United States Patent [19]

Blackburn et al.

[11] Patent Number: 5,705,890
[45] Date of Patent: Jan. 6, 1998

[54] TRICYCLIC INHIBITORS OF THE GPII$_B$III$_A$ RECEPTOR

[75] Inventors: Brent K. Blackburn; Kirk Robarge, both of San Francisco; Todd C. Somers, Foster City, all of Calif.

[73] Assignee: Genentech, Inc., South San Francisco, Calif.

[21] Appl. No.: 313,069

[22] PCT Filed: Jul. 15, 1994

[86] PCT No.: PCT/US94/07989

§ 371 Date: Sep. 26, 1994

§ 102(e) Date: Sep. 26, 1994

[87] PCT Pub. No.: WO95/04057

PCT Pub. Date: Feb. 9, 1995

Related U.S. Application Data

[63] Continuation-in-part of Ser. No. 99,019, Jul. 29, 1993, Pat. No. 5,493,020.

[51] Int. Cl.$^6$ .......................... C07D 487/04; A61K 31/55
[52] U.S. Cl. .......................... 314/220; 514/219; 540/497; 540/498
[58] Field of Search .................. 540/497, 498; 514/219, 220

[56] References Cited

U.S. PATENT DOCUMENTS

| 5,250,679 | 10/1993 | Blackburn et al. | 540/490 |
| 5,403,836 | 4/1995 | Blackburn et al. | 514/213 |
| 5,493,020 | 2/1996 | Blackburn et al. | 540/498 |

FOREIGN PATENT DOCUMENTS

| 519 678 | 12/1992 | European Pat. Off. | A61K 31/55 |
| WO 93/08174 | 4/1993 | WIPO | A61K 31/55 |

OTHER PUBLICATIONS

Ager et al., "Central Nervous System Activity of a Novel Class of Annelated 1,4-Benzodiazephines, Aminomethylene-2,4-dihydro-1H-imidazo [1,2-a][1,4] benzodiazepin-1-ones" *Journal of Medicinal Chemistry* 20(8):1035-1041 (1977).

Hawiger, "Platelet-Vessel Wall Interactions Platelet Adhesion and Aggregation" *Atherosclerosis Reviews* 21:165-186 (1990).

Hynes, "Integrins: A Family of Cell Surface Receptors" *Cell* 48:549-554 (1987).

Kieffer et al., "Platelet Membrane Glycoproteins: Functions in Cellular Interactions" *Annu. Rev. Cell Biol.* 6:329-357 (1990).

Roth, "Platelets and blood vessels: the adhesion event" *Immunology Today* 13(3):100-105 (1992).

Ruoslahti, "Integrins" *J. Clin. Invest.* 87:1-5 (1991).

*Primary Examiner*—Robert T. Bond
*Attorney, Agent, or Firm*—Daryl B. Winter

[57] ABSTRACT

A tricylic benzodiazepine derivative that acts as a nonpeptidyl platelet aggregation inhibitor is provided. This inhibitor potently inhibits fibrinogen binding to the GPII$_b$III$_a$ receptor and is provided in therapeutic compositions for the treatment of diseases for which blocking platelet aggregation is indicated. These nonpeptidyl inhibitors are provided in combination with thrombolytics and anticoagulants.

13 Claims, No Drawings

TRICYCLIC INHIBITORS OF THE GPII$_B$III$_A$ RECEPTOR

This application is a 371 of PCT/US 94/07989, filed 15 Jul. 1994 which is a CIP of Ser. No. 08/099,019, filed 29 Jul. 1993, now U.S. Pat. No. 5,493,020, issued 20 Feb. 1996.

FIELD OF THE INVENTION

The present invention relates to tricyclic integrin receptor inhibitors, especially inhibitors of the platelet GPII$_b$III$_a$ receptor. Specifically, the invention is directed to 1,4-benzodiazepines having one or more 5- or 6-member heterocycle fused to the diazepine moiety that act as antagonists of the final common pathway of platelet aggregation. These antagonists act as potent antithrombotics. The invention further relates to therapeutic applications of these tricyclic inhibitors in diseases for which blocking platelet aggregation is indicated.

BACKGROUND OF THE INVENTION

A. Platelets

Platelets are particles found in whole blood that initiate and provide the structural basis for the hemostatic plug necessary to stop bleeding. Platelets depend on adhesive interactions with extracellular proteins and other cells for proper function (see Hawiger, J. *Atherosclerosis Reviews* 21:165-186 (1990) and Roth J. R. *Immunology Today* 13(2):100-105 (1992)). The external platelet plasma membrane surface is covered with a variety of membrane bound glycoproteins, many of which have recognition and adhesive functions. Perhaps the most abundant platelet membrane adhesive proteins belong to the integrin superfamily which include the glycoproteins; GPII$_b$III$_a$, GPI$_a$II$_a$, GPI$_c$II$_a$, GPI$_b$IX, and the fibronectin and vitronectin receptors (Hynes, R. O., *Cell*, 48: 549 (1987). Each integrin receptor is an αβ heterodimer displaying characteristic affinity and specificity toward various protein ligands found in serum and/or the extracellular matrix including; von Willebrand factor (vWF), collagen, entactin, tenascin, fibronectin (Fn), vitronectin (Vn), and laminin, as well as fibrinogen (Fg) and thrombospondin (see Kieffer et al., *Ann. Rev. Cell Biol.* 6:329-357(1990) and Ruoslahti, *J. Clin. Invest.*, 87:1-5 (1991)). The most abundant integrin found on the surface of normal platelets is GPII$_b$III$_a$ comprising about 50,000 molecules per platelet and representing about 2% of the total platelet protein. GPII$_b$III$_a$ is a non-covalent, calcium ion dependent heterodimeric complex (Jennings, et al., *J. Biol. Chem.* 257: 10458 (1982)) that is restricted in distribution to platelets and other cells of the megakaryocytic lineage (Kieffer et al., supra). On activated platelets, GPII$_b$II$_a$ promiscuously binds a number of protein ligands with varying affinities, including; fibrinogen, fibronectin, von Willebrand factor, vitronectin and thrombospondin (Plow et al., *Biochemistry of Platelets*, Phillips and Shuman eds., p. 225-256, Orlando: Academic Press [1986]). Each of these protein ligands contain at least one tripeptide sequence Arg-Gly-Asp which is commonly referred to as the "recognition sequence". It is believed the most important interactions mediating platelet aggregation involve GPII$_b$III$_a$ binding with the trinodular fibrinogen and, to a lesser extent, with the filamentous von Willebrand factor (Kieffer et al., supra and Albeda et al., *The FASEB Journal*, 4:2868-2880 [1990]).

GPII$_b$III$_a$ binding to its natural ligands can be inhibited to varying degrees by peptides and proteins containing the amino acid recognition sequences; Arg-Gly-Asp (RGD) (Ruoslahti, supra and EPO 0368486, assigned to Merck & Co.), Lys-Gly-Asp (KGD), and the fibrinogen γ-chain carboxy-terminal dodecapeptide HHLGGAKQAGDV and analogues thereof (Timmons et al., *Biochemistry*, 28:2919-2922 [1989]).

B. The Hyperthrombotic State

Many common human disorders are characteristically associated with a hyperthrombotic state leading to intravascular thrombi and emboli. These are a major cause of medical morbidity, leading to infarction, stroke and phlebitis, and of mortality from stroke and pulmonary and cardiac emboli. Patients with atherosclerosis are predisposed to arterial thromboembolic phenomena for a variety of reasons. Atherosclerotic plaques form niduses for platelet plugs and thrombi that lead to vascular narrowing and occlusion, resulting in myocardial and cerebral ischemic disease. This may happen spontaneously or following procedures such as angioplasty or endarterectomy. Thrombi that break off and are released into the circulation cause infarction of different organs, especially the brain, extremities, heart and kidneys.

In addition to being involved in arterial thrombosis, platelets may also play a role in venous thrombosis. A large percentage of such patients have no antecedent risk factors and develop venous thrombophlebitis and subsequent pulmonary emboli without a known cause. Other patients who form venous thrombi have underlying diseases known to predispose them to these syndromes. Some of these patients may have genetic or acquired deficiencies of factors that normally prevent hypercoagulability, such as antithrombin-3. Others have mechanical obstructions to venous flow, such as tumor masses, that lead to low flow states and thrombosis. Patients with malignancy have a high incidence of thrombotic phenomena for unclear reasons. Antithrombotic therapy in this situation with currently available agents is dangerous and often ineffective.

Patients whose blood flows over artificial surfaces, such as prosthetic synthetic cardiac valves or through extracorporeal perfusion devices, are also at risk for the development of platelet plugs, thrombi and emboli. It is standard practice that patients with artificial cardiac valves be treated chronically with anti-coagulants. However, in all instances, platelet activation and emboli formation may still occur despite adequate anticoagulation treatment.

Thus, a large category of patients, including those with atherosclerosis coronary artery disease, artificial heart valves, cancer, and a history of stroke, phlebitis, or pulmonary emboli, are candidates for limited or chronic antithrombotic therapy. The number of available therapeutic agents is limited and these, for the most part, act by inhibiting or reducing levels of circulating clotting factors. These agents are frequently not effective against the patient's underlying hematologic problem, which often concerns an increased propensity for platelet aggregation and adhesion. They also cause the patient to be susceptible to abnormal bleeding. Available antiplatelet agents, such as aspirin, inhibit only part of the platelet activation process and are therefore often inadequate for therapy and also cause the patient to be susceptible to abnormal bleeding. An ideal anti-thrombotic drug would have many properties currently not avialable (see e.g. Sixma, et al. *Thrombosis Research* 67:305-311 [1992]).

C. Therapeutic Agents

An agent which effectively inhibits the final common pathway of platelet activation, namely fibrinogen binding to the GP II$_b$III$_a$ receptor, should accordingly be useful in a large group of disorders characterized by a hyperthrombotic state described above.

Such agents include anti-thrombotic peptides and pseudopeptides capable of inhibiting platelet aggregation. Ruoslahti et al. (U.S. Pat. No. 4,578,079) suggest that tetrapeptides containing the RGD sequence may be used to effect platelet aggregation. Zimmerman et al. (U.S. Pat. No. 4,683,291) disclose that positively charged amino acid residues (e.g. Arg and Lys) and homologues located before or toward the amino terminus of the RGD sequence are superior for inhibiting fibrinogen-platelet binding. Adams et al. (U.S. Pat. No. 4,857,508) describe superior results for in-vitro inhibition of human platelet aggregation in platelet-rich plasma for linear tetrapeptides containing O-methyl-Tyr-amide immediately following the RGD (or homo-RGD) sequence. Barker et al., WO 90/01331, disclose substantially rigid RGD cyclic peptides posessing high affinity for the GP $II_bIII_a$ receptor. A particularly efficacious rigid RGD cyclic peptide described by Barker et al. is represented by the following structure:

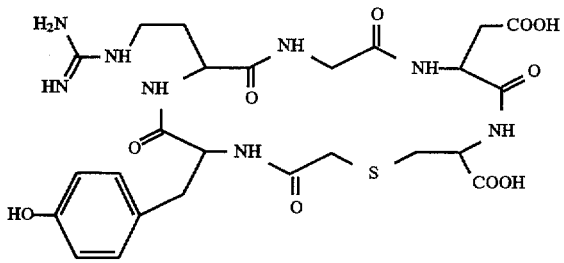

Tjoeng et al. (U.S. Pat. No. 4,879,313) describe peptide mimetic platelet aggregation inhibitors in which the first two residues of the RGD sequence are replaced by the pseudo-dipeptidyl 8-guanidino-octanoyl moiety. Other peptidomimetics in which the Arg of the RGD sequence has been altered include; WO89/07609 (homo-Arg[Har]), EP 341 915 (Har and alkyl-Arg), WO90/15620 (Har and amidino derivatives e.g. imidazolinyl, imidazolyl and substituted imidazolyl), EP 422 937 (aryl-, arylalkyl-, and cycloalkylamines), WO91/07976 (alkylamidino and alkylamino derivatives), WO91/04247 (alkylamino and alkylguanidino proline derivatives), and WO93/07867 (p-(amidino)benzoyl amino substituted β amino acid derivatives). See also EP 384 362 (glycine derivatives) and EP 381 033.

Complete replacement of all residues in the RGD sequence has been described in EP 372 486, assigned to Hoffmann La Roche, where platelet aggregation inhibitors that are derivatives of benzoic and phenylacetic acid are presented. A benzoic acid derivative inhibitor having a particular low $IC_{50}$ in an ELISA measurement of fibrinogen $GPII_bIII_a$ binding has the following structure:

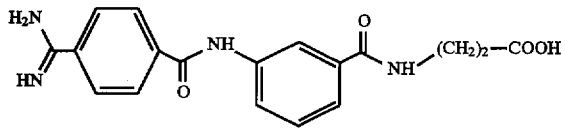

EP 542 708 A1 assigned to Monsanto/Searle discloses related compounds that may be considered p-amidinoaniline derivatives having structures represented by:

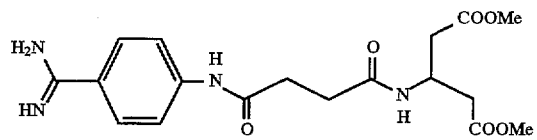

EP 537 980 A1 assigned to Glaxo Ltd. descloses cyclohexaneacetic acids linked through a piperidinyl or piperazinyl group to a p-amidinophenyl moiety, e.g.

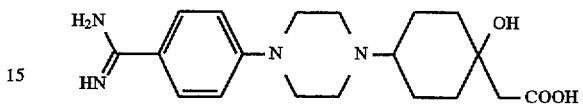

Fibrinogen receptor antagonists possessing alternative structures can be found in EP 478,362, EP 478,363, and EP 478,328, all signed to Merck. A representative Merck compound has the following structure:

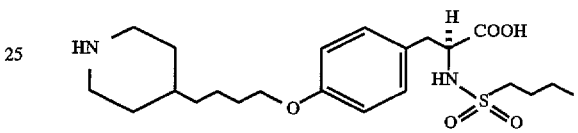

Also of interest are biphenyl derivatives described in EP 483,667 and EP 496,378, the latter publication providing a representitive compound having the structure;

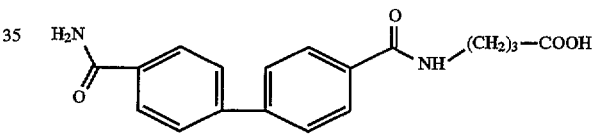

Quinazoline-3-alkanoic acid derivatives are also reported to have an inhibitory effect on platelet aggregation (although possibly by a different mechanism) in EP 456,835 A1. A generic formula representing these compounds is given by:

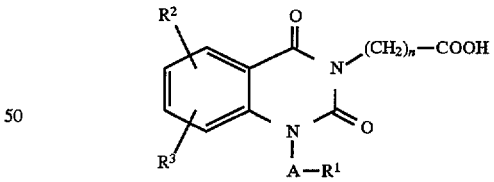

where n is 1 to 3 and $R^2$ and $R^3$ may be interalia hydrogen, lower alkyl, lower alkoxy, aralkyl groups that may be substituted with interalia —$NR^4R^5$, where $R^4$ or $R^5$ may be hydrogen, lower alkyl, or connected with each other to make five- or six-membered heterocycles which may contain another heteroatom, and A—$R^1$ may be lower alkyl.

Substituted benzodiazepines have been reported to be platelet aggregation inhibitors. WO 93/00095 (Smith-Kline Beecham) discloses bicyclic benzodiazepine fibrinogen antagonists in which the benzo moiety is preferably substituted with p-(amidino)benzoyl amino and N-4 may be substituted with carboxyethyl as represented below

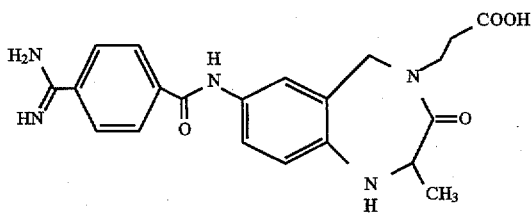

Benzodiazepinedione platelet aggregation inhibitors are described in WO 93/08174 (Genentech). A representative disclosed compound having the p-(amidmo)benzoyl amino benzo substituent is

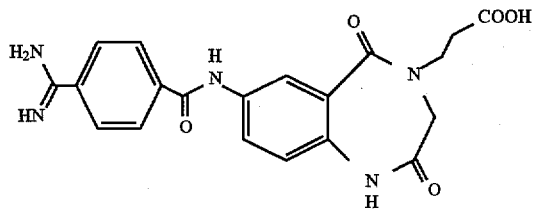

D. Tricyclic 1,4-benzodiazepines 1,4-benzodiazepines with fused 6-membered heterocyclic rings used as CCK antagonists for treatment of panic or anxiety disorders are disclosed in EP 0 519 678 and U.S. Pat. No. 5,210,082(Merck).

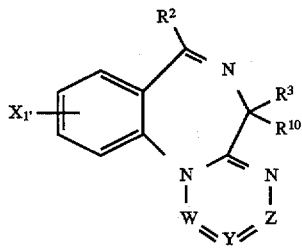

where X is inter alia $NH_2$, $R^2$ is inter alia loweralkyl or carboxyl substituted phenyl, $R^3$ is inter alia NHC(=O)CH($NH_2$)benzyl, $R^{10}$ is H, OH, or methyl, W is CH, CH(alkyl), or C=O, Y is N(alkyl), C(alkyl), or C=O, and Z is N, N(alkyl), C(alkyl), or C=O. None of these tricyclic 1,4-benzodiazepines is disclosed as having platelet aggregation inhibition activity.

E. Objects

It is an object of this invention to produce tricyclic 1,4-benzodiazepines having potent antithrombotic activity. It is another object of the invention to produce such compounds that are essentially free of peptide bonds, substantially rigid, and stable to degradation. It is a further object to produce potent tricyclic 1,4-benzodiazepine antithrombotics that specifically inhibit the $GPII_bIII_a$-Fg interaction but do not strongly inhibit other RGD sensitive integrin interactions including the Vn-VnR, Fn-FnR, and $GPII_bIII_a$-vWF interactions. It is still a further object to produce potent tricyclic 1,4-benzodiazepine platelet aggregation inhibitors that are selective and do not significantly increase cutaneous bleeding time or diminish other hemodynamic factors. It is also an object of this invention to produce tricyclic 1,4-benzodiazepine compounds having a long half-life and a large therapeutic range. Finally it is an object of this invention to produce platelet aggregation inhibitors that have good oral bioavailability.

It is still a further object to produce potent tricyclic 1,4-benzodiazepine inhibitors that are capable of selectively inhibiting other integrin interactions such as the Vn-VnR interaction.

These and other objects of this invention will be apparent from consideration of the invention as a whole.

SUMMARY OF THE INVENTION

The objects of this invention are accomplished by providing a tricyclic compound represented by structural Formula I or II:

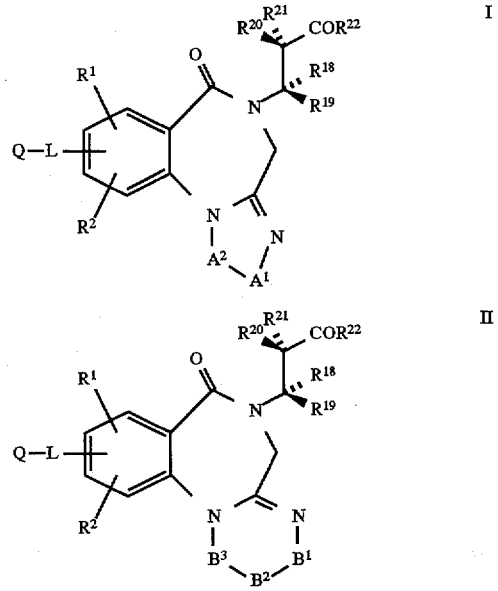

where $R^1$ and $R^2$ are each one or two substituents typically selected from; hydrogen, halo (F, Cl, Br, I), cyano, carboxamido, carboxy, carbamoyloxy, aminocarbonyl, formyloxy, formyl, azido, nitro, imidazolyl, ureido, thioureido, thiocyanato, hydroxy, mercapto, sulfonamido, and an optionally substituted radical selected from; $C_1-C_{12}$alkyl, $C_2-C_{12}$alkenyl, $C_2-C_{12}$alkynyl, $C_3-C_{12}$cycloalkyl, $C_6-C_{14}$aryl, $C_6-C_{10}$aryl-$C_1-C_8$-alkyl, $C_1-C_{12}$alkyloxy, $C_1-C_{12}$alkyloxy$C_1-C_{12}$alky, $C_1-C_{12}$alkyloxycarbonyl, $C_6-C_{14}$ aryloxy, $C_1-C_{12}$acylamino, N,N-di($C_1-C_{12}$)acylamino, N-($C_1-C_{12}$)alkyl-N-($C_1-C_{12}$)-acylamino, $C_1-C_{12}$alkylsulfonamido, N-($C_1-C_{12}$)alkyl-N-($C_1-C_{12}$)alkylsulfonylamino, $C_1-C_{12}$alkylthiocarbonyl, $C_1-C_{12}$alkylthio, $C_1-C_{12}$alkylthio$C_1-C_{12}$alkyl, $C_1-C_{12}$alkylsulfinyl, $C_1-C_6$alkylsulfinyl$C_1-C_6$alkyl, $C_1-C_{12}$alkylsulfonyl, $C_1-C_6$alkylsulfonyl$C_1-C_6$alkyl, $C_1-C_{12}$alkylsulfonato, N-($C_1-C_{12}$)alkylsulfonamido, N,N-di-($C_1-C_{12}$) sulfonamido, N-($C_1-C_{12}$) alkyl-N-thioformylamino, $C_1-C_{12}$thioacylamino, N-($C_1-C_{12}$)alkyl-N-($C_1-C_{12}$) thioacylamino, $C_1-C_{12}$alkylsulfinamido, N-($C_1-C_{12}$)alkyl-N-($C_1-C_{12}$)alkylsulfinylamino, $C_1-C_{12}$carbalkoxy, $C_1-C_{12}$alkylcarbonyl, $C_1-C_{12}$ alkyloxycarbonyl, $C_1-C_{12}$alkanoyloxy, N-($C_1-C_{12}$)alkylcarboxamido, N,N-di-($C_1-C_{12}$)carboxamido, N,N-di-($C_1-C_{12}$) alkylaminocarbonyl, N-($C_1-C_{12}$)alkylcarbamoyloxy, N,N-di-($C_1-C_{12}$)carbamoyloxy, and heterocycloalkyl or heteroaryl having from 1 to 3 rings, each ring having from 5 to 7 atoms with from 0–3 heteroatoms selected from N, O, and S, provided that at least one ring contains a heteroatom, where the substituents are typically selected from halo (F, Cl, Br, I), amino, guanidino, imidazolyl, indolyl, cyano, azido, nitro, hydroxy, mercapto, morpholino, morpholinyl, piperazinyl, piperidinyl, pyrrolinyl, sulfonamido, ureido, thioureido, carboxy, aminocarbonyl, $C_1-C_4$aminocarbonyl, carboxamido, carbamoyloxy, formyloxy, formyl, $C_1$–$C_4$alkyloxycarbonyl, $C_1$–$C_4$alkyl, $C_1$–$C_4$alkylamino, $C_1$–$C_4$alkoxy, phenyl, hydroxyphenyl, and phenoxy. Optionally, $R^1$ and $R^2$ when bonded to adjacent carbon atoms may join to form an unsubstituted or substituted aryl ring, where the substituents are typically selected from halo (F, Cl, Br, I), cyano, azido, nitro, hydroxy, mercapto, sulfonamido, ureido, thioureido, carboxamido, carbamoyloxy, formyloxy, formyl, $C_1$–$C_4$alkyl, $C_1$–$C_4$alkoxy, phenyl, and phenoxy.

Q is a substituted or unsubstituted moiety selected from:
(A) an amino group including;
(1) —$NH_2$,
(2) —$NR^3H$,
(3) —$NR^3R^4$, and
(4) —$NR^3R^4R^5$, where $R^3$, $R^4$, and $R^5$ are typically selected from; (i) an optionally substituted radical selected from (a) —$NR^6R^7$, (b) —C(=$NR^5$)—$NR^6R^7$, (c) —N=$CR^9$—$NR^6R^7$, (d) —$NR^{10}$—$CR^9$=$NR^8$, (e) —$NR^{10}$—C(=$NR^8$)—$NR^6R^7$ where each $R^6$, $R^7$, $R^8$, $R^9$, and $R^{10}$ is independently selected from hydrogen, hydroxy, $C_1$–$C_4$alkoxy, $C_1$–$C_4$alkyl, cyano, and halo(F, Cl, Br, I)$C_1$–$C_4$alkyl, (ii) optionally substituted $C_1$–$C_{12}$alkyl, (iii) optionally substituted $C_3$–$C_7$alkenyl, (iv) optionally substituted $C_3$–$C_7$alkynyl, (v) optionally substituted $C_3$–$C_{12}$cycloalkyl; (vi) optionally substituted $C_5$–$C_{12}$cycloalkenyl, (vii) optionally substituted $C_6$–$C_{14}$aryl, (viii) optionally substituted $C_1$–$C_6$alkyl$C_6$–$C_{14}$aryl, (ix) optionally substituted $C_3$–$C_6$alkenyl-$C_6$–$C_{10}$aryl, (x) optionally substituted heterocyclyl, (xi) optionally substituted $C_1$–$C_6$alkylheterocyclyl, (xii) optionally substituted $C_1$–$C_8$alkoxy, (xiii) optionally substituted $C_1$–$C_8$alkoxycarbonyl, (xiv) optionally substituted $C_1$–$C_8$thioalkoxy, (xv) optionally substituted $C_3$–$C_{10}$alkenoxy, and (xvi) optionally substituted $C_6$–$C_{14}$aryloxy, (xvii) optionally substituted $C_6$–$C_{14}$aryloxycarbonyl, (xviii) optionally substituted $C_6$–$C_{14}$aryl$C_1$–$C_6$alkyloxycarbonyl, where the substituents are usually one to three $R^{11}$, each $R^{11}$ typically selected from (a) optionally substituted $C_6$–$C_{12}$aryloxy, (b) optionally substituted $C_6$–$C_{12}$arylamino, (c) optionally substituted $C_6$–$C_{12}$aroyl, (d) optionally substituted $C_6$–$C_{12}$arylthio, where the substituents are usually one to three $R^{12}$, each $R^{12}$ typically selected from nitro, amino, $C_1$–$C_8$alkylamino, di-($C_1$–$C_8$)alkylamino, amidino, aminomethyleneimino, imino, imino-$C_1$–$C_4$alkyl, iminomethyleneamino, guanidino, $C_6$–$C_{10}$arylamino, $C_1$–$C_8$acylamino, $C_1$–$C_4$alkylsulfonamino, azido, cyano, hydroxy, hydroxy$C_1$–$C_8$alkyl, $C_1$–$C_8$alkoxy, phenyloxy, $C_1$–$C_8$alkanoyloxy, $C_1$–$C_8$alkanoyl, $C_6$–$C_{12}$aroyl, benzamido, phenyl, halo (F, Cl, Br, I), halo$C_1$–$C_8$-alkyl, and $C_1$–$C_8$alkyl, (e) $C_1$–$C_8$alkoxy (f) $C_1$–$C_8$alkthio (g) halo (F, Cl, Br, I), (h) hydroxy, (i) mercapto, (j) $C_1$–$C_8$alkylcarbonyl, (k) carbamoyl, (l) formyl, (m) formyloxy, (n) carboxy, (o) carb-$C_1$–$C_8$alkyloxy, (p) $C_1$–$C_8$alkanoyloxy, (q) N-($C_1$–$C_8$) alkylcarboxamido, (r) N-($C_1$–$C_8$),N-$C_1$–$C_8$) dialkylcarboxamido, (s) carbamoyloxy, (t) N-($C_1$–$C_8$) alkylcarbamoyloxy, (u) N-($C_1$–$C_8$),N-($C_1$–$C_8$) dialkylcarbamoyloxy, (v) $C_1$–$C_8$alkylsulfinyl, (w) $C_1$–$C_8$ alkylsulfonyl, (x) $C_1$–$C_8$alkylsulfonato, (y) sulfo, (z) sulfonamido, (aa) N-($C_1$–$C_8$) alkylsulfonamido, (ab) N-($C_1$–$C_8$), N-($C_1$–$C_8$)dialkylsulfonamido, (ac) amino, (ad) $C_1$–$C_8$ alkylamino, (ae) $C_1$–$C_8$ dialkylamino, (af) $C_1$–$C_8$ acylamino, (ag) N-($C_1$–$C_8$), N-($C_1$–$C_8$)-diacylamino, (ah) N-($C_1$–$C_8$)-alkyl-N-($C_1$–$C_8$)-acylamino, (ai) formylamino, (aj) ureido, (ak) isothioureido, (al) amino-$C_2$–$C_8$ alkylthio, (am) amino-$C_2$–$C_8$alkloxy, (an) amidino, (ao) guanidino, (ap) aminomethyleneimino, (aq) imino, (ar) imino-$C_1$–$C_4$ alkyl, (as) iminomethyleneamino, (at) glycylamino, (au) glycyl, (av) phthalimido, (aw) succinimido, (ax) morpholino, (ay) $C_1$–$C_8$ alkylsulfonamido, (az) N-($C_1$–$C_8$) -alkyl-N-($C_1$–$C_8$)alkyl-N-($C_1$–$C_8$)alkylsulfonoylamino, (ba) $C_1$–$C_8$alkylsulfinamino, (bb) N-($C_1$–$C_8$)alkyl-N-($C_1$–$C_8$) alkylsulfinamino, (bc) $C_1$–$C_8$ lkoxyamino, (bd) $C_1$–$C_8$ alkoxyamino, (be) N-($C_1$–$C_8$)alkyl-N-($C_1$–$C_8$)alkoxyamino, (bf) $C_3$–$C_7$cycloalkyl, (bg) oxo, and (bh) heterocyclyl, optionally any one or two pairs of $R^3$–$R^{10}$ may independently be joined to form one or two optionally substituted heterocyclic rings, each ring optionally fused with one or two optionally substituted homocyclic or heterocyclic rings of from four to seven atoms where any heterocyclic ring contains from one to four heteroatoms selected from N, O, and S and where any ring may be substituted with from one to three $R^{12}$, (B) an amidino (aminoiminomethyl) group including;
(1) —C(=NH)—$NH_2$,
(2) —C(=NH)—$NHR^3$,
(3) —C(=$NR^4$)—$NHR^3$,
(4) —C(=NH)—$NR^3R^4$, and
(5) —C(=$NR^5$)—$NR^3R^4$, where $R^3$, $R^4$, and $R^5$ are defined above, (C) an aminoalkyleneamino group including;
(1) —N=CH—$NH_2$,
(2) —N=CH—$NHR^3$,
(3) —N=CH—$NR^3R^4$, and
(4) —N=$CR^5$—$NR^3R^4$, where $R^3$, $R^4$, and $R^5$ are defined above, (D) an iminoalkyleneamino group, including;
(1) —NH—CH=NH,
(2) —NH —CH=$NR^3$,
(3) —NH—$CR^4$=$NR^3$, and
(4) —$NR^5$—$CR^4$=$NR^3$, where $R^3$, $R^4$, and $R^5$ are defined above, (E) a guanidino (aminoiminomethyleneamino) group including;
(1) —NH—C(=NH)—$NH_2$,
(2) —NH—C(=NH)—$NR^3H$,
(3) —NH—C(=NH)—$NR^3R^4$,
(4) —NH—C(=$NR^5$)—$NR^3R^4$,
(5) —$NR^3$—C(=$NR^3$)—$NR^3R^4$,
(6) —$NR^3$—C(=NH)—$NR^3R^4$,
(7) —$NR^3$—C(=$NR^3$)—$NH_2$,
(8) —$NR^3$—C(=NH)—$NH_2$,
(9) —$NR^3$—C(=$NR^3$)—$NHR^4$, and
(10) —$NR^3$—C(=NH)—$NHR^4$, where $R^3$, $R^4$, and $R^5$ are defined above, (F) an optionally substituted saturated heterocyclic group including;

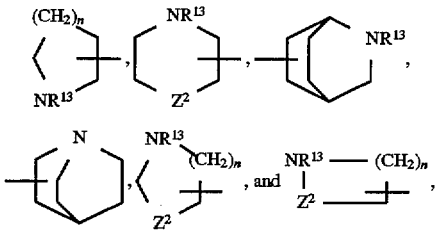

where (1) n is 0, 1, 2, or 3, (2) $R^{13}$ is selected from; $R^6$, —$CR^9$=$NR^8$, —$CR^9$(=$NR^8$)—$NR^6R^7$, —C(=$NR^8$)

—$NR^6R^7$, —$N=CR^9$—$NR^6R^7$, —$NR^{10}$—$CR^9=NR^8$, and —$NR^{10}$—$(C=NR^8)$—$NR^6R^7$ where $R^6$-$R^{10}$ are defined above, (3) $Z^2$ is O, S, or $NR^{13}$, and (4) the substituents are independently one to three $R^{12}$, (G) an optionally substituted unsaturated (nonaromatic) heterocyclyl including;

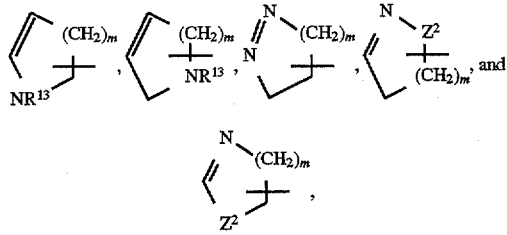

where (1) m is 1, 2, or 3, (2) $Z^2$ and $R^{13}$ are defined above, and (3) the substituents are typically one to three $R^{12}$, (H) an optionally substituted unsaturated (aromatic) heterocyclyl including;

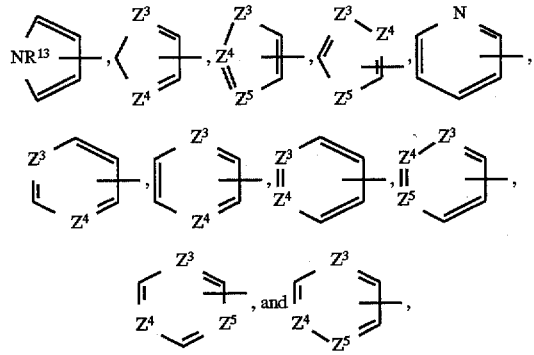

where (1) $Z^3$, $Z^4$, and $Z^5$ are typically selected from O, S, N, and NH, provided at least one $Z^3$, $Z^4$, or $Z^5$ is N or NH, (2) $R^{13}$ is defined above, and the substituents are independently one to three $R^{12}$. Exemplary heterocyclic Q groups include; isoindolmyl, quinuclidinyl, morpholinyl, piperidine, piperazine, pyridine, pyrimidine, and 1,3-diazacyclohex-4-ene. Optionally, any of the nitrogen containing heterocycles described above may be substituted at any accessable position with amino, imino, amidino, aminomethyleneimino, iminomethyleneamino, guanidino, $N^G$-aminoguanidino, alkylamino, dialkylamino, trialkylamino, or alkylideneamino groups.

L is a bivalent radical containing from 3 to 9 methylene groups where any methylene group or groups may be replaced with one or more alkene, alkyne, aryl or functional groups containing the heteroatoms selected from the group N, O, and S. Typically, L is phenyl or a 6-member heteroaryl bonded through two optionally substituted atoms selected from O, N, and C (e.g. —$C(=O)NH$—) to the benzodiazepine nucleus. More specifically, typical L's are benzoylamino and pyridylcarbonylamino. Preferably, L is an optionally substituted bivalent radical including; (A) $C_3$-$C_7$-alkylene, (B) $C_3$-$C_7$-cycloalkylene, (C) $C_3$-$C_7$-alkenylene, (D) $C_3$-$C_7$-alkadienylene, (E) $C_3$-$C_7$-alkynylene, (F) $C_4$-$C_7$-alkadiynylene, (G) $C_4$-$C_7$-alkenynylene, (H) $C_6$-$C_{14}$-arylene, (I) $C_6$-$C_{14}$-aryl-$C_2$-$C_4$-alkynylene, (J) $C_1$-$C_3$-alkyl-$C_6$-$C_{14}$-aryl-$C_2$-$C_4$-alkynylene, (K) $C_6$-$C_{14}$-aryl-$C_2$-$C_4$-alkenylene, (L) $C_1$-$C_3$-alkyl-$C_6$-$C_{14}$-arylene, (M) $C_1$-$C_3$-alkyl-$C_6$-$C_{14}$-aryl-$C_2$-$C_4$-alkenylene, (N) $C_6$-$C_{14}$-aryl-$C_1$-$C_3$-alkylene, (O) $C_6$-$C_{14}$-aryl-$C_1$-$C_3$-alkyloxyene, (P) $C_1$-$C_2$-alkyl-$C_6$-$C_{14}$-aryl-$C_1$-$C_2$-alkylene, (Q) $C_1$-$C_3$-alkyloxy-$C_6$-$C_{14}$-arylene, (R) $C_2$-$C_6$-alkyloxyene, (S) $C_1$-$C_5$-alkyloxy-$C_1$-$C_5$-alkylene, (T) $C_6$-$C_{10}$-aryloxyene, (U) $C_6$-$C_{10}$-aryloxy-$C_1$-$C_5$-alkylene, (V) $C_2$-$C_6$-alkylthioene, (W) $C_1$-$C_5$-alkylthio-$C_1$-$C_5$-alkylene, (X) $C_6$-$C_{10}$-arylthioene, (Y) $C_6$-$C_{10}$-arylthio-$C_1$-$C_5$-alkylene, (Z) $C_1$-$C_5$-alkylsulfoxide-$C_1$-$C_5$-alkylene, (AA) $C_1$-$C_5$-alkylsulfone-$C_1$-$C_5$-alkylene,

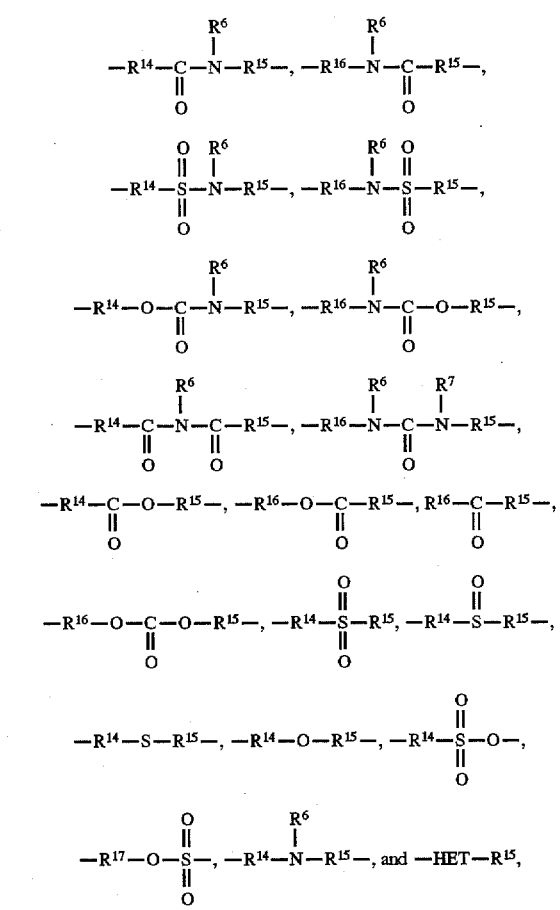

where $R^{14}$ is selected from; (i) a chemical bond, (ii) $C_1$-$C_8$alkyl, (iii) $C_1$-$C_8$alkyloxy, (iv) $C_3$-$C_7$-cycloalkyl, (v) $C_2$-$C_5$-alkenyl, (vi) $C_3$-$C_5$-alkynyl, (vii) $C_6$-$C_{10}$-aryl, (viii) $C_1$-$C_2$-alkyl-$C_6$-$C_{10}$-aryl-$C_1$-$C_2$-alkyl, (ix) $C_1$-$C_3$-alkyl-$C_6$-$C_{12}$-aryl, (x) $C_6$-$C_{10}$-aryl-$C_1$-$C_2$-alkyl, (xi) $C_6$-$C_{10}$-aryloxy-$C_1$-$C_2$-alkyl, (xii) HET, and (xiii) piperizinyl;

$R^{15}$ is selected from; (i) a chemical bond, (ii) $C_1$-$C_4$-alkyl, (iii) $C_2$-$C_4$-alkenyl, (iv) $C_2$-$C_4$-alkynyl, (v) $C_1$-$C_3$-alkyl-$C_6$-$C_{12}$-aryl, and (vi) $C_6$-$C_{10}$-aryl;

$R^{16}$ is selected from; (i) a chemical bond, (ii) $C_1$-$C_5$-alkyl, (iii) $C_3$-$C_7$-cycloalkyl, (iv) $C_3$-$C_5$-alkenyl, (v) $C_3$-$C_5$-alkynyl, (vi) $C_6$-$C_{10}$-aryl, (vii) $C_1$-$C_3$-alkyl-$C_6$-$C_{12}$-aryl, (viii) $C_6$-$C_{10}$-aryl-$C_1$-$C_2$-alkyl, (ix) HET, and (x) piperizinyl;

$R^{17}$ is selected from; (i) $C_3$-$C_4$-alkenyl, (ii) $C_3$-$C_4$-alkynyl, (iii) $C_6$-$C_{10}$-aryl, and (iv) benzyl; HET is a saturated or unsaturated heterocycle having from 5-14 atoms in the cycle(s) and from 1-3 heteroatoms selected from N, O, and S, where the substituents are selected from one to three $R^{12}$;

Where any aryl group comprising substituent L is unsubstituted or substituted with one to four of the groups selected from (i) nitro, (ii) halo (F, Cl, Br, I), (iii) $C_1$–$C_4$alkoxy, (iv) halo(F, Cl, Br, I)$C_1$–$C_4$alkyl, and (v) amino;

$R^{18}$, $R^{19}$, $R^{20}$ and $R^{21}$ are independently selected from hydrogen, $C_1$–$C_5$alkyl, halo(F, Cl, Br, I)$C_1$–$C_5$alkyl, $C_1$–$C_5$alkoxy, halo (F, Cl, Br, I), cyano, carboxy, hydroxy, $C_1$–$C_5$alkoxycarbonyl, and $C_1$–$C_5$alkylsulfonyl$C_0$–$C_3$alkyl;

$R^{22}$ is selected from (a) hydroxy, (b) $C_1$–$C_8$-alkoxy, (c) $C_3$–$C_{12}$-alkenoxy, (d) $C_6$–$C_{12}$-aryloxy, (e) $C_1$–$C_6$-alkyl-$C_6$–$C_{12}$-aryloxy, (f) di-$C_1$–$C_8$-alkylamino-$C_1$–$C_8$-alkoxy, (g) acylamino-$C_1$–$C_8$-alkoxy selected from the group (i) acetylaminoethoxy, (ii) nicotinoylaminoethoxy, and (iii) succinamidoethoxy, (h) $C_1$–$C_8$-alkoyloxy-$C_1$–$C_8$-alkoxy, (i) $C_6$–$C_{12}$-aryl-$C_1$–$C_8$-alkoxy, where any aryl groups are unsubstituted or substituted with one to three of the groups (i) nitro, (ii) halo (F, Cl, Br, I), (iii) $C_1$–$C_4$-alkoxy, and (iv) amino, (j) hydroxy-$C_2$–$C_8$-alkoxy, (k) dihydroxy-$C_3$–$C_8$-alkoxy, and (l) $NR^{23}R^{24}$;

$R^{23}$ and $R^{24}$ are independently selected from the group (a) hydrogen, (b) $C_1$–$C_8$-alkyl, (c) $C_3$–$C_8$-alkenyl, (d) $C_6$–$C_{12}$-aryl, (e) $C_6$–$C_{12}$-aryl-$C_1$–$C_8$-alkyl where any aryl groups are unsubstituted or substituted with one to three of the groups (i) nitro, (ii) halo (F, Cl, Br, I), (iii)$C_1$–$C_4$-alkoxy, and (iv) amino;

$A^1$ is selected from $CR^1N$, and $NR^{25}$;

$A^2$ is selected from $CR^2$, N, O=S=O, S=O, S, O, C=O, C—$OR^{26}$, and C=N—$R^{25}$;

$B^1$ is selected from $CR^1$, N, $NR^{25}$, or C=O;

$B^2$ is selected from $CR^2$, $NR^{25}$, O=S=O, S=O, S, O, or C=O;

$B^3$ is selected from, $CR^1$, $CHR^2$, or C=O;

$R^{25}$ is selected from $R^6$ and $(CH_2)_mR^1$, where m is 1, 2, or 3; and $R^{26}$ is selected from hydrogen, $C_1$–$C_8$-alkyl, $C_6$–$C_{12}$-aryl, and $C_6$–$C_{12}$-aryl-$C_1$–$C_8$-alkyl where any aryl or alkyl groups are unsubstituted or substituted with one to three of the groups nitro, and halo (F, Cl, Br, I).

Preferred tricyclic compounds of this invention are represented by structural Formulae IIIa–VIIIb.

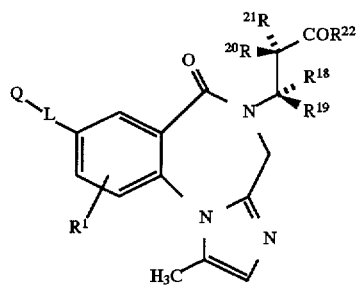
IIIa

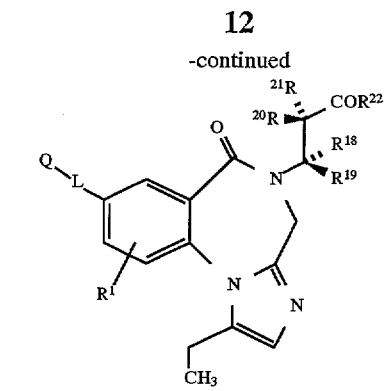
IIIb

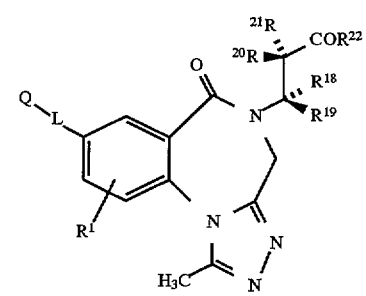
IVa

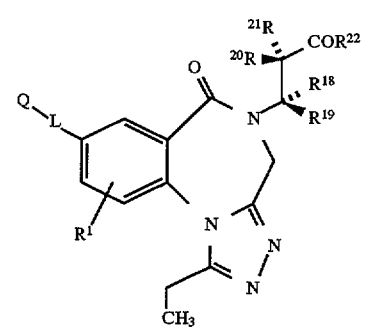
IVb

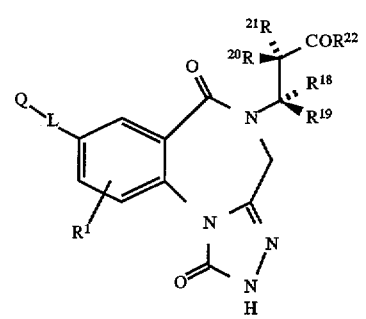
Va

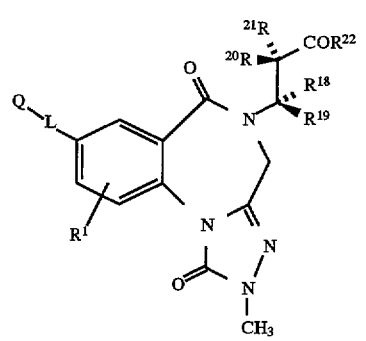
Vb

-continued

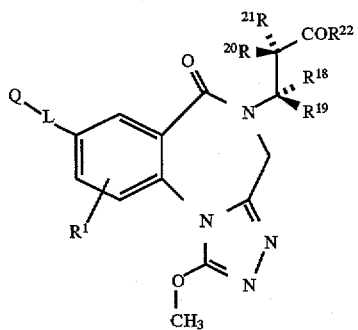

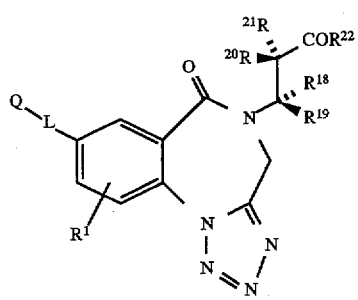

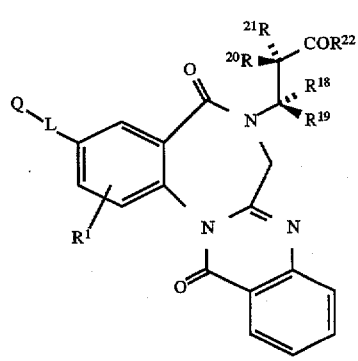

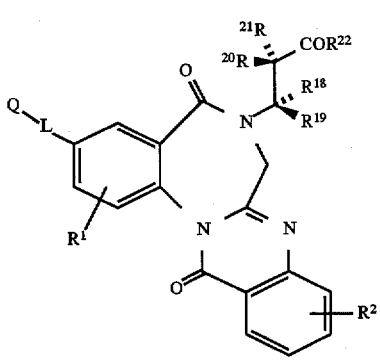

where R¹, R², R¹⁸, R¹⁹, R²⁰, R²¹, R²², Q, and L are as defined above.

More preferred compounds of this invention are represented by structural formula Ia

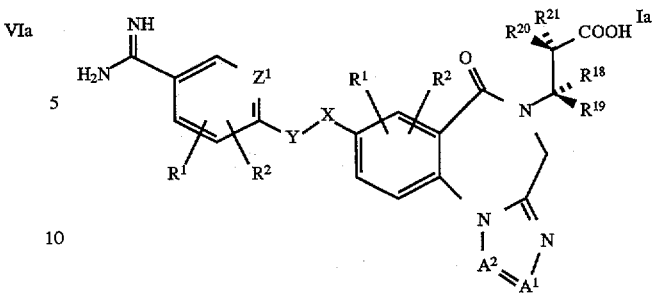

where each $R^1$ and $R^2$ is one or two substituents selected from hydrogen, fluoro, trifluoromethyl and chloro; $R^{18}$, $R^{19}$, $R^{20}$ and $R^{21}$ are selected from $R^1$ and methyl; $A^1$ is CH or N; $A^2$ is CH, C—CH₃, C—CH₂—CH₃ or N; —X—Y— is selected from —NH—C(=O)—, —C(=O)—NH—, —CC—, —CH₂—O—, —O—CH₂— and —CH₂—CH₂—; and $Z^1$ is selected from N and CR¹.

Most preferred compounds of this invention may be selected from:

4H-imidazo[1,2-a][1,4]benzodiazepine-5(6H)-propanoic acid,8-[[4-(aminoiminomethyl)phenyl]ethynyl]-1-methyl-6-oxo, acetate, 4H-imidazo[1,2-a][1,4]benzodiazepine-5(6H)-propanoic acid,8-[[4-(aminoiminomethyl)phenyl]methoxy]-1-methyl-6-oxo, acetate, 4H-imidazo[1,2-a][1,4]benzodiazepine-5(6H)-propanoic acid,8-[[4-(aminoiminomethyl)benzoyl]amino]-1-methyl-6-oxo, acetate, 4H-imidazo[1,2-a][1,4]benzodiazepine-5(6H)-propanoic acid,8-[[4-(aminoiminomethyl)picolinoyl]amino]-1-methyl-6-oxo, acetate, 4H-imidazo[1,2-a][1,4]benzodiazepine-5(6H)-propanoic acid,8-[[4-(aminoiminomethyl)phenyl]ethynyl]-1-phenyl-6-oxo, acetate, 4H-imidazo[1,2-a][1,4]benzodiazepine-5(6H)-propanoic acid,8-[[4-(aminoiminomethyl)phenyl]methoxy]-1-phenyl-6-oxo, acetate, 4H-imidazo[1,2-a][1,4]benzodiazepine-5(6H)-propanoic acid,8-[[4-(aminoiminomethyl)benzoyl]amino]-1-phenyl-6-oxo, acetate, 4H-imidazo[1,2-a][1,4]benzodiazepine-5(6H)-propanoic acid,8-[[4-(aminoiminomethyl)picolinoyl]amino]-1-phenyl-6-oxo, acetate, 4H-[1,2,4]triazolo[4,3-a][1,4]benzodiazepine-5(6H)-propanoic acid,8-[[4-(aminoiminomethyl)phenyl]methoxy]-1-methyl-6-oxo, acetate, 4H-[1,2,4]triazolo[4,3-a][1,4]benzodiazepine-5(6H)-propanoic acid,8-[[4-(aminoiminomethyl)phenyl]ethynyl]-1-methyl-6-oxo, acetate, 4H-[1,2,4]triazolo[4,3-a][1,4]benzodiazepine-5(6H)-propanoic acid,8-[[4-(aminoiminomethyl)benzoyl]amino]-1-methyl-6-oxo, acetate, 4H-[1,2,4]triazolo[4,3-a][1,4]benzodiazepine-5(6H)-propanoic acid,8-[[4-(aminoiminomethyl)picolinoyl]amino]-1-methyl-6-oxo, acetate, 4H-[1,2,4]triazolo[4,3-a][1,4]benzodiazepine-5(6H)-propanoic acid,8-[[4-(ammoiminomethyl)phenyl]methoxy]-1-hydroxy-6-oxo, acetate, 4H-[1,2,4]triazolo[4,3-a][1,4]benzodiazepine-5(6H)-propanoic acid,8-[[4-(aminoiminomethyl)phenyl]ethynyl]-1-hydroxy-6-oxo, acetate, 4H-[1,2,4]triazolo[4,3-a][1,4]benzodiazepine-5(6H)-propanoic acid,8-[[4-(aminoiminomethyl)benzoyl]amino]-1-hydroxy-6-oxo, acetate, 4H-[1,2,4]triazolo[4,3-a][1,4]benzodiazepine-5(6H)-propanoic acid,8-[[4-(aminoiminomethyl)picolinoyl]amino]-1-hydroxy-6-oxo, acetate, 4H-[1,2,4]triazolo[4,3-a][1,4]benzodiazepine-5(6H)-propanoic acid,8-[[4-(aminoiminomethyl)phenyl]methoxy]-1-methoxy-6-oxo, acetate, 4H-[1,2,4]triazolo[4,3-a][1,4]benzodiazepine-5(6H)-propanoic acid,8-[[4-(aminoiminomethyl)phenyl]ethynyl]-1-methoxy-6-oxo, acetate, 4H-[1,2,4]triazolo[4,3-a][1,4]benzodiazepine-5(6H)-propanoic acid,8-[[4-(aminoiminomethyl)benzoyl]amino]-1-methoxy-6-oxo, acetate, 4H-[1,2,4]triazolo[4,3-a][1,4]benzodiazepine-5(6H)-propanoic acid,8-[[4-(aminoiminomethyl)picolinoyl]amino]-1-methoxy-6-oxo, acetate, 4H-[1,2,4]triazolo[4,3-a][1,4]benzodiazepine-5(6H)-propanoic acid,8-[[4-(aminoiminomethyl)phenyl]methoxy]-1-phenyl-6-oxo, acetate, 4H-[1,2,4]triazolo[4,3-a][1,4]benzodiazepine-5(6H)-propanoic acid,8-[[4-(aminoiminomethyl)phenyl]ethynyl]-1-phenyl-6-oxo, acetate, 4H-[1,2,4]triazolo[4,3-a][1,4]benzodiazepine-5(6H)-propanoic acid,8-[[4-(aminoiminomethyl)benzoyl]amino]-1-phenyl-6-oxo, acetate, 4H-[1,2,4]triazolo[4,3-a][1,4]benzodiazepine-5(6H)-propanoic acid,8-[[4-(aminoiminomethyl)picolinoyl]amino]-1-phenyl-6-oxo, acetate, 4H-[1,2,3,4]tetrazolo[4,3-a][1,4]benzodiazepine-5(6H)-propanoic acid,8-[[4-(aminoiminomethyl)phenyl]methoxy]-6-oxo, acetate, 4H-[1,2,3,4]tetrazolo[4,3-a][1,4]benzodiazepine-5(6H)-propanoic acid,8-[[4-(aminoiminomethyl)phenyl]ethynyl]-6-oxo, acetate, 4H-[1,2,3,4]tetrazolo[4,3-a][1,4]benzodiazepine-5(6H)-propanoic acid,8-[[4-(aminoiminomethyl)benzoyl]amino]-6-oxo, acetate, 4H-[1,2,3,4]tetrazolo[4,3-a][1,4]benzodiazepine-5(6H)-propanoic acid,8-[[4-(aminoiminomethyl)picolinoyl]amino]-6-oxo, acetate, 4H-imidazo[1,2-a][1,4]benzodiazepine-5(6H)-(R)-2-methyl,(S)-3-methyl propanoic acid, 8-[[4-(aminoiminomethyl)phenyl]ethynyl]-1-methyl-6-oxo, acetate, 4H-imidazo[1,2-a][1,4]benzodiazepine-5(6H)-(R)-2-methyl,(S)-3-methyl propanoic acid, 8-[[4-(aminoiminomethyl)-3-chloro-phenyl]ethynyl]-1-methyl-6-oxo, acetate, 4H-imidazo[1,2-a][1,4]benzodiazepine-5(6H)-(R)-2-methyl,(S)-3-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(R)-2-methyl,(S)-3-methyl propanoic acid, 8-[[4-(aminoiminomethyl)-pyridyl]ethynyl]-1-methyl-6-oxo, acetate, 4H-imidazo[1,2-a][1,4]benzodiazepine-5(6H)-(S)-2-methyl,(R)-3-methyl propanoic acid, 8-[[4-(aminoiminomethyl)phenyl]ethynyl]-1-methyl-6-oxo, acetate, 4H-imidazo[1,2-a][1,4]benzodiazepine-5(6H)-(S)-2-methyl,(R)-3-methyl propanoic acid, 8-[[4-(aminoiminomethyl)-3-chloro-phenyl]ethynyl]-1-methyl-6-oxo, acetate, 4H-imidazo[1,2-a][1,4]benzodiazepine-5(6H)-(S)-2-methyl,(R)-3-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(S)-2-methyl,(R)-3-methyl propanoic acid, 8-[[4-(aminoiminomethyl)-pyridyl]ethynyl]-1-methyl-6-oxo, acetate, 4H-imidazo[1,2-a][1,4]benzodiazepine-5(6H)-(S)-2-methyl,(R)-3-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(S)-2-methyl,(R)-3-methyl propanoic acid, 8-[[4-(aminoiminomethyl)-pyridyl]ethynyl]-1-methyl-6-oxo, acetate, 4H-imidazo[1,2-a][1,4]benzodiazepine-5(6H)-(R)-2-methyl propanoic acid, 8-[[4-(aminoiminomethyl)phenyl]ethynyl]-1-methyl-6-oxo, acetate, 4H-imidazo[1,2-a][1,4]benzodiazepine-5(6H)-(R)-2-methyl propanoic acid, 8-[[4-(aminoiminomethyl)-3-chloro-phenyl]ethynyl]-1-methyl-6-oxo, acetate, 4H-imidazo[1,2-a][1,4]benzodiazepine-5(6H)-(R)-2-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(R)-2-methyl propanoic acid, 8-[[4-(aminoiminomethyl)-pyridyl]ethynyl]-1-methyl-6-oxo, acetate, 4H-imidazo[1,2-a][1,4]benzodiazepine-5(6H)-(S)-2-methyl propanoic acid, 8-[[4-(aminoiminomethyl)phenyl]ethynyl]-1-methyl-6-oxo, acetate, 4H-imidazo[1,2-a][1,4]benzodiazepine-5(6H)-(S)-2-methyl propanoic acid, 8-[[4-(aminoiminomethyl)-3-chloro-phenyl]ethynyl]-1-methyl-6-oxo, acetate, 4H-imidazo[1,2-a][1,4]benzodiazepine-5(6H)-(S)-2-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(S)-2-methyl propanoic acid, 8-[[4-(aminoiminomethyl)-]pyridyl]ethynyl]-1-methyl-6-oxo, acetate, 4H-imidazo[1,2-a][1,4]benzodiazepine-5(6H)-(S)-3-methyl propanoic acid, 8-[[4-(aminoiminomethyl)phenyl]ethynyl]-1-methyl-6-oxo, acetate, 4H-imidazo[1,2-a][1,4]benzodiazepine-5(6H)-(S)-3-methyl propanoic acid, 8-[[4-(aminoiminomethyl)-3-chloro-phenyl]ethynyl]-1-methyl-6-oxo, acetate, 4H-imidazo[1,2-a][1,4benzodiazepine-5(6H)-(S)-3-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(S)-3-methyl propanoic acid, 8-[[4-(aminoiminomethyl)-]pyridyl]ethynyl]-1-methyl-6-oxo, acetate, 4H-[1,2,3,4,]tetrazolo[4,3a][1,4]benzodiazepine-5(6H)-(R)-2-methyl,(S)-3-methyl-propanoic acid,8-[[4-(aminoiminomethyl)methoxy-6-oxo, acetate, 4H-[1,2,3,4]tetrazolo[4,3a][1,4]benzodiazepine-5(6H)-(S)-2-methyl,(R)-3-methyl-propanoic acid,8-[[4-(aminoiminomethyl)phenyl]methoxy-6-oxo, acetate, 4H-[1,2,3,4]tetrazolo[4,3a][1,4]benzodiazepine-5(6H)-(R)-2-methyl, propanoic acid,8-[[4-(aminoiminomethyl)phenyl]methoxy-6-oxo, acetate, 4H-[1,2,3,4]tetrazolo[4,3a][1,4]benzodiazepine-5(6H)-(S)-2-methyl, propanoic acid,8-[[4-(aminoiminomethyl)phenyl]methoxy-6-oxo, acetate, 4H-[1,2,3,4]tetrazolo[4,3a][1,4]benzodiazepine-5(6H)-(S)-3-methyl, propanoic acid,8-[[4-(aminoiminomethyl)phenyl]methoxy-6-oxo, acetate, 4H-[1,2,3,4]tetrazolo[4,3a][1,4]benzodiazepine-5(6H)-(R)-2-methyl,(S)-3-methyl-propanoic acid,8-[[4-(aminoiminomethyl)-7-chloro-benzoyl]amino-6-oxo, acetate, 4H-[1,2,3,4]tetrazolo[4,3a][1,4]benzodiazepine-5(6H)-(R)-2-methyl,(S)-3-methyl-propanoic acid,8-[[4-(aminoiminomethyl)-benzoyl]amino-6-oxo, acetate, 4-H[1,2,3,4]tetrazolo[4,3a][1,4]benzodiazepine-5(6H)-(S)-2-methyl,(R)-3-methyl-propanoic acid,8-[[4-(aminoiminomethyl)-7-chloro-benzoyl]amino-6-oxo, acetate, 4H-[1,2,3,4]tetrazolo[4,3a][1,4]benzodiazepine-5(6H)-(S)-2-methyl,(R)-3-methyl-propanoic acid,8-[[4-(aminoiminomethyl)-benzoyl]amino]-6-oxo, acetate, 4H-[1,2,3,4]tetrazolo[4,3a][1,4]benzodiazepine-5(6H)-(R)-2-methyl, propanoic acid,8-[[4-(aminoiminomethyl)-7-chloro-benzoyl]amino-6-oxo, acetate, 4H-[1,2,3,4]tetrazolo[4,3a][1,4]benzodiazepine-5(6H)-(R)-2-methyl, propanoic acid,8-[[4-(aminoiminomethyl)-benzoyl]amino]-6-oxo, acetate, 4H-[1,2,3,4]tetrazolo[4,3a][1,4]benzodiazepine-5(6H)-(S)-2-methyl, propanoic acid,8-[[4-(aminoiminomethyl)-7-chloro-benzoyl]amino-6-oxo, acetate, 4H-[1,2,3,4]tetrazolo[4,3a][1,4]benzodiazepine-5(6H)-(S)-2-methyl, propanoic acid,8-[[4-(aminoiminomethyl)-benzoyl]amino]-6-oxo, acetate, 4H-[1,2,3,4]tetrazolo[4,3a][1,4]benzodiazepine-5(6H)-(S)-3-methyl, propanoic acid,8-[[4-(aminoiminomethyl)-7-chloro-benzoyl]amino-6-oxo, acetate, 4H-[1,2,3,4]tetrazolo[4,3a][1,4]benzodiazepine-5(6H)-(S)-3-methyl, propanoic acid,8-[[4-(aminoiminomethyl)-benzoyl]amino]-6-oxo, acetate, The invention further provides a pharmaceutical composition comprising a pharmaceutically acceptable excipient and/or pharmaceutically acceptable hydrates, solvates, and salts of Formulae I and II.

The invention provides a method for inhibiting platelet aggregation or reducing platelet aggregation in a mammal comprising administering a platelet aggregation inhibiting amount of the pharmaceutical composition of Formulae I and II. Optionally, the method includes administering the pharmaceutical composition in combination with a peptidyl antithrombotic and/or a thrombolytic agent and/or an anticoagulant.

DETAILED DESCRIPTION OF THE INVENTION

A. Definitions

The term "alkyl" means a branched or unbranched, saturated aliphatic hydrocarbon radical, having the number of carbon atoms specified, or if no number is specified, having up to 12 carbon atoms. Examples of alkyl radicals include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 2-methylhexyl, and the like. The terms "lower alkyl" "$C_1$–$C_6$ alkyl" and "alkyl of 1 to 6 carbon atoms" are synonymous and used interchangeably. A preferred "$C_1$–$C_6$ alkyl" group is methyl.

The term "substituted $C_n$–$C_m$ alkyl" where m and n are integers identifying the range of carbon atoms contained in the alkyl group, denotes the above alkyl groups that are substituted by one, two or three; halogen, hydroxy, protected hydroxy, amino, protected amino, $C_1$–$C_7$ acyloxy, nitro, carboxy, protected carboxy, carbamoyl, carbamoyloxy, cyano, methylsulfonylamino, morpholino, or $C_1$–$C_4$ alkoxy groups. The substituted alkyl groups may be substituted once, twice or three times with the same or with different substituents.

Examples of the above substituted alkyl groups include but are not limited to; cyanomethyl, nitromethyl, hydroxymethyl, hydroxyethyl, trityloxymethyl, propionyloxymethyl, aminomethyl, carboxymethyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 2-morpholinoethyl, 6-hydroxyhexyl, 2,4-dichloro(n-butyl), 2-amino(iso-propyl), 2-carbamoyloxyethyl and the like. A preferred group of examples within the above "$C_1$–$C_{12}$ substituted alkyl" group includes the substituted methyl group, e.g. a methyl group substituted by the same substituents as the "substituted $C_n$–$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, bromomethyl and iodomethyl.

The terms "$C_1$–$C_{12}$ alkyloxy" or "$C_1$–$C_{12}$ alkoxy" are used interchangeably herein and denote groups such as methoxy, ethoxy, n-propoxy, isopropoxy, n-butoxy, t-butoxy and like groups. Substituted alkoxy groups include those substituents described above for "alkyl".

The terms "$C_1$–$C_{12}$ acyloxy" or "$C_1$–$C_{12}$ alkanoyloxy" are used interchangeably and denote herein groups such as formyloxy, acetoxy, propionyloxy, butyryloxy, pentanoyloxy, hexanoyloxy, heptanoyloxy, and the like.

The terms "$C_1$–$C_{12}$ alkylcarbonyl", "$C_1$–$C_{12}$ alkanoyl" and "$C_1$–$C_{12}$ acyl" are used interchangeably herein and encompass groups such as formyl, acetyl, propionyl, butyryl, pentanoyl, hexanoyl, heptanoyl, benzoyl and the like.

The term "cycloalkyl" as used herein refers to a mono-, bi-, or tricyclic aliphatic ring having 3 to 14 carbon atoms and preferably 3 to 7 carbon atoms.

The term "alkenyl" means a branched or unbranched hydrocarbon radical having the number of carbon atoms designated containing one or more carbon-carbon double bonds, each double bond being independently cis, trans, or a nongeometric isomer.

The term "alkynyl" means a branched or unbranched hydrocarbon radical having the number of carbon atoms designated containing one or more carbon-carbon triple bonds.

The terms "$C_1$–$C_{12}$ alkylthio" and "$C_1$–$C_{12}$ substituted alkylthio" denote $C_1$–$C_{12}$ alkyl and $C_1$–$C_{12}$ substituted alkyl groups, respectively, attached to a sulfur which is in turn the point of attachment for the alkylthio or substituted alkylthio group to the group or substituent designated.

The term "aryl" when used alone means a homocyclic aromatic radical, whether or not fused, having the number of carbon atoms designated. Preferred aryl groups include phenyl, napthyl, biphenyl, phenanthrenyl, naphthacenyl, and the like (see e.g. Lang's Handbook of Chemistry (Dean, J. A., ed) 13th ed. Table 7-2 [1985]).

The term "substituted phenyl" or "substituted aryl" denotes a phenyl group or aryl group substituted with one, two or three substituents chosen from halogen (F, Cl, Br, I), hydroxy, protected hydroxy, cyano, nitro, $C_1$–$C_6$ alkyl, $C_1$–$C_6$ alkoxy, carboxy, protected carboxy, carboxymethyl, protected carboxymethyl, hydroxymethyl, protected hydroxymethyl, aminomethyl, protected aminomethyl, trifluoromethyl N-(methylsulfonylamino) or other groups specified.

Examples of the term "substituted phenyl" includes but is not limited to a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono- or di(alkoxy)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))-phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(N-(methylsulfonylamino))phenyl groups.

The term "arylalkyl" or "aralkyl" means one, two, or three aryl groups having the number of carbon atoms designated, appended to an alkyl radical having the number of carbon atoms designated including but not limited to; benzyl, napthylmethyl, phenethyl, benzhydryl (diphenylmethyl), trityl, and the like. A preferred arylalkyl group is the benzyl group.

The term "substituted $C_6-C_{10}$aryl-$C_1-C_8$alkyl" denotes a $C_1-C_8$alkyl group substituted at any carbon with a $C_6-C_{10}$aryl group bonded to the alkyl group through any aryl ring position and substituted on the $C_1-C_8$alkyl portion with one, two or three groups chosen from halogen (F, Cl, Br, I), hydroxy, protected hydroxy, amino, protected amino, $C_1-C_7$acyloxy, nitro, carboxy, protected carboxy, carbamoyl, carbamoyloxy, cyano, $C_1-C_6$alkylthio, N-(methylsulfonylamino) or $C_1-C_4$alkoxy. Optionally the aryl group may be substituted with one, two, or three groups chosen from halogen, hydroxy, protected hydroxy, nitro, $C_1-C_6$alkyl, $C_1-C_4$alkoxy, carboxy, protected carboxy, carboxymethyl, protected carboxymethyl, hydroxymethyl, protected hydroxymethyl, aminomethyl, protected aminomethyl, or an N-(methyisulfonylamino) group. As before, when either the $C_1-C_8$alkyl portion or the aryl portion or both are disubstituted, the substituents can be the same or different.

Examples of the term "substituted $C_6-C_{10}$aryl$C_1-C_8$alkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl)-3-carboxy(n-hexyl), 5-(4-aminomethylphenyl)-3-(aminomethyl)(n-pentyl), and the like.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl,4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzyisulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the benzodiazepinedione molecule and can be removed at the appropriate point without disrupting the remainder of the molecule. In particular, it is important not to subject the carboxy-protected benzodiazepinedione molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Preferred carboxylic acid protecting groups are the allyl and p-nitrobenzyl groups. Similar carboxy-protecting groups used in the cephalosporin, penicillin and peptide arts can also be used to protect a carboxy group substituents of the benzodiazepinedione. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

As used herein the term "amide-protecting group" refers to any group typically used in the peptide art for protecting the peptide nitrogens from undesirable side reactions. Such groups include p-methoxyphenyl, 3,4-dimethoxybenzyl, benzyl, O-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, trimethylsilyl, t-butyl dimethylsilyl, and the like. Further descriptions of these protecting groups can be found in "Protective Groups in Organic Synthesis", by Theodora W. Greene, 1981, John Wiley and Sons, New York.

Unless otherwise specified, the terms "heterocyclic group" or "heterocyclic" or "HET" or "heterocyclyl" are used interchangeably herein and refer to any mono-, bi-, or tricyclic saturated, unsaturated, or aromatic ring having the number of atoms designated where at least one ring is a 5-, 6- or 7-membered ring containing from one to four heteroatoms selected from nitrogen, oxygen, and sulfur. Preferably at least one heteroatom is nitrogen (*Lang's Handbook of Chemistry, supra*). Typically, the 5-membered ring has 0 to 2 double bonds and the 6- or 7-membered ring has 0 to 3 double bonds and the nitrogen or sulfur heteroatoms may optionally be oxidized, and any nitrogen heteroatom may optionally be quaternized. Included in the definition are any bicyclic groups where any of the above heterocyclic rings are fused to a benzene ring. Heterocyclics in which nitrogen is the heteroatom are preferred.

The following ring systems are examples of the heterocyclic (whether substituted or unsubstituted) radicals denoted by the term "heterocylic": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzthiazolyl, benzimidazolyl and indolyl.

Heterocyclic 5-membered ring systems containing a sulfur or oxygen atom and one to three nitrogen atoms are also suitable for use in the instant invention. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl.

Further suitable specific examples of heterocylic ring systems are 6-membered ring systems containing one to three nitrogen atoms. Such examples include pyridyl, such as pyrid-2-yl, pyrid-3-yl, and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl radicals, are a preferred group.

An alternative suitable group of "heterocyclics" or "HET" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl.

An alternative group of "heterocyclics" includes; piperidyl, piperazinyl, morpholinyl, morpholino, 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

Bivalent radicals L whether branched or unbranched, derived from alkanes, alkenes, alkadienes, alkynes, alkadiynes, and arenes optionally containing O, N and/or S atoms, or homo- and heterocyles either aromatic or aliphatic, are designated by adding the suffix "ene" to the corresponding monovalent radical. Atoms bearing the free valences may include any C, O, N or S.

Each substituent or term used in any formula or expression herein, e.g. $R^n$, $A^n$, $B^n$, Z, X, $C_1$–$C_4$alkyl, etc., when it appears more than once, is independent of its definition elsewhere in that or any other formula or structure.

"Pharmaceutically acceptable salts" include both acid and base addition salts.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-tolenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolmine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

The term "prodrug" as used herein means a derivative of a parent drug molecule that enhances pharmaceutically desirable characteristics or properties (e.g. transport, bioavailablity, pharmacodynamics, etc.) and that requires biotransformation, either spontaneous or enzymatic, within the organism to release the active parent drug.

In the description that follows standard abbreviations as recommended by the *Journal of Organic Chemistry* (see "Guidelines for Authors" in any volume) are employed unless otherwise specified. For convenience, the following standard abbreviations used herein have the meanings provided below.

| ABBREVIATIONS | |
|---|---|
| ACN | acetonitrile |
| Boc or BOC | tert-butyloxycarbonyl |
| BOP | benzotriazolyloxy-trisdimethylamino-phosphonium hexafluorophosphate |
| DCC | dicyclohexylcarbodiimide |
| DCM | dichloromethane |
| DEAD | diethylazodicarboxylate |
| DIPC | diisopropylcarbodiimide |
| DIPEA | diisopropylethylamine |
| DMA | dimethylacetamide |
| DMAP | dimethylaminopyridine |
| DMF | dimethylformamide |
| DMSO | dimethylsulfoxide |
| DTT | dithiothreitol |
| EDC | 1-(3-diethylaminopropyl)-3-ethylcarbodiimide hydrochloride |
| EtN(iPr)$_2$ | diisopropylethylamine |
| Fmoc or FMOC | fluorenylmethyloxycarbonyl |
| HOBt | N-hydroxybenzotriazole |
| HPLC | high pressure liquid chromatography |
| LDA | lithium diisopropylamine |
| MBHA | methylbenzhydrylamine |
| NMM | N-methylmorpholine |
| Ph$_3$P | triphenylphosphine |
| PyBrOP | bromo-tri-pyrrolidinophosphoniumhexafluorophosphate |
| SPPS | solid phase peptide synthesis |
| t-BuO$_2$C | t-butoxycarbonyl |
| TFA | trifluoroacetic acid |

B. Utility

The present invention is the result of the unexpected discovery that substituted fused 6-7-6 or 6-7-5 membered benzodiazepine compounds defined by Formula I and II, referred to hereafter as "substituted tricyclic benzodiazepines", are capable of acting as fibrinogen receptor antagonists inhibiting both platelet aggregation and binding of fibrinogen to the platelet receptor, GPII$_b$III$_a$, at concentrations comparable to many of the more potent anti-aggregatory peptides of the prior art (see e.g. Ali et al. EP 341 915). Thus, the instant fibrinogen receptor antagonists are particularly useful when they inhibit the binding of fibrinogen to the GPII$_b$III$_a$ receptor at an IC$_{50}$ in a Fg/GPII$_b$III$_a$ ELISA as described herein of at least about 35 nM, and an IC$_{50}$ in a platelet aggregation (PA) assay, also described herein, of at least about 3 µM. Since there is some variability in the values obtained for ELISA and PA assays in different laboratories, preferred fibrinogen receptor antagonists represented by Formula I and II will have IC$_{50}$'s for Fg/GPII$_b$III$_a$ ELISA's and PA assays equal to or greater than that of the prior art compound N-[3-(4-amidinobenzamido)benzoyl]-3-aminoproprionoic acid,

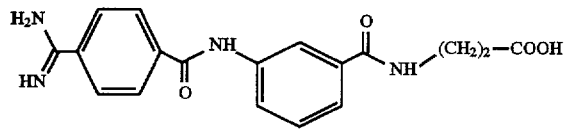

This compound is used as an internal standard and has been found to have an Fg/GPII$_b$III$_a$ ELISA IC$_{50}$ of about 25 nM and a PA inhibition assay IC$_{50}$ of about 3 µM when measured according to the assays described herein. Most preferred fibrinogen receptor antagonists represented by Formula I and II have IC$_{50}$'s in Fg/GPII$_b$III$_a$ ELISA of at least about 15 nM and in platelet aggregation inhibition assays of at least about 1 µM or three times more potent in a platelet aggregation inhibition assay than the reference compound N-[3-(4-amidinobenzamido)benzoyl]-3-aminoproprionoic acid. This reference compound is readily prepared by standard methods from commercially available precursors (e.g. β-alanine, m-aminobenzoic acid, and p-amidinobenzoic acid) or may be synthesized according to the procedures set forth. in EP 372 486 A2.

The compounds described in the present invention may therefore inhibit the binding of fibrinogen to its receptor on platelets, GPII$_b$III$_a$, and thus prevent the aggregation of platelets and the formation of platelet plugs, emboli and thrombi in the circulatory system in mammals. Thromboembolic disorders have been shown to be directly related to the susceptibility of blood platelets to aggregate. Mammals exposed to medical procedures such as angioplasty and thrombolytic therapy are particularly susceptible to thrombus formation. The compounds of the present invention can be used to inhibit thrombus formation following angioplasty. They may also be used in combination with antithrombolytic agents such as tissue plasminogen activator and its derivatives (U.S. Pat. Nos. 4,752,603; 4,766,075; 4,777,043; EP 199 574; EP 238 304; subsequent to the antithrombolytic agent. Mammals exposed to renal dialysis, blood oxygenation, cardiac catheterization and similar medical procedures as well as mammals fitted with certain prosthetic devices are also susceptible to thromboembolic disorders. Physiologic conditions, with or without known cause may also lead to thromboembolic disorders. Thus, the compounds described herein may be useful in treating thromboembolic disorders in mammals. The compounds described herein may also be used as adjuncts to anticoagulant therapy, for example in combination with aspirin, heparin or warfarin and other anticoagulant agents. The application of the compounds described herein for these and related disorders will be apparent to those skilled in the art.

Compounds of this invention are also useful as intermediates generally, or as precursors of inhibitors to GPII$_b$III$_a$ or other integrin receptors and thus in addition to treating cardiovascular disease, these compounds may be usefully employed in metasiatic disease, or for any disease where antagonism of RGD binding integrin receptors is indicated.

Compounds represented by formula I or II are capable of antagonizing the interaction between vitronectin (Vn) and the vitronectin receptor (VnR) and thus are useful in situations where such antogonism is indicated. Thus it is contemplated the instant compounds are useful in treating bone disorders such as osteoporosis. Vn-VnR antagonism is particularly pronounced when substituent Q—L— is bonded to position 8 or 9 based on the benzodiazapinedione numbering system. Exemplary Vn-VnR antagonists are represented by structural formula Ib and IIb below, where the substituents are as previously defined.

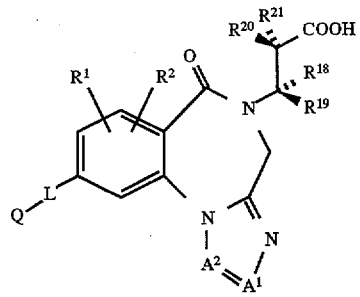

Ib

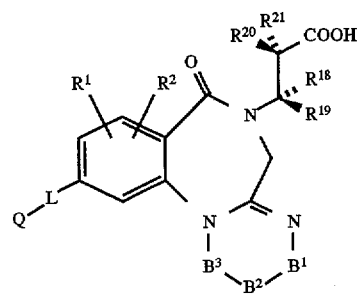

IIb

C. Preferred Embodiments

Nonpeptidyl GPII$_b$III$_a$ Inhibitors

One embodiment of the invention comprises a compound represented by Formula I and II, capable of inhibiting binding of the platelet GPII$_b$III$_a$ receptor to its native in vivo ligands. Preferred nonpeptidyl inhibitors include compounds represented by structural Formulae III–XXI and prodrug forms thereof:

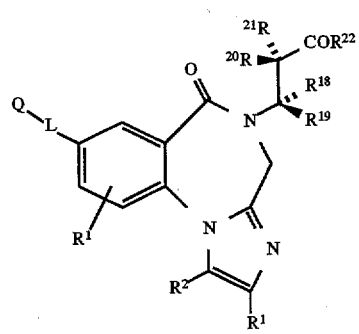

III

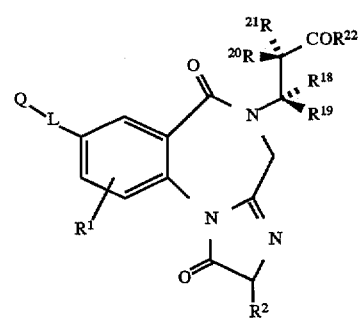

IV

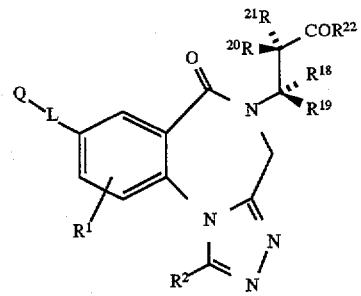

V

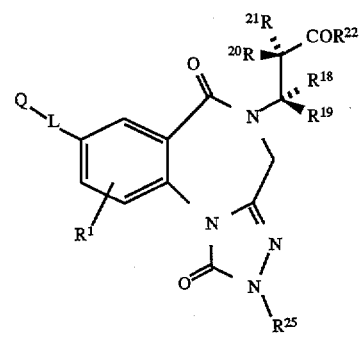

VI

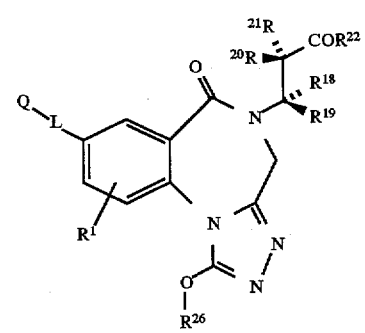

VII

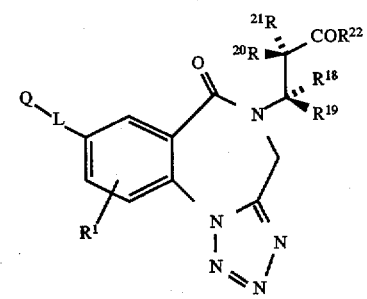

VIII

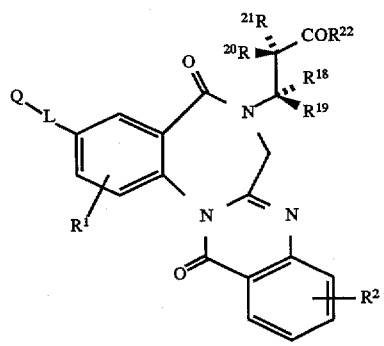

IX

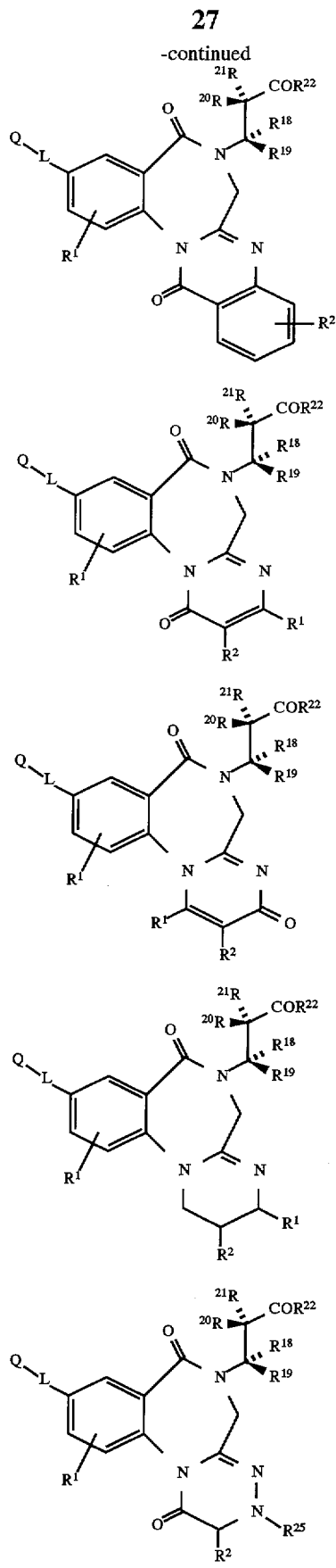
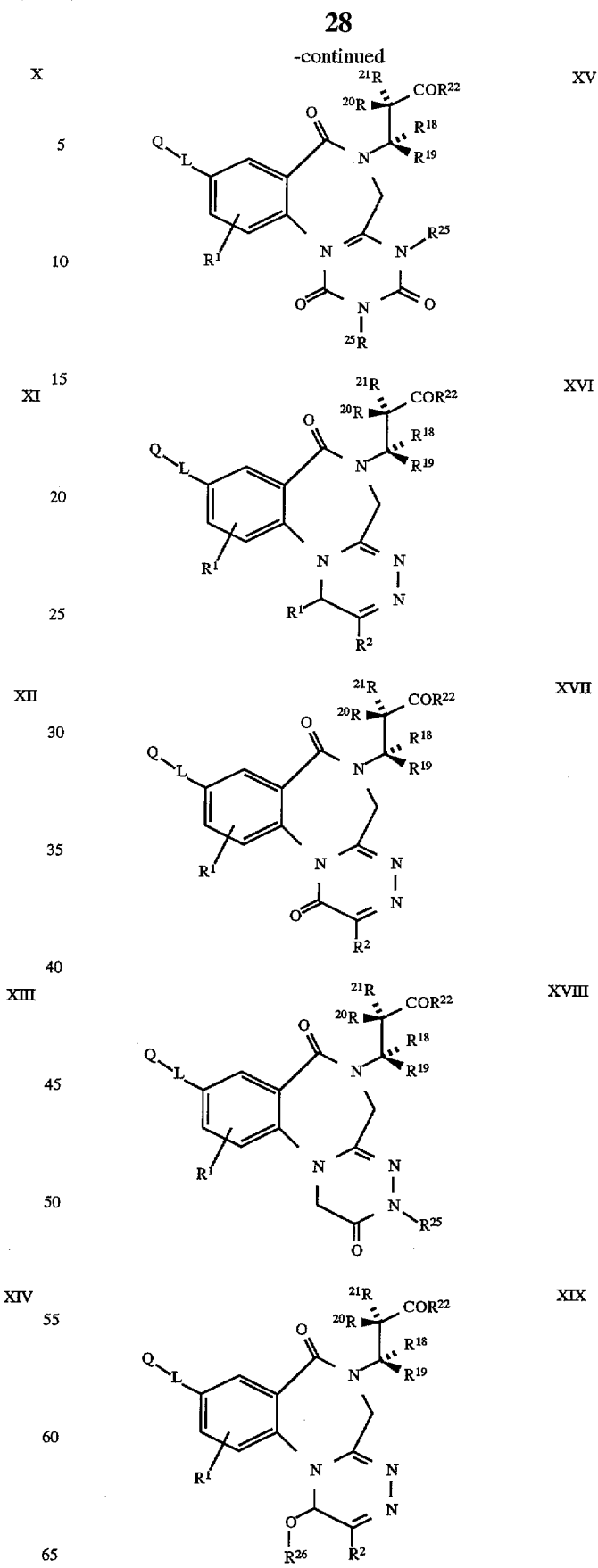

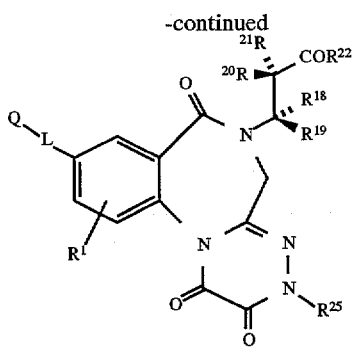

XX

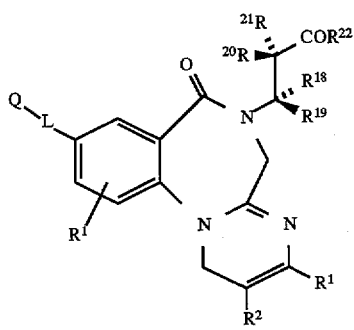

XXI where $R^1, R^2, R^{18}, R^{19}, R^{20}, R^{21}, R^{22}, R^{25}, R^{26}$, Q and L are defined above.

Referring to Formulae I–XXI the following structural features of the instant nonpeptidyl antithrombotic inhibitors can be identified:

a. The positively charged Q moiety;
b. The linking moiety L;
c. The flat aromatic "benzo" ring;
d. The 7-member "diazepine" ring;
e. The fused 5 or 6 member "amidino containing" ring; and
f. The negatively charged acidic moiety $COR^{22}$.

a. Positively charged Q

Suitable groups Q contain one or more nitrogen atoms and have a $pK_b$ sufficiently high so that they are at least 10% positively charged at physiological pH. Q may be one or more primary, secondary, tertiary, or quartinary amines or imines either isolated or conjugated with other nitrogen atoms to form groups including but not limited to; aminomethyleneimino, amidino, and guanidino groups and multiples thereof. Alternatively, Q may be a saturated or unsaturated (including aromatic) heterocyclic group provided the group bears a positive charge at physiological pH. In one embodiment of the invention, Q is preferably selected from; amino ($H_2N$—), imino (=NH), amidino ($H_2NC$(=NH)—), aminomethyleneamino ($H_2N$—CH=N—), iminomethylamino (HN=CH—NH—), guanidino ($H_2N$—C(=NH)—NH—), $N^G$-aminoguanidino ($H_2N$—HN—C(=NH)—NH—), alkylamino ($R^1NH$—), dialkylamino ($R^1{}_2N$—), trialkylamino ($R^1{}_3N$—), alkylideneamino ($R^1{}_2C$=N—), pyranyl, pyrrolyl, imidazolyl, pyrazolyl, pyridyl, pyrazinyl, pyrimidinyl, pyridazinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, pteridinyl, 4aH-carbazolyl, carbazolyl, b-carbolmyl, phenanthridinyl, acridinyl, perimidinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, morpholino, 1,3-diazacyclohex-4-ene, and combinations thereof, where $R^1$ is selected from; hydrogen, $C_1$–$C_6$-alkyl, $C_6$–$C_{10}$-aryl, and $C_3$–$C_{10}$-cycloalkyl. Optionally, any of the nitrogen containing heterocycles described above may be substituted with amino, imino, amidino, aminomethyleneamino, iminomethylamino, guanidino, $N^G$-amino-guanidino, alkylamino, dialkylamino, trialkylamino, or alkylideneamino groups.

Exemplary preferred Q groups include the following:

(A) Amino and ammonio groups;

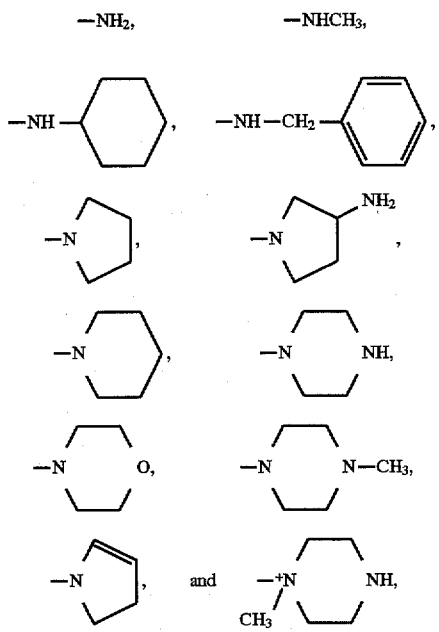

(B) Amidino groups;

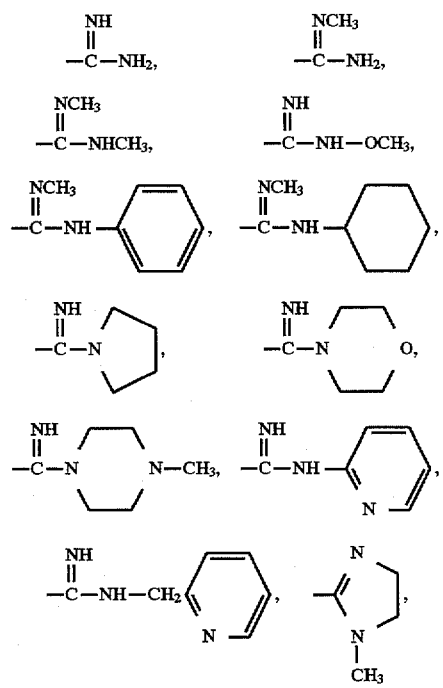

-continued
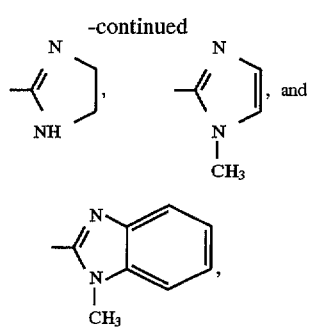
(C) Aminoalkyleneimino groups;
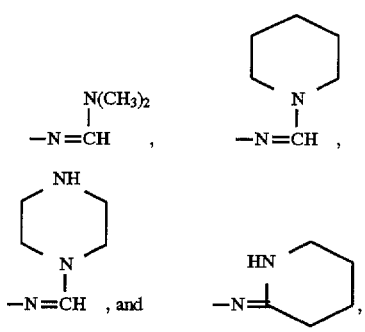
(D) Iminoalkyleneamino groups;
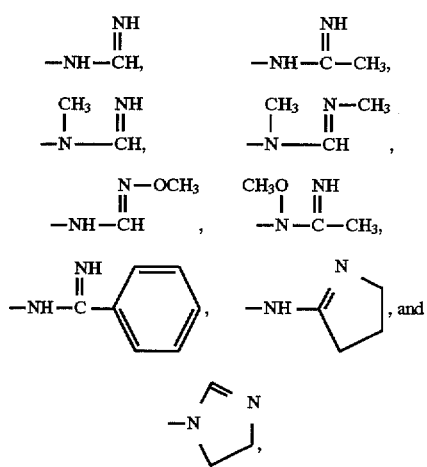
(E) Guanidino groups;
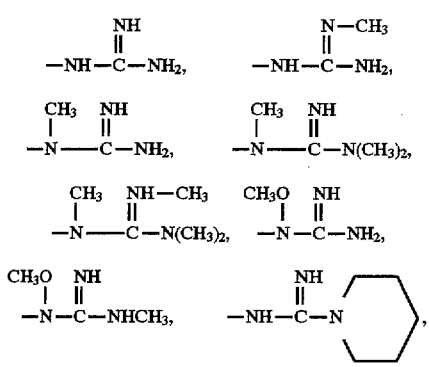
-continued
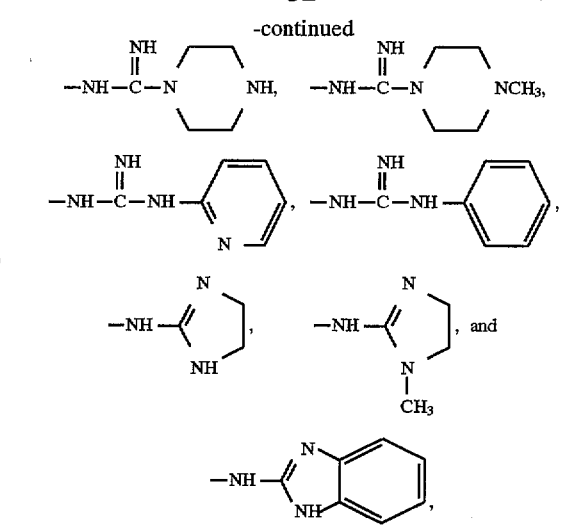
(F) Saturated heterocyclic groups;
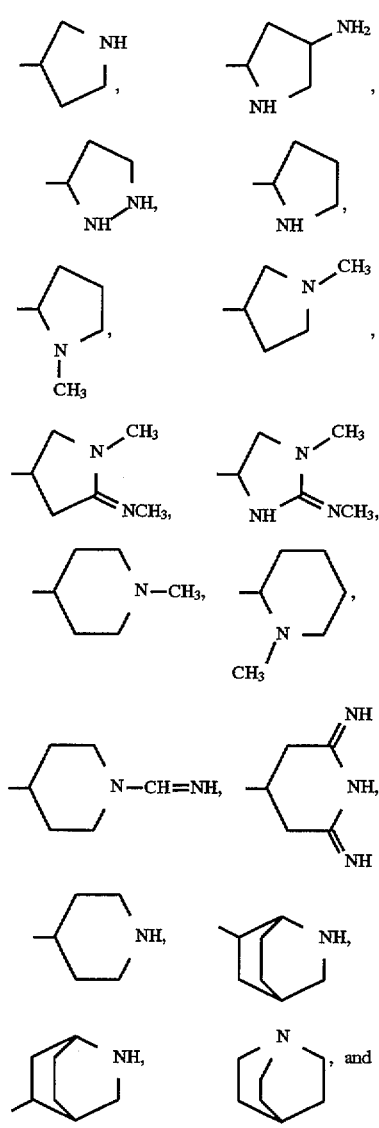

-continued
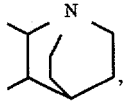
(G) Unsaturated (nonaromatic) heterocyclic groups;
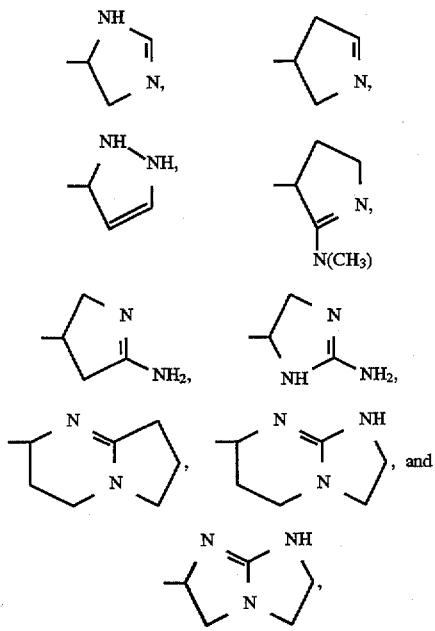
(H) Unsaturated aromatic heterocyclic groups;
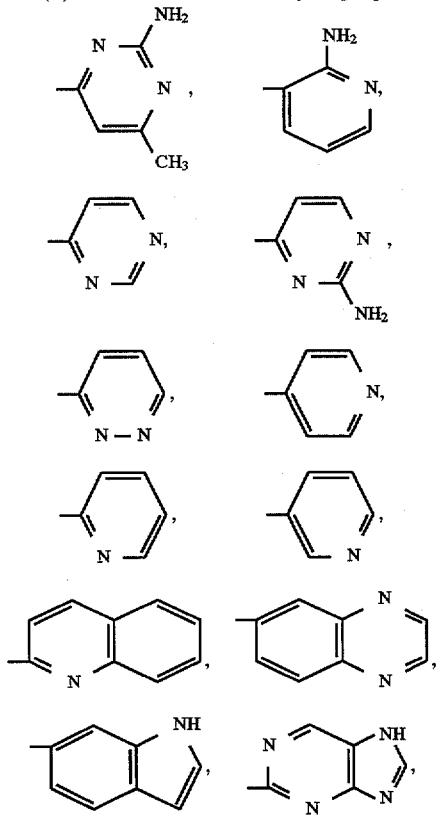
-continued
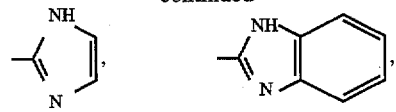
(I) Bicycloheterocyclic groups;
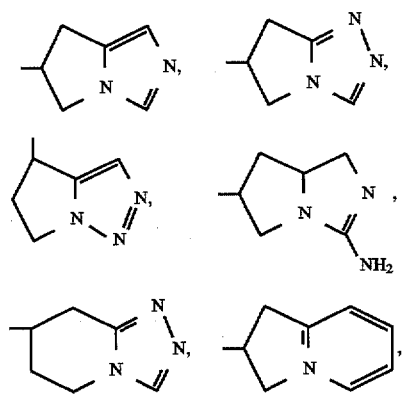

-continued

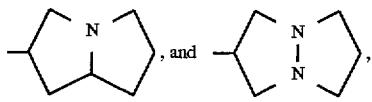

Most preferred Q groups are amino, amidino, and piperazinyl groups.

To increase oral bioavailability the positively charged Q moiety can be made neutral. For example $R^3$, $R^4$, or $R^5$ may be a substituent that transforms compounds represented by structural formulae I–XXI into a prodrug. Exemplary prodrugs include hydroxyamidines and carbamates. Preferred $R^3$, $R^4$, or $R^5$ groups of this embodiment include;

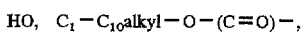

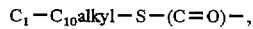

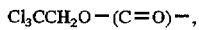

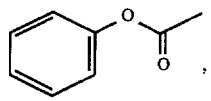

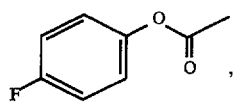

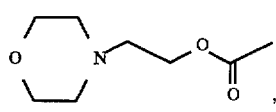

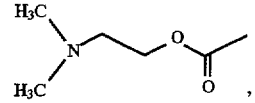

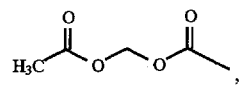

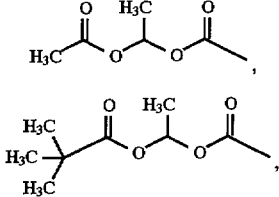

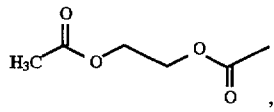

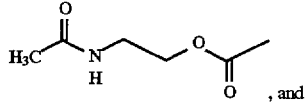

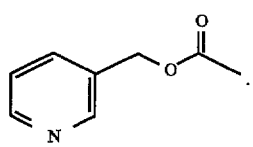

b. The linking group L

The length of the bivalent radical L appears to be important to biological activity. By length is meant the distance between the "benzo" ring and the first charge bearing N of substituent Q. For example, suitable lengths for bivalent radical L range from about 3 to about 9 and preferably 5 or 6 methylene equivalents, where any methylene group or groups may be replaced with one or more or a combination of; alkene, alkyne, aryl, heterocycle or a functional group or groups containing the heteroatoms N, O, and S, so long as the overall length is equivalent to from 3 to 9 methylene groups. These functional groups include one or more of the following:

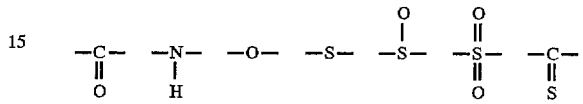

and may be isolated within the linker (e.g. forming ethers, thioethers, ketones, sulfoxides and the like) or combined in any combination, provided only that the compounds so produced are stable in aqueous solution and do not exceed the above stated length requirements. For example, combining these functional groups produces esters, amides, ureidos, carbamates, carbonates, sulfonamides, surfoxides, sulfones, and the like. The linker may optionally be substituted with one or more substituents selected from loweralkyl, haloloweralkyl, loweralkoxy, cyano, hydroxy, halo, haloloweralkoxy and phenyl optionally substituted with halo or haloloweralkyl, provided only that the linker is stable in aqueous solution and does not exceed the length requirements.

Preferred L's are selected from substituted or unsubstituted; $C_3$–$C_7$-alkylene, $C_3$–$C_7$-cycloalkylene, $C_3$–$C_7$-alkenylene, $C_4$–$C_7$-cycloalkenylene, $C_5$–$C_8$-cycloalkadienylene, $C_3$–$C_7$-alkadienylene, $C_3$–$C_7$-alkynylene, $C_4$–$C_7$-alkenynylene, $C_6$–$C_{14}$-arylene, $C_6$–$C_{14}$-aryl-$C_2$–$C_4$-alkynylene, $C_1$–$C_3$-alkyl-$C_6$–$C_{14}$-aryl-$C_2$–$C_4$-alkynylene, $C_6$–$C_{14}$-aryl-$C_2$–$C_4$-alkenylene, $C_1$–$C_3$-alkyl-$C_6$–$C_{14}$-arylene, $C_1$–$C_3$-alkyl-$C_6$–$C_{14}$-aryl-$C_2$–$C_4$-alkenylene, $C_6$–$C_{14}$-aryl-$C_1$–$C_3$-alkylene, $C_6$–$C_{14}$-aryl-$C_1$–$C_3$-alkyloxyene, $C_1$–$C_3$-alkyl-$C_6$–$C_{14}$-aryl-$C_1$–$C_2$-alkylene, $C_1$–$C_3$-alkyloxy-$C_6$–$C_{14}$-arylene, $C_2$–$C_8$-alkyloxyene, $C_1$–$C_5$-alkyloxy-$C_1$–$C_5$-alkylene, $C_6$–$C_{10}$-aryloxyene, $C_6$–$C_{10}$-aryloxy-$C_1$–$C_5$-alkylene, $C_6$–$C_{10}$-arylthio-$C_1$–$C_5$-alkylene,

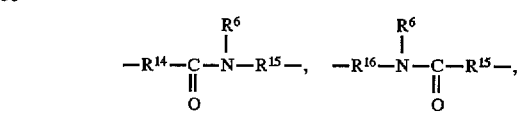

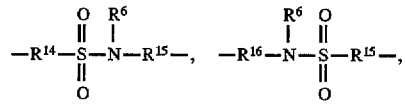

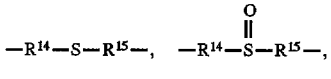

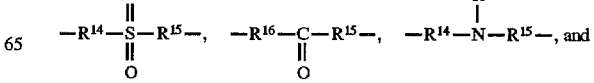

-continued $-R^{14}-O-R^{15}-,$ where $R^{14}$ is selected from; a chemical bond, $C_1$–$C_8$-alkyl, $C_1$–$C_8$-alkyloxy, $C_3$–$C_7$-cycloalkyl $C_2$–$C_5$-alkenyl, $C_3$–$C_5$-alkynyl, $C_6$–$C_{10}$-aryl, $C_1$–$C_3$-alkyl-$C_6$–$C_{12}$-aryl, $C_1$–$C_2$-alkyl-$C_6$–$C_{10}$-aryl-$C_1$–$C_2$-alkyl, $C_6$–$C_{10}$-aryl-$C_1$–$C_2$-alkyl, and $C_6$–$C_{10}$-aryloxy-$C_1$–$C_2$-alkyl. $R^{15}$ is selected from; a chemical bond, $C_1$–$C_4$-alkyl, $C_2$–$C_4$-alkenyl, $C_2$–$C_4$-alkynyl, $C_6$–$C_{10}$-aryl, and $C_1$–$C_3$-alkyl-$C_6$–$C_{12}$-aryl. $R^{16}$ is selected from; a chemical bond, $C_1$–$C_5$-alkyl, $C_3$–$C_7$-cycloalkyl $C_3$–$C_5$-alkenyl, $C_3$–$C_5$-alkynyl, $C_6$–$C_{10}$-aryl, $C_1$–$C_3$-alkyl-$C_6$–$C_{12}$-aryl, and $C_6$–$C_{10}$-aryl-$C_1$–$C_2$alkyl. The substituents are preferably selected from one to three $R^{12}$ defined above.

More preferred bivalent radicals L are selected from the following:

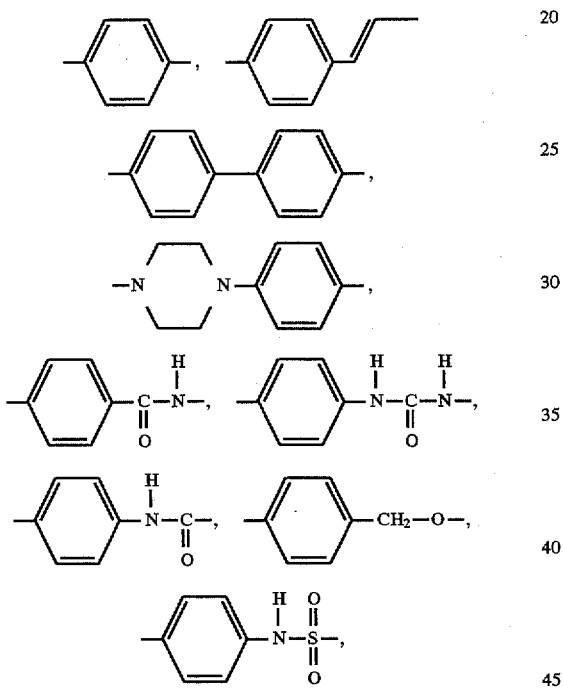

Most preferred Q—L— combinations are selected from:

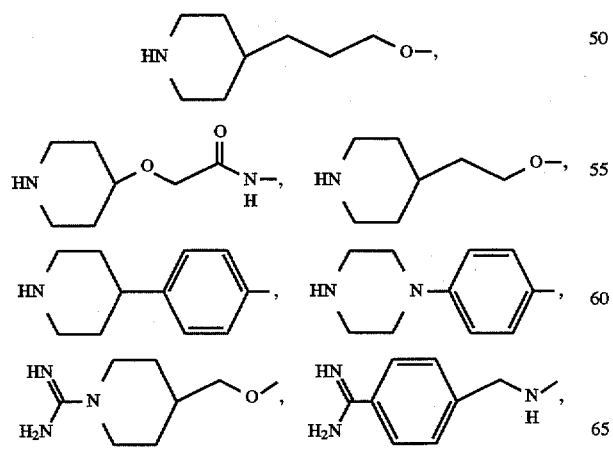

-continued

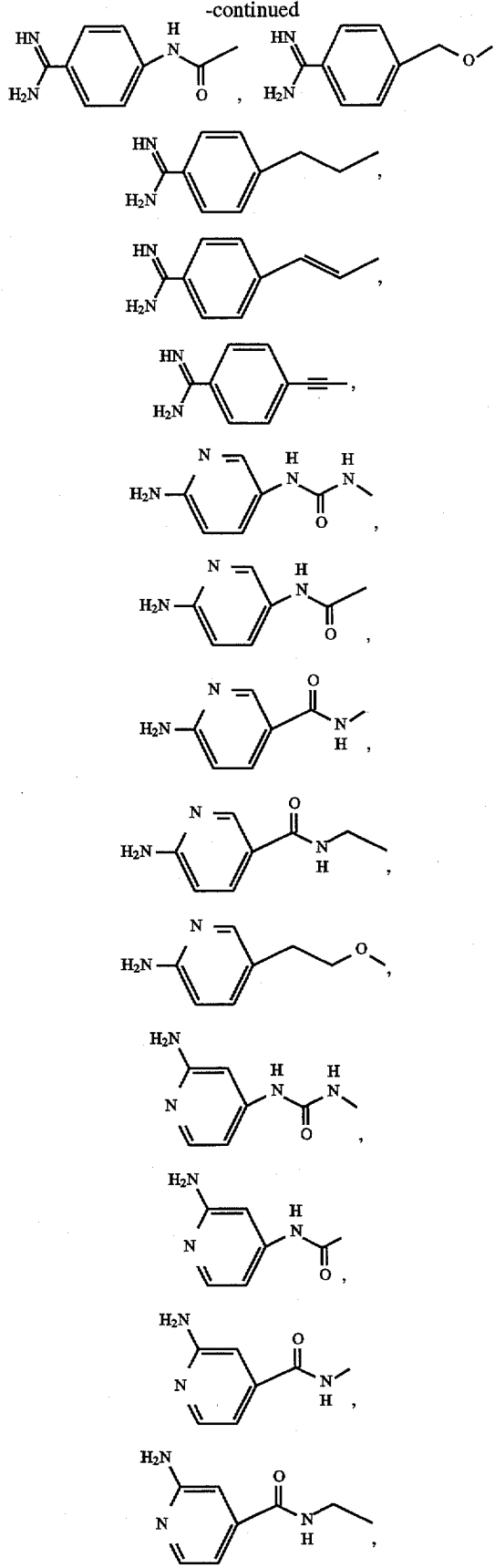

-continued

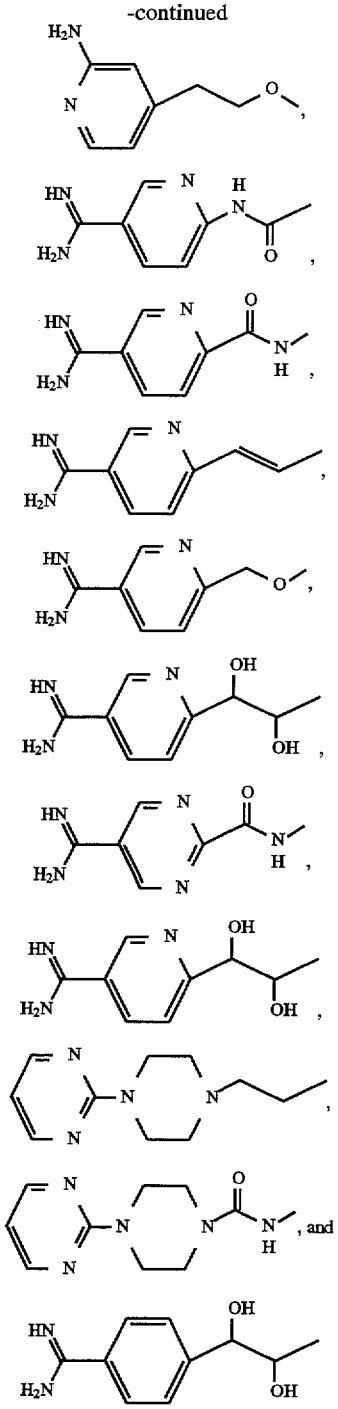

where any amino, amidino, or guanidino nitrogen is optionally derivitized with $C_1$-$C_6$alkoxycarbonyl.

Very most preferred Q—L— combinations are selected from;

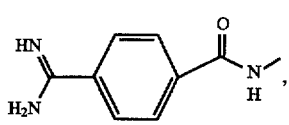

-continued

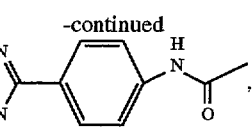

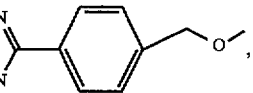

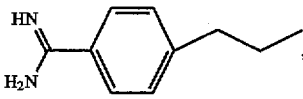

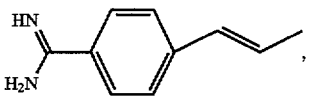

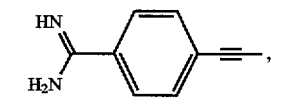

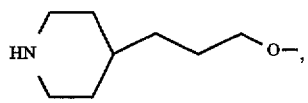

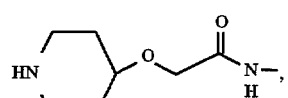

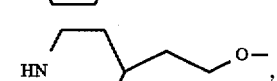

and

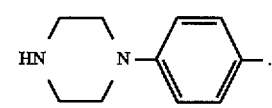

c. The "benzo" ring

Preferred substituents of the "benzo" ring are $R^1$ and $R^2$, where each $R^1$ and $R^2$, is independently selected from hydrogen, halogen (F, Cl, Br, I), cyano, nitro, carboxyl, mercaptocarbonyl, mercapto, pthalimido and a substituent having from 1 to 12 carbon atoms selected from: alkyl, hydroxyalkyl, formyl, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkylnyl, carboxylalkyl, alkylcarbonyloxy, alkylcarbonyloxyalkyl, alkoxycarbonylalkyl, aralkoxycarbonylalkyl, aralkylcarbonyloxyalkyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, alkylsulfinyl, alkylsulfonyl, aralkylsulfinyl, aralkylsulfonyl, arylsulfinyl, arylsulfonyl, pthalimidoalkyl, heteroaryl, heteroarylalkyl, cycloheteroalkyl, cycloheteroalkylalkyl, and cycloheteroalkylcarbonylalkyl where each heteroaryl- and cyclohetero-containing groups has one or more ring hetero atoms selected from oxygen, sulfur and nitrogen. Optionally, each $R^1$ and $R^2$ also may be independently selected from sulfonyl, sulfonylamido, amino and amido radicals of the formula:

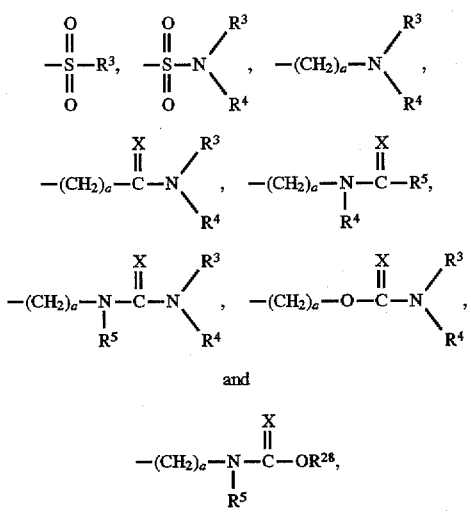

where X is oxygen or sulfur, each "a" is a number independently selected from zero to six, inclusive, and where each of $R^3$ through $R^5$ is independently selected from the groups described above. Optionally, $R^3$ and $R^4$ taken together, $R^4$ and $R^5$ taken together and $R^3$ and $R^5$ taken together may each form a heterocyclic having from five to seven ring members including the hetero atom of the sulfonyl, amino or amido radical and which heterocyclic may further contain one or more hetero atoms as ring members selected from oxygen, nitrogen, and sulfur and which heterocyclic group may be saturated or partially saturated. $R^{28}$ is selected from the groups defined below.

d. The 7-member "diazepine" ring;

Substituents of the 7-member "diazepine" ring are preferably hydrogen or halogen. Optionally any oxo group (=O) may be substituted with an =S group.

e. The fused 5- or 6-member "amidino containing" ring;

Preferred 5-member "amidino containing" rings of Formula I are selected from;

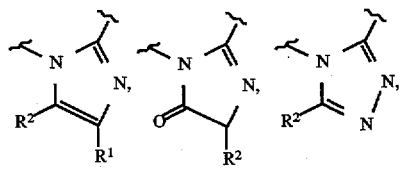

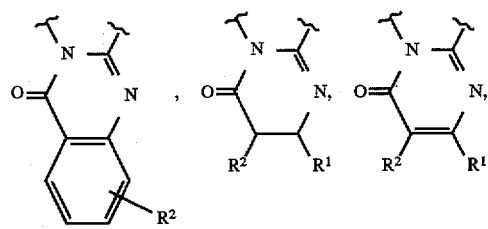

where $R^1$ is preferably hydrogen, lower alkyl, lower alkyl-morpholino, hydroxy lower alkyl, carboxy lower alkyl, amino lower alkyl, and aminocarbonyl lower alkyl; $R^2$ is preferably hydrogen, lower alkyl-morpholino, the side chain of a naturally occurring α-amino acid, or the D stereoisomer thereof; $R^{25}$ is preferably hydrogen, or lower alkyl; and $R^{26}$ is preferably lower alkyl.

Preferred 6-member "amidino containing" rings of Formula II are selected from;

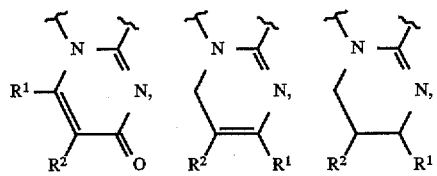

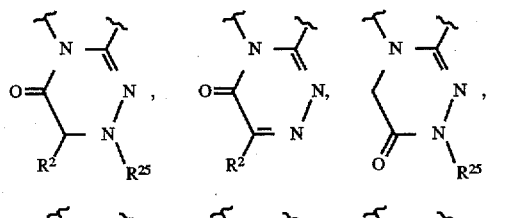

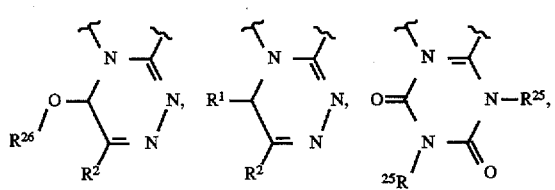

and

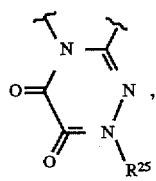

where $R^1$, $R^2$, $R^{25}$, and $R^{26}$ are defined above.

f. The negatively charged acidic moiety $COR^{22}$;

$R^{22}$ is selected from the group consisting of (a) hydroxy, (b) $C_1$–$C_8$-alkoxy, (c) $C_3$–$C_{12}$-alkenoxy, (d) $C_6$–$C_{12}$-aryloxy, (e) $C_1$–$C_6$-alkyl-$C_6$–$C_{12}$-aryloxy, (f) di-$C_1$–$C_8$-alkylamino-$C_1$–$C_8$-alkoxy, (g) acylamino-$C_1$–$C_8$-alkoxy selected from the group (i) acetylaminoethoxy, (ii) nicotinoylaminoethoxy, and (iii) succinamidoethoxy, (h)

$C_1$–$C_8$-alkoyloxy-$C_1$–$C_8$-alkoxy, (i) $C_6$–$C_{12}$-aryl-$C_1$–$C_8$-alkoxy where the aryl group is unsubstituted or substituted with one to three of the groups (i) nitro, (ii) halo (F, Cl, Br, I), (iii) $C_1$–$C_4$-alkoxy, and (iv) amino, (j) hydroxy-$C_2$–$C_8$-alkoxy, (k) dihydroxy-$C_3$–$C_8$-alkoxy, and (l) $NR^{23}R^{24}$.

$R^{23}$ and $R^{24}$ are independently selected from the group (a) hydrogen, (b) $C_1$–$C_8$-alkyl, (c) $C_3$–$C_8$-alkenyl, (d) $C_6$–$C_{12}$-aryl where the aryl group is unsubstituted or substituted with one to three of the groups (i) nitro, (ii) halo (F, Cl, Br, I), (iii) $C_1$–$C_4$-alkoxy, and (iv) amino, and (e) $C_6$–$C_{12}$-aryl-$C_1$–$C_8$-alkyl where the aryl group is unsubstituted or substituted with one to three of the groups (i) nitro, (ii) halo (F, Cl, Br, I), and (iii) $C_1$–$C_4$-alkoxy.

$R^{22}$ is preferably a substituent that transforms compounds represented by structural formulae I–XXI into prodrugs. For example, preferred prodrug forms include simple esters, α-acyloxyalkyl esters, and amides. Preferred esters include compounds where $R^{22}$ is selected from;

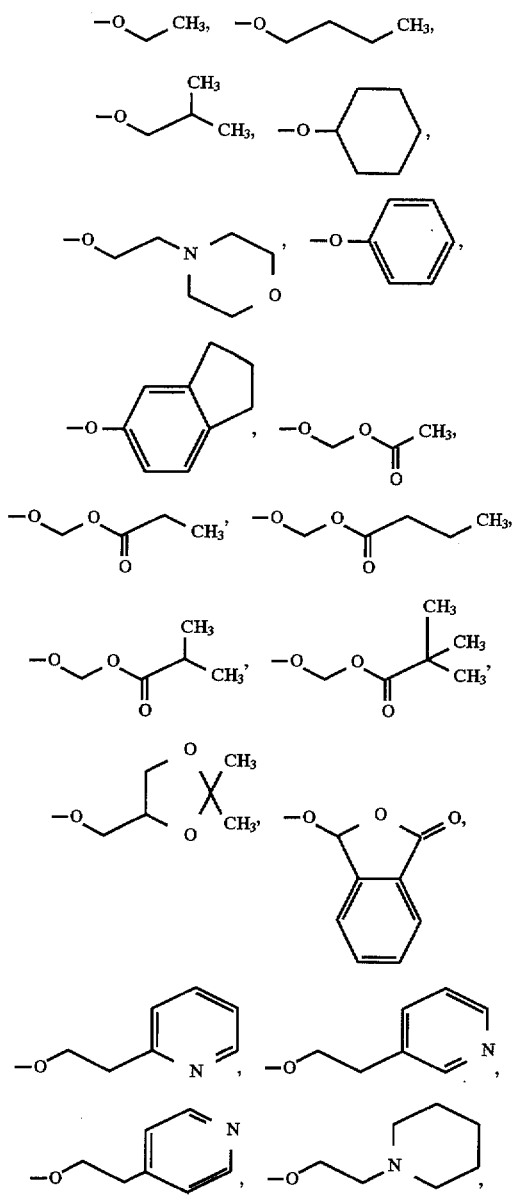

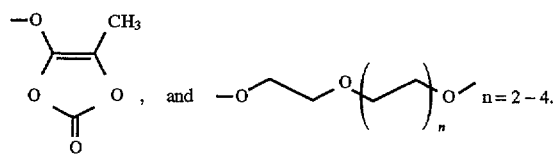

Preferred compounds of this invention are represented by structural Formula I and II and are selected from Tables I and II below, where $R^1$ is hydrogen or chlorine and $R^{18}$, $R^{19}$, $R^{20}$ and $R^{21}$ are hydrogen or methyl, and the other substituents are as set forth in the tables.

TABLE I

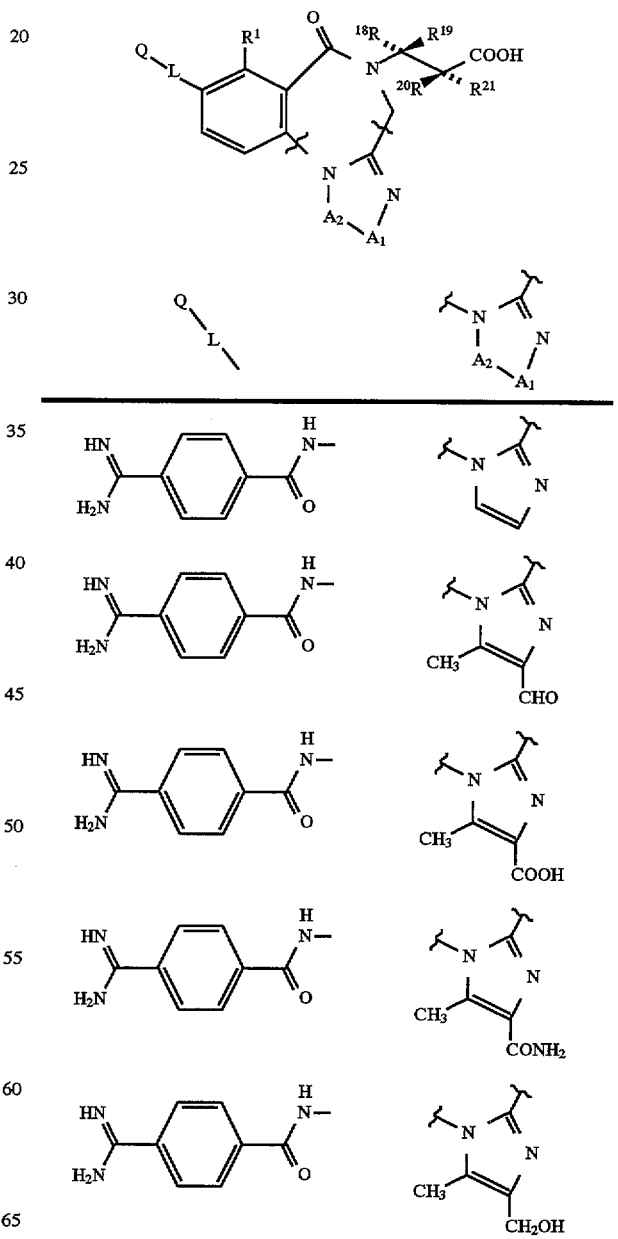

TABLE I-continued
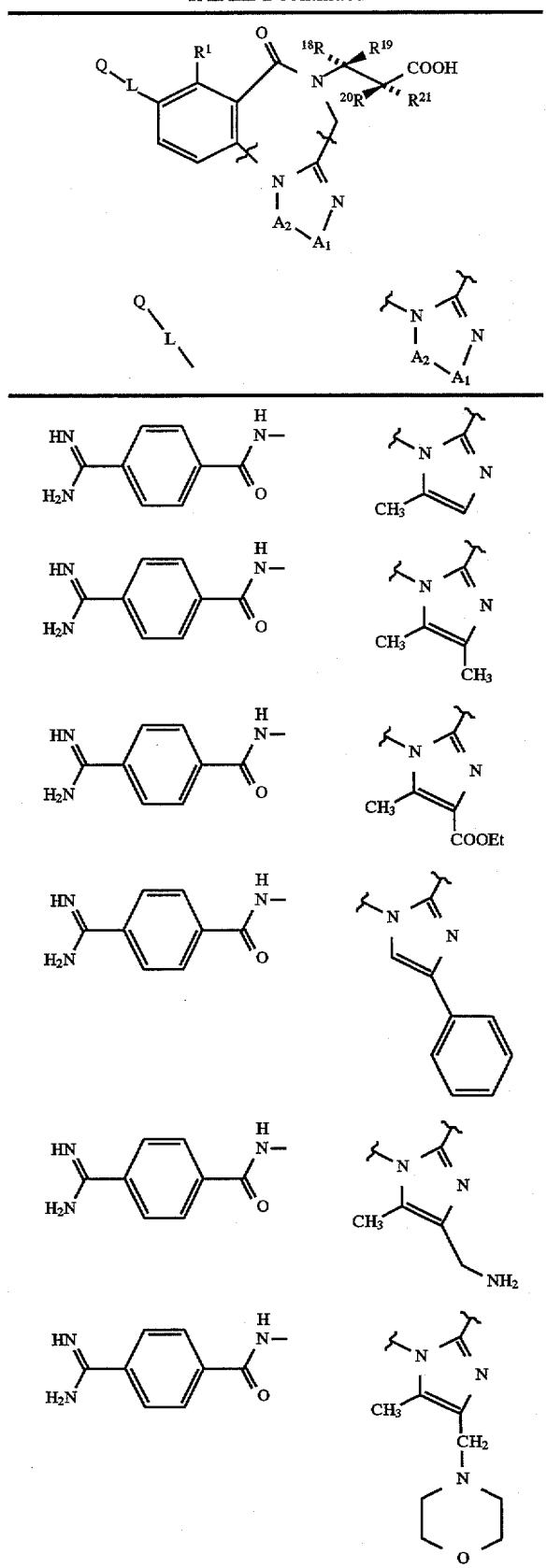
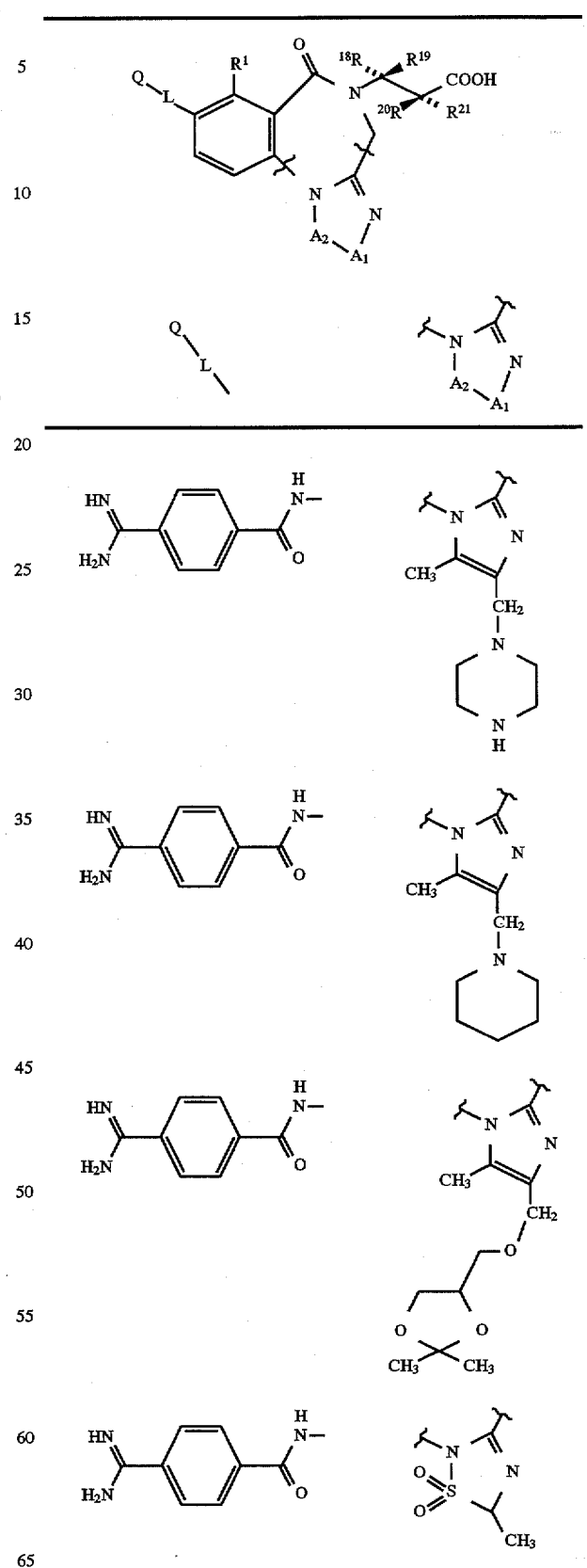

TABLE I-continued
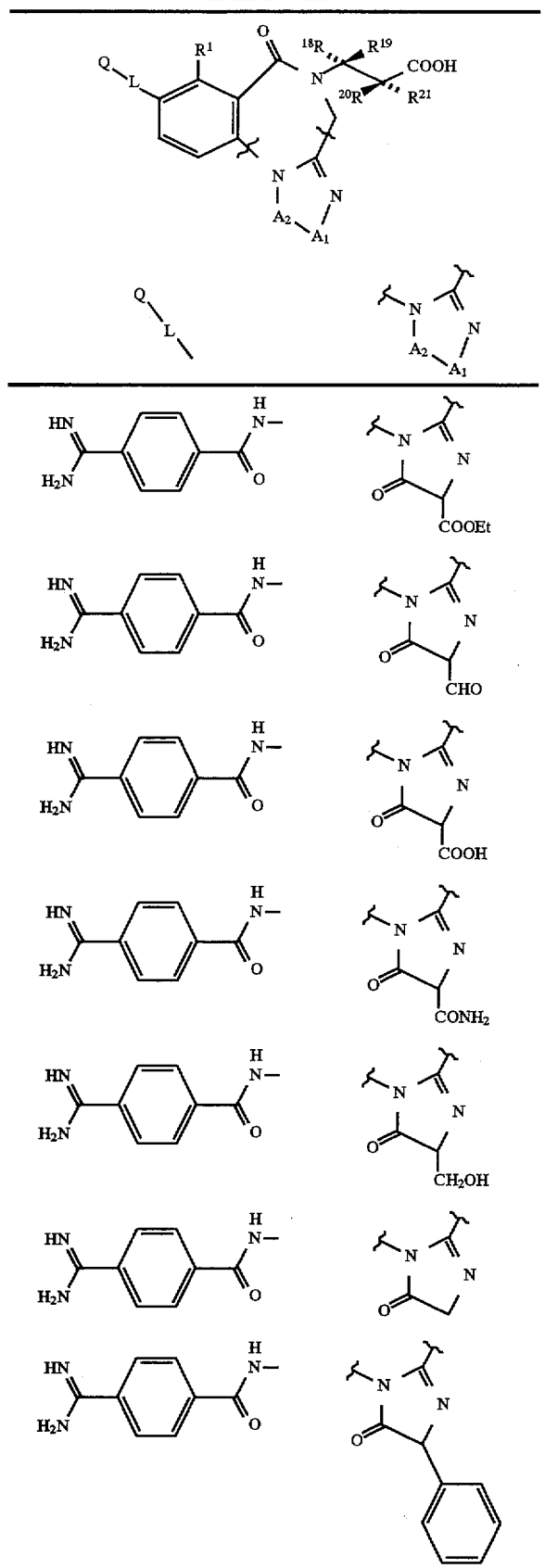
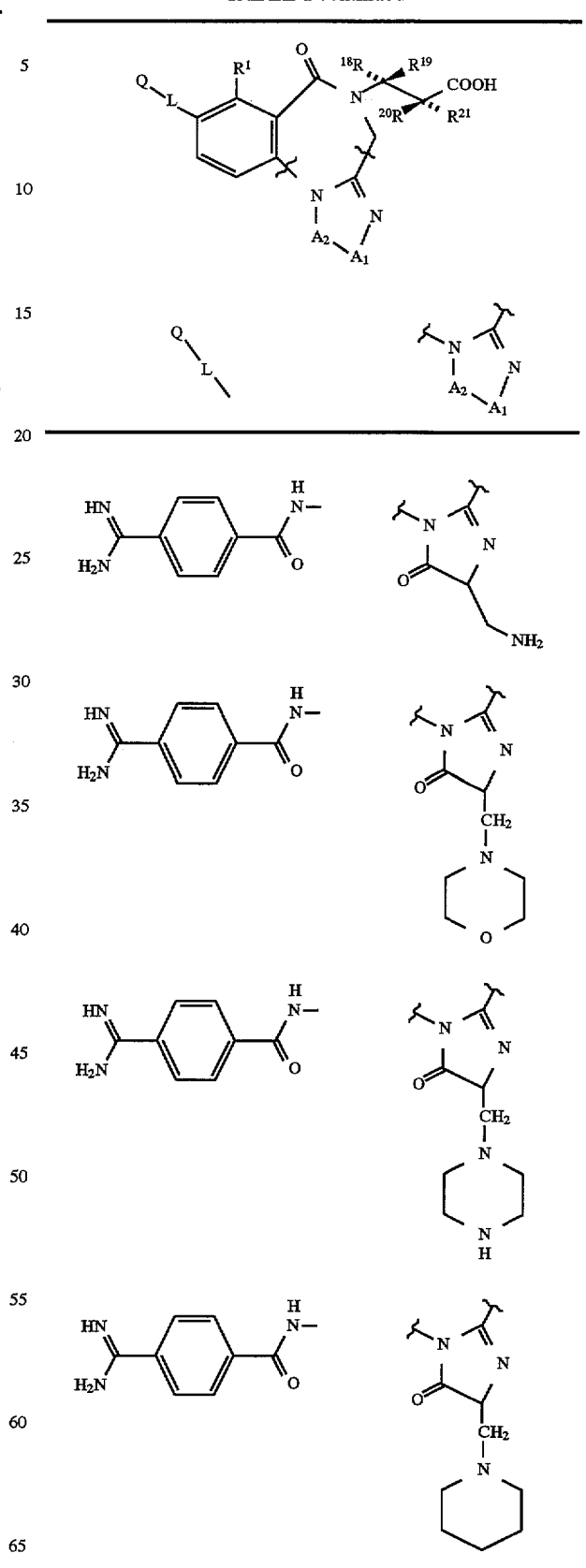

TABLE I-continued
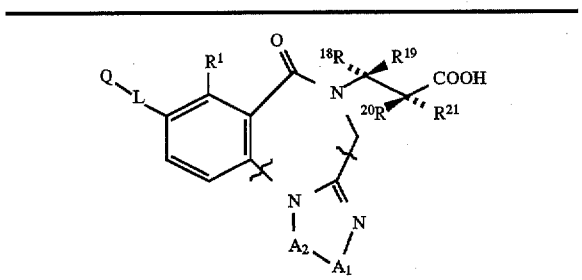
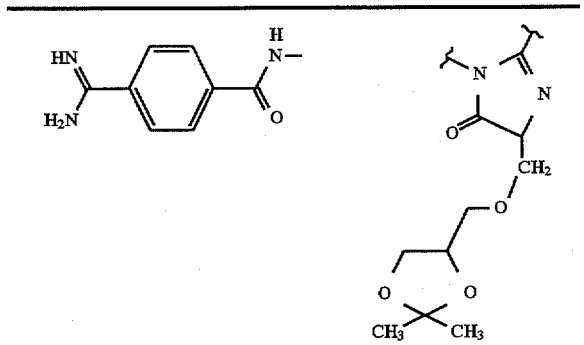
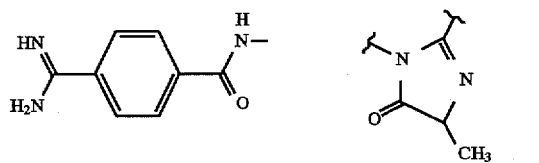
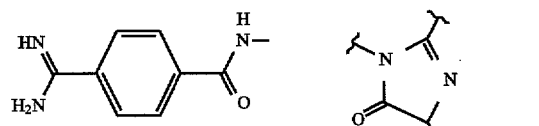
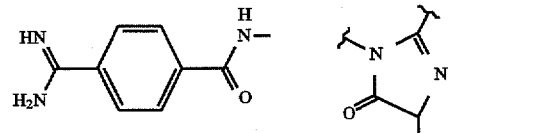
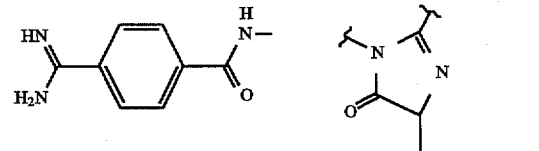
TABLE I-continued
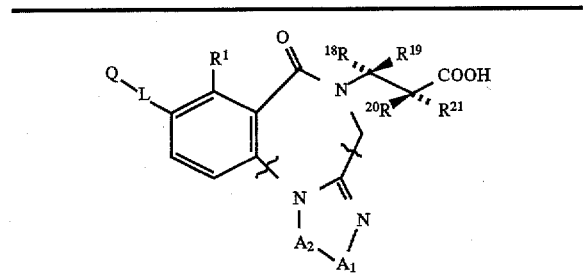
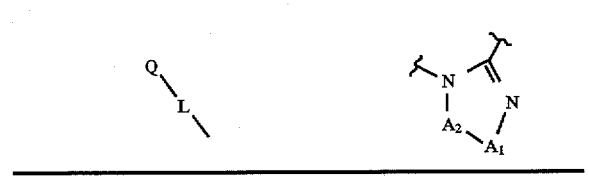
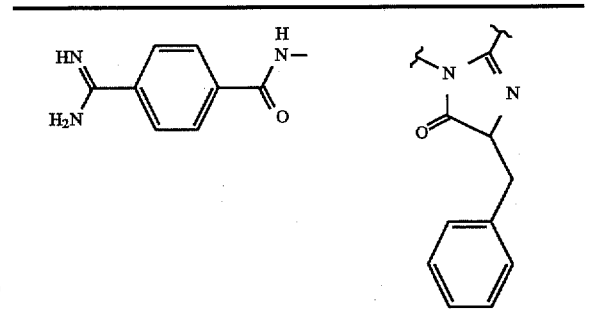
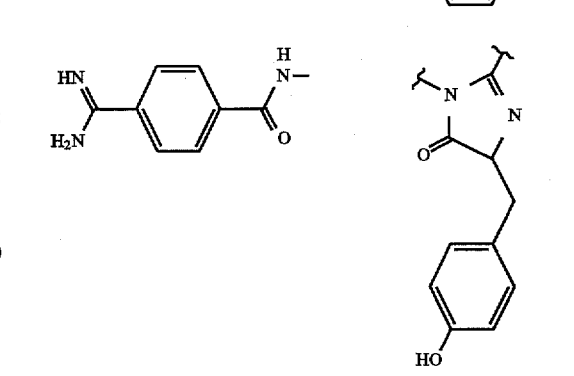
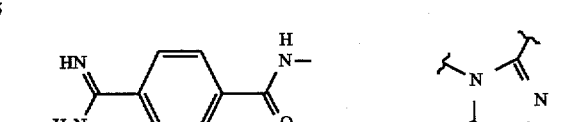
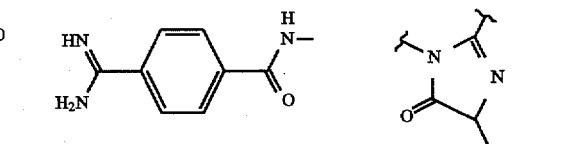

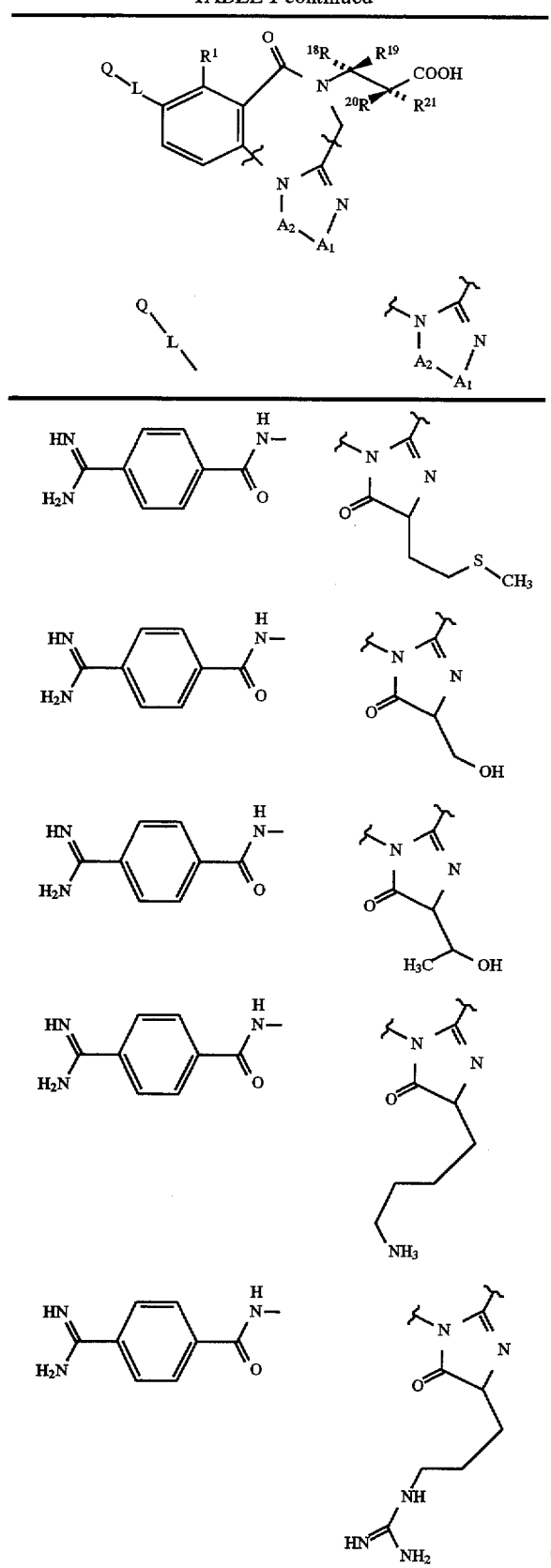

TABLE I-continued
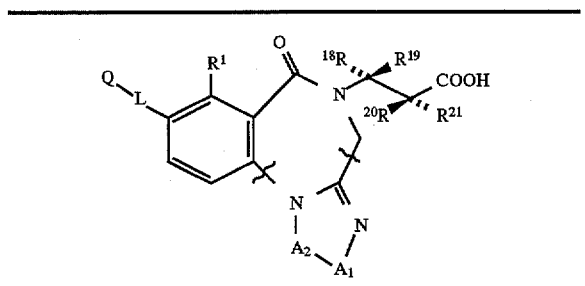
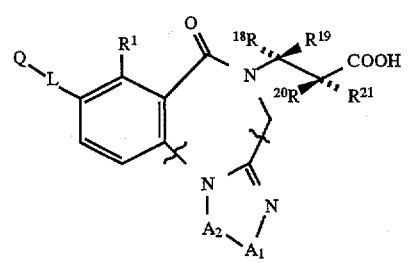
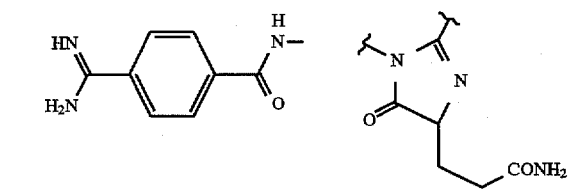
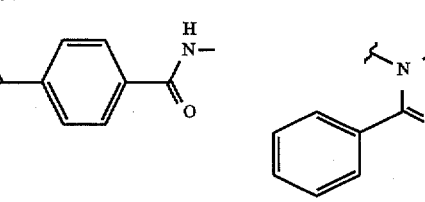
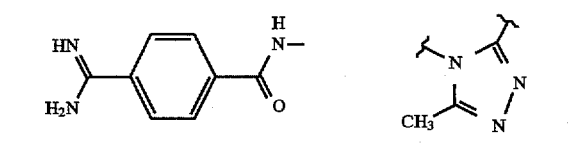
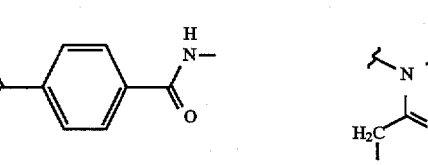
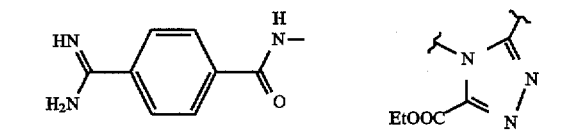
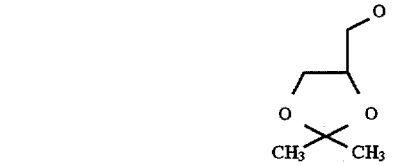
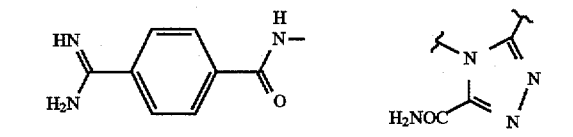
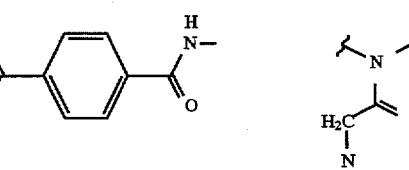
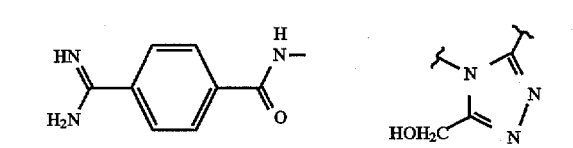
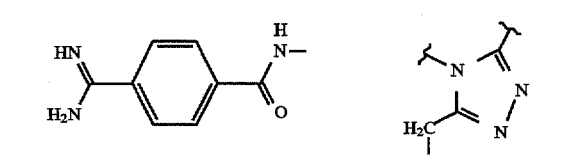
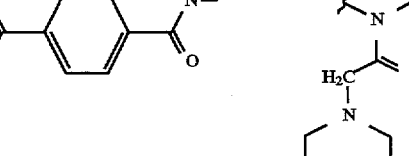
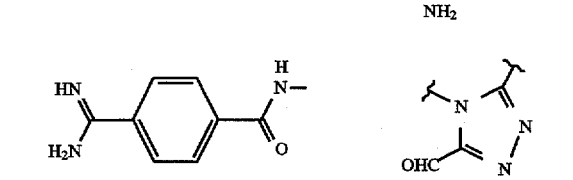

TABLE I-continued
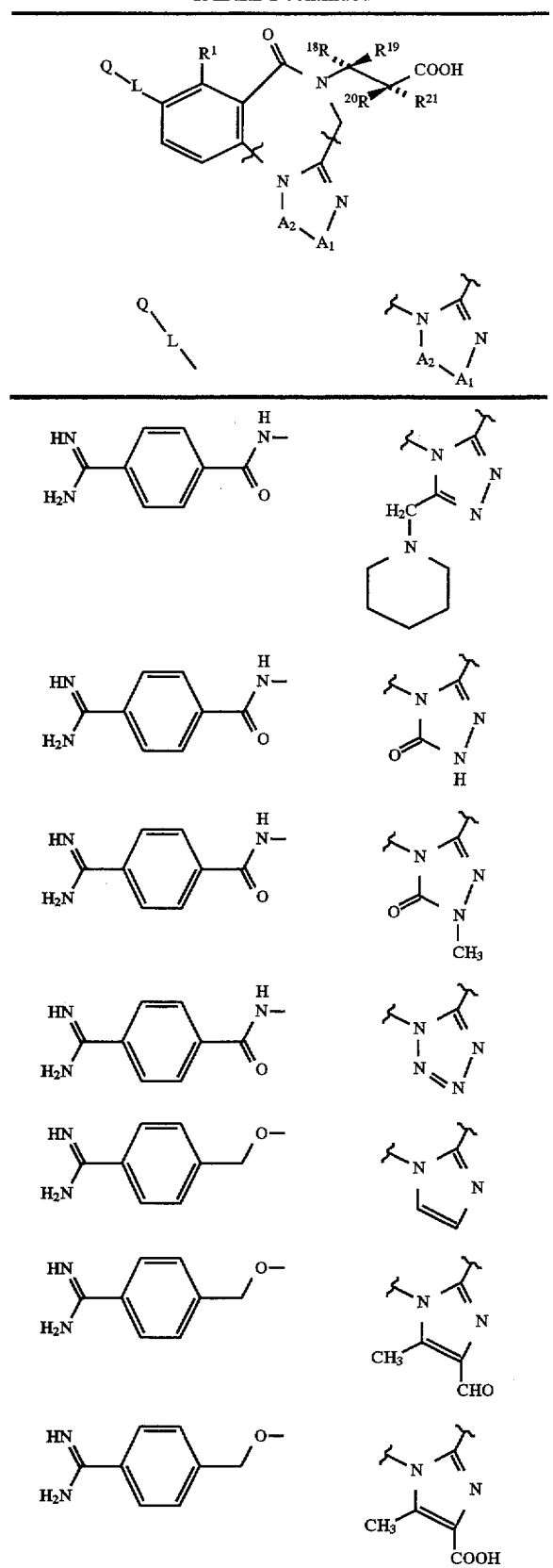
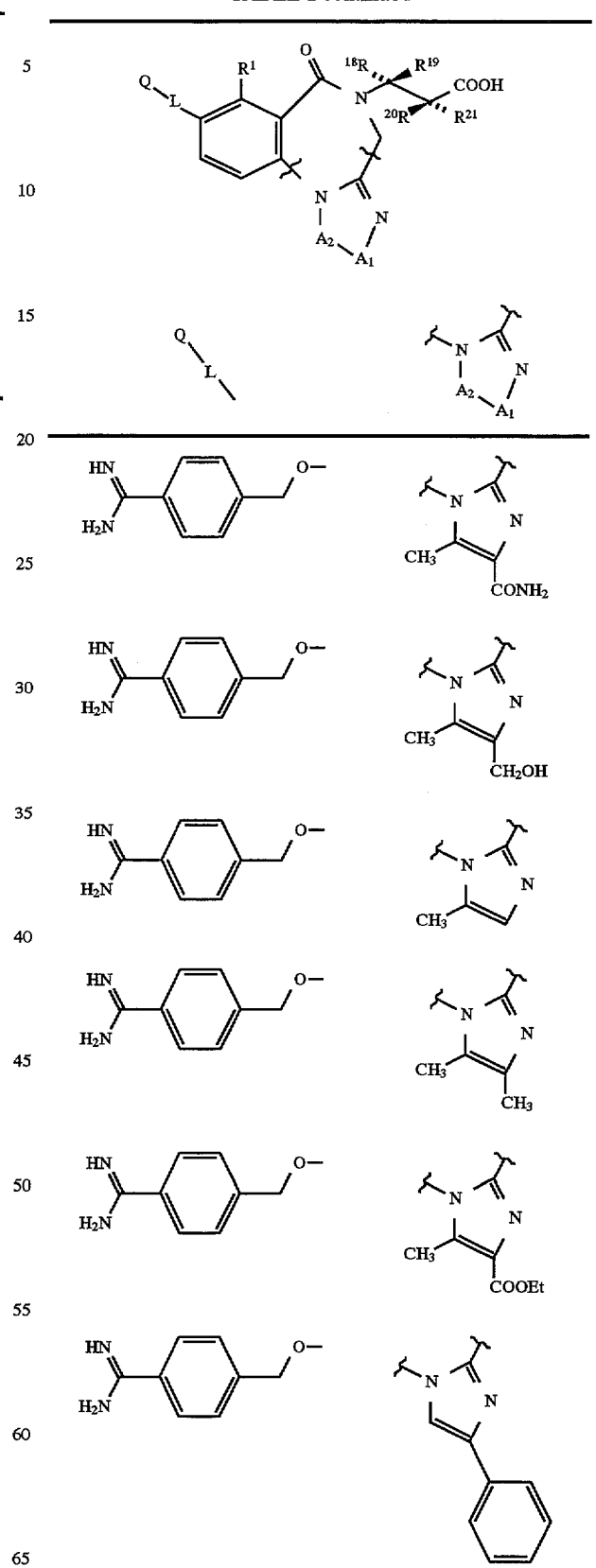

TABLE I-continued
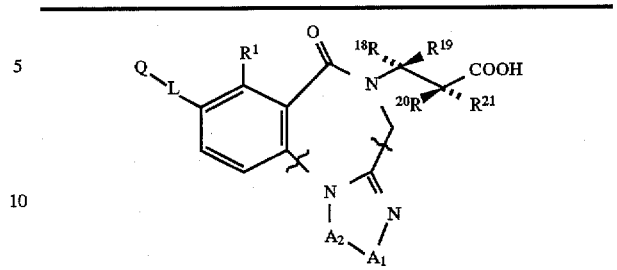
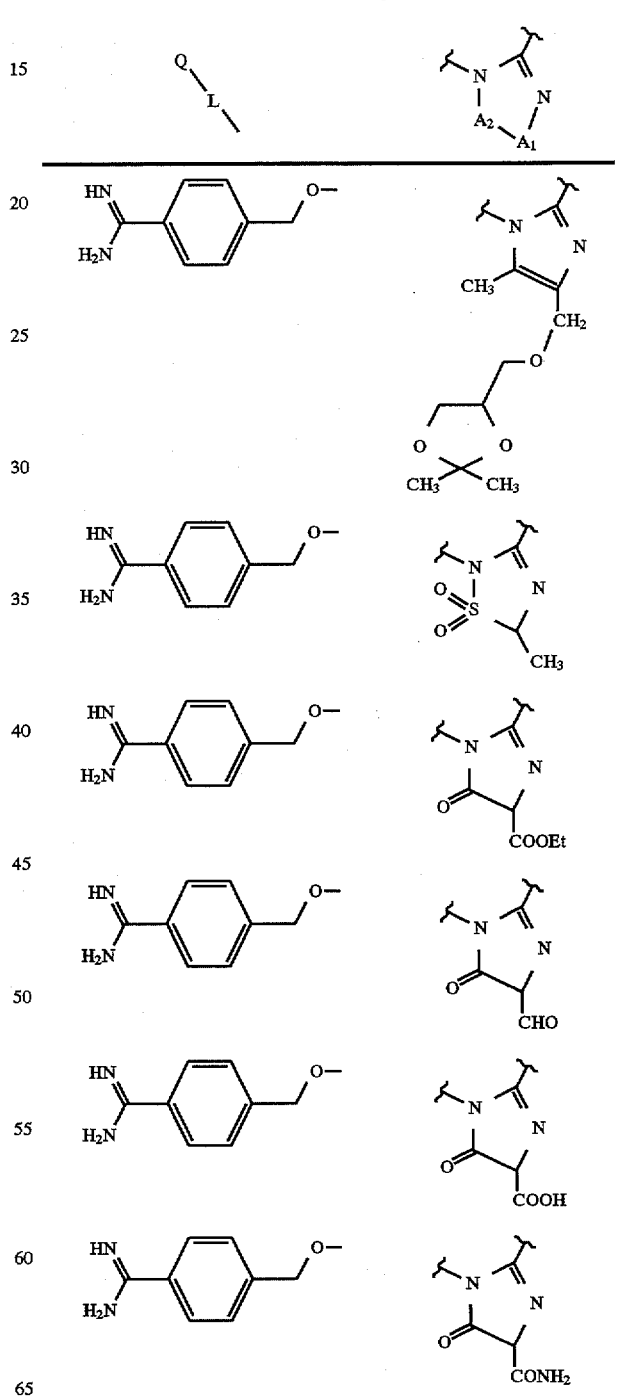

TABLE I-continued
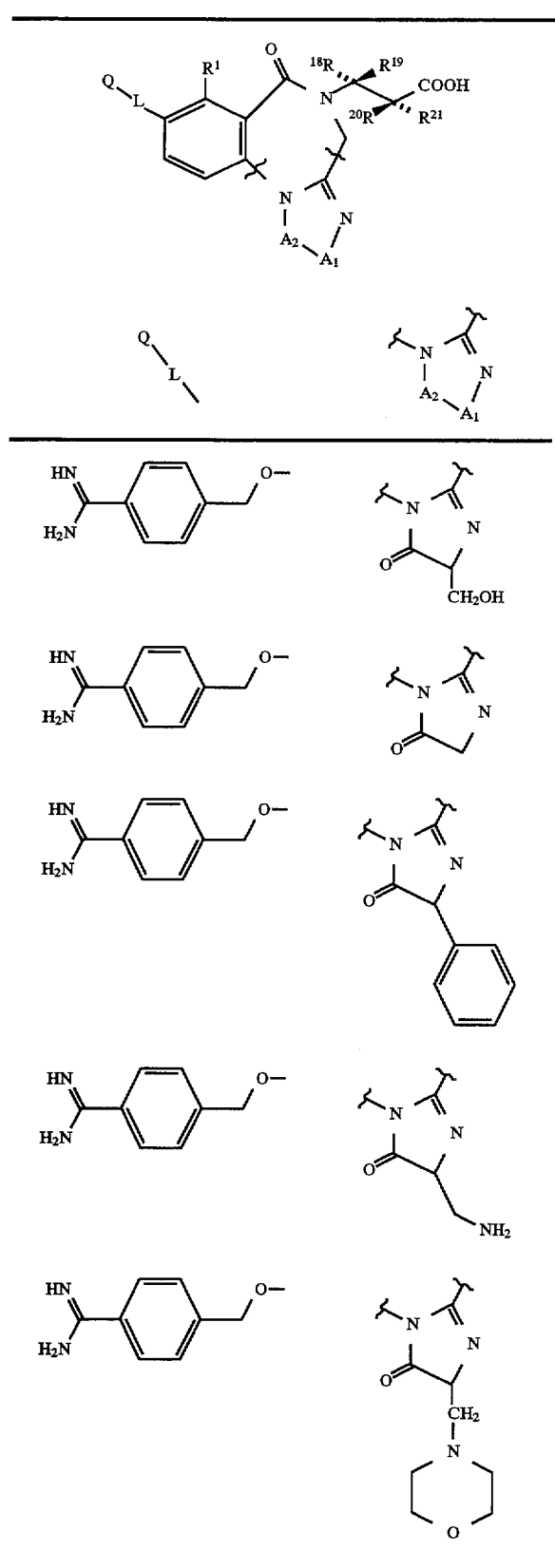
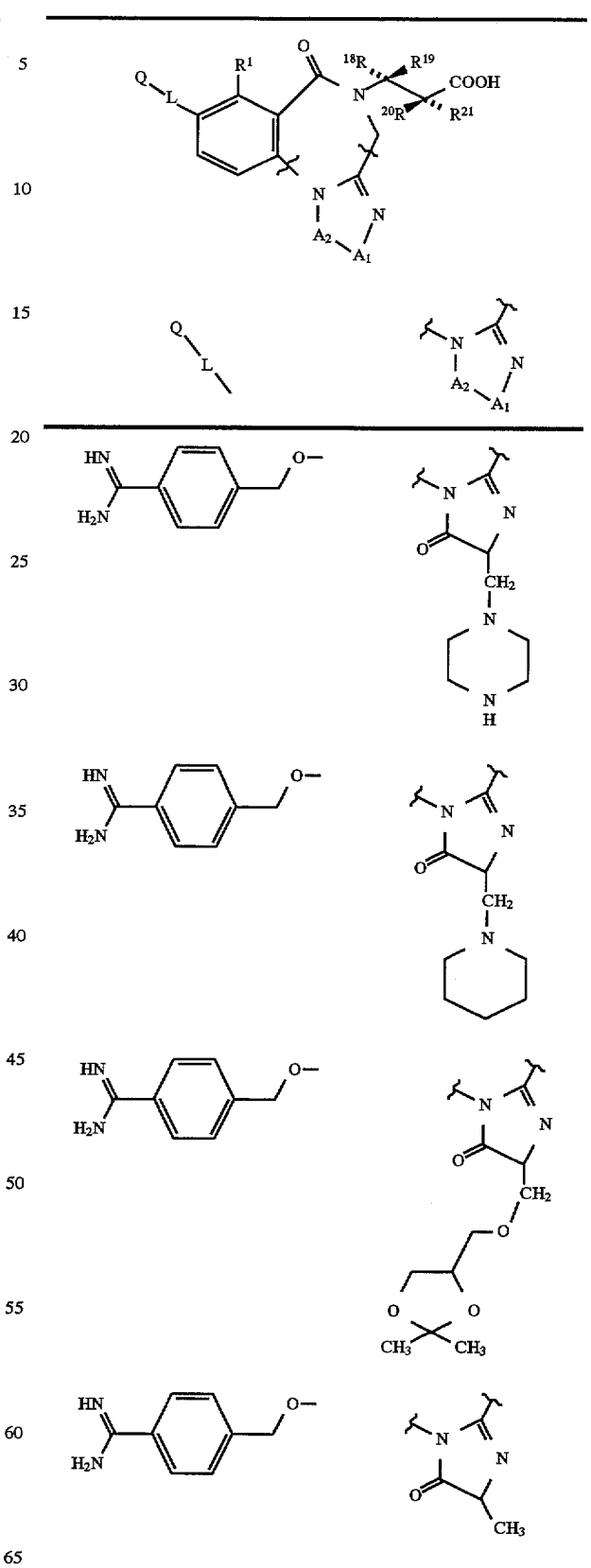

TABLE I-continued
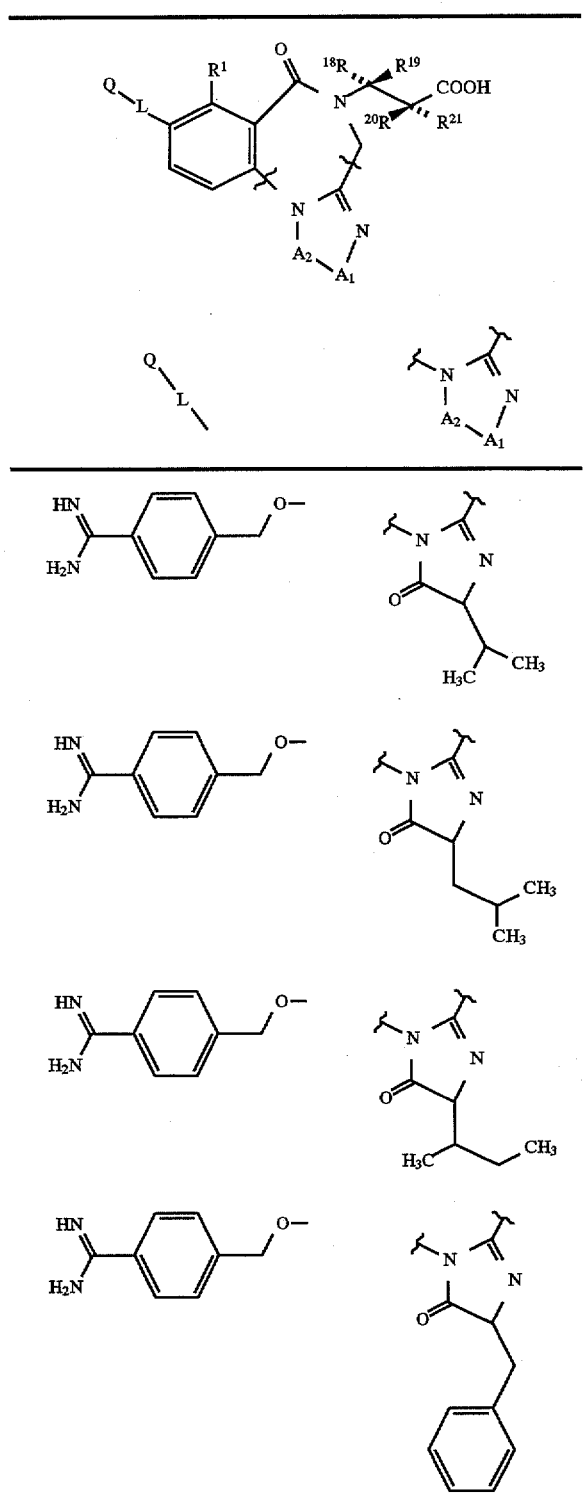
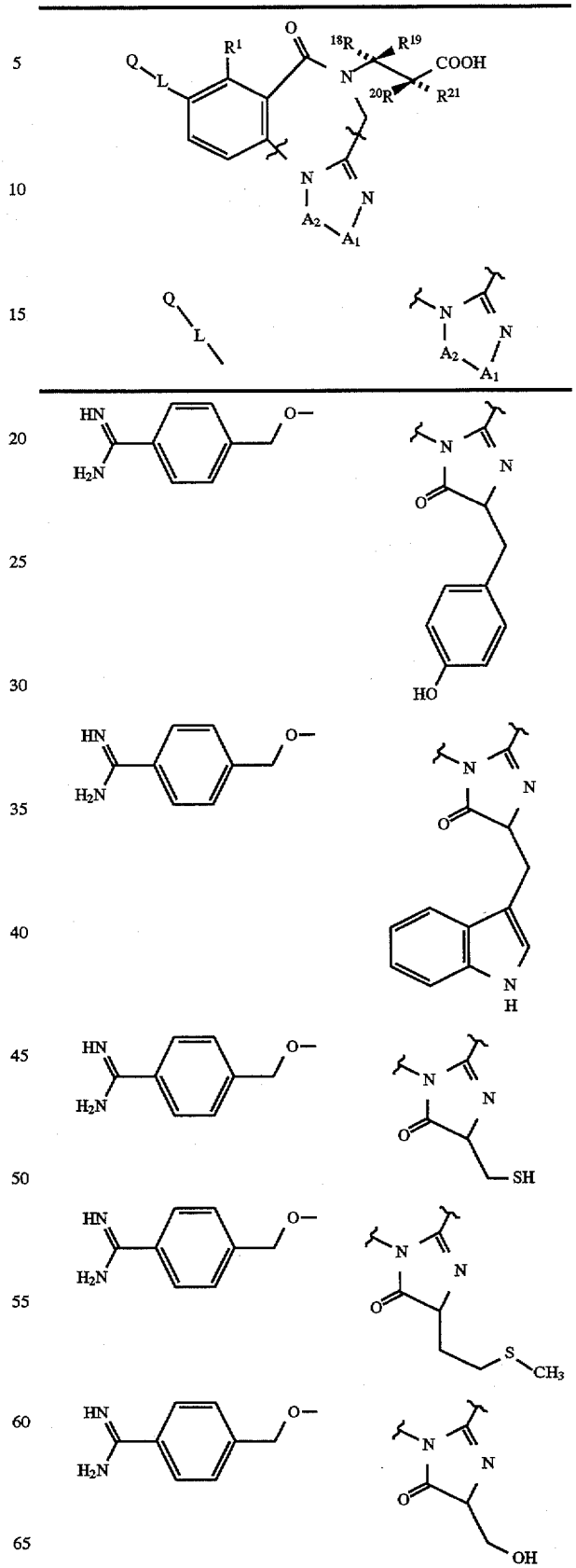

TABLE I-continued
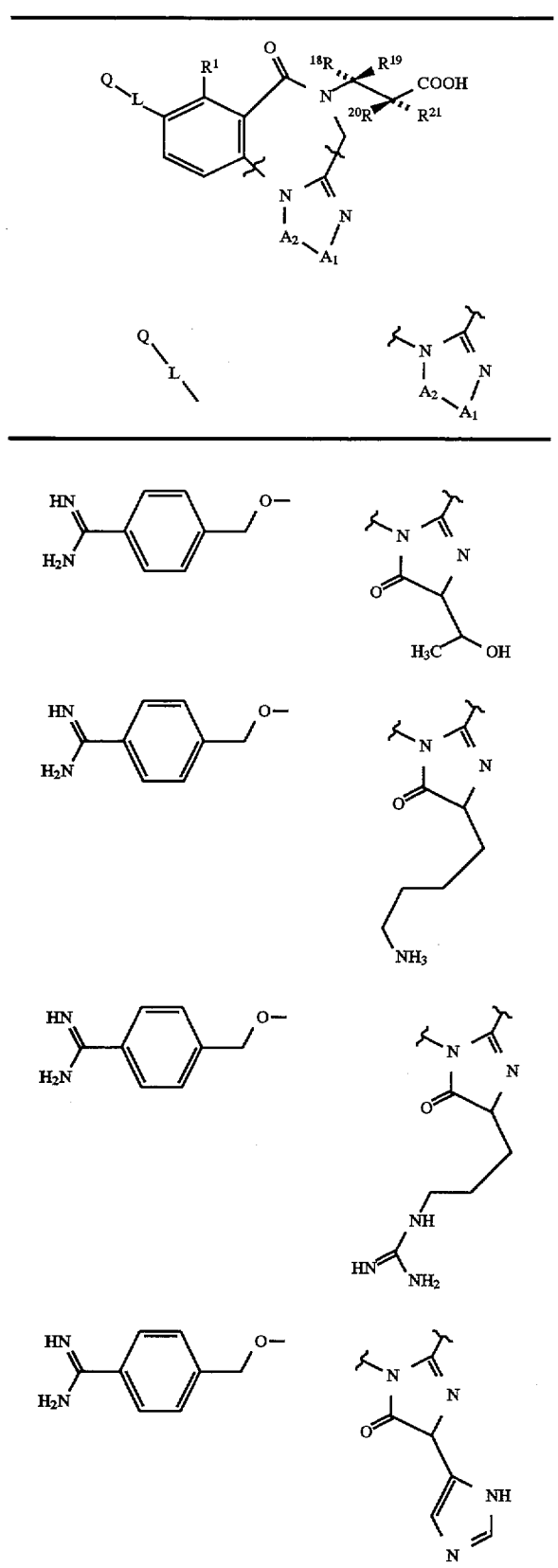
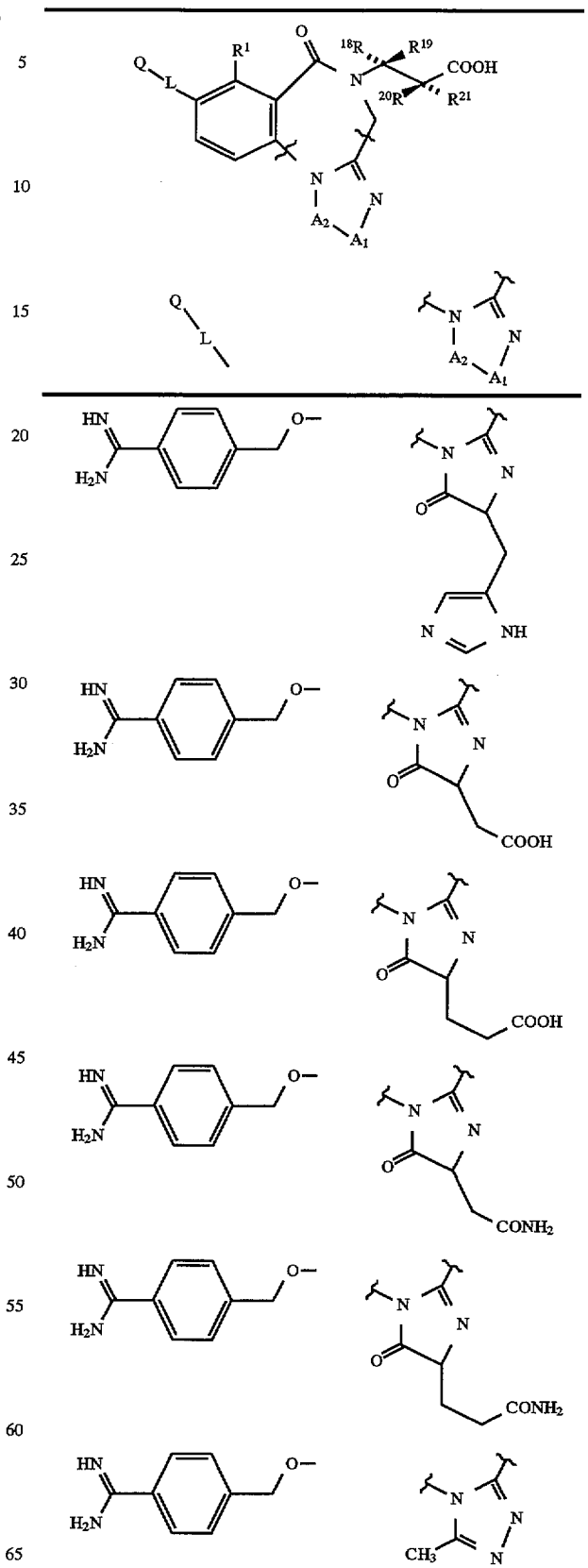

TABLE I-continued
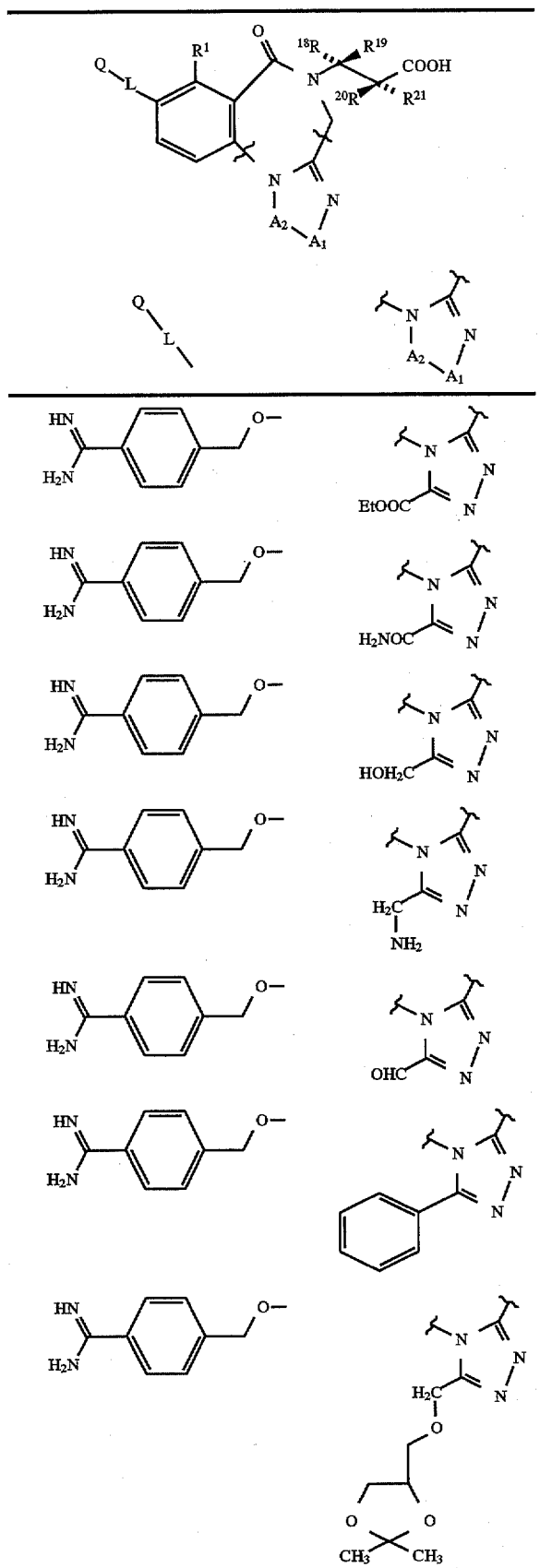
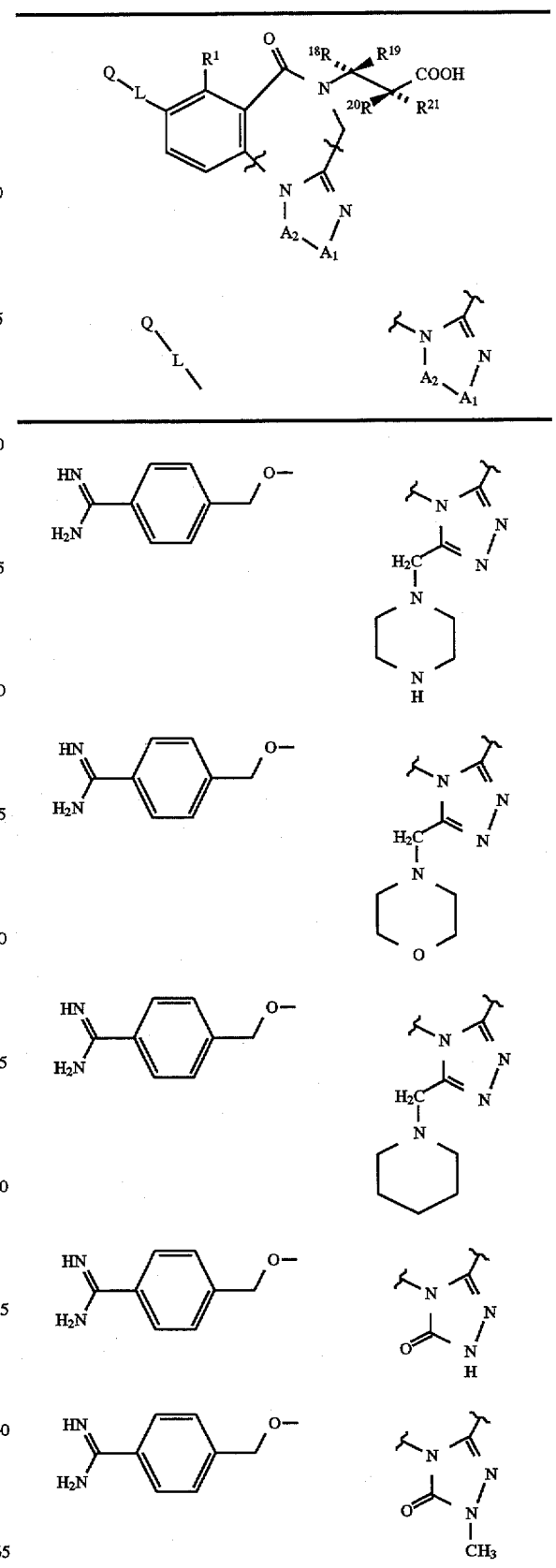

TABLE I-continued
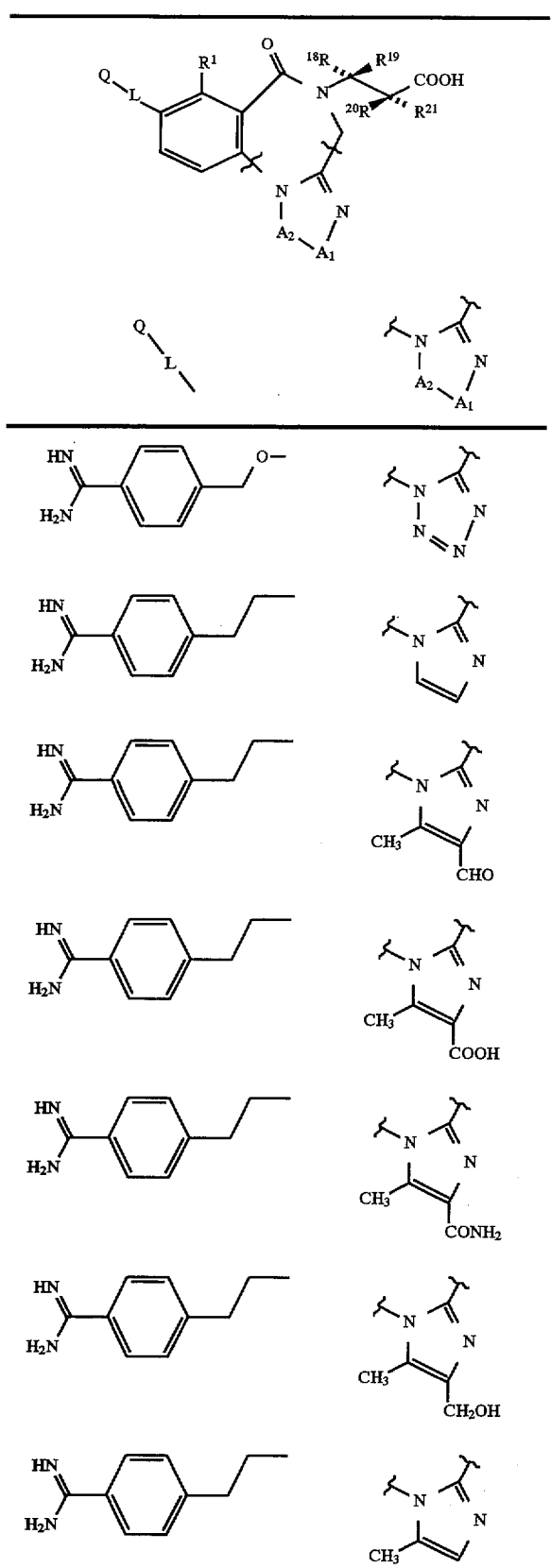
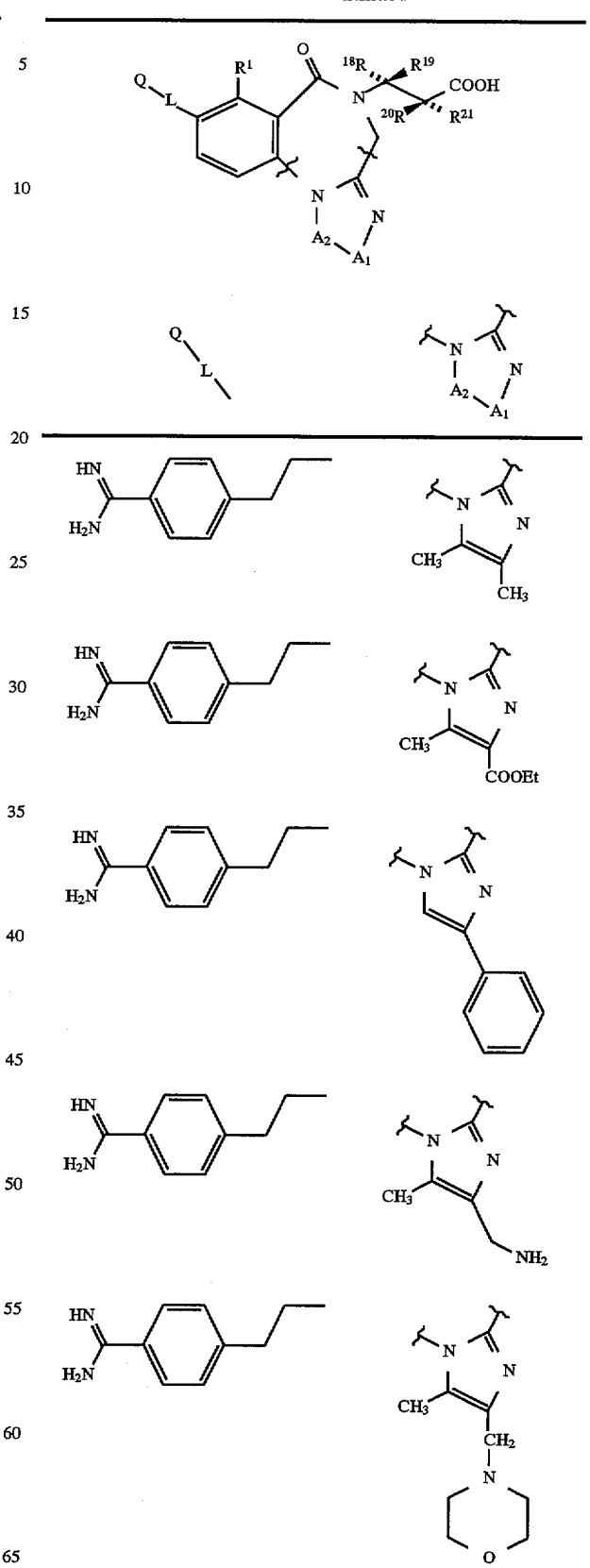

TABLE I-continued
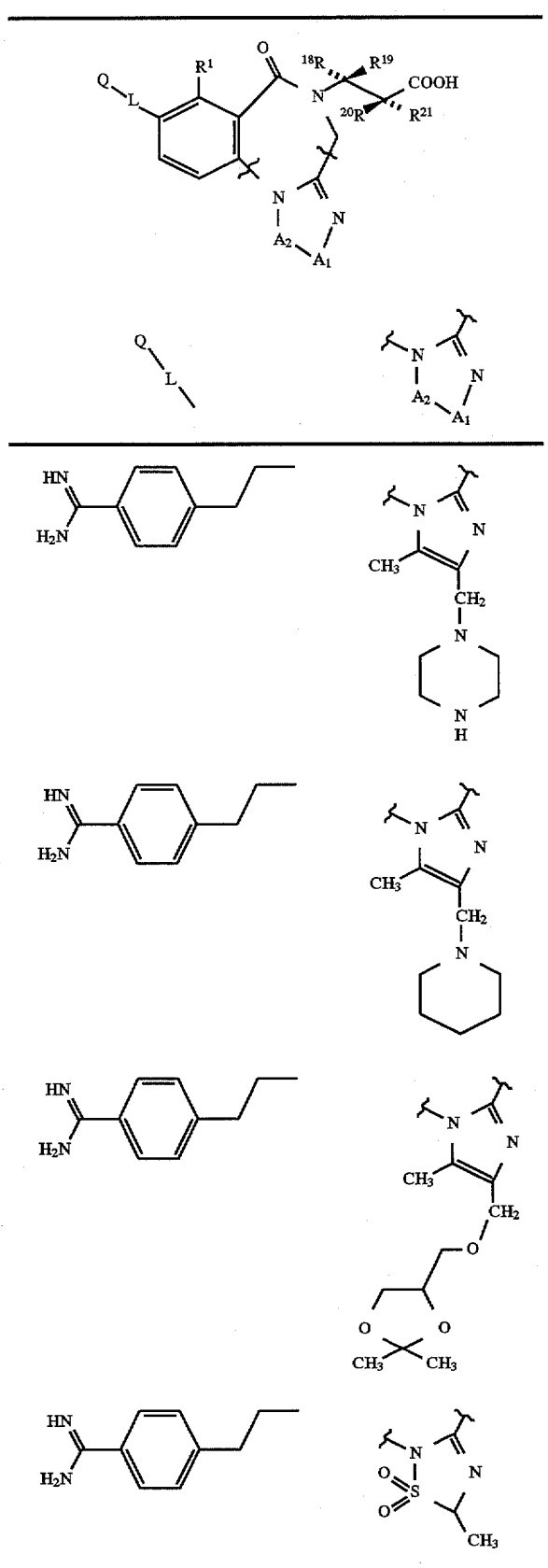
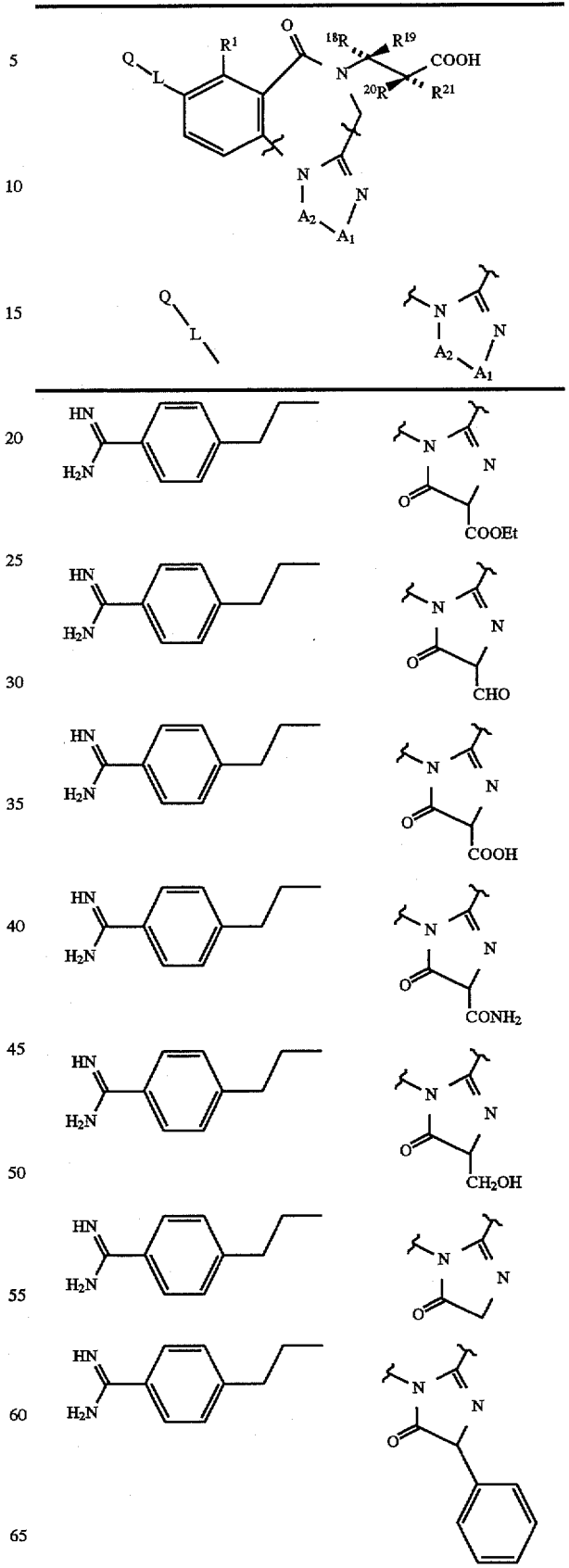

TABLE I-continued

TABLE I-continued
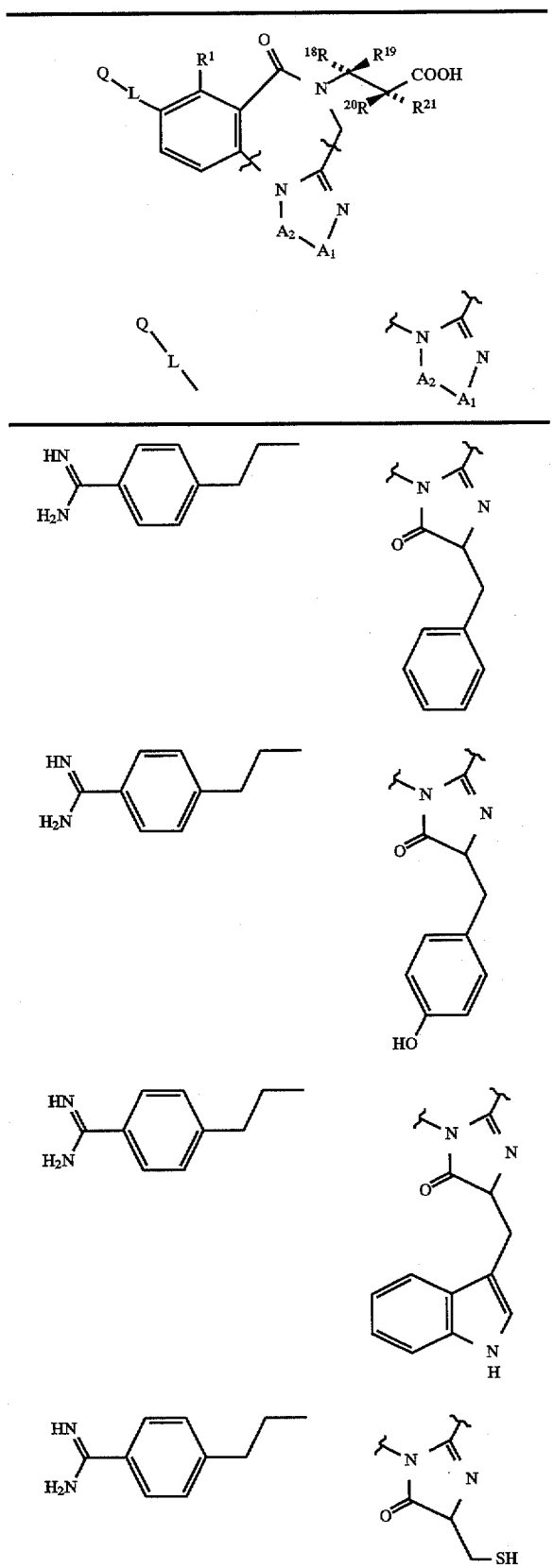
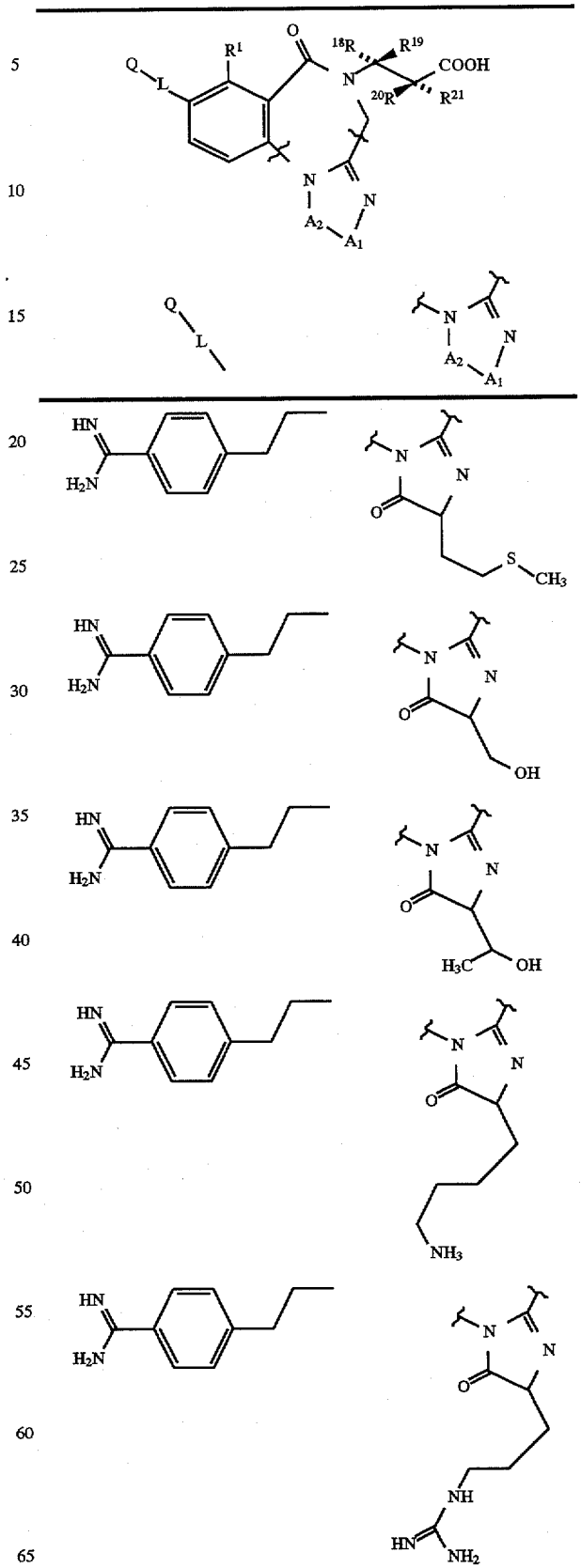

TABLE I-continued
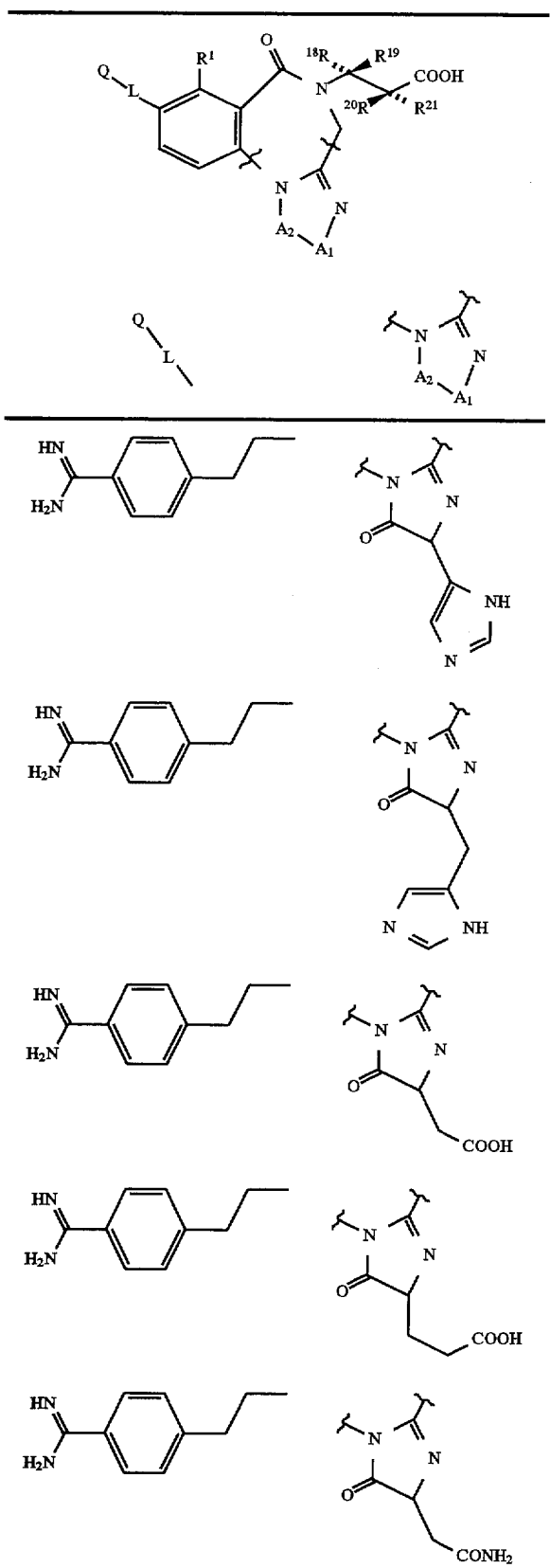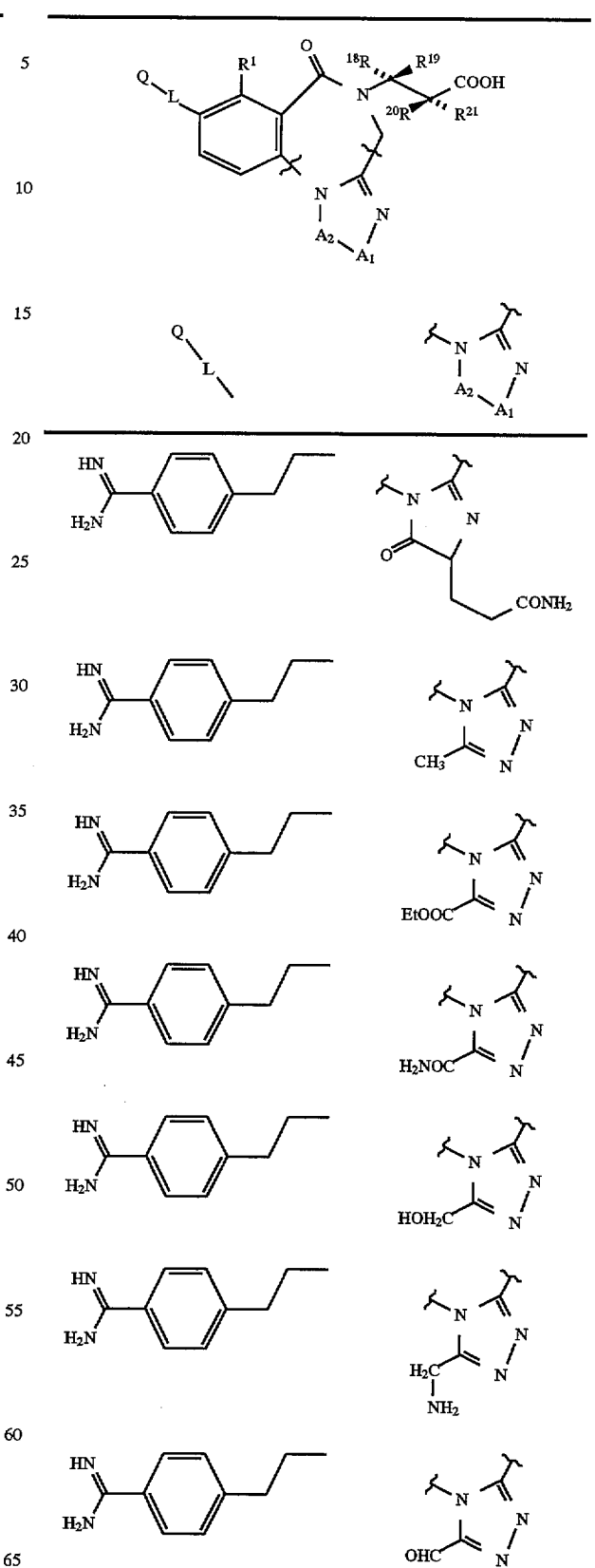

TABLE I-continued
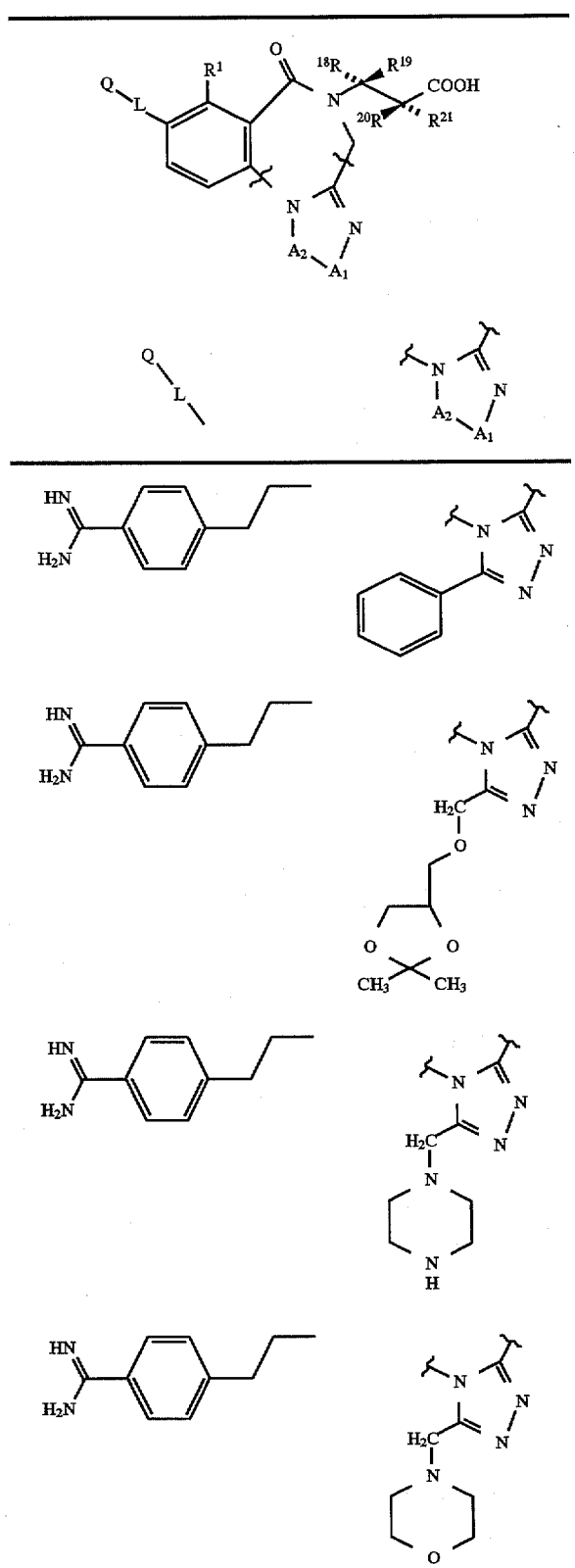
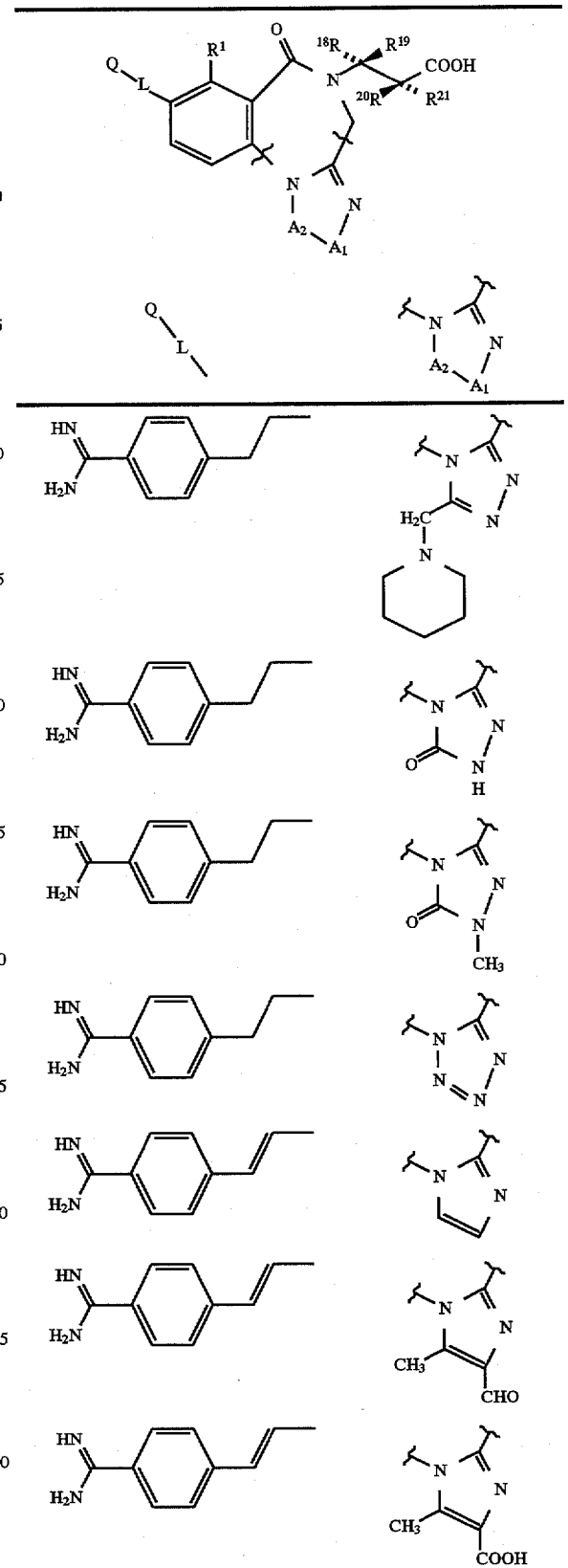

TABLE I-continued
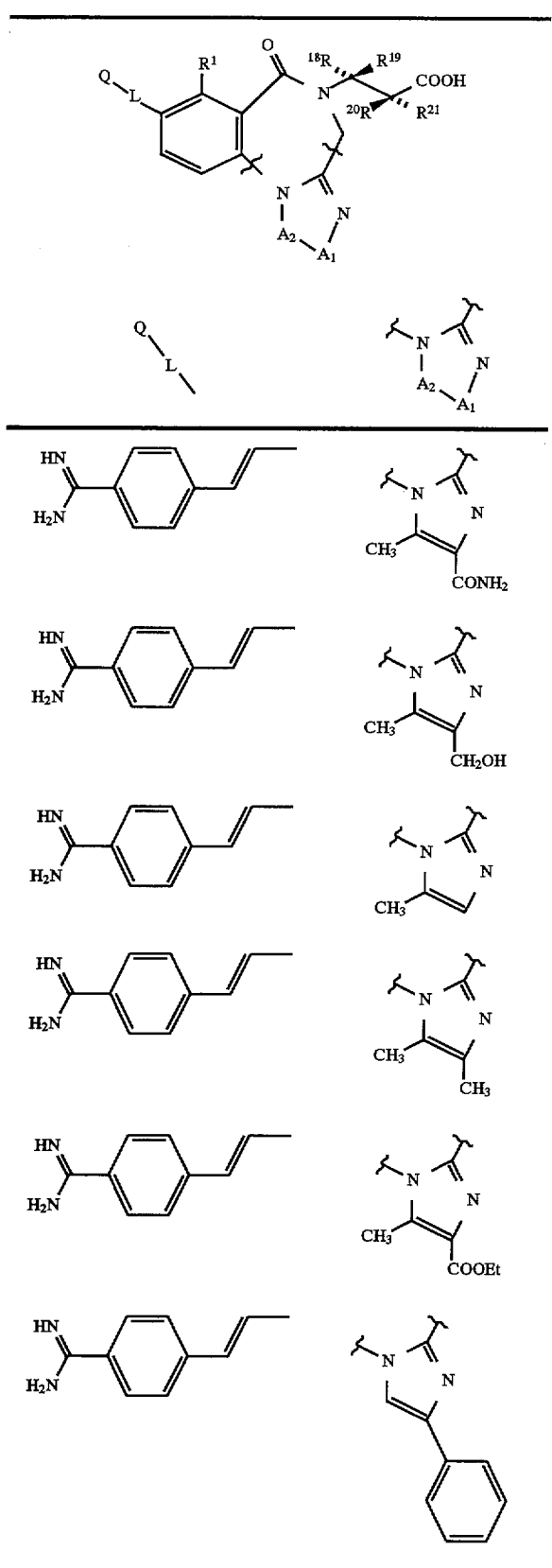
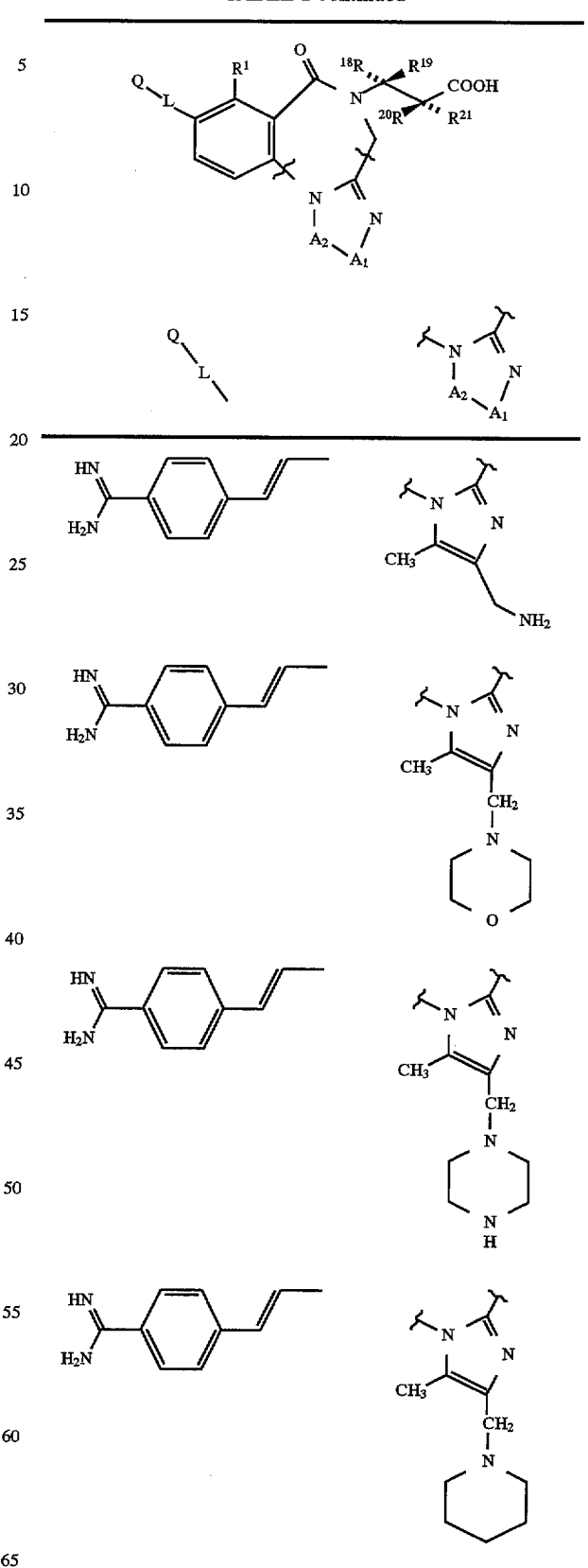

TABLE I-continued
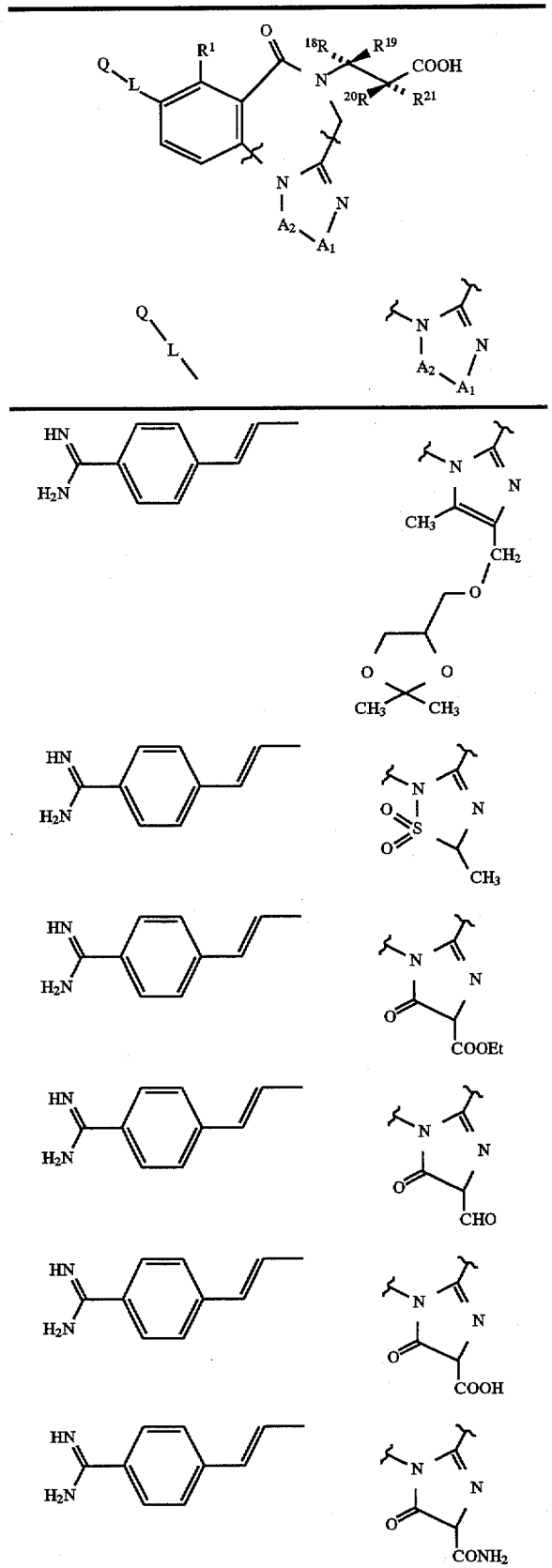
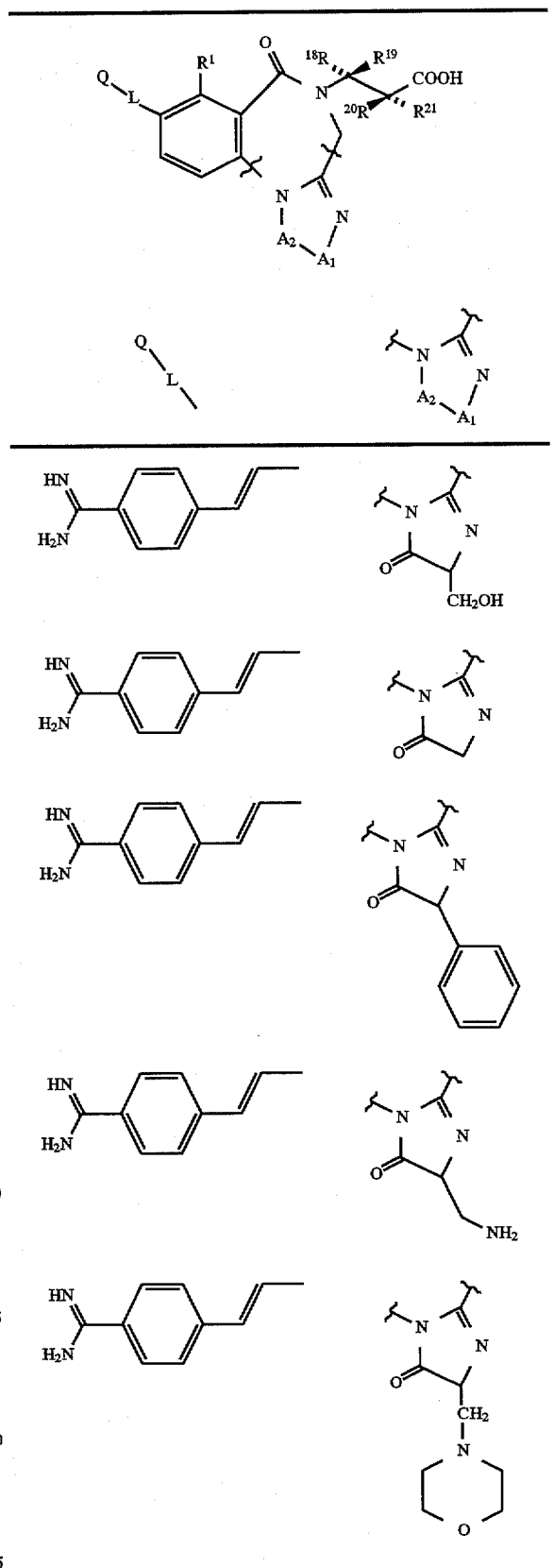

TABLE I-continued
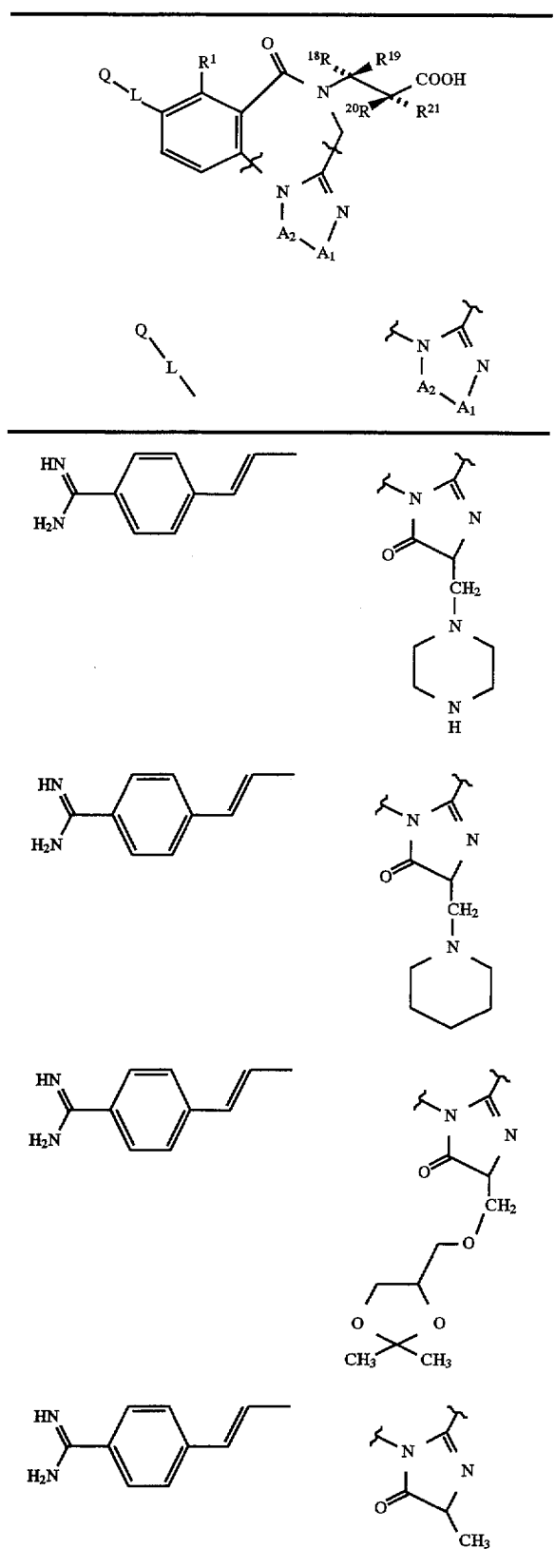
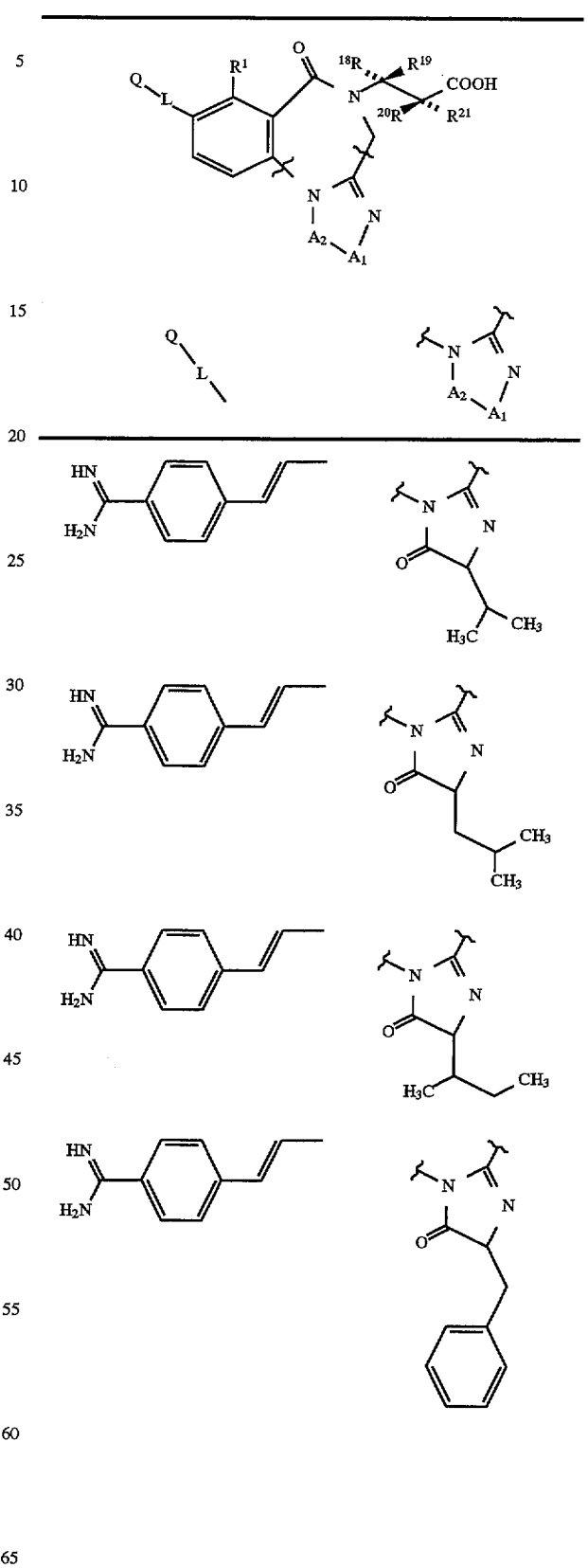

TABLE I-continued
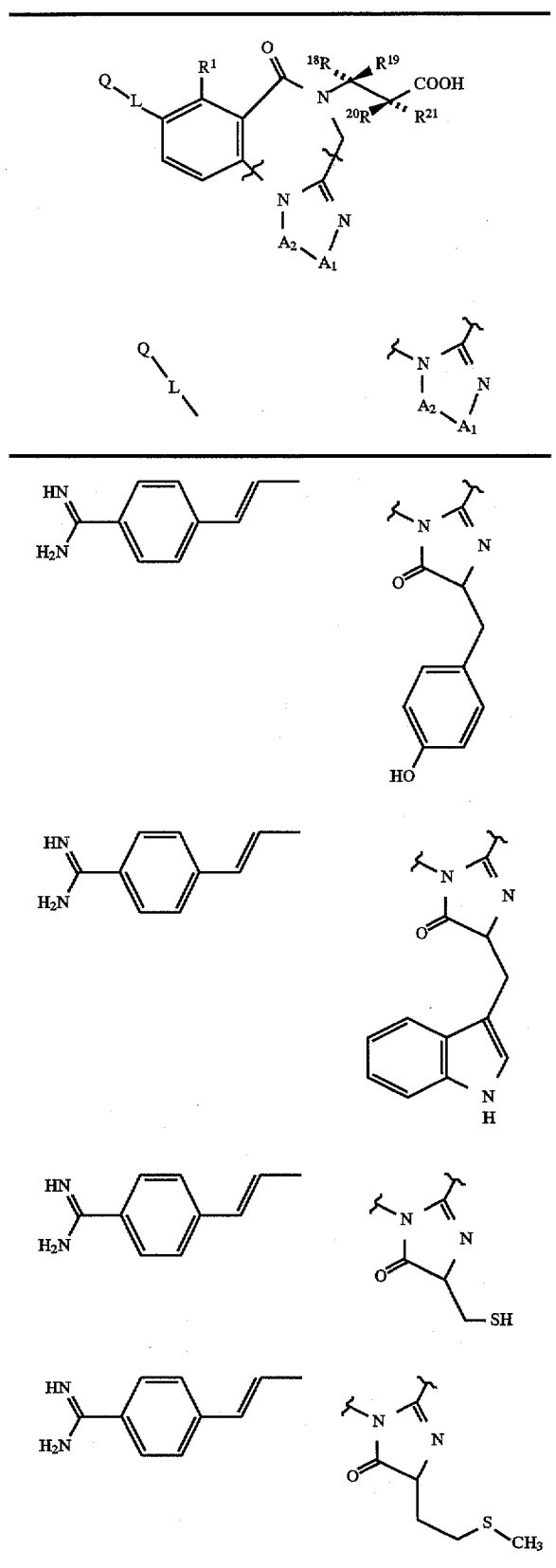
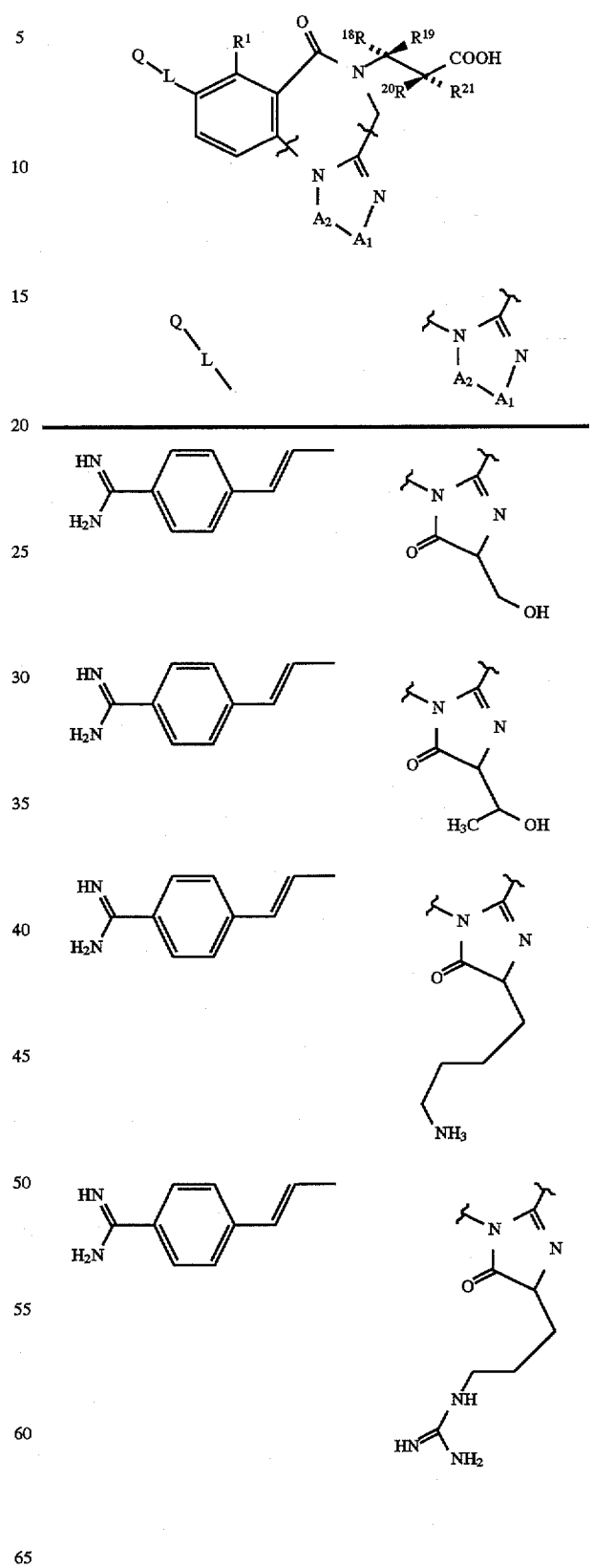

TABLE I-continued
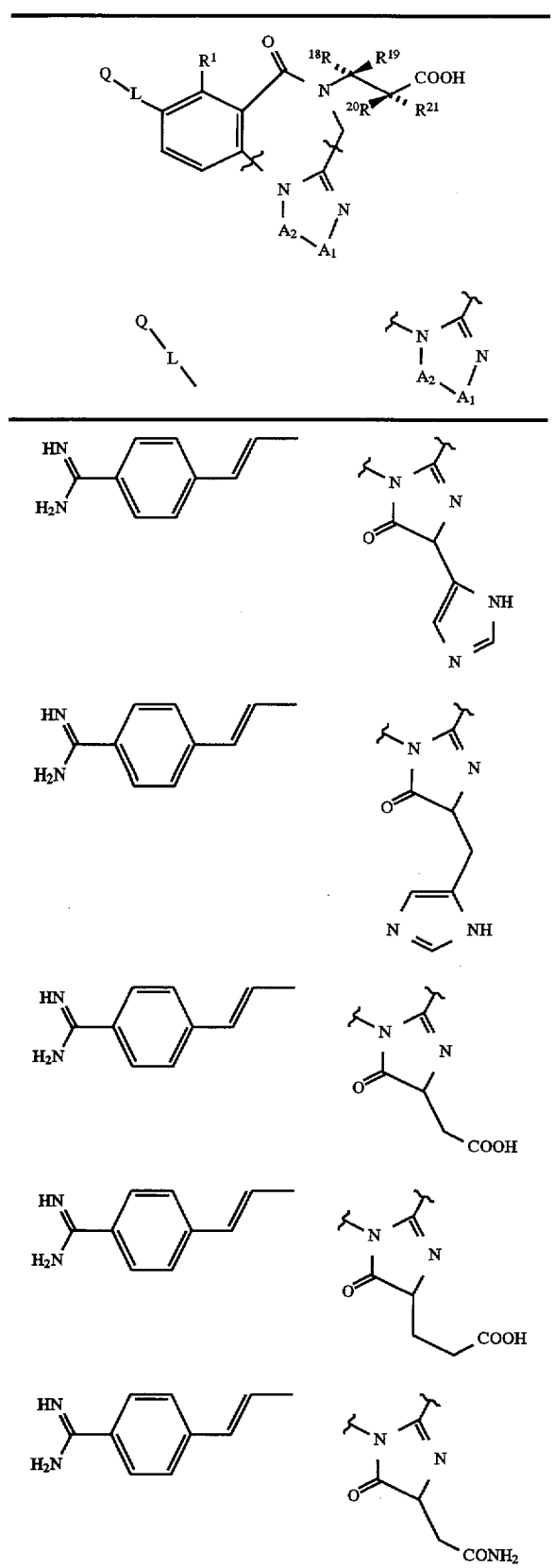
TABLE I-continued
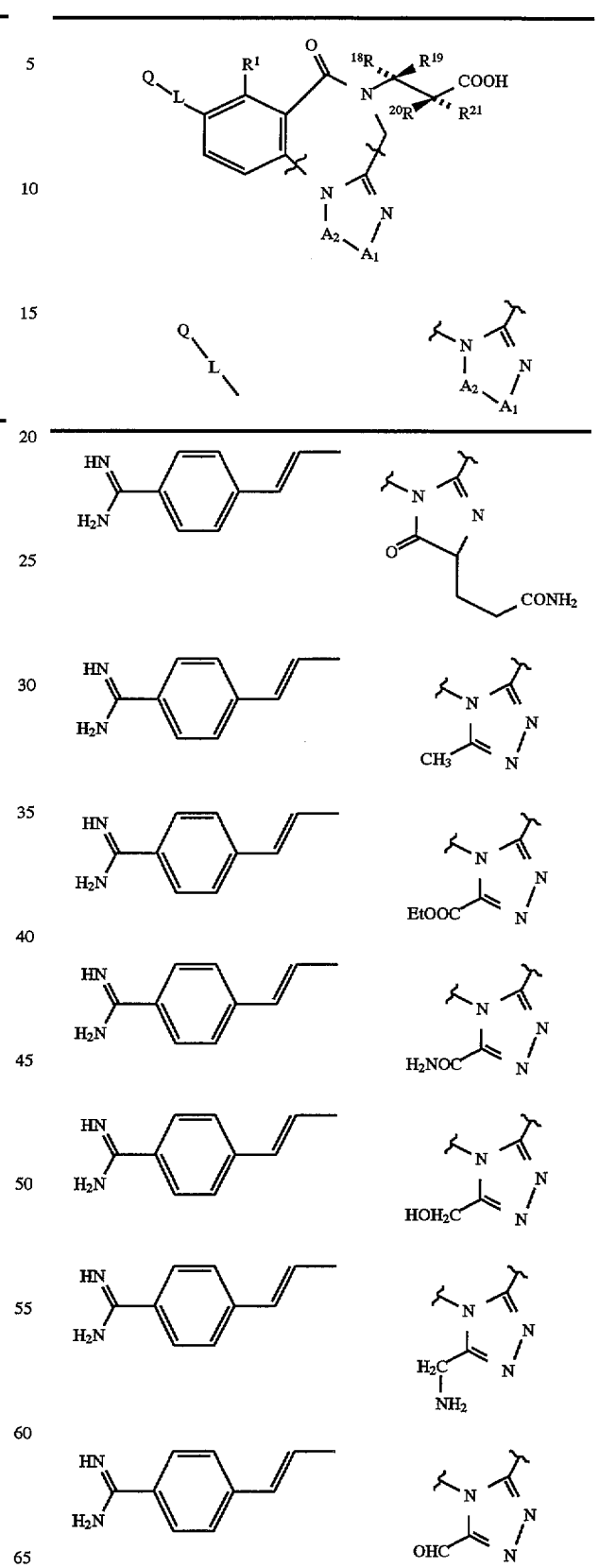

TABLE I-continued
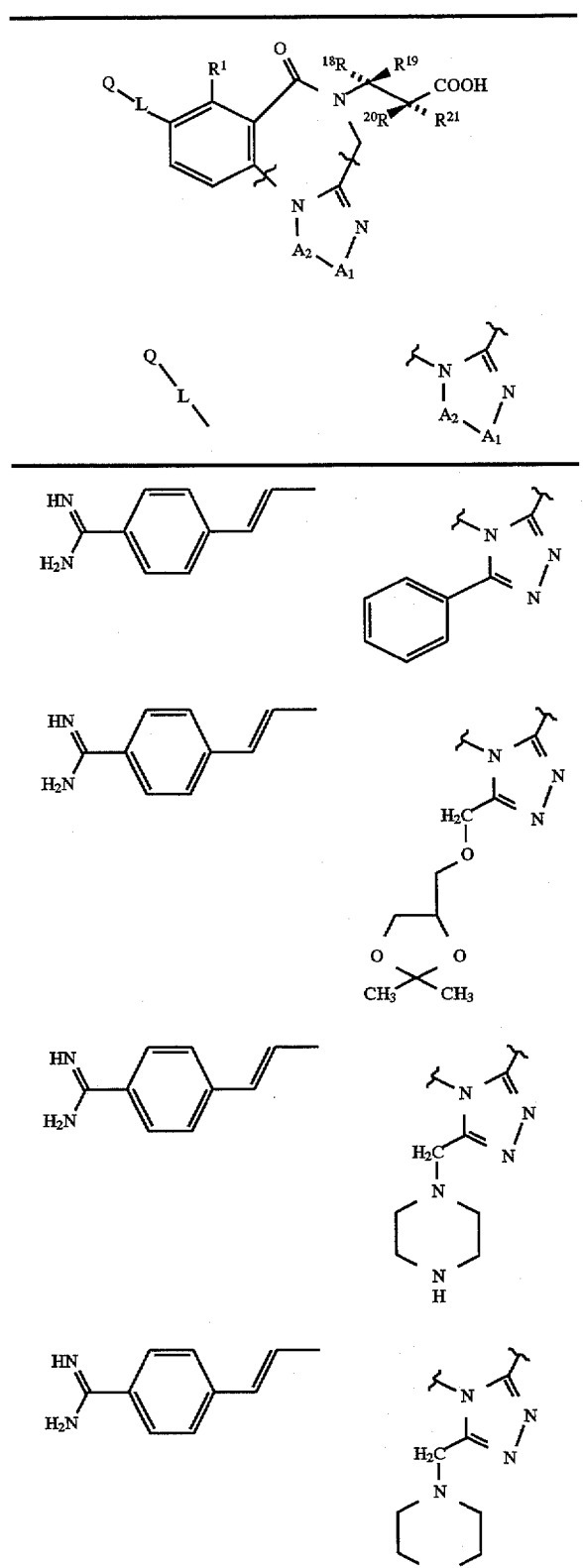
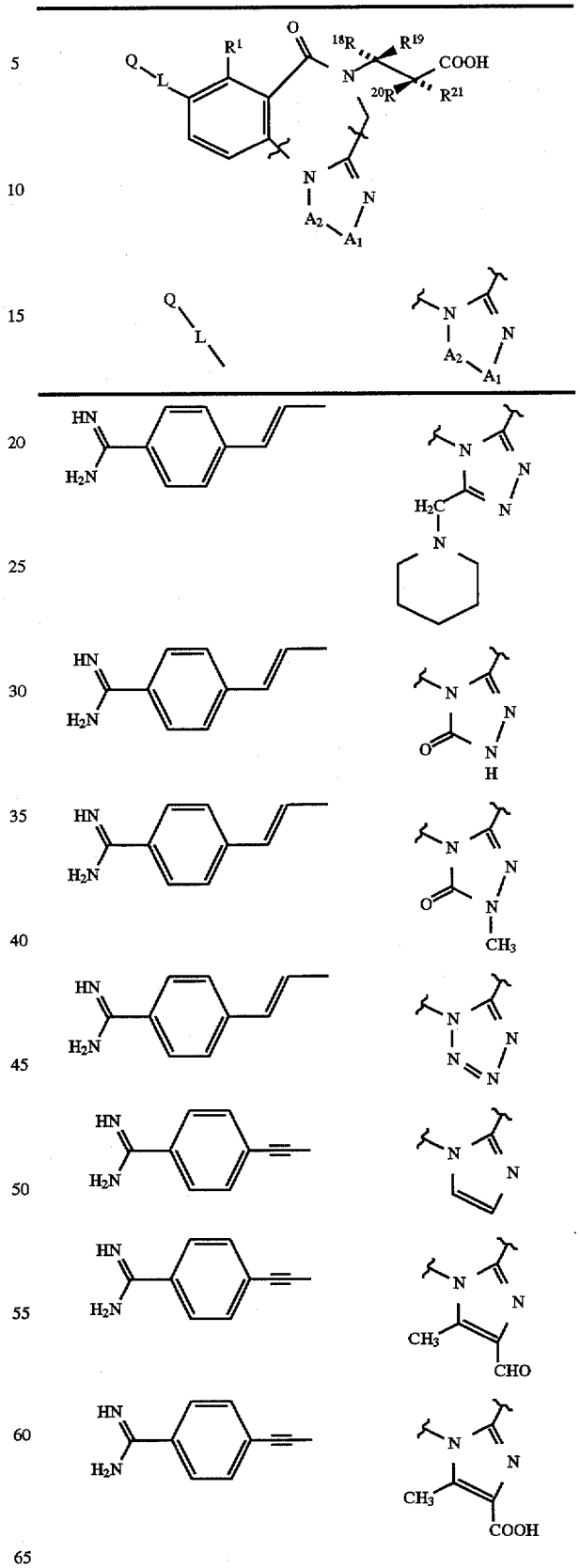

TABLE I-continued
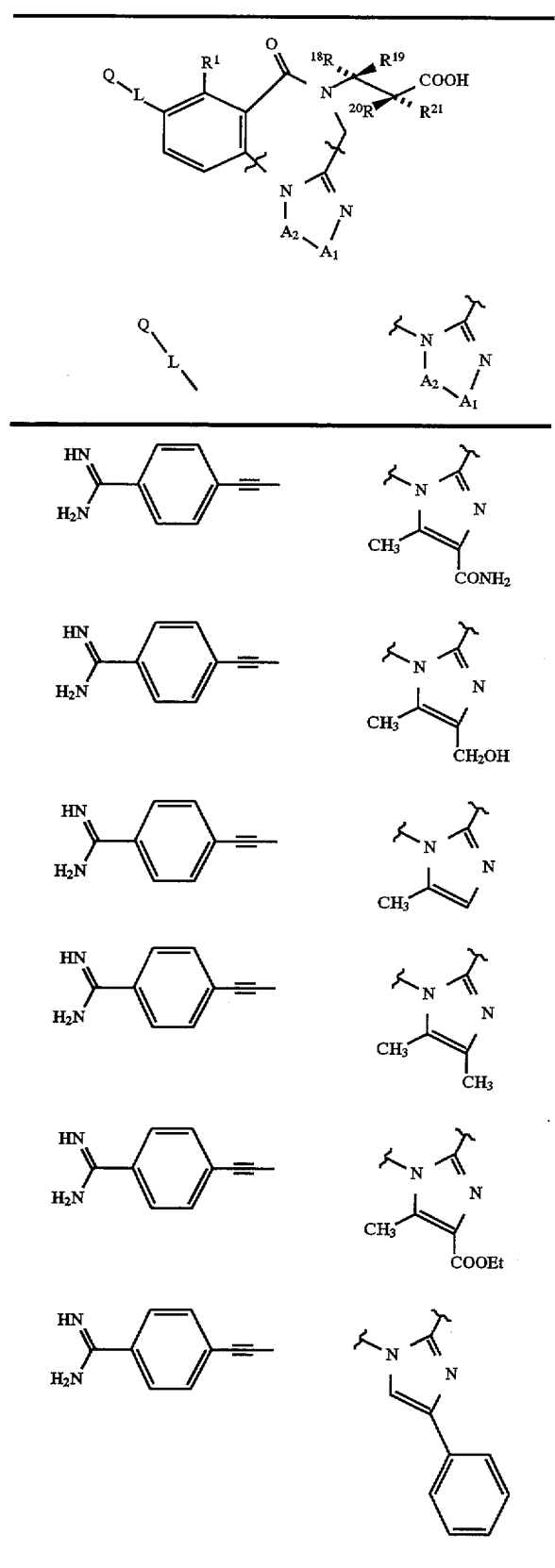
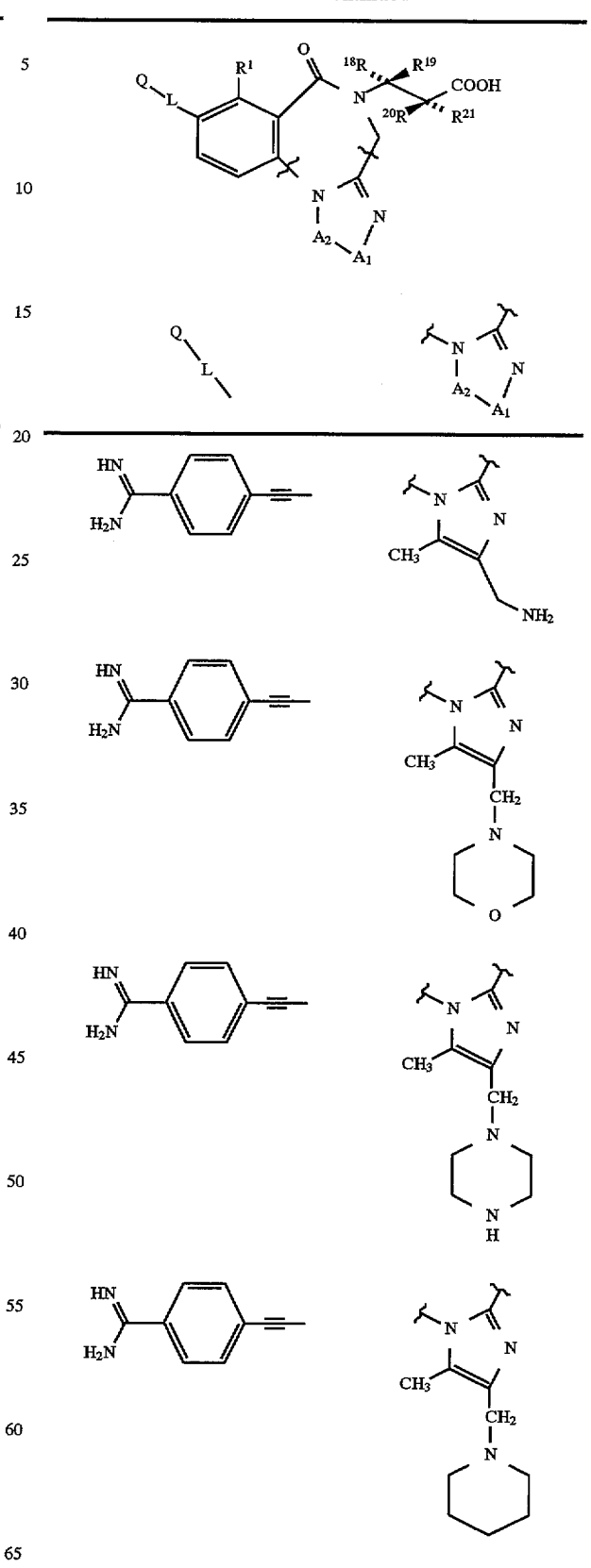

TABLE I-continued
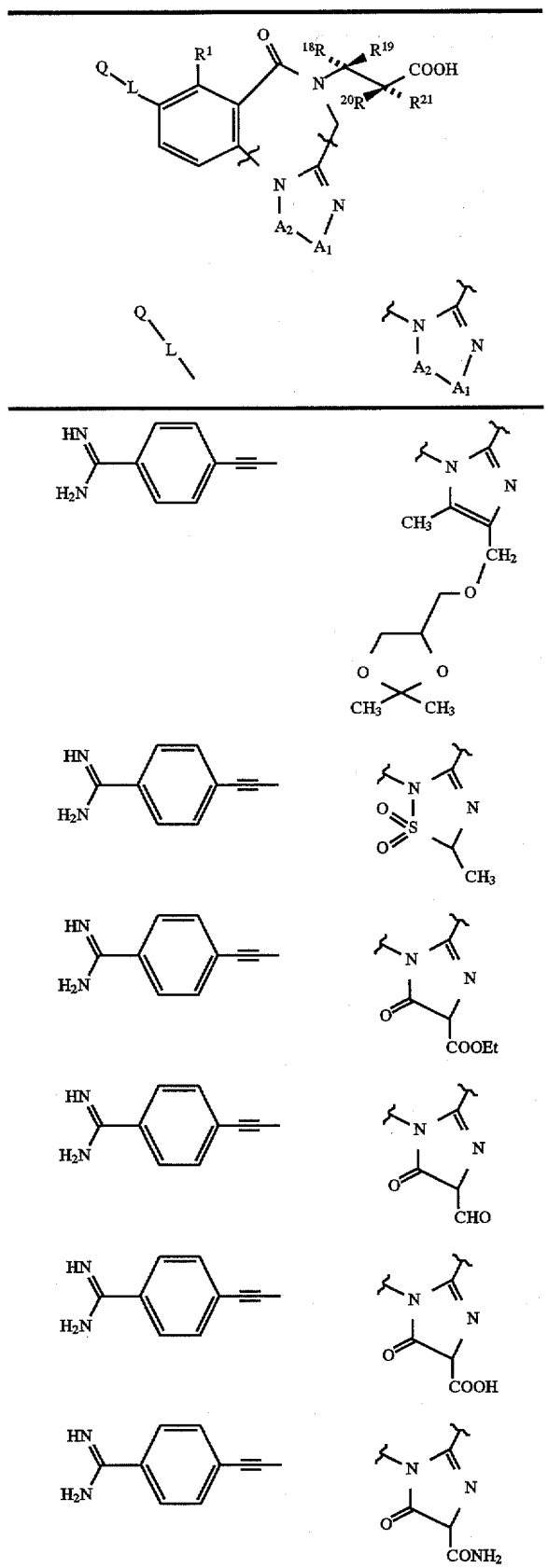
TABLE I-continued
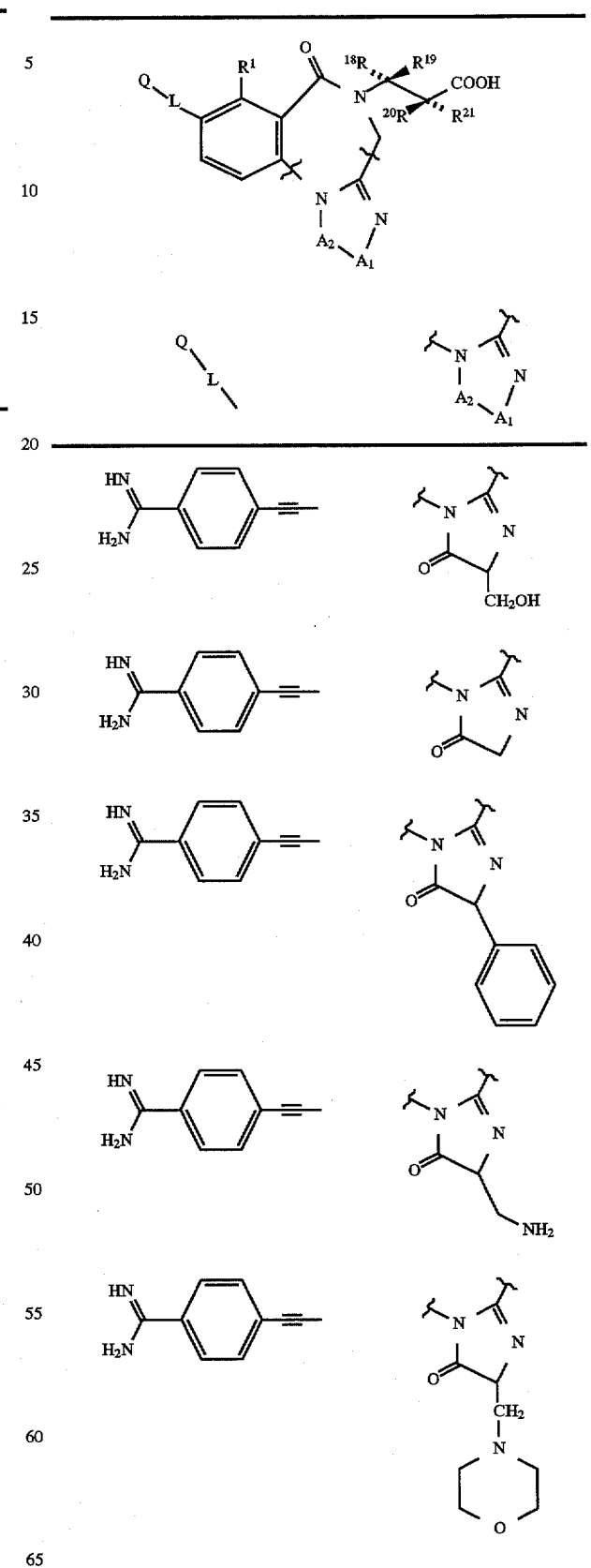

TABLE I-continued
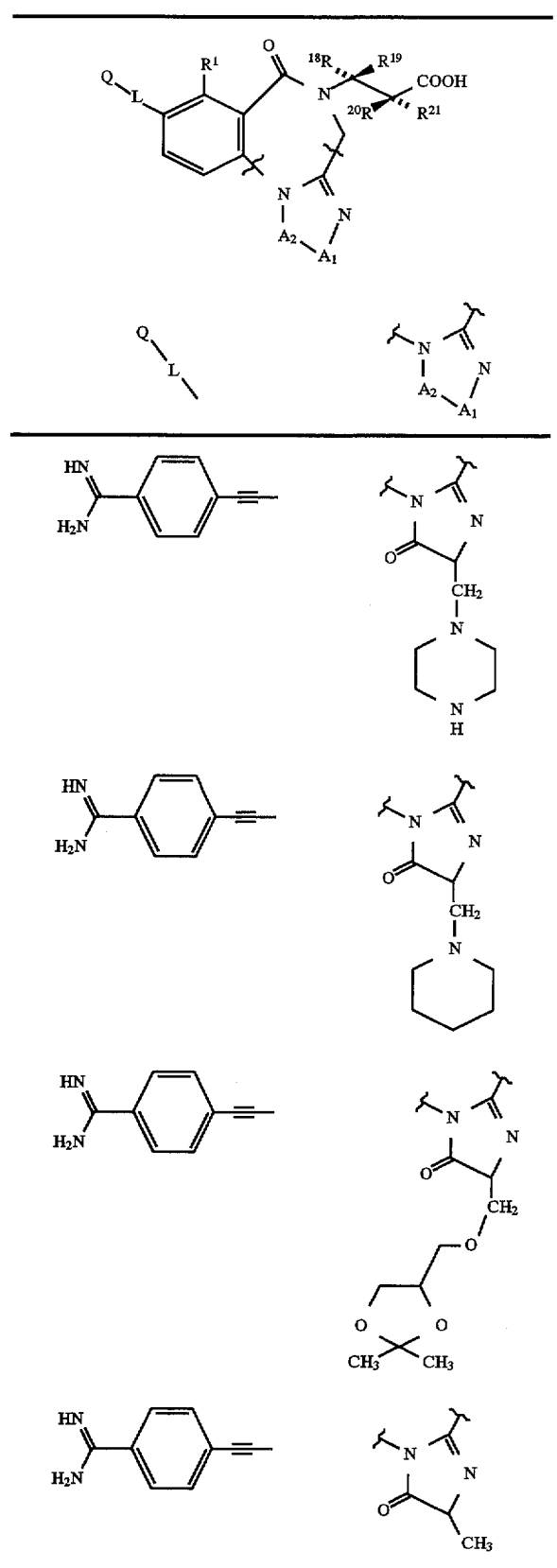
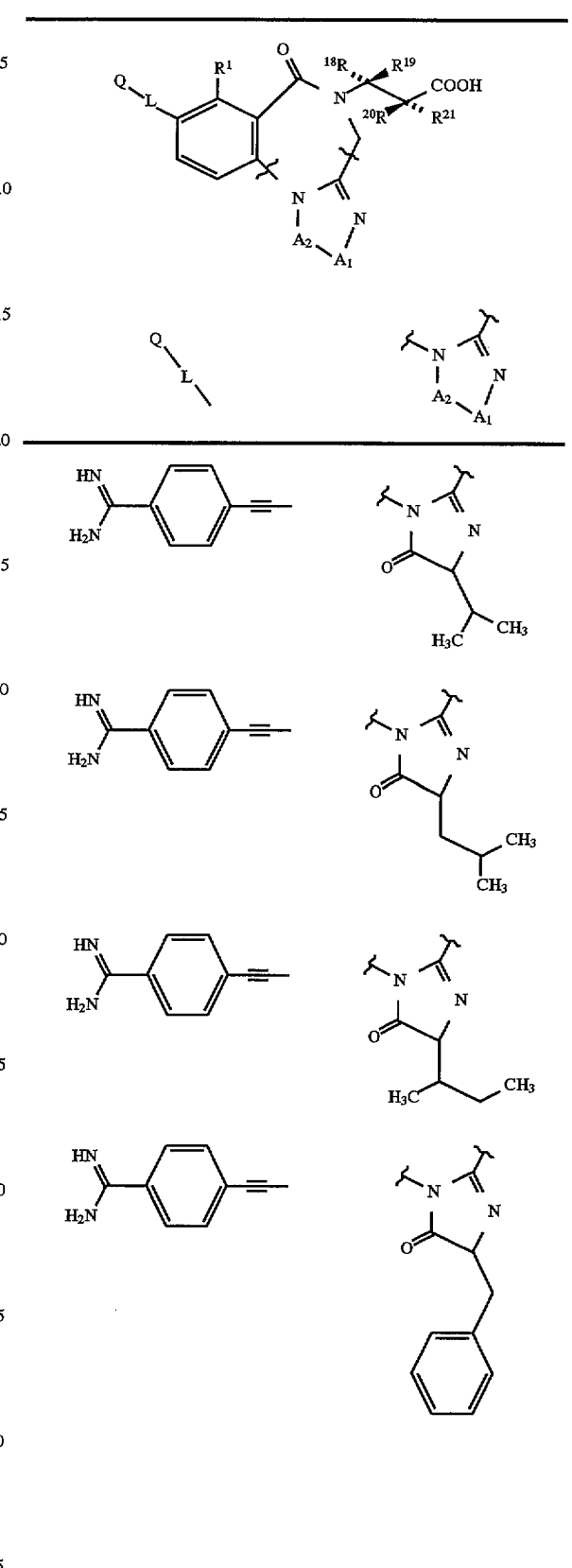

TABLE I-continued
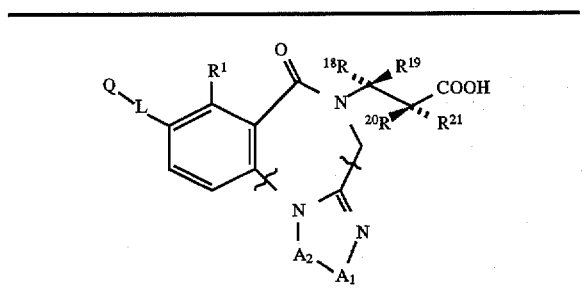
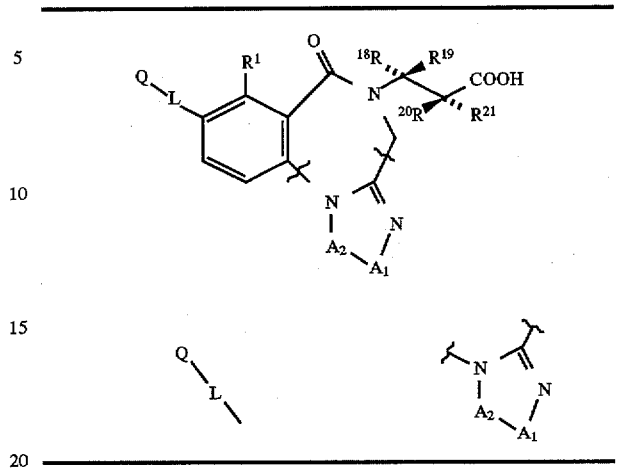
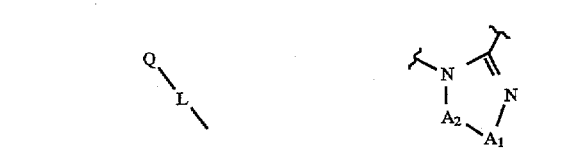
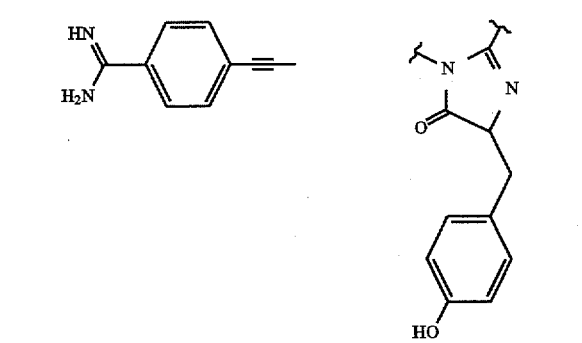
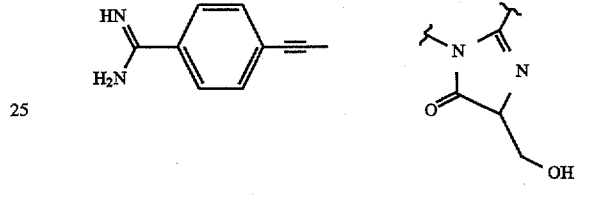
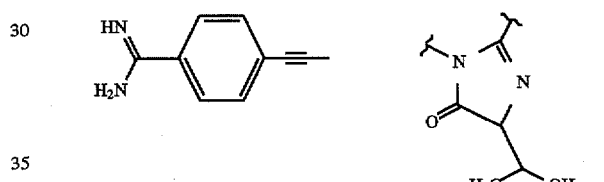
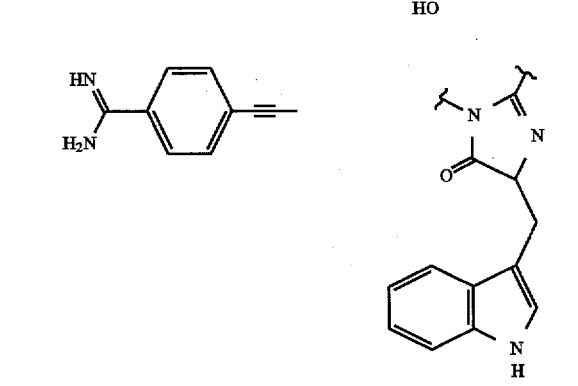
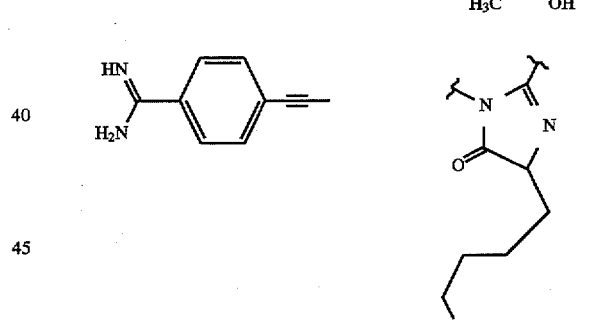
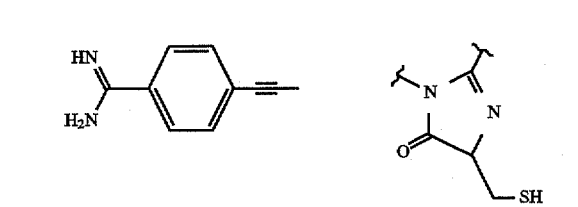
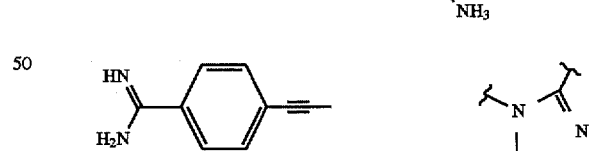
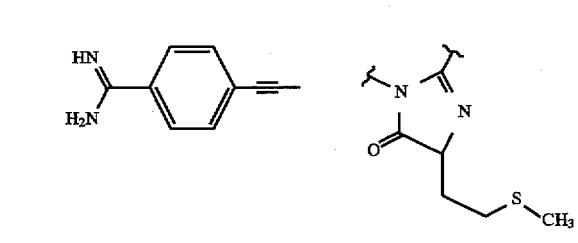
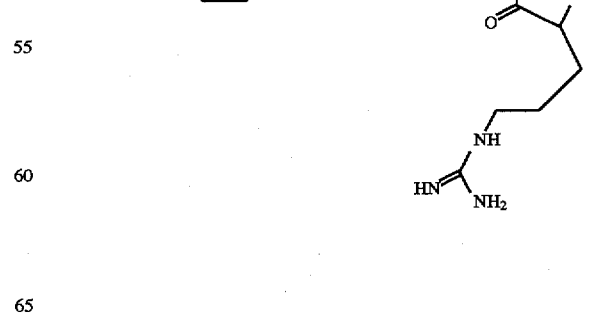

TABLE I-continued
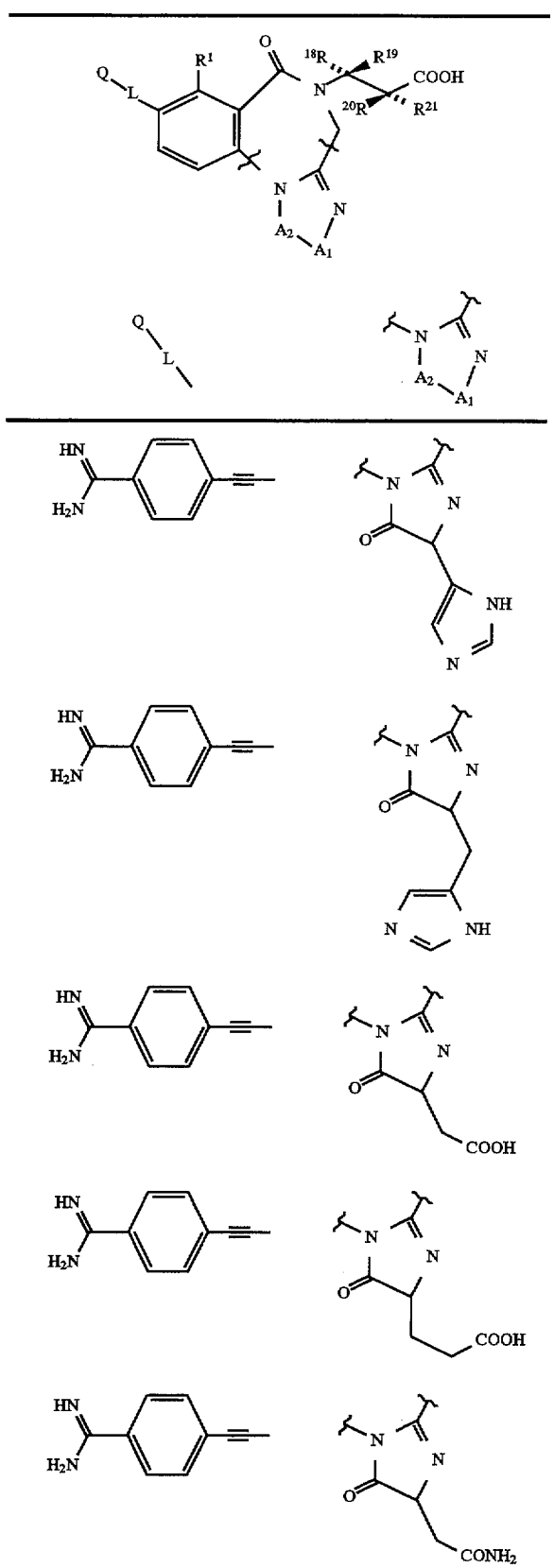
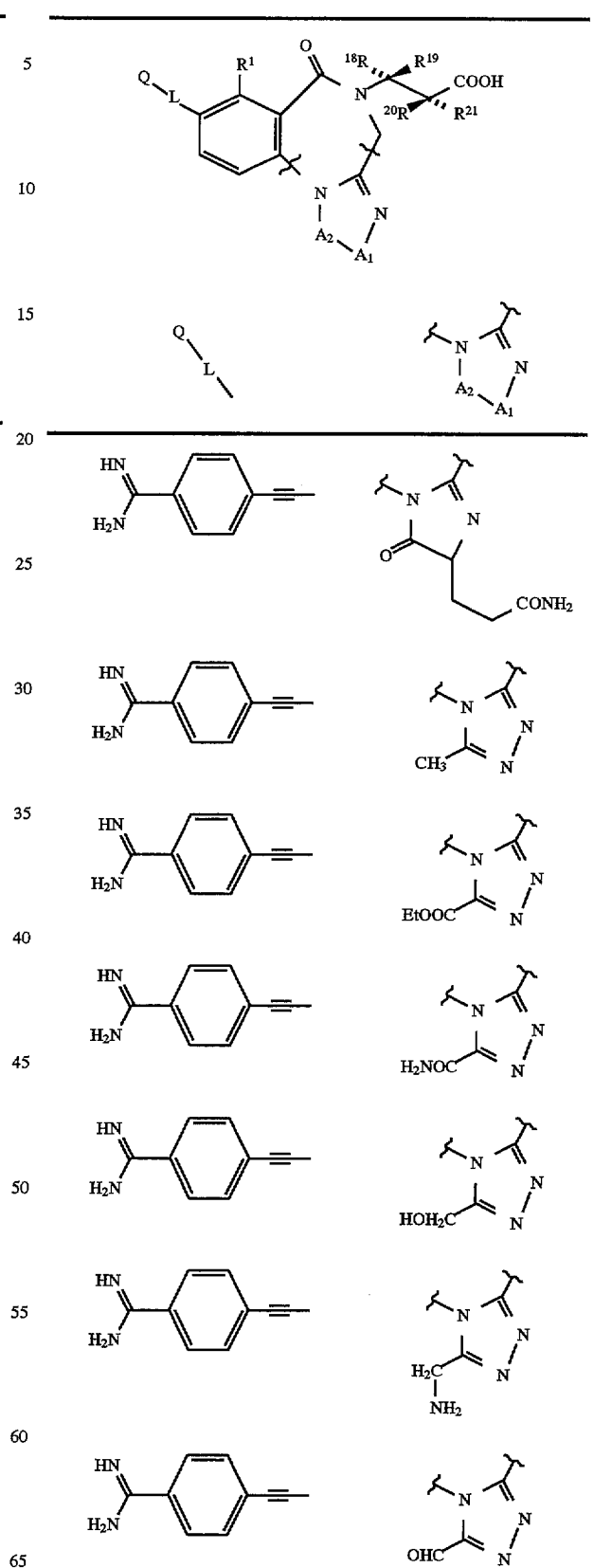

TABLE I-continued
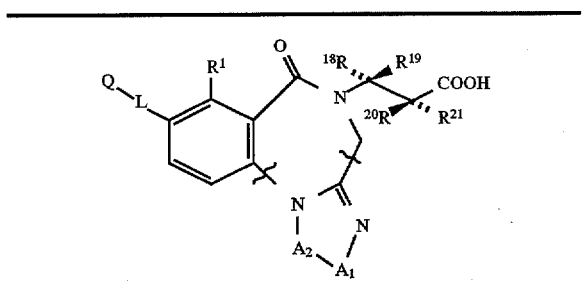
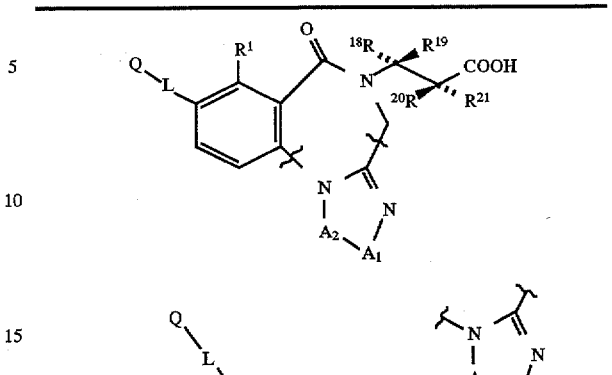
| Q-L- | |
|---|---|
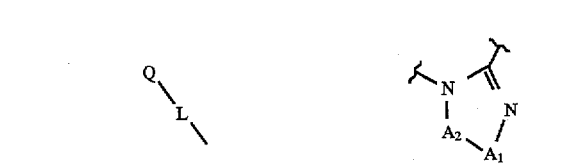
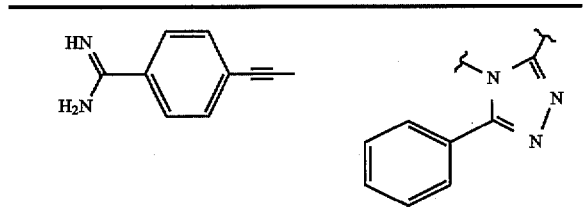
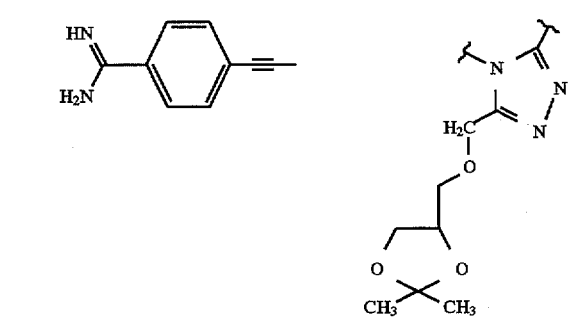
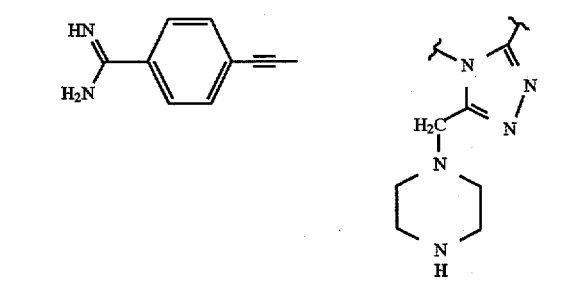
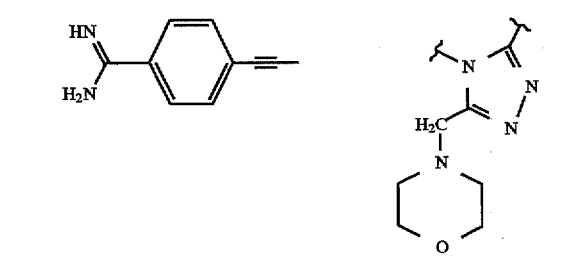
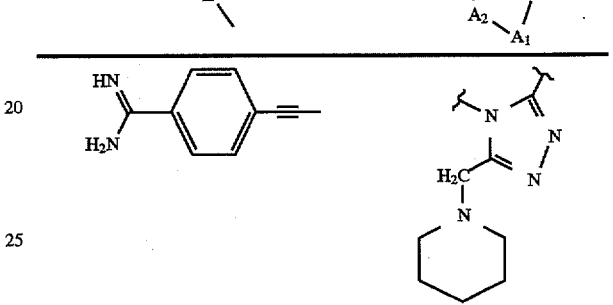
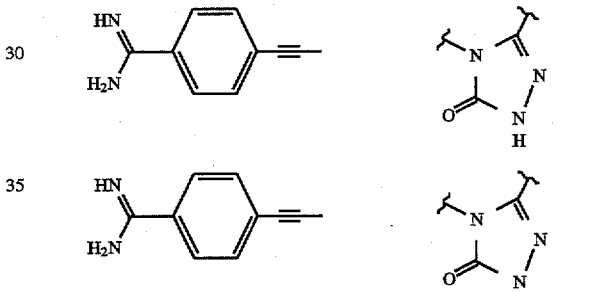
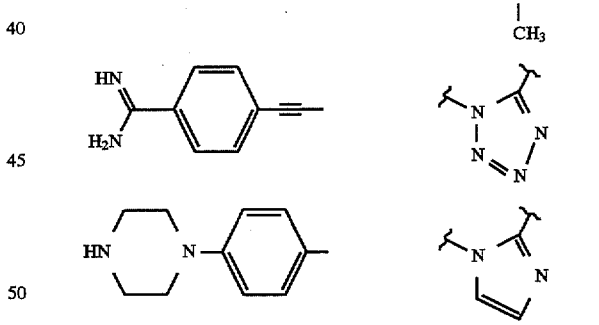
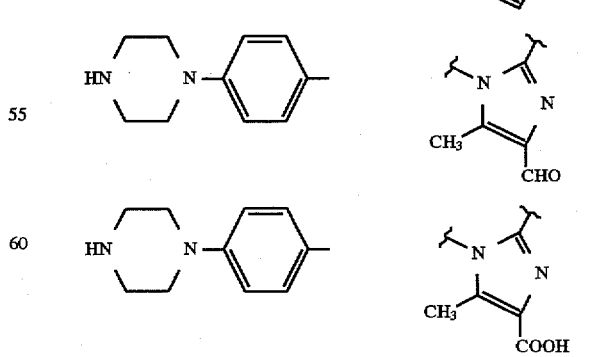

TABLE I-continued
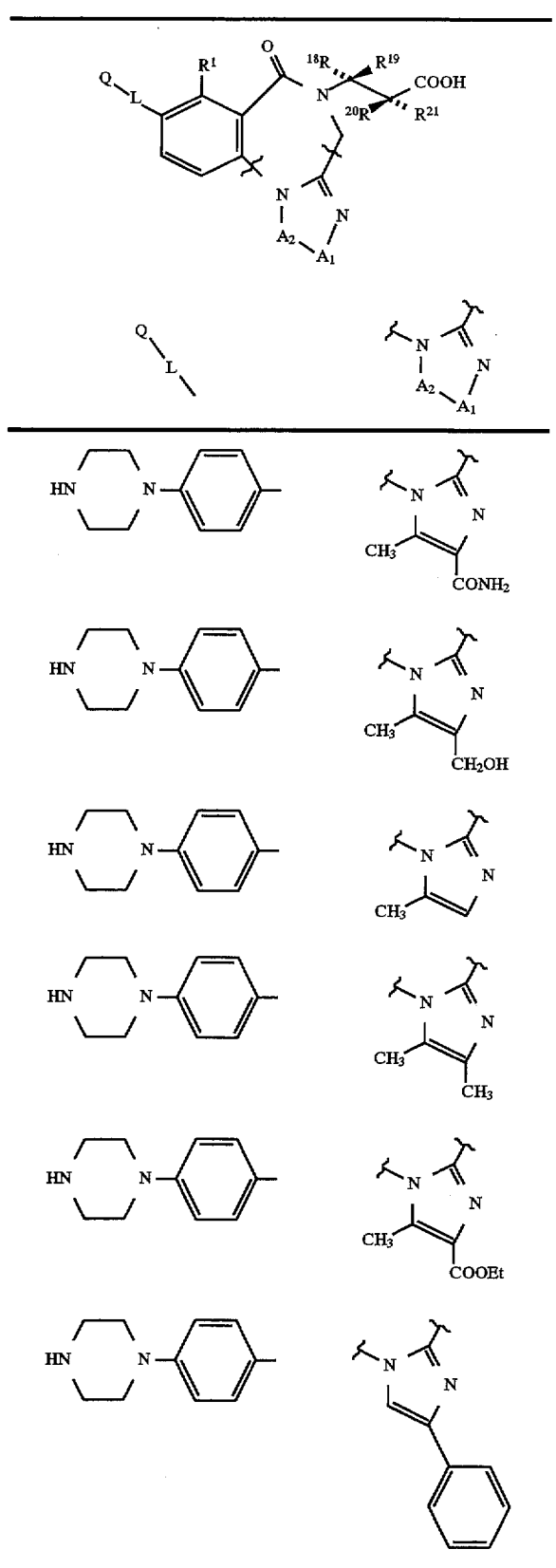
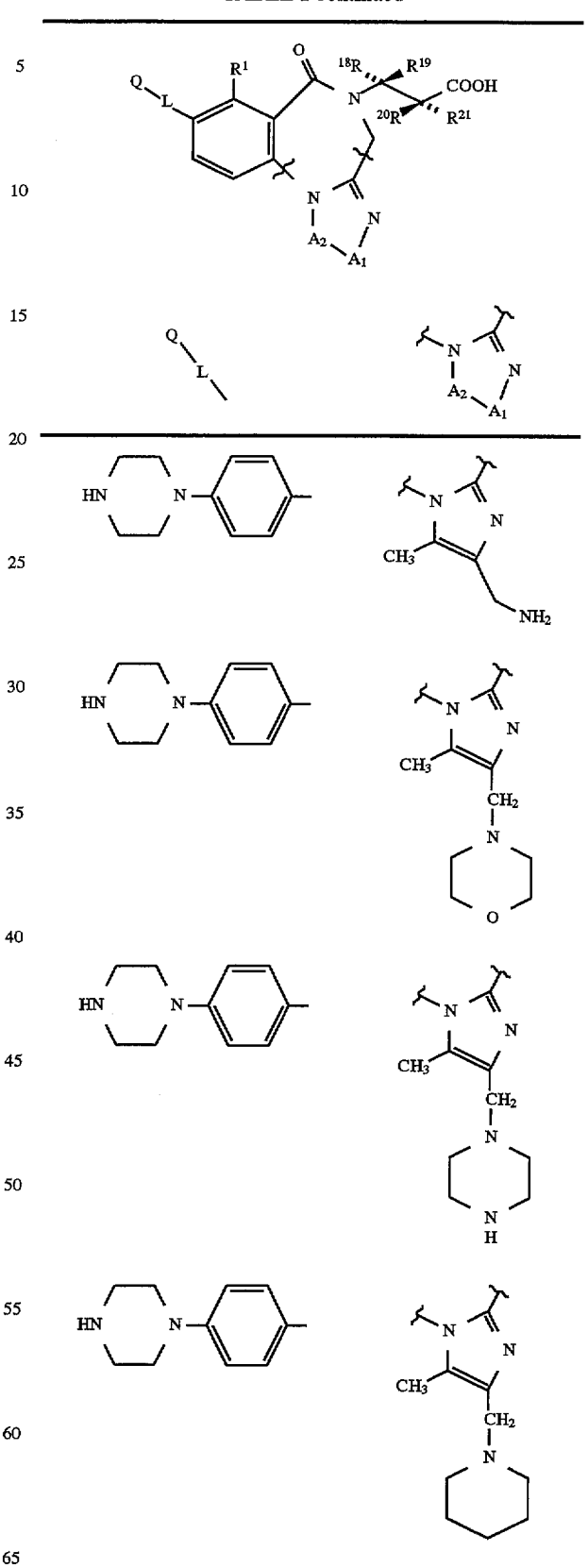

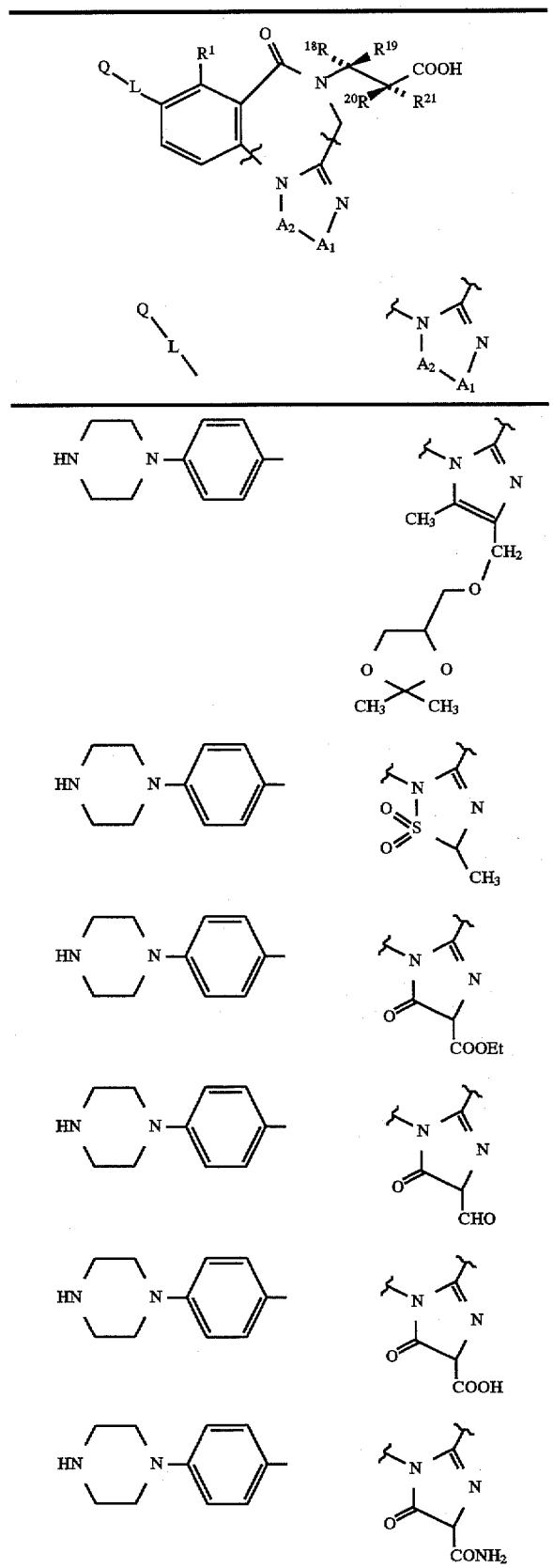

TABLE I-continued
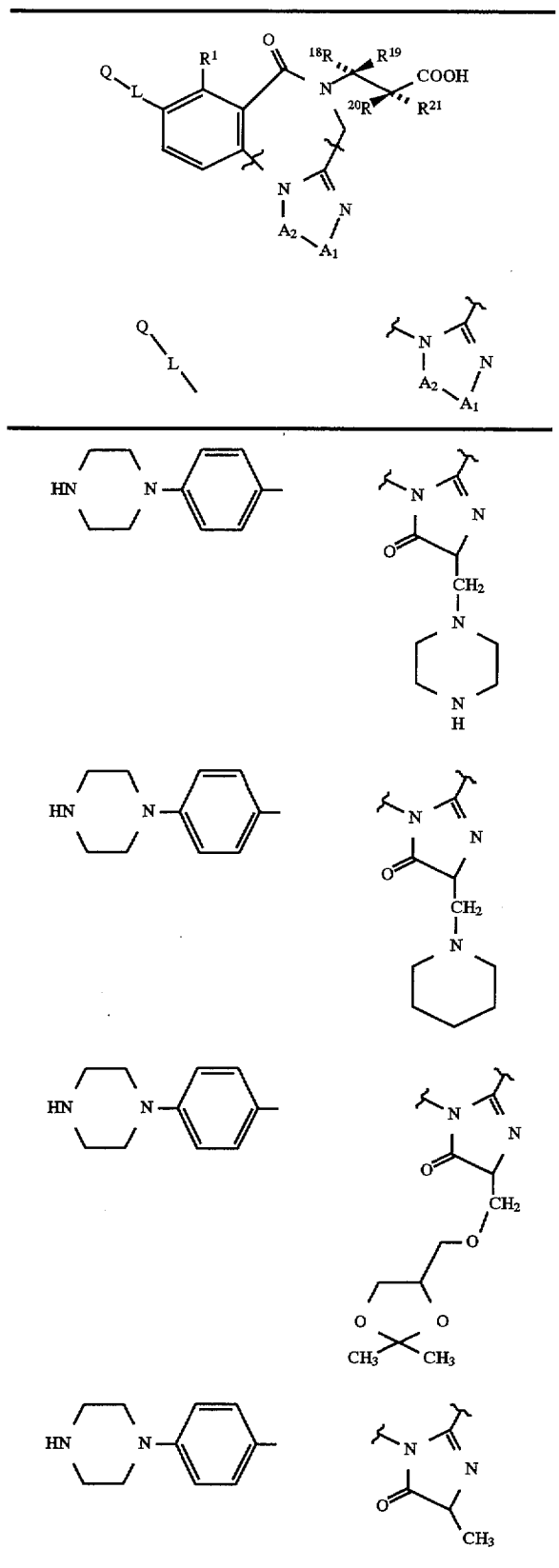
TABLE I-continued
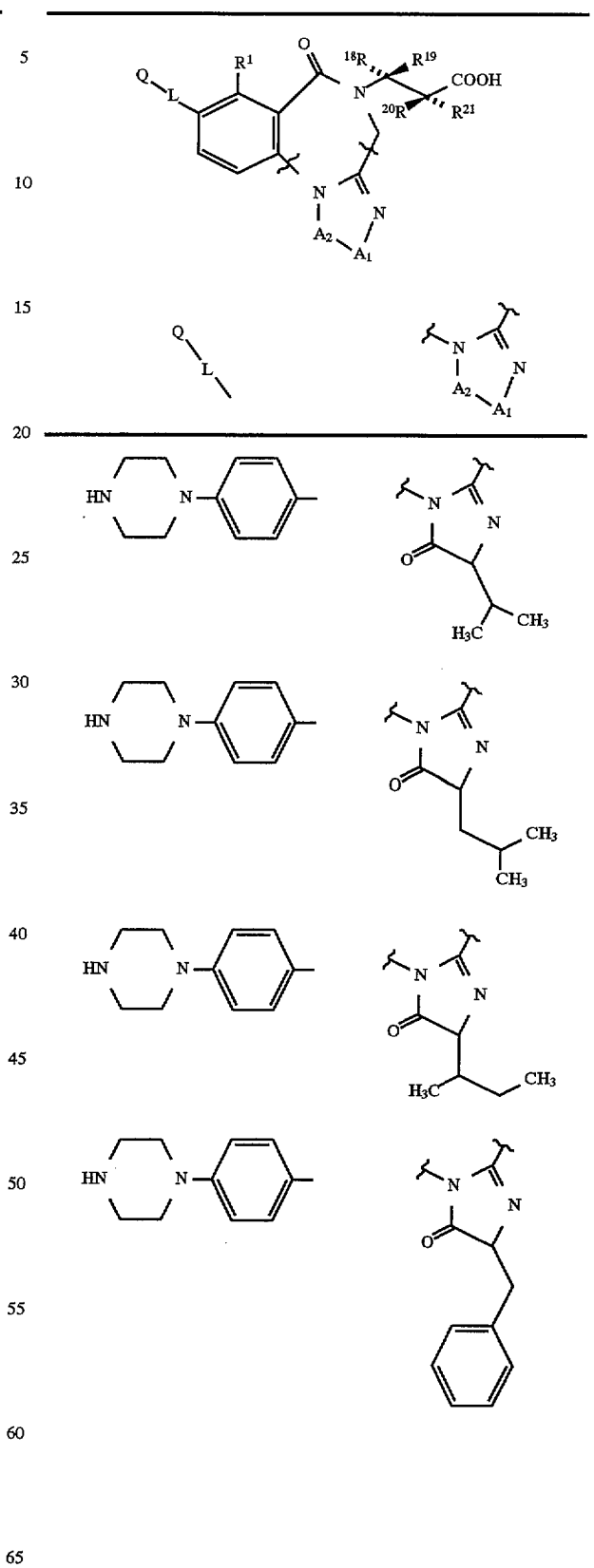

TABLE I-continued
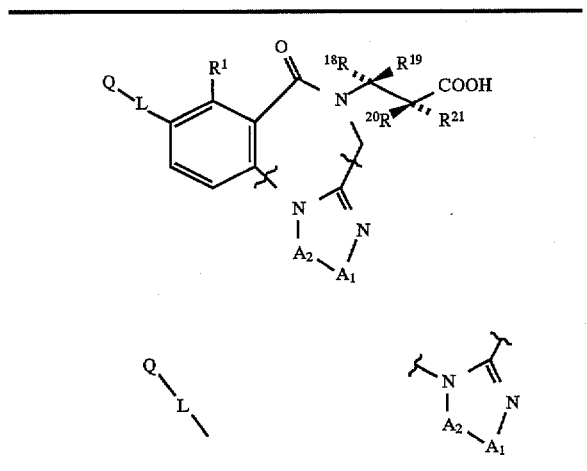
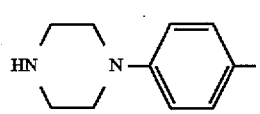 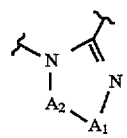
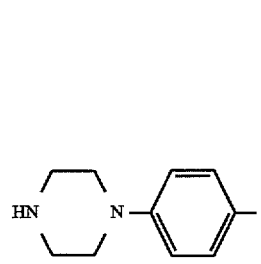 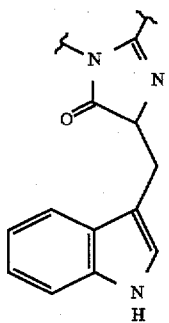
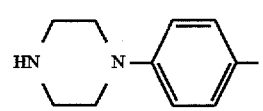 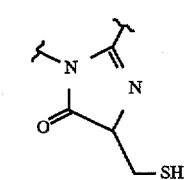
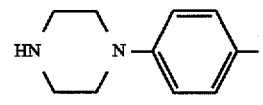 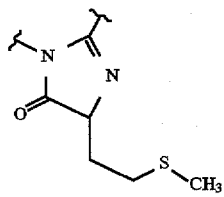
TABLE I-continued
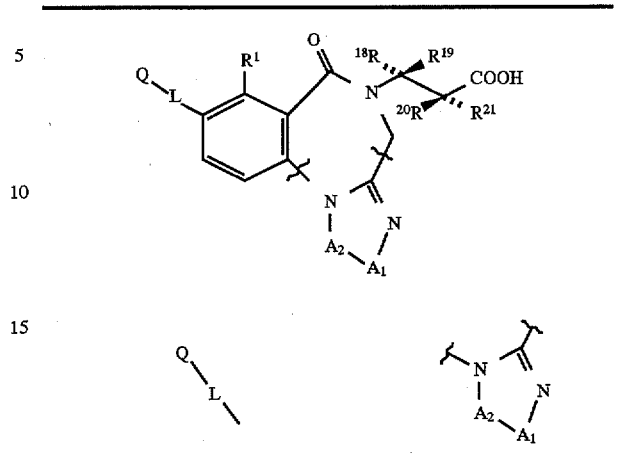
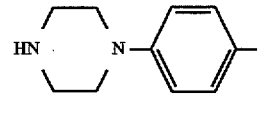 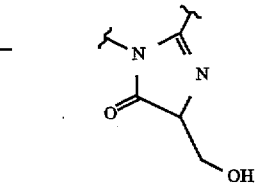
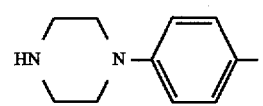 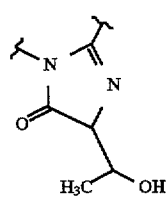
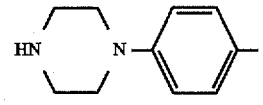 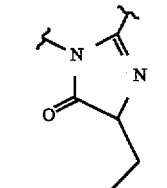
 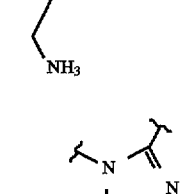
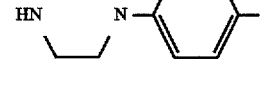 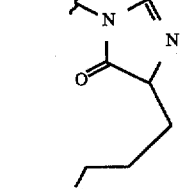
 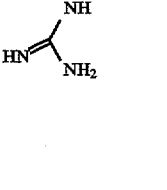

TABLE I-continued
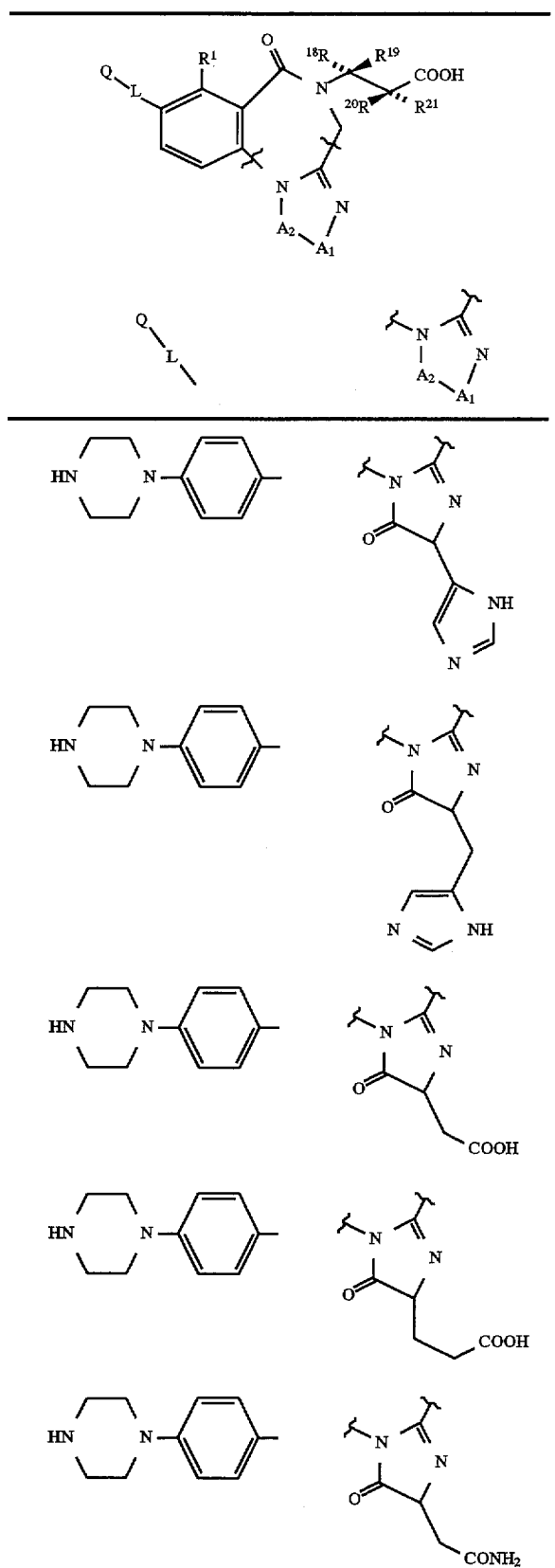
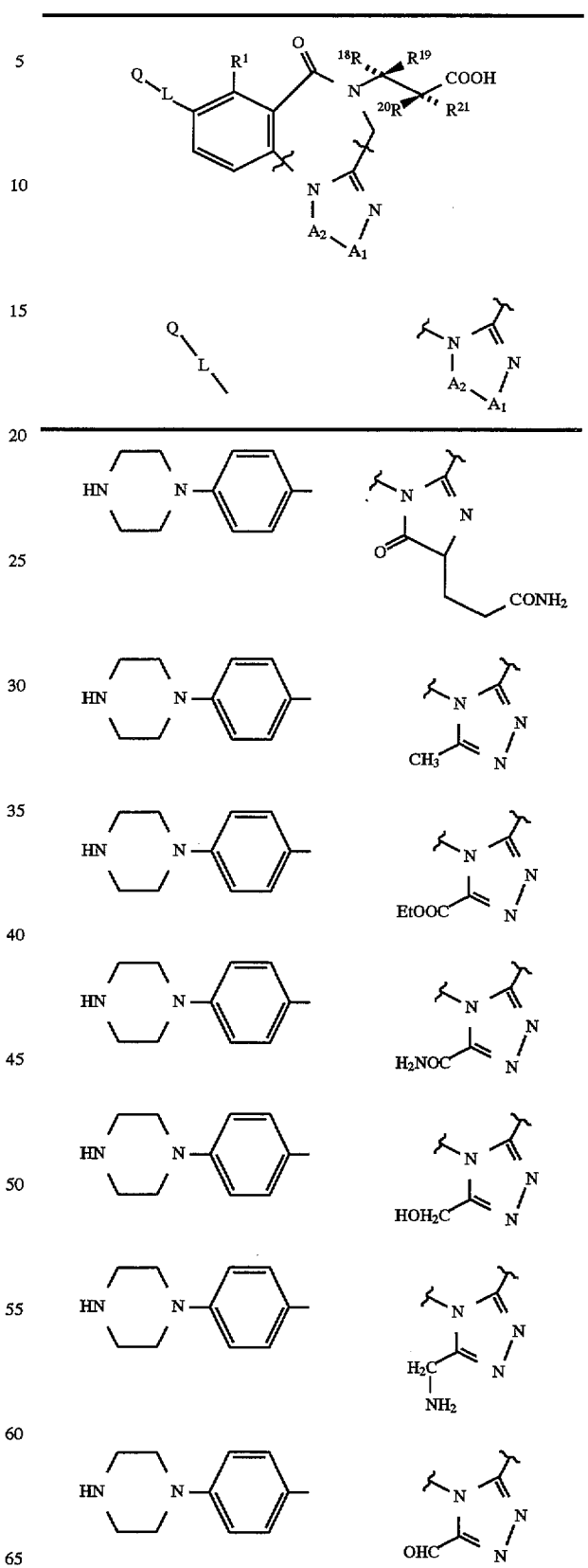

TABLE I-continued
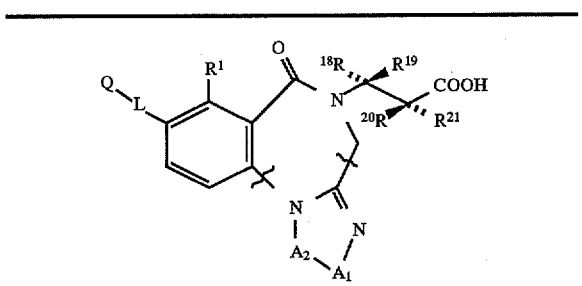
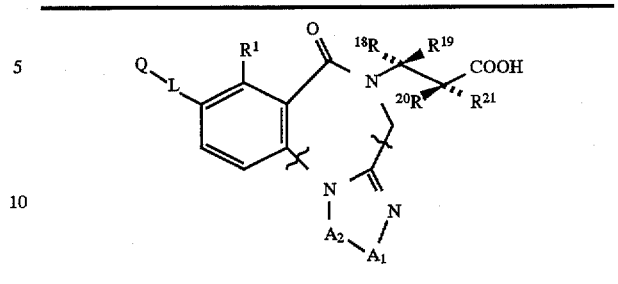
| Q-L- | |
|---|---|
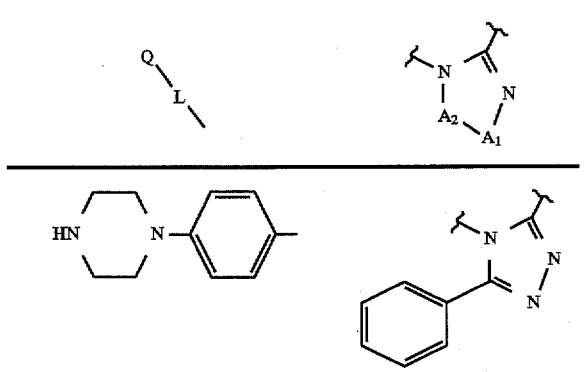
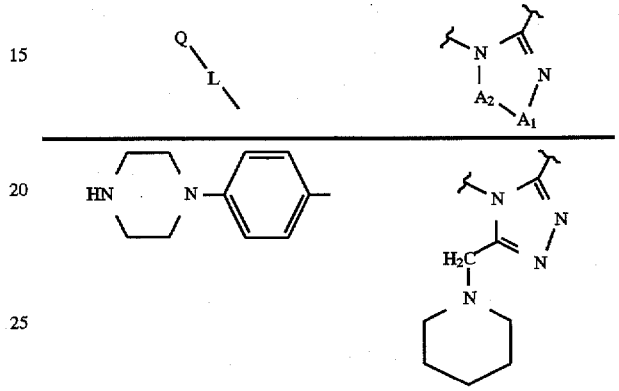
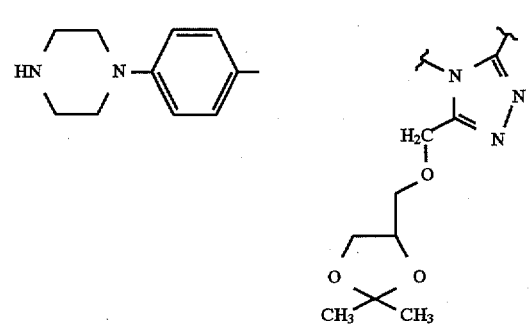
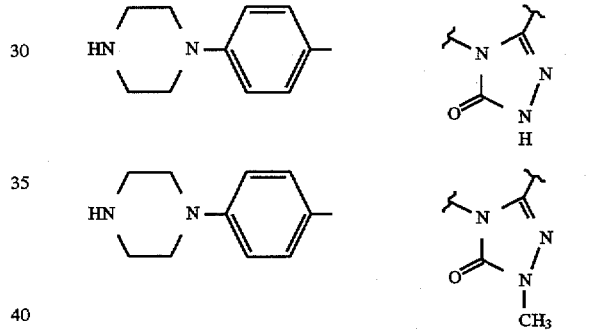
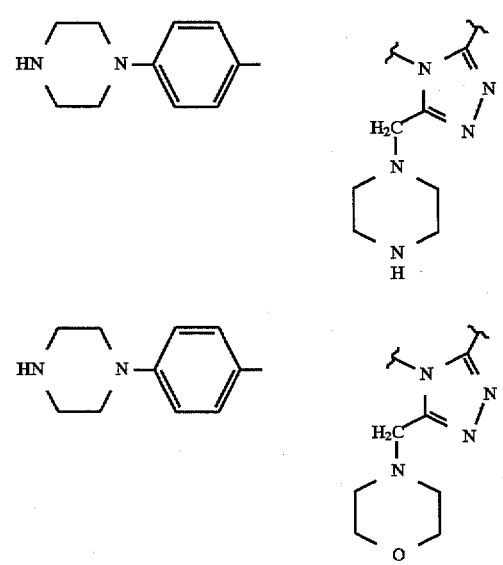
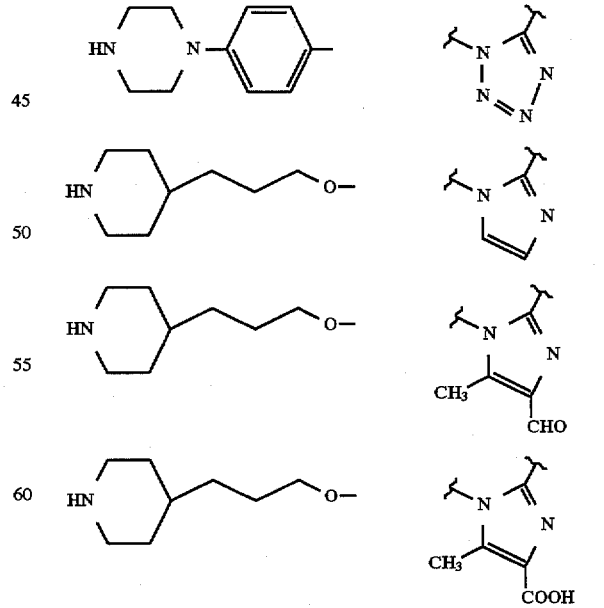

TABLE I-continued
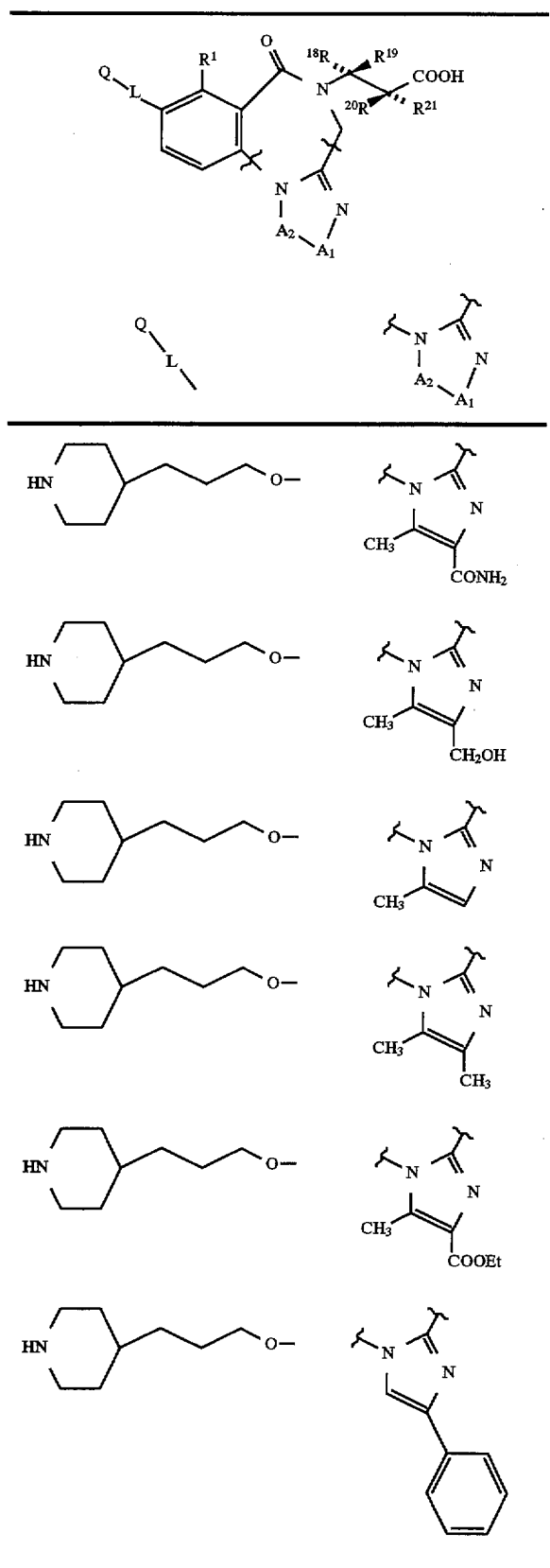
TABLE I-continued
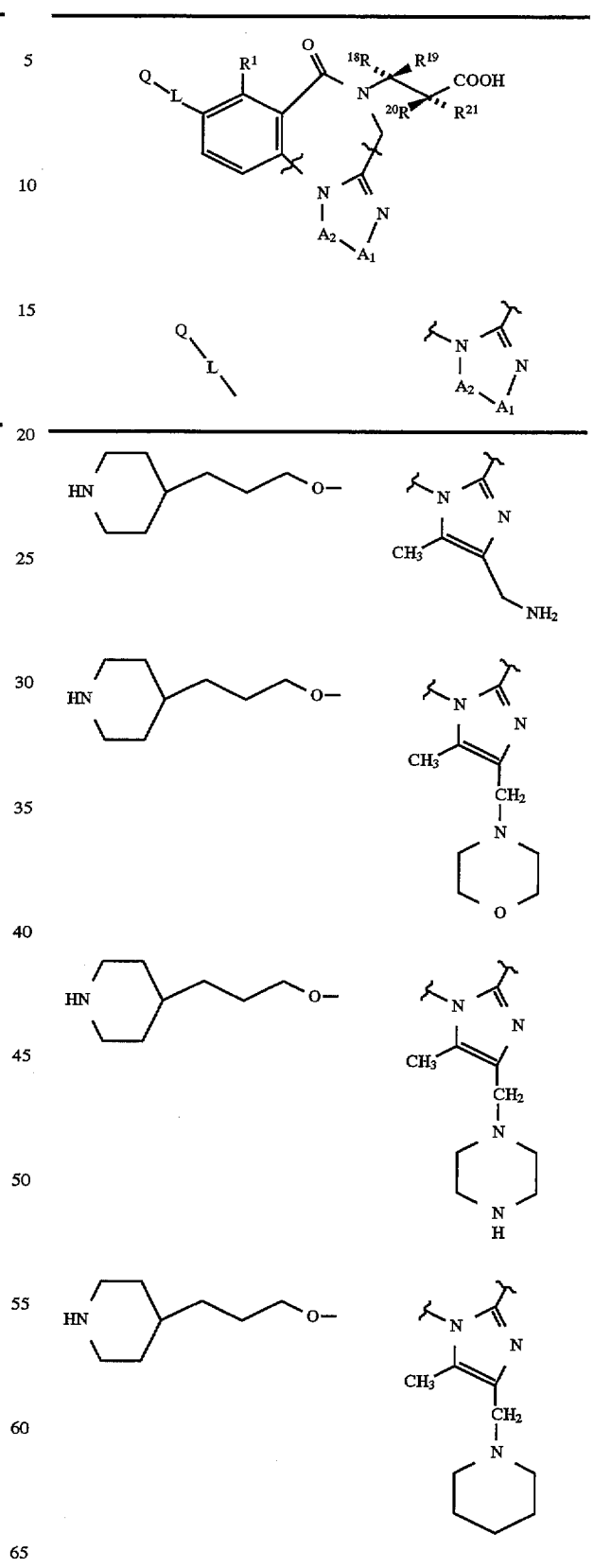

TABLE I-continued
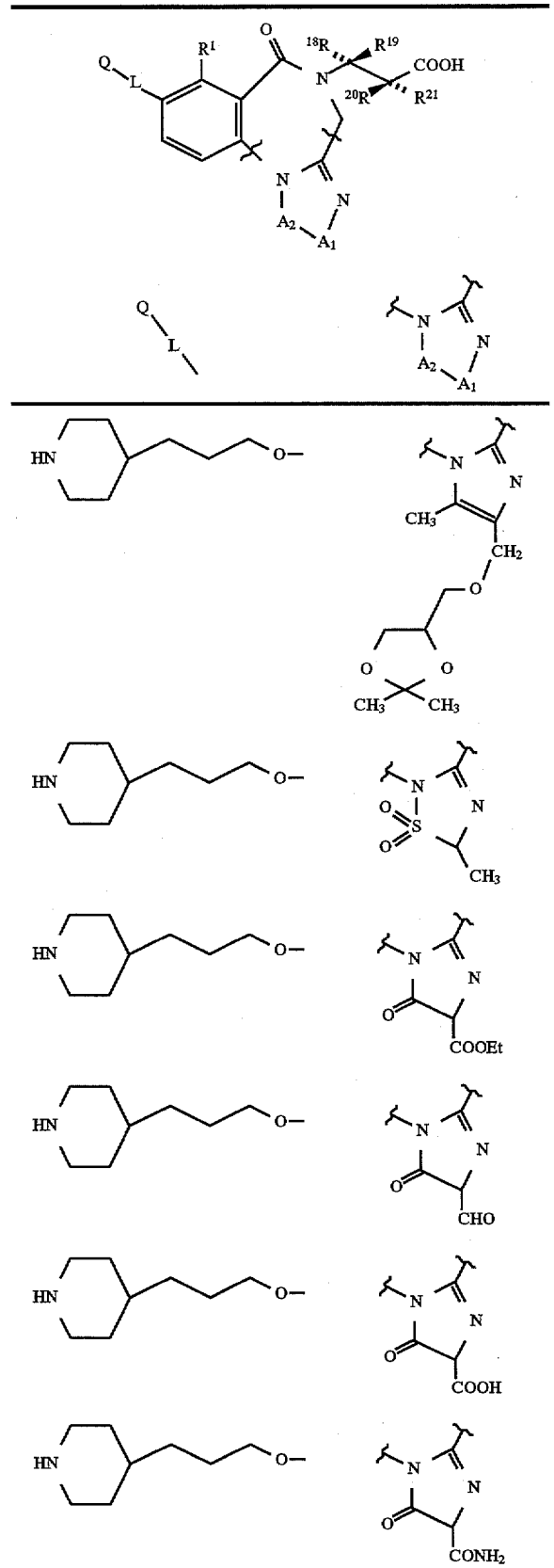
TABLE I-continued
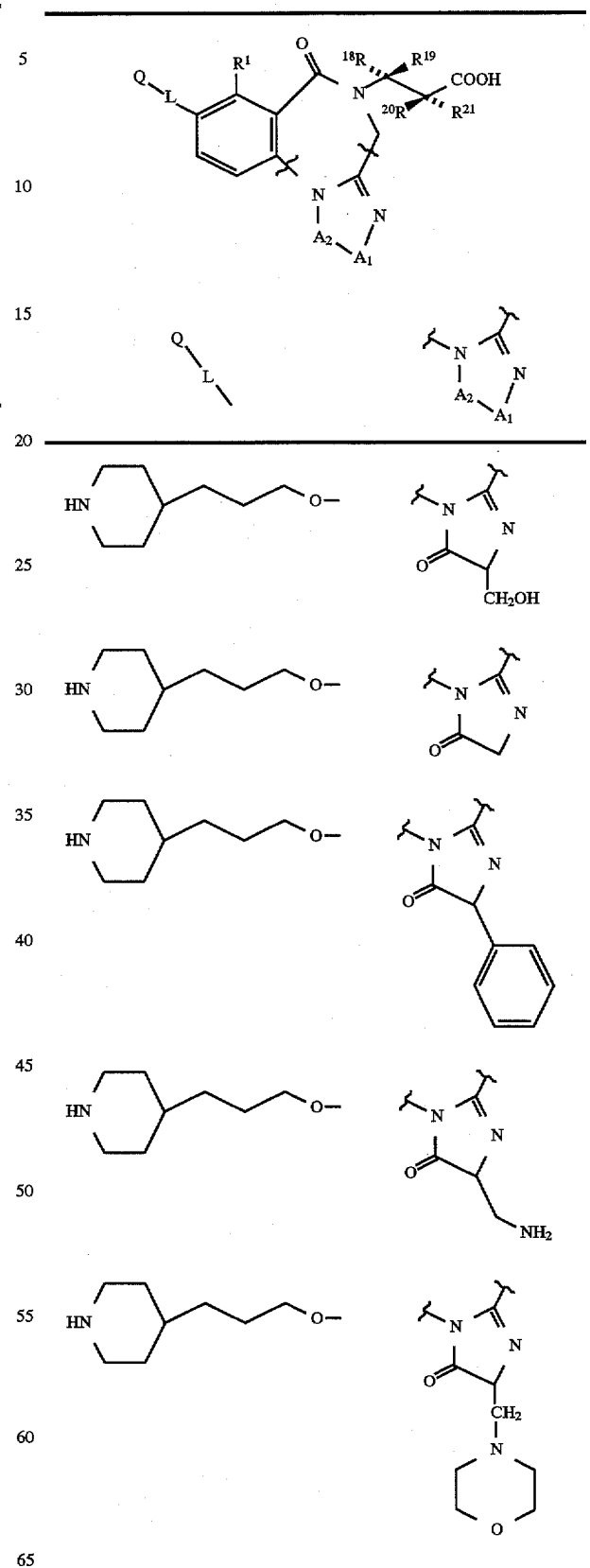

TABLE I-continued
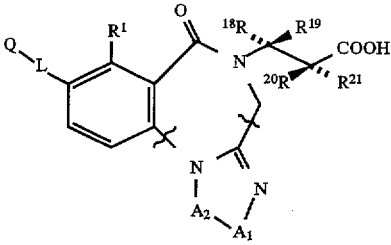

TABLE I-continued
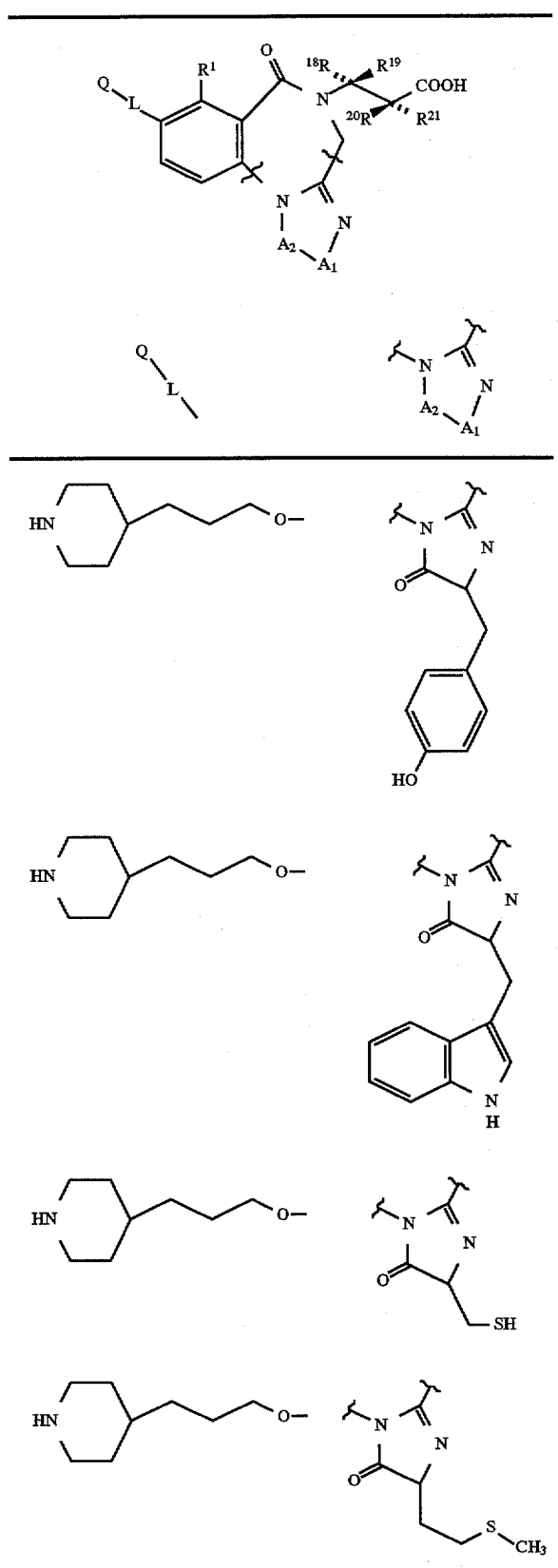
TABLE I-continued
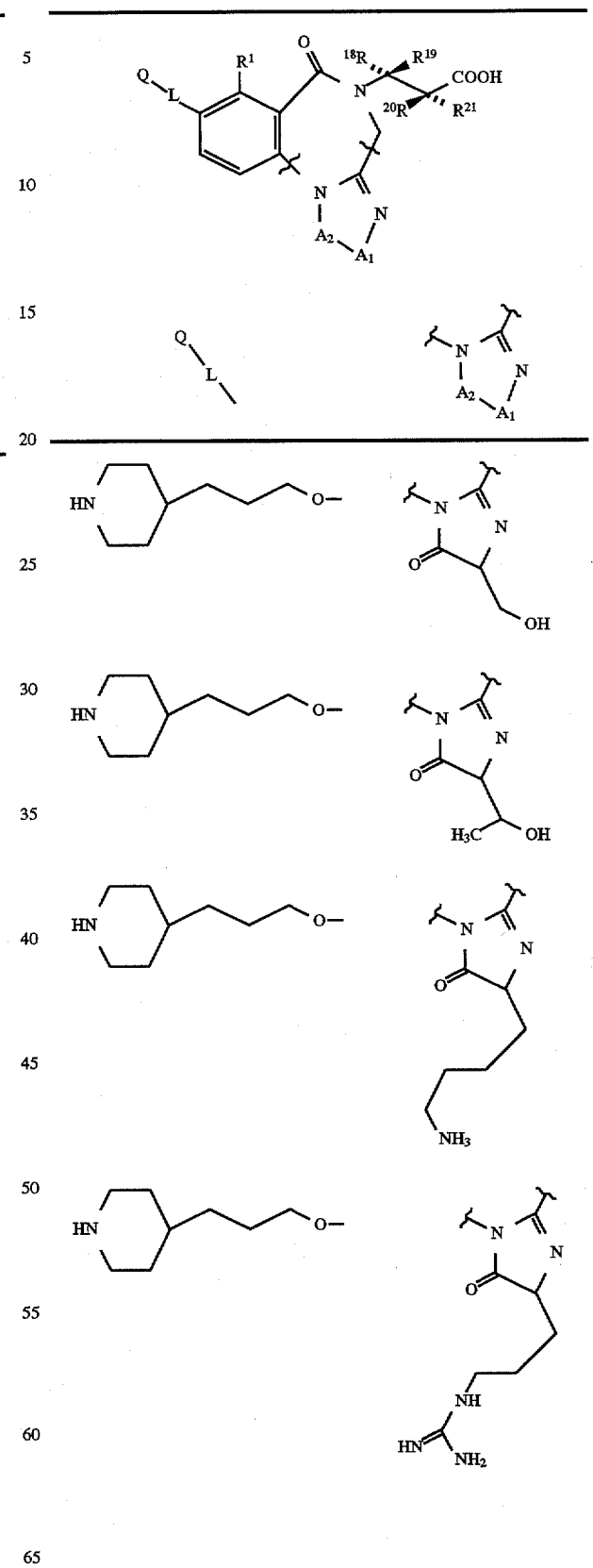

TABLE I-continued
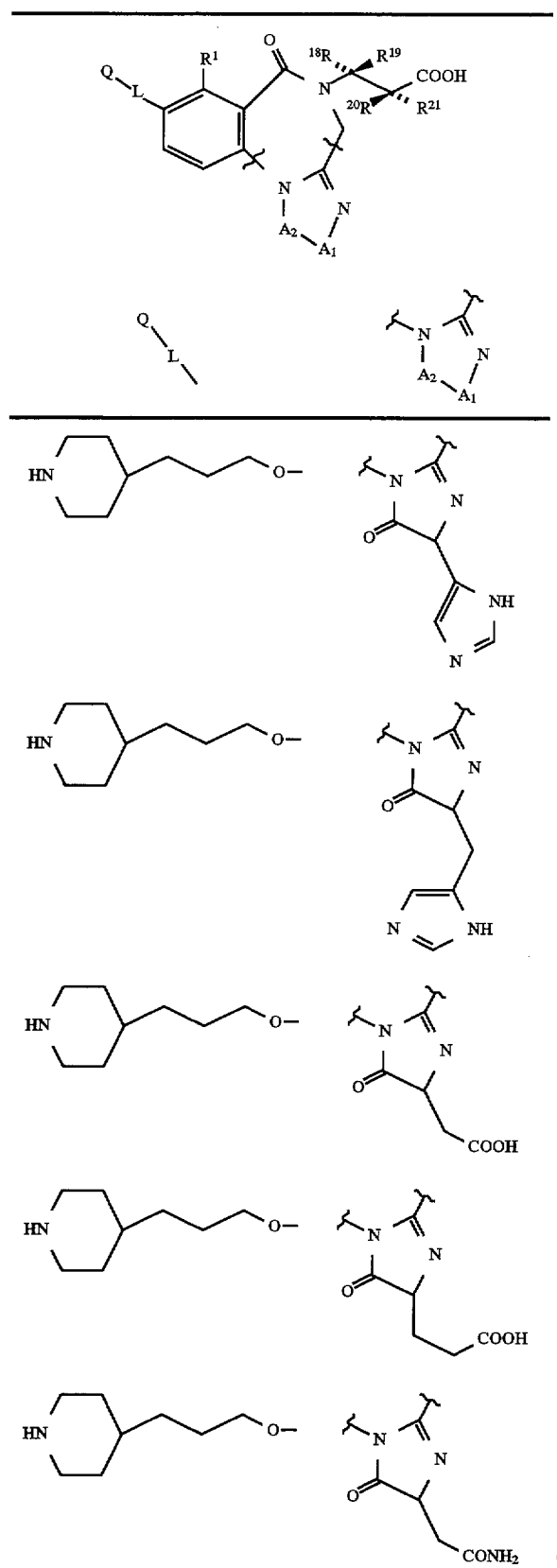
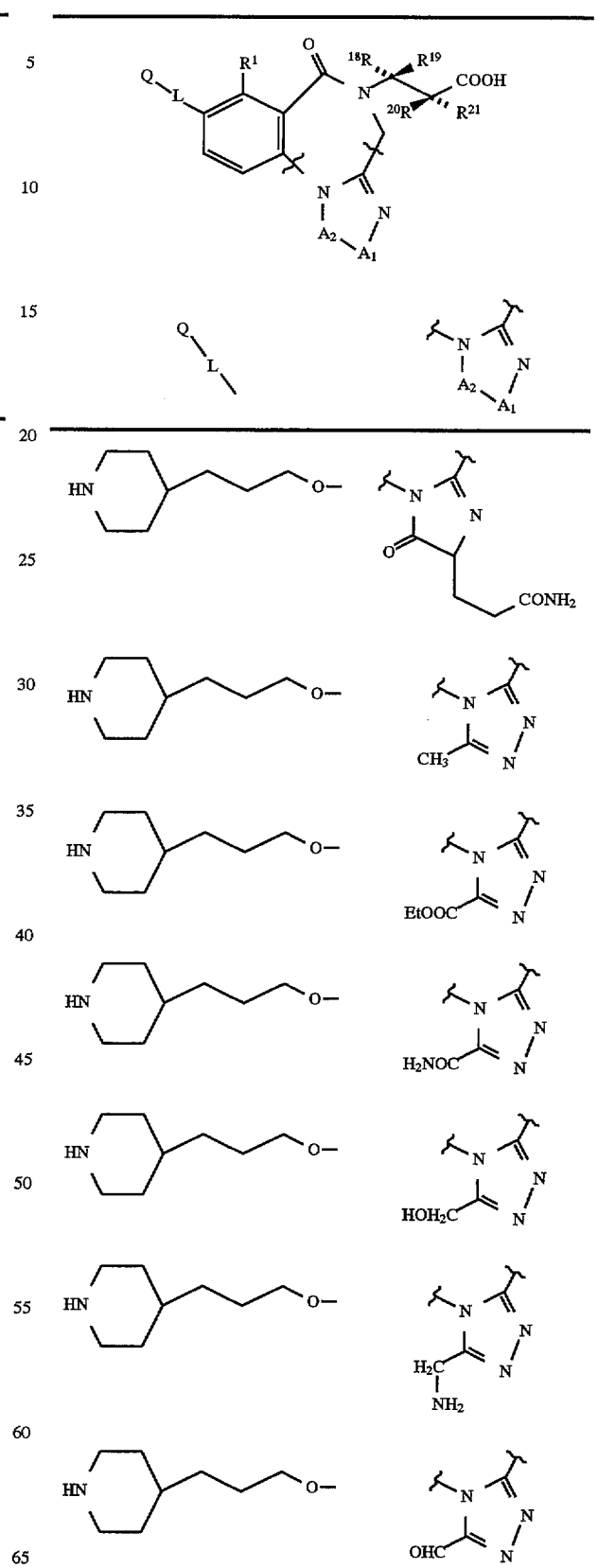

TABLE I-continued
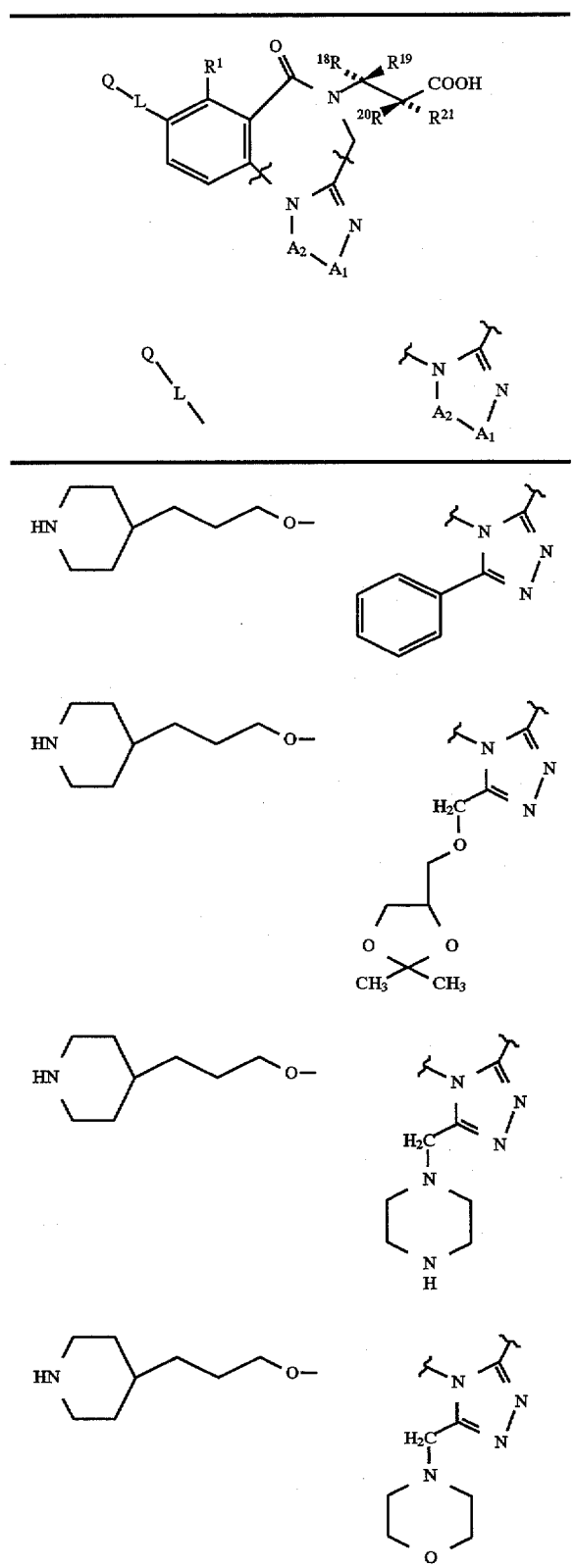
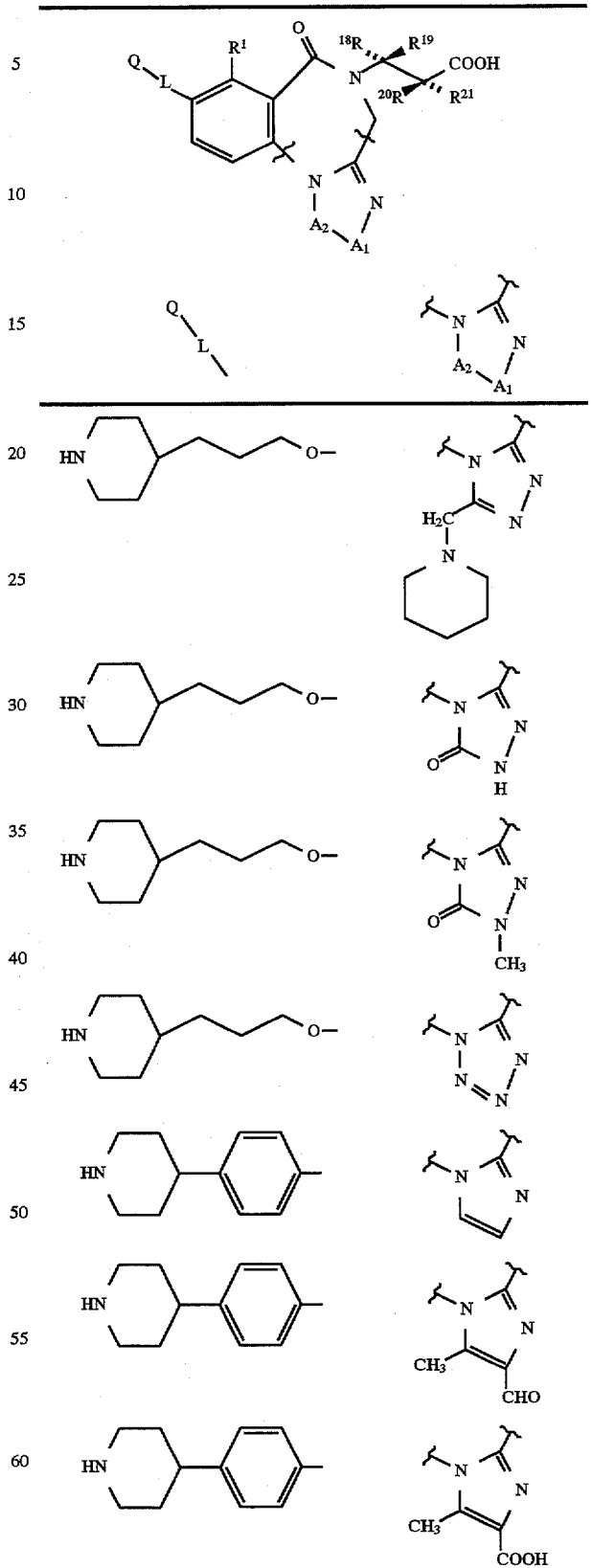

TABLE I-continued
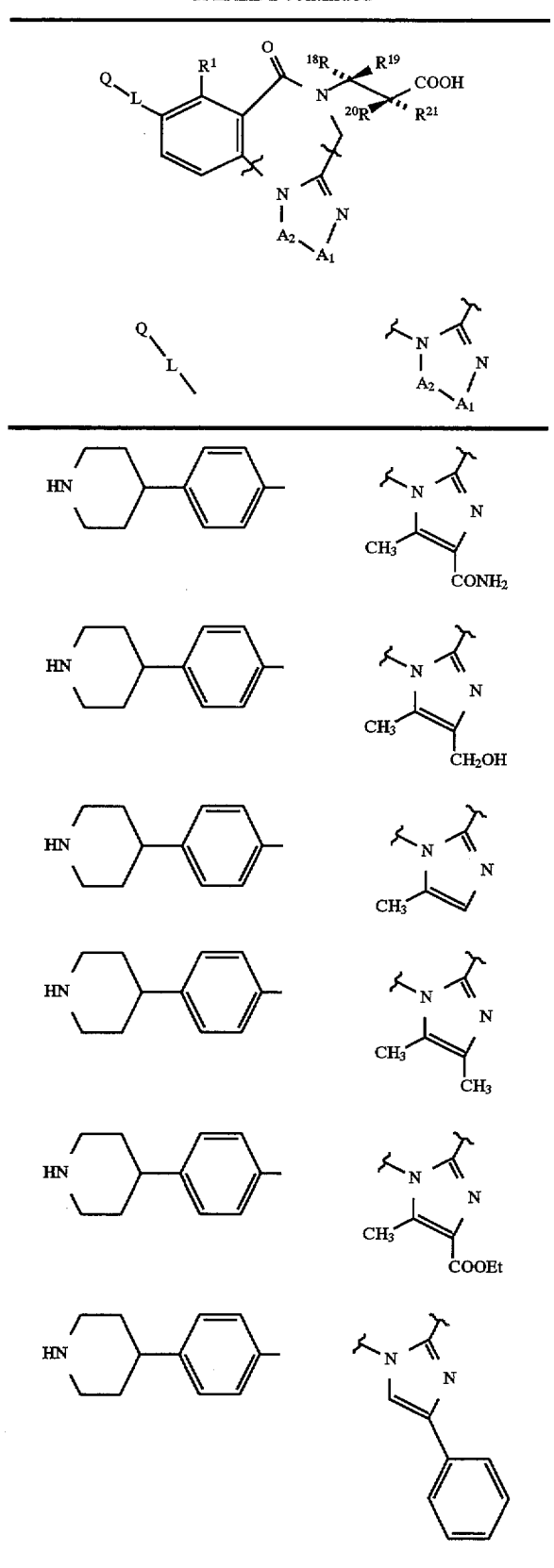
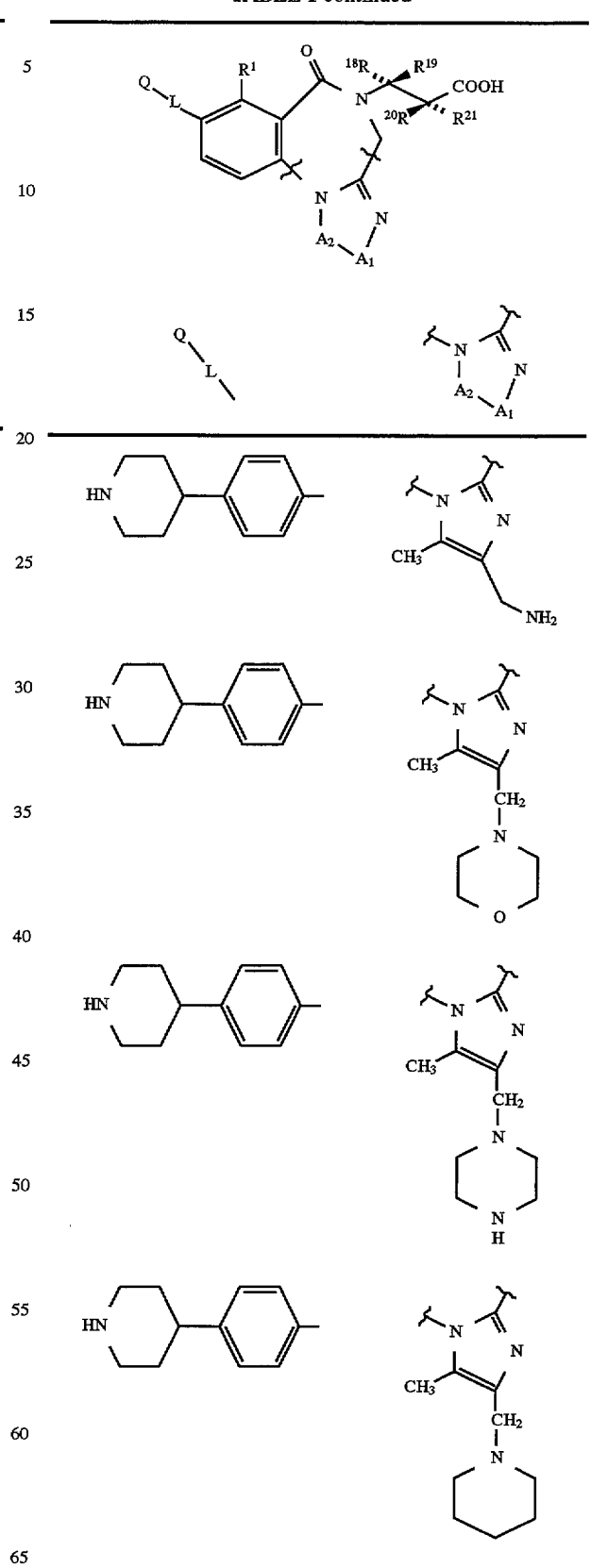

TABLE I-continued
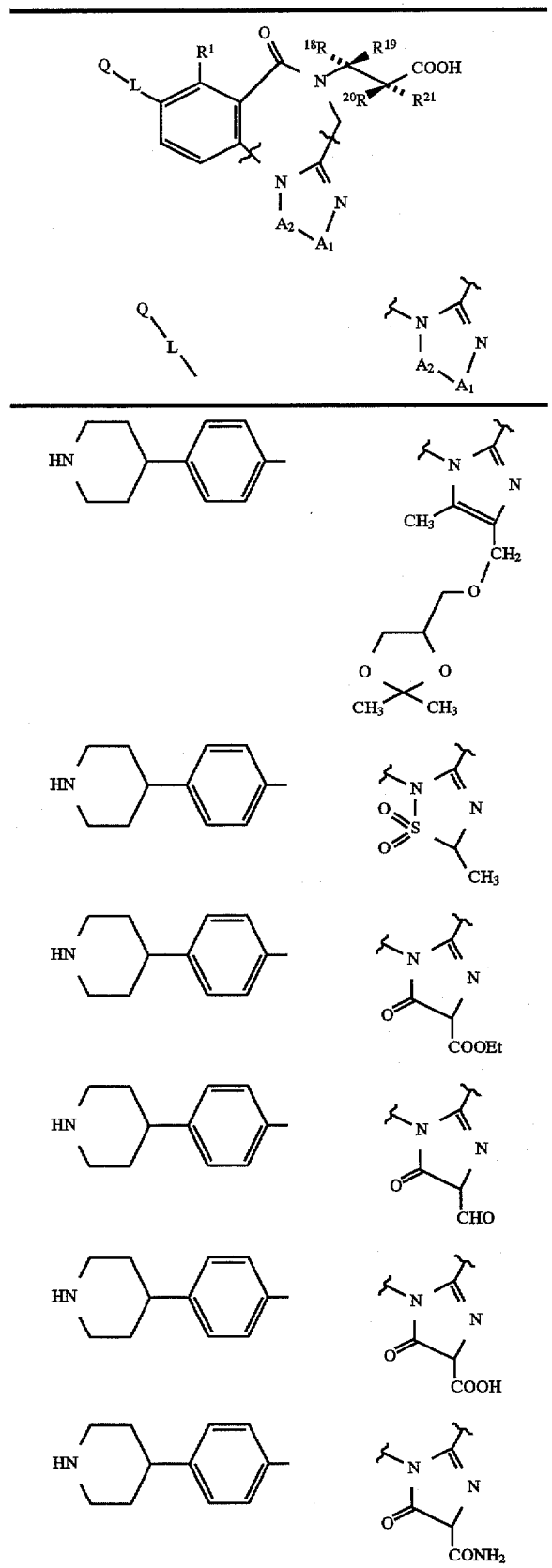
TABLE I-continued
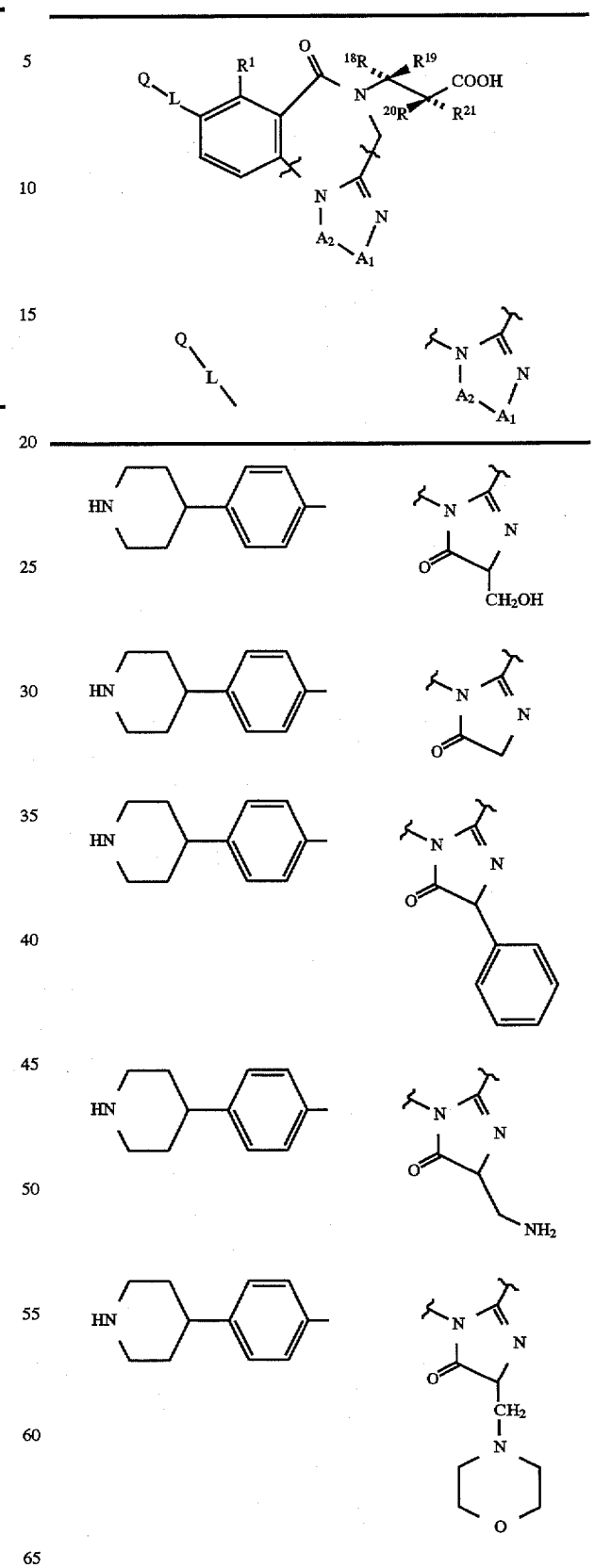

TABLE I-continued
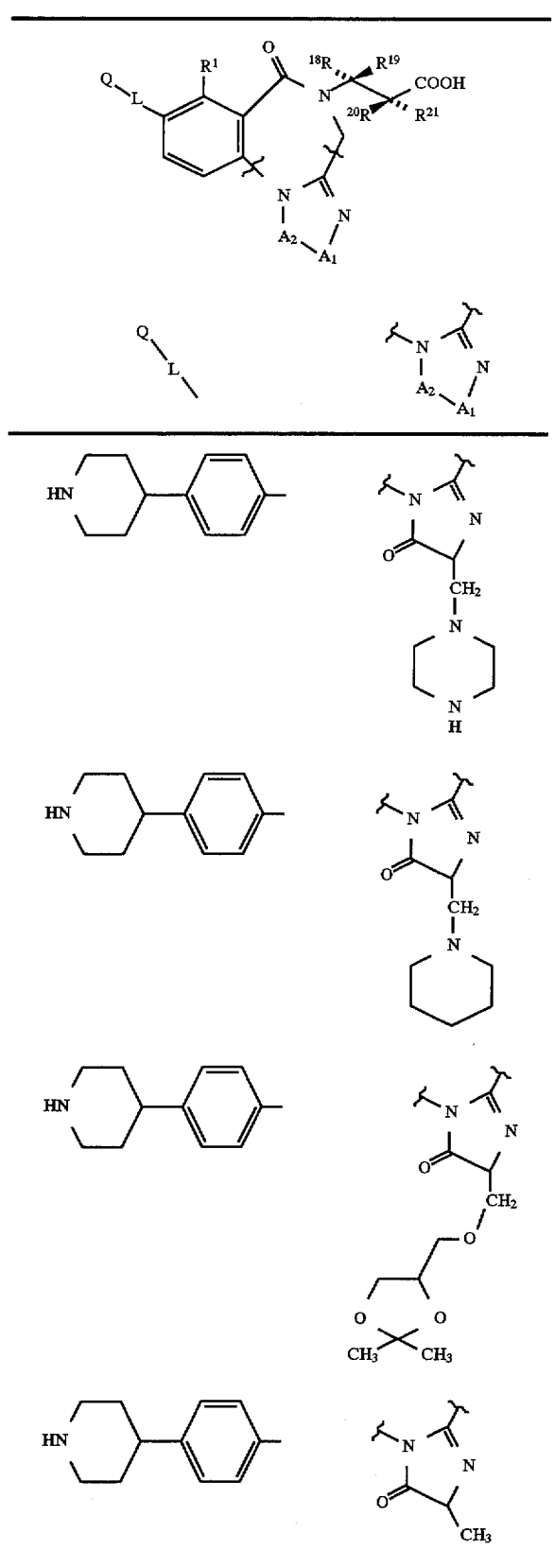
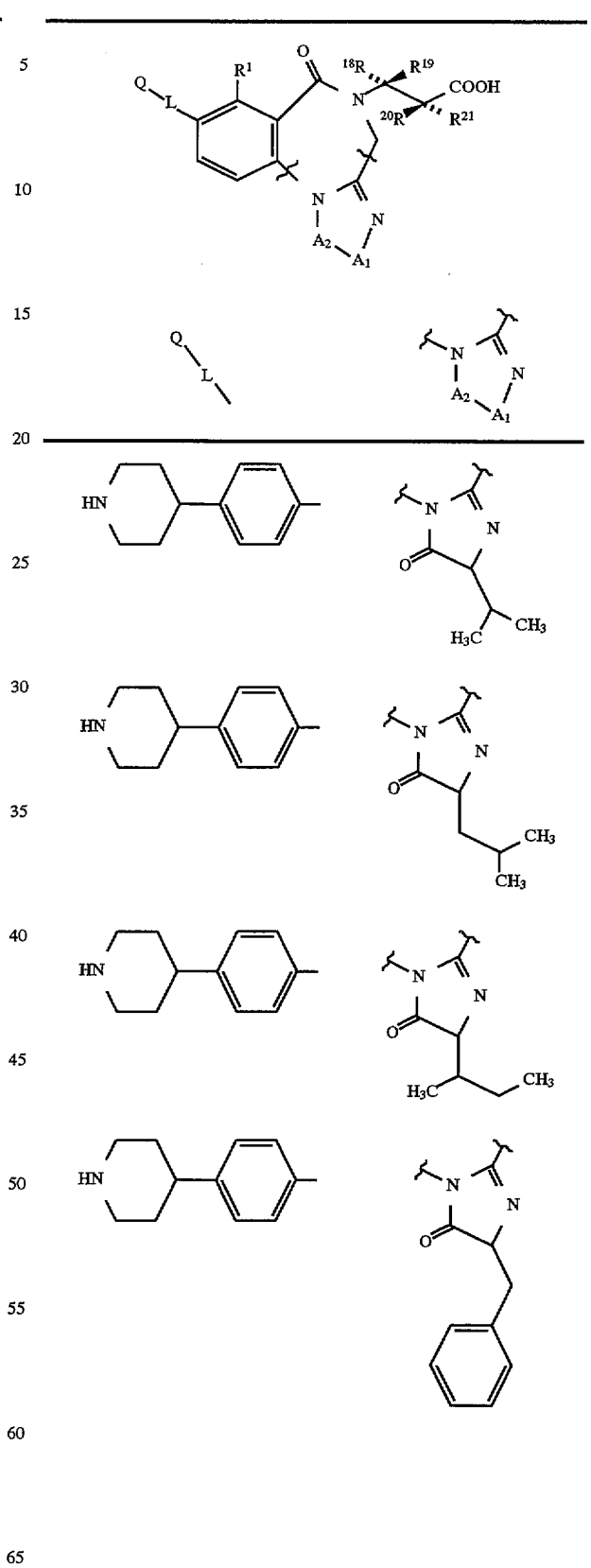

TABLE I-continued
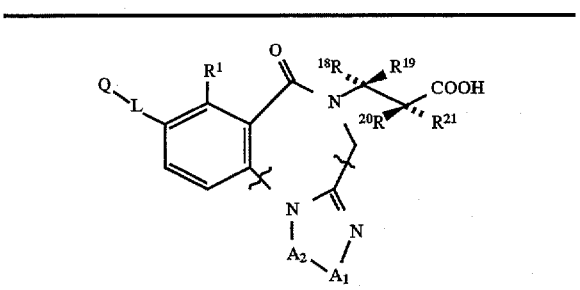
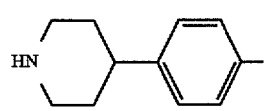 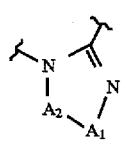
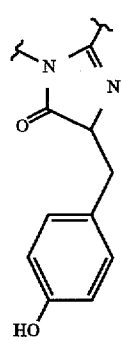
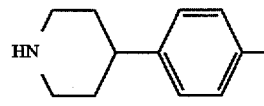 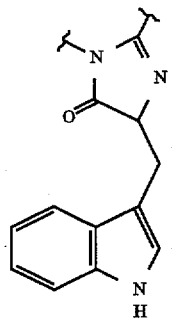
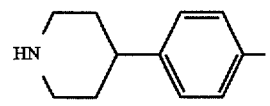 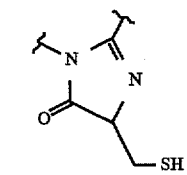
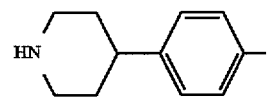 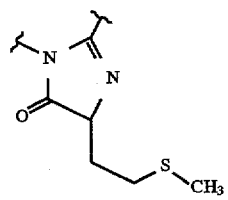
TABLE I-continued
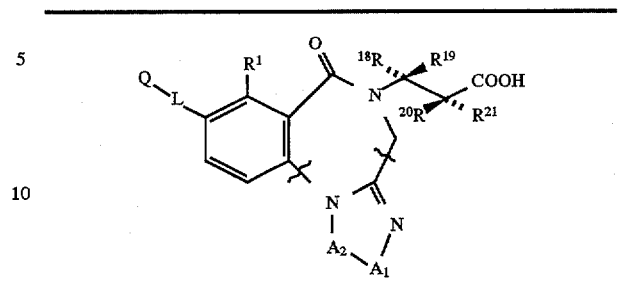
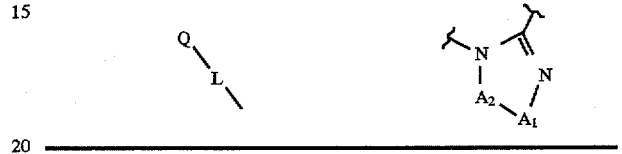
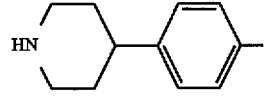 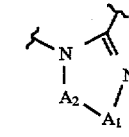
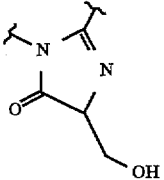
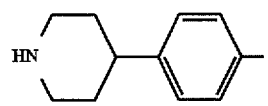 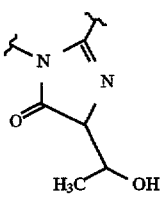
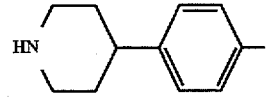 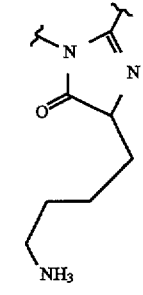
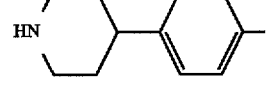 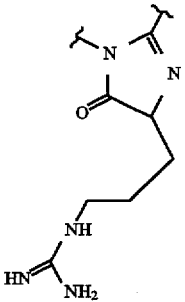

TABLE I-continued
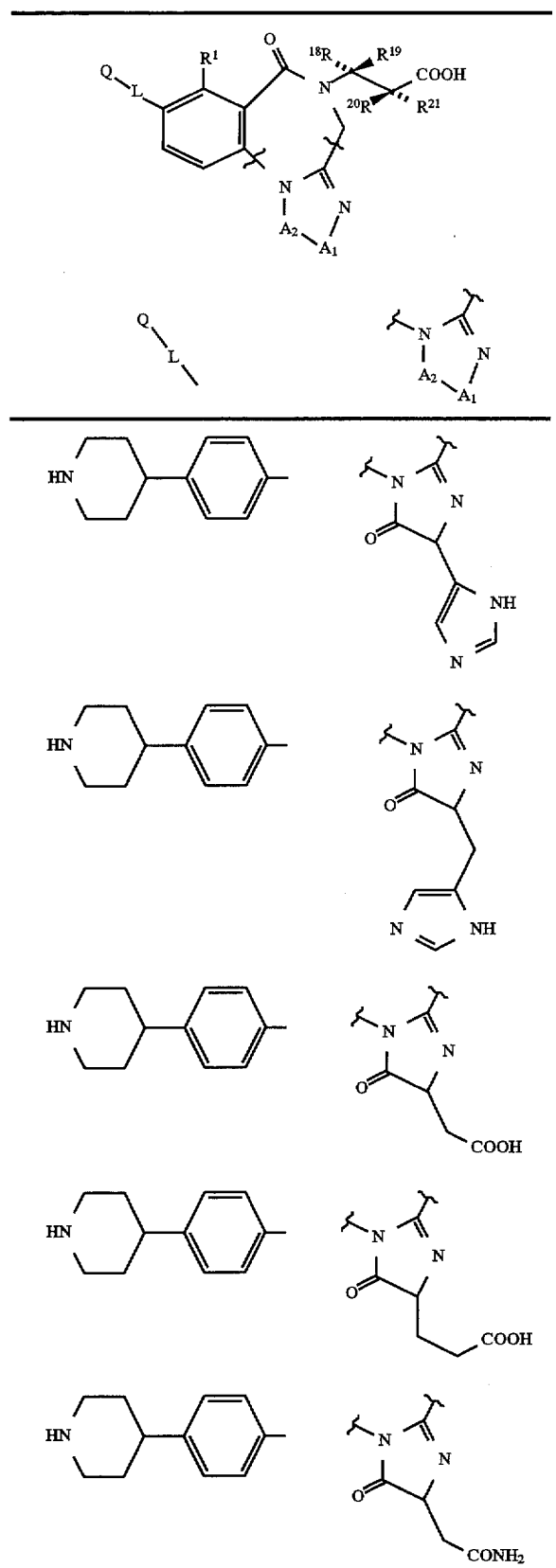
TABLE I-continued
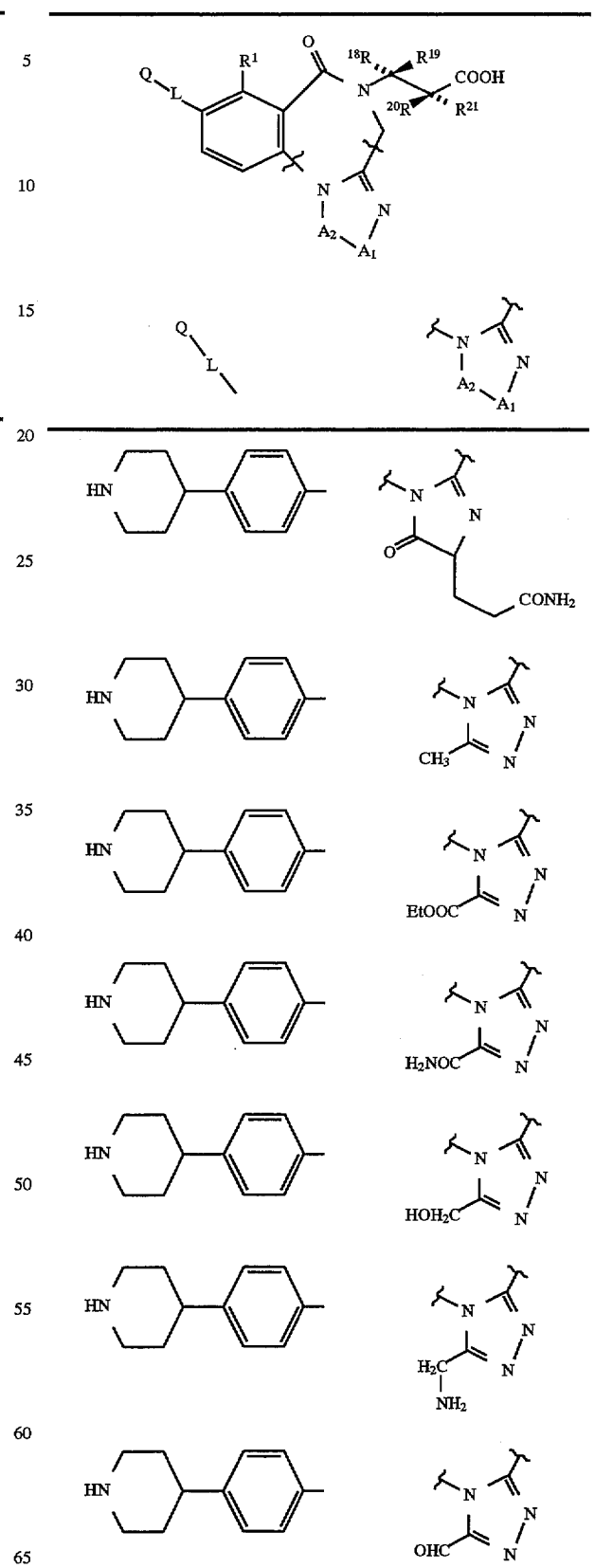

TABLE I-continued
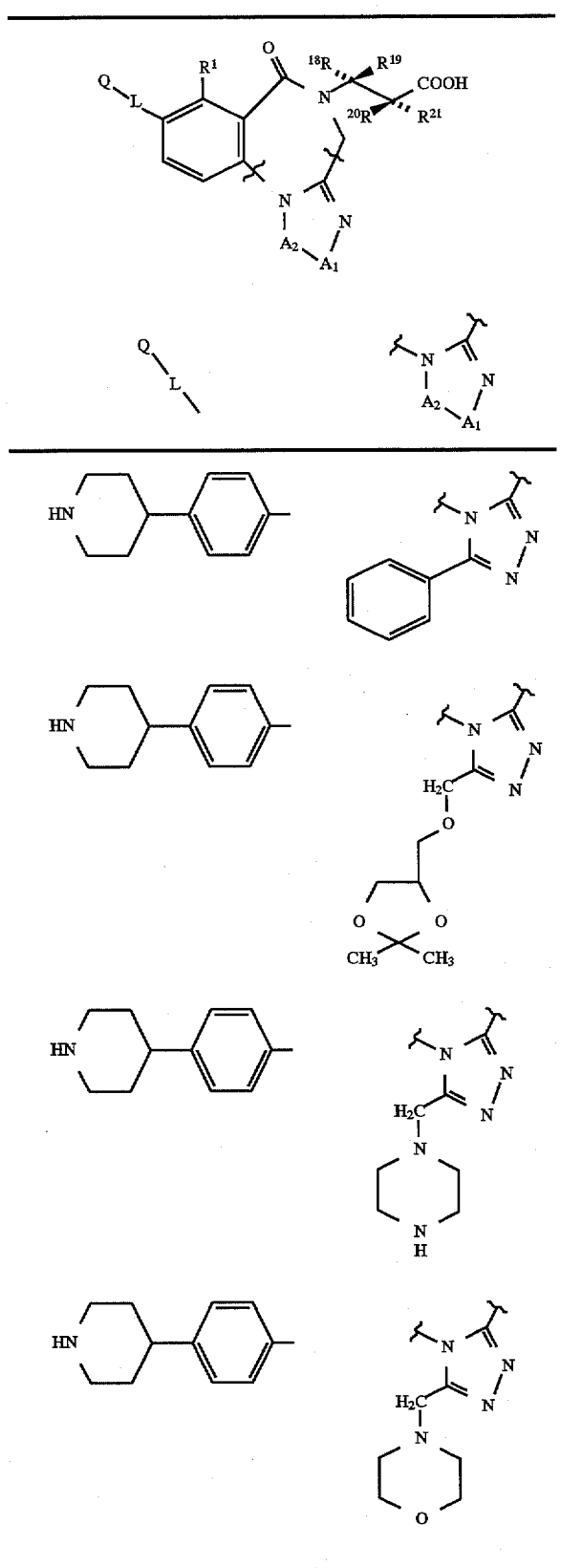
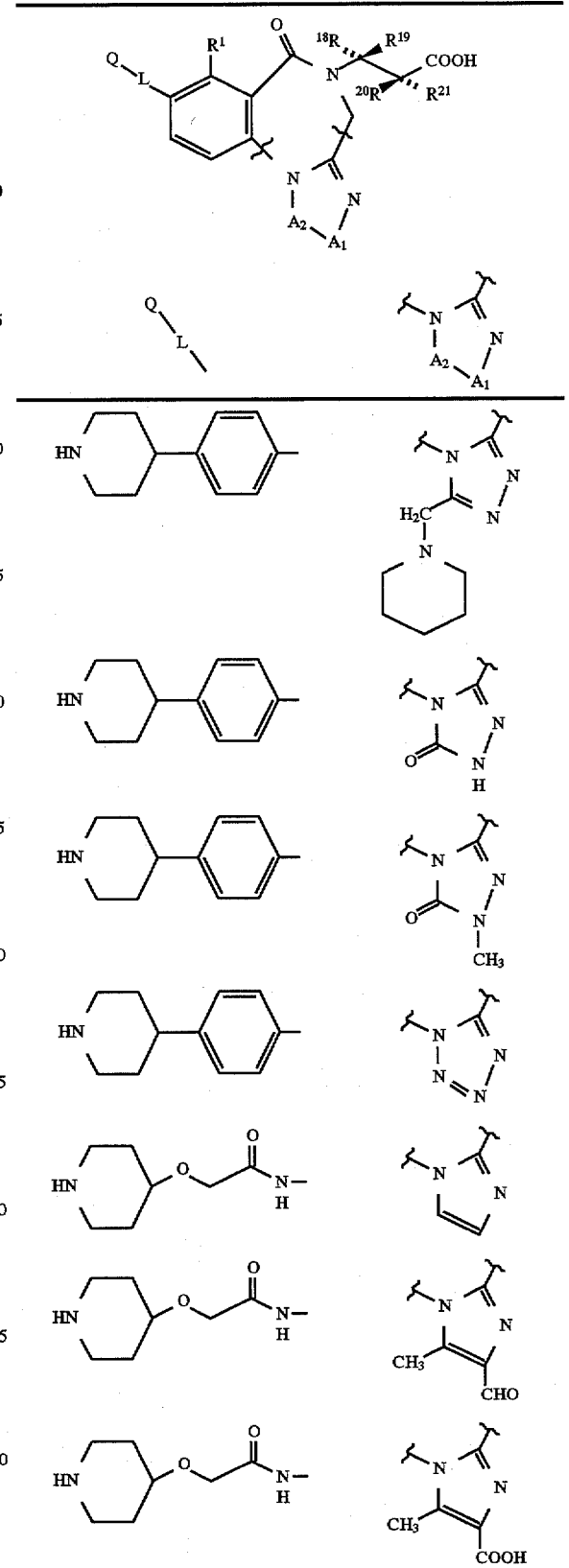

TABLE I-continued
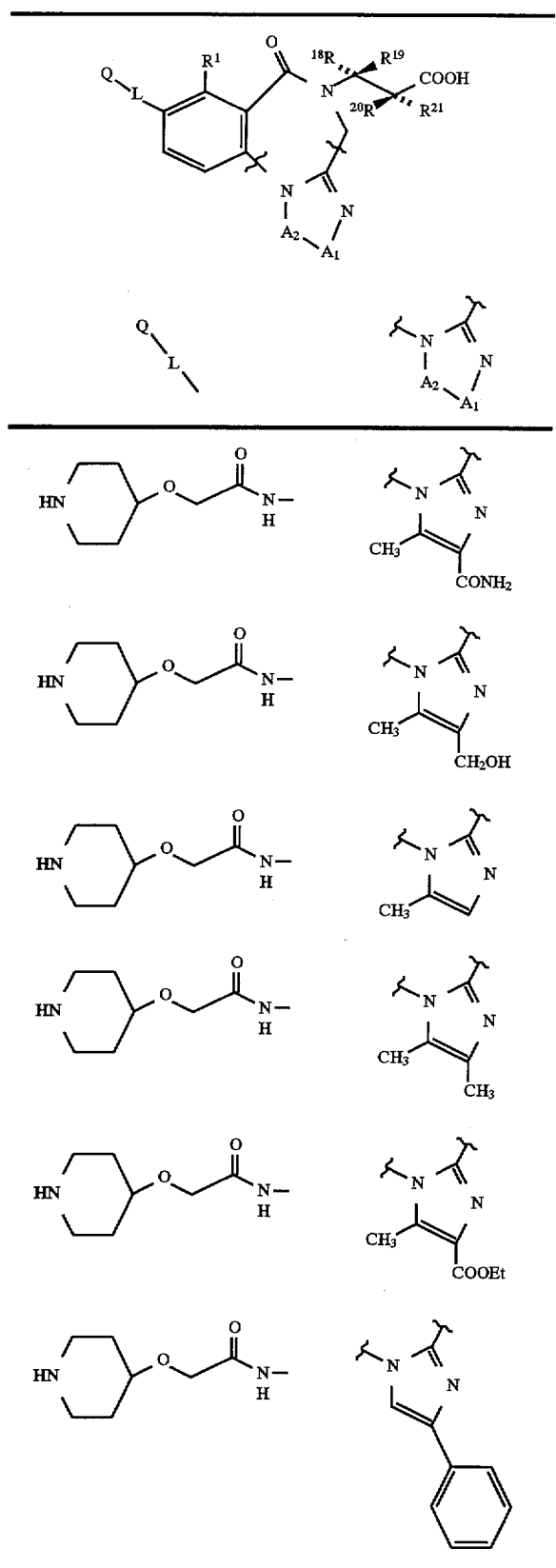
TABLE I-continued
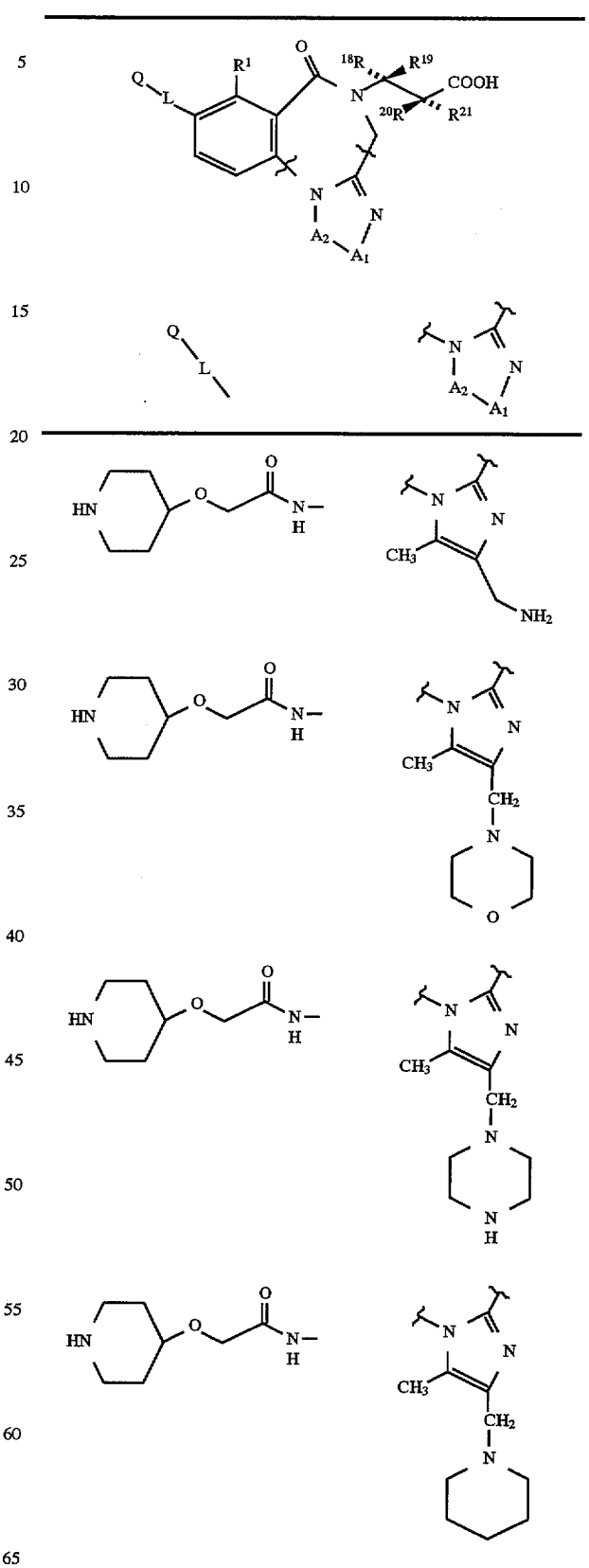

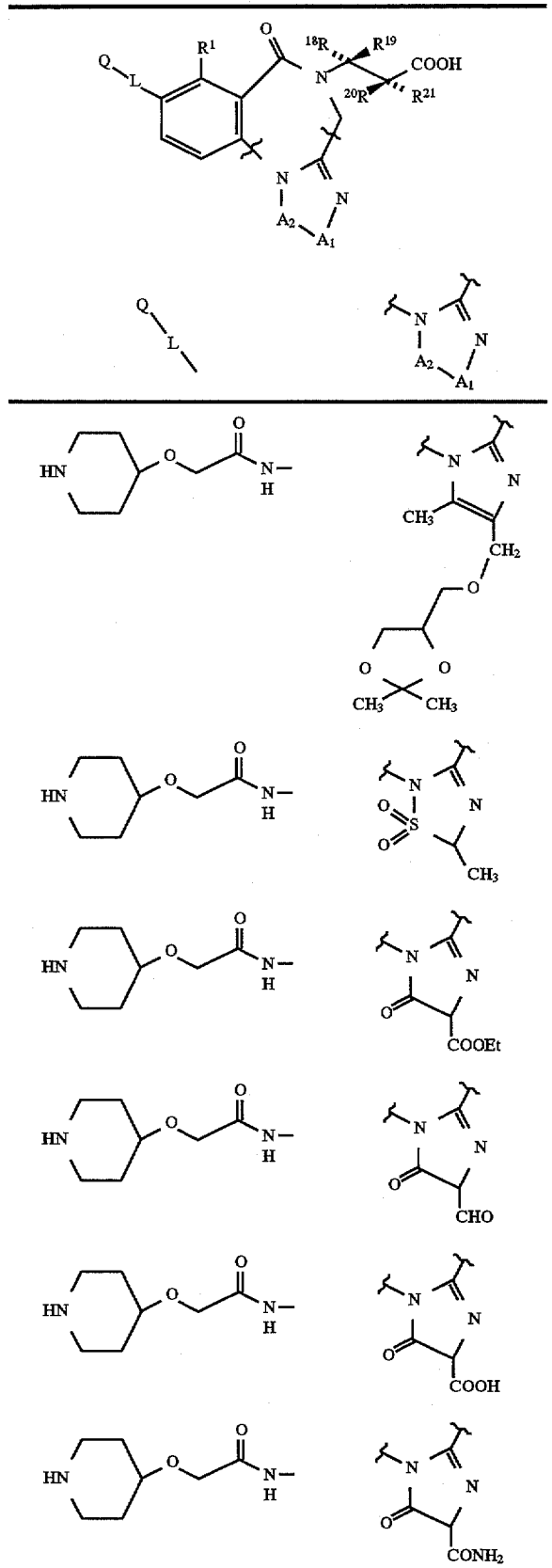

TABLE I-continued
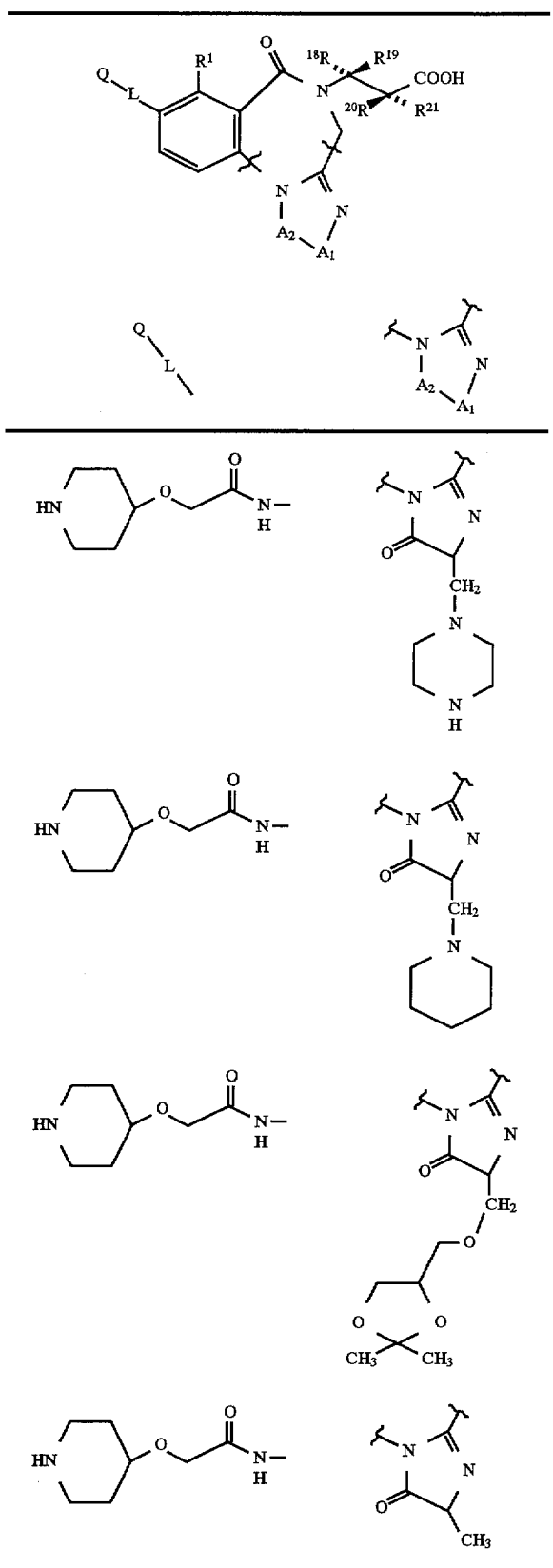
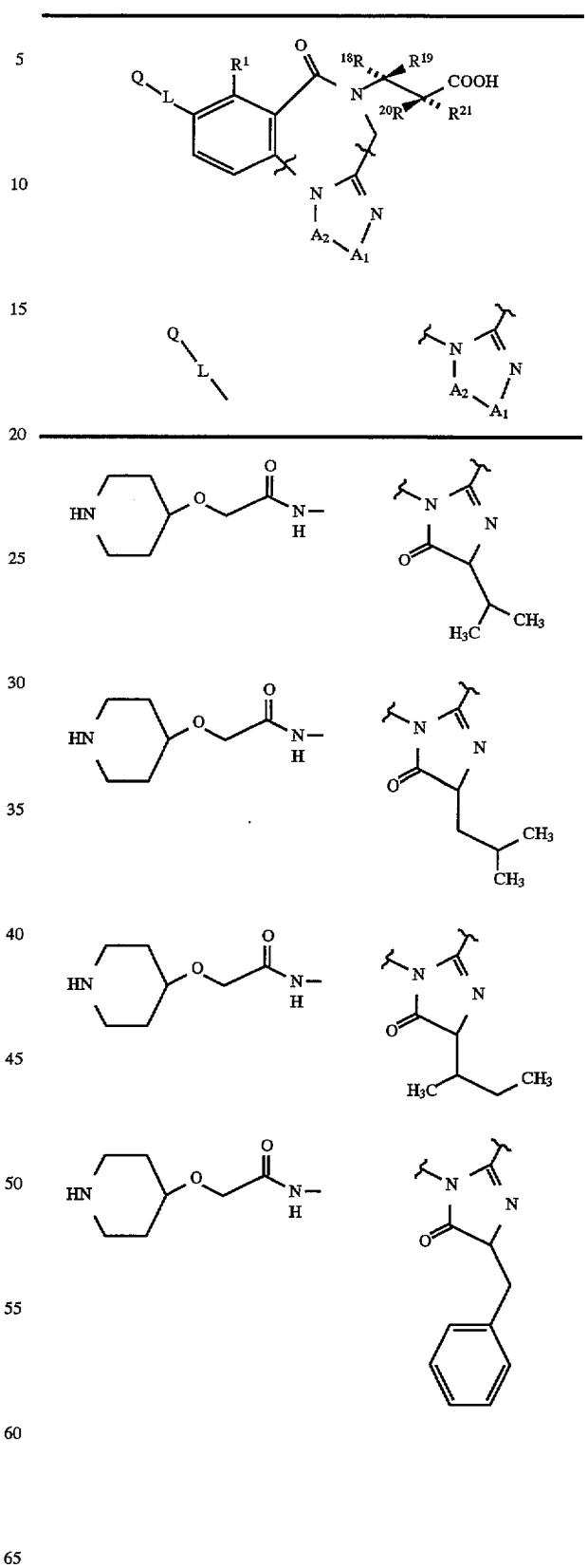

TABLE I-continued
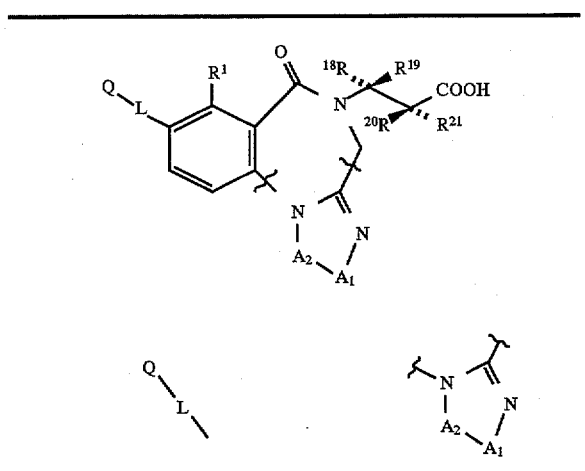
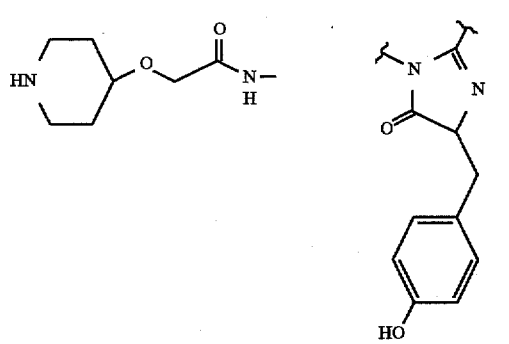
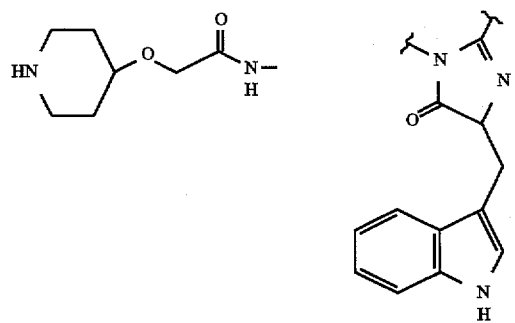
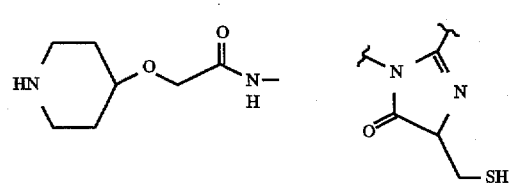
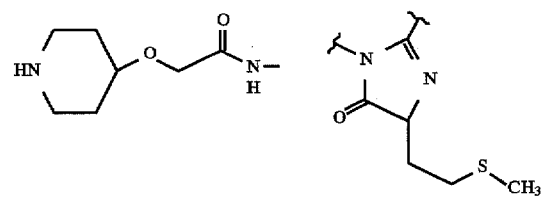
TABLE I-continued
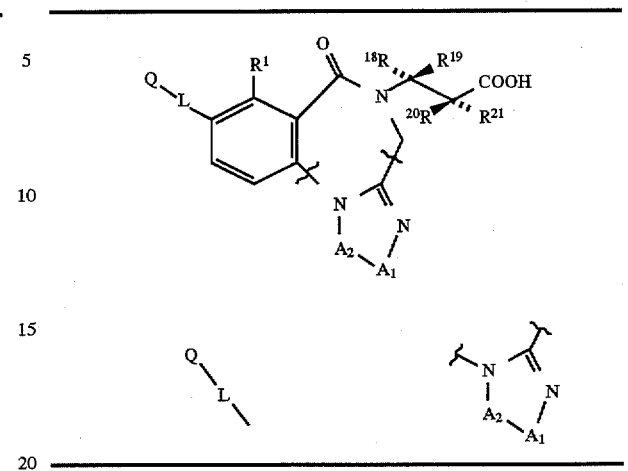
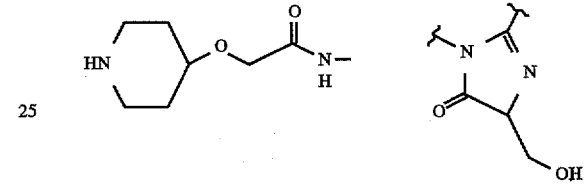
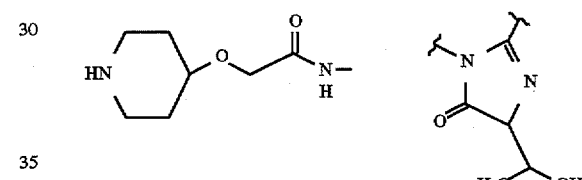
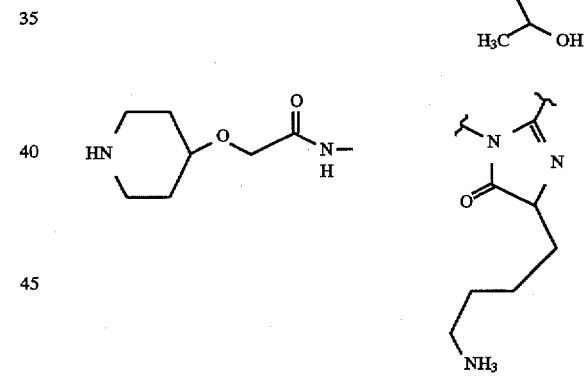
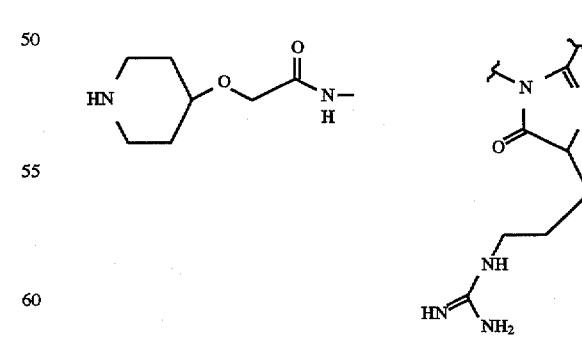

TABLE I-continued
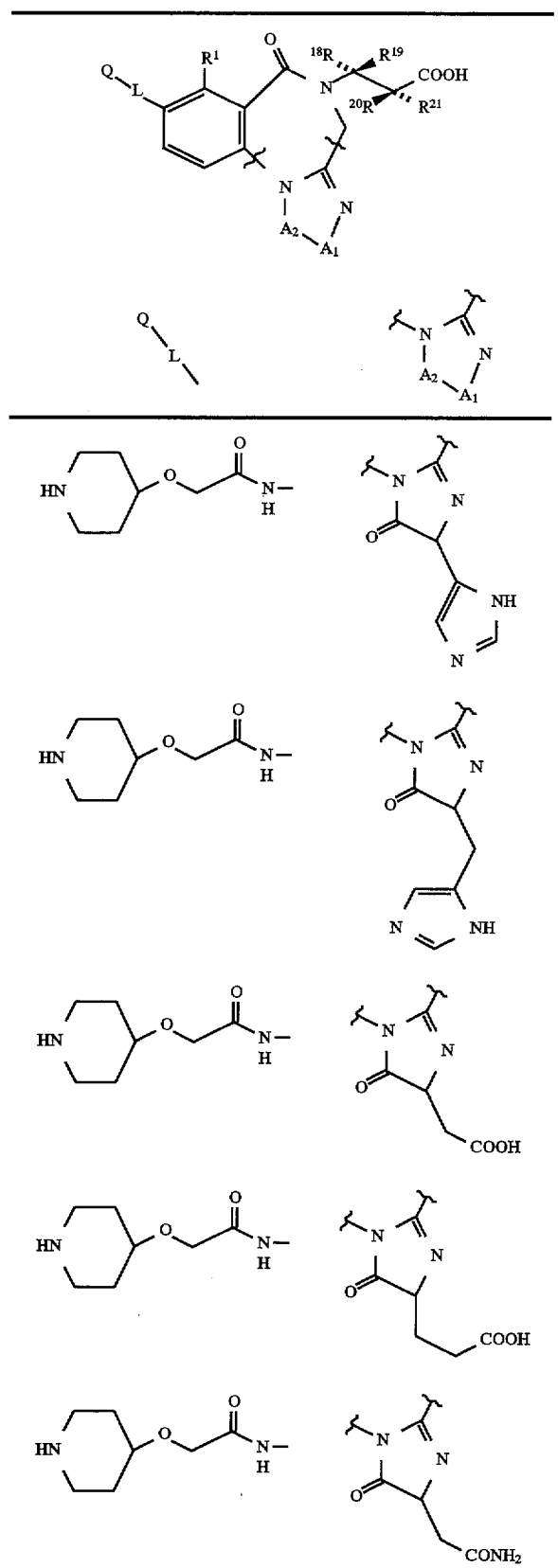
TABLE I-continued
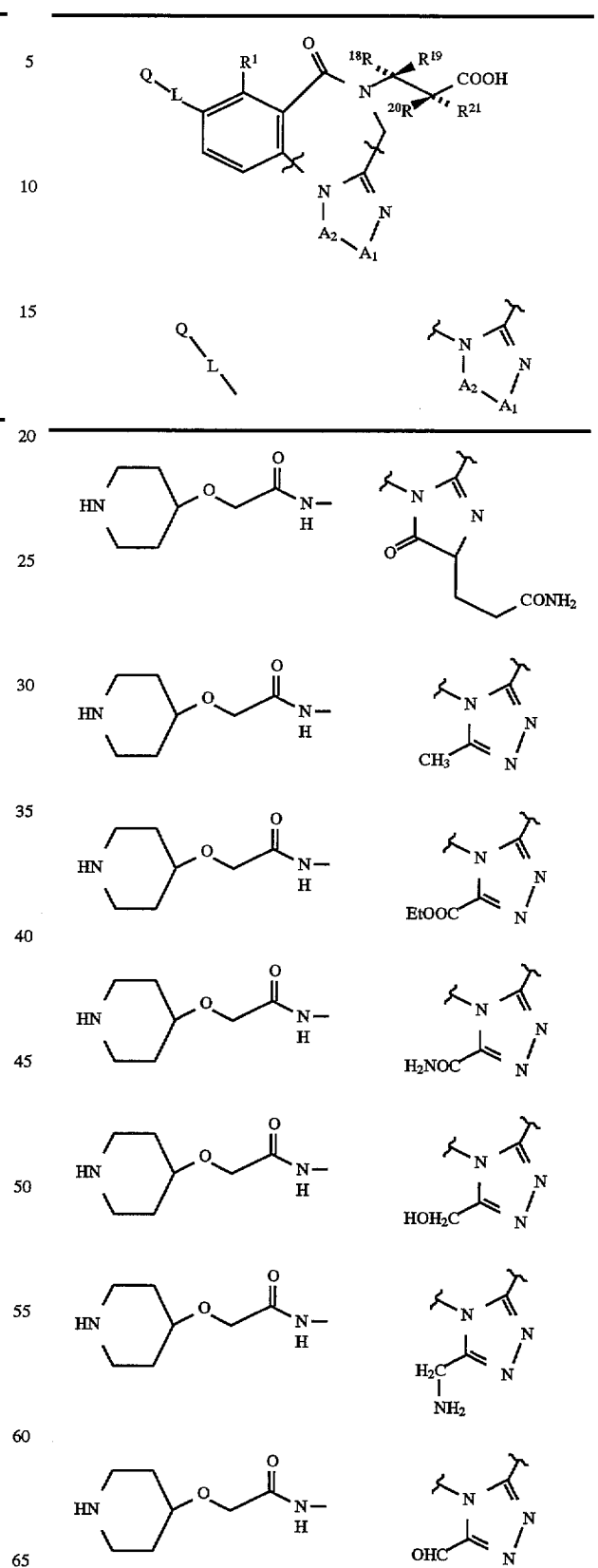

TABLE I-continued
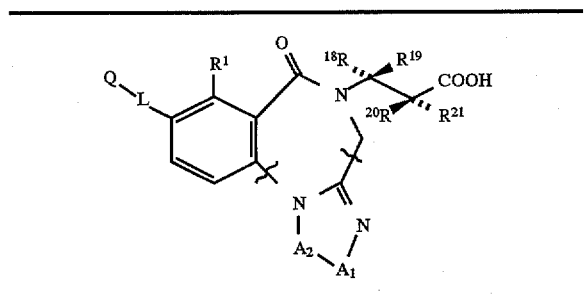
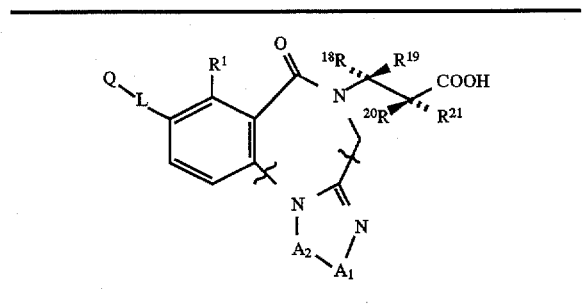
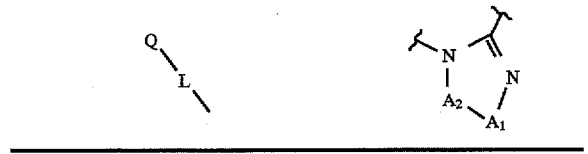
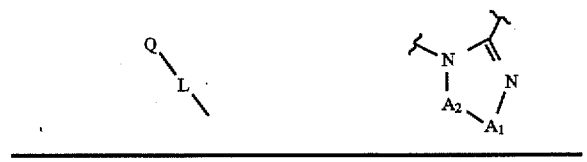
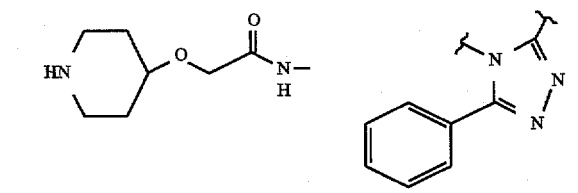
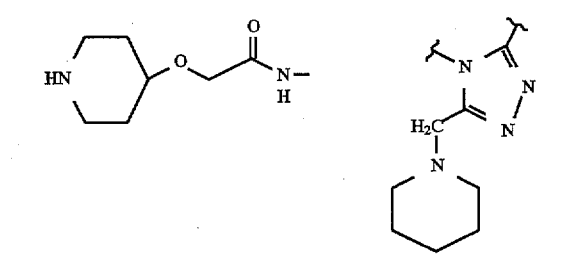
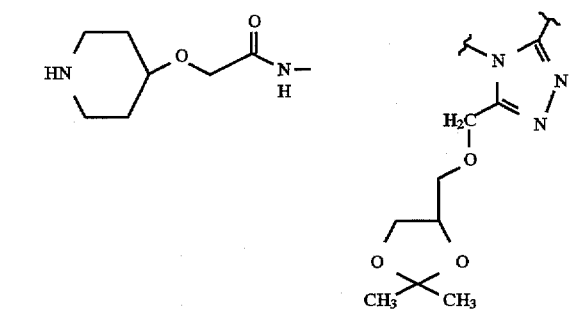
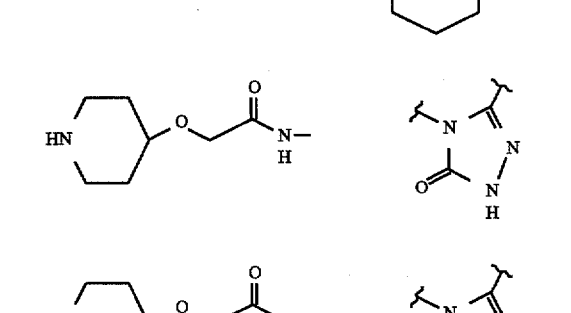
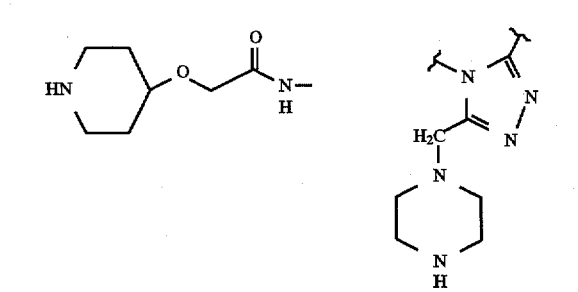
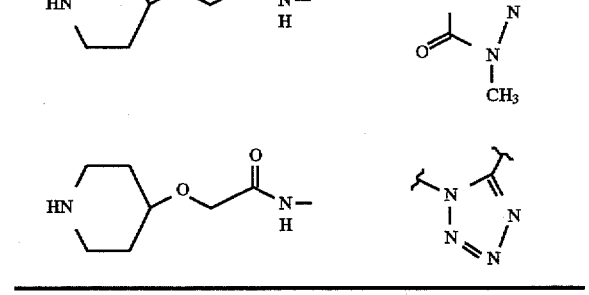
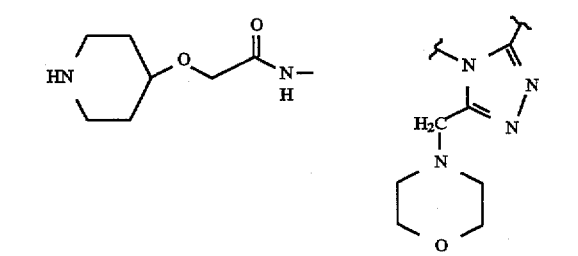

TABLE II
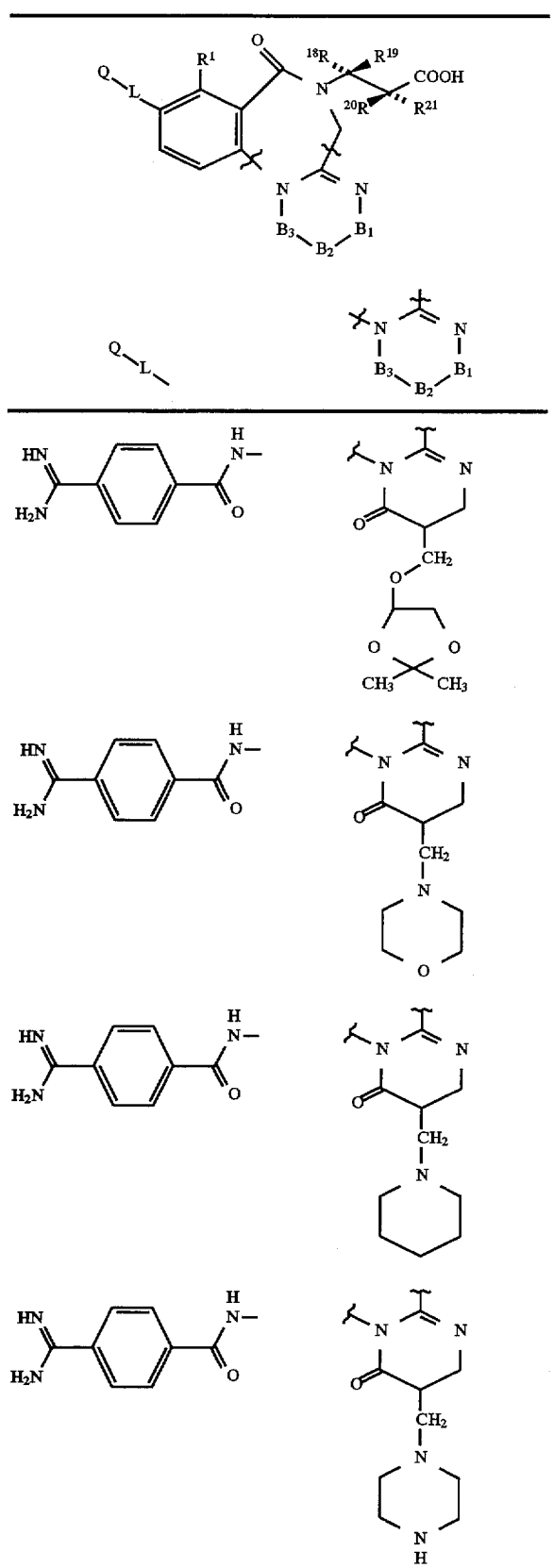
TABLE II-continued
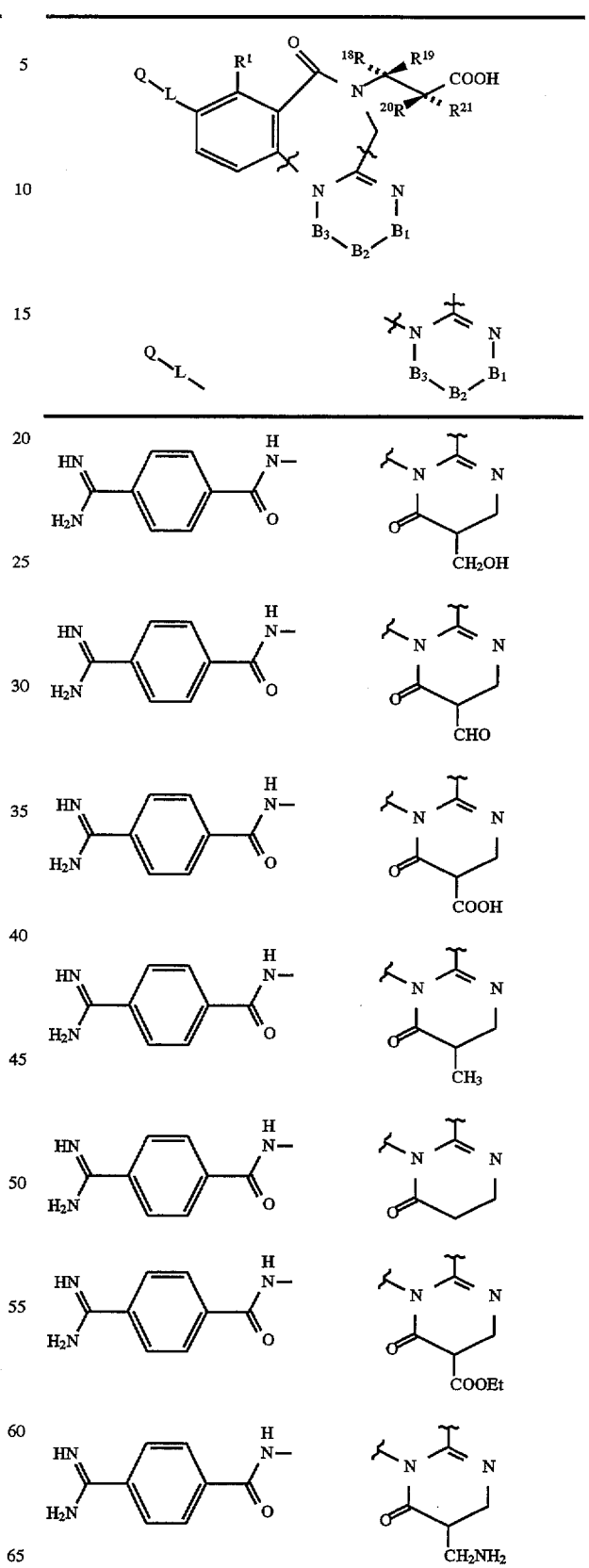

TABLE II-continued
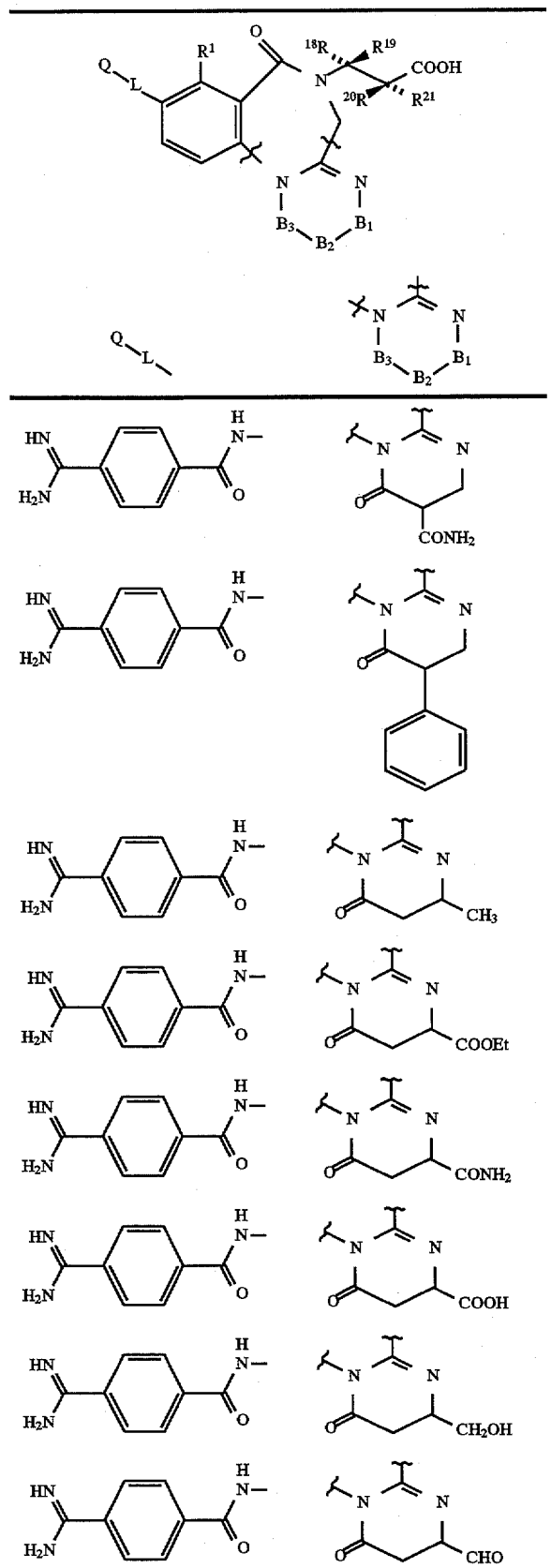
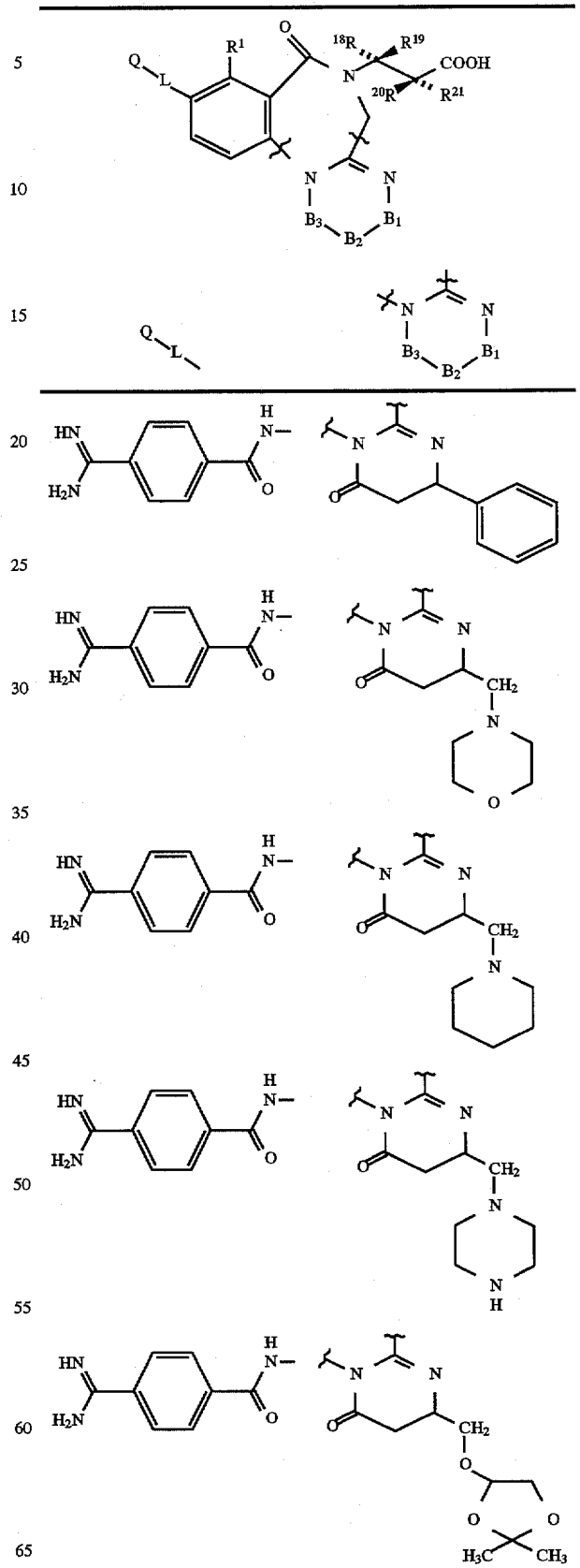

TABLE II-continued
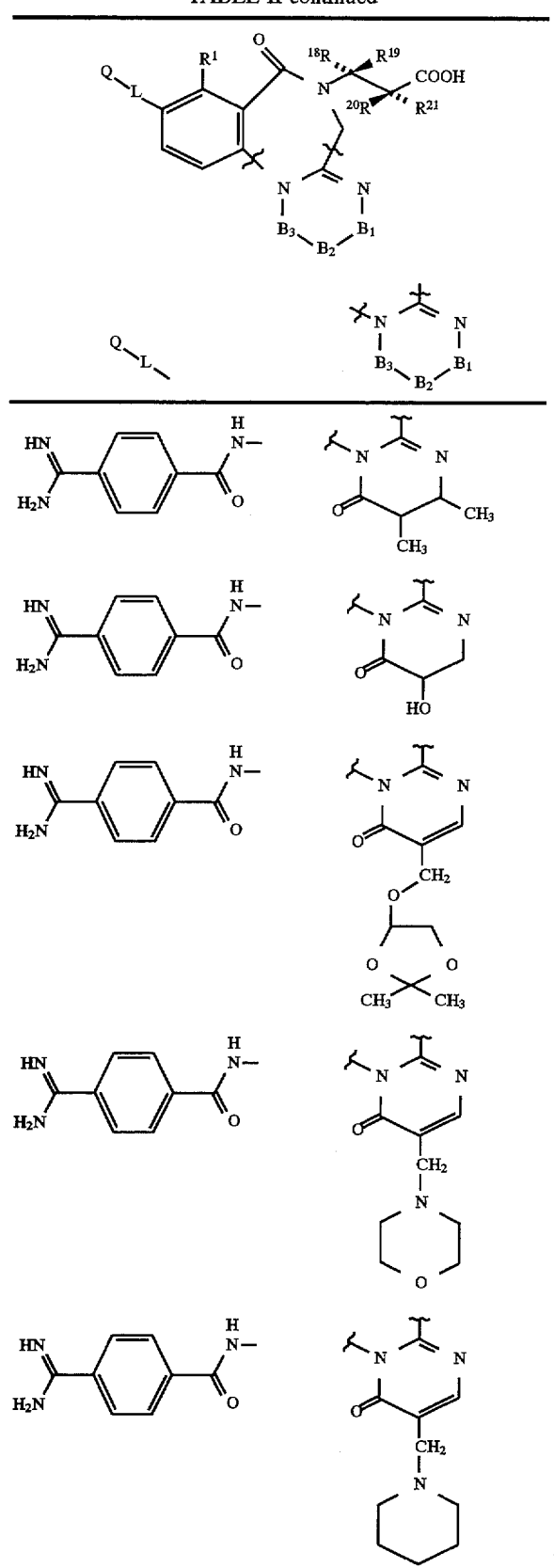
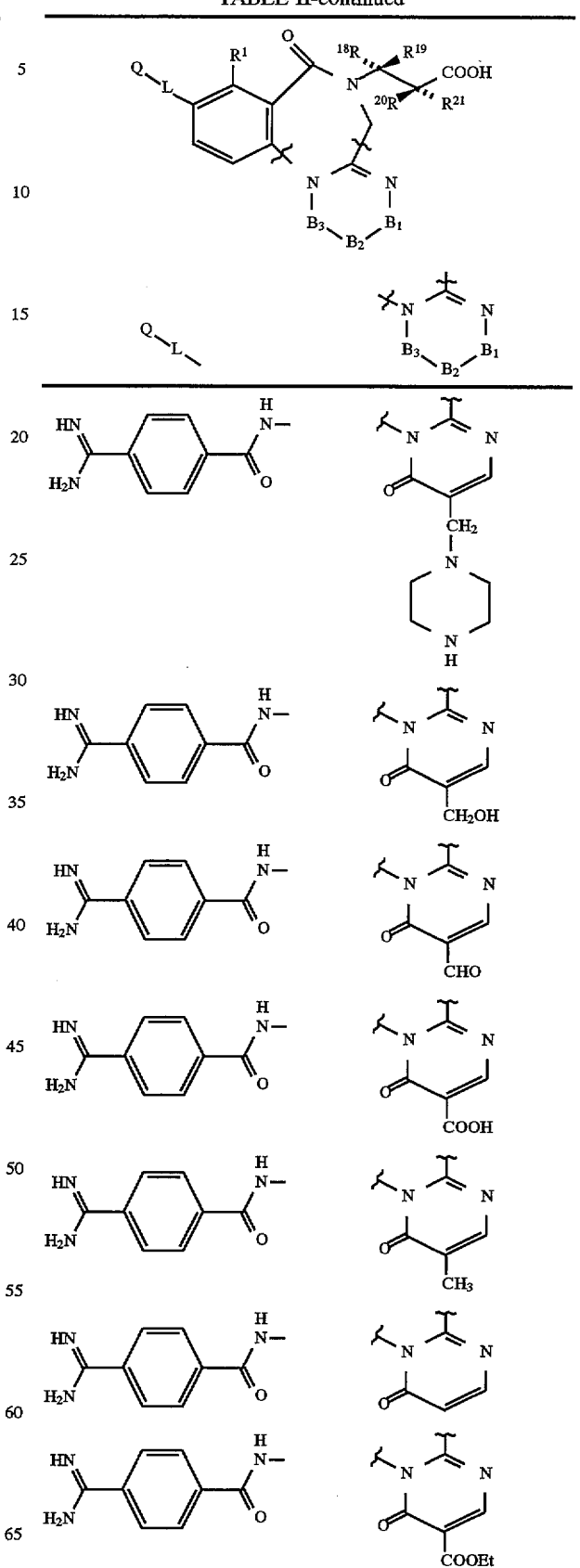

TABLE II-continued
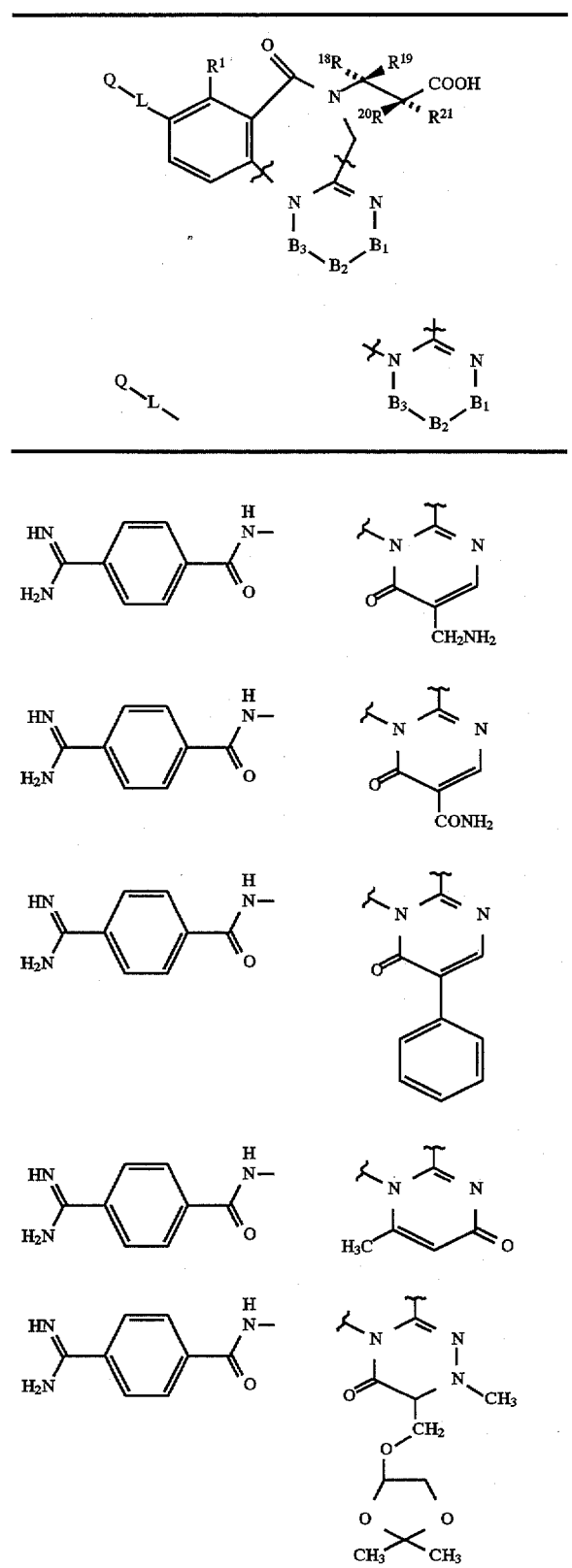
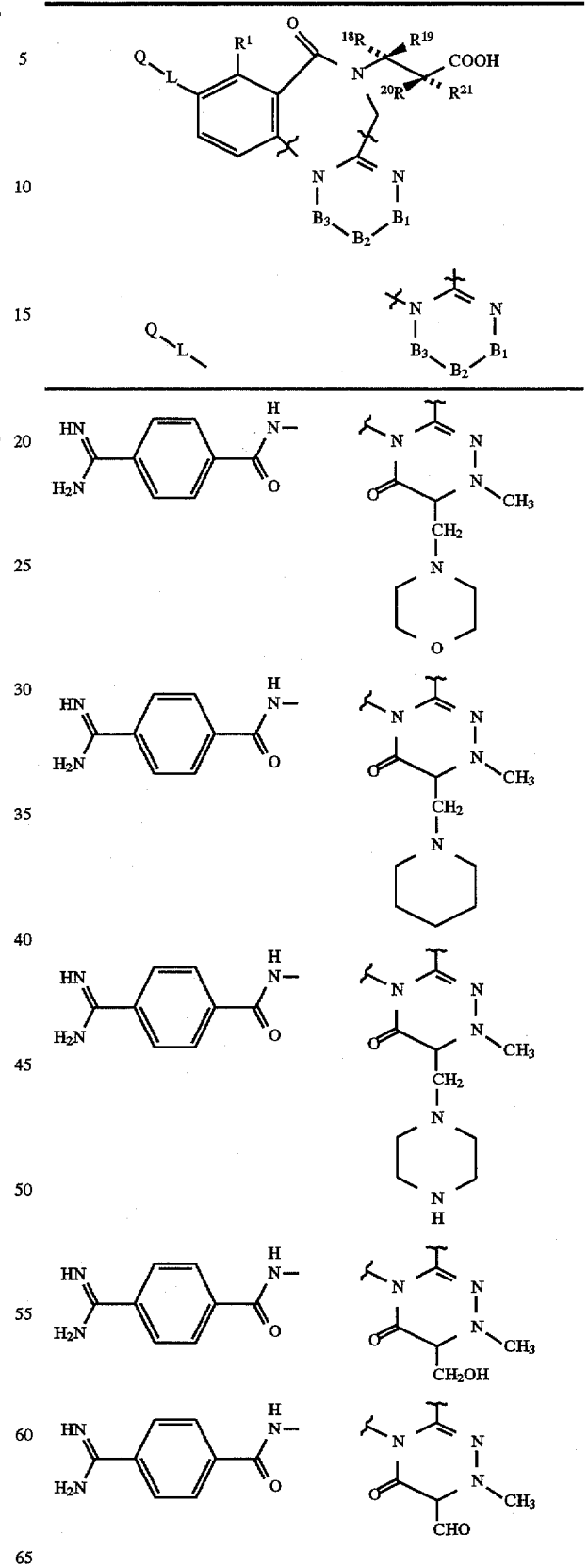

TABLE II-continued
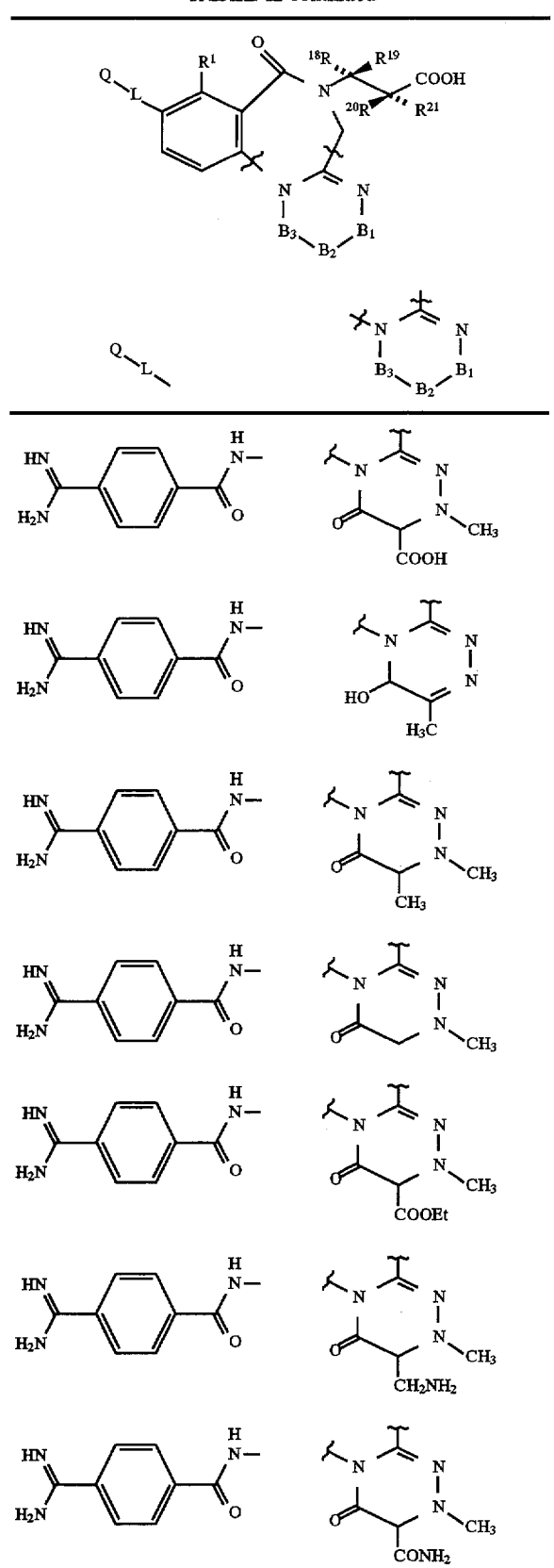
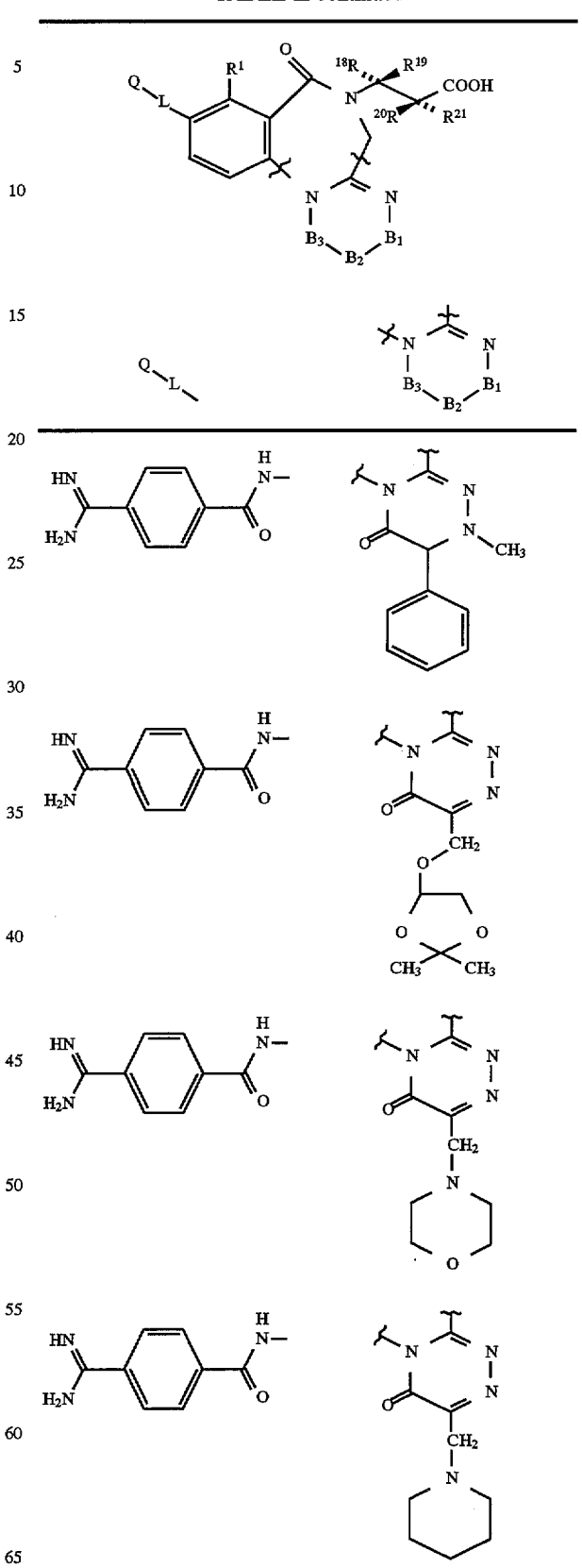

TABLE II-continued
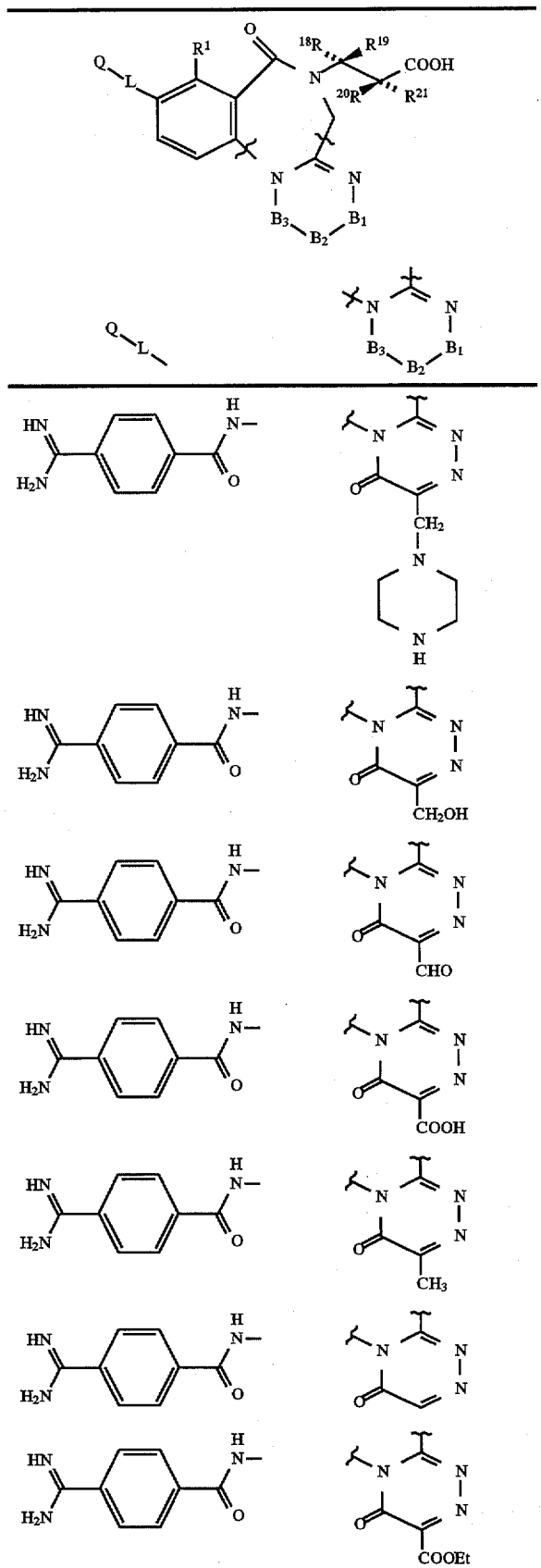
TABLE II-continued
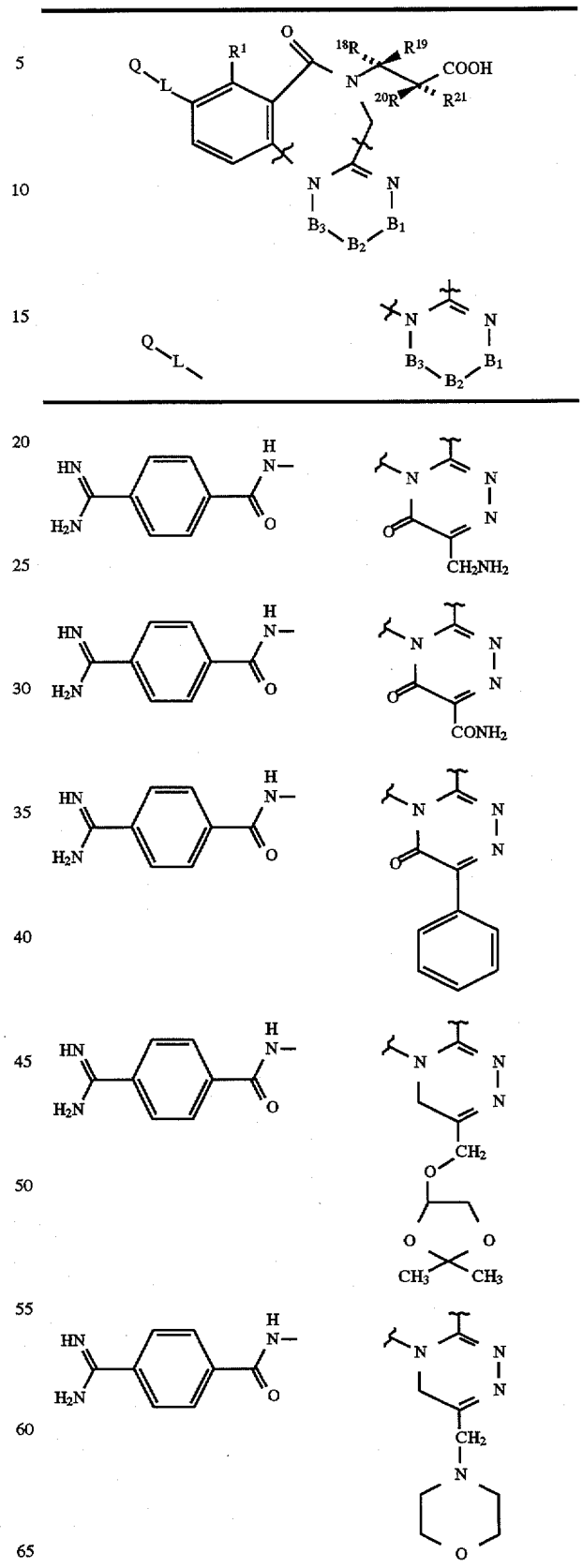

TABLE II-continued
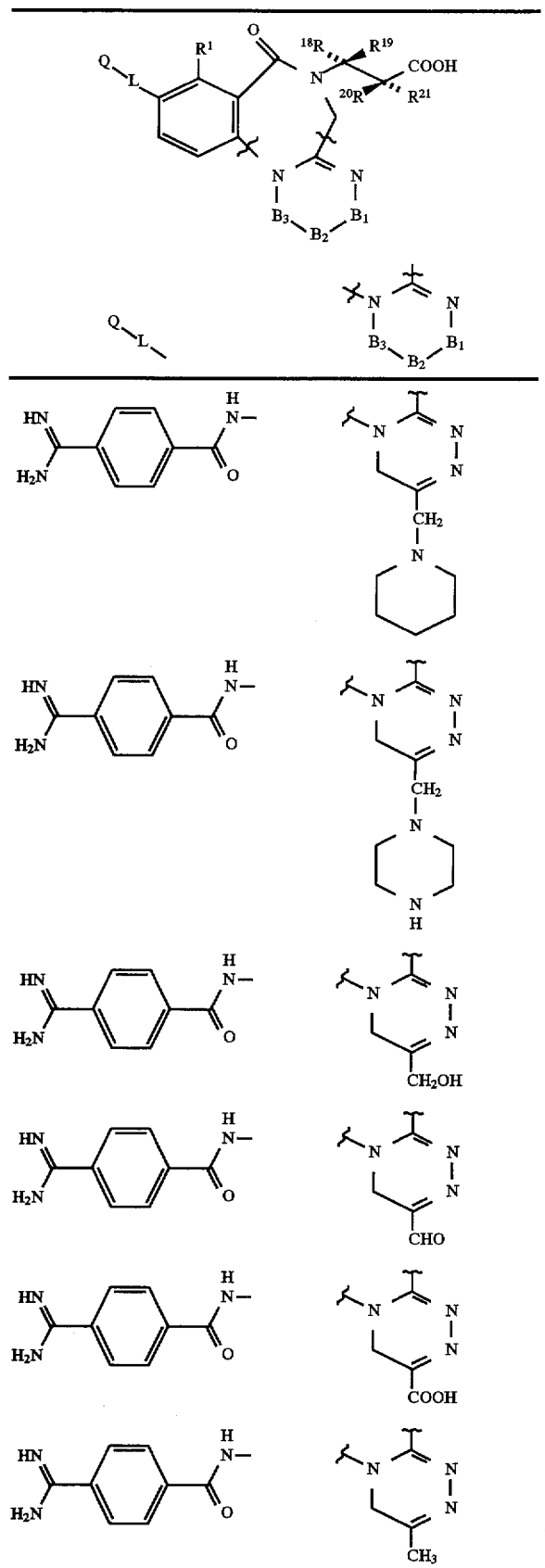
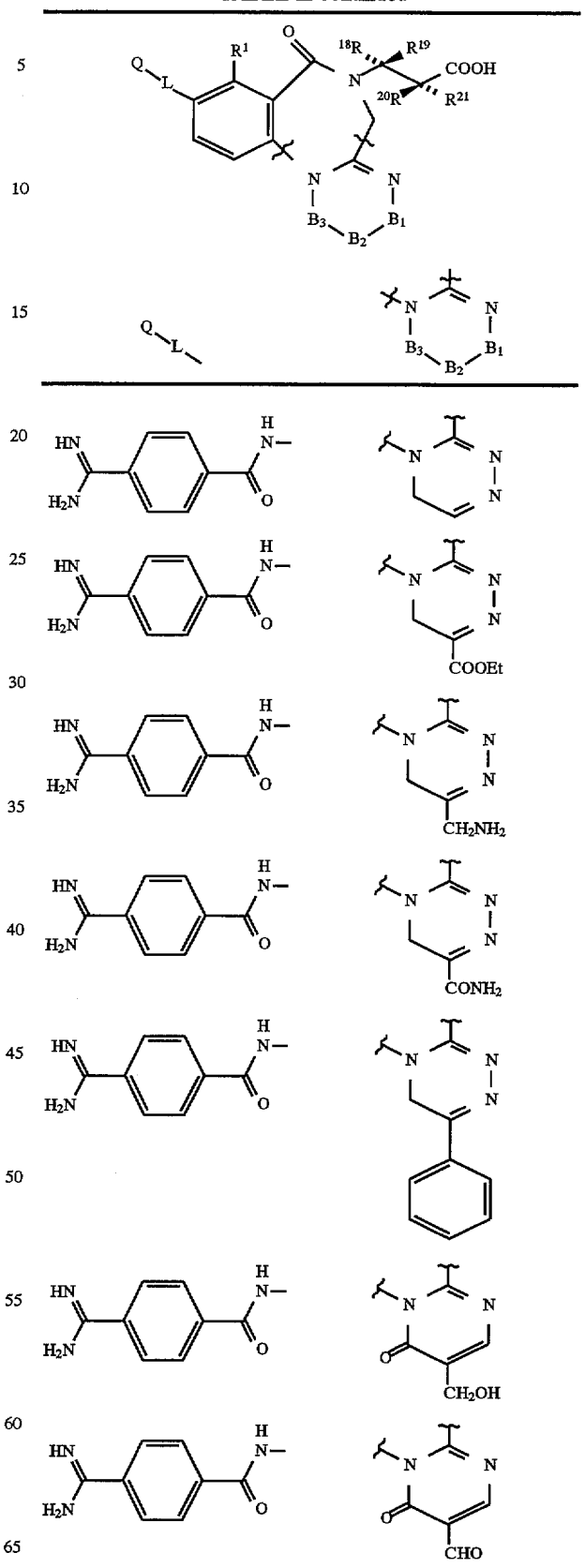

TABLE II-continued
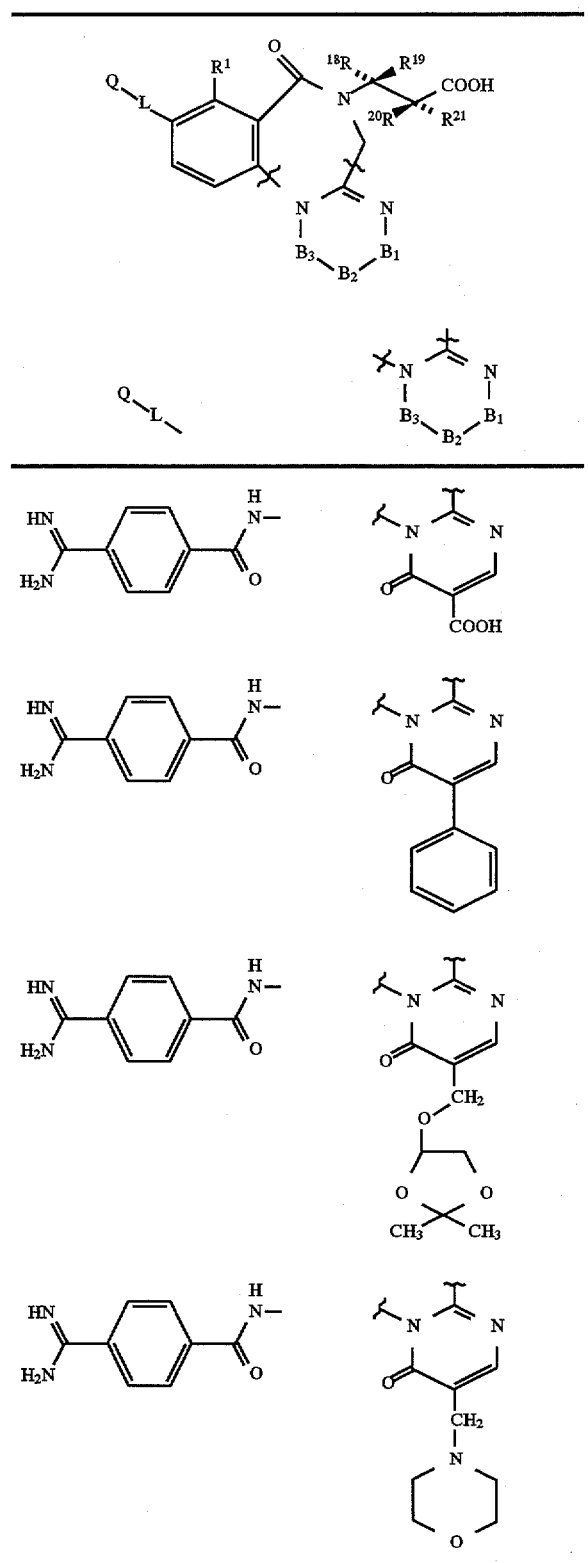
TABLE II-continued
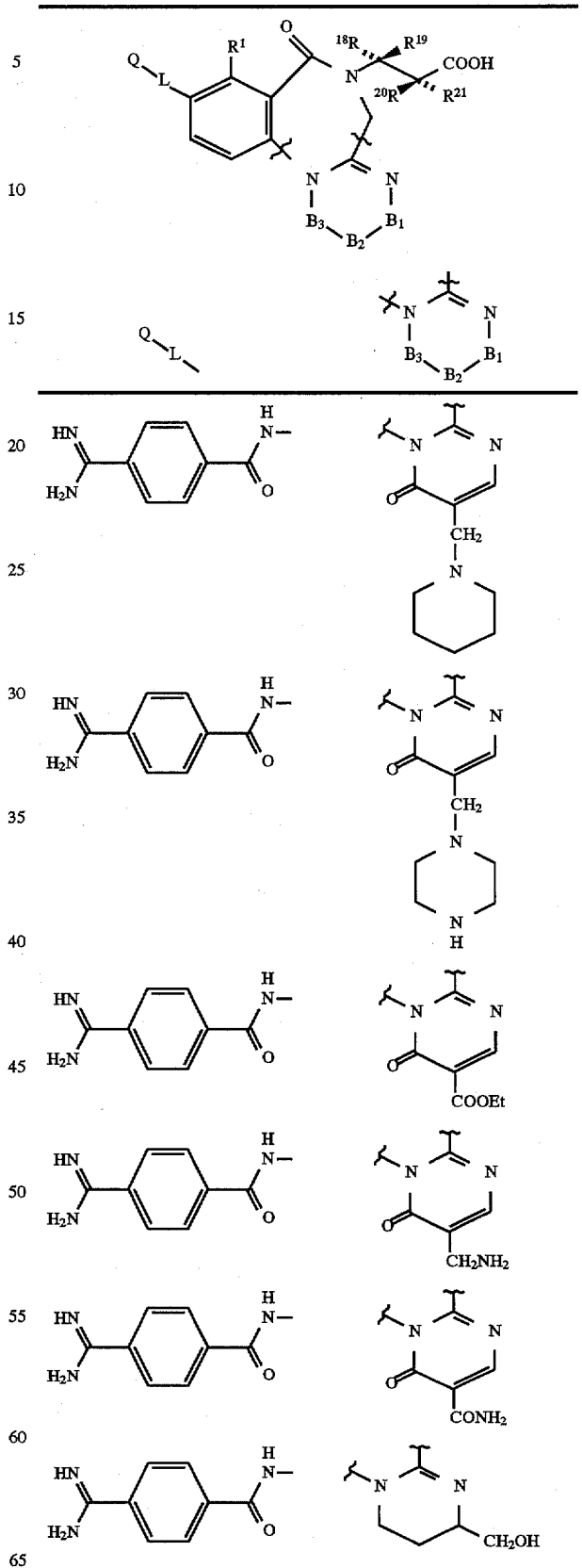

TABLE II-continued
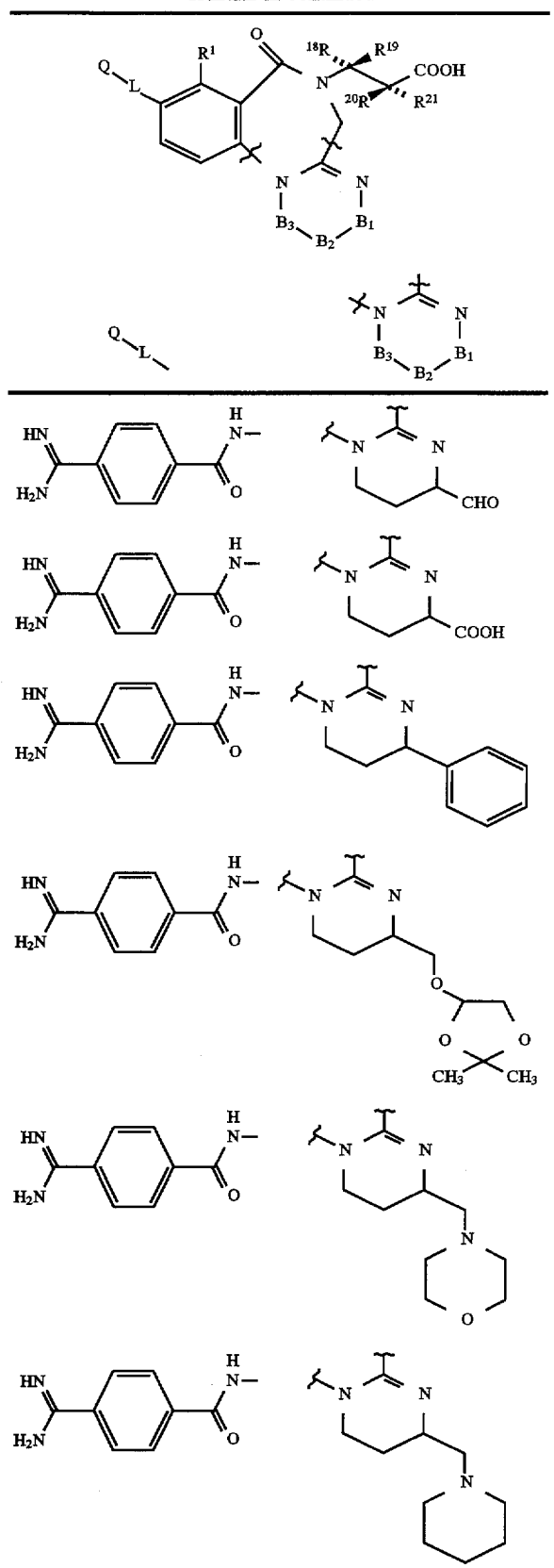
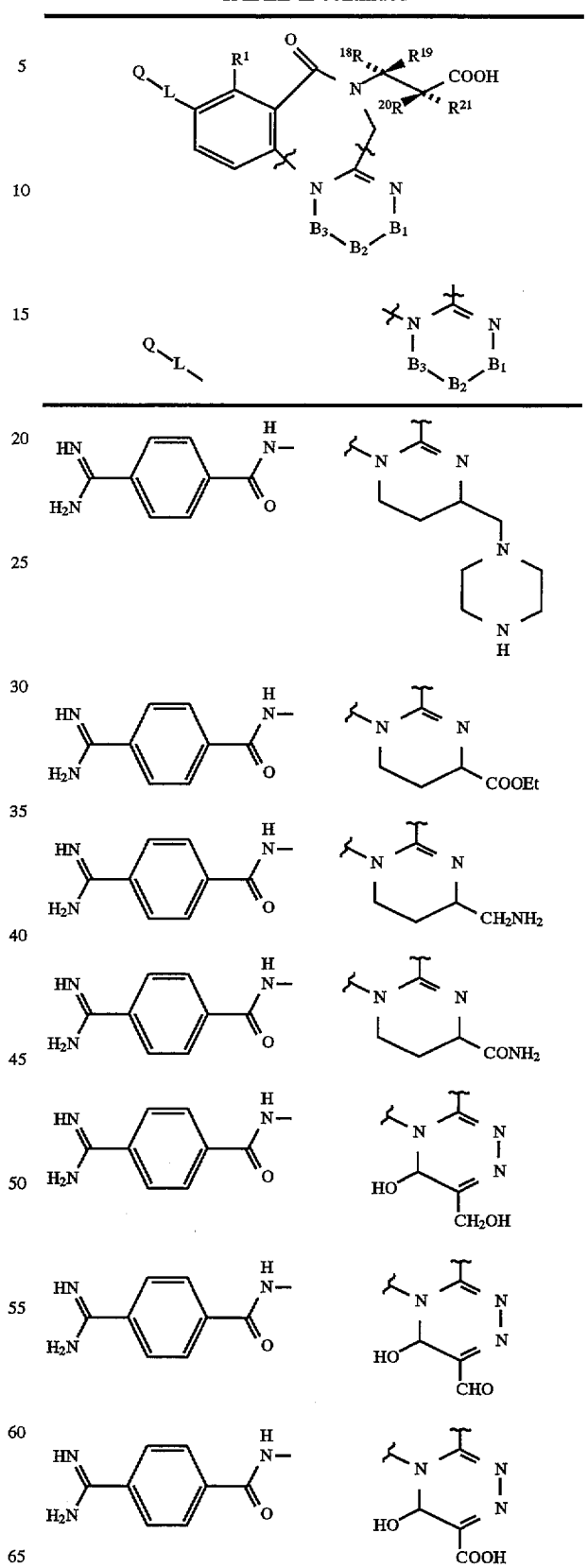

TABLE II-continued
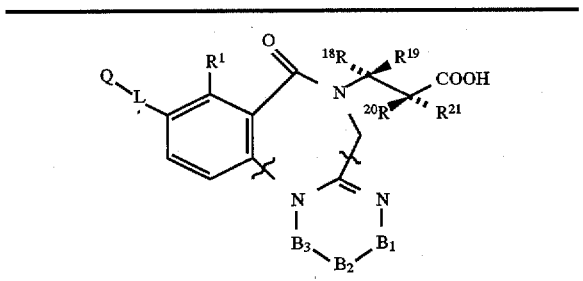
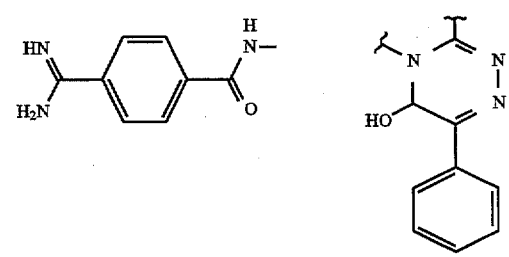
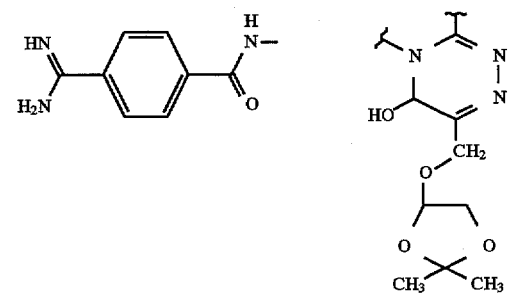
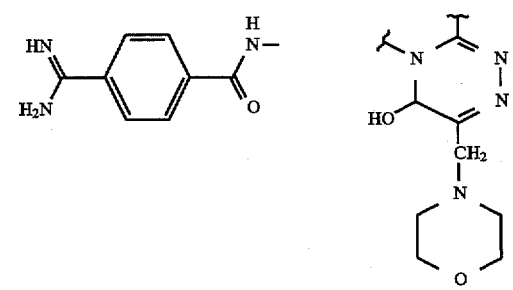
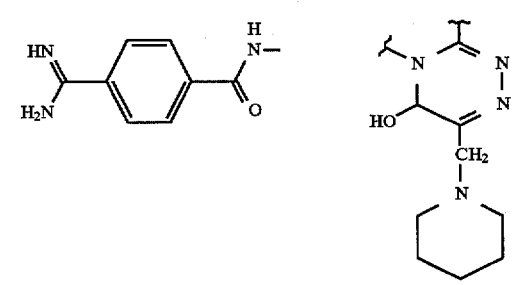
TABLE II-continued
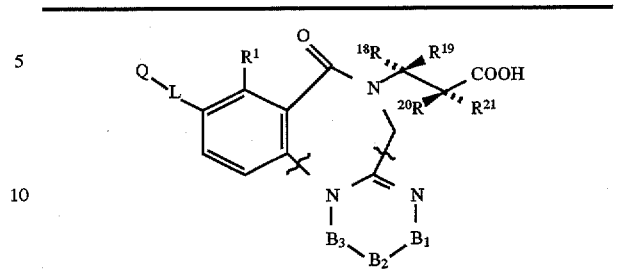
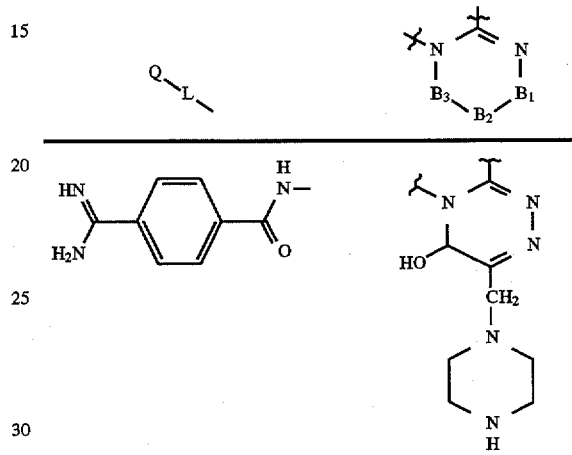
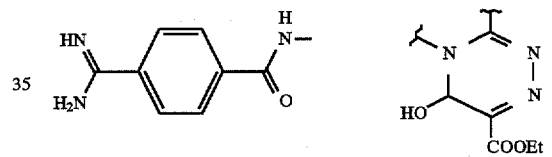
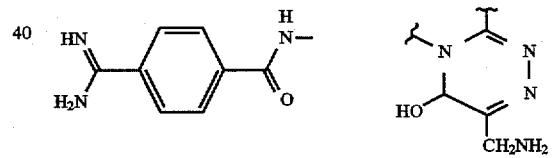
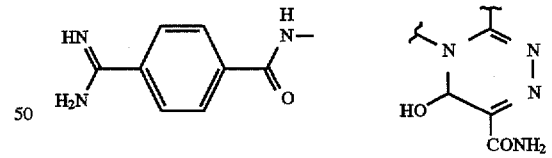
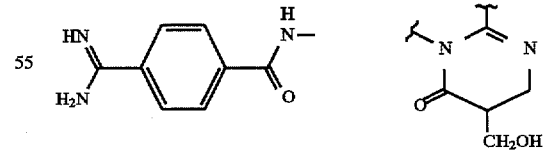
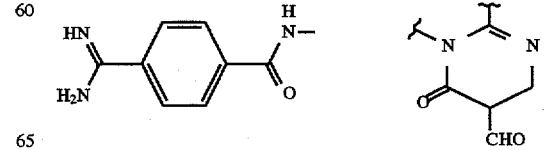

TABLE II-continued
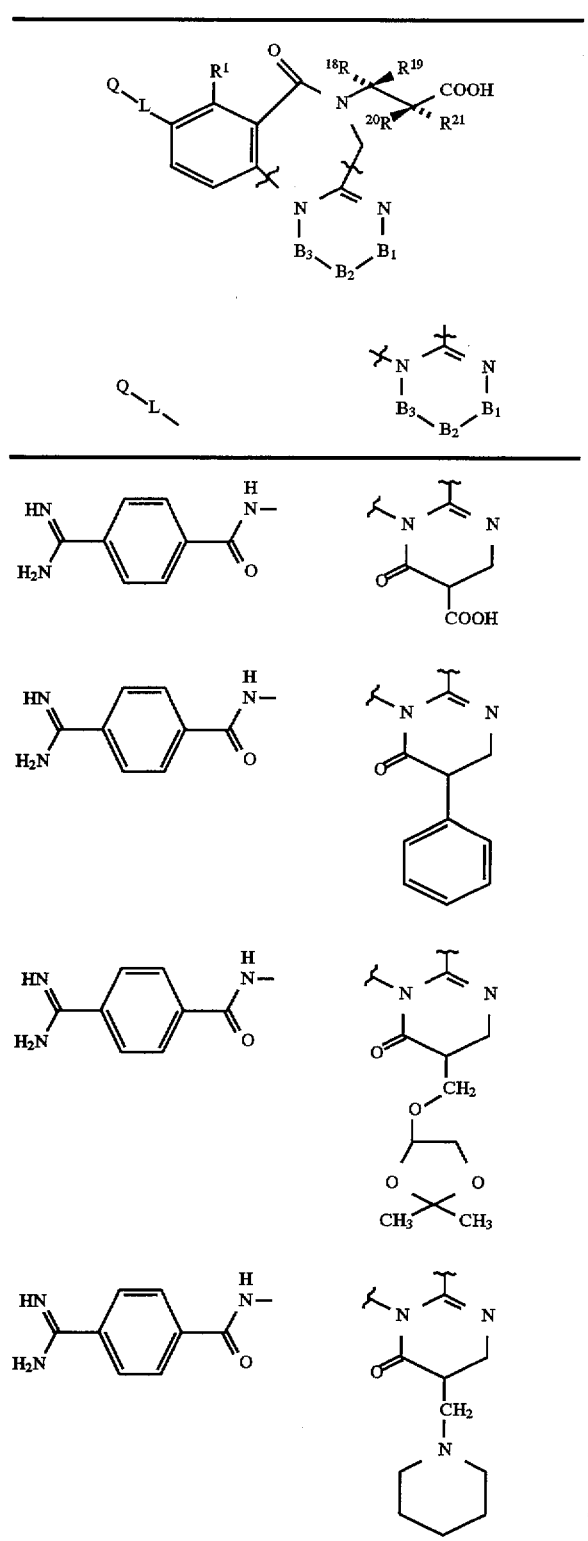
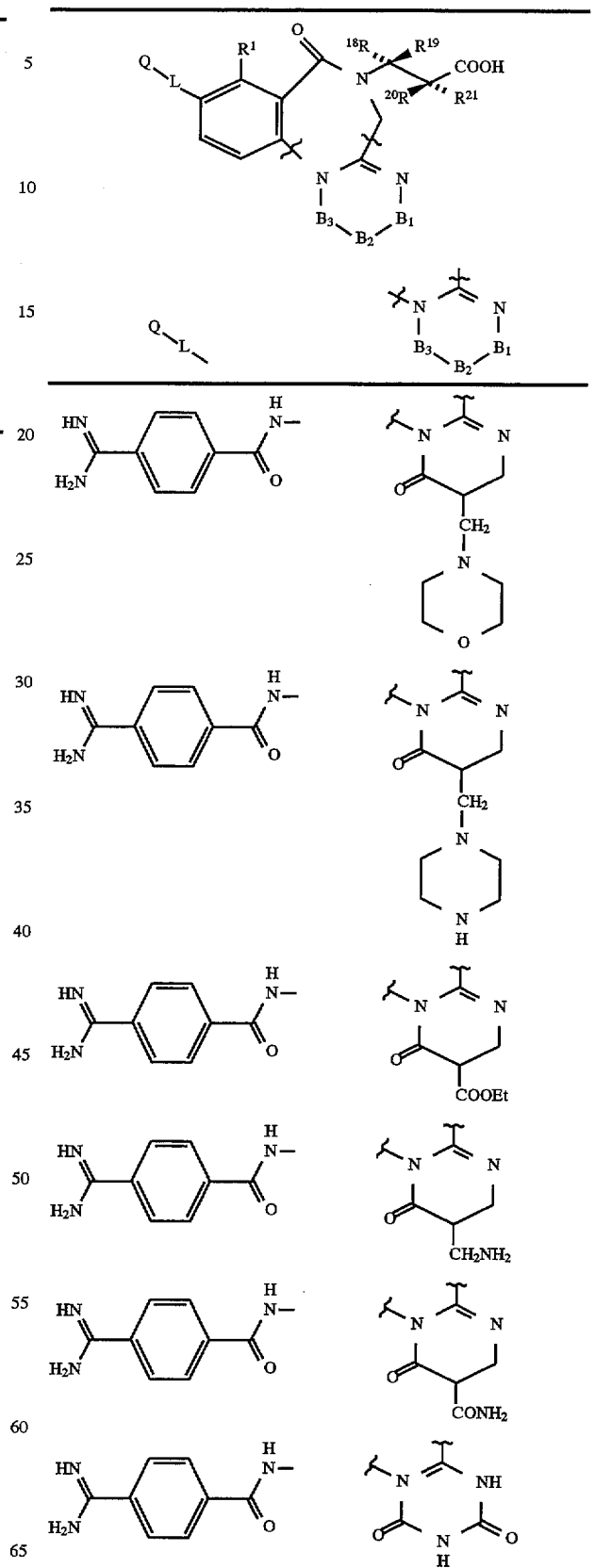

TABLE II-continued
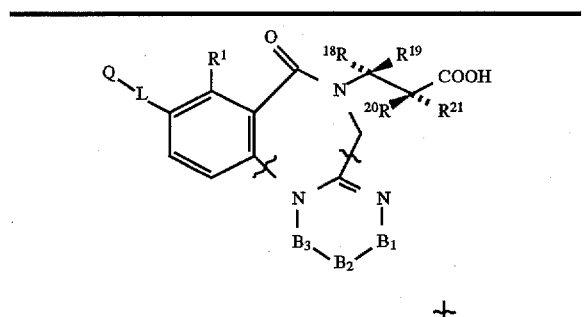
| Q-L- | (B ring) |
|---|---|
| 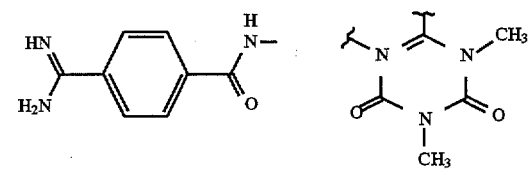 | 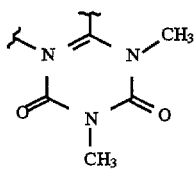 |
| 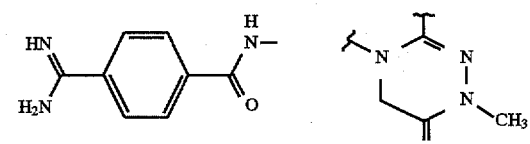 | 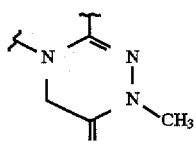 |
| 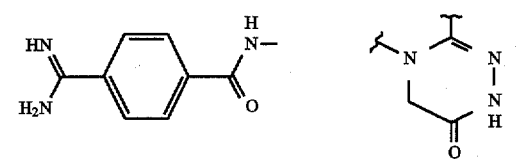 | 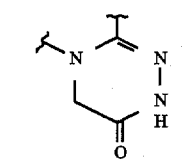 |
| 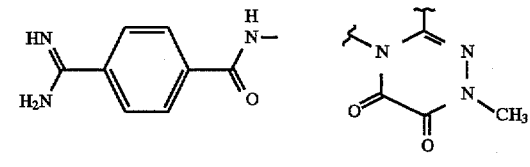 | 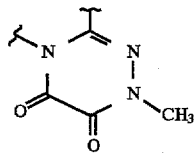 |
| 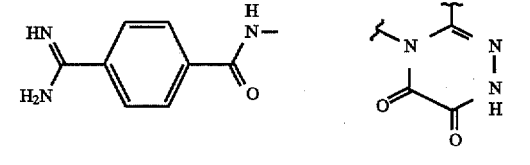 | 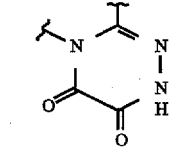 |
| 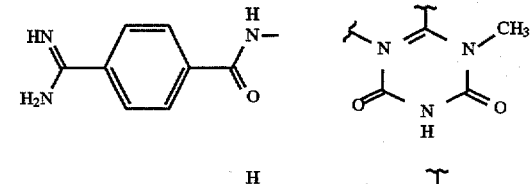 | 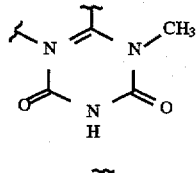 |
| 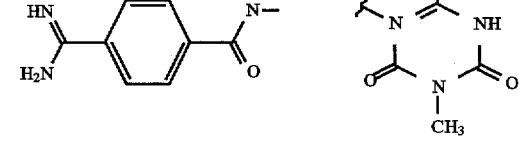 | 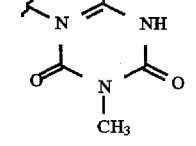 |
TABLE II-continued
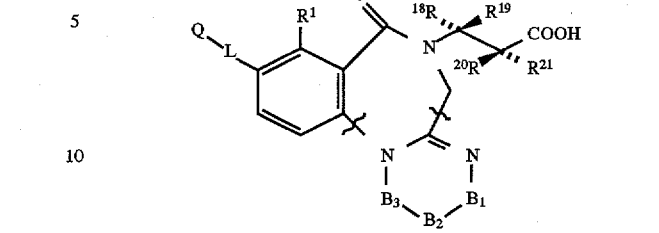
| Q-L- | (B ring) |
|---|---|
| 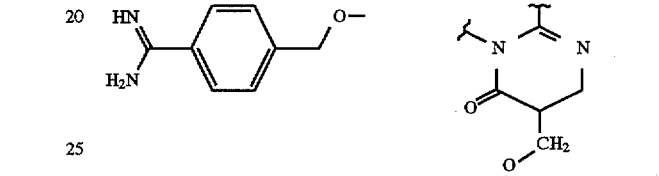 | 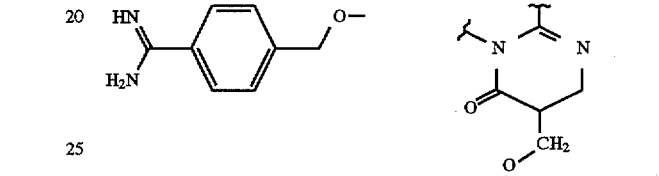 |
|  |  |
| 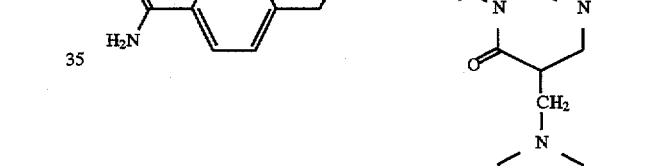 | 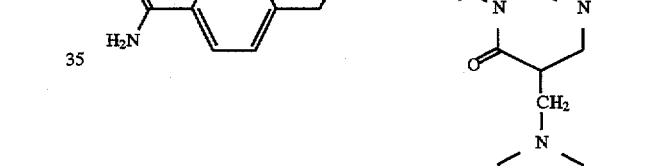 |
| 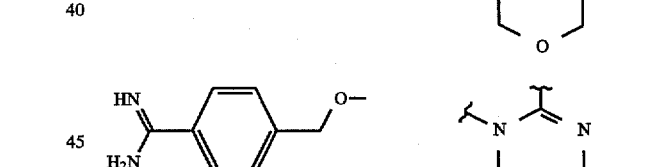 | 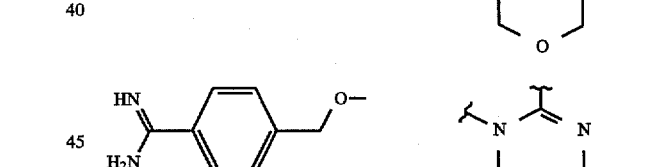 |
|  |  |
| 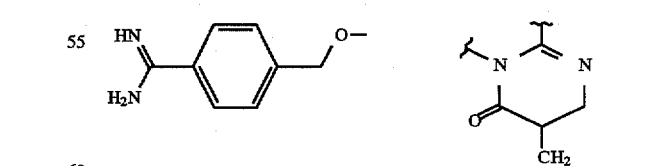 | 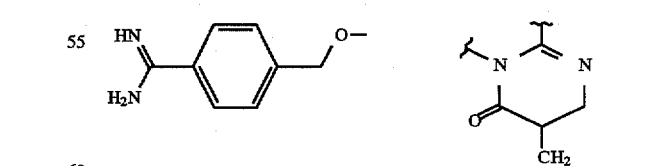 |
|  |  |

TABLE II-continued
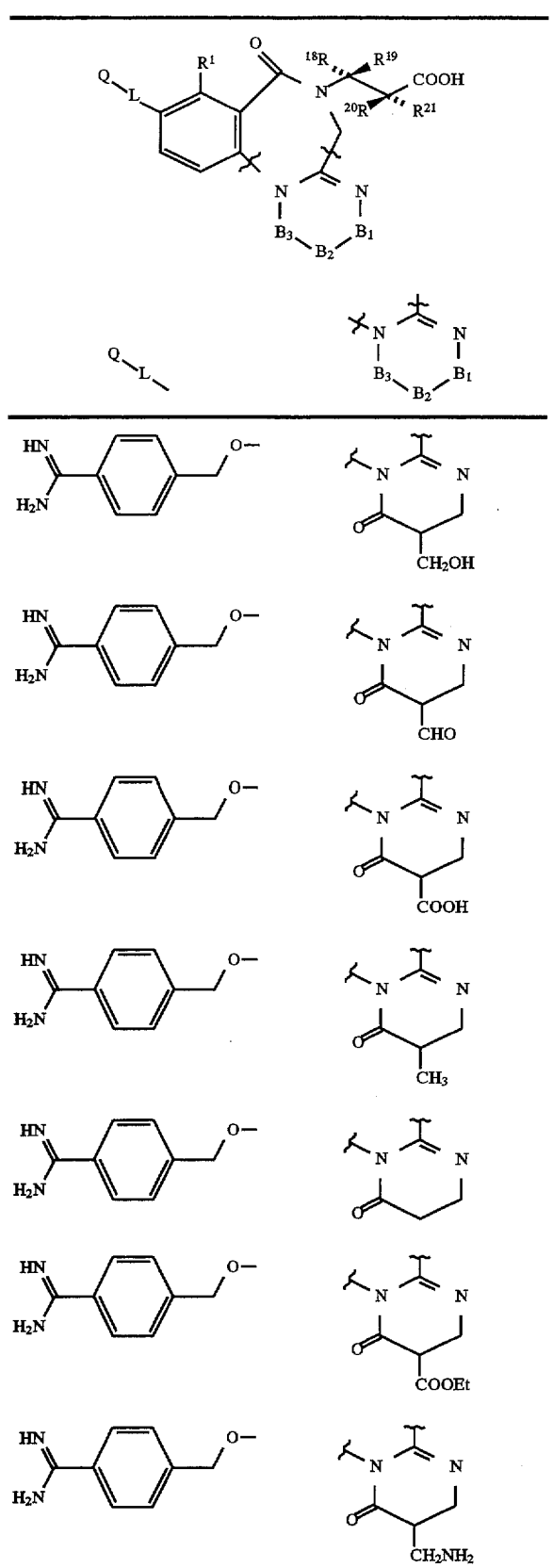
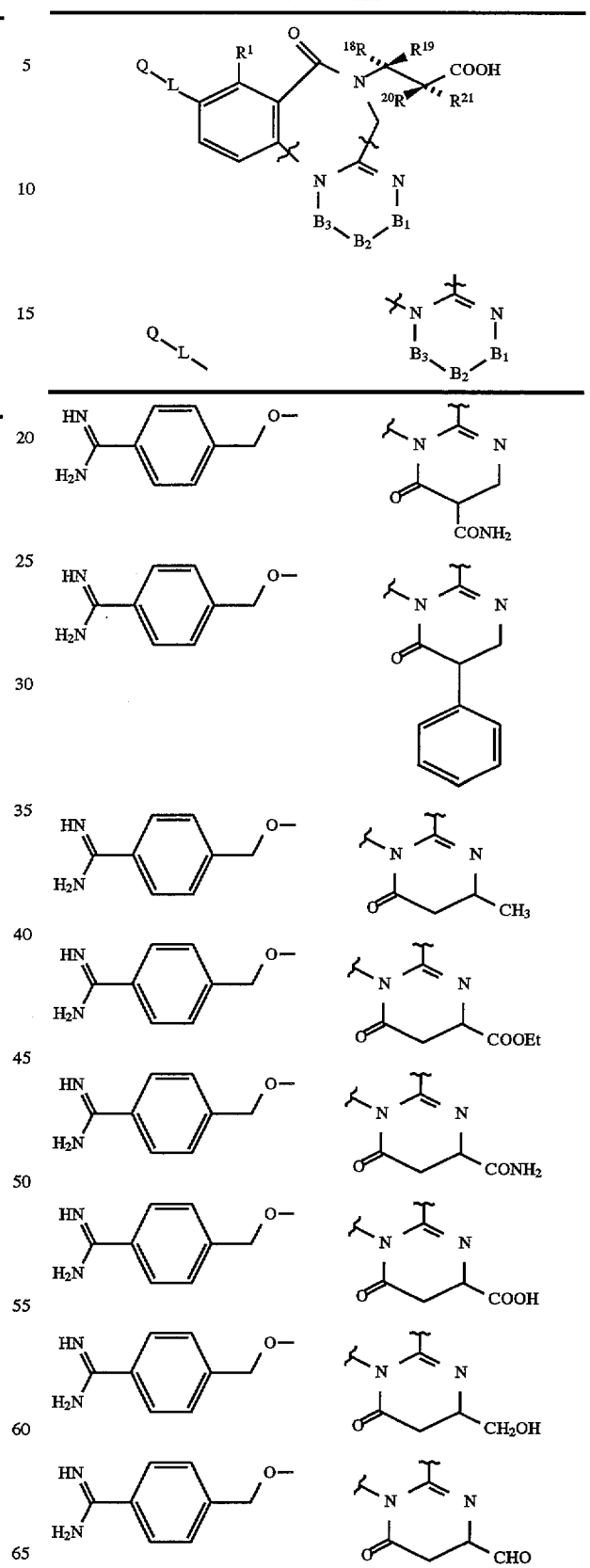

TABLE II-continued
| Q-L- | (structure) |
|---|---|
| 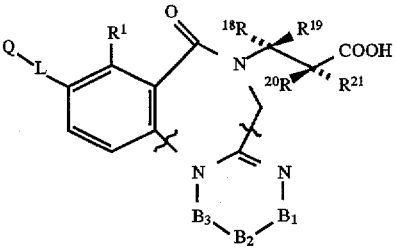 | 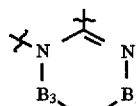 |
| 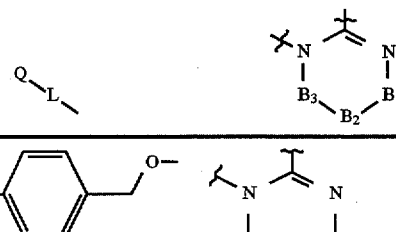 | 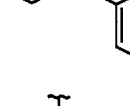 |
| 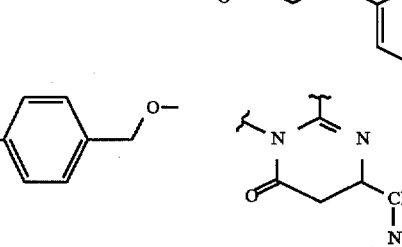 | 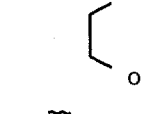 |
| 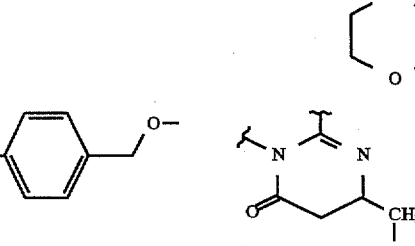 | 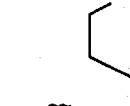 |
| 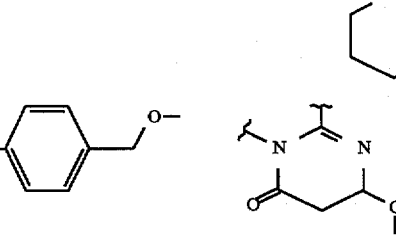 | 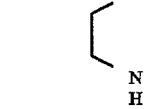 |
TABLE II-continued
| Q-L- | (structure) |
|---|---|
| 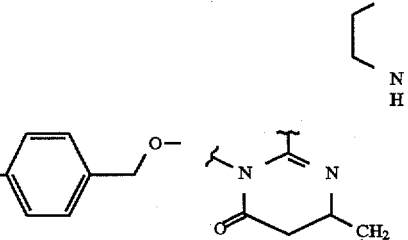 | 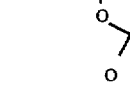 |
|  |  |
| 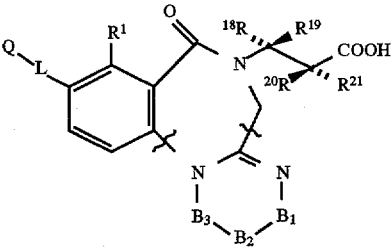 | 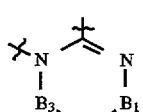 |
| 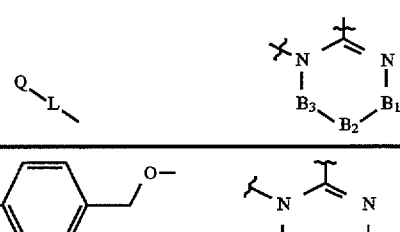 | 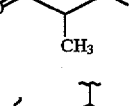 |
| 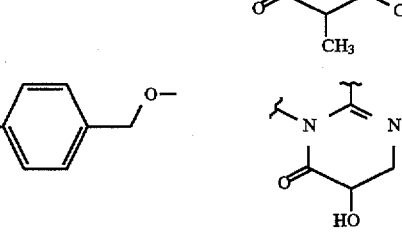 | 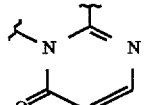 |

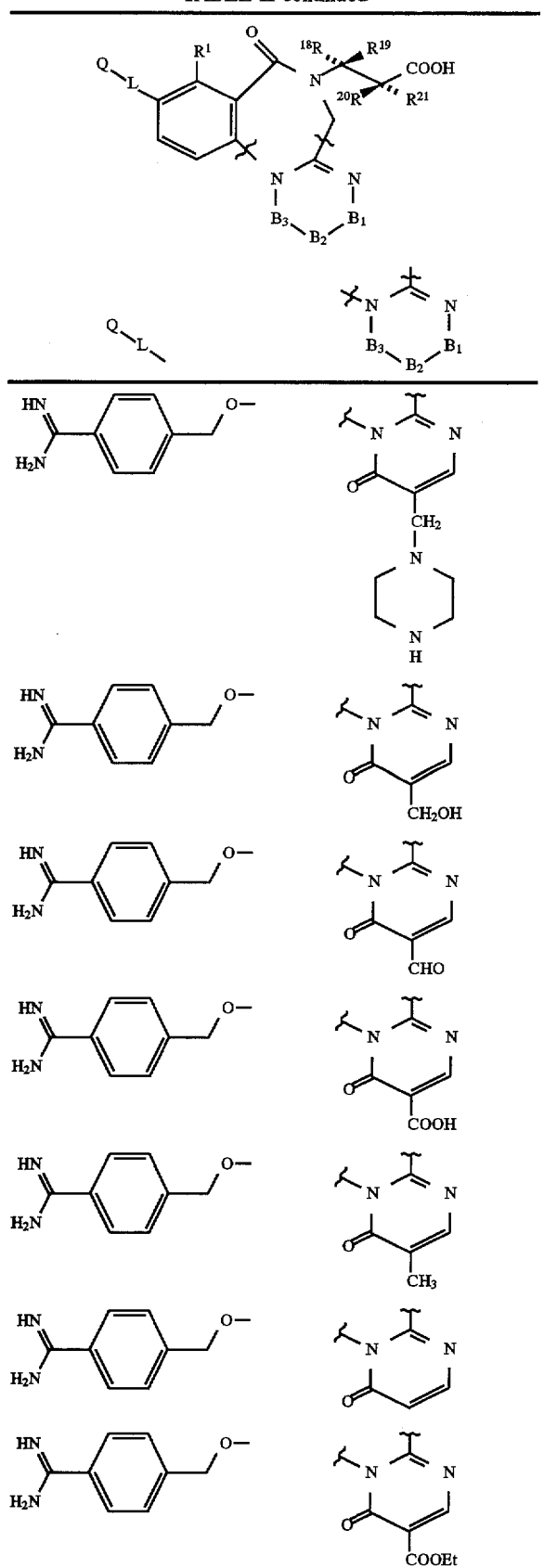

TABLE II-continued
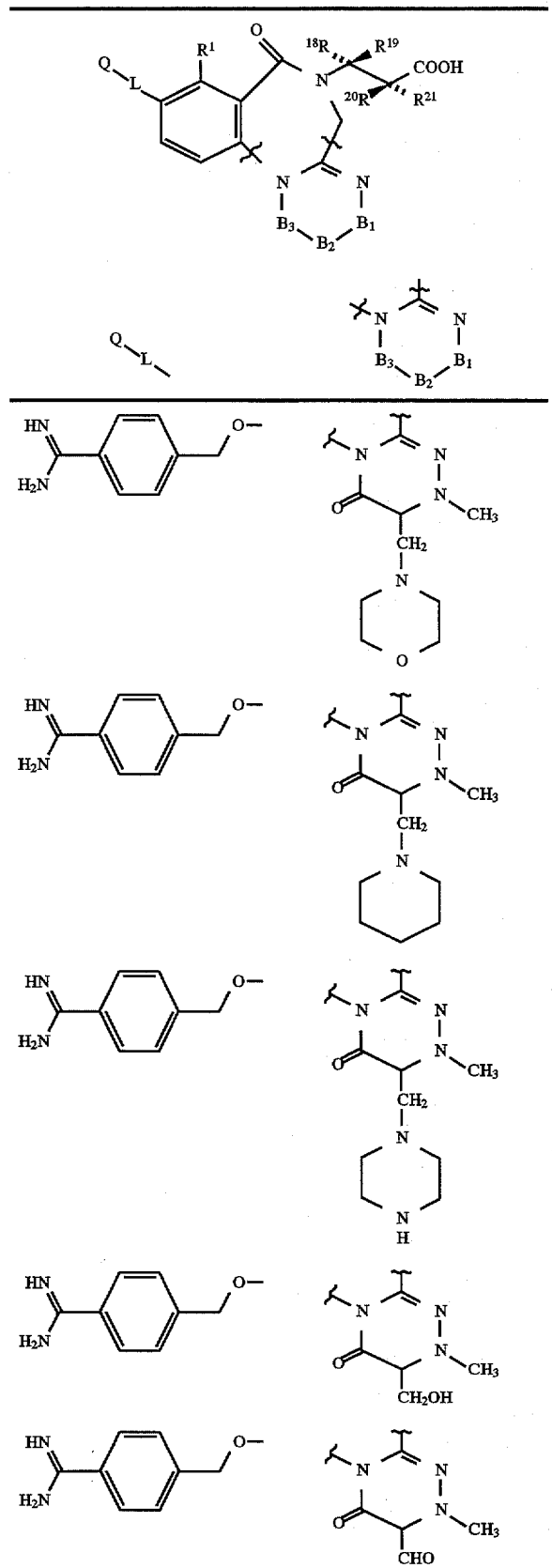
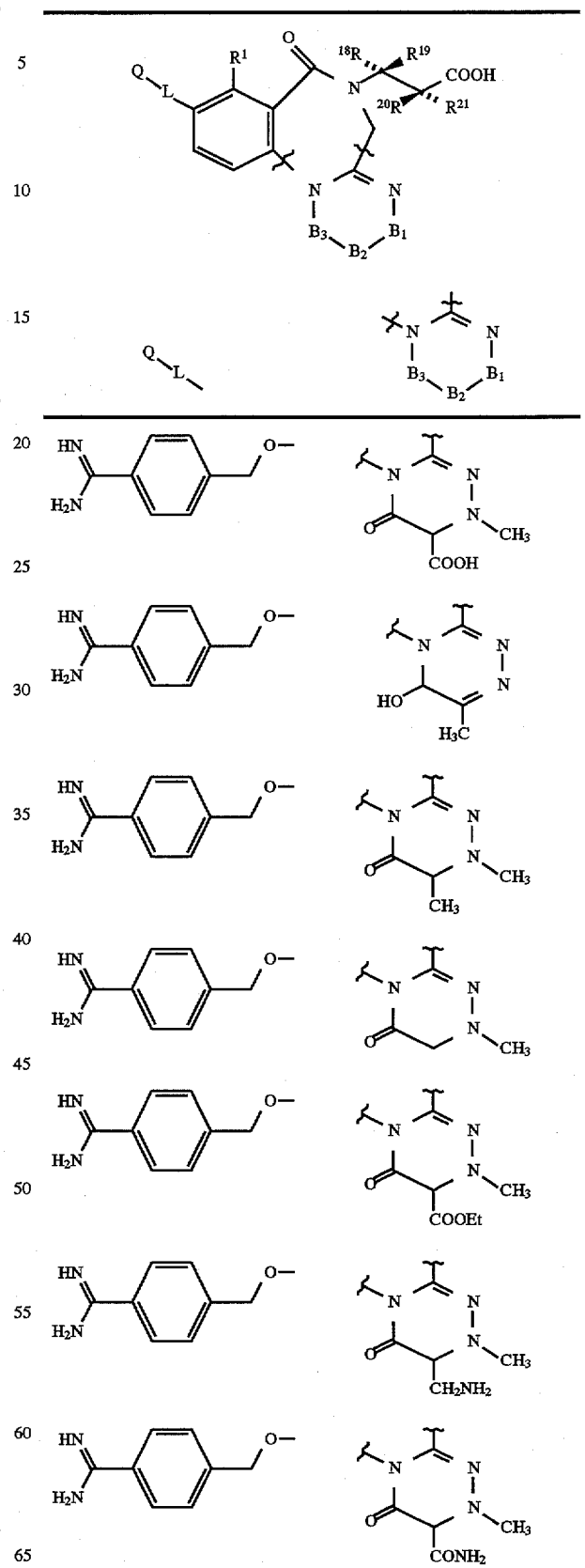

TABLE II-continued
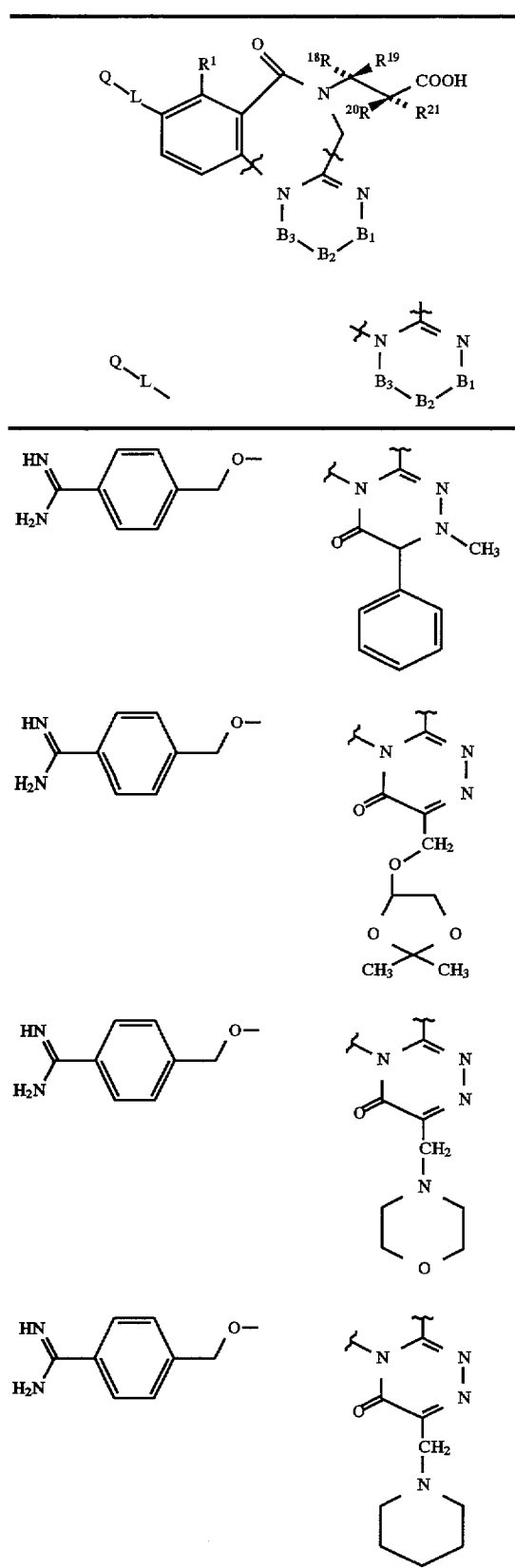
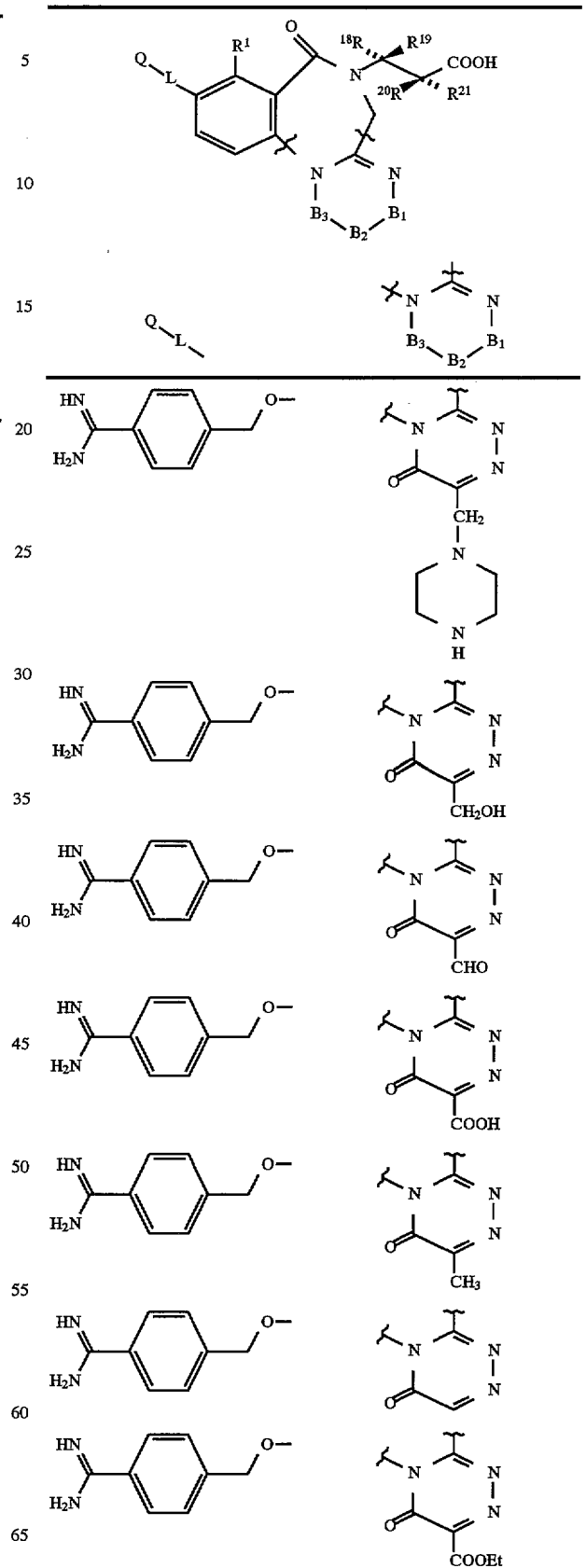

TABLE II-continued
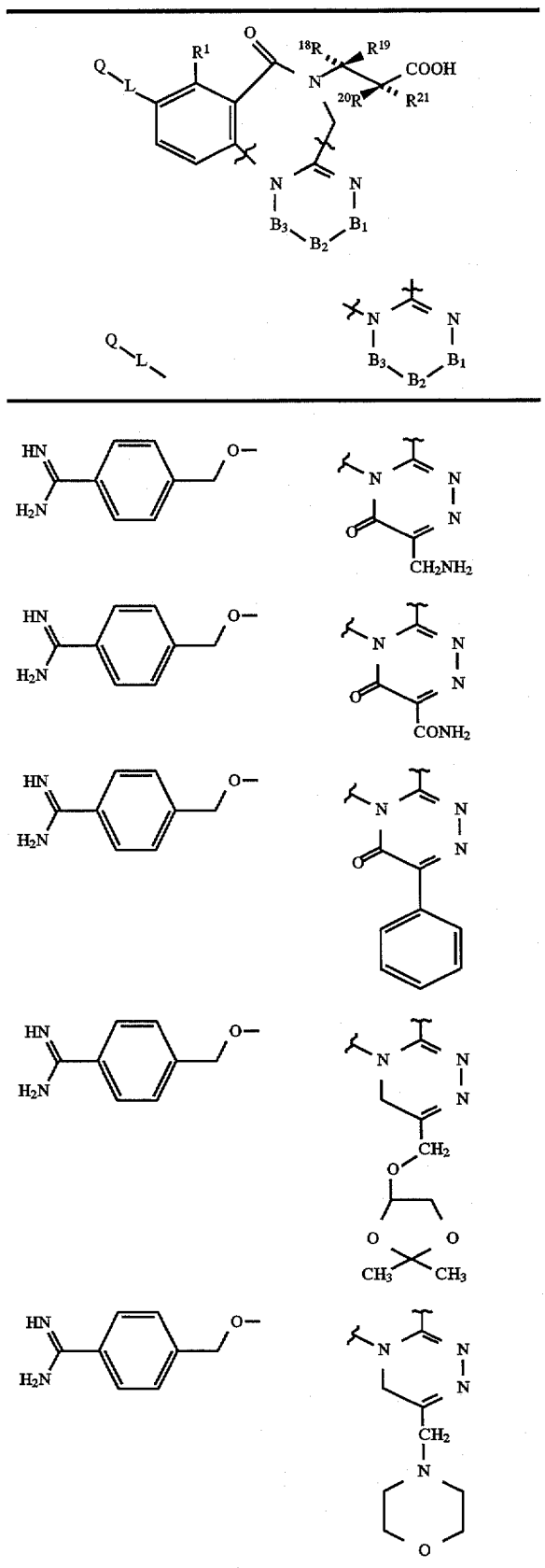
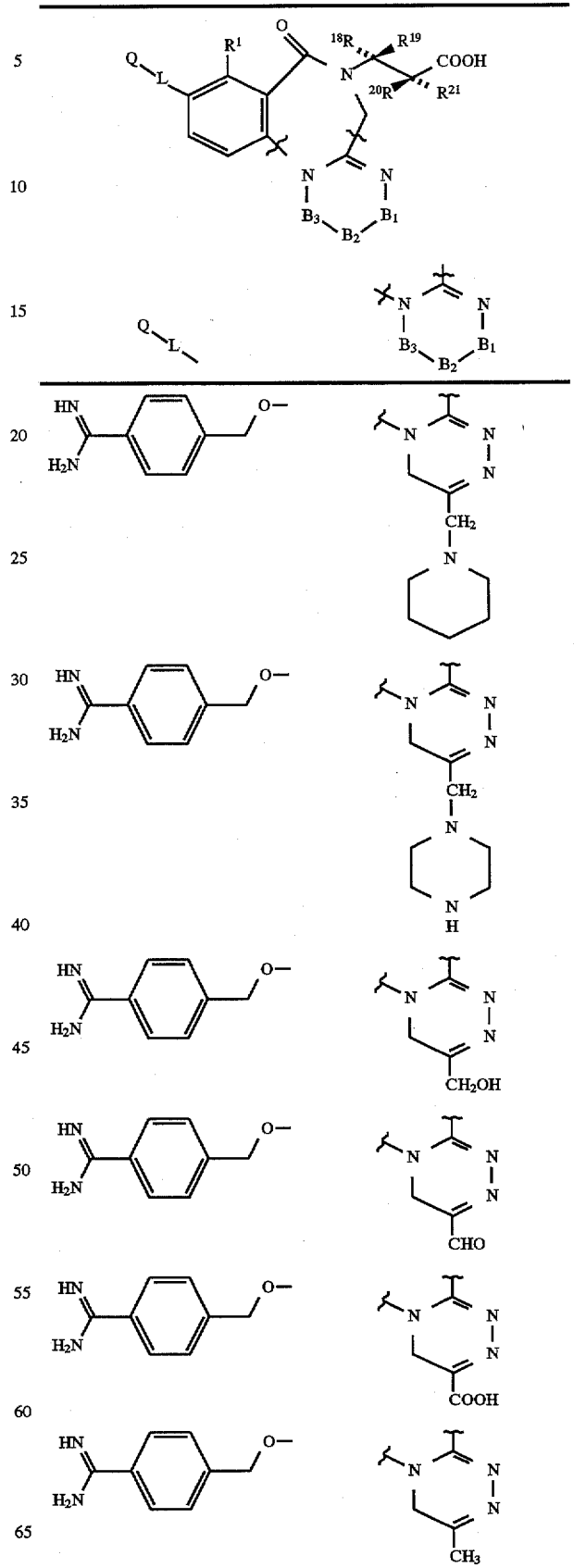

TABLE II-continued
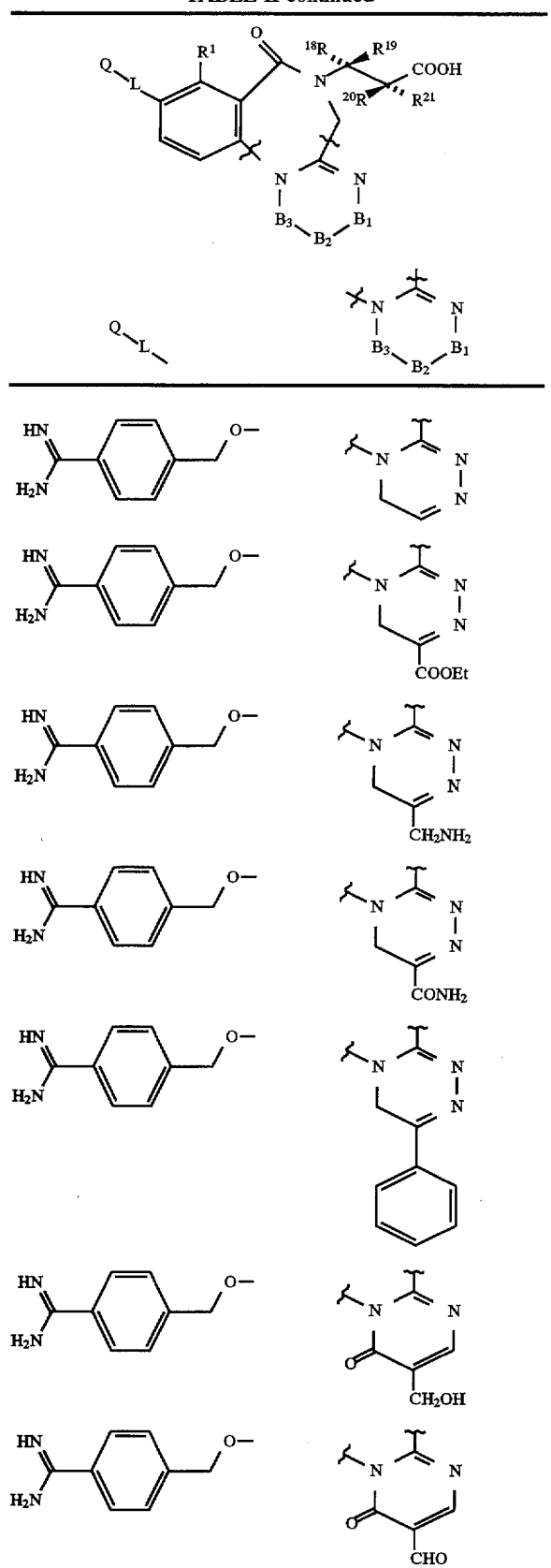
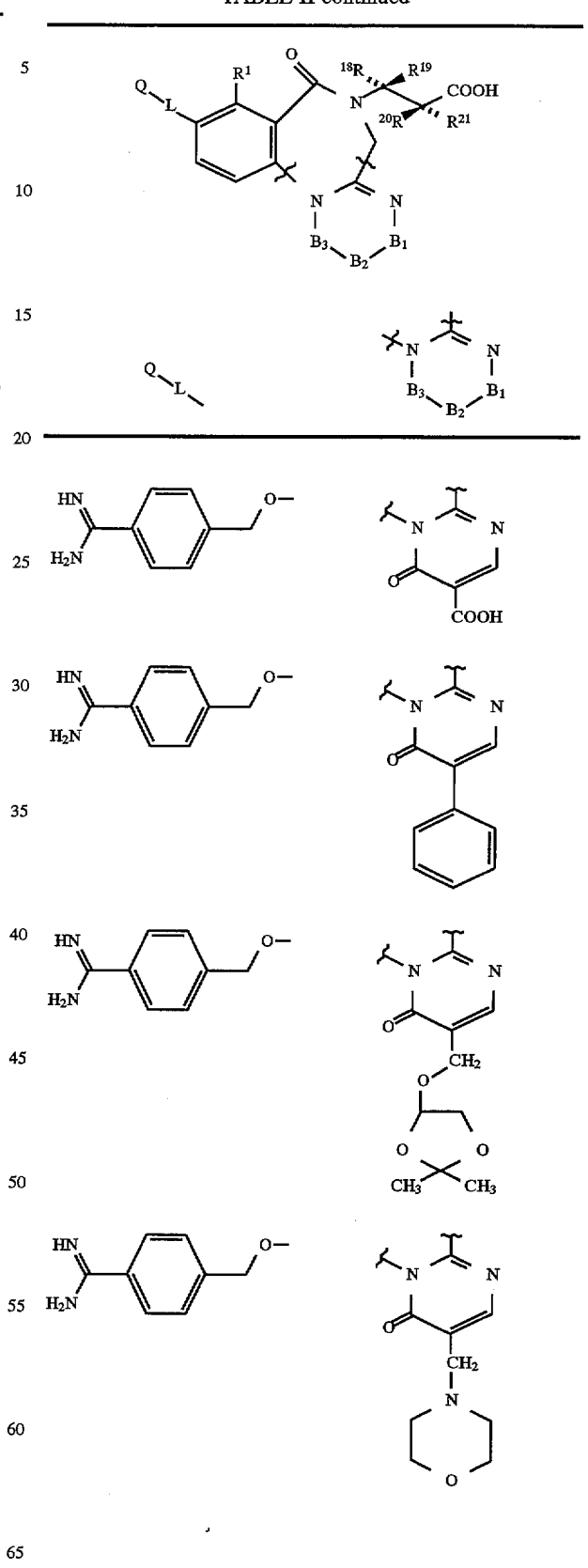

TABLE II-continued
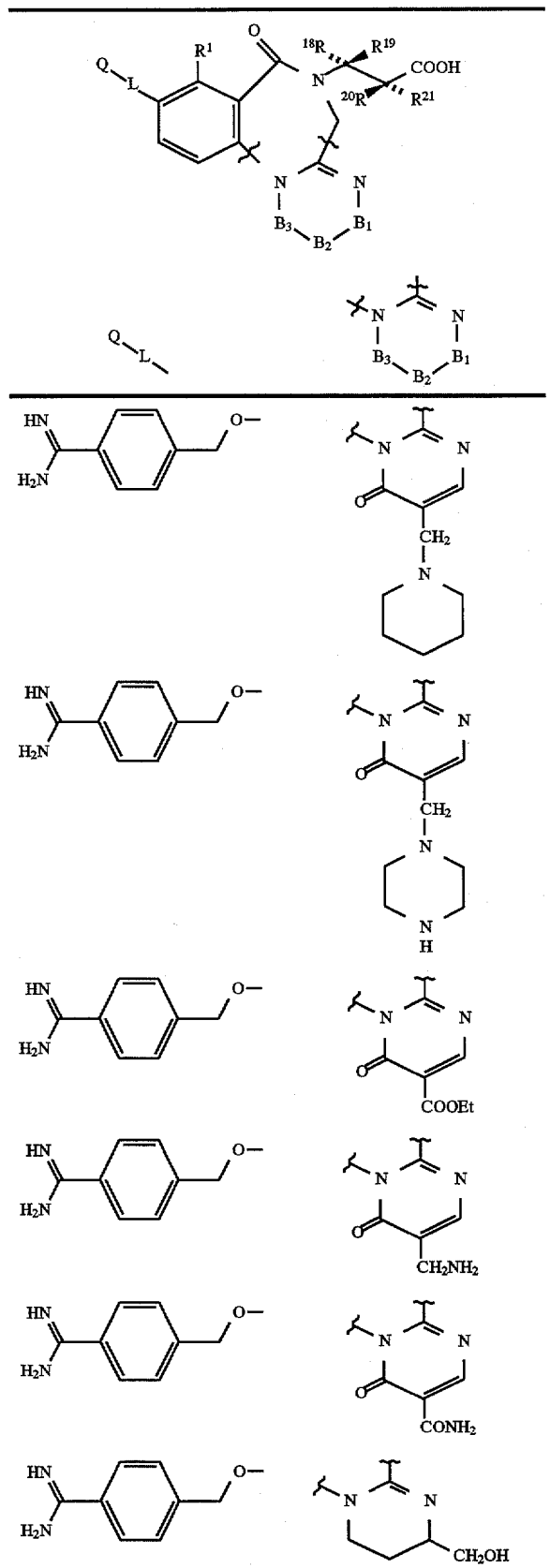
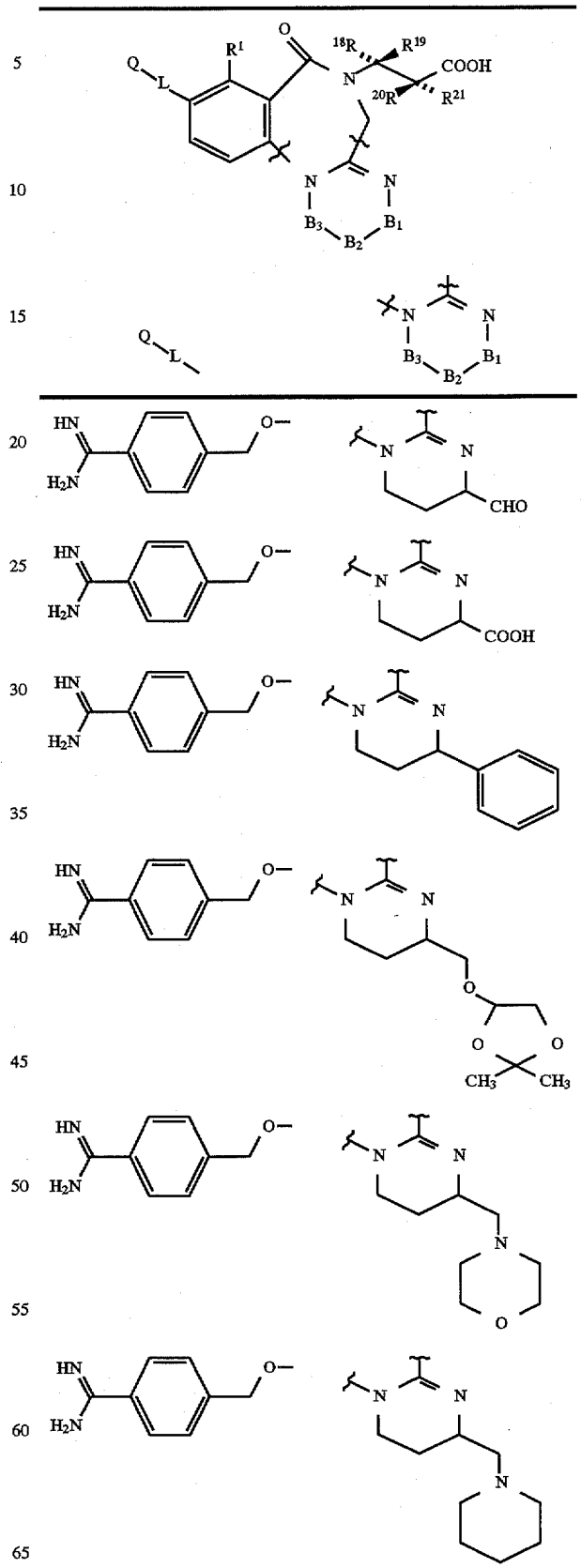

TABLE II-continued
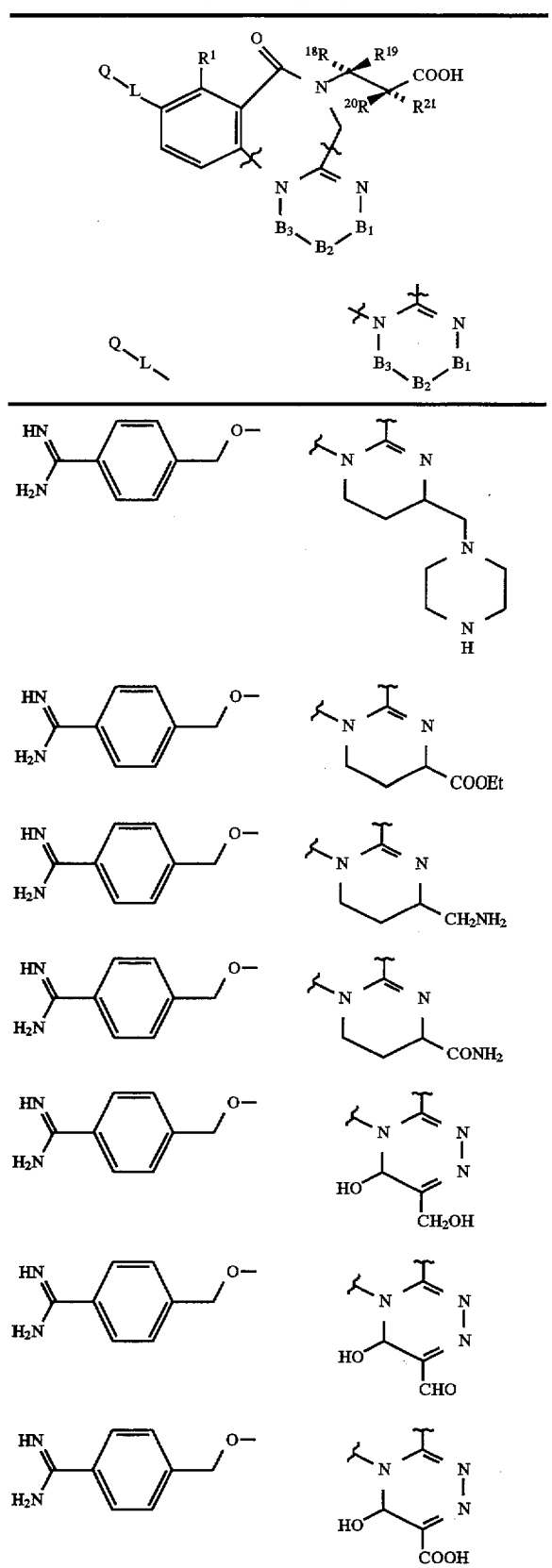
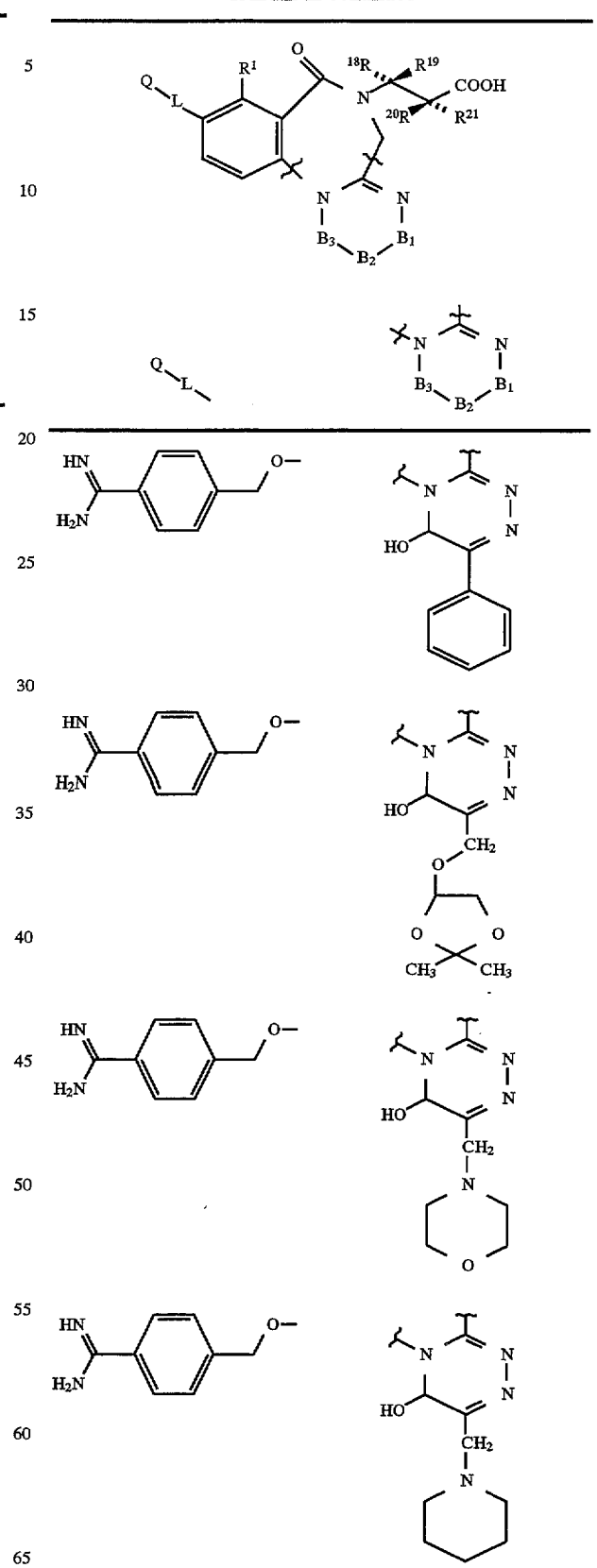

TABLE II-continued
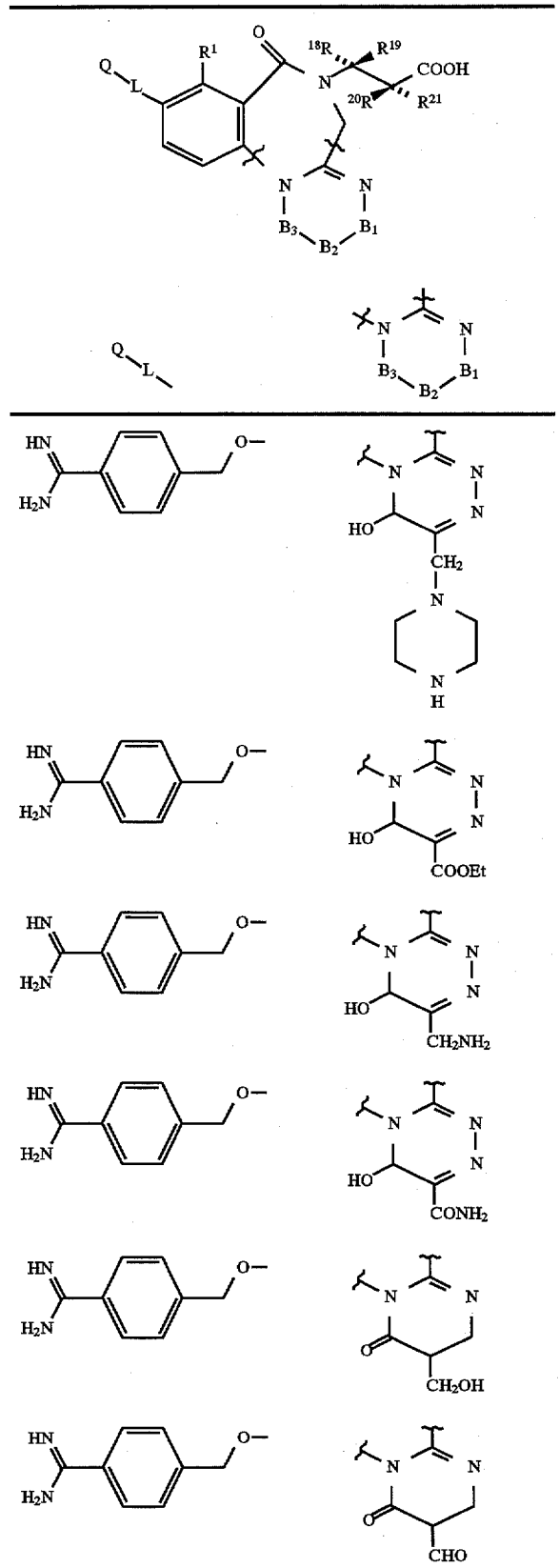
TABLE II-continued
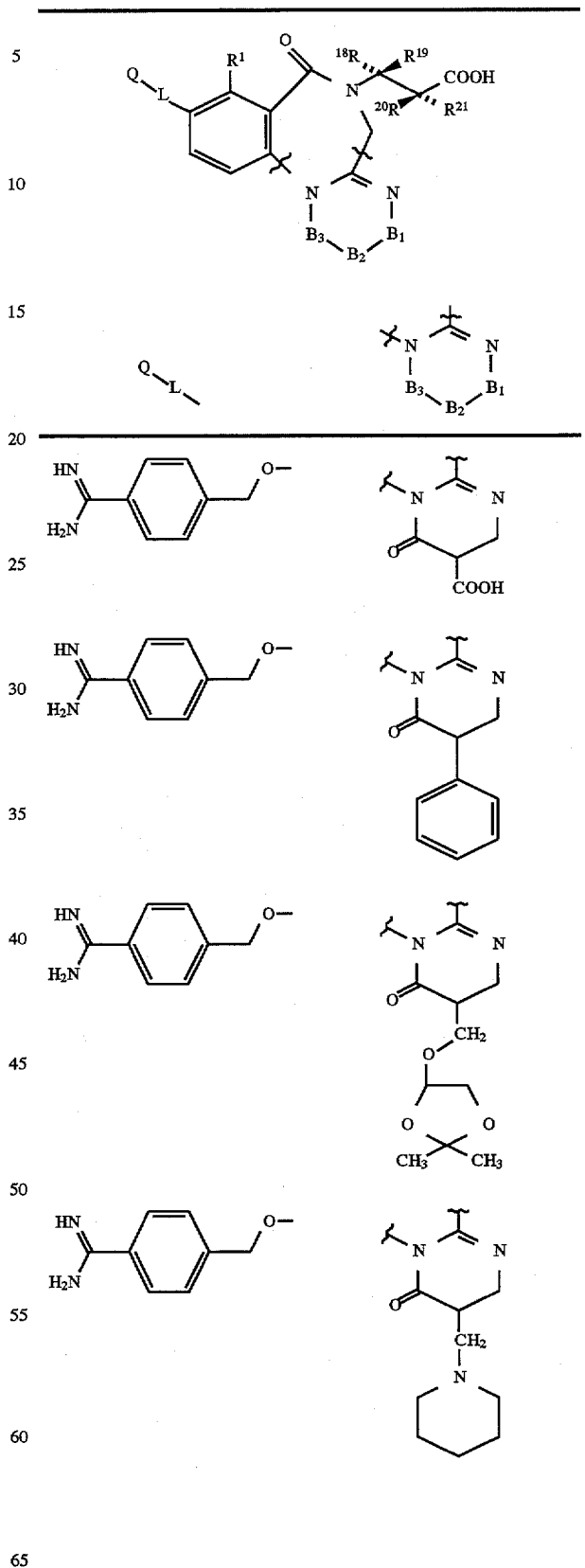

TABLE II-continued
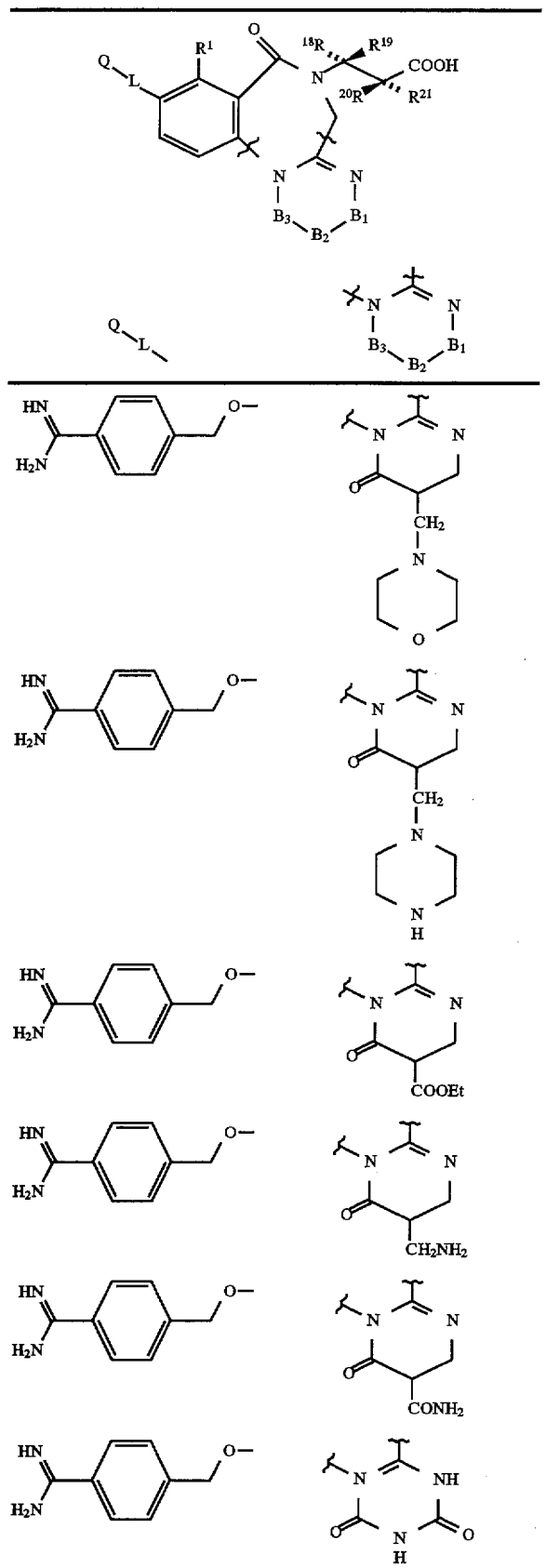
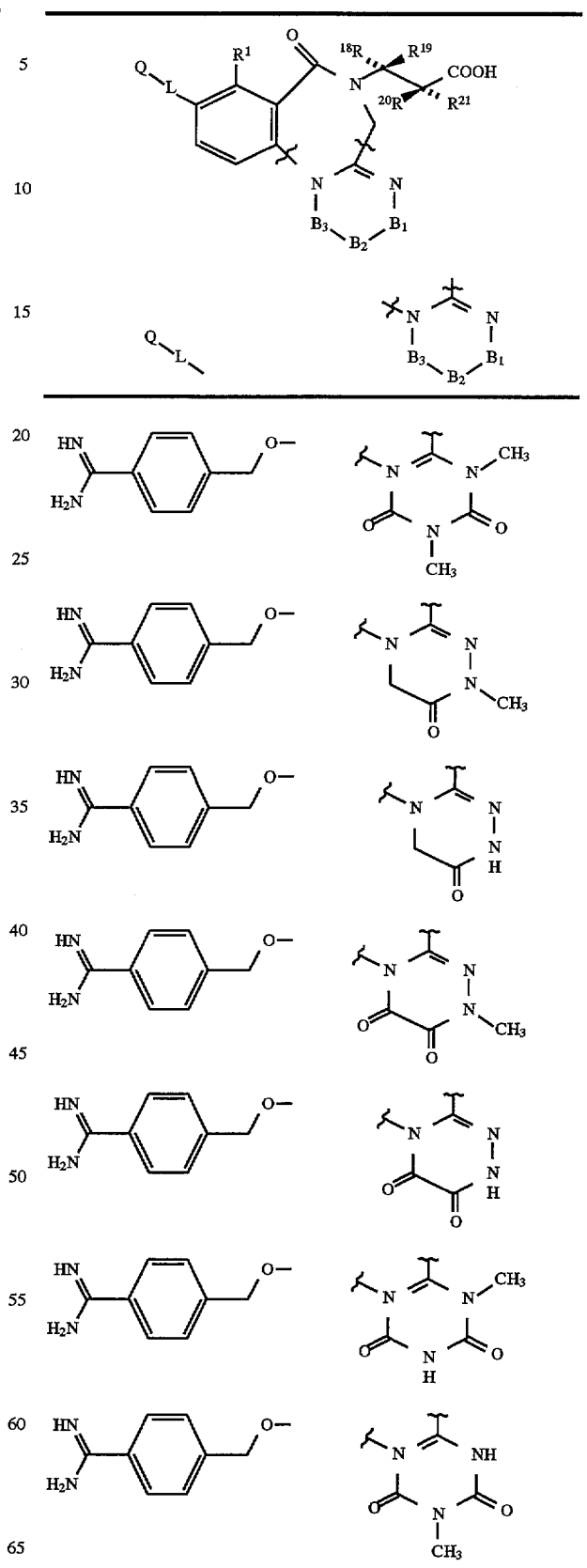

TABLE II-continued
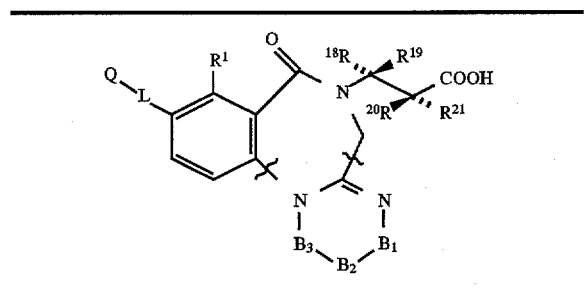
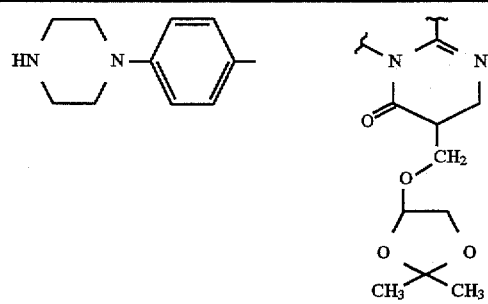
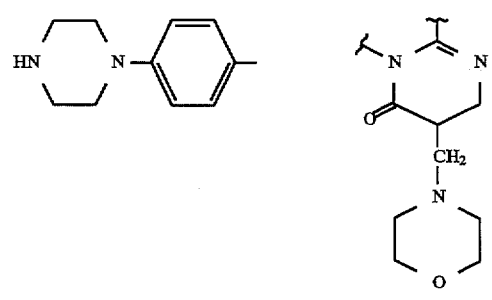
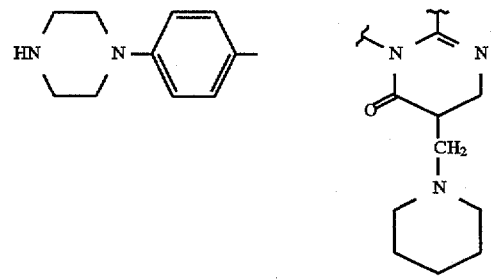
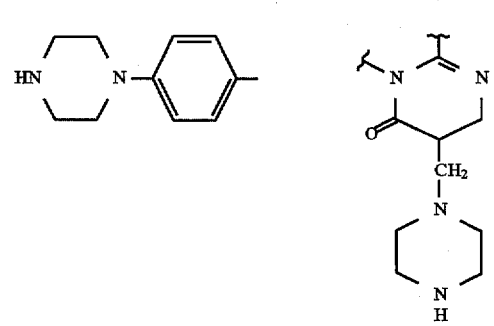
TABLE II-continued
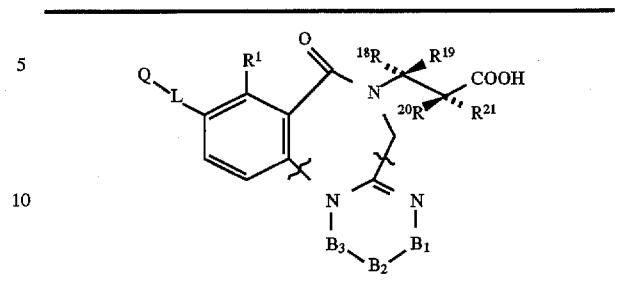
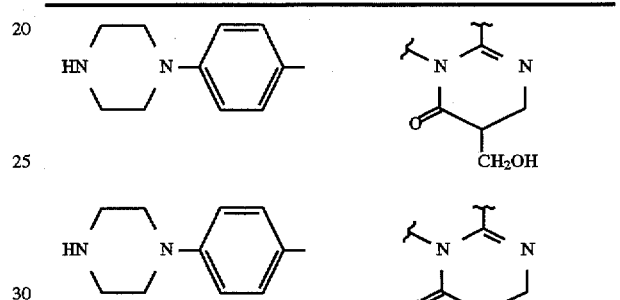
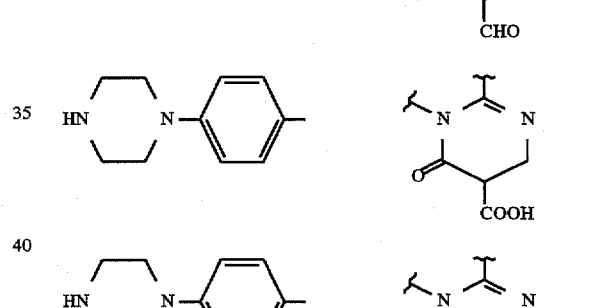
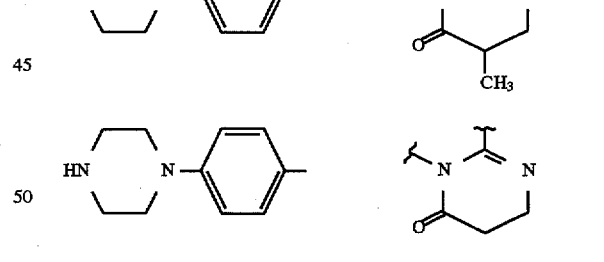
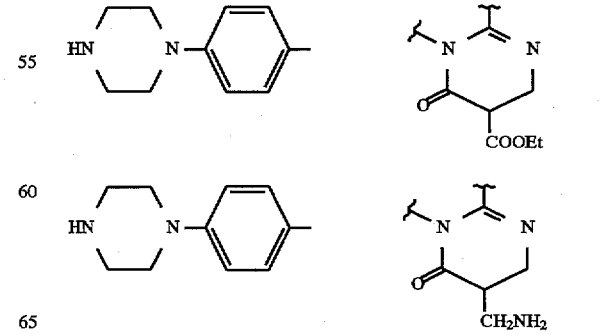

TABLE II-continued
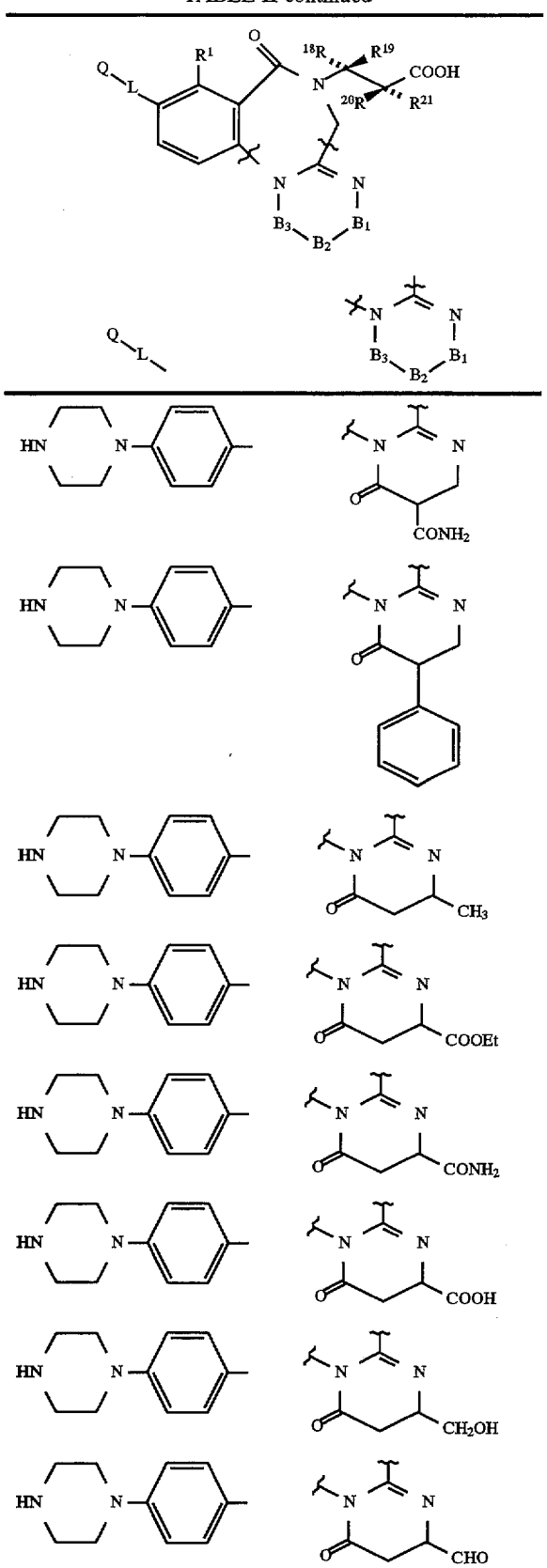
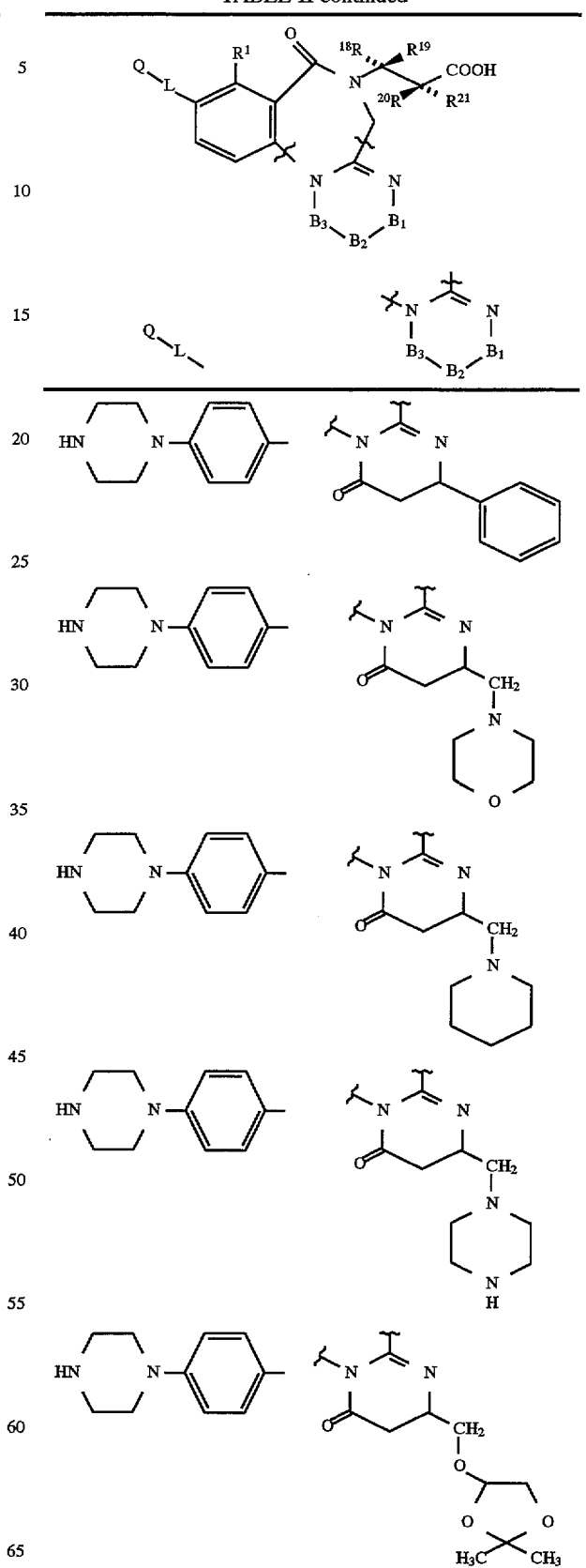

TABLE II-continued
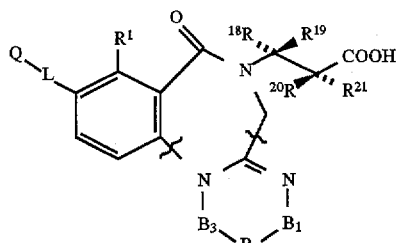

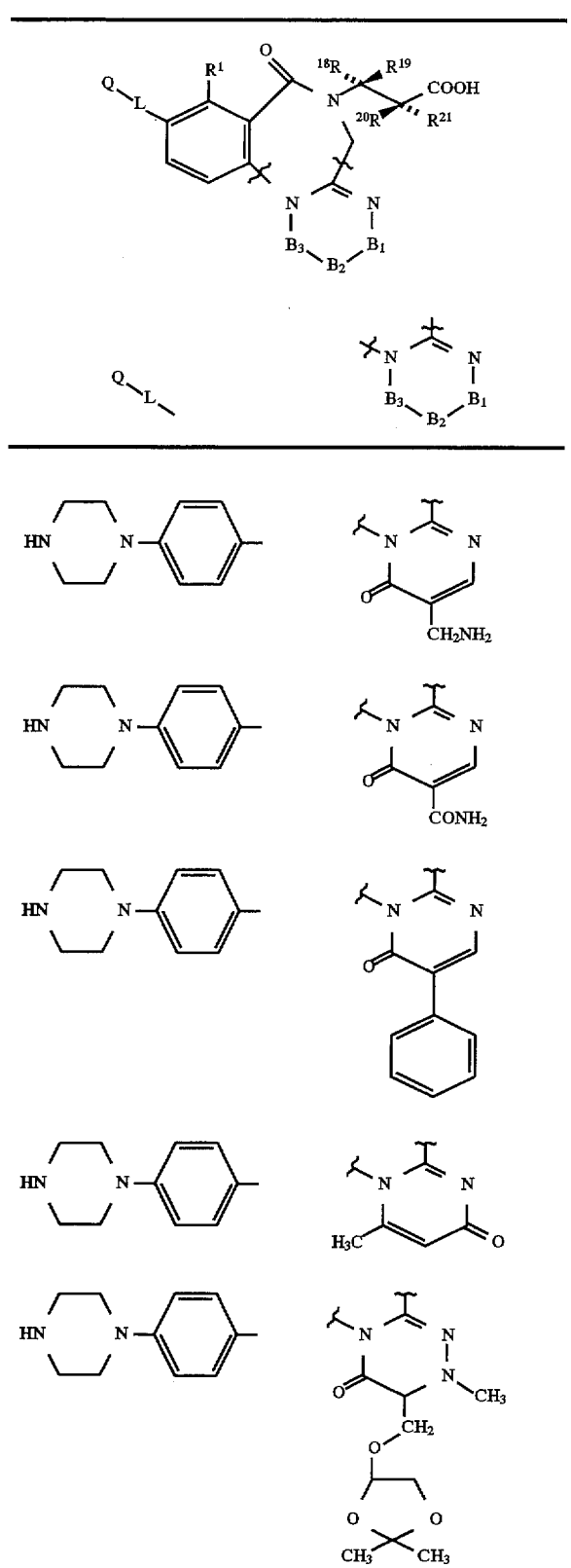
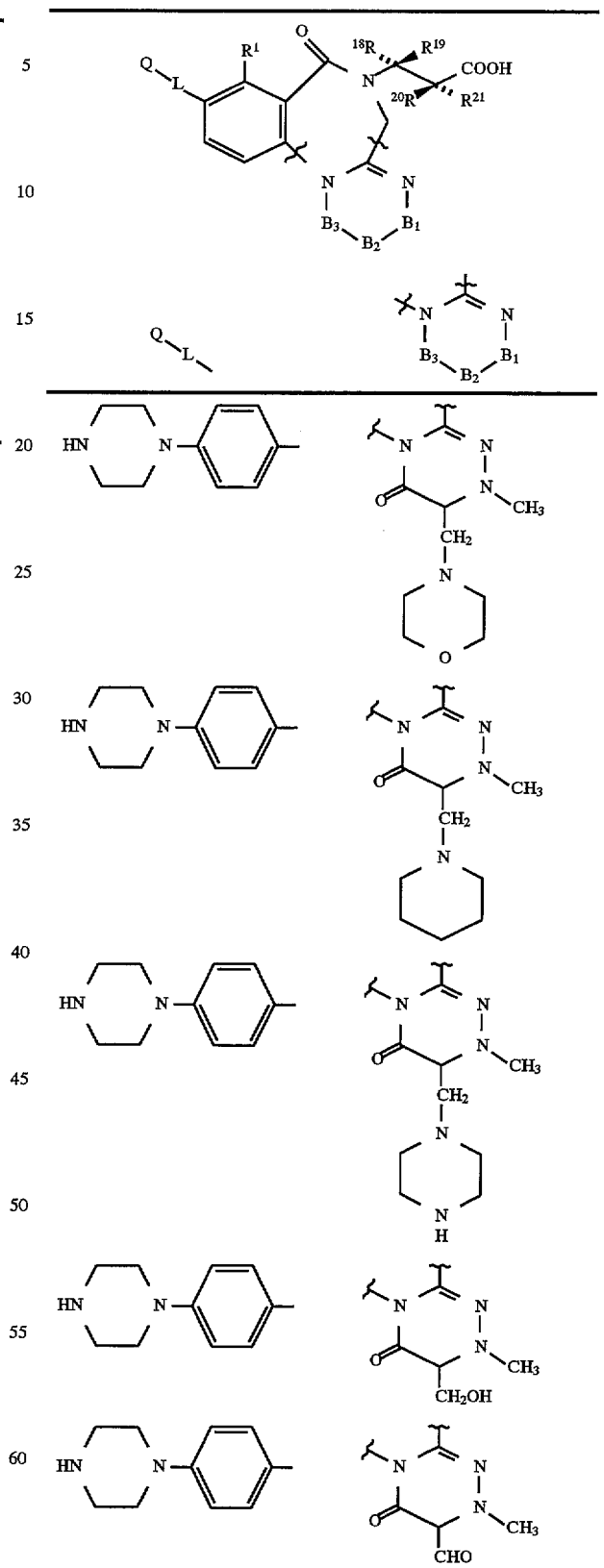

TABLE II-continued
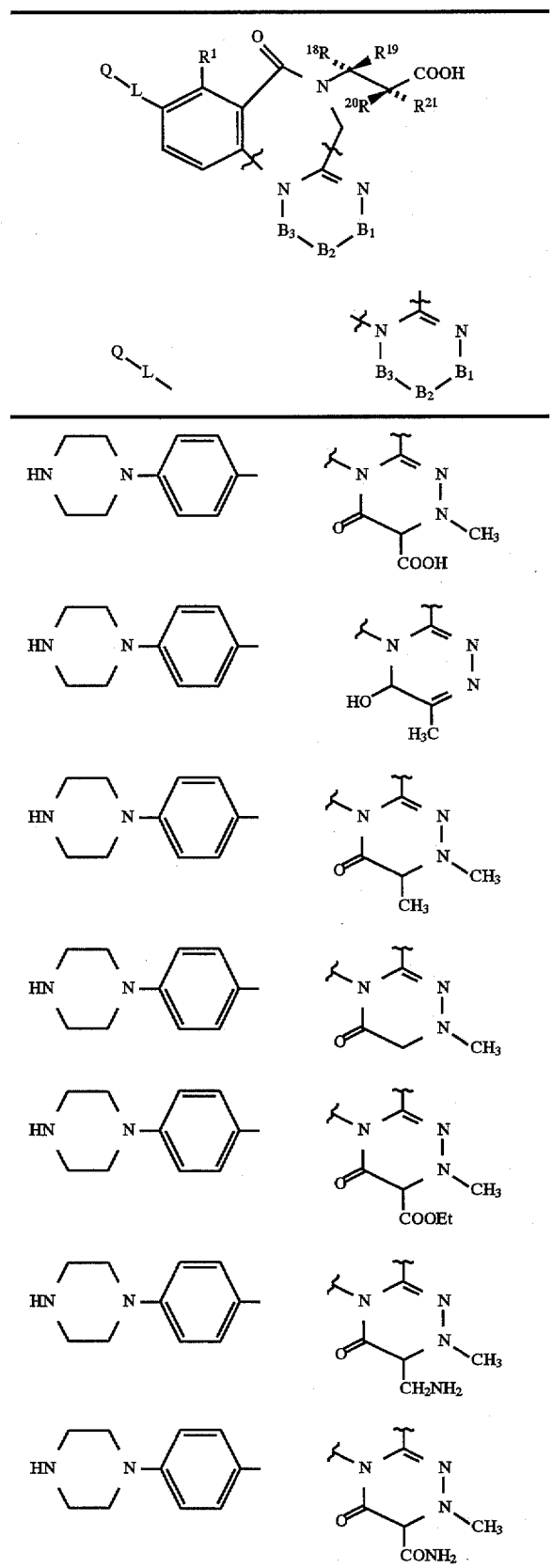
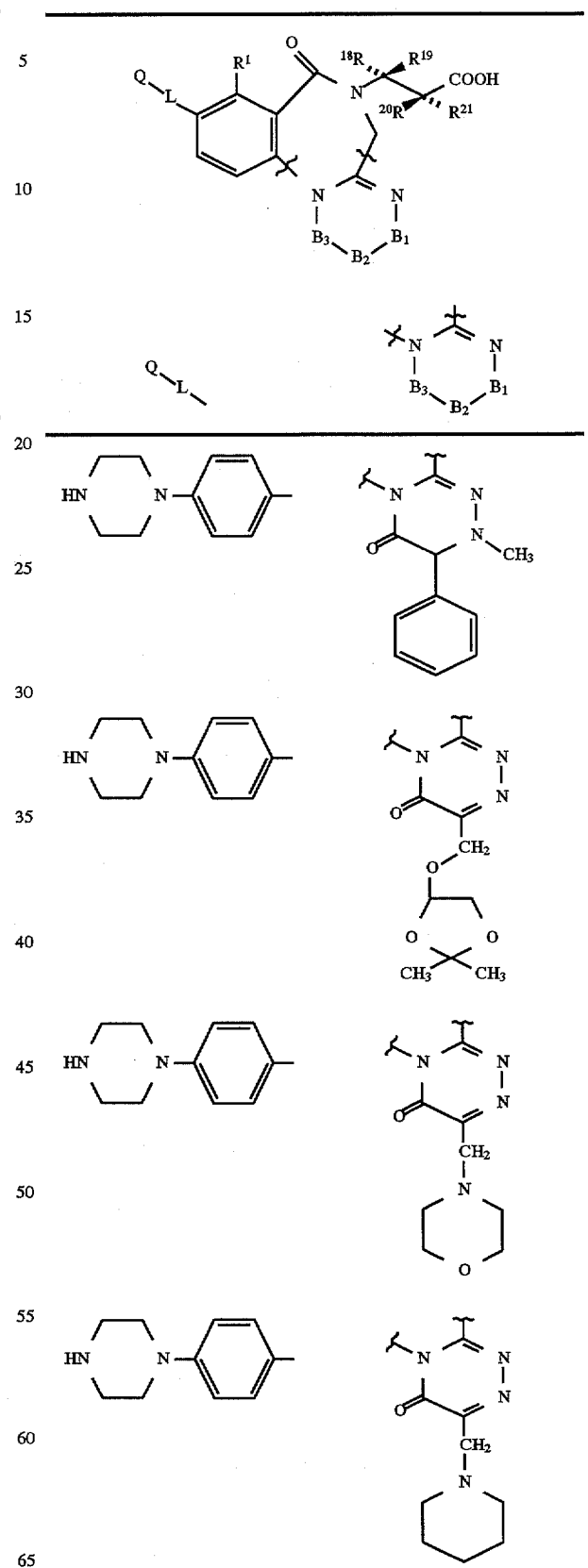

TABLE II-continued
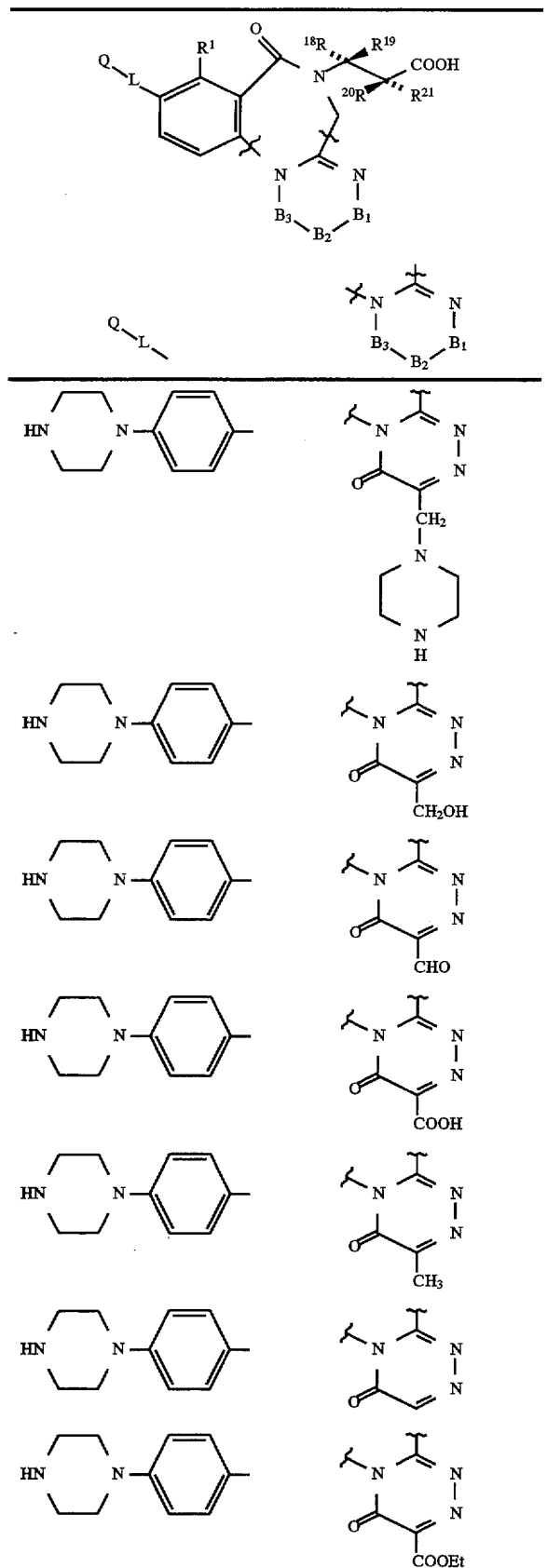
TABLE II-continued
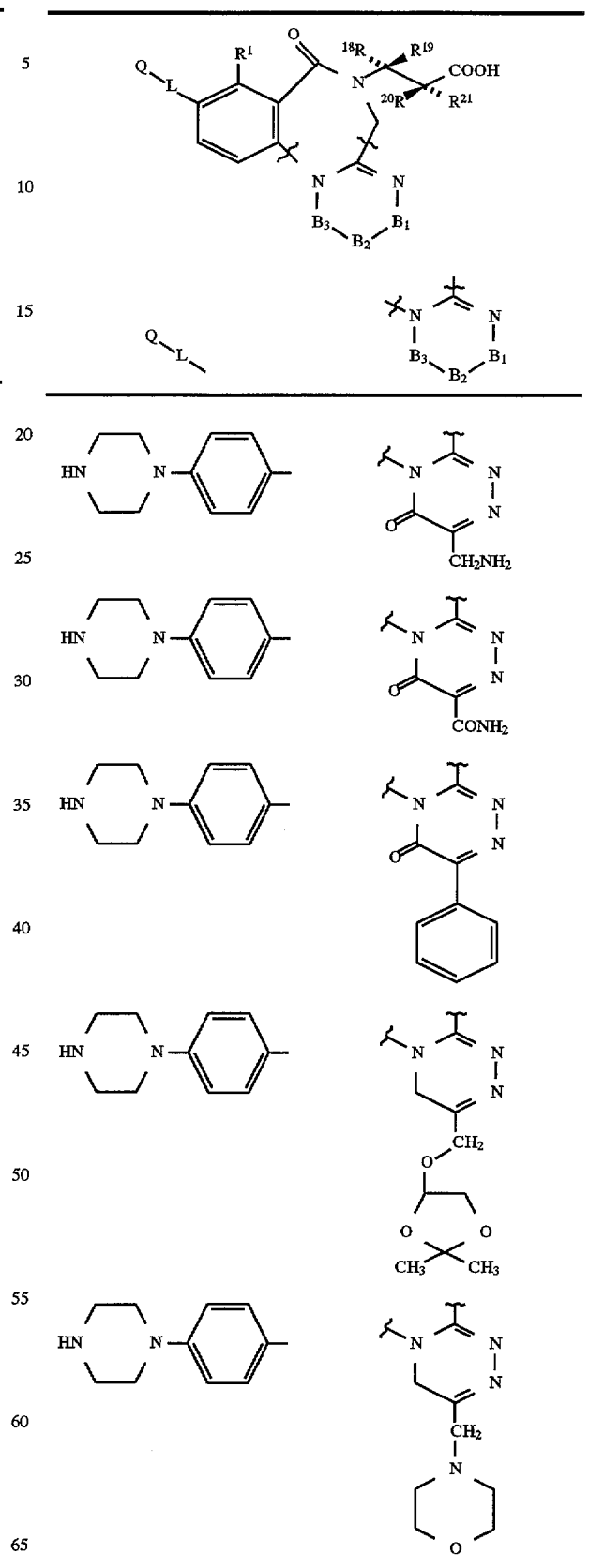

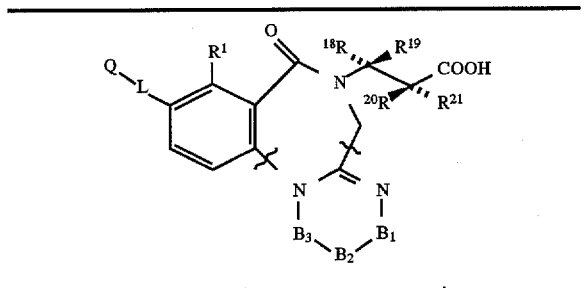
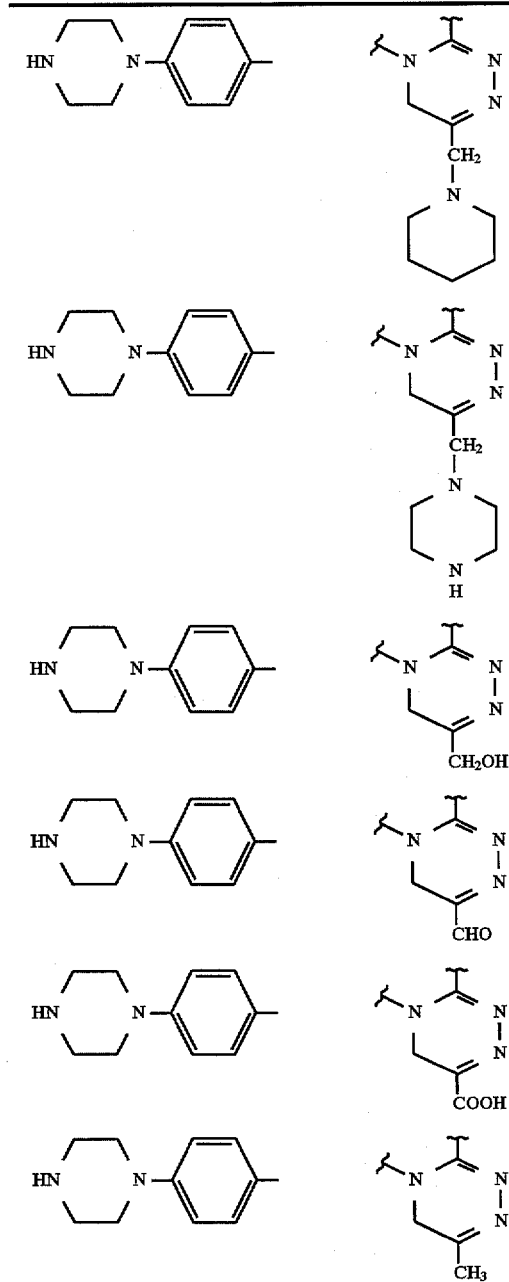
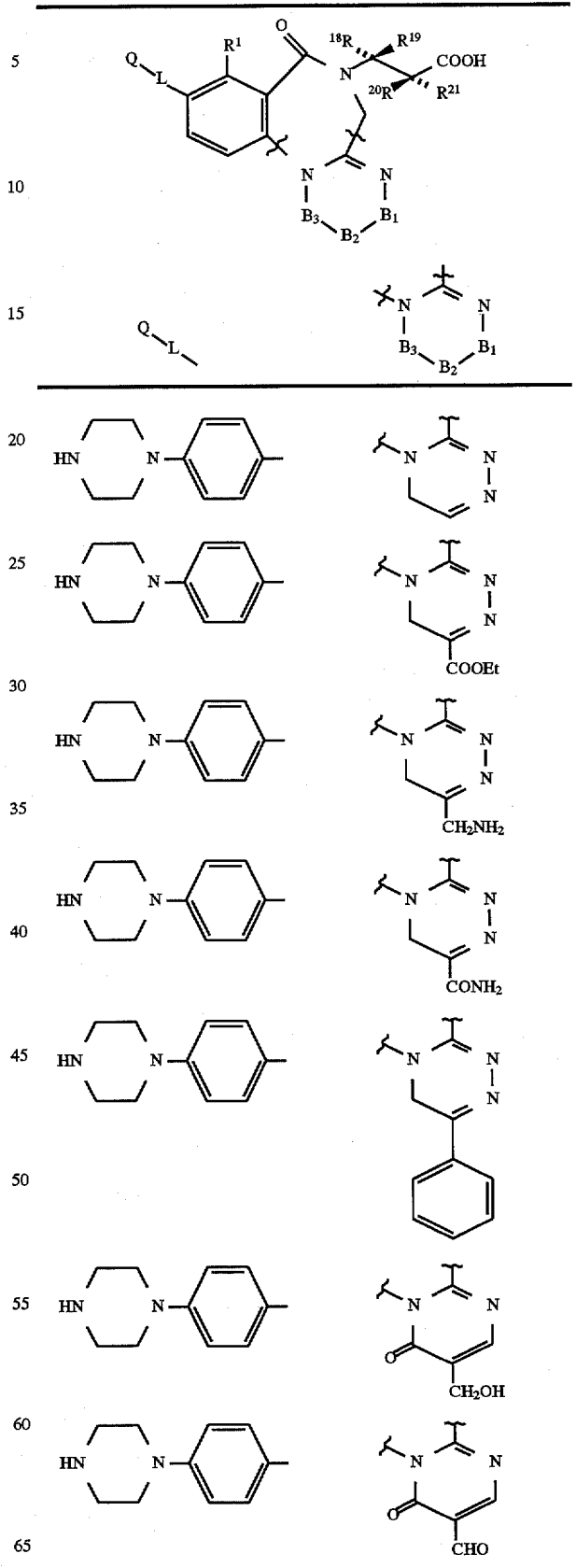

TABLE II-continued
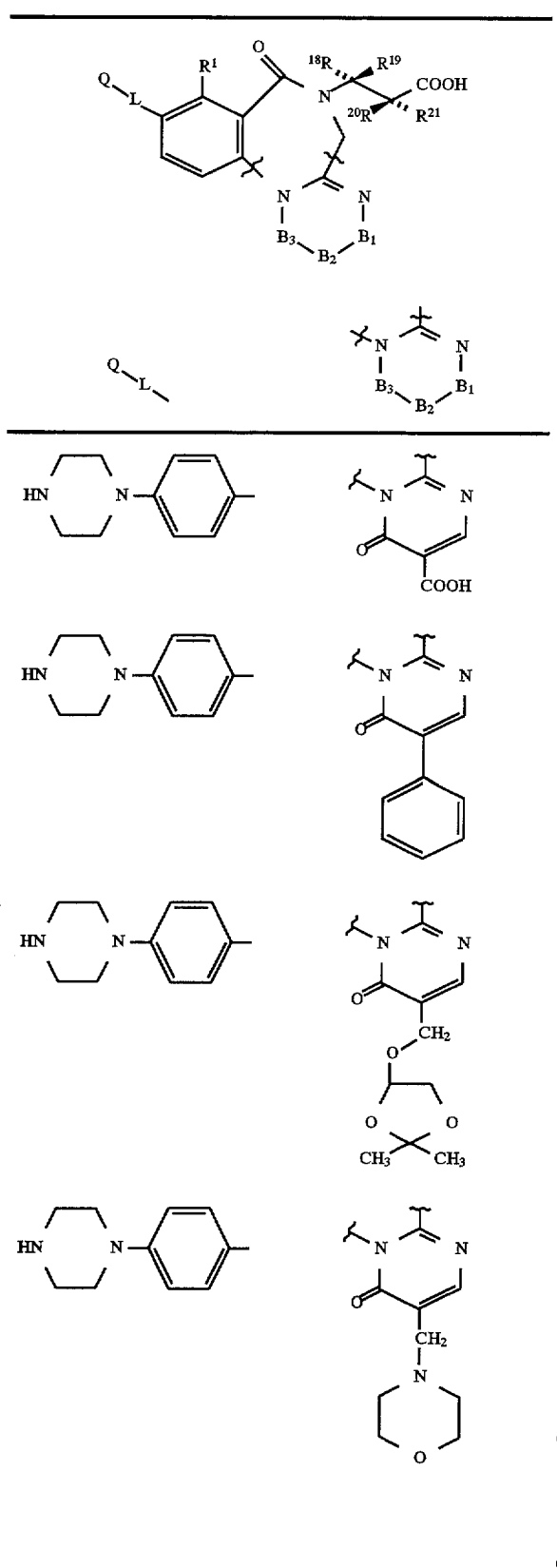
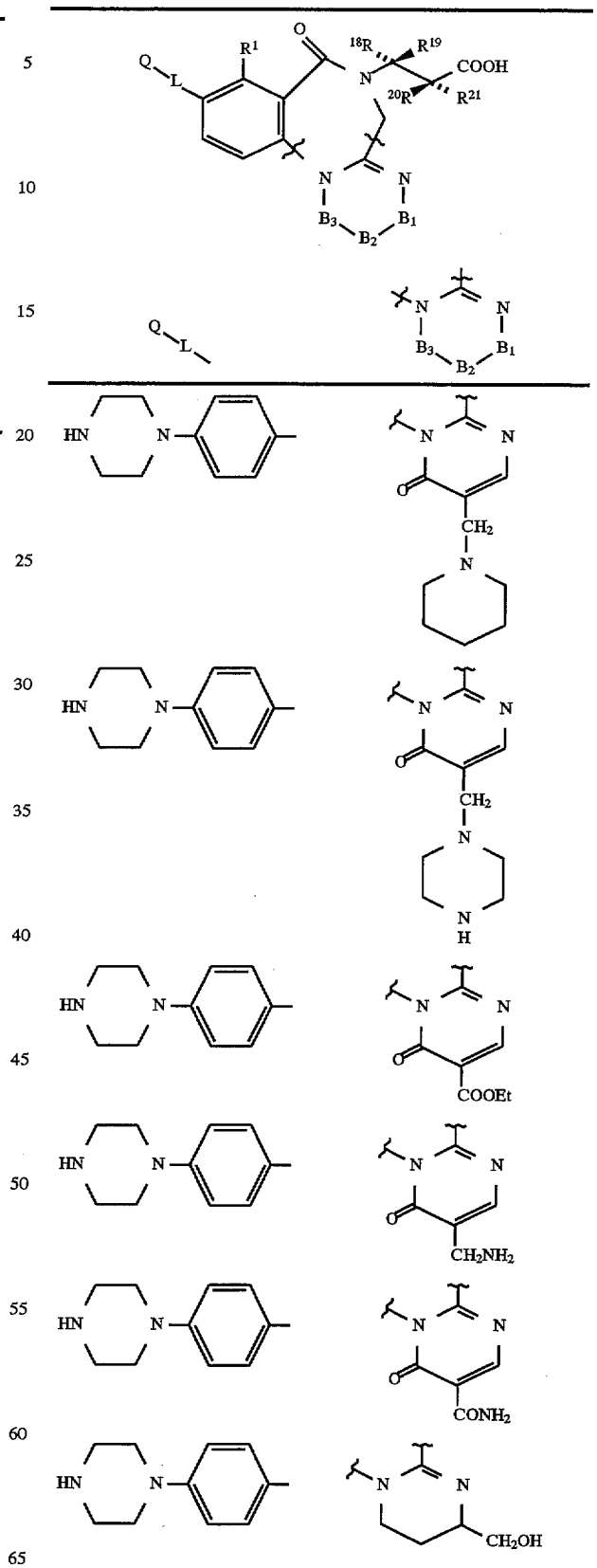

TABLE II-continued
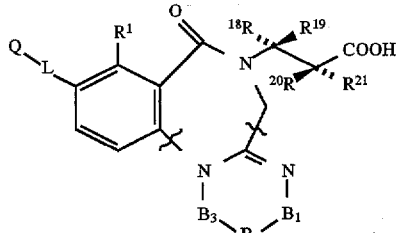

TABLE II-continued
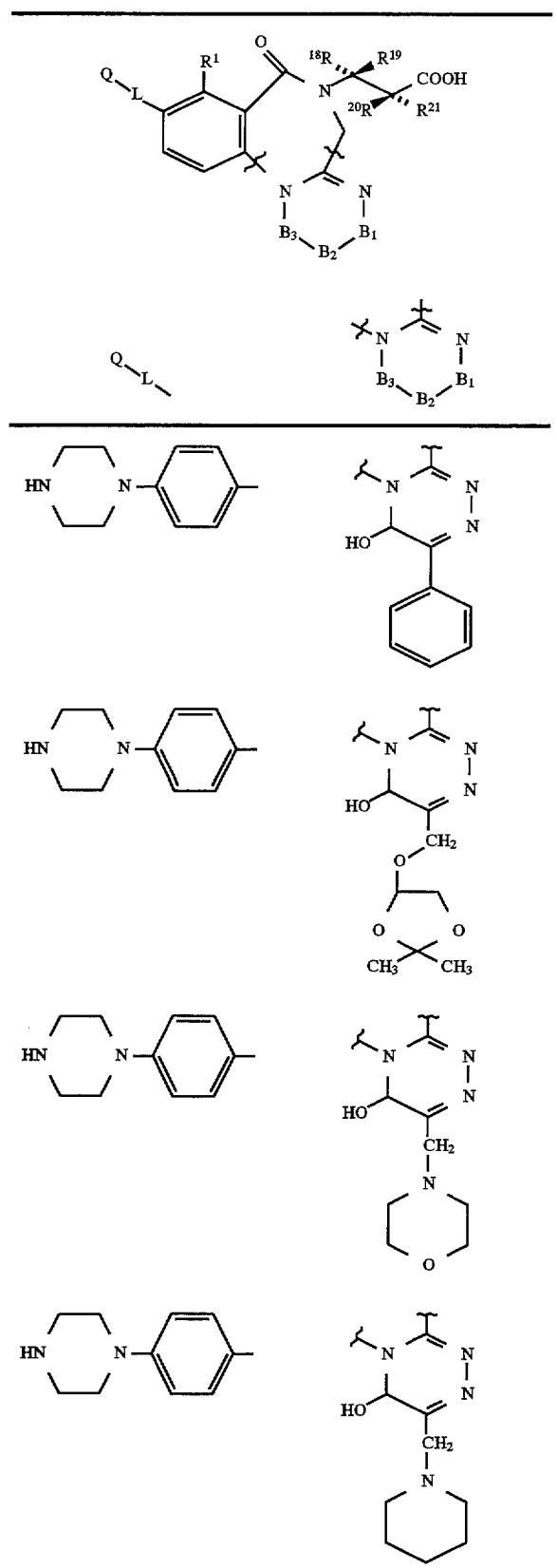
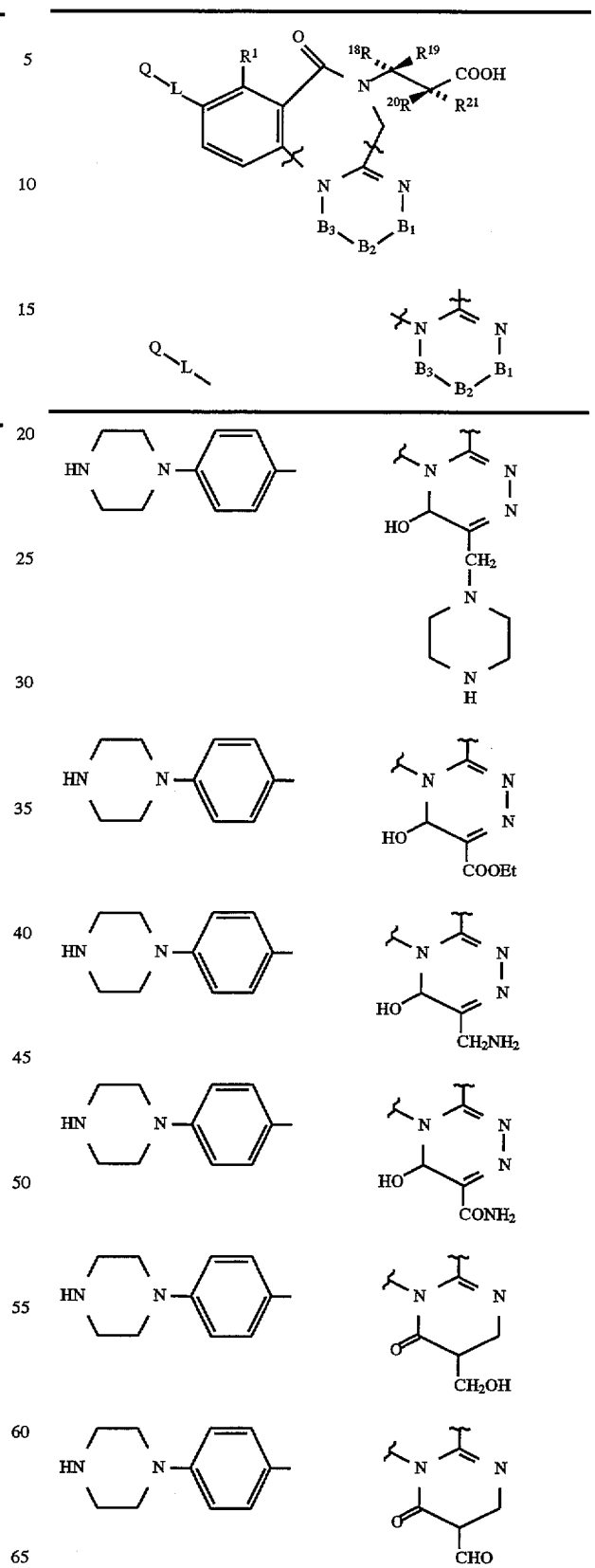

TABLE II-continued
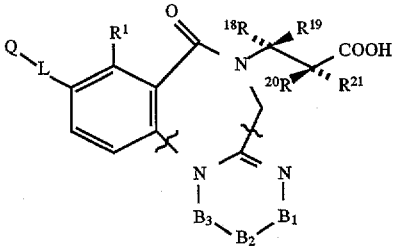

TABLE II-continued

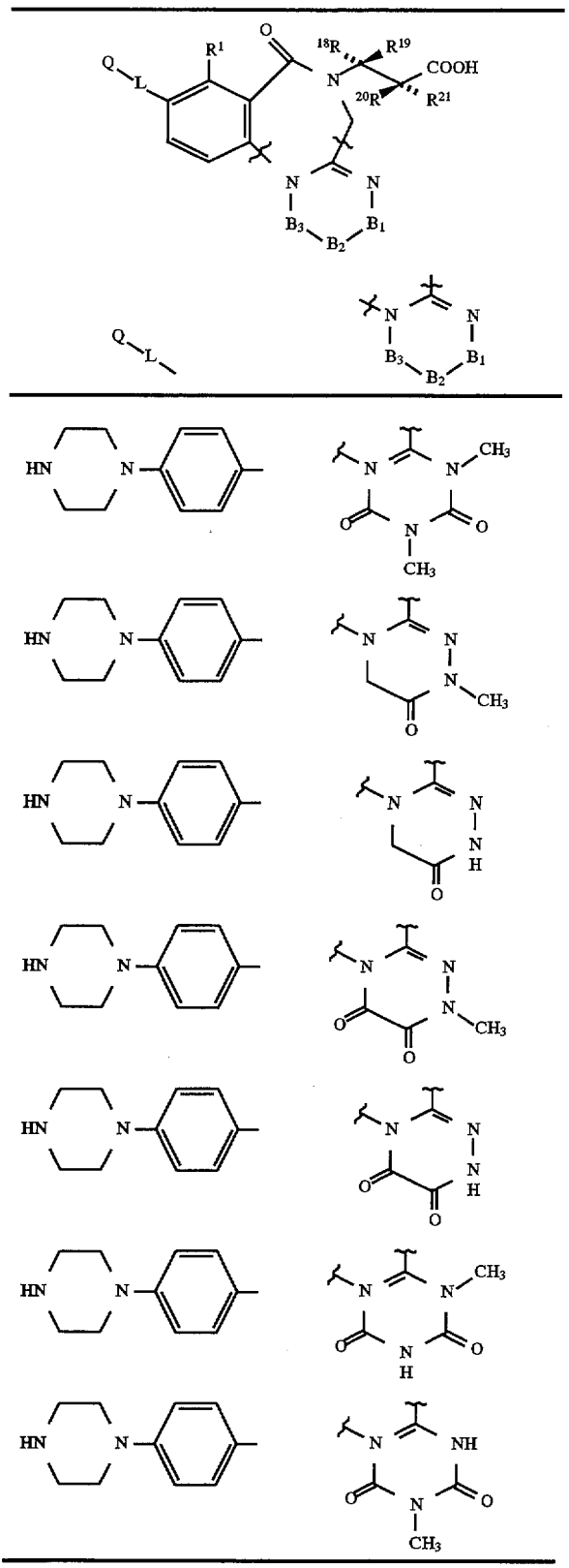

D. Methods of Making

Compounds of the present invention can be prepared by methods employing standard chemical methodologies described and referenced in standard textbooks (e.g. March, J. "Advanced Organic Chemistry" McGraw-Hill, New York, 1977; Collman, J. P., Hegedus, L. S., Norton, J. R., Finke, R. G. "Principles and Applications of Organotransition Metal Chemistry" University Science, Mill Valley, 1987; Larock, R. C. "Comprehensive Organic Transformations" Verlag, New York, 1989). For a detailed description of the preparation of the intermediate, substituted 3,4-dihydro-1H-1,4-benzodiazepine-2,5-dione 4 and of adding the substituent Q—L, see WO 93/08174.

1,5-member heterocycles fused to 1,4-benzodiazepine

The key intermediate for synthesis of 5-member heterocycles fused to 1,4-benzodiazepines is the substituted 3,4-dihydro-1H-1,4-benzodiazepine-2,5-dione 4. The benzodiazepinedione 4 may be prepared from isatoic anhydride 1, a β-alanine ester or a β-amino acid and an α-haloacetyl halide, according to Scheme 1. Methods for preparation of the isatoic anhydrides 1 are known in the art and are available from commercial sources such as Aldrich Chemical Co.

Scheme I

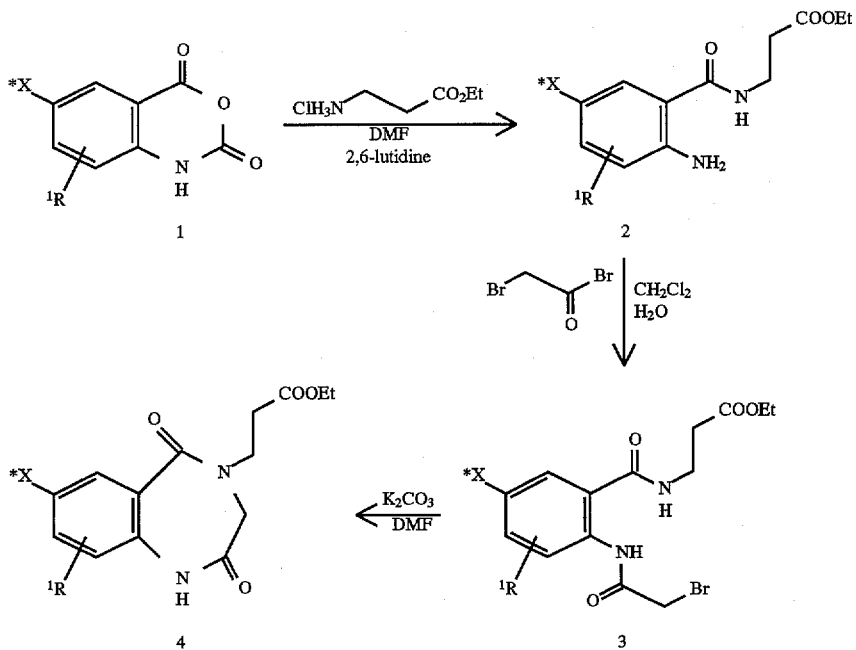

Briefly, isatoic anhydride is converted to N-(2-aminobenzoyl)-β-alanine ester 2 by allowing 1 to react with a β-alanine ester or its salt, in the presence an organic base. The isatoic anhydride 1 may be substituted or unsubstituted, but the 5-iodo isatoic anhydride is preferred (1,X*=I). The β-alanine ester may also be substituted or unsubstituted as the free amine or, more conveniently, as its salt (e.g. HCl). Generally, the reaction is conducted in a dry polar aprotic solvent, such as dimethylformamide or the like, in the presence of an equimolar amount, or up to 30% excess, of a tertiary amine as the organic base, e.g. triethylamine or 2,6-lutidine. Alternatively, the reaction may be catalysed by dimethylaminopyridine (Venuti, M. C. *Synthesis* 266 (1982)). The reaction requires between about 0.5 to 2 days at temperatures between about room temperature and 200° C. Preferably, the reaction is conducted at 80° C. for about 16 hours in dimethylformamide as the solvent. The product is isolated and purified by conventional methods, typically by solvent extraction into a compatible solvent. The product may be further purified by column chromatography or other appropriate methods.

Acylation of 2 with an α-haloacyl halide is carried out in methylene chloride under a dry inert atmosphere, such as nitrogen. The reaction is allowed to run at temperatures between 0° C. and room temperature for about 2 hours, and the product 3 is isolated or purified by conventional methods.

Cyclization of the acylated N-[2-(α-bromoacetylamide) benzoyl]-β-alanine ester 3 may be achieved by reaction with a base such as an alkali metal alkoxide, hydride, or carbonate in a polar solvent at temperatures between about 0° C. and 100° C. for about 0.5 to 2 hours. For example, a solution of the ester 3 is commonly added over a period of approximately 15 to 60 minutes to a slurry of an alkali metal carbonate in an appropriate solvent, cooled to 0° C. It is preferable that the solvent will be a polar aprotic solvent such as dimethylfomamide and the alkali metal carbonate be sodium carbonate, calcium carbonate, or cesium carbonate. Once the addition is complete, the reaction mixture is generally allowed to warm to room temperature and run for an additional 60 to 180 minutes after which the reaction is neutralized by the addition of a solution of an acid, such as 10% citric acid or the like, and the solvent evaporated. The product is then isolated by solvent extraction and further purified by column chromatography.

Preparation of 5-member rings fused to the substituted 3,4-dihydro-1H-1,4-benzodiazepine-2,5-dione 4 is carried out according to Scheme II–III. First, the benzodiazepine-dione 4 is treated with Lawesson's reagent to produce the thiolactam 5. Alkylation of the thiolactam 5 is carried out in a bi-phasic mixture of CH²Cl₂ and basic H₂O by treatment with methyl iodine and a catalytic amount of tetrabutylammonium hydrogen sulfate to produce the intermediate thioimidate ester 6.

Scheme II

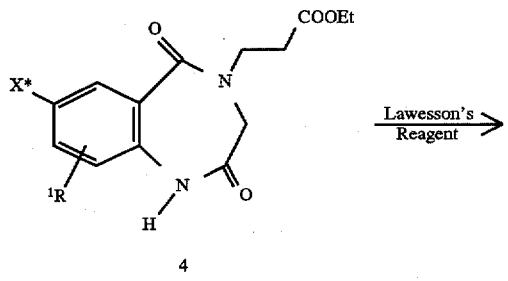

-continued
Scheme II
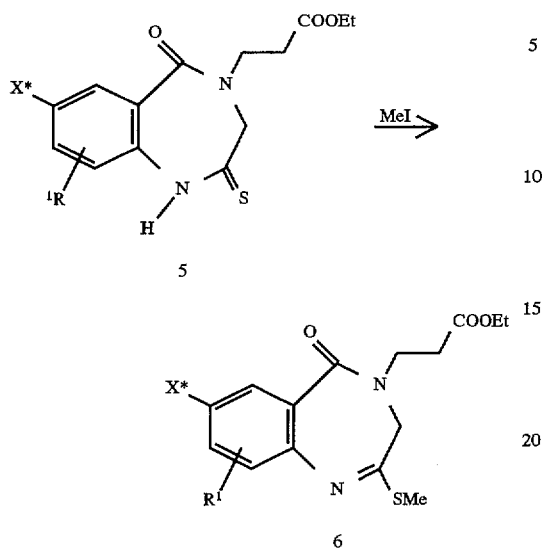
5
6
The thioimidate ester intermediate 6 may then be reacted with a variety of reagents to produce the fused 5-member rings of this invention according to Scheme III.
Scheme III
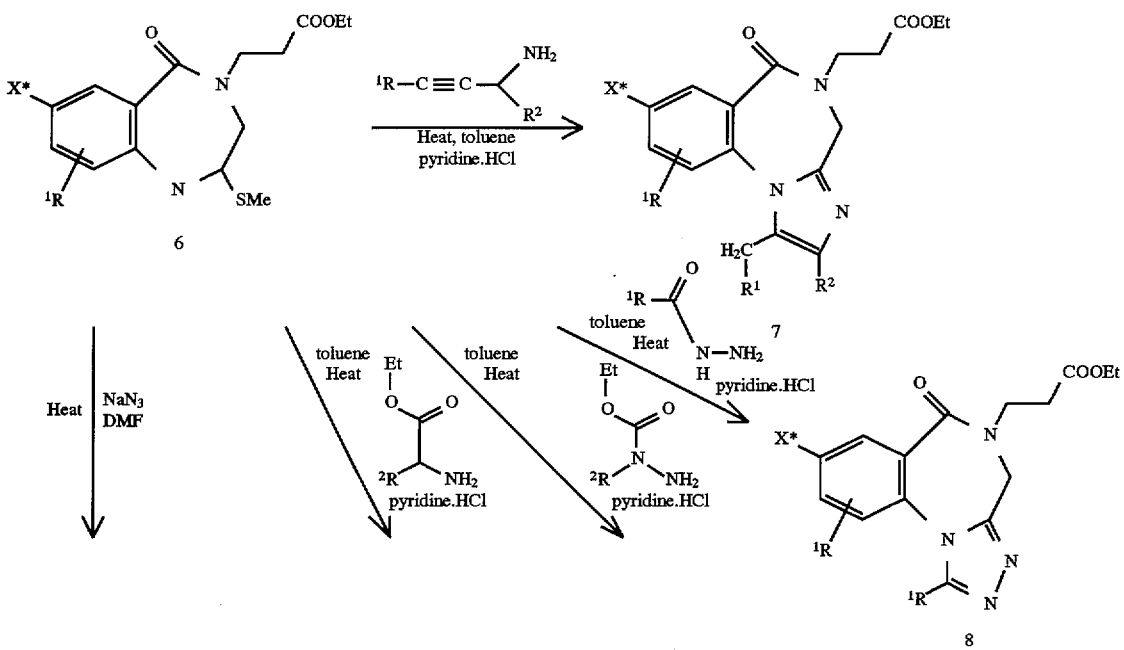

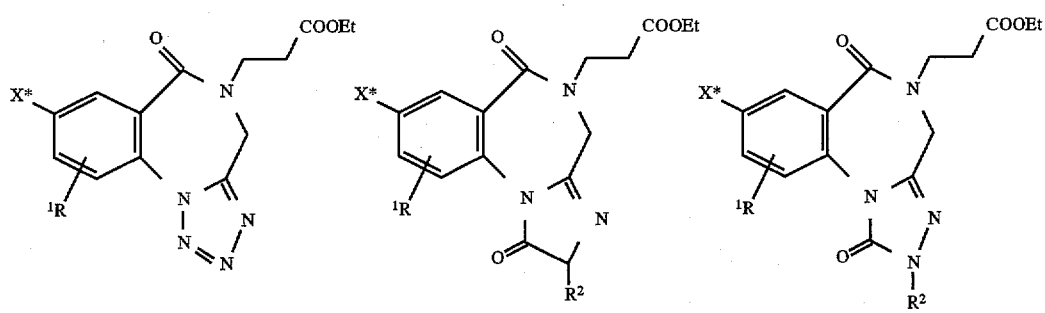

Briefly, 6 may heated to reflux in a toluene/pyridine.HCl solution with a substituted propargylamine to produce the substituted imidazo-benzodiazepine 7. Alternatively, 6 may be similarly refluxed with an appropriately substituted acylhydrazid to give the triazolo-benzodiazepine 8. Optionally, the thiomidate ester intermediate 6 may be reflux in toluene/pyridine.HCl with a substituted carbazate ester or α-amino acid ester to produce respectively the oxotriazolo-benzodiazepine 9 or oxoimidazolo-benzodiazepine 10. Alternatively, the thiolactam 5 (Scheme II) may be reacted with an appropriately protected α-amino acid and cyclized with dicyclohexylcarbodiiimide to yield 10 (see Ager et al., *J. Med. Chem.* 20(8):1035–1040 (1977). Finally, 6 may be heated in DMF with sodium azide to form the tetrazolo-benzodiazepine 11. The tetrazolo-benzodiazepine 11 can also be prepared directly from 4 by conversion of the secondary amide directly into a tetrazole using triphenylphosphine and trimethylsilylazide (see Duncia et al., *J. Org. Chem.* 56(7):2595–2400 (1991).

2. 6-member heterocycles fused to 1,4-benzodiazepine 6-member heterocycles fused to 1,4-benzodiazepines can be prepared by methods known in the art (see e.g. EP 0 519 678 A2). More specifically, beginning with the substituted 3,4-dihydro-1H-1,4-benzodiazepine-2,5-dione 4 (Scheme I) and reacting it with Lawesson's reagent as described in Scheme II produces the thiolactam 5. This intermediate can be further reacted to produce substituted oxodiazines according to Scheme IV.

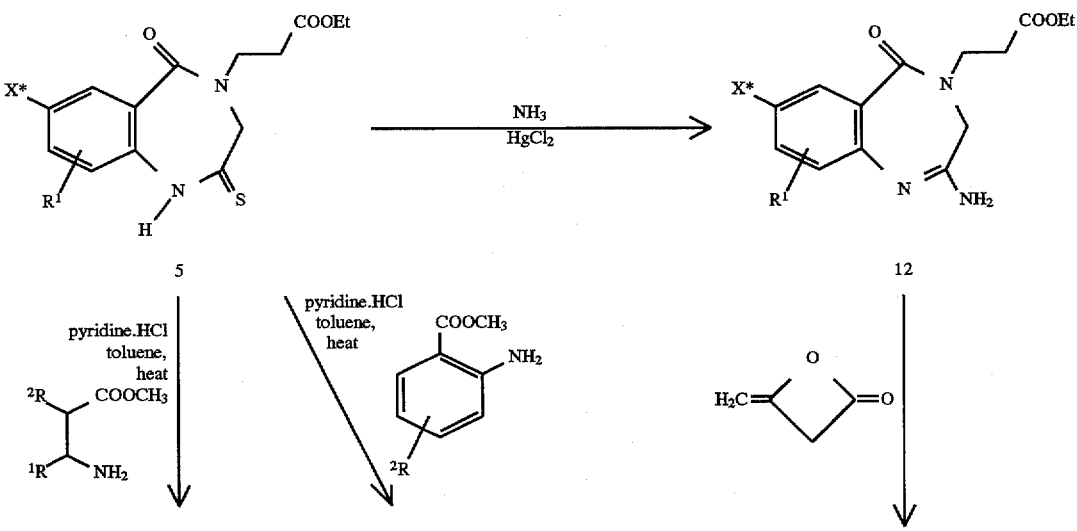

Scheme IV

-continued
Scheme IV

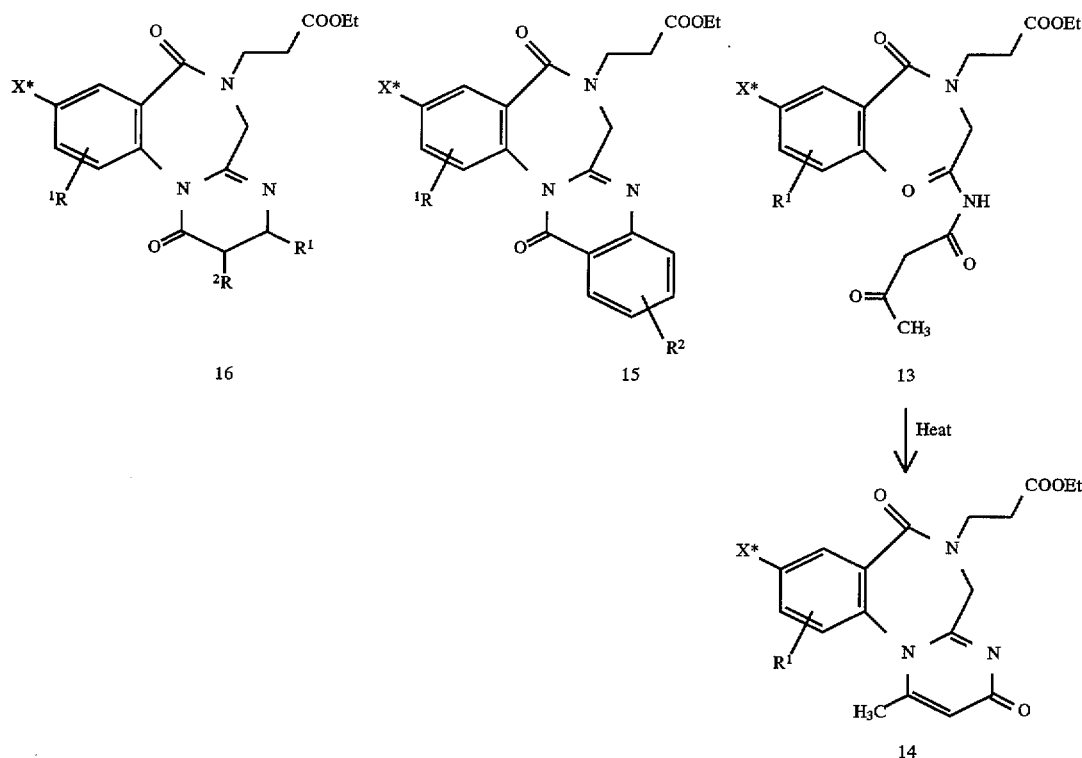

Briefly, the thiolactam 5 may be treated with ammonia in the presence of a mercury (II) salt to form the intermediate amidine 12. Reacting 12 with diketene followed by cyclization with heat treatment yields the substituted pyridinone-benzodiazepine 14. Alternatively, the thiolactam 5 may be treated with methyl iodide and refluxed in toluene/pyridine.HCl with an optionally substituted anthranilate ester or a substituted β-alanine ester to produce respectively the substituted quanizolino-benzodiazepine 15 or substituted pyrimidone-benzodiazepine 16.

Other substituted pyrimidone-benzodiazepines are prepared from the intermediate amidine 12 according to reaction Scheme V.

Scheme V

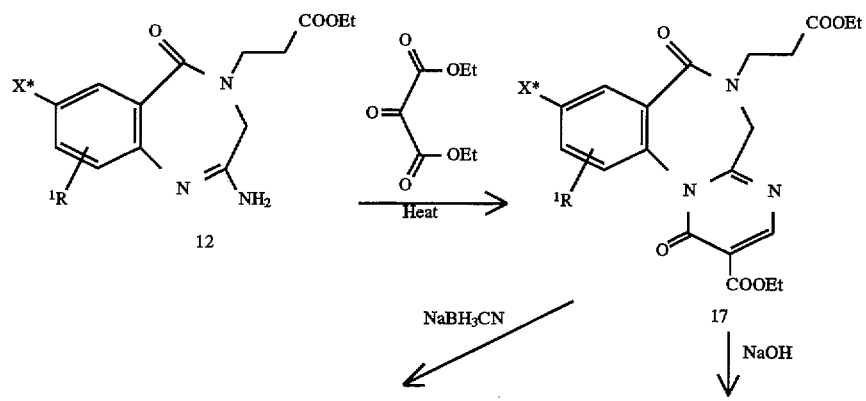

-continued
Scheme V

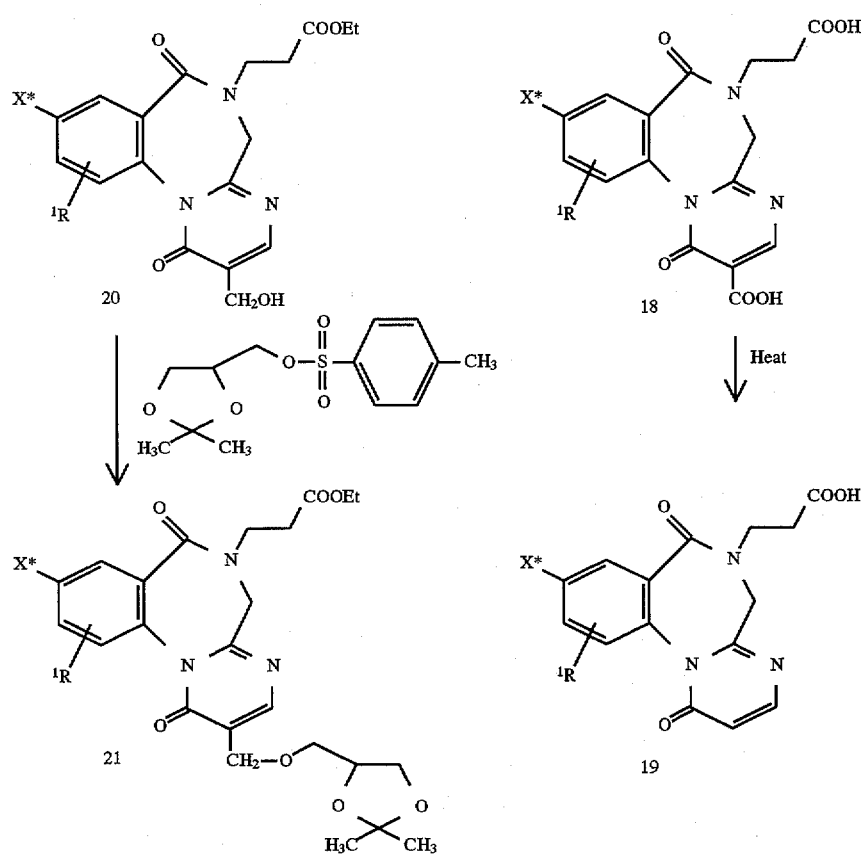

Briefly, the intermediate amidine 12 is heated with ethoxymalonic acid diester to yield the carboxyethyl substituted pyrimidineone-benzodiazepine 17. Saponification of 17 yields the free acid 18 which may be decarboxylated by heating to give compound 19. Alternatively, the carboxyethyl substituted pyrimidineone-benzodiazepine 17 may be reduced with sodium cyanoborohydride to give the corresponding alcohol 20, which can be alkylated with 2,2-dimethyl-1,3-dioxolan-4-ylmethyl-p-toluenesulfonate to yield the glycerol-isopropylidene adduct 21.

The carboxyethyl substituted pyrimidone-benzodiazepine 17 also provides access to a wide variety of primary, secondary, and tertiary amine adducts as shown in Scheme VI.

Scheme VI

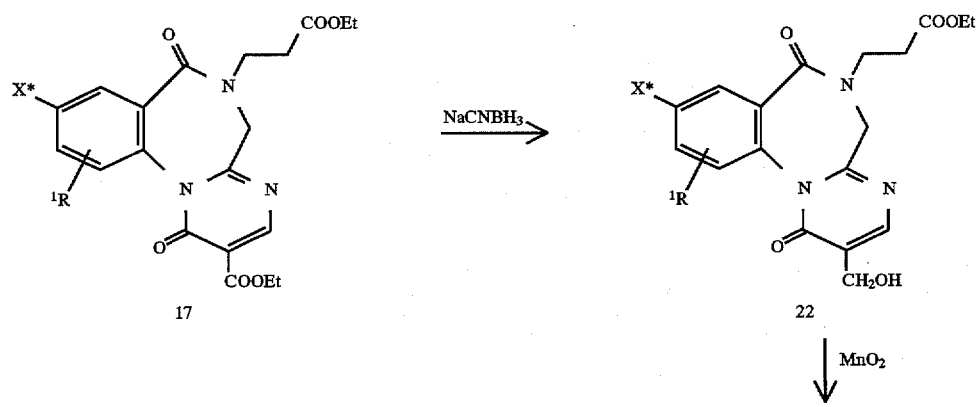

-continued
Scheme VI

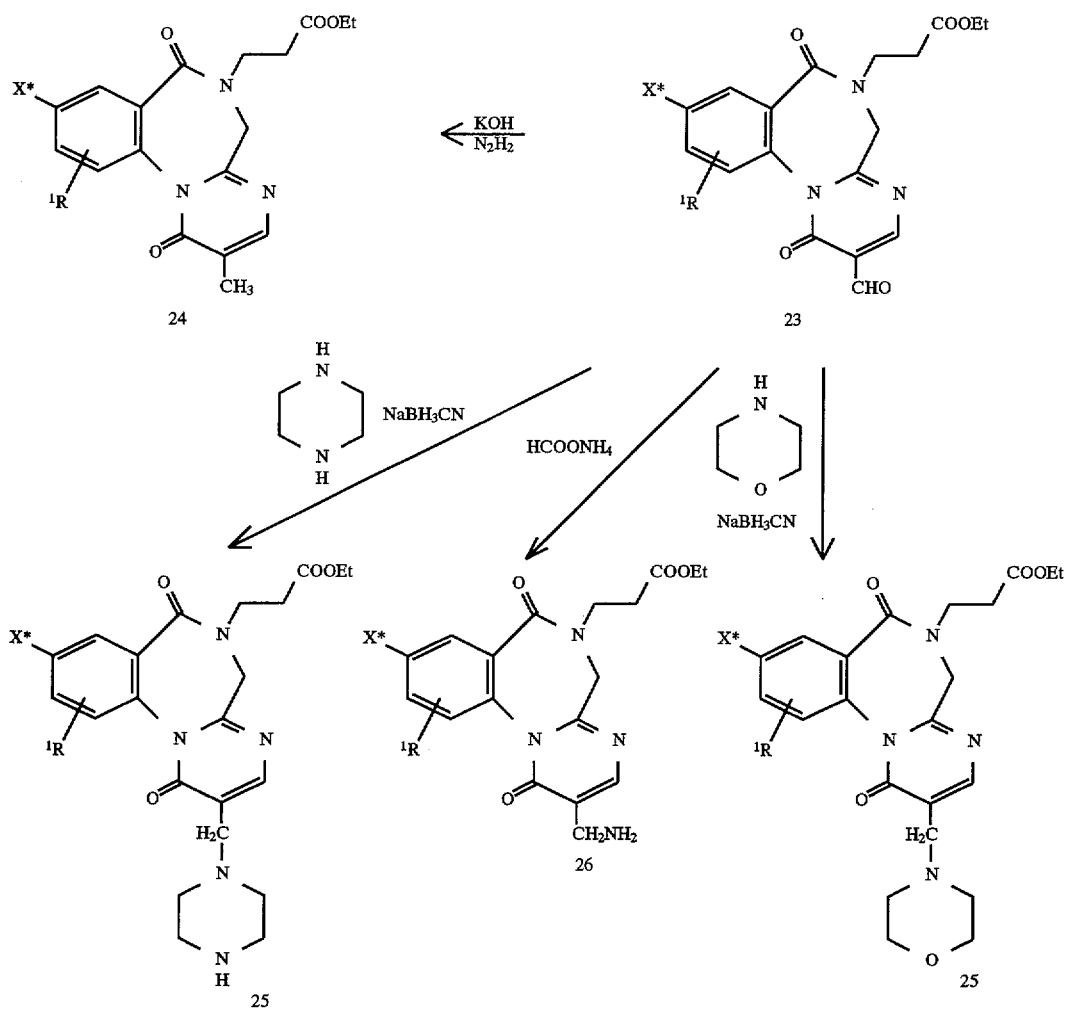

For example, the hydroxyethyl substituted pyrimidineone-benzodiazepine 20 can be treated with a mild oxidizing agent such as manganese dioxide to yield the corresponding aldehyde 23 which in turn can be reductively aminated to produce the primary and tertiary amines 25, 26, and 27. Optionally a Wolff-Kishner reaction converts aldehyde 23 to the methyl compound 24.

The amidine 12 of Scheme V may also be converted into triazinodiones according to Scheme VII.

Scheme VII

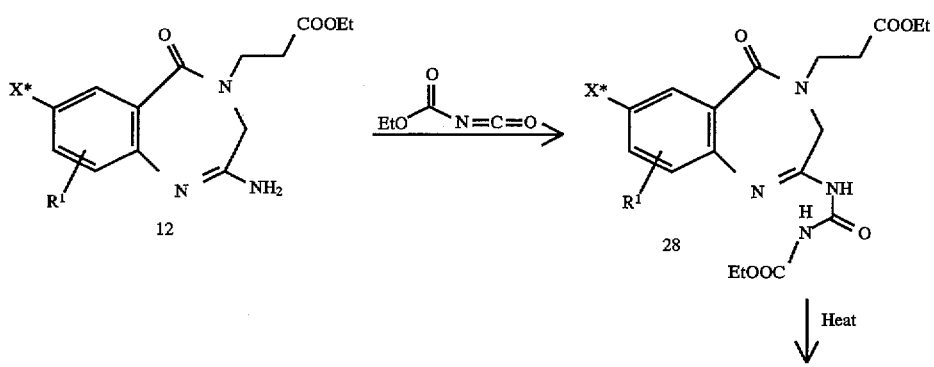

-continued
Scheme VII

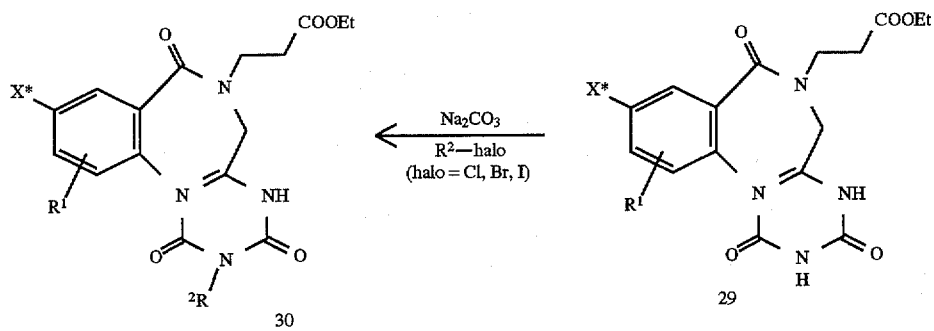

Briefly, amidine 12 is treated with ethoxycarbonyl isocyanate to yield compound 28. Upon heating, 28 is cyclized to the triazinodione 29. Optionally, 29 may be alkylated with an alkyl halide to give the alkyl substituted triazinodione 30.

Triazinobenzodiazepines can be prepared from benzodiazepines according to Scheme VIII.

reagent produces the N-1 alkylated thiolactam 32 which, upon treatment with an alkyl substituted hydrazine, cyclizes to give the triazinobenzodiazepines 33. Alternatively, reaction of thiolactam 32 with hydrazine followed by alkylation with an alkyl halide as shown in Scheme VII yields 33.

Scheme VIII

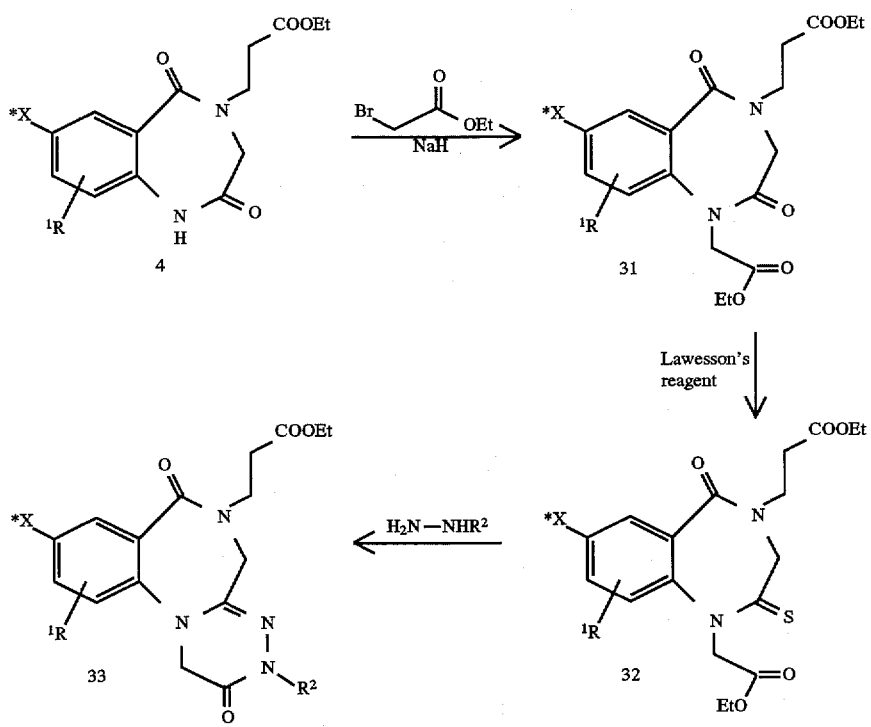

Briefly, 1,4-benzodiazepines 4 are alkylated with ethylbromoacetate and sodium hydride to give the N-1 alkylated carboxyethyl ester 31. Treatment of 31 with Lawesson's Other triazinobenzodiazepines can be prepared from the intermediate thiolactam 5 (Scheme II) according to Scheme IX.

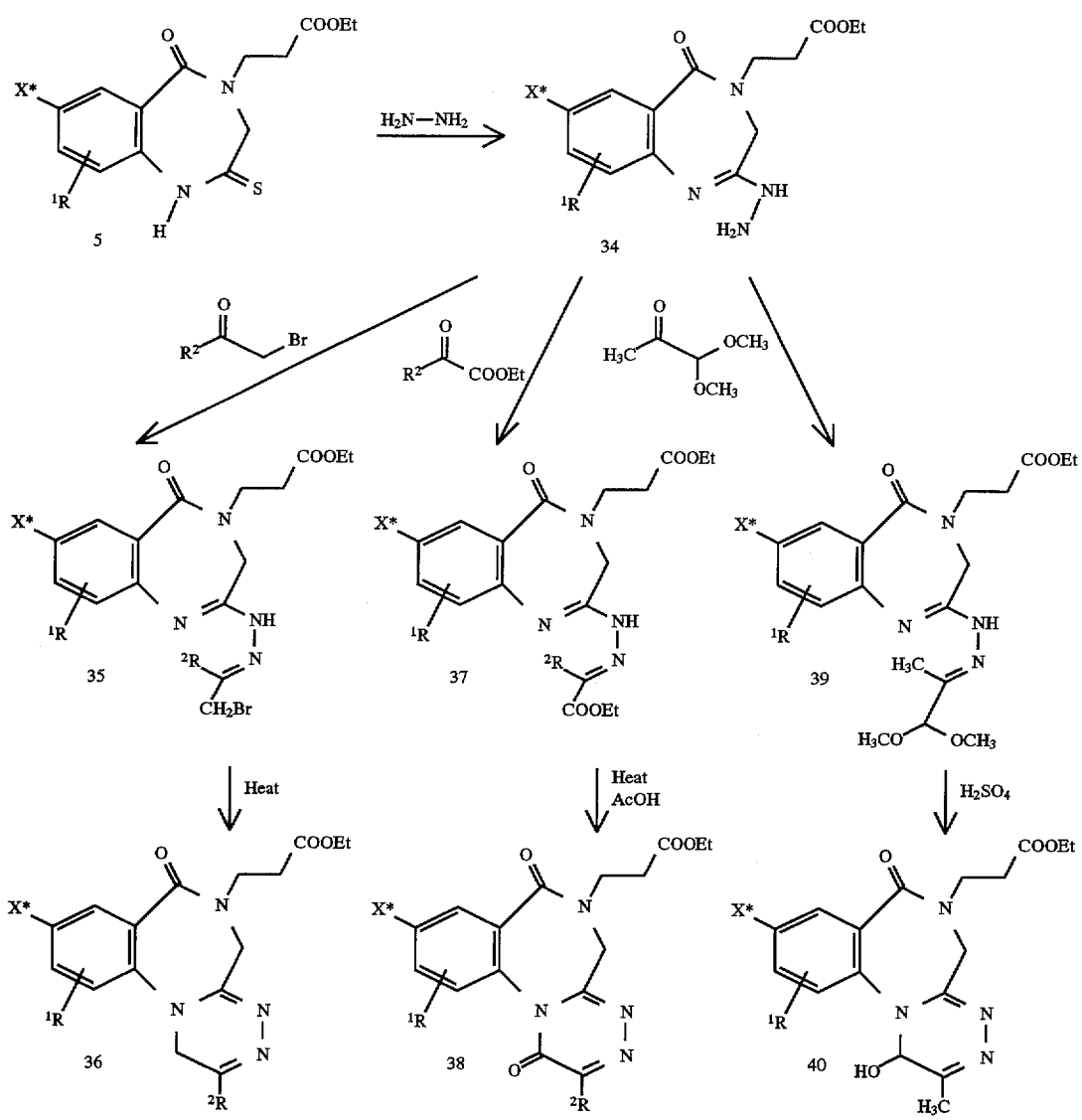

Scheme VIII

Briefly, thiolactam 5 is treated with hydrazine to give the intermediate amidrazone 34. Amidrazone 34 may be reacted with haloaldehydes and ketones to produce hydrazones 35 which, upon heating, gives triazinobenzodiazepine 36. Alternatively, treatment of 34 with α-keto esters yields hydrazones 37 which are cyclized by heating in acetic acid to give oxo-triazinobenzodiazepines 38. Additionally, treatment of 34 with ketoacetals gives hydrazones 39 which upon treatment with concentrated sulfuric acid gives hydroxy-triazinobenzodiazepines 40. Finally, treatment of amidrazone 34 with chlorocarbonylethylformate produces the oxalic ester hydrazid 41 which is cyclized in refluxing pyridine to 1,2-dicarbonyl-triazinobenzodiazepines 42 according to Scheme X.

Scheme X
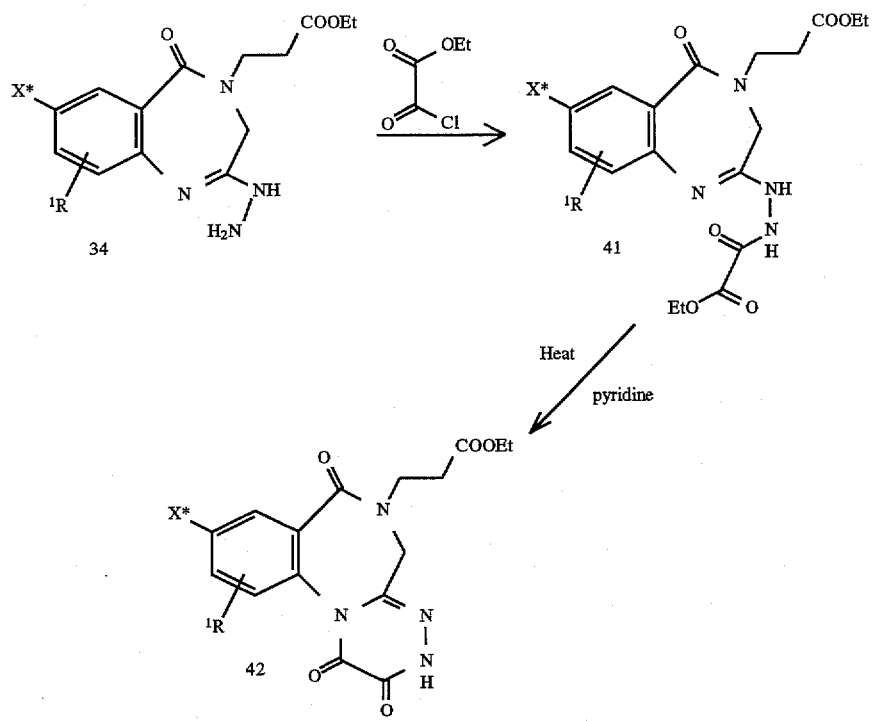
Other oxo-triazinobenzodiazepines and 5-member sulfonamides can be prepared from the intermediate thioimidate ester 6 according to Scheme XI.
Scheme XI
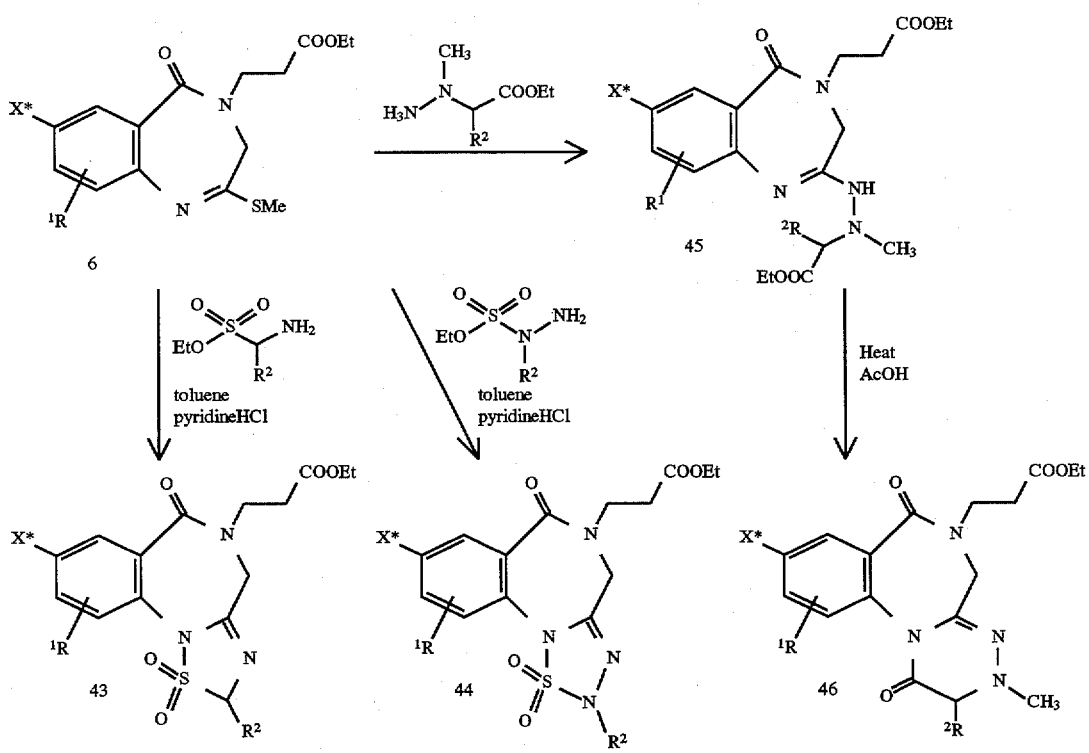

Treatment of 6 with hydrazinoesters yields amidrazonoesters 45 which upon heating in acetic acid gives substituted oxo-triazinobenzodiazepines 46. Compound 6 may also be reacted with α-amino sulfonic acid esters or sulfonamidrazone esters in pyridine/HCl to yield sulfonamides 43 and 44 respectively.

3. The Q—L Group

Referring to Scheme XII, the reaction is allowed to proceed in a dry organic polar aprotic solvent, such as ethyl acetate or the like, with the exclusion of oxygen, at from room temperature to 180° C. for times between about 2 and 48 hours.

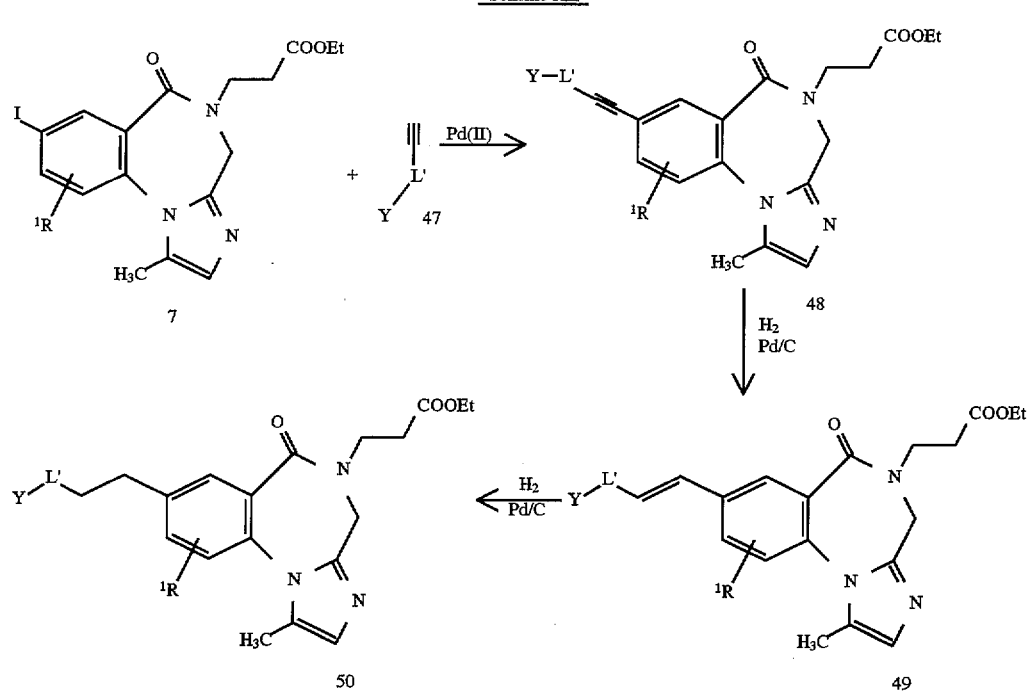

Scheme XII

The nitrogen containing substituents Q or a precursor thereof may be added to the linker L and the combination Q—L—, usually in protected form, bonded to the "benzo" ring. Alternatively, Q or Q plus a portion of L, refered to below as L', may be added to L or a portion thereof after the "benzo" ring and the rest of the molecule have been formed. Q itseft may be prepared and bonded to the "benzo" ring by standard methods published in both the scientific and patent literature (see e.g. U.S. Pat. Nos.; 4,992,542, 4,997,936, 4,194,047, 5,003,076, 5,063,207, 5,063,208, and 5,079,357, and references cited therein).

In the description following, addition of Q—L— (or Q—L') to the benzene moiety of the imidazobenzodiazepine 7 where $R^1$ and $R^2$ are both hydrogen is specified. It will be understood that these same procedures may be applied to other ring systems described in schemes I-IX above and encompassed by formula I and II. For a more comprehensive description of methods for adding Q—L— (or Q—L') to the benzene moiety of the imidazobenzodiazepine see WO 93/08174.

Generally, conversion of the compounds having the structural formula 7 to compounds having the structural formula 48 may be accomplished by allowing 7 to react with an alkyne 47 in the presence of a palladium (II) salt, a copper (I) salt, and an organic base. Preferably, the alkyne 47 is substituted in a way such that the Y group can be synthetically converted to the positively charged Q group of structural Formula I and II. More preferably, the Y group is a protected form of the positively charged Q group. For example, alkyne 47 may be a N-Boc-amino alkyne, a benzo or alkylnitrile alkyne, a nitrobenzo alkyne, or the like.

Preferably, the reaction will run with a catalytic amount of palladium(II) salt at 10 molar percent end copper (I) salt at 5 molar percent. A 2 fold excess of the alkyne 47 and a 5 fold excess of a tertiary amine as the organic base, such as triethylamine or the like, is preferred. The product 48 can be isolated by solvent extraction in to a suitable organic solvent, such as ethyl acetate, and washed with a solution of 10% ethylenediaminetetraacetic acid and the solvent evaporated. 48 may be further purified by column chromatography.

Preparation of compounds 49 and 50 may be achieved by selective reduction of the alkyne moiety in compounds of the general formula 48 to yield alkene 49 and alkane 50 by allowing the alkyne to stir under an atmosphere of hydrogen in the presence of a small amount of palladium on carbon. Typically, the reaction is run in an inert solvent, such as ethyl acetate, with a 5–10 molar percent by weight of 10% palladium on carbon at temperatures between about room temperature and 50° C. for times between about 15 and 240 minutes. Preferably, the reaction is carried out at room temperature for 1 hour. The products are isolated by filtration of the mixture through a filter agent, such as Celite®, and evaporation of solvent.

Conversion of the compounds of the general formula 48, 49, or 50 in which Y is a N-(tert-butoxycarbonyl) amino protected moiety (N-BOC) to the amino ester can be accomplished by allowing the material to react with a strong acid. Generally, the reaction is carried out by mixing the N-BOC amino ester with a large excess of concentrated solution of a strong acid, such as hydrogen chloride, dissolved in an appropriate inert solvent, such as ethyl acetate. The reaction can be conducted at a temperature between about minus 30° C. and room temperature for about 0.5 to 24 hours. The reaction can be run in the presence of a molar amount of trialkylsilane, such as triethylsilane or the like. Preferably, the reaction will be carried out at room temperature for 2 hours with a molar equivalent of triethylsilane in ethyl acetate. The solvent is evaporated and the products can be further purified by high-pressure liquid chromatography using a reverse phase column.

Conversion of compounds of the general formula 48, 49, or 50 in which the Y functional group is an arylnitrile to the benzylamine ester can be achieved by allowing the arylnitriles to react with dicobalt octacarbonyl in the presence of trimethylsilane. The reduction of a benzonitrile to a benzylamine is a known reaction (Mural, T.; Sakane, T.; Kato, S. *Tetrahedron Lett.* 26: 5145–5148 [1985]) and is generally carried out in an inert solvent, such as toluene or the like, at 60° C. for 20 hours with an 8 molar percent of dicobalt octacarbonyl and a 10 fold excess of trimethylsilane. The solvent is evaporated and the resulting material diluted with methanol and allowed to react with a 5 fold excess of potassium fluoride. The products are then isolated by solvent extraction and further purified by high-pressure liquid chromatography using a reverse phase column. Conversion of the same arylnitrile compounds to their corresponding amidino esters can be accomplished by sequential reaction with hydrogen sulphide, methyl iodide, and ammonium acetate. The resulting amidino esters may be purified by either column chromatography, crystallization, or preparative high-pressure liquid chromatography using a reverse phase column.

From commercially available precursors, alkynyl benzonitriles containing substituents on the nitrile containing benzo ring can be prepared by known methods. These substituents specifically include a chlorine (positioned either ortho or meta to the aryl nitrile), an amino (suitably protected, positioned ortho to the arylnitrile), fluorine (tetra, i.e., fluorines at both ortho and meta positions relative to the arylnitrile), and a methyl group (positioned ortho and meta to the aryl nitrile). Palladium mediated coupling of these alkynyl benzonitriles containing the substituents described to 7, followed by treatment with hydrogen sulfide, methyl iodide, ammonium acetate and purification via silica, reverse phase chromatography, or recrystallization would afford amidino esters of interest. It is also possible to prepare from a commercially available material an amidino benzodiazepinedione ester where L' is a pyridine ring rather than a benzene ring. In the synthesis of the alkynyl pyridyl nitrile which would be reacted with 7, it may be preferable to use a nickel catalyst (rather than palladium) to effect the coupling of 2-chloro-5-cyano-pyridine with the acetylene synthon (most likely trimethylsilyl acetylene).

Conversion of the compounds of the general formula 48, 49, or 50 in which the Y functional group is a nitroarene, to the anilino ester can be executed by a selective reduction (Bellamy, F. D.; Ou, K. *Tetrahedron Lett.* 25: 839–842 [1984]). The reaction is generally run with a five molar excess of stannous chloride dihydrate in either ethyl acetate or ethanol as the solvent at temperatures between about 50° and 100° C. for times between about 15–120 minutes under an inert atmosphere, such as nitrogen. Preferably, the reaction is carried out at 70° C. in ethanol for approximately 30 minutes. The products are then isolated by solvent extraction and further purified by high-pressure liquid chromatography using a reverse phase column.

Conversion of the amino esters to their corresponding amino acids of the structural Formula I and II involves saponification using well known conditions and reagents. For example, an aqueous solution of a strong alkali metal base, such as sodium hydroxide, lithium hydroxide or the like, is added to an alcohol-water (1:3) solution of the ester. Alcohols which may be used as the solvent for this reaction may include, for example, methanol, ethanol, and isopropanol, but, methanol is preferred. The preferred base is sodium hydroxide at a concentration between about 1 to 6N, though 2N is preferred. The reaction may be conducted at a temperature between about 0° to 50° C. for times between about 10 to 60 minutes. Preferably, the reaction is carried out at room temperature for 30 minutes after which the reaction is neutralized with a concentrated solution of a strong acid, such as hydrochloric acid or the like, and the solvent evaporated. The products are isolated by high-pressure liquid chromatography using a reverse phase column.

The conversion of the amino acids to their corresponding guanidino acids of the structural Formula I and II is a known reaction (Kim, K. Lin, Y.-L.; H. S. *Tetrahedron Lett.* 3183–3186 [1988]). The reaction can be accomplished by allowing the amino acid to react with aminoiminomethanesulfonic acid. Generally, the reaction can be conducted with a equimolar to a 10 fold molar excess of aminoiminomethanesulfonic acid at temperatures between 0° to 50° C. for times between about 15 to 120 minutes in a polar protic solvent, such as methanol, water or the like. The solution, prior to the addition of aminoiminomethanesulfonic acid, may be made neutral or basic by the addition of weak base, such as an alkali metal carbonate. Preferably, for alkyl amines the amino acid will be allowed to react with a 5 fold excess aminoiminomethanesulfonic acid at room temperature for 30 minutes with 5% potassium bicarbonate in water as the reaction medium, whereas for aryl amines the amino acid will be allowed to react with an equimolar amount of aminoiminomethanesulfonic acid at room temperature for 1 hour in methanol. Generally, the reaction mixture will be made acidic by the addition of a dilute solution of an acid, such as acetic acid and the solvent evaporated. The products are isolated by high-pressure liquid chromatography using a reverse phase column.

Preparation of other tricyclic compounds containing preferred L—Q groups bonded to the benzo moiety may also be prepared from key intermediate 7 according to Schemes XIII and XIV below.

Scheme XIII

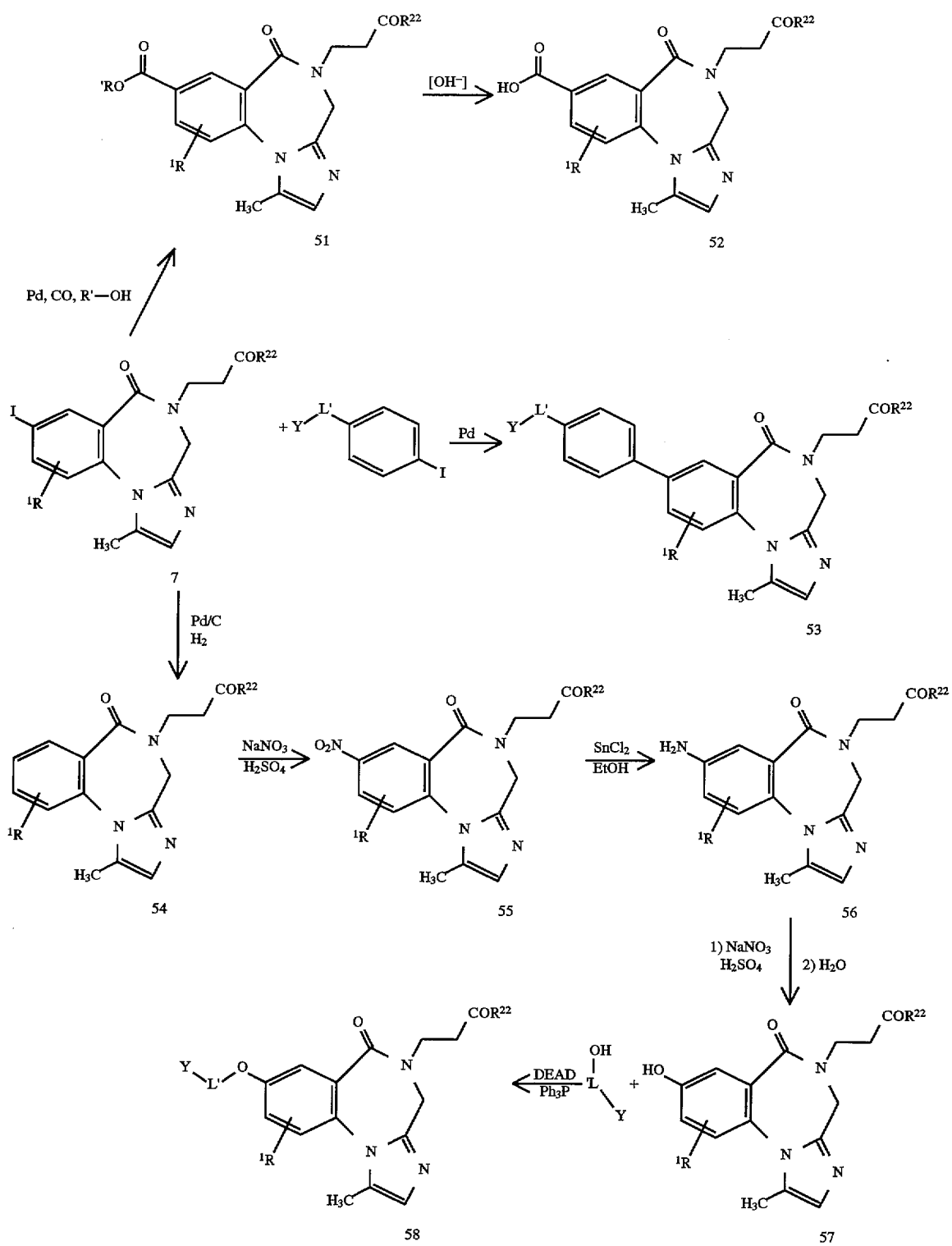

Conversion of the iodoarene 7 to a synthetic precursors of 59 may be accomplished by carbonylation in an alcoholic solvent (R'OH) under a carbon monoxide atmosphere utilizing a palladium(0) catalyst. The alcoholic solvent (R'OH) must be chosen so as to allow for the selective removal of the R' group of the diester 51. For example, when R'=CH$_3$ and R$^{22}$=tert-butyl, the alcoholic solvent is methanol, and this methyl ester functionality in 51 can be moved by mild basic hydrolysis to afford acid 52.

For preparation of the biaryl adducts 53, 7 may be allowed to react with substituted iodoaryls or arylboronates, where Y and L' are defined as above, in the presence of palladium(0). Alternatively, synthetic precursors of 58 and 60 may be prepared by converting iodoarene 7 into the aniline 56 or phenol 57 by standard procedures. Phenol 57 may be converted to ether 58 by combining with the appropriately protected alcohol and dehydrating with diethyl azodicarboxylate-triphenylphosphene (DEAD).

Precursor carboxylates 52 and anilines 56 may be converted into amides 59 and 60 in a dehydration reaction utilizing dicyclohexylcarbodiimide (DCC) with the appropriate amine or acid according to Scheme XIV.

example, using hydrochloric, hydrobromic, surfuric, phosphoric, trifluoroacetic, methanesulfonic, malic, maleic, fumaric and the like. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of Formula I and II with one or more molar equivalents of the desired acid or base in a solvent or solvent mixture in which the salt is insoluble; or in a solvent like water after which the solvent is removed by evaporation,

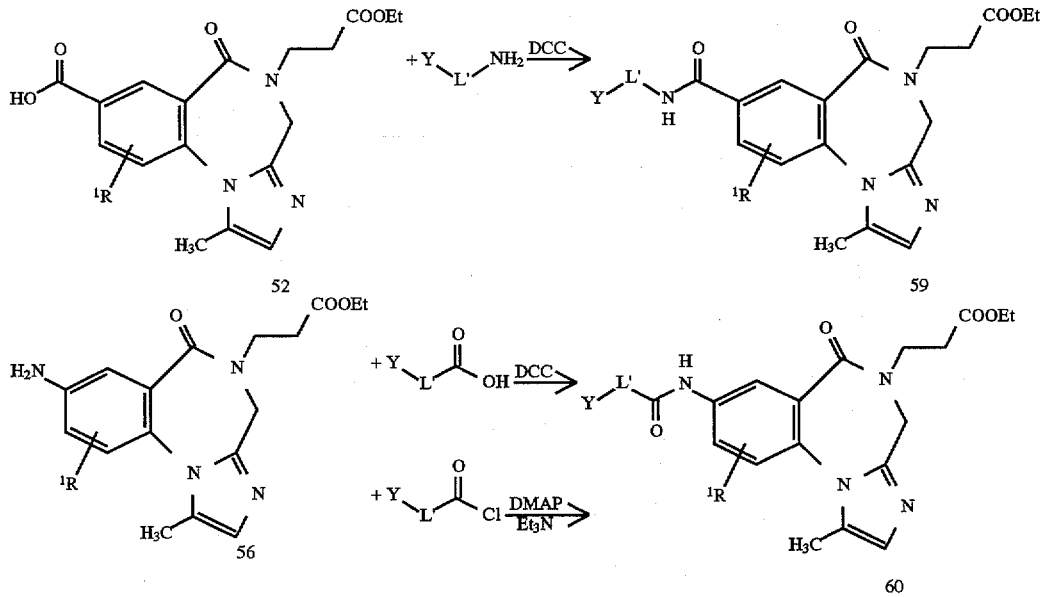

Scheme XIV

The latter reaction preferably is carried out with an acyl chloride in the presence of triethylammine and 4-dimethylaminopyridine (DMAP).

4. Isomeric Products

In products of Formula I and II carbon atoms bonded to four nonidentical substituents are asymmetric. Accordingly, the compounds may exist as diastereoisomers, enantiomers or mixtures thereof. The syntheses described above may employ racemates, enantiomers or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present in compounds of Formula I and II, may be in one of two configurations (R or S) and both are within the scope of the present invention.

E. Pharmaceutical Compositions

The compounds described in this invention may be isolated as the free acid or base or converted to salts of various inorganic and organic acids and bases. Such salts are within the scope of this invention. Examples of such salts include ammonium, metal salts like sodium, potassium, calcium and magnesium; salts with organic bases like dicyclohexylamine, N-methyl-D-glucamine and the like; and salts with amino acids like arginine or lysine. Salts with inorganic and organic acids may be likewise prepared, br distillation or freeze drying. Alternatively, the free acid or base form of the product may be passed over an ion exchange resin to form the desired salt or one salt form of the product may be converted to another using the same general process.

In the management of thromboembolic disorders the compounds of this invention may be utilized in compositions such as tablets, capsules or elixirs for oral administration; suppositories for rectal administration; sterile solutions or suspensions for injectable administration, and the like. Animals in need of treatment using compounds of this invention can be administered dosages that will provide optimal efficacy. The dose and method of administration will vary from animal to animal and be dependent upon such factors as weight, diet, concurrent medication and other factors which those skilled in the medical arts will recognize.

Dosage formulations of the nonpeptidyl inhibitors of the present invention are prepared for storage or administration by mixing the inhibitor having the desired degree of purity with physiologically acceptable carriers, excipients, or stabilizers. Such materials are non-toxic to the recipients at the dosages and concentrations employed, and include buffers such as phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as Tween, Pluronics or polyethyleneglycol.

Dosage formulations of the nonpeptidyl inhibitors of the present invention to be used for therapeutic administration must be sterile. Sterility is readily accomplished by filtration through sterile filtration membranes such as 0.2 micron membranes. Nonpeptidyl inhibitor formulations ordinarily will be stored in lyophilized form or as an aqueous solution. The pH of the cyclic inhibitor preparations typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by hypodermic injection needle, other methods of administration are also anticipated such as suppositories, aerosols, oral dosage formulations and topical formulations such as ointments, drops and dermal patches.

Therapeutic nonpeptidyl inhibitor formulations generally are placed into a container having a sterile access port, for example, an intravenous solution bag or vial having a stopper pierceable by hypodermic injection needle.

Therapeutically effective dosages may be determined by either in vitro or in vivo methods. For each particular nonpeptidyl inhibitor of the present invention, individual determinations may be made to determine the optimal dosage required. The range of therapeutically effective dosages will naturally be influenced by the route of administration. For injection by hypodermic needle it may be assumed the dosage is delivered into the body's fluids. For other routes of administration, the absorption efficiency must be individually determined for each inhibitor by methods well known in pharmacology.

The range of therapeutic dosages is from about 0.001 nM to 1.0 mM, more preferably from 0.1 nM to 100 mM, and most preferably from 1.0 nM to 50 mM.

Typical formulation of compounds of Formula I and II as pharmaceutical compositions are discussed below.

About 0.5 to 500 mg of a compound or mixture of compounds of Formula I and II, as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The mount of active ingredient in these compositions is such that a suitable dosage in the range indicated is obtained.

Typical adjuvants which may be incorporated into tablets, capsules and the like are a binder such as acacia, corn starch or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen or cherry. When the dosage form is a capsule, in addition to the above materials it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

F. Platelet Inhibition Assays

Evaluation of the Formula I and II inhibitors of the fibrinogen-platelet interaction is guided by in vitro receptor binding assays and in vitro platelet aggregation inhibition assays.

In-vitro biological activity of the compounds of Formula I and II are monitored using a modified fibrinogen-GPIIbIIIa ELISA based on the method of Nachman and Leung (*J. Clin. Invest.* 69:263–269 (1982)) which measures the inhibition of fibrinogen binding to purified human platelet GPIIbIIIa receptor. Human fibrinogen is prepared by the method of Lipinska, et al. (*J. Lab. Clin. Med.* 84:509–516 (1974)). Platelet $GPII_bIII_a$ is prepared by the method of Fitzgerald, et al., *Anal. Biochem.*, 151:169–177 (1985).

Briefly, microtiter plates are coated with fibrinogen (10 mg/ml) and then blocked with TACTS buffer containing 0.5% bovine serum albumin (BSA). (TACTS buffer contains 20 mM Tris.HCl, pH 7.5, 0.02% sodium azide, 2 mM calcium chloride, 0.05% Tween 20, 150 mM sodium chloride.) The plate is washed with phosphate buffered saline (PBS) containing 0.01% Tween 20 and the sample to be determined added, followed by addition of solubilized GP IIbIIIa receptor (40 mg/ml) in TACTS, 0.5% BSA. After incubation, the plate is washed and 1 mg/ml of murine anti-platelet monoclonal antibody AP3 (Newman et al., *Blood* 65:227–232 (1985)) is added. After another wash a goat anti-mouse IgG conjugated to horseradish peroxidase is added. A final wash is performed and developing reagent buffer (10 mg o-phenylenediamine dihydrochloride, 0.0212% hydrogen peroxide, 0.22 mM citrate, 50 mM phosphate, pH 5.0) is added and then incubated until color develops. The reaction is stopped with 1N sulfuric acid and the absorbance at 492 nm is recorded.

In addition to the $GPII_bIII_a$ ELISA assay, platelet aggregation assays may be performed in human platelet rich plasma (PRP). Fifty milliliters of whole human blood (9 parts) is drawn on 3.6% sodium citrate (1 part) from a donor who has not taken aspirin or related medications for at least two weeks. The blood is centrifuged at 160×g for 10 min at 22° C. and then allowed to stand for 5 min after which the PRP is decanted. Platelet poor plasma (PPP) is isolated from the remaining blood after centrifugation at 2000×g for 25 min. The platelet count of the PRP is adjusted to ca. 300,000 per microliter with PPP.

A 225 mL aliquot of PRP plus 25 mL of either a dilution of the test sample or a control (PBS) is incubated for 5 min in a Chrono-log Whole Blood Aggregometer at 25° C. An aggregating agent (collagen, 1 mg/ml; U46619, 100 ng/ml; or ADP, 8 mM) is added and the platelet aggregation recorded.

Without further description, it is believed that one of ordinary skill in the art can, using the preceding description and illustrative examples, make and utilize the present example to the fullest extent. The following working examples therefore, specifically point out preferred embodiments of the present invention, and are not to be construed as limiting in any way the remainder of the disclosure.

EXAMPLE 1

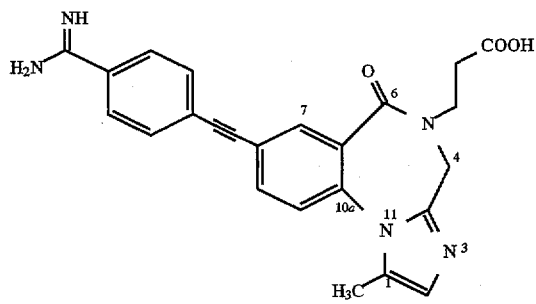

4H-imidazo[1,2-a][1,4]benzodiazepine-5(6H)-propanoic acid,8-[[4-(aminoiminomethyl)phenyl] ethynyl]-1-methyl-6-oxo, acetate a) A slurry of 1-(diphenylmethyl)-4-(2-carboxyethyl)-7-iodo-3,4-dihydro-1H-1,4-benzodiazepine-2,5-dione ethyl ester (15 grams, 0.0264 mol), (Blackburn, B. K., Barker, P.; Gadek, T; McDowell, R. S.; McGee, L.; Somers, T.; Webb, R.; Robarge, K. International Patent Application WO 93/08174), 15 mL anisole, and 3 mL ethyl methyl sulfide in a teflon tube was cooled to −196° C. ($N_2$) and condensed 70 mL hydrogen fluoride. The reaction was stirred for 2 hrs and concentrated in vacuo. The resulting residue was purified on column chromatography ($SiO_2$, using 30% ethyl acetate in hexane to 80% ethyl acetate in hexane). The material can be further purified by crystalization using a minimum volume of ethyl acetate (heating was required to dissolve the material) followed by the addition of an equal volume of hexanes to yield 8.5 grams (80%) of m.p. 129°–130° C. 4-(2-carboxyethyl)-7-iodo-3,4-dihydro-1H-1,4-benzodiazepine-2,5-dione ethyl ester. $^1$H NMR ($CDCl_3$, δTMS) 9.60 (1H, s, NH), 8.21 (1H, d, $^4J_{HH}$=2 Hz, C6 Ar—H), 7.72 (1H, dd, $^4J_{HH}$=2 Hz, $^3J_{HH}$=9 Hz, C8 Ar—H), 6.81 (1H, d, $^3J_{HH}$=9 Hz, C9 ArH), 4.12 (2H, q, $^3J_{HH}$=7 Hz, $OCH_2$), 3.97 (2H, s, $NCH_2CO$), 3.91 (2H, t, $^3J_{HH}$=7 Hz, $NCH_2CH_2CO_2$), 2.72 (2H, t, $^3J_{HH}$=7 Hz, $CH_2CO_2$), 1.23 (3H, t, $^3J_{HH}$=7 Hz, $CH_3$). $^{13}$C NMR ($CDCl_3$) 171.3, 170.7, 165.7, 141.1, 140.1, 135.6, 127.9, 122.4, 88.5, 60.8, 51.5, 45.7, 32.8, 14.1.

Using the above procedure, but substituting the appropriate 1-(diphenylmethyl)-4-(2-carboxyethyl)-3,4-dihydro-1H-1,4-benzodiazepine-2,5-dione ethyl ester for 1-(diphenylmethyl)-4-(2-carboxyethyl)-7-iodo-3,4-dihydro-1H-1,4-benzodiazepine-2,5-dione ethyl ester there may be prepared, for example, the following compounds:

4-(2-carboxyethyl)-7-[3-(4-piperidine)-propoxy]-3,4-dihydro-1H-1,4-benzodiazepine-2,5-dione ethyl ester, 4-(2-carboxyethyl)-7-[4-(1-piperazine)-phenyl]-3,4-dihydro-1H-1,4-benzodiazepine-2,5-dione ethyl ester, 4-(2-carboxyethyl)-7-[3-(1-piperazine)-propoxy]-3,4-dihydro-1H-1,4-benzodiazepine-2,5-dione ethyl ester, 4-(2-carboxyethyl)-7-[4-(4-piperidine)-2-oxobutyl]-3,4-dihydro-1H-1,4-benzodiazepine-2,5-dione ethyl ester, 4-(2-carboxyethyl)-7-[2-(4-cyanophenyl)-2-oxoethyl]-3,4-dihydro-1H-1,4-benzodiazepine-2,5-dione ethyl ester, 4-(2-carboxyethyl)-7-[(4-cyanoanalino)-carbonyl]-3,4-dihydro-1H-1,4-benzodiazepine-2,5-dione ethyl ester, 4-(2-carboxyethyl)-7-[[4-(cyano)-phenylsulphonyl]-amino]-3,4-dihydro-1H-1,4-benzodiazepine-2,5-dione ethyl ester, 7-[[4-(cyano)benzoyl]amino]-1H-[1,4]benzodiazepine-2,5-dione-4-propanoic acid ethyl ester.

b) To a solution of 4-(2-carboxyethyl)-7-iodo-3,4-dihydro-1H-1,4-benzodiazepine-2,5-dione ethyl ester (1.0 grams, 2.49 mmol), in 10 mL THF at room temperature under an atmosphere of nitrogen was added 1.0 equiv. of Lawesson's reagent (1.0 grams) and the reaction heated to 50° C. for 2 hrs. The reaction mixture was allowed to cool to room temperature and concentrated in vacuo. The resulting residue was purified on column chromatography ($SiO_2$, using 40% ethyl acetate in hexanes to 60% ethyl acetate in hexanes, TLC (1:1, ethyl acetate/hexane): Rf=0.44, μv positive) to yield 0.95 grams (91%) of 4-(2-carboxyethyl)-7-iodo-3,4-dihydro-1H-1,4-benzodiazepine-2-thione-5-one ethyl ester (m.p. 187°–189° C). $^1$H NMR ($CDCl_3$, δTMS) 8.21 (1H, d, $4J_{HH}$=2 Hz, C6 Ar—H), 7.78 (1H, dd, $^4J_{HH}$=2 Hz, $^3J_{HH}$=9 Hz, C8 Ar—H), 6.88 (1H, d, $^3J_{HH}$=9 Hz, C9 ArH), 4.28 (2H, s, $NCH_2CS$), 4.15 (2H, q, $^3J_{HH}$=7 Hz, $OCH_2$), 3.94 (2H, t, $^3J_{HH}$=7 Hz, $NCH_2CH_2CO_2$), 2.72 (2H, t, $^3J_{HH}$=7 Hz, $CH_2CO_2$), 1.27 (3H, t, $^3J_{HH}$=7 Hz, $CH_3$). $^{13}$C NMR ($CDCl_3$) 198.8, 171.4, 165.3, 141.2, 140.4, 135.9, 128.9, 121.9, 90.4, 60.8, 58.0, 45.4, 32.8, 14.1.

Using the above procedure, but substituting the appropriate 4-(2-carboxyethyl)-3,4-dihydro-1H-1,4-benzodiazepine-2,5-dione ethyl ester for 4-(2-carboxyethyl)-7-iodo-3,4-dihydro-1H-1,4-benzodiazepine-2,5-dione ethyl ester there may be prepared, for example, the following compounds:

4-(2-carboxyethyl)-7-[3-(1-(N-Boc)-4-piperidine)-propoxy]-3,4-dihydro-1H-1,4-benzodiazepine-2-thione-5-one ethyl ester, 4-(2-carboxyethyl)-7-[4-(4-(N-Boc)-1-piperazine)-phenyl]-3,4-dihydro-1H-1,4-benzodiazepine-2-thione-5-one ethyl ester, 4-(2-carboxyethyl)-7-[3-(4-(N-Boc )-1-piperazine)-propoxy]-3,4-dihydro-1H-1,4-benzodiazepine-2-thione-5-one ethyl ester, 4-2-carboxyethyl)-7-[4-(1-(N-Boc)-4-piperidine)-2-oxobutyl]-3,4-dihydro-1H-1,4-benzodiazepine-2-thione-5-one ethyl ester, 4-(2-carboxyethyl)-7-[2-(4-cyanophenyl)-2-oxoethyl]-3,4-dihydro-1H-1,4-benzodiazepine-2-thione-5-one ethyl ester, 4-(2-carboxyethyl)-7-[(4-cyanoanalino)-carbonyl]-3,4-dihydro-1H-1,4-benzodiazepine-2-thione-5-one ethyl ester, 4-(2-carboxyethyl)-7-[[4-(cyano)-phenylsulphonyl]-amino]- 3,4-dihydro-1H-1,4-benzodiazepine-2-thione-5-one ethyl ester, 7-[[4-(cyano)benzoyl]amino]-1H-[1,4]benzodiazepine-2-thione-5-one-4-propanoic acid ethyl ester.

c) To a biphasic solution of the 4-(2-carboxyethyl)-7-iodo-3,4-dihydro-1H-1,4-benzodiazepine-2-thione-5-one ethyl ester (0.95 grams, 2.27 mmol), $CH_2Cl_2$ (10 mL), water (10 mL), methyl iodide (0.2 grams) and a catalytic amount of tetrabutylammonium hydrogen sulfate at room temperature with vigorous stirring was added 1.2 mL 2N sodium hydroxide. The reaction was monitored by TLC. After 2 hrs, the layers were seperated and the aqueous layer was washed 2×25 mL $CH_2Cl_2$. The combined organics were dried over sodium sufate, decanted and concentrated in vacuo. The resulting residue was dissolved in 10 mL toluene and allowed to react with propargyl amine (4-fold excess, 0.64 mL) and pyridine hydrogen chloride (1 molar equiv., 0.23 grams). The reaction was heated to reflux and the reaction monitored by TLC. After 6 hrs, the reaction mixture was allowed to cool to room temperature, concentrated in vacuo, and purified by column chromatography ($SiO_2$, 100% ethyl acetate), to yield 0.653 grams (66% yield) of 4H-imidazo[1,2-a][1,4]benzodiazepine-5(6H)-propanoic acid, 8-iodo-1-methyl-6-oxo, ethyl ester. $^1$H NMR ($CDCl_3$, δTMS) 8.33

(1H, d, $^4J_{HH}$=2 Hz, C7 Ar—H), 7.90 (1H, dd, $^4J_{HH}$=2 Hz, $^3J_{HH}$=9 Hz, C9 Ar—H), 7.00 (1H, d, $^3J_{HH}$=9 Hz, C10 ArH), 6.89 (1H, bq, $^4J_{HH}$=1 Hz), 4.49 (1H, d, $^2J_{HH}$=15 Hz, NCHHCN), 4.32 (1H, d, 2JHH=15 Hz, NCHHCN) 4.17 (2H, q, $^3J_{HH}$=7 Hz, OCH$_2$), 3.94 (2H, m, NCH$_2$CH$_2$CO$_2$), 2.69 (2H, m, CH$_2$CO$_2$), 2.33 (3H, d, $^4J_{HH}$=1 Hz, CH$_3$),1.27 (3H, t, $^3J_{HH}$=7 Hz, CH$_3$). $^{13}$C NMR (CDCl$_3$) 171.3, 145.9, 140.7, 140.5, 140.4,132.8, 128.1, 124.6, 91.9, 60.8, 45.7, 45.1, 32.8, 14.1, 11.0.

Using the above procedure, but substituting the appropriate 4-(2-carboxyethyl)-3,4-dihydro-1H-1,4-benzodiazepine-2-thione-5-one ethyl ester for 4-(2-carboxyethyl)-7-iodo-3,4-dihydro-1H-1,4-benzodiazepine-2-thione-5-one ethyl ester there may be prepared, for example, the following compounds:

4H-imidazo[1,2-a][1,4]benzodiazepine-5(6H)-propanoic acid, 8-[3-[1-(N-Boc)-4-piperidine]-propoxy]-1-methyl-6-oxo, ethyl ester, 4H-imidazo[1,2-a][1,4]benzodiazepine-5(6H)-propanoic acid, 8-[4-[4-(N-Boc)-1-piperazine]-phenyl]-1-methyl-6-oxo, ethyl ester, 4H-imidazo[1,2-a][1,4]benzodiazepine-5(6H)-propanoic acid, 8-[3-[4-(N-Boc)-1-piperazine]-propoxy]-1-methyl-6-oxo, ethyl ester, 4H-imidazo[1,2-a][1,4]benzodiazepine-5(6H)-propanoic acid, 8-[4-[1-(N-Boc)-4-piperidine]-2-oxobutyl]-1-methyl-6-oxo, ethyl ester, 4H-imidazo[1,2-a][1,4]benzodiazepine-5(6H)-propanoic acid, 8-[2-(4-cyanophenyl)-2-oxoethyl]-1-methyl-6-oxo, ethyl ester, 4H-imidazo[1,2-a][1,4]bertzodiazepine-5(6H)-propanoic acid, 8-[(4-cyanoanalino)-carbonyl]-1-methyl-6-oxo, ethyl ester, 4H-imidazo[1,2-a][1,4]benzodiazepine-5(6H)-propanoic acid, 8-[[4-(cyano)phenylsulphonyl]-amino]-1-methyl-6-oxo, ethyl ester, 4H-imidazo[1,2-a][1,4]benzodiazepine-5(6H)-propanoic acid,8-[[4-(cyano)benzoyl]amino]-1-methyl-6-oxo, ethyl ester.

d) To a slurry of the 4H-imidazo[1,2-a][1,4]benzodiazepine-5(6H)-propanoic acid, 8-iodo-1-methyl-6-oxo, ethyl ester (0.15 grams, 0.34 mmol), 4 mL ethyl acetate (degassed), 4-cyanophenylacetylene (2 molar eqiuv. 0.135 grams), bis(triphenylphosphine)palladium dichloride (10 mgs), copper iodide (10 mgs), at room temperature under an atmosphere of nitrogen was added triethylamine (0.24 grams), and the reaction allowed to stir overnight. The reaction was con centrated in vacuo and the residue purified by column chromatography (SiO$_2$, using 100% ethyl acetate) to yield 0.157 grams (78%) of 4H-imidazo[1,2-a][1,4]benzodiazepine-5(6H)-propanoic acid, 8-[[4-cyanophenyl]ethynyl]-1-methyl-6-oxo, ethyl ester. $^1$H NMR (CDCl$_3$, δTMS) 8.01 (1H, d, $^4J_{HH}$=2 Hz, C7 Ar—H), 7.92 (2H, d, $^3J_{HH}$=8 Hz, o-CN ArH), 7.84 (1H, dd, $^4J_{HH}$=2 Hz, $^3J_{HH}$=9 Hz, C9 Ar—H), 7.78 (2H, d, 3JHH=8 Hz, m-CN ArH), 7.61 (1H, d, $^3J_{HH}$=9 Hz, C10 ArH), 6.82 (1H, bq, $^4J_{HH}$=1 Hz), 4.49 (1H, d, $^2J_{HH}$=15 Hz, 4.35 (1H, d, 2JHH=15 Hz, NCHHCN) 4.00 (2H, q, $^3J_{HH}$=7 Hz, OCH$_2$), 3.77 (2H, bt, NCH$_2$CH$_2$CO$_2$), 2.58 (2H, CH$_2$CO$_2$), 2.30 (3H, d, $^4J_{HH}$=1 Hz, CH$_3$),1.13 (3H, t, $^3J_{HH}$=7 Hz, CH$_3$). $^{13}$C NMR (CDCl$_3$) 171.3, 166.1, 135.5, 134.2, 133.1, 132.1, 128.1, 127.3, 121.6, 118.3, 111.9, 91.4 89.5, 60.7, 45.7, 45.1, 32.7, 14.1, 11.1.

e) To a solution of 0.15 grams of 4H-imidazo[1,2-a][1,4]benzodiazepine-5(6H)-propanoic acid, 8-[[4-cyanophenyl]ethynyl]-1-methyl-6-oxo, ethyl ester and pyridine (2 mL) and diethylamine (2 mL) was bubbled via a pipette for 5 mins. hydrogen sulfide (gas). The reaction was stirred for 2 hrs at room temperature, concentrated in vacuo, and purified by column chromatography (SiO$_2$, 100% ethyl acetate). The yellow compound was further allowed to react with methyl iodide (2 mL) in methylene chloride (4 mL), heating to 50° C. for 30 mins. The mixture was concentrated in vacuo and the resulting residue allowed to react with ammonium acetate (0.5 grams) in ethanol (5 mL). The mixture was again heated to 50° C. for 30 mins. After cooling to room temperature the reaction was purified by HPLC (0–10 mins. (30% acetonitrile(0.5% acetic acid)/70% water(0.5% acetic acid) 10–50 mins. ramp to 70% acetonitrile (0.5% acetic acid)/30% water (0.5% acetic acid), 15 mL/min., Detector: 254 nM, R$_f$=27.6 mins.) to yield 0.025 grams of 4H-imidazo[1,2-a][1,4]benzodiazepine-5(6H)-propanoic acid, 8-[[4-(aminoiminomethyl)phenyl]ethynyl]-1-methyl-6-oxo, ethyl ester acetate (16%). MS (FAB) cald. for C$_{26}$H$_{25}$N$_5$O$_3$ 455.1, found MH$^+$ 456.1.

Using the above procedure, but substituting the appropriate 4H-imidazo[1,2-a][1,4]benzodiazepine-5(6H)-propanoic acid,1-methyl-6-oxo, ethyl ester for 4H-imidazo[1,2-a][1,4]benzodiazepine-5(6H)-propanoic acid, 8-[[4-cyanophenyl]ethynyl]-1-methyl-6-oxo, ethyl ester there may be prepared, for example, the following compounds:

4H-imidazo[1,2-a][1,4]benzodiazepine-5(6H)-propanoic acid, 8-[2-[4-(aminoiminomethyl)]-2-oxoethyl]-1-methyl-6-oxo, ethyl ester, 4H-imidazo[1,2-a][1,4]benzodiazepine-5(6H)-propanoic acid, 8-[[4-(aminoiminomethyl)-anilino]-carbonyl]-1-methyl-6-oxo, ethyl ester, 4H-imidazo[1,2-a][1,4]benzodiazepine-5(6H)-propanoic acid, 8-[[4-(aminoiminomethyl)phenylsulphonyl]-amino]-1-methyl-6-oxo, ethyl ester, 4H-imidazo[1,2-a][1,4]benzodiazepine-5(6H)-propanoic acid,8-[[4-(aminoiminomethyl)benzoyl]amino]-1-methyl-6-oxo, ethyl ester.

f) 4H-imidazo[1,2-a][1,4]benzodiazepine-5(6H)-propanoic acid, 8-[[4-(aminoiminomethyl)phenyl]ethynyl]-1-methyl-6-oxo, ethyl ester acetate taken from part (e) above was saponified in 2 mL methanol with 2 mL 2N sodium hydroxide for 20 mins. The reaction mixture was quenched with acetic acid and purified by HPLC (0–10 mins. (30% acetonitrile(0.5% acetic acid)/70% water(0.5% acetic acid) 10–50 mins. ramp to 70% acetonitrile (0.5% acetic acid)/ 30% water (0.5% acetic acid), Detector: 2.54 nM, R$_f$=23.5 mins.) to yield 20 mgs (85%) of 4H-imidazo[1,2-a][1,4]benzodiazepine-5(6H)-propanoic acid, 8-[[4-(aminoiminomethyl)phenyl]ethynyl]-1-methyl-6-oxo, acetate. Exact mass (FAB, MH$^+$) cald for C$_{24}$H$_{25}$N$_5$O$_3$: 428.1723, found 428.1705.

Using the above procedure, but substituting the appropriate 4H-imidazo[1,2-a][1,4]benzodiazepine-5(6H)-propanoic acid, 1-methyl-6-oxo, ethyl ester for 4H-imidazo [1,2-a][1,4]benzodiazepine-5(6H)-propanoic acid, 8-[[4-(aminoiminomethyl)phenyl]ethynyl]-1-methyl-6-oxo, ethyl ester there may be prepared, for example, the following compounds:

4H-imidazo[1,2-a][1,4]benzodiazepine-5(6H)-propanoic acid, 8-[2-[4-(aminoiminomethyl)]-2-oxoethyl]-1-methyl-6-oxo, acetate, 4H-imidazo[1,2-a][1,4]benzediazepine-5(6H)-propanoic acid, 8-[[4-(aminoiminomethyl)anilino]-carbonyl]-1-methyl-6-oxo, acetate, 4H-imidazo[1,2-a][1,4]benzodiazepine-5(6H)-propanoic acid, 8-[[4-(aminoiminomethyl)phenylsulphonyl]-amino]- 1-methyl-6-oxo, acetate 4H-imidazo[1,2-a][1,4]benzodiazepine-5(6H)-propanoic acid,8-[[4-(aminoiminomethyl)benzoyl]amino]-1-methyl-6-oxo, acetate.

EXAMPLE 2

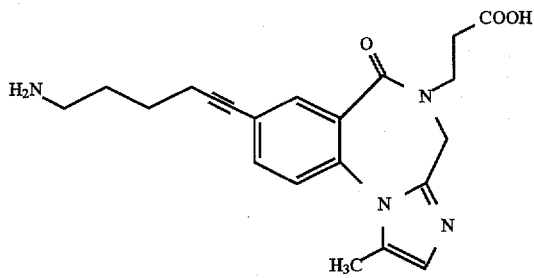

4H-imidazo[1,2-a][1,4]benzodiazepine-5(6H)-
propanoic acid,8-[6-aminohex-1-ynyl]-1-methyl-6-
oxo, acetate a) To a slurry 4H-imidazo[1,2-a][1,4]benzodiazepine-5 (6H)-propanoic acid, 8-iodo-1-methyl-6-oxo, ethyl ester, prepared as described in part (c) of example 1, (0.15 grams, 0.34 mmol), 4 mL ethyl acetate (degassed), N-Boc-6-aminohexyne (0.135 grams, 0.68 mmol), bistriphenylphosphine palladium dichloride (10 mgs), copper iodide (10 mgs), at room temperature under an atmosphere of nitrogen was added triethylamine (0.16 mL, 5× excess) and the reaction allowed to stir overnight. The reaction was concentrated in vacuo and the residue chromatographed (60 mL $SiO_2$, ethyl acetate) to yield the desired product, 4H-imidazo [1,2-a][1,4]benzodiazepine-5(6H)-propanoic acid,8-[[N-Boc]6-aminohex-1-ynyl]-1-methyl-6-oxo, ethyl ester (0.113 grams, 65%). $_1$H NMR ($CDCl_3$, δTMS) 7.84 (1H, d, $^4J_{HH}$=2 Hz, C7 Ar—H), 7.40 (1H, dd, $^4J_{HH}$=2 Hz, $^3J_{HH}$=9 Hz, C8 Ar—H), 7.04 (1H, d, $^3J_{HH}$=9 Hz, C9 ArH), 6.64 (1H, s, C2-H), 4.45 (1H, bq, NH), 4.32 (1H, d, $^2J_{HH}$=16 Hz, C4H), 4.13 (1H, d, $^2J_{HH}$=16 Hz, C4H), 3.97 (2H, q, $^3J_{HH}$=7 Hz, $OCH_2$), 3.76 (2H, m, $NCH_2CH_2$), 3.03 (2H, bq, $NHCH_2$), 2.51 (2H, m, $CH_2CO_2$), 2.3 (2H, t, $^3J_{HH}$=7 Hz, C≡$CCH_2$), 2.17 (3H, s, Me), 1.49 (4H, m, $CH_2CH_2$), 1.28 (9H, s, t-Bu), 1.08 (3H, t, $^3J_{HH}$=7 Hz, $CH_2CH_3$); $^{13}C$ NMR ($CDCl_3$) 171.3, 166.4, 145.9, 135.1, 134.2, 131.9, 130.3, 127.9, 123.5, 123.0, 92.2, 79.2, 60.7, 45.6, 44.9 32.8, 29.3, 28.4, 25.7, 19.0, 14.1, 11.1; MS (FAB) cald. for $C_{28}H_{36}N_4O_5$ 508.3, found $MH^+$ 509.3.

b) A solution of 4H-imidazo[1,2-a][1,4]benzodiazepine-5(6H)-propanoic acid,8-[[N-Boc]6-aminohex-1-ynyl]-1-methyl-6-oxo, ethyl ester (0.113 grams, 0.22 mmol) in 2 mL ethyl acetate and 0.5 mL triethylsilane was added to 2 mL of a saturated solution of hydrogen chloride in ethyl acetate and the reaction monitored by TLC. After 30 mins., the reaction was concentrated in vacuo, diluted with 2 mL ethanol and allowed to react with 0.5 mL 2N sodium hydroxide. After 15 mins. the reaction was quenched with 0.5 mL glacial acetic acid and purified by HPLC (C18, 0–10 mins. (30% acetonitrile(0.5% acetic acid)/70% water(0.5% acetic acid) 10–50 mins. ramp to 70% acetonitrile (0.5% acetic acid)/ 30% water (0.5% acetic acid), Detector: 254 nM) to yield 44.2 mgs (52%) of 4H-imidazo[1,2-a][1,4]benzodiazepine-5(6H)-propanoic acid,8-[6-aminohex-1-ynyl]-1-methyl-6-oxo, acetate. $^1H$ NMR ($D_2O$, δHOD) 7.63 (1H, d, $^4J_{HH}$=2 Hz, C7 Ar—H), 7.42 (1H, dd, $^4J_{HH}$=2 Hz, $^3J_{HH}$=9 Hz, C8 Ar—H), 7.29 (1H, d, $^3J_{HH}$=9 Hz, C9 ArH), 6.98 (1H, bs, C2H), 4.50 (1H, bd, $^2J_{HH}$=16 Hz, $C_4H$), 4.24 (1H, bd, $^2J_{HH}$=16 Hz, C4H), 3.64 (2H, bs, $NCH_2CH_2$), 2.92 (2H, t, $^3J_{HH}$=7 Hz, $NH_3CH_2$), 2.41 (2H, m, $CH_2CO_2$), 2.2 (5H, m, C≡$CCH_2$, Me), 1.63 (2H, m, $NH_3CH_2CH_2CH_2$), 1.42 (2H, m, $NH_3CH_2CH_2CH_2$). Exact mass (FAB, $MH^+$) cald for $C_{21}H_{24}N_4O_3$: 381.1927, found 381.1943.

Using the above procedure, but substituting the appropriate 4H-imidazo[1,2-a][1,4]benzodiazepine-5(6H)-propanoic acid,1-methyl-6-oxo, ethyl ester for 4H-imidazo [1,2-a][1,4]benzodiazepine-5(6H)-propanoic acid,8-[[N-Boc]6-aminohex-1-ynyl]-1-methyl-6-oxo, ethyl ester there may be prepared, for example, the following compounds:

4H-imidazo[1,2-a][1,4]benzodiazepine-5(6H)-propanoic acid, 8-[3-(4-piperidine)-propoxy]-1-methyl-6-oxo, acetate, 4H-imidazo[1,2-a][1,4]benzodiazepine-5(6H)-propanoic acid, 8-[4-(1-piperazine)-phenyl]-1-methyl-6-oxo, acetate, 4H-imidazo[1,2-a][1,4]benzodiazepine-5(6H)-propanoic acid, 8-[3-(1-piperazine)-propoxy]-1-methyl-6-oxo, acetate, 4H-imidazo[1,2-a][1,4]benzodiazepine-5(6H)-propanoic acid, 8-[4-(4-piperidine)-2-oxobutyl]-1-methyl-6-oxo, acetate, 4H-[1,2,4]triazolo[4,3-a][1,4]benzodiazepine-5(6H)-propanoic acid, 8-[3-[4-piperidine]-propoxy]-1-methyl-6-oxo, acetate, 4H-[1,2,4]triazolo[4,3-a][1,4]benzodiazepine-5(6H)-propanoic acid, 8-[4-[1-piperazine]-phenyl]-1-methyl-6-oxo, acetate, 4H-[1,2,4]triazolo[4,3-a][1,4]benzodiazepine-5(6H)-propanoic acid, 8-[3-[1-piperazine]-propoxy]-1-methyl-6-oxo, acetate, 4H-[1,2,4]triazolo[4,3-a][1,4]benzodiazepine-5(6H)-propanoic acid, 8-[4-[4-piperidine]-2-oxobutyl]-1-methyl-6-oxo, acetate, 4H-[1,2,4]triazolo[4,3-a][1,4]benzodiazepine-5(6H)-propanoic acid, 8-[3-[4-piperidine]-propoxy]-1-hydroxy-6-oxo, acetate, 4H-[1,2,4]triazolo[4,3-a][1,4]benzodiazepine-5(6H)-propanoic acid, 8-[4-[1-piperazine]-phenyl]-1-hydroxy-6-oxo, acetate, 4H-[1,2,4]triazolo[4,3-a][1,4]benzodiazepine-5(6H)-propanoic acid, 8-[3-[1-piperazine]-propoxy]-1-hydroxy-6-oxo, acetate, 4H-[1,2,4]triazolo[4,3-a][1,4]benzodiazepine-5(6H)-propanoic acid, 8-[4-[4-piperidine]-2-oxobutyl]-1-hydroxy-6-oxo, acetate, 4H-[1,2,3,4]tetrazolo[1,5-a][1,4]benzodiazepine-5(6H)-propanoic acid, 8-[3-[4-piperidine]-propoxy]-6-oxo, acetate, 4H-[1,2,3,4]tetrazolo[1,5-a][1,4]benzodiazepine-5(6H)-propanoic acid, 8-[4-[1-piperazine]-phenyl]-[1]6-oxo, acetate, 4H-[1,2,3,4]tetzazolo[1,5-a][1,4]benzodiazepine-5(6H)-propanoic acid, 8-[3-[1-piperazine]-propoxy]-6-oxo, acetate, 4H-[1,2,3,4]tetrazolo[1,5-a][1,4]benzodiazepine-5(6H)-propanoic acid, 8-[4-[4-piperidine]-2-oxobutyl]-6-oxo, acetate, quinazolino[3,2-a][1,4]benzodiazepine-6(5H)-propanoic acid, 8-[3-[4-piperidine]-propoxy]-7,13-dihydro-5,13-dioxo, acetate, quinazolino[3,2-a][1,4]benzodiazepine-6(5H)-propanoic acid, 8-[4-[piperazine]-phenyl]-7,13-dihydro-5,13-dioxo, acetate, quinazolino[3,2-a][1,4]benzodiazepine-6(5H)-propanoic acid, 8-[3-[1-piperazine]-propoxy]-7,13-dihydro-5,13-dioxo, acetate, quinazolino[3,2-a][1,4]benzodiazepine-6(5H)-propanoic acid, 8-[4-[4-piperidine]-2-oxobutyl]-7,13-dihydro-5,13-dioxo, acetate.

EXAMPLE 3

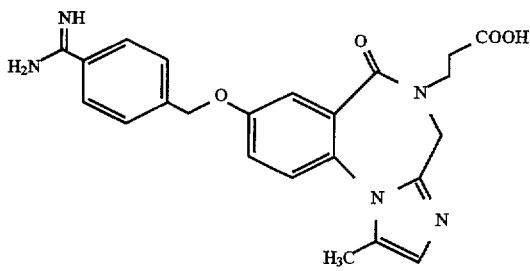

4H-imidazo[1,2-a][1,4]benzodiazepine-5(6H)-propanoic acid,8-[[4-(aminoiminomethyl)phenyl]methoxy]-1-methyl-6-oxo, acetate a) A solution of 1.44 g (7.15 mmol, 1.1 eq.) bromoacetyl bromide in 10 mL of methylene chloride was added over 10 mins. to a stirred biphasic solution of 2.38 g (6.5 mmol, 1.0 eq.) of N-(5-(4-cyanobenzyloxy)-2-aminobenzoyl)-β-alanine ethyl ester in 100 ml of methylene chloride and 30 mL of water cooled to 0° C. The reaction was complete in ½ hr. (TLC, 96 $CH_2Cl_2$:4 MeOH, product $R_f$=0.71) and was partitioned between dilute aqueous sodium bicarbonate and methylene chloride. The organic phase was dried over sodium sulfate, filtered and concentrated to give 3.11 g (98%) of off white crystals of N-(5-(4-cyanobenzyloxy)-2-(bromoacetyl)aminobenzoyl)-β-alanine ethyl ester which was used unpurified but may be recrystallized from ethyl acetate/hexane. $^1$H NMR ($CDCl_3$, δTMS) 8.41(1H,d,ArH), 7.60 (4H,abq,ArH), 7.02(2H,d,ArH), 6.98(1H,t,NH), 5.12 (2H,s,$ArCH_2O$),4.16 (2H,q,$COOCH_2$),3.97 (2H,s,$CH_2Br$), 3.68 (2H, q, $NCH_2$), 2.61 (2H,t,$CH_2COO$), 1.25 (3H,t, $CH_3$). IR (KBr): 3389(NH), 3355(NH), 2226(CN), 1735(ester), 1675,1642(amides),1609,1523,1423,1244,1184,819. MS (FAB,M+H$^+$) cald for $C_{22}H_{22}N_3O_5Br$ 488.3, found (M+H$^+$) 489.

b) A mixture of 3.11 g (6.37 mmol, 1.0 eq.) of N-(5-(4-cyanobenzyloxy)-2-(bromoacetyl)aminobenzoyl)-β-alanine ethyl ester, 1.32 g (9.55 mmol, 1.5 eq.) powdered potassium carbonate and 350 mL of dry DMF were combined and stirred at 50° C. for 2 hrs. TLC (70 EtOAc:30 hexane, product $R_f$=0.31) indicated complete reaction. The reaction mixture was partitioned between ethyl acetate and water, the organic phase washed twice with water, once with brine, dried over sodium sulfate and evaporated to yield the crystalline product. The crystals were slurried in ether/ethyl acetate and filtered to give 1.5 g of 4-(2-carboxyethyl)-7-(4-cyanobenzyloxy)-3,4-dihydro-1H-1,4-benzodiazepine-2,5-dione ethyl ester. The residual ether/ethyl acetate solution was concentrated and chromatographed on silica to recover an additional 0.5 g of product. Total yield=2.0 g (77%). $^1$H NMR (300 MHz, acetone-$d_6$): 9.32 (1H,s,NH), 7.78 (4H, abq,ArH), 7.41 (1H,d,Ar), 7.20 (1H,d,Ar), 7.15 (1H,d,Ar), 5.24 (2H,s,$ArCH_2O$), 4.10 (2H,q,$COOCH_2$), 3.98 (2H,s, $COCH_2N$), 3.88 (2H,t,$NCH_2$), 3.77 (HOD), 2.66 (2H,t, $CH_2COO$), 2.03(acetone), 1.20(3H,t,$CH_3$). IR(KBr): 3521 (NH), 2226(CN), 1735(ester), 1682, 1642, 1609, 1503, 1277, 1204, 819. Exact mass: (FAB,M+H$^+$) cald for $C_{22}H_{22}N_3O_5$: 408.1559, found: 408.1538. A 19% yield of dimer was observed (TLC, 70 EtOAc: 30 hexane, $R_f$=0.23).

c) To a solution of 7-[[4-cyanophenyl]methoxy]-4-propanoic acid, 3,4-dihydro-1H-1,4-benzodiazepine-2,5-dione, ethyl ester (1.0 grams, 2.45 mmol), in THF (20 mL) at room temperature under an atmosphere of nitrogen was added 1.0 molar equivalent of Lawesson's reagent (1.0 grams) and the mixture heated to 50° C. for 2 hours. The mixture was allowed to cool to room temperature, concentrated in vacuo, and purified by column chromatography ($SiO_2$, 4:6 ethyl acetate:hexanes to 6:4 ethyl acetate:hexanes) to yield 1.0 grams (96%) of 7-[[4-cyanophenyl]methoxy]-4-propanoic acid, 3,4-dihydro-1H-1,4-benzodiazepine-2-thione-5-one, ethyl ester. $^1$H NMR ($CDCl_3$, δTMS) 9.65 (1H, s, NH), 7.71 (2H, d, $^3J_{HH}$=8 Hz, 3,5H:4-$NCC_6H_4$), 7.55 (2H, $^3J_{HH}$=8 Hz, 2,6H:4-$NCC_6H_4$), 7.51 (1H, d, $^4J_{HH}$=3 Hz, C6 ArH), 7.13 (1H, dd, $^4J_{HH}$=3 Hz, $^3J_{HH}$=9 Hz, C8 ArH), 7.01 (1H, d, $^3J_{HH}$=9 Hz, C9 ArH), 5.17 (2H, s, $OCH_2Ar$), 4.29 (2H, s, C(S)CH2), 4.16 (2H, q, $^3J_{HH}$=7 Hz, $OCH_2$), 3.96 (2H, t, $^3J_{HH}$=7 Hz, $NCH_2$), 2.79 (2H, t, $^3J_{HH}$=7 Hz, $CH_2CO_2$), 1.27 (3H, t, $^3J_{HH}$=7 Hz, $CH_2CH_3$); MS (FAB) cald. for $C_{22}H_{21}N_3O_4S$ 423.1, found MH$^+$ 424.1.

d) To a biphasic solution of 7-[[4-cyanophenyl]methoxy]-4-propanoic acid, 3,4-dihydro-1H-1,4-benzodiazepine-2-thione-5-one, ethyl ester (1 gram, 2.36 mmol), methylene chloride (10 mL), water (10 mL), methyl iodide (0.2 mL) and a catalytic amount of tetrabutyl ammonium hydrogen sulphate at room temperature with vigorous stirring was added 1.2 mL of a 2N solution of sodium hydroxide. After 16 hours (overnight) the layers were seperated, the aqueous layer was washed 2×60 mL methylene chloride, and the combined organics were dried over sodium sulfate, decanted, and concentrated in vacuo. The resulting residue, 7-[[4-cyanophenyl]methoxy]-4-propanoic acid, 3,4-dihydro-1,4-benzodiazepine-2-methylmercaptyl-5-one, ethyl ester ($^1$H NMR ($CDCl_3$, δTMS) 7.70 (2H, d, $^3J_{HH}$=8 Hz, 3,5H:4-$NCC_6H_4$), 7.56 (2H, $^3J_{HH}$=8 Hz, 2,6H:4-$NCC_6H_4$), 7.49 (1H, d, $^4J_{HH}$=3 Hz, C6 ArH), 7.18 (1H, d, $^3J_{HH}$=9 Hz, C9 ArH), 7.15 (1H, dd, $^4J_{HH}$=3 Hz, $^3J_{HH}$=9 Hz, C8 ArH), 5.18 (2H, s, $OCH_2Ar$), 4.16 (2H, q, $^3J_{HH}$=7 Hz, $OCH_2$), 3.94 (2H, t, $^3J_{HH}$=7 Hz, $NCH_2$), 3.91 (2H, s, C(S)$CH_2$), 2.78 (2H, t, $^3J_{HH}$=7 Hz, $CH_2CO_2$), 2.52 (3H, s, SMe), 1.24 (3H, t, $^3J_{HH}$=7 Hz, $CH_2CH_3$); MS (FAB) cald. for $C_{23}H_{23}N_3O_4S$ 437.1, found MH$^+$ 438.1), was dissolved in dry toluene (15 mL) and allowed to react with 0.23 grams pyridinium hydrogen chloride and 0.64 mL propargyl amine. The reaction was heated to reflux. After 5 hours, the reaction was allowed to cool to room temperature and the reaction concentrated in vacuo. The crude material was purified by column chromatography ($SiO_2$, using ethyl acetate as the eluting solvent, $R_f$=0.1) to yield 4H-imidazo [1,2-a][1,4]benzodiazepine-5(6H)-propanoic acid,8-[[∝-cyanophenyl]methoxy]-1-methyl-6-oxo, ethyl ester (0.23 grams, 22%). $^1$H NMR ($CDCl_3$, δTMS) 7.71 (2H, d, $^3J_{HH}$=8 Hz, 3,5H:4-$NCC_6H_4$), 7.56 (2H, $^3J_{HH}$=8 Hz, 2,6H:4-$NCC_6H_4$), 7.53 (1H, d, $^4J_{HH}$=3 Hz, C6 ArH), 7.24 (1H, d, $^3J_{HH}$=9 Hz, C9 ArH), 7.18 (1H, dd, $^4J_{HH}$=3 Hz, $^3J_{HH}$=9 Hz, C8 ArH), 5.21 (2H, dd, $OCH_2Ar$), 4.52 (1H, d, $^2J_{HH}$=16 Hz, C5H), 4.30 (1H, d, $^2J_{HH}$=16 Hz, C5H), 4.16 (2H, q, $^3J_{HH}$=7 Hz, $OCH_2$), 3.89 (2H, m, $NCH_2$), 2.66 (2H, m, $CH_2CO_2$), 2.29 (3H, s, C1-Me), 1.22 (3H, t, $^3J_{HH}$7 Hz, $CH_2CH_3$).

e) To a solution of 4H-imidazo[1,2-a][1,4] benzodiazepine-5(6H)-propanoic acid,8-[[4-cyanophenyl]methoxy]-1-methyl-6-oxo, ethyl ester (0.1 grams, 0.22 mmol), in 2 mL pyridine and 2 mL triethylamine was added hydrogen sulfide gas via a pipette to saturation and the reaction stirred for 20 mins. A stream of nitrogen was passed over the reaction mixture for 20 mins., The mixture was concentrated in vacuo, diluted with methylene chloride (2 mL) and allowed to react with methyl iodide (2 mL). The mixture was heated briefly to 50° C., stirred for 30 mins., concentrated in vacuo, diluted with methanol and the reaction allowed to react with ammonium acetate (0.25 grams). Again the reaction was heated breifly to 50° C. and stirred for an additional 30 mins. The mixture was concentrated in vacuo and purified by HPLC (solvent gradient 1:4 acetonitrile:water(0.5% acetic acid) (time 0 to 10 mins.) to 3:2 acetonitrile:water(0.5% acetic acid) (time 50). The major component isolated by HPLC was diluted in methanol (2 mL) and allowed to react 2N sodium hydroxide (2 mL). After 15 mins. the mixture was quenched with glacial acetic acid (0.5 mL) and purified by HPLC (same eluting conditions as those described above) to yield 4H-imidazo[1,2-a][1,4]benzodiazepine-5(6H)-propanoic acid, 8-[[4-(aminoiminomethyl)phenyl]methoxy]-1-methyl-6-oxo, acetate (0.005 grams, 5%). $^1$H NMR (D$_2$O, δHOD) 7.63 (2H, d, $^3J_{HH}$=8 Hz, 3,5H:4-NCC$_6$H$_4$), 7.53 (2H, $^3J_{HH}$=8 Hz, 2,6H:4-NCC$_6$H$_4$), 7.44 (1H, d, $^3J_{HH}$=9 Hz, C6 ArH), 7.36 (1H, d, $^4J_{HH}$=3 Hz, C9 ArH), 7.26 (1H, dd, $^4J_{HH}$=3 Hz, $^3J_{HH}$=9 Hz, C8 ArH), 7.17 (1H, bq, C2H), 5.21 (2H, dd, OCH$_2$Ar), 3.78 (1H, d, 2J$_{HH}$=16 Hz, C4H), 3.79 (1H, dt, NCHH), 3.63 (1H, dt, NCHH), 2.54 (2H, m, CH$_2$CO$_2$), 2.22 (3H, s, C1-Me). Exact mass (FAB, MH$^+$) cald for C$_{23}$H$_{24}$N$_5$O$_4$: 434.1828, found 434.1794.

EXAMPLE 4

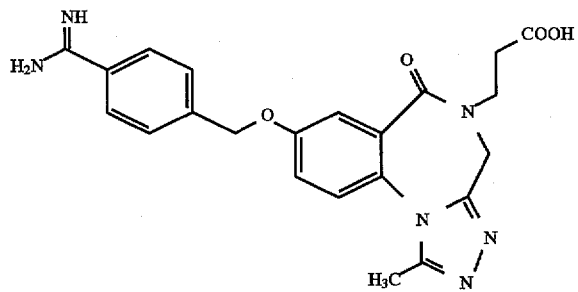

4H-[1,2,4]Triazolo[4,3-a][1,4]benzodiazepine-5(6H)-propanoic acid,8-[[4-(aminoiminomethyl)phenyl]methoxy]-1-methyl-6-oxo, acetate a) To a biphasic solution of 7-[[4-cyanophenyl]methoxy]-4-propanoic acid, 3,4-dihydro-1H-1,4-benzodiazepine-2-thione-5-one, ethyl ester (0.75 grams, 1.77 mmol), prepared as described in part (c) of Example 3, methylene chloride (20 mL), water (20 mL), 0.2 mL methyl iodide, and a catalytic amount of tetrabutyl ammonium hydrogen sulfate was added 1.2 mL 2N sodium hydroxide. After 16 hrs, overnight, of vigorous stirring the layers were seperated. The aqueous layer was washed 3×30 mL methylene chloride and the cobined organics were dried over sodium sulfate, decanted, and concentrated in vacuo. the resulting residue was dissolved in toluene (15 mL) and allowed to react with 0.23 grams (2.0 mmol) pyridinium hydrogen chloride and 0.64 grams (8.6 mmol) acetic hydrazide and the reaction was heated to reflux. After 5 hours, the reaction was allowed to cool to room temperature and concentrated in vacuo. The resulting residue was purified by column chromatography (SiO2, using 5:95 methanol:methylene chloride as the eluting solvent) to yield 0.5 grams (63%) of 4H-[1,2,4]triazolo[4,3-a][1,4]benzodiazepine-5(6H)-propanoic acid, 8-[[4-cyanophenyl]methoxy]-1-methyl-6-oxo, ethyl ester. $^1$H NMR (CDCl$_3$, δTMS) 7.59 (2H, d, $^3J_{HH}$=8 Hz, 3,5H:4-NCC$_6$H$_4$), 7.46 (2H, $^3J_{HH}$=8 Hz, 2,6H:4-NCC$_6$H$_4$), 7.45 (1H, d, $^4J_{HH}$=3 Hz, C6 ArH), 7.17 (1H, d, $^3J_{HH}$=9 Hz, C9 ArH), 7.12 (1H, dd, $^4J_{HH}$=3 Hz, $^3J_{HH}$=9 Hz, C8 ArH), 5.12 (2H, dd, OCH$_2$Ar), 4.61 (1H, d, $^2J_{HH}$16 Hz, C5H), 4.25 (1H, d, $^2J_{HH}$=16 Hz, C5H), 4.01 (2H, q, $^3J_{HH}$=7 Hz, OCH$_2$), 3.77 (2H, m, NCH$_2$), 2.57 (2H, m, CH$_2$CO$_2$), 2.46 (3H, s, C1-Me), 1.13 (3H, t, $^3J_{HH}$=7 Hz, CH$_2$CH$_3$); $^{13}$C NMR (CDCl$_3$) 171.1 165.9, 157.6, 152.4, 150.5, 141.0, 132.4, 131.2, 127.5, 124.1, 119.4, 118.3, 116.8, 111.9, 69.3, 60.6, 45.2, 43.3, 32.4, 14.0, 12.1.

Using the above procedure, but substituting the appropriate 4-propanoic acid, 3,4-dihydro-1H-1,4-benzodiazepine-2-thione-5-one, ethyl ester for 7-[[4-cyanophenyl]methoxy]-4-propanoic acid, 3,4-dihydro-1H-1,4-benzodiazepine-2-thione-5-one, ethyl ester and hydrazide or azide for acetic hydrazide there may be prepared, for example, the following compounds:

4H-[1,2,4]triazolo[4,3-a][1,4]benzodiazepine-5(6H)-propanoic acid, 8-[3-[1-(N-Boc)-4-piperidine]-propoxy]-1-methyl-6-oxo, ethyl ester, 4H-[1,2,4]triazolo[4,3-a][1,4]benzodiazepine-5(6H)-propanoic acid, 8-[4-[4-(N-Boc)-1-piperazine]-phenyl]-1-methyl-6-oxo, ethyl ester, 4H-[1,2,4]triazolo[4,3-a][1,4]benzodiazepine-5(6H)-propanoic acid, 8-[3-[4-(N-Boc)-1-piperazine]-propoxy]-1-methyl-6-oxo, ethyl ester, 4H-[1,2,4]triazolo[4,3-a][1,4]benzodiazepine-5(6H)-propanoic acid, 8-[4-[1-(N-Boc)-4-piperidine]-2-oxobutyl]-1-methyl-6-oxo, ethyl ester, 4H-[1,2,4]triazolo[4,3-a][1,4]benzo-diazepine-5(6H)-propanoic acid, 8-[2-(4-cyanophenyl)-2-oxoethyl]-1-methyl-6-oxo, ethyl ester, 4H-[1,2,4]-triazolo[4,3-a][1,4]benzodiazepine-5(6H)-propanoic acid, 8-[(4-cyanoanalino)-carbonyl]-1-methyl-6-oxo, ethyl ester, 4H-[1,2,4]triazolo[4,3-a][1,4]benzodiazepine-5(6H)-propanoic acid, 8-[[4-(cyano)-phenylsulphonyl]-amino]-1-methyl-6-oxo, ethyl ester, 4H-[1,2,4]triazolo[4,3-a][1,4]benzodiazepine-5(6H)-propanoic acid, 8-[3-[1-(N-Boc)-4-piperidine]-propoxy]-1-hydroxy-6-oxo, ethyl ester, 4H-[1,2,4]triazolo[4,3-a][1,4]benzodiazepine-5(6H)-propanoic acid, 8-[4-[4-(N-Boc)-1-piperazine]-phenyl]-1-hydroxy-6-oxo, ethyl ester, 4H-[1,2,4]triazolo[4,3-a][1,4]benzodiazepine-5(6H)-propanoic acid, 8-[3-[4-(N-Boc)-1-piperazine]-propoxy]-1-hydroxy-6-oxo, ethyl ester, 4H-[1,2,4]triazolo[4,3-a][1,4]benzodiazepine-5(6H)-propanoic acid, 8-[4-[1-(N-Boc)-4-piperidine]-2-oxobutyl]-1-hydroxy-6-oxo, ethyl ester, 4H-[1,2,4]triazolo[4,3-a][1,4]benzo-diazepine-5(6H)-propanoic acid, 8-[2-(4-cyanophenyl)-2-oxoethyl]-1-hydroxy-6-oxo, ethyl ester, 4H-[1,2,4]triazolo[4,3-a][1,4]benzodiazepine-5(6H)-propanoic acid, 8-[(4-cyanoanalino)-carbonyl]-1-hydroxy-6-oxo, ethyl ester, 4H-[1,2,4]triazolo[4,3-a][1,4]benzodiazepine-5(6H)-propanoic acid, 8-[[4-(cyano)-phenylsulphonyl]-amino]-1-hydroxy-6-oxo, ethyl ester, 4H-[1,2,4]triazolo[4,3-a][1,4]benzodiazepine-5(6H)-propanoic acid, 8-[[4-(cyano)benzoyl]amino]-1-hydroxy-6-oxo, ethyl ester, 4H-[1,2,3,4]tetrazolo[1,5-a][1,4]benzodiazepine-5(6H)-propanoic acid, 8-[3-[1-(N-Boc)-4-piperidine]-propoxy]-6-oxo, ethyl ester, 4H-[1,2,3,4]tetrazolo[1,5-a][1,4]benzodiazepine-5(6H)-propanoic acid, 8-[4-[4-(N-Boc)-1-piperazine]-phenyl]-6-oxo, ethyl ester, 4H-[1,2,3,4]tetrazolo[1,5-a][1,4]benzodiazepine-5(6H)-propanoic acid, 8-[3-[4-(N-Boc)-1-piperazine]-propoxy]-1-methyl-6-oxo, ethyl ester, 4H-[1,2,3,4]tetrazolo[1,5-a][1,4]benzodiazepine-5(6H)-propanoic acid, 8-[4-[1-(N-Boc)-4-piperidine]-2-oxobutyl]-1-methyl-6-oxo, ethyl ester, 4H-[1,2,3,4]tetrazolo[1,5-a][1,4]benzo-diazepine-5(6H)-propanoic acid, 8-[2-(4-cyanophenyl)-2-oxoethyl]-6-oxo, ethyl ester, 4H-[1,2,3,4]tetrazolo[1,5-a][1,4]benzodiazepine-5(6H)-propanoic acid, 8-[(4-cyanoanalino)-carbonyl]-6-oxo, ethyl ester, 4H-[1,2,3,4]tetrazolo[1,5-a][1,4]benzodiazepine-5(6H)-propanoic acid, 8-[[4-(cyano)-phenylsulphonyl]-amino]-6-oxo, ethyl ester, 4H-[1,2,3,4]tetrazolo[1,5-a][1,4]benzodiazepine-5(6H)-propanoic acid, 8-[[4-(cyano)benzoyl]-amino]-6-oxo, ethyl ester, quinazolino[3,2-a][1,4]benzodiazepine-6(5H)-propanoic acid, 8-[3-[1-(N-Boc)-4-piperidine]-propoxy]-7,13-dihydro-5,13-dioxo, ethyl ester, quinazolino[3,2-a][1,4]benzodiazepine-6(5H)-propanoic acid, 8-[4-[4-(N-Boc)-1-piperazine]-phenyl]-7,13-dihydro-5,13-dioxo, ethyl ester, quinazolino[3,2-a][1,4]benzodiazepine-6(5H)-propanoic acid, 8-[3-[4-(N-Boc)-1-piperazine]-propoxy]-7,13-dihydro-5,13-dioxo, ethyl ester, quinazolino[3,2-a][1,4]benzodiazepine-6(5H)-propanoic acid, 8-[4-[1-(N-Boc)-4-piperidine]-2-oxobutyl]-7,13-dihydro-5,13-dioxo, ethyl ester, quinazolino[3,2-a][1,4]benzodiazepine-6(5H)-propanoic acid, 8-[2-(4-cyanophenyl)-2-oxoethyl]-7,13-dihydro-5,13-dioxo, ethyl ester, quinazolino[3,2-a][1,4]benzodiazepine-6(5H)-propanoic acid, 8-[(4-cyanoanalino)-carbonyl]-7,13-dihydro-5,13-dioxo, ethyl ester, quinazolino[3,2-a][1,4]benzodiazepine-6(5H)-propanoic acid, 8-[[4-(cyano)phenylsulphonyl]amino]-7,13-dihydro-5,13-dioxo, ethyl ester, quinazolino[3,2-a][1,41benzodiazepine-6(5H)-propanoic acid, 8-[[4-(cyano)benzoyl]amino]-7,13-dihydro-5,13-dioxo, ethyl ester.

b) A solution of 4H-[1,2,4]triazolo[4,3-a][1,4]benzodiazepine-5(6H)-propanoic acid, 8-[[4-cyanophenyl]methoxy]-1-methyl-6-oxo, ethyl ester (grams, mmol) in 3 mL pyridine and 3 mL diethylamine was saturated with hydrogen sulfide gas, bubbled through the solution via a pipette. The reaction was monitored by TLC (SiO$_2$, 100% ethyl acetate) and was complete after 3 hours. The mixture was concentrated in vacuo and dissolved in 3 mL methylene chloride. The mixture was allowed to react with an excess of methyl iodide (2 mL), heating to 50° C. for 30 mins. The reaction was concentrated in vacuo, dissolved in ethanol (5 mL) and heated to 50° C. with ammonium acetate (0.5 grams) for 30 mins. The reaction was cooled to room temperature and purified by HPLC (solvent gradient 1:4 acetonitrile:water(0.5% acetic acid) (time 0 to 10 mins.) to 3:2 acetonitrile:water(0.5% acetic acid) (time 50 mins.), 20 mL/mins., C18 2" column, R$_t$=36.1 mins.) to yield 4H-[1,2,4]triazolo[4,3-a][1,4]benzodiazepine-5(6H)-propanoic acid, 8-[[4-(iminoaminomethyl)phenyl]methoxy]-1-methyl-6-oxo, ethyl ester. $^1$H NMR (D$_2$O, δHOD) 7.60 (2H, d, $^3J_{HH}$=8 Hz, 3,5H:4-NCC$_6$H$_4$), 7.46 (2H, $^3J_{HH}$=8 Hz, 2,6H:4-NCC$_6$H$_4$), 7.33 (1H, d, $^3J_{HH}$=9 Hz, C9 ArH), 7.23 (1H, d, $^4J_{HH}$=3 Hz, C6 ArH), 7.18 (1H, dd, $^4J_{HH}$=3 Hz, $^3J_{HH}$=9 Hz, C8 ArH), 5.05 (2H, s, OCH$_2$Ar), 4.48 (1H, d, $^2J_{HH}$=16 Hz, C5H), 4.27 (1H, d, $^2J_{HH}$=16 Hz, C5H), 3.93 (1H, m, NCHH), 3.74 (2H, q, $^3J_{HH}$=7 Hz, OCH$_2$), 3.48 (1H, dt, $^2J_{HH}$=14 Hz, $^3J_{HH}$=7 Hz, NCHH), 2.55 (1H, m, CHHCO$_2$), 2.40 (1H, dt, $^2J_{HH}$=15 Hz, $^3J_{HH}$=6 Hz, CHHCO2), 2.33 (3H, s, C1-Me), 0.85 (3H, t, $^3J_{HH}$7 Hz, CH$_2$CH$_3$).

Using the above procedure, but substituting the appropriate 4H-[1,2,4]triazolo[4,3-a][1,4]benzodiazepine-5(6H)-propanoic acid,1-methyl-6-oxo, ethyl ester for 4H-[1,2,4]triazolo[4,3-a][1,4]benzodiazepine-5(6H)-propanoic acid, 8-[[4-cyanophenyl]methoxy]-1-methyl-6-oxo, ethyl ester there may be prepared, for example, the following compounds:

4H-[1,2,4]triazolo[4,3-a][1,4]benzo-diazepine-5(6H)-propanoic acid, 8-[2-[4-(iminoaminomethyl)phenyl]-2-oxoethyl]-1-methyl-6-oxo, ethyl ester, 4H-[1,2,4]triazolo[4,3-a][1,4]benzodiazepine-5(6H)-propanoic acid, 8-[[4-(iminoaminomethyl)anilino]carbonyl]-1-methyl-6-oxo, ethyl ester, 4H-[1,2,4]triazolo[4,3-a][1,4]benzodiazepine-5(6H)-propanoic acid, 8-[[4-(iminoaminomethyl)phenylsulphonyl]-amino]-1-methyl-6-oxo, ethyl ester, 4H-[1,2,4]triazolo[4,3-a][1,4]benzo-diazepine-5(6H)-propanoic acid, 8-[2-[4-(iminoaminomethyl)phenyl]-2-oxoethyl]-1-hydroxy-6-oxo, ethyl ester, 4H-[1,2,4]triazolo[4,3-a][1,4]benzodiazepine-5(6H)-propanoic acid, 8-[[4-(iminoaminomethyl)analino]-carbonyl]-1-hydroxy-6-oxo, ethyl ester, 4H-[1,2,4]triazolo[4,3-a][1,4]benzodiazepine-5(6H)-propanoic acid, 8-[[4-(iminoaminomethyl)phenylsulphonyl]-amino]-1-hydroxy-6-oxo, ethyl ester, 4H-[1,2,3,4]tetrazolo[1,5-a][1,4]benzo-diazepine-5(6H)-propanoic acid, 8-[2-[4-(iminoaminomethyl)phenyl]-2-oxoethyl]-6-oxo, ethyl ester, 4H-[1,2,3,4]tetrazolo[1,5-a][1,4]benzodiazepine-5(6H)-propanoic acid, 8-[[4-(iminoaminomethyl)analino]-carbonyl]-6-oxo, ethyl ester, 4H-[1,2,3,4]tetrazolo[1,5-a][1,4]benzodiazepine-5(6H)-propanoic acid, 8-[[4-(iminoaminomethyl)phenylsulphonyl]amino]-6-oxo, ethyl ester, 4H-[1,2,3,4]tetrazolo[1,5-a][1,4]benzodiazepine-5(6H)-propanoic acid, 8-[[4-(iminoaminomethyl)benzoyl]amino]-6-oxo, ethyl ester, quinazolino[3,2-a][1,4]benzodiazepine-6(5H)-propanoic acid, 8-[2-[4-(iminoaminomethyl)phenyl]-2-oxoethyl]-7,13-dihydro-5,13-dioxo, ethyl ester, quinazolino[3,2-a][1,4]benzodiazepine-6(5H)-propanoic acid, 8-[[4-(iminoaminomethyl)analino]-carbonyl]-7,13-dihydro-5,13-dioxo, ethyl ester, quinazolino[3,2-a][1,4]benzodiazepine-6(5H)-propanoic acid,8-[[4-(iminoaminomethyl)phenylsulphonyl]-amino]-7,13-dihydro-5,13-dioxo, ethyl ester, quinazolino[3,2-a][1,4]benzodiazepine-6(5H)-propanoic acid, 8-[[4-(iminoaminomethyl)benzoyl]-amino]-7,13-dihydro-5,13-dioxo, ethyl ester.

c) To a solution of 4H-[1,2,4]triazolo[4,3-a][1,4]benzodiazepine-5(6H)-propanoic acid, 8-[[4-(iminoaminomethyl)phenyl]methoxy]-1-methyl-6-oxo, ethyl ester in 3 mL ethanol at room temperature was added 0.75 mL 2N sodium hydroxide and the reaction stirred for 45 mins. The mixture was quenched with 0.5 mL glacial acetic acid and purified by HPLC (solvent gradient 1:4 acetonitrile:water(0.5% acetic acid) (time 0 to 10 mins.) to 3:2 acetonitrile:water(0.5% acetic acid) (time 50 mins.), 20 mL/min, C$_{18}$ 2" column, R$_t$=33.2 mins.) to yield 4H-[1,2,4]triazolo[4,3-a][1,4]benzodiazepine-5(6H)-propanoic acid, 8-[[4-(iminoaminomethyl)phenyl]methoxy]-1-methyl-6-oxo, acetate. Exact mass (FAB, MH$^+$) cald for C$_{22}$H$_{23}$N$_6$O$_4$: 435.1781, found 435.1744.

Using the above procedure, but substituting the appropriate 4H-[1,2,4]triazolo[4,3-a][1,4]benzodiazepine-5(6H)-propanoic acid,1-methyl-6-oxo, ethyl ester for 4H-[1,2,4]triazolo[4,3-a][1,4]benzodiazepine-5(6H)-propanoic acid, 8-[[4-(iminoaminomethyl)phenyl]methoxy]-1-methyl-6-oxo, ethyl ester there may be prepared, for example, the following compounds:

4H-[1,2,4]triazolo[4,3-a][1,4]benzo-diazepine-5(6H)-propanoic acid, 8-[2-[4-(iminoaminomethyl)phenyl]-2-oxoethyl]-1-methyl-6-oxo, acetate, 4H-[1,2,4]triazolo[4,3-a][1,4]benzodiazepine-5(6H)-propanoic acid, 8-[[4-(iminoaminomethyl)anilino]carbonyl]-1-methyl-6-oxo, acetate, 4H-[1,2,4]triazolo[4,3-a][1,4]benzodiazepine-5(6H)-propanoic acid, 8-[[4-(iminoaminomethyl)phenylsulphonyl]-amino]-1-methyl-6-oxo, acetate, 4H-[1,2,4]triazolo[4,3-a][1,4]benzo-diazepine-5(6H)-propanoic acid, 8-[2-[4-(iminoaminomethyl)phenyl]-2-oxoethyl]-1-hydroxy-6-oxo, acetate, 4H-[1,2,4]triazolo[4,3-a][1,4]benzodiazepine-5(6H)-propanoic acid, 8-[[4-(iminoaminomethyl)analino]-carbonyl]-1-hydroxy-6-oxo, acetate, 4H-[1,2,4]triazolo[4,3-a][1,4]benzodiazepine-5(6H)-propanoic acid, 8-[[4-(iminoaminomethyl)phenylsulphonyl]-amino]-1-hydroxy-6-oxo, acetate, 4H-[1,2,4]triazolo[4,3-a][1,4]benzodiazepine-5(6H)-propanoic acid, 8-[[4-(iminoaminomethyl)benzoyl]amino]-1-hydroxy-6-oxo, acetate, 4H-[1,2,3,4]tetrazolo[1,5-a][1,4]benzo-diazepine-5(6H)-propanoic acid, 8-[2-[4-(iminoaminomethyl)phenyl]-2-oxoethyl]-6-oxo, acetate, 4H-[1,2,3,4]tetrazolo[1,5-a][1,4]benzodiazepine-5(6H)-propanoic acid, 8-[[4-(iminoaminomethyl)analino]-carbonyl]-6-oxo, acetate, 4H-[1,2,3,4]tetrazolo[1,5-a][1,4]benzodiazepine-5(6H)-propanoic acid, 8-[[4-(iminoaminomethyl)phenylsulphonyl]amino]-6-oxo, acetate, 4H-[1,2,3,4]tetrazolo[1,5-a][1,4]benzodiazepine-5(6H)-propanoic acid, 8-[[4-(iminoaminomethyl)benzoyl]amino]-6-oxo, acetate, quinazolino[3,2-a][1,4]benzodiazepine-6(5H)-propanoic acid, 8-[2-[4-(iminoaminomethyl)phenyl]-2-oxoethyl]-7,13-dihydro-5,13-dioxo, acetate, quinazolino[3,2-a][1,4]benzodiazepine-6(5H)-propanoic acid, 8-[[4-(iminoaminomethyl)analino]-carbonyl]-7,13-dihydro-5,13-dioxo, acetate, quinazolino[3,2-a][1,4]benzodiazepine-6(5H)-propanoic acid, 8-[[4-(iminoaminomethyl)phenylsulphonyl]amino]-7,13-dihydro-5,13-dioxo, acetate, quinazolino[3,2-a][1,4]benzodiazepine-6(5H)-propanoic acid, 8-[[4-(iminoaminomethyl)benzoyl]amino]-7,13-dihydro-5,13-dioxo, acetate.

EXAMPLE 5

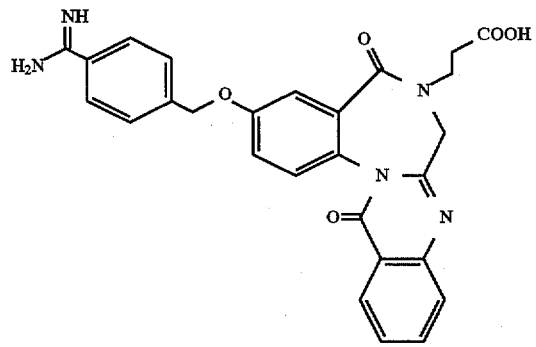

Quinazolino[3,2-a][1,4]benzodiazepine-6-(5H)-propanoic acid,8-[[4-(aminoiminomethyl)phenyl]methoxy]-7,13-dihydro-5,13-dioxo, acetate a) Quinazolino[3,2-a][1,4]benzodiazepine-6(5H)-propanoic acid,8-[[4-cyanophenyl]methoxy]-7,13-dihydro-5,13-dioxo, ethyl ester was prepared using the method described in part (a) of example 4, substituting methyl anthranilate (1.42 mL, 11.0 mmol) for acetic hydrazide; yield 0.3 grams (33%). $^1$H NMR (CDCl$_3$, δTMS) 8.33 (1H, d, 3JHH=8 Hz, ArH), 7.78 (2H, m, ArH), 7.71 (2H, d, $^3J_{HH}$=8 Hz, 3,5H:4-NCC$_6$H$_4$), 7.56 (4H, m, 2,6H:4-NCC$_6$H$_4$, ArH), 7.43 (1H, d, $^4J_{HH}$=3 Hz, C6 ArH), 7.17 (1H, d, $^3J_{HH}$=9 Hz, C9 ArH), 5.20 (2H, s, OCH$_2$Ar), 4.52 (1H, d, $^2J_{HH}$=16 Hz, C5H), 4.34 (1H, d, $^2J_{HH}$=16 Hz, C5H), 4.04 (2H, q, $^3J_{HH}$=7 Hz, OCH$_2$), 3.93 (2H, bt, NCH$_2$), 2.78 (1H, dt, $^2J_{HH}$=15 Hz, $^3J_{HH}$=6 Hz, CHHCO$_2$), 2.62 (1H, dt, 2J$_{HH}$=15 Hz, $^3J_{HH}$=6 Hz, CHHCO$_2$), 1.18 (3H, t, $^3J_{HH}$=7 Hz, CH$_2$CH$_3$).

b) Quinazolino[3,2-a][1,4]benzodiazepine-6(5H)-propanoic acid,8-[[4-(iminoaminomethyl)phenyl]methoxy]-7,13-dihydro-5,13-dioxo, ethyl ester was prepared using the method described in part (b) of example 4. Thus, from 0.3 grams (0.6 mmol) quinazolino[3,2-a][1,4]benzodiazepine-6(5H)-propanoic acid,3-[[4-cyanophenyl]methoxy]-7,13-dihydro-5,13-dioxo, ethyl ester was prepared quinazolino[3,2-a][1,4]benzodiazepine-6(5H)-propanoic acid,3-[[4-(aminoiminomethyl)phenyl]methoxy]-7,13-dihydro-5,13-dioxo, ethyl ester (0.22 grams, 71%, mp=235°–238° C.). The product precipitates from the crude reaction mixture and was isolated by suction filtration. The white powder was washed with a 1:1 mixture of ethanol:ether, and then ether.

c) Quinazolino[3,2-a][1,4]benzodiazepine-6(5H)-propanoic acid,3-[[4-(aminoiminomethyl)phenyl]methoxy]-7,13-dihydro-5,13-dioxo, acetate was prepared by disolving quinazolino[3,2-a][1,4]benzodiazepine-6(5H)-propanoic acid,3-[[4-(iminoaminomethyl)phenyl]methoxy]-7,13-dihydro-5,13-dioxo, ethyl ester (50 mgs, 0.085 mmol), in 4 mL THF and 2 mL water at room temperature and sequentally adding 0.77 mL 30% solution of hydrogen peroxide (9× excess) and 0.006 grams lithium hydroxide (0.256 mmol, 3× excess). The mixture was stirred for 2 hours, quenched with a saturated solution of sodium bisufite and 0.25 mL glacial acetic acid. The mixture was concentrated in vacuo and purified by HPLC (solvent gradient 1:4 acetonitrile:water (0.5% acetic acid) (time 0 to 10 mins.) to 3:2 acetonitrile:water(0.5% acetic acid) (time 50 mins.), 20 mL/min, C18 2" column) to yield quinazolino[3,2-a][1,4]benzodiazepine-6(5H)-propanoic acid,3-[[4-(aminoiminomethyl)phenyl]methoxy]-7,13-dihydro-5,13-dioxo, acetate (0.005 grams, 10%).

EXAMPLE 6

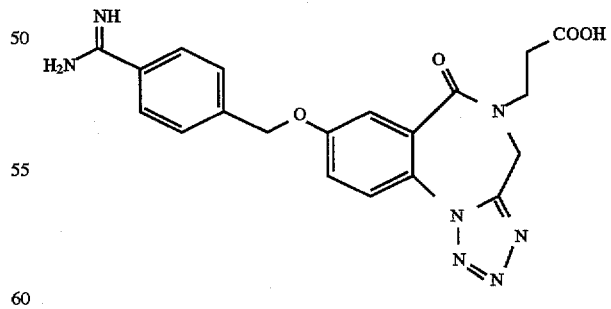

4H-[1,2,3,4]Tetrazolo[4,3a][1,4]benzodiazepine-5 (6H)-propanoic acid,8-[[4-(aminoiminomethyl) phenyl]methoxy]-6-oxo, acetate a) A solution of 4-(2-carboxyethyl)-7-[(4-cyanophenyl) methoxy]-3,4-dihydro-1H-1,4-benzodiazepine-2,5-dione ethyl ester (prepared in part (b) of Example 3, 1 g, 2.5 mmol) diethyl diazodicarboxylate (DEAD, 0.39 mL, 2.5 mmol), triphenylphosphine (0.65 g, 2.5 mmol), and trimethylsilylazide (0.33 mL, 2.5 mmol) in 20 mL dry tetrahydrofuran was magnetically stirred for for 24 hrs. An additional equivalent of DEAD, triphenylphosphine, and trimethylsilylazide were added and the mixture stirred for an additional 48 hrs. The mixture was concentrated in vacuo and purified by column chromatography (SiO$_2$, elution gradient of 30% ethyl acetate/70% hexane to 100% ethyl acetate) followed by a second column (SiO$_2$, elution gradient 5% acetone/methylene chloride to 10% acetone/methylene chloride) to yield 0.787 g (72%) of 4H-[1,2,3,4]tetrazolo[4,3a][1,4]benzodiazepine-5(6H)-propanoic acid, 8-[(4-cyanophenyl) methoxy]-6-oxo ethyl ester: mp=64°–67° C.; TLC (SiO$_2$, 1:1 ethyl acetate:hexane) R$_f$=0.11; $^1$H NMR (CDCl$_3$, δTMS) 7.87 (1H, d, $^3J_{HH}$=9 Hz, ArH C10-H), 7.72 (2H, d, $^3J_{HH}$=8 Hz, ArH), 7.66 (1H, d, $^4J_{HH}$=3 Hz, ArH C7-H), 7.59 (2H, d, $^3J_{HH}$=8 Hz, ArH), 7.34 (1H, dd, $^3J_{HH}$=9 Hz, $^4J_{HH}$=3 Hz, ArH C9-H), 5.27 (2H, s, OCH$_2$Ar) 4.85 (2H, s, C4H), 4.13 (2H, q, $^3J_{HH}$=7 Hz, OCH$_2$), 3.93 (2H, t, $^3J_{HH}$=6 Hz, NCH$_2$CH$_2$CO$_2$), 2.70 (2H, t, $^3J_{HH}$=6 Hz, CH$_2$CO$_2$), 1.24 (3H, s, CH$_3$); $^{13}$C NMR (CDCl$_3$) 171.4, 165.2, 158.7, 151.7, 141.0, 132.5, 128.5, 127.6, 121.0, 123.8, 120.7, 118.4, 117.0, 112.1, 69.4, 61.0, 46.2, 41.3, 33.0, 30.9, 14.1. HRMS (FAB, M+H$^+$) calcd. for C$_{22}$H$_{21}$N$_6$O$_4$ 433.1624, found 433.1596.

b) The amidino ester 4H-[1,2,3,4]tetrazolo[4,3a][1,4]benzodiazepine-5(6H)-propanoic acid, 8-[(4-(iminoaminomethyl)phenyl) methoxy]-6-oxo ethyl ester, acetate was prepared using the method described in part (e) of Example 1. Thus 0.5 grams of 4H-[1,2,3,4]tetrazolo[4,3a][1,4]benzodiazepine-5(6H)-propanoic acid, 8-[(4-cyanophenyl)methoxy]-6-oxo ethyl ester (1.16 mmol) yielded 0.343 grams (66%) of the amidino ester acetate salt. [Analytical HPLC Microsorb Short-One 80-200-C3, 9 mm×85 mm; elution gratient 0–100% acetonitrile (0.1% TFA)/water (0.1% TFA) over 11 min] R$_t$=5.51 min: mp=213°–216° C.; $^1$H NMR (CD$_3$OD, δTMS) 7.88 (1H, d, $^3J_{HH}$=9 Hz, ArH C10-H), 7.84 (2H, d, $^3J_{HH}$=8 Hz, ArH) 7.73 (2H, d, $^3J_{HH}$=8 Hz, ArH), 7.62 (1H, d, $^4J_{HH}$=3 Hz, ArH C7-H), 7.47 (1H, dd, $^3J_{HH}$=9 Hz, $^4J_{HH}$=3 Hz, ArH C9-H), 5.36 (2H, s, OCH$_2$Ar) 4.90 (2H, s, C4H), 4.01 (2H, q, $^3J_{HH}$=7 Hz, OCH$_2$), 3.93 (2H, t, $^3J_{HH}$=6 Hz, NCH$_2$CH$_2$CO$_2$), 2.64 (2H, t, $^3J_{HH}$=6 Hz, CH$_2$CO$_2$), 1.14 (3H, t, $^3J_{HH}$=7 Hz, CH$_3$); $^{13}$C NMR (CDCl$_3$) 172.9, 168.2, 167.3, 160.4, 154.0, 144.4, 129.9, 129.2, 125.5, 125.1, 121.6, 118.3, 70.6, 61.9, 47.1, 41.7, 33.9, 22.6, 14.5; HRMS (FAB, M+H$^+$) calc'd. for C$_{22}$H$_{21}$H$_7$O$_4$ 450.1890, found 450.1869.

c) 4H-[1,2,3,4]tetrazolo[4,3a][1,4]benzodiazepine-5(6H)-propanoic acid, 8-[(4-(iminoaminomethyl)phenyl)methoxy]-6-oxo ethyl ester, acetate was saponified using the conditions described in part (f) of Example 1. Thus 50 mgs of the amidino ester (0.1 mmol) yielded 30 mgs of 4H-[1,2,3,4]tetrazolo[4,3a][1,4]benzodiazepine-5(6H)-propanoic acid, 8-[(4-(iminoaminomethyl)phenyl)methoxy]-6-oxo, acetate. [Analytical HPLC Microsorb Short-One 80-200-C3, 9 mm×85 mm; elution gratient 0–100% acetonitrile (0.1% TFA)/water (0.1% TFA) over 11 min] R$_t$=4.60 min.; mp=238°–240° C. (dec.); $^1$H NMR (DMSO-d$_6$, δTMS) 9.32(1H,bs, NH), 9.06 (1H, bs, NH), 7.87 (1H, d,$^3J_{HH}$=9.0 Hz, ArH C$_{10}$-H), 7.84 (2H, d, $^3J_{HH}$=8.0 Hz, ArH), 7.71(2H, d,$^3J_{HH}$=8 Hz, ArH), 7.58 (1H, d, $^4J_{HH}$=3 Hz, ArH C7-H), 7.50 (1H, dd, $^3J_{HH}$=9 Hz, $^4J_{HH}$=3 Hz, ArH C9-H), 5.40 (2H, s, C4H), 490 (2H,s, OCH$_2$Ar), 3.78 (2H, t, $^3J_{HH}$=7 Hz, NCH$_2$CH$_2$CO$_2$H), 2.49 (2H, m, NCH$_2$CH$_2$CO$_2$H, coincident with reference peak for DMSO-d$_6$); HRMS (FAB, M+H$^+$) calc'd for C$_{20}$H$_{20}$N$_7$O$_4$ 422.1577, found 422.1547.

EXAMPLE 7

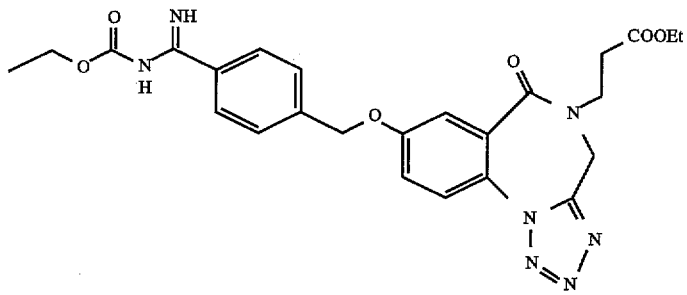

4H-[1,2,3,4]tetrazolo[4,3a][1,4]benzodiazepine-5 (6H)-propanoic acid, 8-[[4-[N-(ethylcarbamoyl) iminoaminomethyl]phenyl]methoxy]-6-oxo ethyl ester a) To a solution of 4H-[1,2,3,4]tetrazolo[4,3a][1,4]benzodiazepine-5(6H)-propanoic acid, 8-[[4-(iminoaminomethyl)phenyl]methoxy]-6-oxo ethyl ester, acetate (0.15 grams, 0.334 mmol), sodium bicarbonate (70 mgs, 2.5 molar equiv.) tetrahydrofuran(4 mL), and water (2 mL) was added ethyl chloroformate (48 μL, 1.5 molar equiv.). The reaction was stirred for 2 hrs, concentrated in vacuo, and purified by column chromatography (SiO$_2$, elution gradient acetone/methylene chloride) to 20% acetone/methylene chloride to yield 69.4 mg (40%) of 4H -[1,2,3,4]tetrazolo[4,3a][1,4]benzodiazepine-5(6H)-propanoic acid, 8-[[4-[N-(ethylcarbamoyl)iminoaminomethyl]phenyl] methoxy]-6-oxo ethyl ester:TLC (SiO$_2$, 100% ethyl acetate) R$_f$=0.42 uv positive; mp=78°–82 C.; $^1$H NMR (CDCl$_3$, δTMS) 9.57 (1H, bs, NH), 7.92 (2H, d, $^3J_{HH}$=8 Hz, ArH), 7.82 (1H, d, $^3J_{HH}$=9 Hz, ArH C10-H), 7. 61 (1, d $^4J_{HH}$=3 Hz, ArH C7-H), 7.48 (2H, d, $^3J_{HH}$=8 Hz, ArH), 7.30 (1H, dd, $^3J_{HH}$=9 Hz, $^4J_{HH}$=3 Hz, ArH C9-H), 5.22 (2H, s, OCH$_2$Ar) 4.82 (2H, s, C4H), 4.19 (2H, q, $^3J_{HH}$=7 Hz, H$_3$CCH$_2$OCONH), 4.12 (2H, q, $^3J_{HH}$=7 Hz, OCH$_2$), 3.91 (2H, t, $^3J_{HH}$=6 Hz, NCH$_2$CH$_2$CO$_2$), 2.69 (2H, t, $^3J_{HH}$=6 Hz, CH$_2$CO$_2$), 1.32 (3H, t, $^3J_{HH}$=7 Hz, CH$_3$), 1.22 (3H, t, $^3J_{HH}$=7 Hz CH$_3$); $^{13}$C NMR (CDCl$_3$) 171.4, 165.3, 158.9, 151.7, 139.9, 134.5, 128.3, 127.7, 127.2, 123.7, 120.7, 117.1, 69.8, 61.3, 61.0, 46.2, 41.3, 33.0, 14.4, 14.0; HRMS (FAB, M+H$^+$) calc'd for C$_{25}$H$_{28}$N$_7$O$_6$ 522.2101, found 522.2088.

EXAMPLE 8

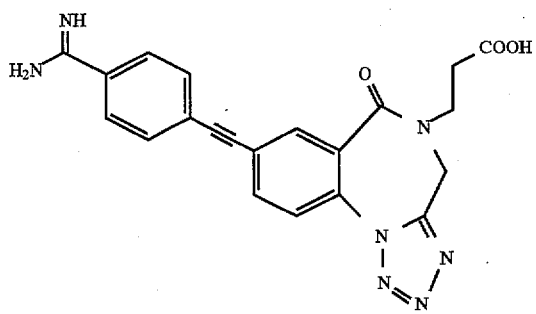

4H-[1,2,3,4]tetrazolo[4,3a][1,4]benzodiazepine-5 (6H)-propanoic acid, 8-[[4-(iminoaminomethyl) phenyl]acetylene]-6-oxo, acetate a) 4H-[1,2,3,4]tetrazolo[4,3a][1,4]benzodiazepine-5(6H)-propanoic acid, 8-[[4-cyanophenyl]acetylene]-6-oxo was prepared from 4-(2-carboxyethyl)-7-[(4-cyanophenyl) acetylene]-3,4-dihydro-1H-1,4-benzodiazepine-2,5-dione ethyl ester (see part (b) of Example 1 for prep of the ethyl ester) using the method described in part (a) of Example 6 for conversion of the secondary amide into the tetrazole ring. Thus 1 gram (2.49 mmol) of the 7-[(4-cyanophenyl) acetylene]benzodiazepinedione yielded 0.5 gram (47%) of the tetrazole: TLC (SiO$_2$, 1:1 ethyl acetate/hexane) R$_f$=0.21, uv positive; mp=167°–169° C.; $^1$H NMR (CDCl$_3$, δTMS) 8.30 (1H, d, $^4J_{HH}$=2 Hz, ArH C$_7$-H), 7.97 (1H, d, $^3J_{HH}$=9 Hz, ArH C10-H), 7.86 (1H, dd, $^4J_{HH}$=2 Hz, $^3J_{HH}$=9 Hz, ArH C9-H), 7.68 (2H, d, $^3J_{HH}$=8 Hz, ArH), 7.64 (2H, d, $^3J_{HH}$=8 Hz, ArH), 4.88 (2H, s, C4H), 4.15 (2H, q, $^3J_{HH}$=7 Hz, OCH$_2$), 3.95 (2H, t $^3J_{HH}$=6 Hz, NCH$_2$CH$_2$CO$_2$), 2.73 (2H, t, $^3J_{HH}$=6 Hz, CH$_2$CO$_2$), 1.25 (3H, s, CH$_3$); $^{13}$C NMR (CDCl$_3$) 171.5, 164.8, 152.1, 136.3, 135.8, 132.2, 129.7, 127.3, 126.9, 124.5, 122.3, 118.2, 112.4, 90.7, 64.1, 46.5, 41.3, 33.0, 14.2. HRMS (FAB, M+H$^+$) calc'd. for C$_{23}$H$_{18}$N$_6$O$_3$ 427.1519, found 427.1489.

b) 4H-[1,2,3,4]tetrazolo[4,3a][1,4]benzodiazepine-5(6H)-propanoic acid, 8-[[4-(iminoaminomethyl)phenyl] acetylene]-6-oxo, ethyl ester, acetate was prepared as in part (e) of Example 1. Thus, 4H-[1,2,3,4]tetrazolo[4,3a][1,4] benzodiazepine-5(6H)-propanoic acid, 8-[[4-cyanophenyl] acetylene]-6-oxo ethyl ester, acetate (0.5 grams, 1.17 mmol) yielded the desired amidino ester (0.175 grams, 34%): $^1$H NMR (CD$_3$OD, δTMS) 8.23 (1H, d, $^4J_{HH}$=2 Hz, ArH C$_7$-H), 8.03 (1H, d, $_3J_{HH}$=9 Hz, ArH C10-H), 7.97 (1H, dd, $^4J_{HH}$=2 Hz, $^3J_{HH}$=9 Hz, ArH C9-H), 7.84 (2H, d, $^3J_{HH}$=9 Hz, ArH), 7.74 (2H, d, $^3J_{HH}$=9 Hz, ArH), 4.96 (2H, s, C4H), 4.04 (2H, q, $^3J_{HH}$=7 Hz, OCH$_2$), 3.97 (2H, t, $^3J_{HH}$=6 Hz, NCH$_2$CH$_2$CO$_2$), 2.67 (2H, t, $^3J_{HH}$=6 Hz, CH$_2$CO$_2$), 1.15 (3H, s, CH$_3$); $^{13}$C, HRMS c) Saponification of the amidino ester 4H-[1,2,3,4] tetrazolo[4,3a][1,4]benzodiazepine-5(6H)-propanoic acid, 8-[[4-(iminoaminomethyl)phenyl]acetylene]-6-oxo ethyl ester, acetate was accomplished using the method described in part (f) of Example 1 to yield 4H-[1,2,3,4]tetrazolo[4,3a][1,4]benzodiazepine-5(6H)-propanoic acid, 8-[[4-(iminoaminomethyl)phenyl]acetylene]-6-oxo, acetate in 95% yield; $^1$H NMR (DMSO-d$_6$, δTMS) 8.64 (1H, bs, ArH C7-H), 8.44 (2H, bs, ArH C9,10-H), 8.26 (4H, bs, ArH), 5.33 (2, s C4H), 3.03 (2H, t, $^3J_{HH}$=6 Hz, NCH$_2$CH$_2$CO$_2$), 2.45 (2H, t, $^3J_{HH}$=6 Hz, CH$_2$CO$_2$); HRMS (M+H$^+$) calc'd. for C$_{21}$H$_{18}$N$_7$O$_3$ 416.1471, found 416.1448.

EXAMPLE 9

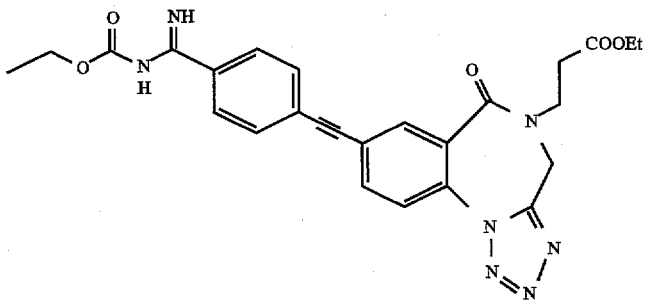

4H-[1,2,3,4]tetrazolo[4,3a][1,4]benzodiazepine-5 (6H)-propanoic acid, 8-[[4-[N-(ethylcarbamoyl) iminoaminomethyl]phenyl]acetylene]-6-oxo, ethyl ester a) The carbamate ester 4H-[1,2,3,4]tetrazolo[4,3a][1,4] benzodiazepine-5(6H)-propanoic acid, 8-[[4-[N-(ethylcarbamoyl)iminoaminomethyl]phenyl]acetylene]-6-oxo, ethyl ester was prepared as described in part (a) of Example 7 to afford the carbamate ester in a 30% yield; TLC (SiO$_2$, 100% ethyl acetate) R$_f$=0.73, uv positive; mp=91°–95° C.; $^1$H NMR (CDCl$_3$, δTMS) 9.6 (1H, bs, NH), 7.92 (2H, d, $^3J_{HH}$=8 Hz, ArH), 8.26 (1H, d, $^4J_{HH}$=2 Hz, ArH C7-H), 7.93 (2H, d, $^3J_{HH}$=8 Hz, ArH), 7.86 (2H, d, $^3J_{HH}$=8 Hz, ArH), 7.82 (1H, dd, $^3J_{HH}$=9 Hz, $^4J_{HH}$=3 Hz, ArH C9-H), 7.59 (1H, d, $^3J_{HH}$=9 Hz, ArH C10-H), 4.87 (2H, s, C4H), 4.23 (2H, q, $^3J_{HH}$=7 Hz, H$_3$CCH$_2$OCONH), 4.15 (2H, q, $^3J_{HH}$=7 Hz, OCH$_2$), 3.94 (2H, t, $^3J_{HH}$=6 Hz, NCH$_2$CH$_2$CO$_2$), 2.70 (2H, t, $^3J_{HH}$=6 Hz, CH$_2$CO$_2$), 1.38 (3H, t, $^3J_{HH}$=7 Hz, CH$_3$), 1.22 (3H, t, $^3J_{HH}$=7 Hz CH$_3$); $^{13}$C NMR (CDCl$_3$) 171.5, 164.9, 152.1, 136.1, 135.8 134.8, 131.9, 129.5, 127.4, 126.1, 125.1, 122.3, 91.8, 89.3, 61.5, 61.1, 46.4, 41.4, 33.0, 14.4, 14.1; HRMS (M+H$^+$) calc'd. for C$_{26}$H$_{26}$N$_7$O$_5$ 516.1995, found 516.1976.

EXAMPLE 10

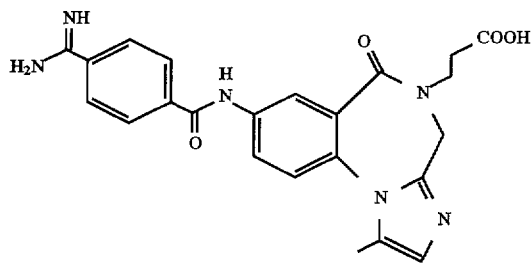

4H-imidazo[1,2-a][1,4]benzodiazepine-5(6H)-propanoic acid, 8-[[4-(aminoiminomethyl)benzoyl]amino]-1-methyl-6-oxo, trifluoroacetate a) A slurry of 2-amino-5-[4-cyanobenzoyl]amino-1-benzoyl-(ethyl-3-aminopropanoate) (8 grams, 2.12 mmol) in 1,2-dichloroethane (100 ml) was charged with 2,6-lutidine (2.5 ml, 21.2 mmol) and heated to 60° C. Over a 3 hour period diphenylmethylbromide (10 grams, 40 mmol, Aldrich) dissolved in 1,2-dichloroethane (50 ml) was added in 4 equal portions. The reaction mixture was allowed to cool to room temperature and concentrated in vacuo. The residue was dissolved in ethyl acetate (50 ml), transferred to a separatory funnel and washed with water (50 ml), 5% sodium bicarbonate solution (50 ml) and brine (50 ml). The organic phase was dried over magnesium sulfate, filtered, concentrated in vacuo, and purified by column chromatography (SiO$_2$, 1:1 ethyl acetate:hexane) to yield 10 grams (86% yield) of N-(2-diphenylmethylamino)-5-[4-cyanobenzoyl]amino-1-benzoyl-(ethyl-3-aminopropanoate). $^1$H NMR (CDCl$_3$, δTMS) 8.25 (1H, s, Ar—CONH—Ar), 7.88 (2H, d, $^3J_{HH}$=7.8 Hz, o—CN ArH), 7.74 (1H, br s, C6 aniline ArH), 7.65 (2H, d, $^3J_{HH}$=7.8 Hz, m—CNArH), 7.15–7.35 (12H, m, ArCHAr, ArNH(CH)Ar$_2$, C4 aniline ArH), 6.96 (1H, br t, $^3J_{HH}$=6.0 Hz, Ar CONHCH$_2$), 6.48 (1H, d, $^3J_{HH}$=9 Hz, C3 aniline ArH), 5.54 (1H, s, ArCHAr), 4.11 (2H, q, $^3J_{HH}$=6.8 Hz, CO$_2$CH$_2$CH$_3$), 3.59 (2H, q, $^3J_{HH}$=5.9 Hz, CONHCH$_2$CH$_2$CO$_2$Et), 2.56 (2H, t, CONHCH$_2$CH$_2$CO$_2$Et), 1.23 (3H, t, $^3J_{HH}$=6.8 Hz, CO$_2$CH$_2$CH$_3$). $^{13}$C NMR (CDCl$_3$) 172.6, 169.2, 163.9, 146.2, 142.4, 138.7, 132.3, 128.8, 128.4, 127.8, 127.7, 127.3, 127.2, 126.3, 125.6, 120.8, 118.0, 115.2, 114.9, 113.5, 62.1, 60.8, 35.2, 34.0, 14.1. Exact mass (FAB M+H$^+$) C$_{33}$H$_{30}$N$_4$O$_4$ calc'd. 547.2346, found 547.2309 b) To a biphasic CH$_2$Cl$_2$/H$_2$O (50 ml/50 ml) solution of N-(2-diphenyl methylamino)-5-[4-cyanobenzoyl]amino-1-benzoyl-(ethyl-3-aminopropanoate) (9 grams, 16 mmol), bromoacetylbromide (5.90 grams, 29.2 mmol) and potassium carbonate (4.14 grams, 30 mmol) were added in 3 equal portions over 25 minutes. The pH was maintained at 7–8. After stirring at room temperature for 1 hour, the reaction was transferred to a separatory funnel and the layers separated. The organic phase was dried over magnesium sulfate, filtered, concentrated in vacuo, and purified by column chromatography (SiO$_2$, 2:1 ethyl acetate:hexane) to yield 6.68 grams (61% yield) of N-[2-diphenylmethylamino]-N-bromoacetyl-5-[4-cyanobenzoyl]amino-1-benzoyl-(ethyl-3-aminopropanoate). $^1$H NMR (CDCl$_3$, δTMS) 9.75 (1H, s, Ar—CONH—Ar), 8.05 (2H, d, $^3J_{HH}$=7.2 Hz, o—CN ArH), 7.98 (1H, br s, C6 aniline ArH), 7.71, (2H, d, $^3J_{HH}$=7.2 Hz, m—CNArH), 7.58 (1H, br d, $^3J_{HH}$=8.7 Hz, C4 aniline ArH), 7.30–7.00 (10H, m, ArCHAr), 6.82 (1H, s, ArCHAr), 6.74 (1H, d, $^3J_{HH}$=8.7 Hz, C3 aniline ArH), 5.73 (1H, br t, $^3J_{HH}$=5.4 Hz, Ar CONHCH$_2$), 4.18 (2H, q, $^3J_{HH}$=7.2 Hz, CO$_2$CH$_2$CH$_3$), 3.83 (2H, br s, NCOCH H Br), 3.47 (1H, m, $^3J_{HH}$=6.9 Hz, CONHCHHCH$_2$CO$_2$Et), 3.13 (1H, m, $^3J_{HH}$=6.9 Hz, CONHCHHCH$_2$CO$_2$Et), 2.46 (2H, br t, CONHCH$_2$CH$_2$CO$_2$Et), 1.28 (3H, t, $^3J_{HH}$=7.2 Hz, CO$_2$CH$_2$CH$_3$). $^{13}$C NMR (CDCl$_3$) 172.0, 169.3, 166.5, 164.5, 139.6, 139.3, 138.1, 136.6, 135.4, 132.7, 132.3, 131.3, 128.3, 128.2, 128.0, 127.4, 127.2, 122.6, 119.2, 118.0, 115.0, 64.4, 60.8, 35.3, 33.5, 29.9, 14.1.Mass spec. (FAB M+H$^+$) calc'd 667.15, found 667.2 Exact mass (FAB M+H$^+$) C$_{35}$H$_{32}$BrN$_4$O$_5$ calc'd 667.1556, found 667.1538.

c) To a stirring DMF (400 ml) solution of N-[2-diphenylmethylamino]-N-bromoacetyl-5-[4-cyanobenzoyl]amino-1-benzoyl-(ethyl-3-aminopropanoate) (6.56 grams, 9.83 mmol) at room temperature, solid cesium carbonate (6.41 grams, 19.6 mmol) was added in one portion. The heterogeneous solution was stirred at rt for 2 hours, then poured into a separatory funnel containing ethyl acetate (500 ml) and water (500 ml). After thorough mixing, the aqueous phase was removed and the organic phase was washed with water (200 ml), brine (300 ml), dried over magnesium sulfate, filtered and concentrated in vacuo to give 5.36 grams (93% yield) of 1-(diphenylmethyl)-4-(2-carboxyethyl)-(7-[4-[cyano)benzoyl]-amino]-3,4-dihydro-1H-1,4-benzodiazepine-2,5-dione ethyl ester. $^1$H NMR (CDCl$_3$, δTMS) 9.47 (1H, s, ArCONHAr), 7.83 (2H, d, $^3J_{HH}$=7.8 Hz, o—CNArH), 7.77 (1H, s, C6 ArH), 7.46 (2H, d, $^3J_{HH}$=8.4 Hz, m—CNArH), 7.25–7.0 (11H, m, ArCHAr, upon expansion of this region C8 ArH appears @ 7.09 as a dd, $^3J_{HH}$=7.8 Hz, $^4J_{HH}$=2.0 Hz), 6.97 (1H, d, $^3J$=HH=8.4 Hz, C9 ArH), 6.62 (1H, s, ArCHAr), 4.09 (1H, d, $^2J_{HH}$=14.4 Hz, ArN(R') COCHHN(R)CO), 3.96 (2H, q, $^3J_{HH}$=7.2 Hz, CO$_2$CH$_2$CH$_3$), 3.81 (1H, m, $^3J_{HH}$=7.2 Hz, CONHCHHCH$_2$CO$_2$Et), 3.70 (1H, d, $^2J_{HH}$=14.4 Hz, ArN(R')COCHHN(R)CO), 3.55 (1H, m, $^3J_{HH}$=7.2 Hz, (CONHCHHCH$_2$CO$_2$Et), 2.39 (2H, br t, CONHCH$_2$CH$_2$CO$_2$Et), 1.10, (3H, t, $^3J_{HH}$=7.2 Hz, CO$_2$CH$_2$CH$_3$). $^{13}$C NMR (CDCl$_3$) 170.8, 168.2, 166.6, 164.2, 138.1, 138.0, 137.6, 136.4, 135.5, 132.0, 130.3, 129.1, 128.2, 128.1, 128.0, 127.9, 127.6, 127.4, 124.4, 123.1, 121.9, 117.8, 114.9, 67.0, 60.6, 44.6, 32.0, 14.0. Exact mass (FAB M+H$^+$) C$_{35}$H$_{30}$N$_4$O$_5$ calc'd 587.2295, found 587.2324 d) A slurry of 1-(diphenylmethyl)-4-(2-carboxyethyl)-7-[4-[(cyano)benzoyl]-amino]-3,4-dihydro-1H-1,4-benzodiazepine-2,5-dione ethyl ester (5.36 grams, 9.14 mmol), anisole (5 ml) and ethyl methyl sulfide (5 ml) in a teflon tube was cooled to –196° C. (N$_2$) and hydrogen fluoride (30 ml) was condensed into the teflon tube. The reaction was stirred for 30 min at –196° C., allowed to warm to 0° C., and concentrated in vacuo over 2 hrs. The resulting residue was triturated with ethyl ether, collected in a filter and dried in vacuo, to give 3.22 grams (56% yield) of 4-(2-carboxyethyl)-7-[4-(cyano)benzoyl]-amino]-3,4-dihydro-1H-1,4-benzodiazepine-2,5-dione ethyl ester. TLC R$_f$=0.46 (SiO$_2$, 1:1 hexane:ethyl acetate, uv positive), mp=253°–257° C (dec.) $^1$H NMR (DMSO-d$_6$, δTMS) 10.63 (1H, s, ArCONHAr), 10.45 (1H, s, ArNHCOCH$_2$N(R)CO), 8.16 (1H, d, $^4J_{HH}$=3.3 Hz, C6 ArH), 8.12 (2H, d, $^3J_{HH}$=8 Hz, o—CN ArH), 8.03 (2H, d, $^3J_{HH}$=8 Hz, m—CN ArH), 7.95 (1H, dd, $^3J_{HH}$=8.7 Hz, $^4J_{HH}$=3.3 Hz, C8 ArH), 7.10 (1H, d, $^3J_{HH}$=8.7 Hz, C9 ArH), 4.06 (2H, q, $^3J_{HH}$=7.2 Hz, CO$_2$CH$_2$CH$_3$), 3.91 (2H, s, ArNHCOCH$_2$N(R)CO), 3.81 (2H, t, $^3J_{HH}$=7.2 Hz, NCH$_2$CH$_2$CO$_2$Et), 2.62 (2H, t, $^3J_{HH}$=7.2 Hz, NCH$_2$CH$_2$CO$_2$Et), 1.18 (3H, t, $^3J_{HH}$=7.2 Hz, CO$_2$CH$_2$CH$_3$). $^{13}$C NMR (DMSO-d$_6$) 170.9, 170.0, 166.2, 164.0, 138.6, 134.8, 133.2, 132.5, 128.5, 126.2, 124.4, 122.3, 121.2, 118.3, 114.0, 60.1, 50.9, 44.5, 32.4, 14.0. Mass spec. (FAB M+H$^+$) calc'd 421.4, found 421.4. Exact mass (FAB M+H$^+$) $C_{22}H_{21}N_4O_5$ calc'd 421.1512, found 421.1501.

e) 4-(2-Carboxyethyl)-7-[4-(cyano)benzoyl]-amino]-3,4-dihydro-1H-1,4-benzodiazepine-2,5-dione ethyl ester, (1.5 grams, 3.6 mmol), Lawesson's reagent (2,4-bis(4-methoxyphenyl)1,3,2,4-dithiadiphosphetane 2,4-disulfide, 1.43 grams, 3.6 mmol) and anhydrous THF (20 ml) were combined and heated to 50° C. The slurry was stirred for 2 hours, cooled to room temperature and the resulting solid was collected and washed with THF to give 1.1 grams of 4-(2-carboxyethyl)-7-[4-(cyano)benzoyl]-amino)-3,4-dihydro-1H-1,4-benzodiazepine-2-thio-5-oxo ethyl ester (70% yield). TLC R$_f$=0.47 (SiO$_2$, 1:2 hexane:ethyl acetate, uv positive) $^1$H NMR (DMSO-d$_6$, δTMS) 10.72 (1H, s, ArCONHAr), 8.24 (1H, br s, C6 ArH), 8.14 (2H, d, $^3J_{HH}$=7.8 Hz, o —CN ArH), 8.04 (2H, d, $^3J_{HH}$=7.8 Hz, m —CN ArH), 8.01 (1H, br d, $^3J_{HH}$=8.7 Hz, C8 ArH), 7.26 (1H, d, $^3J_{HH}$=8.7 Hz, C9 ArH), 4.25 (2H, s, ArNHCSCH$_2$N(R)CO), 4.06 (2H, q, $^3J_{HH}$=6.9 Hz, CO$_2$CH$_2$CH$_3$), 3.80 (2H, t, $^3J$=HH=6.9 Hz, NCH$_2$CH$_2$CO$_2$Et), 2.71 (2H, t, $^3J_{HH}$=6.9 Hz, NCH$_2$CH$_2$CO$_2$Et), 1.18 (3H, t, $^3J_{HH}$=6.9 Hz, CO$_2$CH$_2$CH$_3$). Mass spec. (FAB M+H$^+$) calc'd 437.1 found 437.1. Exact mass (FAB M+H$^+$) $C_{22}H_{21}N_4SO_4$ calc'd 437.1284, found 437.1269.

f) A slurry of 4-(2-carboxyethyl)-7-[4-(cyano)benzoyl]-amino]-3,4-dihydro-1H-1,4-benzodiazepine-2-thio-5-oxo ethyl ester (1 gram, 2.3 mmol) in anhydrous acetonitrile (60 mL) was treated with methyl iodide (0.65 grams, 4.6 mmol) and heated to reflux. The reaction flask was charged with additional methyl iodide (0.65 grams, 4.6 mmol) at six, seven and eight hours of reflux. Soon after the last charge with methyl iodide (t=8 h) the reaction turned clear. The solution was dried in vacuo, taking care to avoid exposure to moisture. The crude reaction mixture was treated with a solution of propargyl amine (0.73 ml, 11.5 mmol) and pyridinium chloride (0.27 grams, 2.3 mmol) in anhydrous toluene (250 ml). The resulting slurry was heated to reflux for 6 hours and the warm toluene solution decanted from the solids to give 350 mg of the crude imidazole. The crude product was purified (RP-Dynamax 60A C18, methanol/water/0.1% TFA, gradient elution 5% methanol for 15 minutes, 5 to 90% methanol in 70 minutes, product collected from 60–70 minutes, UV @ 254 nm) to give 4H-imidazo[1,2-a][1,4]benzodiazepine-5(6H)-propanoic acid, 8-[[4-cyanobenzoyl]amino-1-methyl-6-oxo, ethyl ester, (240 mg, 23% yield) after lyophilization. $^1$H NMR (DMSO-d$_6$, δTMS) 10.89 (1H, s, ArCONHAr), 8.36 (1H, d, $^4J_{HH}$=2.4 Hz, C7 ArH), 8.22 (1H, dd, $^3J_{HH}$=9 Hz, $^4J_{HH}$=2.4 Hz, C9 ArH), 8.16 (2H, d, $^3J_{HH}$=8.2 Hz, o —CN ArH), 8.08 (2H, d, $^3J_{HH}$=8.2 HZ, m —CN ArH), 7.74 (1H, d, $^3J_{HH}$=9 Hz, C10 ArH), 7.30 (1H, s, C2 imidazole CH), 4.68 (1H, d, $^2J_{HH}$=16 Hz, ArNCNCHHN(R)CO), 4.51 (1H, d, $^2J_{HH}$=16 Hz, ArNCNCHHN(R)CO), 4.03 (2H, q, $^3J_{HH}$=6.9 Hz, CO$_2$CH$_2$CH$_3$), 3.79 (2H, m, NCH$_2$CH$_2$CO$_2$Et), 2.62 (2H, t, $^3J_{HH}$=7.2 Hz, NCHCH$_2$CO$_2$Et), 2.39 (3H, s, imidazole CH$_3$), 1.14 (3H, t, $^3J_{HH}$=6.9 Hz, CO$_2$CH$_2$CH$_3$). Mass spec. (FAB M+H$^+$) calc'd 458.2, found 458.1 Exact mass (FAB M+H$^+$) $C_{25}H_{24}N_5O_4$ calc'd 458.1828, found 458.1819.

g) 4H-imidazo[1,2-a][1,4]benzodiazepine-5(6H)-propanoic acid, 8-[[4-cyanobenzoyl]amino]-1-methyl-6-oxo, ethyl ester (80 mg, 0.17 mmol) was dissolved in anhydrous pyridine/triethylamine (2 ml/1 ml), transferred to a pressure tube, and the pyridine/Et$_3$N solution saturated with hydrogen sulfide. The pressure tube was sealed, heated to 65° C. and stirred for 30 min. After cooling to room temperature, the reaction solution was poured into a separatory funnel containing ethyl acetate (30 ml) and water (30 ml). After thorough mixing, the aqueous phase was removed and the organic phase was washed with water (20 ml), brine (30 ml), dried over magnesium sulfate, filtered and concentrated in vacuo to give 75 mg (90% yield) 4H-imidazo[1,2-a][1,4]benzodiazepine-5(6H)-propanoic acid, 8-[[4-thioamidobenzoyl]amino-1-methyl-6-oxo, ethyl ester. $^1$H NMR (CDCl$_3$, δTMS) 9.47 (1H, s, ArCONHAr), 8.46 (1H, dd, $^3J_{HH}$=8.7 Hz, $^4J_{HH}$=2.4 Hz, C$_9$ ArH), 8.23 (1H, brs, NH), 8.11 (1H, d, $^4J_{HH}$=2.7 Hz, C7 ArH), 8.03 (1H, brs, NH), 7.71 (2H, d, $^3J_{HH}$=8.0 Hz, o —H$_2$NCS ArH), 7.67 (1H, m, C10 ArH), 7.30 (2H, m, m —H$_2$NCS ArH), 6.88 (1H, s, C2-imidazole CH), 4.45 (1H, d, $^2J_{HH}$=15.6 Hz, ArNCNCHHN(R)CO), 4.33 (1H, d, $^2J_{HH}$=15.6 Hz, ArNCNCHHN(R)CO), 4.13 (2H, q, $^3J_{HH}$=7.0 Hz, CO$_2$CH$_3$CH$_3$), 3.68 (2H, m, NCH$_2$CH$_2$CO$_2$Et), 2.57 (2H, t, $^3J_{HH}$=6.9 Hz, NCH$_2$CH$_2$CO$_2$Et), 2.33 (3H, s, imidazole CH$_3$), 1.25 (3H, t, $^3J_{HH}$=7.0 Hz, CO$_2$CH$_2$CH$_3$). Mass spec. (FAB M+H$^+$) calc'd 492, found 492. Exact mass (FAB M+H$^+$) $C_{25}H_{26}N_5SO_4$ calc'd 492.1706, found 492.1715.

h) 4H-imidazo[1,2-a][1,4]benzodiazepine-5(6H)-propanoic acid, 8-[[4-thioamidobenzoyl]amino-1-methyl-6-oxo, ethyl ester (75 mg, 0.16 mmol) was suspended in anhydrous acetonitrile (3 ml) in a pressure tube. The slurry was treated with methyl iodide (15 ml, 0.25 mmol), the pressure tube sealed, and the stirred heterogeneous solution heated to 85° C. (oil bath) for 1 hour. After heating for one hour the reaction mixture was homogeneous. The solution was dried in vacuo, taking care to avoid exposure to moisture. The crude product was dissolved m ethanol (3 ml), treated with ammonium acetate (52 mg, 0.68 mmol), stoppered, and stirred overnight at room temperature. The reaction mixture was concentrated in vacuo and the crude product purified by prep RP HPLC (RP-Dynamax 60A C18, methanol/water/0.1% TFA, gradient elution 5% methanol for 15 minutes, 5 to 90% methanol in 70 minutes, retention time 33–minutes, UV @ 254 nm) to give 4H-imidazo[1,2-a][1,4]benzodiazepine-5(6H)-propanoic acid, 8-[[4-(aminoiminomethyl)benzoyl]amino]-1-methyl-6-oxo, ethyl ester, trifluoroacetate (24.5 mg, 24% yield) after lyophilization. $^1$H NMR (CDCl$_3$, δTMS) 10.8 (1H, s, ArCONHAr), 9.45 (1H, brs, NH), 9.12 (2H, brs, NH), 8.33 (1H, d, $^4J_{HH}$=2.7 Hz, C7 ArH), 8.21 (1H, dd, $^3J_{HH}$=11.7 Hz, $^4J_{HH}$=2.7 Hz, C$_9$ ArH), 8.20 (2H, d, $^3J_{HH}$=8.4 Hz, o —H$_2$NCNH ArH), 7.97 (2H, d, $^3J_{HH}$=8.4 Hz, m —H$_2$NCNH ArH), 7.66 (1H, d, $^3J_{HH}$=11.7 Hz, C10 ArH), 7.06 (1H, s, C2 imidazole CH), 4.58 (2H, d, $^2J_{HH}$=15.9 Hz,ArNCNCHHN(R)CO), 4.41 (2H, d, $^2J_{HH}$=15.9 Hz, ArNCNCHHN(R)CO), 4.03 (2H, q, $^3J_{HH}$=7.2 Hz, CO$_2$CH$_2$CH$_3$), 3.77 (2H, t, $^3J_{HH}$=7.5 Hz, NCH$_2$CH$_2$CO$_2$Et), 2.59 (2H, t, $^3J_{HH}$=7.5 Hz, NCH$_2$CH$_2$CO$_2$Et), 2.35 (3H, s, imidazole CH$_3$), 1.15 (3H, t $^3J_{HH}$=7.2 Hz, CO$_2$CH$_2$CH$_3$). Mass spec. (FAB M+H$^+$) $C_{25}H_{27}N_6O_4$ calc'd 475 found 475.2 Exact mass (FAB M+H$^+$) $C_{25}H_{27}N_6O_4$ calc'd 475.2090, found 475.2096.

i) 4H-imidazo[1,2-a][1,4]benzodiazepine-5(6H)-propanoic acid, 8-[[4-(aminoiminomethyl)benzoyl]amino]-1-methyl-6-oxo, ethyl ester, trifluoroacetate (23 mg, 0.40 mmol) was dissolved in 3:2:1 tetrahydrofuran:methanol:water (0.5 ml), treated with 1N sodium hydroxide solution (1.25 ml, 3.0 equiv) and stirred at room temperature overnight. The reaction mixture was concentrated in vacuo. and the crude product purified (RP-Dynamax 60A C$_{18}$, methanol/water/0.1% TFA, gradient elution 0% methanol for 20 minutes, 0 to 24% methanol in 40 minutes, product collected from 50–52.5 minutes, UV @ 254 nm) to give 4H-imidazo[1,2-a][1,4]benzodiazepine-5(6H)-propanoic acid, 8-[[4-(aminoiminomethyl)benzoyl]amino]-methyl-6-oxo, trifluoroacetate (24.5 mg, 24% yield). 1H NMR (DMSO-$d_6$, δTMS) 10.8 (1H, s, ArCONHAr), 9.45 (1H, brs, NH), 9.11 (2H, brs, $NH_2$), 8.33 (1H, d, $^4J_{HH}$=2.4 Hz, $C_7$ ArH), 8.20 (2H, d, $^3J_{HH}$=8.4 Hz, o —$H_2$NCNH ArH plus hidden under the resonance @ 8.20, 1H, dd, J values could not be determ'd C9 ArH), 7.97 (2H, d, $^3J_{HH}$=8.4 Hz, m —$H_2$NCNH ArH), 7.66 (1H, d, $^3J_{HH}$=11.7 Hz, C10 ArH), 7.03 (1H, s, C2 imidzole CH), 4.58 (2H, d, $^2J_{HH}$=16.2 Hz, ArNCNCHHN(R)CO), 4.41 (2H, d, $^2J_{HH}$=16.2 Hz, ArNCNCHHN(R)CO), ~3.7 hidden partially by water peak, (2H, t, $NCH_2CH_2CO_2H$), ~2.5 hidden under DMSO, (2H, t, $^3J_{HH}$=7.5 Hz, $NCH_2CH_2CO_2H$), 2.35 (3H, s, imidazole $CH_3$). Exact mass (FAB M+H$^+$) $C_{23}H_{23}N_6O_4$ calc'd 447.1781, found 447.1764. Fg IIbIIIa ELISA $IC_{50}$=9 nM. PA (citrate)$IC_{50}$=85 nM

EXAMPLE 11

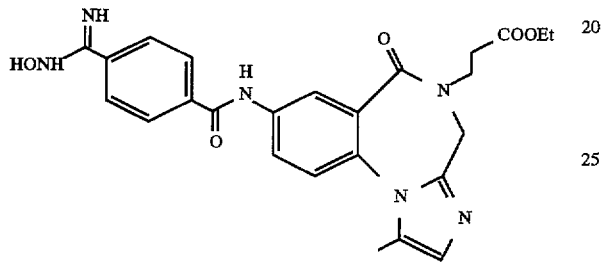

4H-[1,2,3,4]tetrazolo[4,3a][4]benzodiazepine-5(6H)-propanoic acid, 8-[[4-(hydroxyiminoaminomethyl)-benzoyl]amino]-6-oxo, a) An ethanolic solution (0.6 ml, anhydrous absolute EtOH, over 3A molecular sieves for 48 h prior to use) of 4H-imidazo[1,2-a][1,4]benzodiazepine-5(6H)-propanoic acid, 8-[[4-cyanobenzoyl]amino-1-methyl-6-oxo, ethyl ester (see Example 11, part (f), 113 mg, 0.25 mmol) was treated with hydroxylamine hydrochloride (28 mg, 0.41 mmol) followed by sodium ethoxide (24.5 mg, 0.360 mmol). After stirring at room temperature for five minutes the reaction flask was stoppered and placed in a 50° C. oil bath for 16 hours. TLC ($SiO_2$, 4% MeOH, 15% acetone in EtOAc) indicated complete consumption of the nitrile. The reaction mixture was diluted to a volume of approximately 2.5 ml by addition of EtOH(approx 0.4 ml), $H_2O$ (approx. 10 ml), and acetic acid(approx. 0.5 ml) and the crude purified directly by prep RP HPLC (Dynamax 60A, C18 83-221 C., acetonitrile/water/0.5% HOAc, gradient elution 5% $CH_3CN$ to 31% $CH_3CN$ in 55 minutes, retention time 31-42 minutes, UV @ 254) to afford 70 mg (58%) of the desired amidooxime/ethyl ester, 4H-imidazo[1,2-a][1,4]benzodiazepine-5(6H)-propanoic acid, 8-[[4-(hydroxyaminoiminomethyl)benzoyl]amino]-$_1$-methyl-6-oxo, ethyl ester. TLC $R_f$=0.04 ($SiO_2$, 4% MeOH, 15% acetone in EtOAc); $^1$H NMR ($CD_3OD$, δTMS) 8.26 (1H, d, $^4J_{HH}$=2.0 Hz, C7 ArH), 8.19 (1H, dd, $^3J_{HH}$=9.0 Hz, $^4J_{HH}$=20 Hz, C9 ArH), 8.0 (2H, d, $^3J_{HH}$=8.4 Hz, o —HONHCNH ArH), 7.82 (2H, d, $^3J_{HH}$=8.4 Hz, m —HONHCNH ArH), 7.55 (1H, d, $^3J_{HH}$=9.0 Hz, $C_{10}$ ArH), 6.87 (1H, brs, C2, imidazole CH), 4.46 (2H, brs, ArNCNCHHN(R)CO), 4.10 (2H, q, $^3J_{HH}$=7.2 Hz, $CO_2CH_2CH_3$), 3.93 (1H, m, $NCHHCH_2CO_2Et$), 3.86 (1H, m, $NCHHCH_2CO_2Et$), 2.67 (2H, m, $NCH_2CH_2CO_2Et$), 2.38 (3H, s, imidazole $CH_3$), 1.21 (3H, t, $^3J_{HH}$=7.2 Hz, $CO_2CH_2CH_3$). $^{13}$C NMR ($CD_3OD$) 172.87, 168.63, 168.11, 154.33, 147.50, 139.62, 137.62, 136.64, 131.67, 130.11, 130.01, 129.42, 128.83, 128.32, 127.64, 127.34, 125.46, 125.32, 124.10, 61.79, 49.83, 45.88, 33.5, 14.40, 10.93. Mass spec. (FAB M+H$^+$) calc'd 491.2, found 491.2. Exact mass (FAB M+H$^+$)$C_{25}H_{27}N_6O_5$ calc'd 491.2042, found 491.2043.

EXAMPLE 12

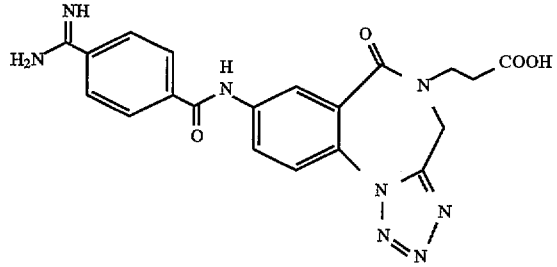

4H-1-[1,2,3,4]tetrazolo[4,3a][1,4]benzodiazepine-5(6H)-propanoic acid, 8-[[4-(iminoaminomethyl)-benzoyl]amino]-6-oxo, trifluoroacetate a) 4-(2-Carboxyethyl)-7-[4-(cyano)benzoyl]amino-3,4-dihydro-1H-1,4-benzodiazepine-2,5-dione ethyl ester (Example 10, part (d), 0.312 grams, 0.74 mmol), triphenylphosphine (0.126 grams, 1.48 mmol), trimethylsilylazide (0.200 ml, 1.48 mmol) diethyl azodicarboxylate and anhydrous glyme (2 ml) were stirred at room temperature for 16 hours. The reaction mixture was concentrated in vacuo and the crude product purified by sequential column chromatography ($SiO_2$, 1:1 hexane:ethyl acetate, then RP C18 Dynamax 60A 83-221 acetonitrile/water/0.1% TFA gradient elution 15 to 50% acetonitrile in 75 minutes, retention time 50-56 minutes, UV @ 254 nm) to give 4-H-[1,2,3,4] tetrazolo[4,3-a][1,4]benzodiazepine-5(6H)-propanoic acid, 8-[[4-cyanobenzoyl]amino]-6-oxo, ethyl ester (170 mg, 52% yield). TLC $R_f$=0.3 ($SiO_2$, 1:2 hexane:ethyl acetate, uv positive); $^1$H NMR (DMSO-$d_6$, δTMS) 10.94 (1H, s, ArCONHAr), 8.46 (1H, d, $^4J_{HH}$=2.4 Hz, C7 ArH), 8.30 (1H, dd, $^4J_{HH}$=2.4 Hz, $^3J_{HH}$=8.7 Hz, C9 ArH), 8.17 (2H, d, $^3J_{HH}$=8.1 Hz, o —CN ArH), 8.06 (2H, d, $^3J_{HH}$=8.1 Hz, m —CN ArH), 7.97 (1H, d, $^3J_{HH}$=8.7 Hz, C10 ArH), 4.97 (2H, s, ArNCNCH$_2$N(R)CO), 3.95 (2H, q, $^3J_{HH}$=6.9 Hz, $CO_2CH_2CH_3$), 3.86.(2H, t, $^3J_{HH}$=6.9 Hz, $NCH_2CH_2CO_2Et$), 2.59 (2H, t, $^3J_{HH}$=6.9 Hz, $NCH_2CH_2CO_2Et$), 1.09 (3H, t, $^3J_{HH}$=6.9 Hz, $CO_2CH_2CH_3$). $^{13}$C NMR ($CDCl_3$) 171.4, 165.7, 164.5, 151.8, 139.8, 137.8, 132.3, 128.3, 127.2, 125.9, 125.0, 123.8, 122.9, 117.8, 115.5, 61.1, 46.3, 41.3, 32.9, 14.0. Mass spec. (FAB M+H$^+$) calc'd 446.1, found 446.1. Exact mass (FAB M+H$^+$) $C_{22}H_{20}N_7O_4$ calc'd 446.1577, found 446.1561.

b) 4-H-[1,2,3,4]tetrazolo[4,3-a][1,4]benzodiazepine-5(6H)-propanoic acid, 8-[[4-cyanobenzoyl]amino]-6-oxo, ethyl ester (93 mg, 0.17 mmol) was dissolved in anhydrous pyridine (2 ml)/triethylamine (1 ml), transferred to a pressure tube, and the pyridine/triethylamine solution saturated with hydrogen sulfide. The vessel was sealed, heated to 50° C. and stirred for 90 min. After cooling to room temperature, the reaction mixture was concentrated in vacuo and transferred to a separatory funnel containing ethyl acetate (30 ml) and water (30 ml). After thorough mixing, the aqueous phase was removed and the organic phase was washed with water (20 ml), brine (30 ml), dried over magnesium sulfate, filtered and concentrated in vacuo to give 60 mg (76% yield) 4-H-[1,2,3,4]tetrazolo[4,3-a][1,4]benzodiazepine-5(6H)- propanoic acid, 8-[[4-thioamidobenzoyl]amino]-6-oxo, ethyl ester. TLC $R_f$=0.55 (SiO$_2$, ethyl acetate, uv positive). Analytical HPLC Dynamax 300 A, C8 83-303-C5, elution gradient 30–100% acetonitrile (0.1% TFA) over 10 minutes, retention time 4.27 min (UV @ 214 nm). $^1$H NMR (CD$_3$OD, δTMS) 8.46 (1H, d, $^4J_{HH}$=2.4 Hz, C7 ArH), 8.26 (1H, dd, $^4J_{HH}$=2.4 Hz, $^3J_{HH}$=9.0 Hz, C9 ArH), 8.00 (2H, s, o —H$_2$NCS ArH), 7.99 (2H, s, m —H$_2$NCS ArH), 7.96 (1H, d, $^3J_{HH}$=9.0 Hz, C10 ArH), 4.94 (2H, s, NCNCH$_2$N(R)CO), 4.05 (2H, q, $^3J_{HH}$=7.2 Hz, CO$_2$CH$_2$CH$_3$), 3.97 (2H, t, $^3J_{HH}$=6.3 Hz, NCH$_2$CH$_2$CO$_2$Et), 2.69 (2H, t, $^3J_{HH}$=6.3 Hz, NCH$_2$CH$_2$CO$_2$Et), 1.09 (2H, t, $^3J_{HH}$=7.2 Hz, CO$_2$CH$_2$CH$_3$). Mass spec. FAB (M+H$^+$) calc'd 480, found 480. Exact mass (FAB M+H$^+$)C$_{22}$H$_{22}$N$_7$SO$_4$ calc'd 480.1454, found 480.1450.

c) Treated 4-H[1,2,3,4]tetrazolo[4,3-a][1,4]benzodiazepine-5(6H)-propanoic acid, 8-[[4-thioamidobenzoyl]amino]-6-oxo, ethyl ester (0.21 gm, 0.47 mmol) with methyl iodide (20 ml) and addition of N-methyl pyrrolidinone (2 ml) was necessary to achieve a homogeneous solution (the thioamide is sparingly soluble in most typical organic solvents). The reaction was stirred overnight at room temperature. The crude reaction was concentrated in vacuo to a volume of 2 ml, taking care to avoid exposure to moisture. Chloroform (5 ml) was added and removed in vacuo to chase off traces of methyl iodide and the resulting crude residue placed under high vacuum for 15 minutes. The crude methyl iodide adduct was dissolved in ethanol (3 ml), saturated with anhydrous ammonium acetate (decanted from the 3A sieves and undissolved ammonium acetate), stoppered and stirred overnight at room temperature (anhydrous ammonium acetate was prepared by stirring ammonium acetate (1.2 gm, 15.0 mmol) in anhydrous ethanol (9 ml) with freshly activated 3A sieves for 16 h at room temperature). The reaction mixture was concentrated in vacuo and the crude product purified by prep RP HPLC (RP-Dynamax 60A C18 83-221-C, acetonitrile/water/0.1% TFA, gradient elution 0% acetonitrile for 20 minutes, 0 to 50% acetonitrile in 60 minutes, retention time 46–52 minutes, UV @ 254 nm) to give 4-H-[1,2,3,4]tetrazolo[4,3-a][1,4]benzodiazepine-5(6H)-propanoic acid, 8-[[4-(iminoaminomethyl)benzoyl]amino]-6-oxo, ethyl ester, trifluoroacetate (24.5 mg, 24% yield). Analytical HPLC Dynamax 300 A, C8 83-303-C5, isocratic elution @ 35% acetonitrile (0.1% TFA) over 6 minutes, retention time 2.78 min (UV @ 214 nm). $^1$H NMR (DMSO-d$_6$, δTMS) 11.0 (1H, bs, ArCONHAr), 8.46 (1H, d, $^4J_{HH}$=2.4 Hz,C7 ArH), 8.31 (1H, dd, $^3J_{HH}$=8.7 Hz, $^4J_{HH}$=2.4 Hz, C9 ArH), 8.17 (2H, d, $^3J_{HH}$=8.4 Hz, o —H$_2$NCNH ArH), 8.06 (2H, d, $^3J_{HH}$=8.4 Hz, m —H$_2$NCNH ArH), 7.96 (1H, d, $^3J_{HH}$=8.7 Hz, C10 ArH), 4.97 (2H, br s, NCNCHHN(R)CO), 3.95 (2H, q, $^3J_{HH}$=7.0 Hz, CO$_2$CH$_2$CH$_3$), 3.86 (2H, t, $^3J_{HH}$=7.0 Hz, NCH$_2$CH$_2$CO$_2$Et), 2.59 (2H, t, $^3J_{HH}$=7.5 Hz, NCH$_2$CH$_2$CO), 2.59 (2H, t, $^3J_{HH}$=7.0 Hz, NCH$_2$CH$_2$CO$_2$Et), 1.09 (3H, t, $^3J_{HH}$=7.0 Hz, CO$_2$CH$_2$CH$_3$) Mass spec. FAB (M+H$^+$) calc'd 463.1 found 463.1. Exact mass FAB (M+H$^+$) C$_{22}$H$_{23}$N$_8$O$_4$ calc'd 463.1842, found 463.1835.

d) 4-H-[1,2,3,4]tetrazolo[4,3-a][1,4]benzodiazepine-5(6H)-propanoic acid, 8-[[4-(iminoaminomethyl)benzoyl]amino]-6-oxo, ethyl ester, trifluoroacetate (7.0 mg, 0.015 mmol) was dissolved in THF:MeOH:H$_2$O (3:2:1, 0.25 ml:0.17 ml:0.08 ml, total volume=0.5 ml) and treated with 1.0N NaOH (15 µl, 0.015 mmol). The reaction mixture was stirred at room temperature for 2 hr and additional 1.0N NaOH was added (15 gl, 0.015 mmol). After stirring additionally for 16 h at room temperature another one equivalent of 1.0N NaOH (15 µl, 0.015 mmol) was added and the reaction mixture heated to 60° C. for 1 hr. After cooling to room temperature, the reaction mixture was acidified (neat TFA), and purified by prep RP HPLC (RP-Dynamax 60A C18 83-221-C, acetonitrile/water/0.1% TFA, gradient elution 0% acetonitrile for 20 minutes, 0 to 30% acetonitrile in 60 minutes, retention time 63–64 minutes, UV @ 254 nm) to give 4-H-[1,2,3,4]tetrazolo[4,3-a][1,4]benzodiazepine-5(6H)-propanoic acid, 8-[[4-(iminoaminomethyl)benzoyl]amino]-6-oxo, trifluoroacetate (1.7 mg, 17% yield). Analytical HPLC Dynamax 300 A, C8 83-303-C5, isocratic elution @ 15% acetonitrile (0.1% TFA) over 10 minutes, retention time 4.07 min (UV @ 214 nm). $^1$H NMR (D$_2$O, δTMS) 8.23 (1H, apparent t due to two sets of overlapping doublets in a 1:1 ratio, $^4J_{HH}$=2.1 Hz, C7 ArH), 8.09 (1H, d of apparent t, $^3J_{HH}$=9.0 H.z, $^4J_{HH}$=2.1 Hz, C9 ArH), 8.06, 8.05 (2H, d, $^3J_{HH}$=8.7, 8.4 Hz, o —H$_2$NCNH ArH), 7.98,7.97 (2H, d, $^3J_{HH}$=9.3, 8.7 Hz, C10 ArH), 7.86,7.85 (2H, d, $^3J_{HH}$=8.10 Hz, m —H$_2$NCNH), 4.98 (2H, br s, NCNCHHN(R)CO), 3.97 (2H, t, $^3J_{HH}$=6.0 Hz, NCH$_2$CH$_2$CO$_2$H), 2.71(2H, t, $^3J_{HH}$=6.0 Hz, NCH$_2$CH$_2$CO$_2$H). Mass spec. FAB (M+H$^+$) calc'd 435.1 found 435.1. Exact mass FAB (M+H$^+$) C$_{20}$H$_{19}$N$_8$O$_4$ calc'd 435.1529, found 435.1509.Fg IIbIIIa ELISA IC$_{50}$=1.2 nM, PA (citrate) IC$_{50}$ 32 23 nM.

EXAMPLE 13

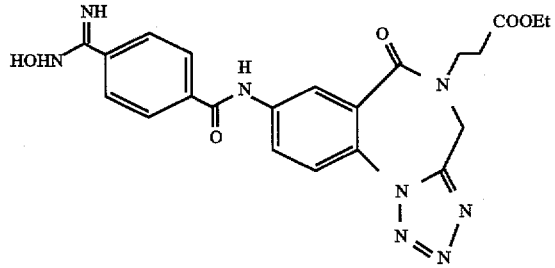

4H-[1,2,3,4]tetrazolo[4,3a][1,4]benzodiazepine-5(6H)-propanoic acid, 8-[[4-(hydroxyiminoaminomethyl)-benzoyl]amino]-6-oxo, ethyl ester a) 4H-[1,2,3,4]tetrazolo[4,3a][1,4]benzodiazepine-5(6H)-propanoic acid, 8-[[4-(hydroxyiminoaminomethyl)-benzoyl]amino]-6-oxo, ethyl ester was prepared by the method described in Example 11, part (a). 4-H -[1,2,3,4]tetrazolo[4,3-a][1,4]benzodiazepine-5(6H)-propanoic acid, 8-[[4-cyanobenzoyl]amino]-6-oxo, ethyl ester (see Example 12, part (a), for preparation, 64.5 mg, 0.115 mmol) yielded the desired hydroxyamidine/tetrazole (29 mg, 53% yield) after treatment with hydroxylamine hydrochloride (17.1 mg, 0.246 mmol)/NaOEt (14.8 mg, 0.217 mmol) in EtOH (60° C.) and purification by prep RP HPLC (RP-Dynamax 60A C18 83-221-C, acetonitrile/water/0.1% TFA, gradient elution 5% acetonitrile to 31% acetonitrile in 60 minutes, retention time 30–44 minutes, UV @ 254 nm). Analytical HPLC Dynamax 300 A, C8 83-303-C5, isocratic elution @ 35% acetonitrile (0.1% TFA) over 10 minutes, retention time 2.90 min (UV @ 214 nm). $^1$H NMR (DMSO-d$_6$) 10.78 (1H, brs, ArCONHAr), 9.85 (1H, brs, HONHCNH), 8.48 (1H, brs, C7 ArH), 8.23 (1H, br dd, $^4J_{HH}$=1.5 Hz, $^3J_{HH}$=8.7 Hz, C9 ArH), 8.02 (2H, d, $^3J_{HH}$=8.10 Hz, o —HONHCNH ArH), 7.95 (2H, d, $^3J_{HH}$=8.70 Hz, C10 ArH), 7.86 (2H, d, $^3J_{HH}$=9.0 Hz, m —HONHCNH ArH) 5.94 (br, s 1H, HONHCNH), 4.97 (br s, 2H, ArNCNCHH N(R)CO), 3.93 (2H, q, $^3J_{HH}$=6.9 Hz, CO$_2$CH$_2$CH$_3$), 3.86 (2H, t, $^3J_{HH}$=6.9 Hz, NCH$_2$CH$_2$CO$_2$Et), 2.59 (2H, t, $^3J_{HH}$=6.9 Hz, NCH$_2$CH$_2$CO$_2$Et), 1.09 (3H, t, $^3J_{HH}$=6.9 Hz, CO$_2$CH$_2$CH$_3$). Mass spec. FAB (M+H$^+$) C$_{22}$H$_{23}$N$_8$O$_5$ calc'd 479.0 found 479.0. Exact mass FAB (M+H$^+$) calc'd 479.1791, found 479.1796.

EXAMPLE 14

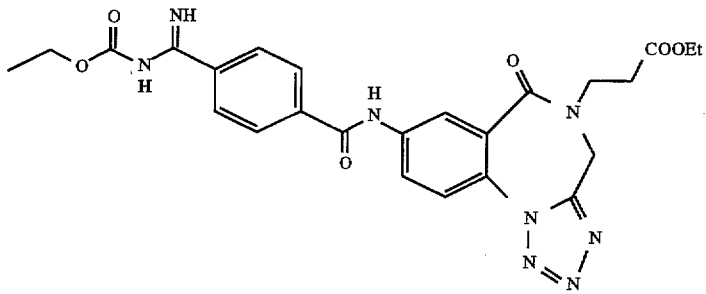

4H-[1,2,3,4]tetrazolo[4,3a][1,4]benzodiazepine-5(6H)-propanoic acid, 8-[[4-[N-(ethylcarbamoyl)iminoaminomethyl]-benzoyl]amino]-6-oxo, ethyl ester a) A THF/H$_2$O (2:1, 0.2 ml:0.1 ml) solution of 4-H-[1,2,3,4]tetrazolo[4,3-a][1,4]benzodiazepine-5(6H)-propanoic acid, 8-[[4-(iminoaminomethyl)benzoyl]amino]-6-oxo, ethyl ester, trifluoroacetate (mono) (Example 12, part (c), 36.2 mg, 0.062 mmol) was treated with sodium bicarbonate (19.6 mg, 0.234 mmol) and ethyl chloroformate (9.32 µl. 0.098 mmol). After stirring at room temperature for 45 minutes, analytical HPLC analysis (Dynamax 300 A, C8 83-303-C5, isocratic elution @ 35% acetonitrile (0.1% TFA) over 10 minutes) indicated complete consumption of the amidino ester. The THF/H$_2$O solution was transferred to a separatory funnel and shaken with ethyl acetate and water. The layers were separated and the organic layer washed with water (2×), brine, dried (MgSO$_4$), filtered, and concentrated in vacuo to afford 4H-[1,2,3,4]tetrazolo[4,3a][1,4]benzodiazepine-5(6H)-propanoic acid, 8-[[4-[N-(ethylcarbamoyl)iminoaminomethyl]-benzoyl]amino]-6-oxo, ethyl ester (27 mg, 79% based on the amidinoester being a mono TFA salt). Analytical HPLC Dynamax 300 A, C8 83-303-C5, isocratic elution @ 35% acetonitrile (0.1% TFA) over 6 minutes, retention time 2.90 min (UV @ 214 nm). $^1$H NMR (CDCl$_3$/CD$_3$OD, δTMS) 8.39 (1H, dd, $^3J_{HH}$= 9.0 Hz, $^4J_{HH}$=2.4 Hz, C9 ArH), 8.26 (1H, d, $^4J_{HH}$=2.4 Hz, C7 ArH), 8.01(2H, d, $^3J_{HH}$=8.7 Hz, o —RO$_2$CHNCNHAr), 7.97 (2H, d, $^3J_{HH}$=8.7 Hz, m —RO$_2$CHNCNHAr), 7.96 (1H, d, $^3J_{HH}$=9.0 Hz, C10 ArH), 4.89 (2H, br s, NCNCHHN(R) CO), 4.24 (2H, q, $^3J_{HH}$=7.0 Hz, H$_3$CCH$_2$OCONH), 4.15 (2H, q, $^3J_{HH}$=7.0 Hz, CO$_2$CH$_2$CH$_3$), 3.96 (2H, t, $^3J_{HH}$=6.3 Hz, NCH$_2$CH$_2$CO$_2$Et), 2.73 (2H, t, $^3J_{HH}$=6.3 Hz, NCH$_2$CH$_2$CO$_{Et}$), 1.37 (3H, t, $^3J_{HH}$=7.5 Hz, H$_3$CCH$_2$OCONH), 1.25 (3H, t, $^3J_{HH}$=7.0 Hz, CO$_2$CH$_2$CH$_3$). $^{13}$C NMR (CDCl$_3$/CD$_3$OD) 171.49, 166.32, 165.69, 151.86, 140.18, 137.59, 137.22, 127.69, 127.61, 127.19, 125.62, 125.18, 123.43, 122.75, 61.28, 60.99, 41.04, 32.76, 14.13, 13.81. Mass spec. FAB (M+H$^+$) C$_{25}$H$_{27}$N$_8$O$_6$ calc'd 535.2 found 535.2. Exact mass FAB (M+H$^+$) calc'd 535.2053, found 535.2056.

EXAMPLE 15

ELISA and platelet aggregation assay results

| Q—L— | IC$_{50}$ (µM) Fg/IIbIIIa | IC$_{50}$ (µM) PA (citrate) | IC$_{50}$ (µM) PA (heparin) |
|---|---|---|---|
| H$_2$N(CH$_2$)$_4$CC | 0.057 | 8.29 | ND |
| p-H$_2$N(NH)CC$_6$H$_4$CC | 0.004 | 0.093 | 0.24 |
| p-H$_2$N(NH)CC$_6$H$_4$CH$_2$O | 0.009 | 0.133 | 0.22 |
| p-H$_2$N(NH)CC$_6$H$_4$CONH | 0.009 | 0.086 | ND |
| p-H$_2$N(NH)CC$_6$H$_4$CH$_2$O | 0.54 | 1.7 | |

-continued

| Q—L— | IC$_{50}$ (μM) Fg/IIbIIIa | IC$_{50}$ (μM) PA (citrate) | IC$_{50}$ (μM) PA (heparin) |
|---|---|---|---|
| 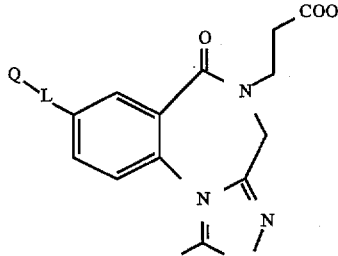 | | | |
| p-H$_2$N(NH)CC$_6$H$_4$CH$_2$O | 0.005 | | 0.086 |
| 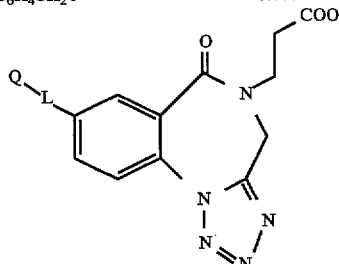 | | | |
| p-H$_2$N(NH)CC$_6$H$_4$CH$_2$O | 0.116 | | ND |
| p-H$_2$N(NH)CC$_6$H$_4$CC | 0.449 | | ND |
| p-H$_2$N(NH)CC$_6$H$_4$CONH | 0.0256 | | ND |

What is claimed is:

1. A compound represented by structural Formula I or II:

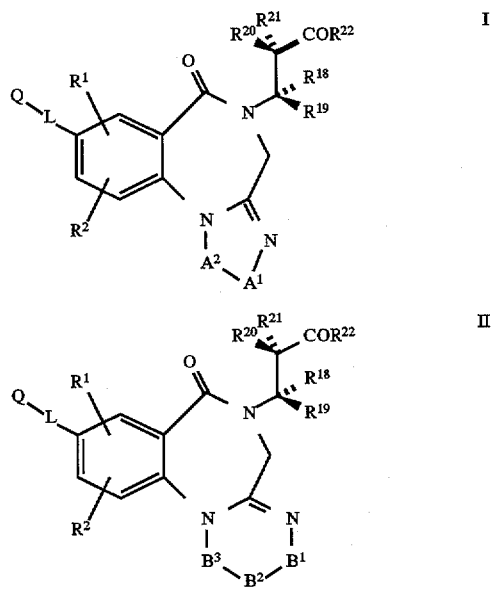

where
R$^1$ and R$^2$ are independently selected from
  hydrogen,
  halo (F, Cl, Br, I),
  cyano,
  carboxy,
  aminocarbonyl,
  carboxamido,
  carbamoyloxy,
  formyloxy,
  formyl,
  azido,
  nitro,
  imidazolyl,
  ureido,
  thioureido,
  thiocyanato,
  hydroxy,
  mercapto,
  sulfonamido and
  an optionally substituted group selected from
    C$_1$–C$_{12}$alkyl,
    C$_2$–C$_{12}$alkenyl,
    C$_3$–C$_{12}$alkynyl,
    C$_3$–C$_{12}$cycloalkyl,
    phenyl,
    phelyl-C$_1$–C$_8$alkyl,
    C$_1$–C$_{12}$alkyloxy,
    C$_1$–C$_{12}$alkyloxyC$_1$–C$_{12}$alkyl,
    phenoxy,
    C$_1$–C$_{12}$alkanoylamino,
    N,N-di(C$_1$–C$_{12}$)alkanoylamino,
    N-(C$_1$–C$_{12}$)alkyl-N-(C$_1$–C$_{12}$)alkylsulfonylamino,
    C$_1$–C$_{12}$alkylthiocarbonyl,
    C$_1$–C$_{12}$alkylthio,
    C$_1$–C$_{12}$alkylthioC$_1$–C$_{12}$alkyl,
    C$_1$–C$_{12}$alkylsulfinyl,
    C$_1$–C$_{12}$alkylsulfinylC$_1$–C$_{12}$alkyl,
    C$_1$–C$_{12}$alkylsulfonyl,
    C$_1$–C$_{12}$alkylsulfonylC$_1$–C$_{12}$alkyl,
    C$_1$–C$_{12}$alkylsulfonato,
    N-(C$_1$–C$_{12}$)alkylsulfonamido,
    N,N-di-(C$_1$–C$_{12}$)sulfonamido,
    N-(C$_1$–C$_{12}$)alkyl-N-thioformylamino,
    C$_1$–C$_{12}$thioalkanoylamino,
    N-(C$_1$–C$_{12}$)alkyl-N-(C$_1$–C$_{12}$)thioalkanoylamino,
    C$_1$–C$_{12}$alkylsulfinamido,
    N-(C$_1$–C$_{12}$)alkyl-N-(C$_1$–C$_{12}$)alkylsulfinylamino,
    C$_1$–C$_{12}$carbalkoxy,
    C$_1$–C$_{12}$alkylcarbonyl,
    C$_1$–C$_{12}$alkyloxycarbonyl,
    C$_1$–C$_{12}$alkanoyloxy,
    N-(C$_1$–C$_{12}$)alkylcarboxamido,
    N-(C$_1$–C$_{12}$)alkylaminocarbonyl,
    N,N-di-(C$_1$–C$_{12}$)carboxamido,
    N,N-di-(C$_1$–C$_{12}$)alkylaminocarbonyl,
    N-(C$_1$–C$_{12}$)alkylcarbamoyloxy and
    N,N-di-(C$_1$–C$_{12}$)carbamoyloxy,
  where the substituents are one to three groups selected from
    halo (F, Cl, Br, I),
    amino,
    amidino,
    guanidino,
    imidazolyl,
    indolyl,
    cyano,
    azido,
    nitro,
    hydroxy,
    mercapto,
    morpholino,
    morpholinyl,
    piperazinyl,
    piperidinyl,
    pyrrolinyl,
    sulfonamido,
    ureido,
    thioureido, carboxy,
aminocarbonyl,
$C_1$-$C_4$aminocarbonyl,
carboxamido,
carbamoyloxy,
formyloxy,
formyl,
$C_1$-$C_4$alkyloxycarbonyl,
$C_1$-$C_4$alkyl,
$C_1$-$C_4$alkylamino,
di-($C_1$-$C_4$)alkylamino,
$C_1$-$C_4$alkoxy,
hydroxyphenyl,
phenyl, and
phenoxy optionally, $R^1$ and $R^2$ when bonded to adjacent carbon atoms may join to form a fused unsubstituted or substituted napthyl, phenanthrenyl or napthacenyl ring, where the substituents are selected from
halo (F, Cl, Br, I),
cyano,
azido,
nitro,
hydroxy,
mercapto,
sulfonamido,
ureido,
thioureido,
carboxamido,
carbamoyloxy,
formyloxy,
formyl,
$C_1$-$C_4$alkyl,
halo$C_1$-$C_4$alkyl,
$C_1$-$C_4$alkoxy,
phenyl, and
phenoxy;

Q is selected from the group consisting of
1) an amino group selected from
$NH_2$,
$NR^3H$,
$NR^3R^4$, and
$NR^3R^4R^5$, $R^3$, $R^4$, and $R^5$ are independently selected from
hydrogen,
cyano,
$NR^6R^7$,
$C(=NR^8)-NR^6R^7$,
$N=CR^9-NR^6R^7$,
$NR^{10}-CR^9=NR^8$,
$NR^{10}-C(=NR^8)-NR^6R^7$,
halo(F, Cl, Br, I)-$C_1$-$C_4$alkyl, and
an optionally substituted group selected from
$C_1$-$C_{12}$alkyl,
$C_2$-$C_7$alkenyl,
$C_3$-$C_{12}$cycloalkyl,
$C_5$-$C_{12}$cycloalkenyl,
phenyl,
$C_1$-$C_6$alkylphenyl,
$C_2$-$C_6$alkenylphenyl,
$C_1$-$C_8$alkoxy,
$C_1$-$C_8$alkoxycarbonyl,
phenoxy,
phenoxycarbonyl and
phenyl-$C_1$-$C_6$alkyloxycarbonyl,
where each $R^6$, $R^7$, $R^8$, $R^9$, and $R^{10}$ is independently selected from
hydrogen,
cyano,
$C_1$-$C_6$alkyl and
$R^{11}$, and where the substituents are one to three $R^{11}$,
$R^{11}$ is selected from optionally substituted
phenoxy,
phenylamino,
benzoyl,
$C_1$-$C_8$alkoxy,
$C_1$-$C_8$alkoxyalkyl,
$C_1$-$C_8$alkoxyalkyloxy,
$C_1$-$C_8$alkoxycarbonyl,
$C_1$-$C_8$alkylcarbonyl,
phenyl$C_1$-$C_8$alkylthiocarbonyl,
$C_2$-$C_8$alkoxythiocarbonyl,
phenyl,
$C_1$-$C_4$alkanoylamino,
$C_1$-$C_6$alkoxycarbonyl-$C_0$-$C_6$alkylamino,
$C_1$-$C_8$alkylsulfonylamino,
$C_1$-$C_8$alkylthio,
$C_1$-$C_8$alkylsulfinyl,
$C_1$-$C_8$alkylsulfonyl,
$C_1$-$C_8$alkylaminosulfonyl and
$C_2$-$C_8$alkenyl,
where the substituents are one to three $R^{12}$,
$R^{12}$ is selected from
nitro,
amino,
$C_1$-$C_8$alkylamino,
di-($C_1$-$C_8$)alkylamino,
amidino,
aminomethyleneimino,
imino,
imino$C_1$-$C_4$alkyl,
iminomethyleneamino,
guanidino,
$C_1$-$C_8$alkanoylamino,
$C_1$-$C_4$alkylsulfonamino,
azido,
cyano,
hydroxy,
hydroxy$C_1$-$C_8$alkyl,
$C_1$-$C_8$alkoxy,
phenyloxy,
$C_1$-$C_8$alkanoyloxy,
$C_1$-$C_8$alkanoyl,
benzoyl,
benzamido,
phenyl,
halo (F, Cl, Br, I),
halo$C_1$-$C_8$alkyl, and
$C_1$-$C_8$alkyl,
aminosulfonyl,
oxo,
thio,
thiocarbonyl,
hydroxy,
mercapto,
formyl,
formyloxy,
carboxy,
ureido,
glycyl,
phthalimido,
succinimido,
morpholino and $C_3$-$C_7$cycloalkyl;

optionally $R^3$ and $R^4$ taken together may form optionally substituted
tetramethylene,
pentamethylene,
3-oxopentamethylene and
3-azapentamethylene, where the substituents are selected from one to three $R^{12}$;

2) an amidino group selected from
C(=NH)—$NH_2$,
C(=NH)—$NHR^3$,
C(=$NR^4$)—$NHR^3$,
C(=NH)—$NR^3R^4$ and
C(=$NR^5$)—$NR^3R^4$, where $R^3$, $R^4$, and $R^5$ are defined above or are selected from the group HO—, $C_1$-$C_{10}$alkyl-O—(C=O)—, $C_1$-$C_{10}$alkyl-S—(C=O)—, $Cl_3CCH_2O$—(C=O)—, 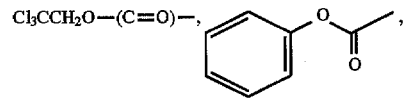

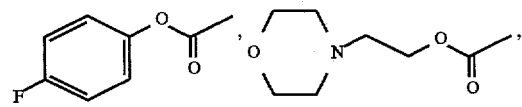

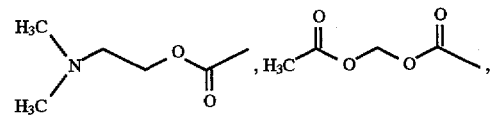

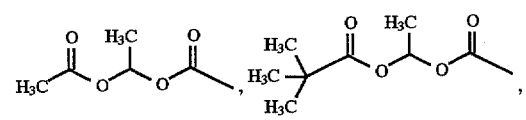

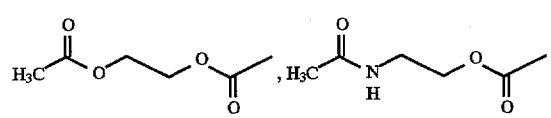

and

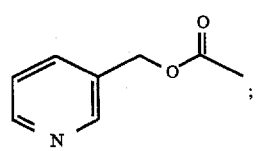

3) an aminoalkyleneimino group selected from
N=CH—$NH_2$,
N=CH—$NHR^3$,
N=CH—$NR^3R^4$ and
N=$CR^5$—$NR^3R^4$, where $R^3$, $R^4$, and $R^5$ are defined above;

4) an iminoalkyleneamino group selected from
NH—CH=NH,
NH—CH=$NR^3$,
NH—$CR^4$=$NR^3$ and
$NR^5$—$CR^4$=$NR^3$, where $R^3$, $R^4$, and $R^5$ are defined above;

5) a guanidino group selected from
NH—C(=NH)—$NH_2$,
NH—C(=NH)—$NR^3H$,
NH—C(=NH)—$NR^3R^4$,
NH—C(=$NR^5$)—$NR^3R^4$,
$NR^3$—C(=$NR^3$)—$NR^3R^4$,
$NR^3$—C(=NH)—$NR^3R^4$,
$NR^3$—C(=$NR^3$)—$NH_2$,
$NR^3$—C(=NH)—$NH_2$,
$NR^3$—C(=$NR^3$)—$NHR^4$ and
$NR^3$—C(=NH)—$NHR^4$, where $R^3$, $R^4$, and $R^5$ are defined above;

6) an optionally substituted saturated group selected from

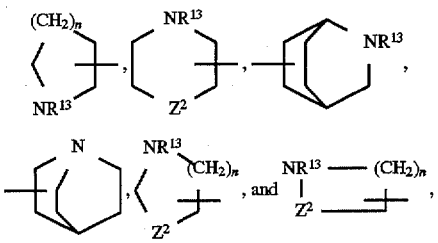

where n is 0, 1, 2, or 3,
$R^{13}$ is selected from $R^6$,
$CR^9$=$NR^8$,
$CR^9$(=$NR^8$)—$NR^6R^7$,
C(=$NR^8$)—$NR^6R^7$,
N=$CR^9$—$NR^6R^7$,
$NR^{10}$—$CR^9$=$NR^8$ and
$NR^{10}$—(C=$NR^8$)—$NR^6R^7$, where $R^6$-$R^{10}$ are defined above, $Z^2$ is O, S, or $NR^{13}$,
and the substituents are independently one to three $R^{12}$;

7) an optionally substituted unsaturated group selected from

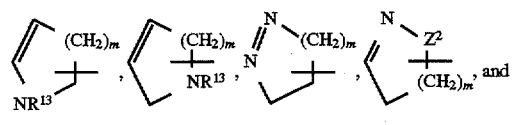

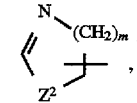

where
m is 1, 2, or 3,
$Z^2$ and $R^{13}$ are defined above and
the substituents are independently one to three $R^{12}$;

8) an optionally substituted unsaturated group selected from

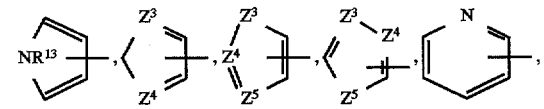

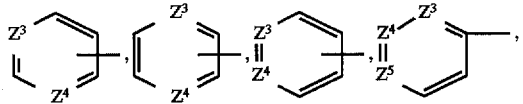

-continued

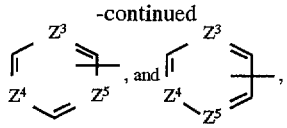

where $Z^3$, $Z^4$, and $Z^5$ are selected from O, S, N, and $NR^6$, provided that at least one $Z^3$, $Z^4$, or $Z^5$ is N or $NR^6$, $R^{13}$ is defined above, and the substituents are independently one to three $R^{12}$;

L is an optionally substituted bivalent radical selected from the group
$C_3-C_7$-alkylene,
$C_3-C_7$-cycloalkylene,
$C_3-C_7$-alkenylene,
$C_3-C_7$-alkadienylene,
$C_3-C_7$-alkynylene,
$C_4-C_7$-alkadiynylene,
$C_4-C_7$-alkenynylene,
phenylene,
phenyl-$C_2-C_4$alkynylene,
phenyl-$C_2-C_4$alkenylene,
$C_1-C_3$alkylphenylene,
$C_1-C_3$alkyloxyphenylene,
$C_2-C_6$-alkyloxyene,
$C_1-C_5$-alkyloxy-$C_1-C_5$-alkylene,
phenoxyene,
phenoxy-$C_1-C_5$alkylene,
$C_2-C_6$-alkylthioene,
$C_1-C_5$-alkylthio-$C_1-C_5$-alkylene,
$C_1-C_5$-alkylsulfoxide-$C_1-C_5$-alkylene,
$C_1-C_5$-alkylsulfone-$C_1-C_5$-alkylene,

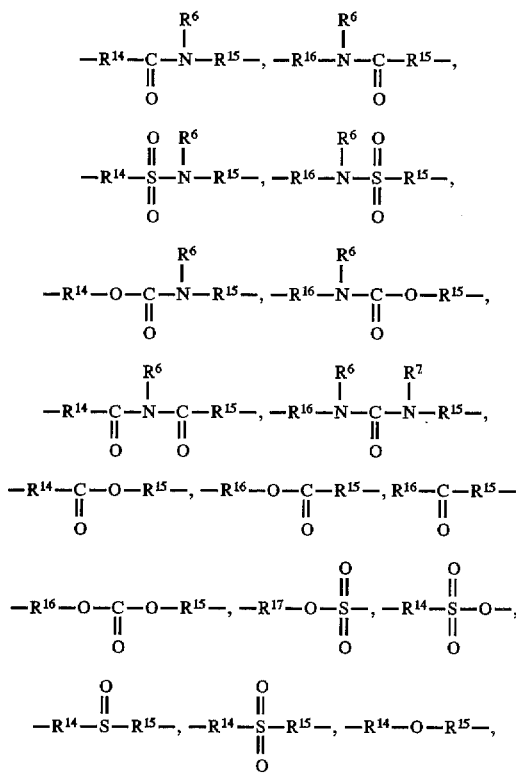

-continued

where
$R^{14}$ is selected from
a chemical bond,
$C_1-C_8$-alkylene,
$C_1-C_8$-alkyloxyene,
$C_3-C_7$-cycloalkylene,
$C_2-C_5$-alkenylene,
$C_3-C_5$-alkynylene,
phenylene,
napthylene,
$C_1-C_3$alkylphenylene
$C_1-C_2$alkylphenyl$C_1-C_2$alkylene, and
piperizinyl;

$R^{15}$ is selected from
a chemical bond,
$C_1-C_4$-alkylene,
$C_2-C_4$-alkenylene,
$C_2-C_4$-alkynylene, and
phenyl $R^{16}$ is selected from
a chemical bond,
$C_1-C_5$-alkylene,
$C_3-C_7$-cycloalkylene,
$C_3-C_5$-alkenylene,
$C_3-C_5$-alkynylene,
phenylene,
napthylene, and
pyridyl;

$R^{17}$ is selected from
$C_3-C_4$-alkenylene,
$C_3-C_4$-alkynylene and
phenylene;

$R^{18}$, $R^{19}$, $R^{20}$ and $R^{21}$ are independently selected from
hydrogen,
$C_1-C_4$alkyl,
halo(F, Cl, Br, I)$C_1-C_4$alkyl,
$C_1-C_4$alkoxy,
halo (F, Cl, Br, I),
cyano,
carboxy,
hydroxy,
$C_1-C_4$alkoxycarbonyl and
$C_1-C_4$alkylsulfonyl$C_0-C_3$alkyl;

$R^{22}$ is selected from the group consisting of
hydroxy,
$C_1-C_8$-alkoxy,
$C_3-C_{12}$-alkenoxy,
phenoxy,
$C_1-C_6$-alkylphenoxy,
di-$C_1-C_8$-alkylamino-$C_1-C_8$-alkoxy,
alkanoylamino-$C_1-C_8$-alkoxy selected from the group
acetylaminoethoxy,
nicotinoylaminoethoxy and
succinamidoethoxy,
$C_1-C_8$-alkanoyloxy and
phenyl-$C_1-C_8$alkoxy,
where any phenyl groups are unsubstituted or substituted with one to three of the groups
nitro,
halo (F, Cl, Br, I),
$C_1-C_4$-alkoxy and
amino, hydroxy-$C_2$-$C_8$-alkoxy,
dihydroxy-$C_3$-$C_8$-alkoxy,
morpholino-$C_2$-$C_8$-alkoxy,
morpholinyl-$C_1$-$C_8$-alkoxy and
$NR^{23}R^{24}$;

$R^{23}$ and $R^{24}$ are independently selected from the group
hydrogen,
$C_1$-$C_8$-alkyl,
$C_3$-$C_8$-alkenyl and
phenyl,
where any phenyl group is unsubstituted or substituted
with one to three of the groups
nitro,
halo (F, Cl, Br, I),
$C_1$-$C_4$-alkoxy and
amino;

$A^1$ is selected from
N and
$NR^{25}$;

$A^2$ is selected from
$CHR^1$,
$CR^2$,
N,
O=S=O,
S=O,
S,
O,
C=O,
C—$OR^{26}$ and
C=N—$R^{25}$;

$B^1$ is selected from
$CR^1$,
$CHR^2$,
N,
$NR^{25}$ and
C=O;

$B^2$ is selected from
$CR^2$,
$CHR^1$,
$NR^{25}$,
O=S=O,
S=O,
S,
O and
C=O;

$B^3$ is selected from
$CR^1$,
$CHR^2$ and
C=O;

$R^{25}$ is selected from
$R^6$ and
$(CH_2)_mR^1$, where m is 1, 2, or 3;

$R^{26}$ is selected from
hydrogen,
$C_1$-$C_8$-alkyl,
phenyl and
phenyl-$C_1$-$C_8$-alkyl,
where any phenyl or alkyl groups are unsubstituted or
substituted with one to three of the groups
nitro and
halo (F, Cl, Br, I); and
pharmaceutically acceptable salts thereof.

2. A compound represented by Formula IV–VIII:

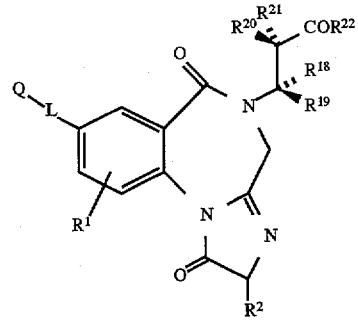

IV

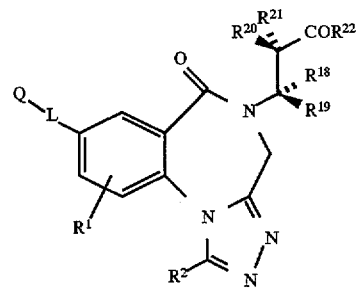

V

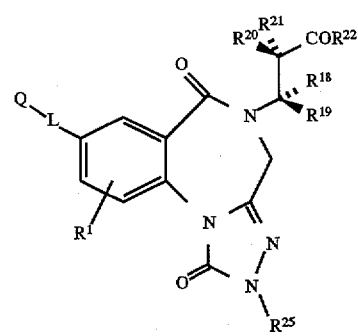

VI

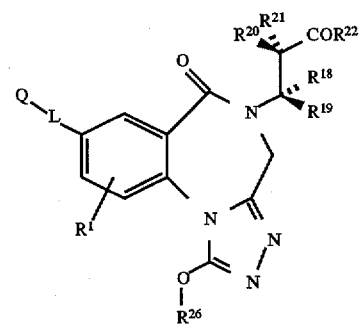

VII

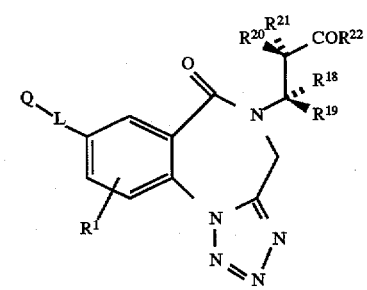

VIII where
$R^1$ and $R^2$ are independently selected from
hydrogen,
halo (F, Cl, Br, I), cyano,
carboxy,
aminocarbonyl,
carboxamido,
carbamoyloxy,
formyloxy,
formyl,
azido,
nitro,
imidazolyl,
ureido,
thioureido,
thiocyanato,
hydroxy,
mercapto,
sulfonamido and
an optionally substituted group selected from
 $C_1$–$C_{12}$alkyl,
 $C_1$–$C_{12}$alkyloxycarbonyl,
 $C_1$–$C_{12}$alkyloxy$C_1$–$C_{12}$alkyl,
 $C_2$–$C_{12}$alkenyl,
 $C_2$–$C_{12}$alkynyl,
 $C_3$–$C_{12}$cycloalkyl,
 phenyl,
 phenyl-$C_1$–$C_8$alkyl,
 $C_1$–$C_{12}$alkyloxy,
 phenoxy and
 $C_1$–$C_{12}$alkanoylamino,
 where the substituents are selected from
  halo (F, Cl, Br, I),
  amidino,
  guanidino,
  imidazolyl,
  indolyl,
  cyano,
  azido,
  nitro,
  hydroxy,
  mercapto,
  morpholino,
  morpholinyl,
  piperazinyl,
  piperidinyl,
  pyrrolinyl,
  sulfonamido,
  ureido,
  thioureido,
  carboxy,
  aminocarbonyl,
  $C_1$–$C_4$aminocarbonyl,
  carboxamido,
  carbamoyloxy,
  formyloxy,
  formyl,
  $C_1$–$C_4$alkyloxycarbonyl,
  $C_1$–$C_4$alkyl,
  $C_1$–$C_4$alkylamino,
  di-($C_1$–$C_4$)alkylamino,
  $C_1$–$C_4$alkoxy,
  $C_1$–$C_4$alkthio,
  hydroxyphenyl,
  phenyl and
  phenoxy;
Q is selected from the group consisting of
1) an amino group selected from
 $NH_2$,
 $NR^3H$,
 $NR^3R^4$ and
 $NR^3R^4R^5$,
 where $R^3$, $R^4$, and $R^5$ are independently hydrogen an optionally substituted group selected from
  halo(F, Cl, Br, I)$C_1$–$C_4$-alkyl,
  $C_1$–$C_{12}$ alkyl,
  $C_3$–$C_{12}$ cycloalkyl,
  phenyl,
  $C_1$–$C_6$alkylphenyl,
  $C_1$–$C_8$ alkoxy,
  $C_1$–$C_8$ alkoxycarbonyl,
  phenoxy,
  phenoxycarbonyl,
  $NR^6R^7$,
  $C(=NR^8)$—$NR^6R^7$,
  $N=CR^9$—$NR^6R^7$,
  $NR^{10}$—$CR^9=NR^8$ and
  $NR^{10}$—$C(=NR^8)$—$NR^6R^7$,
 where each $R^6$, $R^7$, $R^8$, $R^9$, and $R^{10}$ is independently selected from
  hydrogen, and
  $C_1$–$C_4$ alkyl,
 where the substituents are one to three $R^{12}$,
 $R^{12}$ is selected from
  nitro,
  amino,
  $C_1$–$C_8$alkylamino,
  di-($C_1$–$C_8$)alkylamino,
  amidino,
  aminomethyleneimino,
  imino,
  imino-$C_1$–$C_4$alkyl,
  iminomethyleneamino,
  guanidino,
  phenylamino,
  $C_1$–$C_8$alkanoylamino,
  $C_1$–$C_4$alkylsulfonamino,
  azido,
  cyano,
  hydroxy,
  hydroxy-$C_1$–$C_8$alkyl,
  $C_1$–$C_8$alkoxy,
  phenyloxy,
  $C_1$–$C_8$alkanoyloxy,
  $C_1$–$C_8$alkanoyl,
  benzoyl,
  benzamido,
  phenyl,
  halo (F, Cl, Br, I),
  halo-$C_1$–$C_8$alkyl,
  $C_1$–$C_8$alkyl,
  aminosulfonyl,
  oxo,
  thio,
  thiocarbonyl,
  hydroxy,
  mercapto,
  formyl,
  formyloxy,
  carboxy,
  ureido,
  glycyl,
  phthalimido,
  succinimido,
  morpholino and
  $C_3$–$C_7$cycloalkyl;
 optionally $R^3$ and $R^4$ taken together may form optionally substituted tetramethylene,
pentamethylene,
3-oxopentamethylene and
3-azapentamethylene,
where the substituents are selected from one to three $R^{12}$, 2) an amidino group selected from
$C(=NH)—NH_2$,
$C(=NH)—NHR^3$,
$C(=NR^4)—NHR^3$,
$C(=NH)—NR^3R^4$ and
$C(=NR^5)—NR^3R^4$,
where $R^3$, $R^4$, and $R^5$ are defined above or are selected from the group

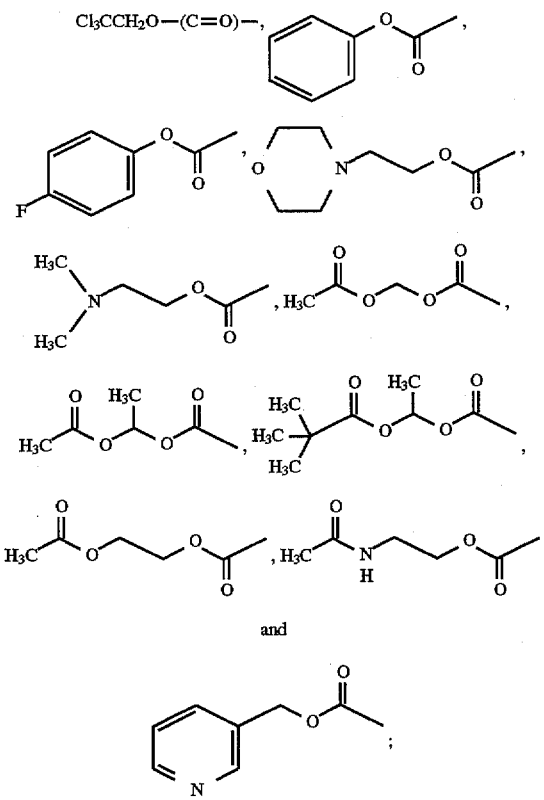

and 3) an aminoalkyleneamino group selected from
$N=CH—NH_2$,
$N=CH—NHR^3$,
$N=CH—NR^3R^4$ and
$N=CR^5—NR^3R^4$,
where $R^3$, $R^4$, and $R^5$ are defined above, 4) an imninoalkyleneimino group selected from
$NH—CH=NH$,
$NH—CH=NR^3$,
$NH—CR^4=NR^3$ and
$NR^5—CR^4=NR^3$,
where $R^3$, $R^4$, and $R^5$ are defined above, 5) a guanidino group selected from
$NH—C(=NH)—NH_2$,
$NH—C(=NH)—NR^3H$,
$NH—C(=NH)—NR^3R^4$,
$NH—C(=NR^5)—NR^3R^4$,
$NR^3—C(=NR^3)—NR^3R^4$,
$NR^3—C(=NH)—NR^3R^4$,
$NR^3—C(=NR^3)—NH_2$,
$NR^3—C(=NH)—NH_2$,
$NR^3—C(=NR^3)—NHR^4$ and
$NR^3—C(=NH)—NHR^4$,
where $R^3$, $R^4$, and $R^5$ are defined above;

L is an optionally substituted bivalent radical selected from the group
$C_3$-$C_7$-alkylene,
$C_3$-$C_7$-cycloalkylene,
$C_3$-$C_7$-alkenylene,
$C_4$-$C_7$-cycloalkenylene,
$C_5$-$C_5$-cycloalkadienylene,
$C_3$-$C_7$-alkadienylene,
$C_3$-$C_7$-alkynylene,
$C_4$-$C_7$-alkenynylene,
$C_2$-$C_8$-alkyloxyene,
$C_1$-$C_5$-alkyloxy-$C_1$-$C_5$-alkylene,

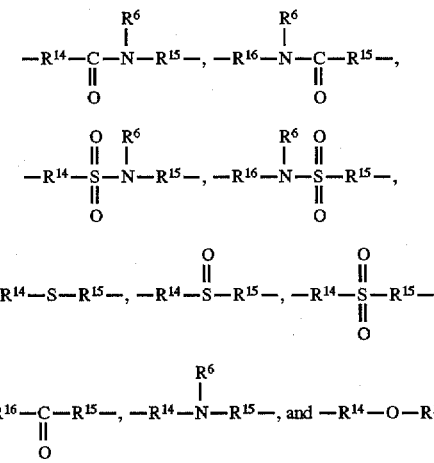

where
$R^{14}$ is selected from a chemical bond,
$C_1$-$C_8$-alkylene,
$C_1$-$C_8$-alkyloxyene,
$C_3$-$C_7$-cycloalkylene,
$C_2$-$C_5$-alkenyene,
$C_3$-$C_5$-alkynylene,
phenylene,
$C_1$-$C_3$alkyl-phenylene,
$C_1$-$C_2$alkyl-phenyl-$C_1$-$C_2$-alkylene,
phenyl-$C_1$-$C_2$-alkylene and
pyridyl;
$R^{15}$ is selected from a chemical bond,
$C_1$-$C_4$-alkylene,
$C_2$-$C_4$-alkenylene,
$C_2$-$C_4$-alkynylene and
phenylene;
$R^{16}$ is selected from a chemical bond,
$C_1$-$C_5$-alkylene,
$C_3$-$C_7$-cycloalkylene,
$C_3$-$C_5$-alkenylene,
$C_3$-$C_5$-alkynylene,
phenylene,
$C_1$-$C_3$-alkylphenylene,
phenyl$C_1$-$C_2$alkylene and
pyridyl;
$R^{18}$, $R^{19}$, $R^{20}$ and $R^{21}$ are independently selected from
hydrogen,
$C_1$-$C_4$alkyl and
halo(F, Cl, Br, I)$C_1$-$C_4$alkyl, R²² is selected from the group consisting of
hydroxy,
$C_1$–$C_8$-alkoxy,
$C_3$–$C_{12}$-alkenoxy,
phenoxy,
$C_1$–$C_6$alkylphenoxy,
di-$C_1$–$C_8$-alkylamino-$C_1$–$C_8$-alkoxy,
acylamino-$C_1$–$C_8$-alkoxy selected from the group
    acetylaminoethoxy,
    nicotinoylaminoethoxy and
    succinamidoethoxy,
$C_1$–$C_8$-alkoyloxy-$C_1$–$C_8$-alkoxy,
phenyl-$C_1$–$C_8$alkoxy where the phenyl group is unsubstituted or substituted with one to three of the groups
    nitro,
    halo (F, Cl, Br, I),
    $C_1$–$C_4$-alkoxy and
    amino,
hydroxy-$C_2$–$C_8$-alkoxy,
dihydroxy-$C_3$–$C_8$-alkoxy,
morpholino-$C_2$–$C_8$-alkoxy and
$NR^{23}R^{24}$,
$R^{23}$ and $R^{24}$ are independently selected from
hydrogen,
$C_1$–$C_8$-alkyl,
$C_3$–$C_8$-alkenyl and
phenyl,
where the phenyl group is unsubstituted or substituted with one to three groups selected from
    nitro,
    halo (F, Cl, Br, I),
    $C_1$–$C_4$-alkoxy and
    amino
$R^{25}$ is selected from
$R^6$ and
$(CH_2)_mR^1$, where m is 1, 2, or 3;
$R^{26}$ is selected from
hydrogen,
$C_1$–$C_8$-alkyl,
phenyl and
phenyl-$C_1$–$C_8$alkyl,
where any phenyl or alkyl groups are unsubstituted or substituted with one to three groups selected from
    nitro and
    halo (F, Cl, Br, I); and
pharmaceutically acceptable salts thereof.

3. A compound represented by Formula IX–XX:

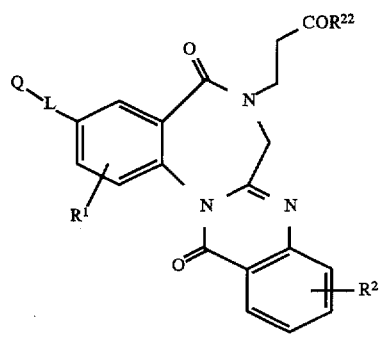
IX

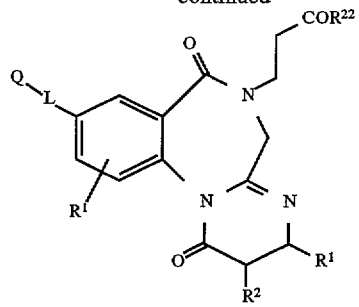
X

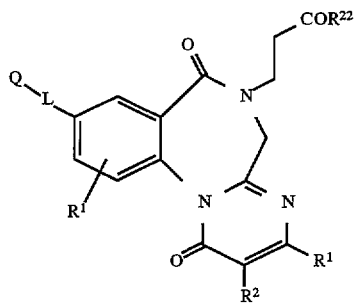
XI

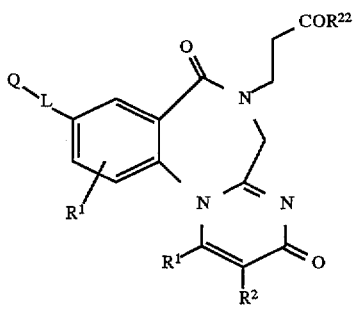
XII

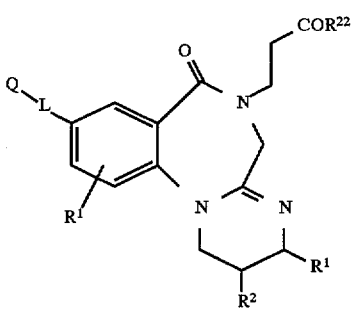
XIII

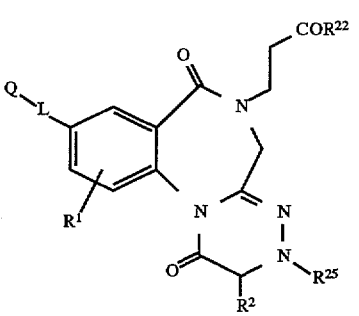
XIV

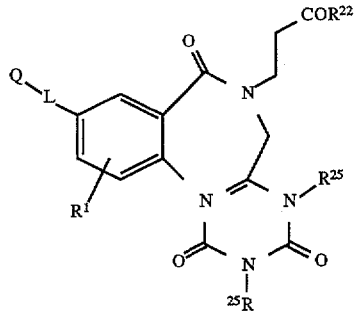

XV

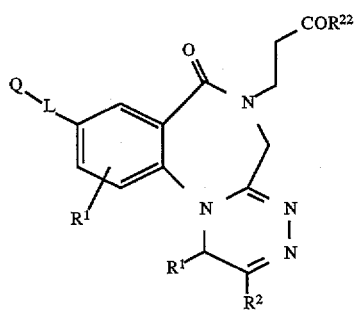

XVI

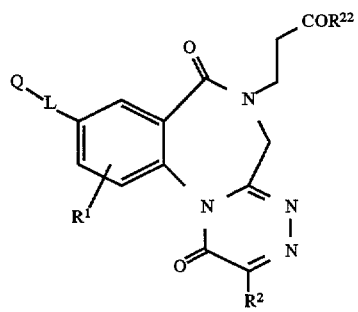

XVII

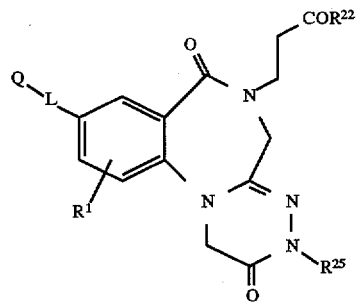

XVIII

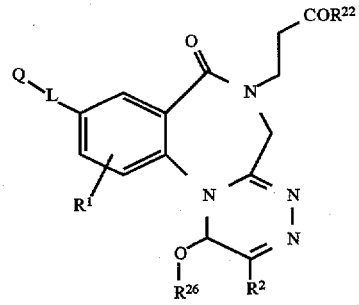

XIX

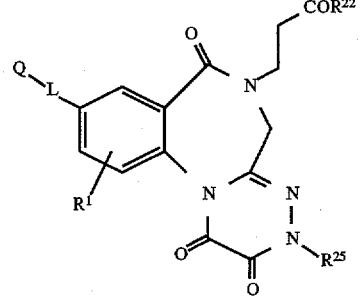

XX where
R$^1$ and R$^2$ are independently selected from
hydrogen,
halo (F, Cl, Br, I),
cyano,
carboxy,
aminocarbonyl,
carboxamido,
carbamoyloxy,
formyloxy,
formyl,
azido,
nitro,
imidazolyl,
ureido,
thioureido,
thiocyanato,
hydroxy,
mercapto,
sulfonamido and
an optionally substituted groups selected from
    C$_1$-C$_{12}$alkyl,
    C$_1$-C$_{12}$alkyloxycarbonyl,
    C$_1$-C$_{12}$alkyloxyC$_1$-C$_{12}$alkyl,
    C$_2$-C$_{12}$alkenyl,
    C$_2$-C$_{12}$alkynyl,
    C$_3$-C$_{12}$cycloalkyl,
    phenyl,
    phenyl-C$_1$-C$_8$alkyl,
    C$_1$-C$_{12}$alkyloxy,
    phenoxy and
    C$_1$-C$_{12}$alkanoylamino,
where the substituents are selected from
    halo (F, Cl, Br, I),
    amino,
    amidino,
    guanidino,
    imidazolyl,
    indolyl,
    cyano,
    azido,
    nitro,
    hydroxy,
    mercapto,
    morpholino,
    morpholinyl,
    piperazinyl,
    piperidinyl,
    pyrrolinyl,
    sulfonamido,
    ureido,
    thioureido,
    carboxy,
    aminocarbonyl, $C_1-C_4$aminocarbonyl,
carboxamido,
carbamoyloxy,
formyloxy,
formyl,
$C_1-C_4$alkyloxycarbonyl,
$C_1-C_4$alkyl,
$C_1-C_4$alkylamino,
di-$(C_1-C_4)$alkylamino,
$C_1-C_4$alkoxy,
$C_1-C_4$alkthio,
hydroxyphenyl,
phenyl and
phenoxy;

Q is selected from the group consisting of
an amino group selected from
$NH_2$,
$NR^3H$,
$NR^3R^4$ and
$NR^3R^4R^5$, $R^3$, $R^4$, and $R^5$ are independently hydrogen or an optionally substituted group selected from
halo(F, Cl, Br, I)$C_1-C_4$alkyl,
$C_1-C_{12}$ alkyl,
$C_3-C_{12}$ cycloalkyl,
phenyl,
$C_1-C_6$alkylphenyl,
$C_1-C_8$ alkoxy,
$C_1-C_8$ alkoxycarbonyl,
phenoxy,
phenoxycarbonyl,
$NR^6R^7$,
$C(=NR^8)$—$NR^6R^7$,
$N=CR^9$—$NR^6R^7$,
$NR^{10}$—$CR^9=NR^8$, and
$NR^{10}$—$C(=NR^8)$—$NR^6R^7$,
where each $R^6$, $R^7$, $R^8$, $R^9$, and $R^{10}$ is independently selected from
hydrogen and
$C_1-C_4$ alkyl,
where the substituents are one to three $R^{12}$, $R^{12}$ is selected from
nitro,
amino,
$C_1-C_8$alkylamino,
di-$(C_1-C_8)$alkylamino,
amidino,
aminomethyleneimino,
imino,
imino-$C_1-C_4$alkyl,
iminomethyleneamino,
guanidino,
phenylamino,
$C_1-C_8$alkanoylamino,
$C_1-C_4$alkylsulfonamino,
azido,
cyano,
hydroxy,
hydroxy-$C_1-C_8$alkyl,
$C_1-C_8$alkoxy,
phenyloxy,
$C_1-C_8$alkanoyloxy,
$C_1-C_8$alkanoyl,
benzoyl,
benzamido,
phenyl,
halo (F, Cl, Br, I),
halo-$C_1-C_8$alkyl,
$C_1-C_8$alkyl,
aminosulfonyl,
oxo,
thio,
thiocarbonyl,
hydroxy,
mercapto,
formyl,
formyloxy,
carboxy,
ureido,
glycyl,
phthalimido,
succinimido,
morpholino and
$C_3-C_7$cycloalkyl;

optionally $R^3$ and $R^4$ taken together may form optionally substituted
tetramethylene,
pentamethylene,
3-oxopentamethylene and
3-azapentamethylene,
where the substituents are selected from one to three $R^{12}$, an amidino group selected from
$C(=NH)$—$NH_2$,
$C(=NH)$—$NHR^3$,
$C(=NR^4)$—$NHR^3$,
$C(=NH)$—$NR^3R^4$ and
$C(=NR^5)$—$NR^3R^4$,
where $R^3$, $R^4$, and $R^5$ are defined above, an aminoalkyleneamino group selected from
$N=CH$—$NH_2$,
$N=CH$—$NHR^3$,
$N=CH$—$NR^3R^4$ and
$N=CR^5$—$NR^3R^4$,
where $R^3$, $R^4$, and $R^5$ are defined above, an iminoalkyleneimino group selected from
$NH$—$CH=NH$,
$NH$—$CH=NR^3$,
$NH$—$CR^4=NR^3$ and
$NR^5$—$CR^4=NR^3$,
where $R^3$, $R^4$, and $R^5$ are defined above, a guanidino group selected from
$NH$—$C(=NH)$—$NH_2$,
$NH$—$C(=NH)$—$NR^3H$,
$NH$—$C(=NH)$—$NR^3R^4$,
$NH$—$C(=NR^5)$—$NR^3R^4$,
$NR^3$—$C(=NR^3)$—$NR^3R^4$,
$NR^3$—$C(=NH)$—$NR^3R^4$,
$NR^3$—$C(=NR^3)$—$NH_2$,
$NR^3$—$C(=NH)$—$NH_2$,
$NR^3$—$C(=NR^3)$—$NHR^4$ and
$NR^3$—$C(=NH)$—$NHR^4$,
where $R^3$, $R^4$, and $R^5$ are defined above;

L is an optionally substituted bivalent radical selected from the group
$C_3-C_7$-alkylene,
$C_3-C_7$-cycloalkylene,
$C_3-C_7$-alkenylene,
$C_4-C_7$-cycloalkenylene,
$C_5-C_8$-cycloalkadienylene,
$C_3-C_7$-alkadienylene,
$C_3-C_7$-alkynylene,
$C_4-C_7$-alkenynylene, $C_2$–$C_8$-alkyloxyene,
$C_1$–$C_5$-alkyloxy-$C_1$–$C_5$-alkylene,

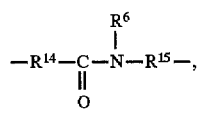

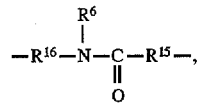

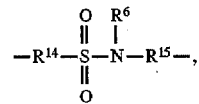

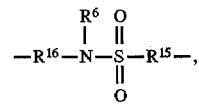

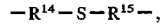

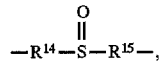

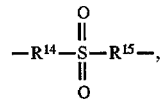

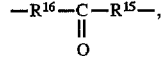

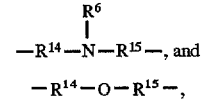

where
$R^{14}$ is selected from a chemical bond,
  $C_1$–$C_8$-alkylene,
  $C_1$–$C_8$-alkyloxyene,
  $C_3$–$C_7$-cycloalkylene,
  $C_2$–$C_5$-alkenyene,
  $C_3$–$C_5$-alkynylene,
  phenylene,
  $C_1$—$C_3$-alkylphenylene,
  $C_1$–$C_2$alkylphenyl-$C_1$–$C_2$alkylene,
  phenyl-$C_1$–$C_2$alkylene and
  pyridyl;
$R^{15}$ is selected from a chemical bond,
  $C_1$–$C_4$-alkylene,
  $C_2$–$C_4$-alkenylene,
  $C_2$–$C_4$-alkynylene and
  phenylene;
$R^{16}$ is selected from a chemical bond,
  $C_1$–$C_5$-alkylene,
  $C_3$–$C_7$-cycloalkylene,
  $C_3$–$C_5$-alkenylene,
  $C_3$–$C_5$-alkynylene,
  phenylene,
  $C_1$–$C_3$-alkylphenylene,
  phenyl$C_1$–$C_2$alkylene and
  pyridyl;
$R^{22}$ is selected from the group consisting of
  hydroxy,
  $C_1$–$C_8$-alkoxy,
  $C_3$–$C_{12}$-alkenoxy,
  phenoxy,
  $C_1$–$C_6$-alkyl-$C_6$–$C_{12}$-aryloxy,
  $C_1$–$C_6$alkyl-phenoxy,
  di-$C_1$–$C_8$-alkylamino-$C_1$–$C_8$-alkoxy,
  acylamino-$C_1$–$C_8$-alkoxy selected from the group
    acetylaminoethoxy,
    nicotinoylaminoethoxy and
    succinamidoethoxy,
  $C_1$–$C_8$-alkoyloxy-$C_1$–$C_8$-alkoxy,
  phenyl-$C_1$–$C_8$alkoxy where the phenyl group is unsubstituted or substituted with one to three of the groups
    nitro,
    halo (F, Cl, Br, I),
    $C_1$–$C_4$-alkoxy and
    amino,
  hydroxy-$C_2$–$C_8$-alkoxy,
  dihydroxy-$C_3$–$C_8$-alkoxy,
  morpholino-$C_2$–$C_8$-alkoxy, and
  $NR^{23}R^{24}$,
$R^{23}$ and $R^{24}$ are independently selected from
  $C_1$–$C_8$-alkyl,
  $C_3$–$C_8$-alkenyl,
  hydrogen and
  phenyl,
  where the phenyl group is unsubstituted or substituted with one to three groups selected from
    nitro,
    halo (F, Cl, Br, I),
    $C_1$–$C_4$-alkoxy and
    amino;
$R^{25}$ is selected from
  $R^6$ and
  $(CH_2)_m R^1$, where m is 1, 2, or 3;
$R^{26}$ is selected from
  hydrogen,
  $C_1$–$C_8$-alkyl,
  phenyl and
  phenyl-$C_1$–$C_8$alkyl,
  where any phenyl or alkyl groups are unsubstituted or substituted with one to three of the groups selected from
    nitro and
    halo (F, Cl, Br, I); and
pharmaceutically acceptable salts thereof.

4. A compound selected from the group:

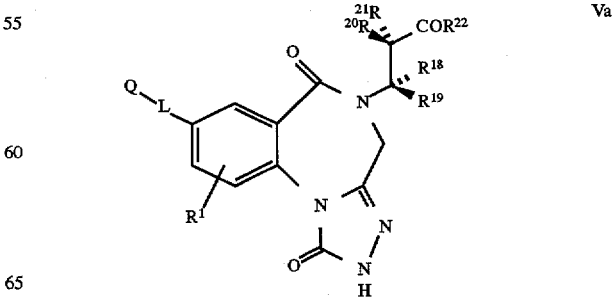

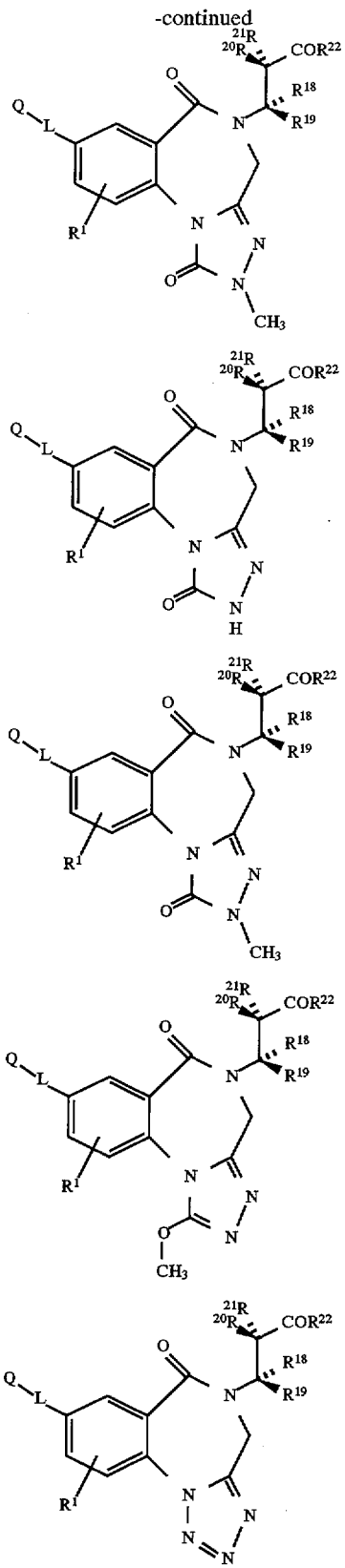

cyano,
carboxy,
aminocarbonyl,
carboxamido,
carbamoyloxy,
formyloxy,
formyl,
azido,
nitro,
imidazolyl,
ureido,
thioureido,
thiocyanato,
hydroxy,
mercapto,
sulfonamino and
an optionally substituted radical selected from
  $C_1$–$C_{12}$alkyl,
  $C_1$–$C_{12}$alkyloxycarbonyl,
  $C_1$–$C_{12}$alkyloxy$C_1$–$C_{12}$alkyl,
  $C_2$–$C_{12}$alkenyl,
  $C_2$–$C_{12}$alkynyl,
  $C_3$–$C_{12}$cycloalkyl,
  phenyl,
  phenyl-$C_1$–$C_8$alkyl,
  $C_1$–$C_{12}$alkyloxy,
  phenoxy and
  $C_1$–$C_{12}$alkanoylamino,
where the substituents are selected from
  halo (F, Cl, Br, I),
  amino,
  amidino,
  guanidino,
  imidazolyl,
  indolyl,
  cyano,
  azido,
  nitro,
  hydroxy,
  mercapto,
  morpholino,
  morpholinyl,
  piperazinyl,
  piperidinyl,
  pyrrolinyl,
  sulfonamido,
  ureido,
  thioureido,
  carboxy,
  aminocarbonyl,
  $C_1$–$C_4$aminocarbonyl,
  carboxamido,
  carbamoyloxy,
  formyloxy,
  formyl,
  $C_1$–$C_4$alkyloxycarbonyl,
  $C_1$–$C_4$alkyl,
  $C_1$–$C_4$alkylamino,
  di-($C_1$–$C_4$)alkylamino,
  $C_1$–$C_4$alkoxy,
  $C_1$–$C_4$alkthio,
  hydroxyphenyl,
  phenyl and
  phenoxy;
Q is selected from the group consisting of
  an amino group selected from
    $NH_2$, where
$R^1$ is selected from
  hydrogen,
  halo (F, Cl, Br, I), NR$^3$H,
NR$^3$R$^4$ and
NR$^3$R$^4$R$^5$,
R$^3$, R$^4$, and R$^5$ are independently hydrogen or an optionally substituted group selected from
halo(F, Cl, Br, I)C$_1$-C$_4$-alkyl,
C$_1$-C$_{12}$ alkyl,
C$_3$-C$_{12}$ cycloalkyl,
phenyl,
C$_1$-C$_6$alkylphenyl,
C$_1$-C$_8$ alkoxy,
C$_1$-C$_8$ alkoxycarbonyl,
phenoxy,
phenoxycarbonyl,
NR$^6$R$^7$,
C(=NR$^8$)—NR$^6$R$^7$,
N=CR$^9$—NR$^6$R$^7$,
NR$^{10}$—CR$^9$=NR$^8$, and
NR$^{10}$—C(=NR$^8$)—NR$^6$R$^7$
R$^6$, R$^7$, R$^8$, R$^9$, and R$^{10}$ are independently selected from
hydrogen and
C$_1$-C$_4$ alkyl,
where the substituents are one to three R$^{12}$,
R$^{12}$ is selected from
nitro,
amino,
C$_1$-C$_8$alkylamino,
di-(C$_1$-C$_8$)alkylamino,
amidino,
aminomethyleneimino,
imino,
imino-C$_1$-C$_4$alkyl,
iminomethyleneamino,
guanidino,
phenylamino,
C$_1$-C$_8$alkanoylamino,
C$_1$-C$_4$alkylsulfonamino,
azido,
cyano,
hydroxy,
hydroxy-C$_1$-C$_8$alkyl,
C$_1$-C$_8$alkoxy,
phenyloxy,
C$_1$-C$_8$alkanoyloxy,
C$_1$-C$_8$alkanoyl,
C$_6$-C$_{12}$aroyl,
benzamido,
phenyl,
halo (F, Cl, Br, I),
halo-C$_1$-C$_8$alkyl,
C$_1$-C$_8$alkyl,
aminosulfonyl,
oxo,
thio,
thiocarbonyl,
hydroxy,
mercapto,
formyl,
formyloxy,
carboxy,
ureido,
glycyl,
phthalimido,
succinimido,
morpholino,
C$_3$-C$_7$cycloalkyl and
optionally R$^3$ and R$^4$ taken together may form optionally substituted
tetramethylene,
pentamethylene,
3-oxopentamethylene and
3-azapentamethylene,
where the substituents are selected from one to three R$^{12}$,
an amidino group selected from
C(=NH)—NH$_2$,
C(=NH)—NHR$^3$,
C(=NR$^4$)—NHR$^3$,
C(=NH)—NR$^3$R$^4$ and
C(=NR$^5$)—NR$^3$R$^4$,
where R$^3$, R$^4$ and R$^5$ are defined above or are selected from the group HO—,
C$_1$-C$_{10}$alkyl-O—(C=O)—,
C$_1$-C$_{10}$alkyl-S—(C=O)—,
Cl$_3$CCH$_2$O—(C=O)—,

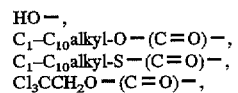

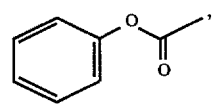

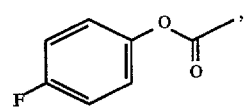

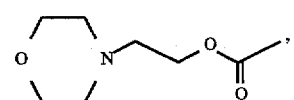

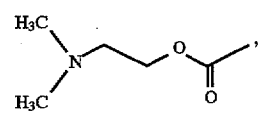

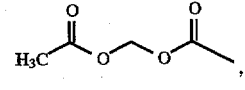

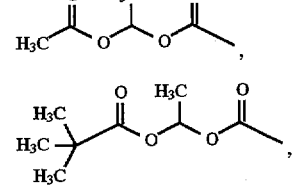

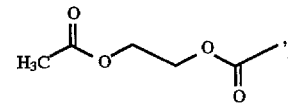

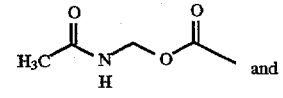 and

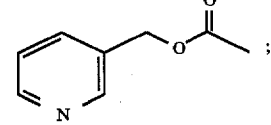 ;

an aminoalkyleneimino group selected from
N=CH—NH$_2$,
N=CH—NHR$^3$,

N=CH—NR³R⁴ and
N=CR⁵—NR³R⁴,
where R³, R⁴, and R⁵ are defined above,
an iminoalkyleneamino group selected from
NH—CH=NH,
NH—CH=NR³,
NH—CR⁴=NR³ and
NR⁵—CR⁴=NR³,
where R³, R⁴, and R⁵ are defined above,
a guanidino group selected from
NH—C(=NH)—NH₂,
NH—C(=NH)—NR³H,
NH—C(=NH)—NR³R⁴,
NH—C(=NR⁵)—NR³R⁴,
NR³—C(=NR³)—NR³R⁴,
NR³—C(=NH)—NR³R⁴,
NR³—C(=NR³)—NH₂,
NR³—C(=NH)—NH₂,
NR³—C(=NR³)—NHR⁴ and
NR³—C(=NH)—NHR⁴,
where R³, R⁴, and R⁵ are defined above;
L is an optionally substituted bivalent group selected from
$C_3$–$C_7$-alkylene,
$C_3$–$C_7$-cycloalkylene,
$C_3$–$C_7$-alkenylene,
$C_4$–$C_7$-cycloalkenylene,
$C_5$–$C_8$-cycloalkadienylene,
$C_3$–$C_7$-alkadienylene,
$C_3$–$C_7$-alkynylene,
$C_4$–$C_7$-alkenynylene,
$C_2$–$C_8$-alkyloxyene,
$C_1$–$C_5$-alkyloxy-$C_1$–$C_5$-alkylene,

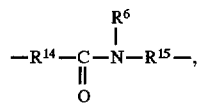

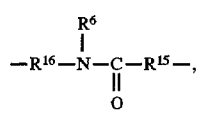

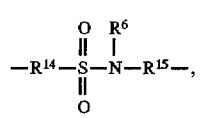

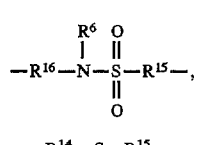

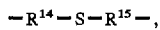

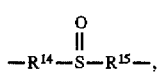

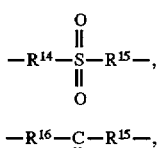

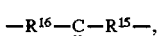

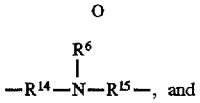

where
R¹⁴ is selected from a chemical bond,
$C_1$–$C_8$-alkylene,
$C_1$–$C_8$-alkyloxyene,
$C_3$–$C_7$-cycloalkylene,
$C_2$–$C_5$-alkenylene,
$C_3$–$C_5$-alkynylene,
phenylene,
$C_1$–$C_3$alkylphenylene,
$C_1$–$C_2$alkylphenyl$C_1$–$C_2$alkylene,
phenyl-$C_1$–$C_2$alkylene and
pyridyl;
R¹⁵ is selected from a chemical bond,
$C_1$–$C_4$-alkylene,
$C_2$–$C_4$-alkenylene,
$C_2$–$C_4$-alkynylene and
phenylene;
R¹⁶ is selected from a chemical bond,
$C_1$–$C_5$-alkylene,
$C_3$–$C_7$-cycloalkylene,
$C_3$–$C_5$-alkenylene,
$C_3$–$C_5$-alkynylene,
phenylene,
$C_1$–$C_3$alkylphenylene,
phenyl-$C_1$–$C_2$alkylene and
pyridyl;
R¹⁸, R¹⁹, R²⁰ and R²¹ are independently selected from
hydrogen,
$C_1$–$C_4$alkyl and
halo(F, Cl, Br, I)$C_1$–$C_4$alkyl;
R²² is selected from the group consisting of
hydroxy,
$C_1$–$C_8$-alkoxy,
$C_3$–$C_{12}$-alkenoxy,
phenoxy,
$C_1$–$C_6$alkyl-phenoxy,
di-$C_1$–$C_8$-alkylamino-$C_1$–$C_8$-alkoxy,
acylamino-$C_1$–$C_8$-alkoxy selected from the group
  acetylaminoethoxy,
  nicotinoylaminoethoxy, and
  succinamidoethoxy,
$C_1$–$C_8$-alkoyloxy-$C_1$–$C_8$-alkoxy,
phenyl-$C_1$–$C_8$alkoxy where the phenyl group is unsubstituted or substituted with one to three of the groups
  nitro,
  halo (F, Cl, Br, I),
  $C_1$–$C_4$-alkoxy and
  amino,
hydroxy-$C_2$–$C_8$-alkoxy,
dihydroxy-$C_3$–$C_8$-alkoxy,
morpholino-$C_2$–$C_8$-alkoxy and
NR²³R²⁴,
R²³ and R²⁴ are independently selected from
hydrogen,
$C_1$–$C_8$-alkyl,
$C_3$–$C_8$-alkenyl and
phenyl,
where the phenyl group is unsubstituted or substituted with one to three groups selected from
  nitro,
  halo (F, Cl, Br, I),
  $C_1$–$C_4$-alkoxy and
  amino; and pharmaceutically acceptable salts thereof.
5. The compound of claim 2 where Q—L— is selected from the group consisting of
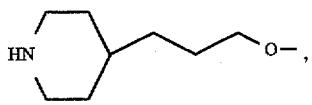
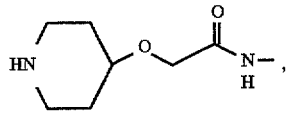
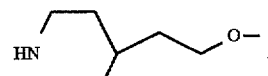
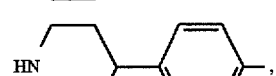
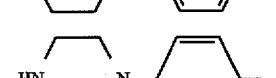
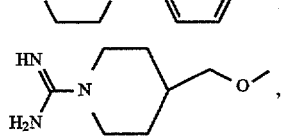
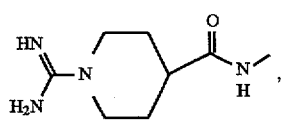
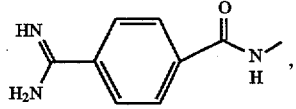
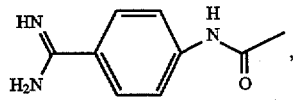
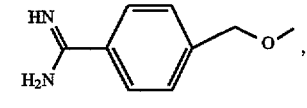
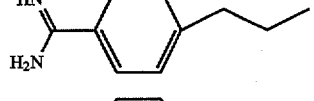
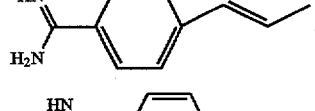
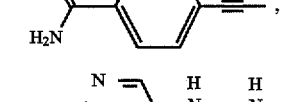
-continued
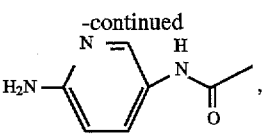
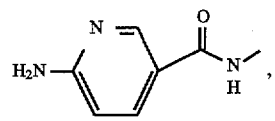
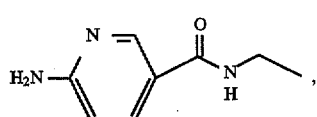
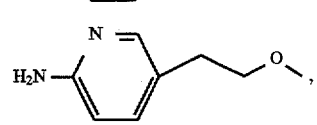
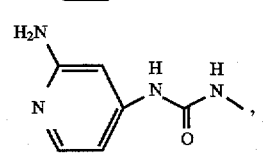
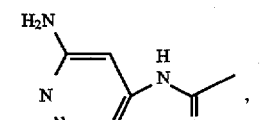
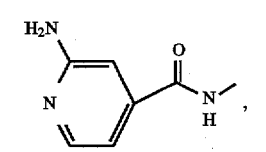
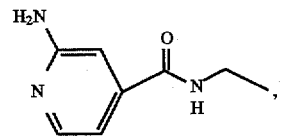
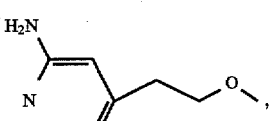
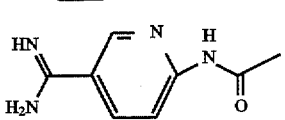
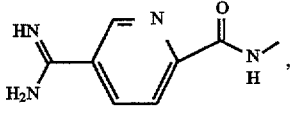
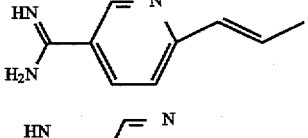

-continued

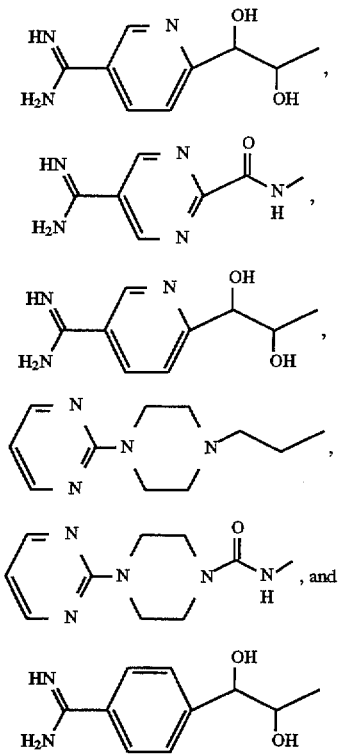

where any amino, amidino, or guanidino nitrogen is optionally derivitized with $C_1$–$C_6$ alkoxycarbonyl.

6. A compound represented by structural formula Ia

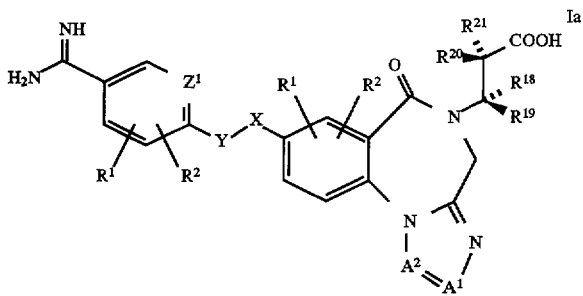

where $R^1$ and $R^2$ are each one or two substituents independently selected from hydrogen, fluro, trifluromethyl and chloro;
$R^{18}$, $R^{19}$, $R^{20}$ and $R^{21}$ are independently selected from $R^1$ and methyl;
$A^1$ is CH or N;
$A^2$ is CH, C—$CH_3$, C—$CH_2$—$CH_3$, or N;
—X—Y— is selected from —NH—C(=O)—, —C(=O)—NH—, —CC—, —$CH_2$—O—, —O—$CH_2$— and —$CH_2$—$CH_2$—; and
$Z^1$ is selected from N and $CR^1$.

7. A compound selected from the group consisting of
4H-imidazo[1,2-a][1,4]benzodiazepine-5(6H)-propanoic acid,8-[[4-(aminoiminomethyl)phenyl]ethynyl]-1-methyl-6-oxo, acetate,
4H-imidazo[1,2-a][1,4]benzodiazepine-5(6H)-propanoic acid,8-[[4-(aminoiminomethyl)phenyl]methoxy]-1-methyl-6-oxo, acetate,
4H-imidazo[1,2-a][1,4]benzodiazepine-5(6H)-propanoic acid,8-[[4-(aminoiminomethyl)benzoyl]amino]-1-methyl-6-oxo, acetate,
4H-imidazo[1,2-a][1,4]benzodiazepine-5(6H)-propanoic acid,8-[[4-(aminoiminomethyl)picolinoyl]amino]-1-methyl-6-oxo, acetate,
4H-imidazo[1,2-a][1,4]benzodiazepine-5(6H)-propanoic acid,8-[[4-(aminoiminomethyl)phenyl]ethynyl]-1-phenyl-6-oxo, acetate,
4H-imidazo[1,2-a][1,4]benzodiazepine-5(6H)-propanoic acid,8-[[4-(aminoiminomethyl)phenyl]methoxy]-1-phenyl-6-oxo, acetate,
4H-imidazo[1,2-a][1,4]benzodiazepine-5(6H)-propanoic acid,8-[[4-(aminoiminomethyl)benzoyl]amino]-1-phenyl-6-oxo, acetate,
4H-imidazo[1,2-a][1,4]benzodiazepine-5(6H)-propanoic acid,8-[[4-(aminoiminomethyl)picolinoyl]amino]-1-phenyl-6-oxo, acetate,
4H-[1,2,4]triazolo[4,3-a][1,4]benzodiazepine-5(6H)-propanoic acid,8-[[4-(aminoiminomethyl)phenyl]methoxy]-1-methyl-6-oxo, acetate,
4H-[1,2,4]triazolo[4,3-a][1,4]benzodiazepine-5(6H)-propanoic acid,8-[[4-(aminoiminomethyl)phenyl]ethynyl]-1-methyl-6-oxo, acetate,
4H-[1,2,4]triazolo[4,3-a][1,4]benzodiazepine-5(6H)-propanoic acid,8-[[4-(aminoiminomethyl)benzoyl]amino]-1-methyl-6-oxo, acetate,
4H-[1,2,4]triazolo[4,3-a][1,4]benzodiazepine-5(6H)-propanoic acid,8-[[4-(aminoiminomethyl)picolinoyl]amino]-1-methyl-6-oxo, acetate,
4H-[1,2,4]triazolo[4,3-a][1,4]benzodiazepine-5(6H)-propanoic acid,8-[[4-(aminoiminomethyl)phenyl]methoxy]-1-hydroxy-6-oxo, acetate,
4H-[1,2,4]triazolo[4,3-a][1,4]benzodiazepine-5(6H)-propanoic acid,8-[[4-(aminoiminomethyl)phenyl]ethynyl]-1-hydroxy-6-oxo, acetate,
4H-[1,2,4]triazolo[4,3-a][1,4]benzodiazepine-5(6H)-propanoic acid,8-[[4-(aminoiminomethyl)benzoyl]amino]-1-hydroxy-6-oxo, acetate,
4H-[1,2,4]triazolo[4,3-a][1,4]benzodiazepine-5(6H)-propanoic acid,8-[[4-(aminoiminomethyl)picolinoyl]amino]-1-hydroxy-6-oxo, acetate,
4H-[1,2,4]triazolo[4,3-a][1,4]benzodiazepine-5(6H)-propanoic acid,8-[[4-(aminoiminomethyl)phenyl]methoxy]-1-methoxy-6-oxo, acetate,
4H-[1,2,4]triazolo[4,3-a][1,4]benzodiazepine-5(6H)-propanoic acid,8-[[4-(aminoiminomethyl)phenyl]ethynyl]-1-methoxy-6-oxo, acetate,
4H-[1,2,4]triazolo[4,3-a][1,4]benzodiazepine-5(6H)-propanoic acid,8-[[4-(aminoiminomethyl)benzoyl]amino]-1-methoxy-6-oxo, acetate,
4H-[1,2,4]triazolo[4,3-a][1,4]benzodiazepine-5(6H)-propanoic acid,8-[[4-(aminoiminomethyl)picolinoyl]amino]-1-methoxy-6-oxo, acetate,
4H-[1,2,4]triazolo[4,3-a][1,4]benzodiazepine-5(6H)-propanoic acid,8-[[4-(aminoiminomethyl)phenyl]methoxy]-1-phenyl-6-oxo, acetate,
4H-[1,2,4]triazolo[4,3-a][1,4]benzodiazepine-5(6H)-propanoic acid,8-[[4-(aminoiminomethyl)phenyl]ethynyl]-1-phenyl-6-oxo, acetate,
4H-[1,2,4]triazolo[4,3-a][1,4]benzodiazepine-5(6H)-propanoic acid,8-[[4-(aminoiminomethyl)benzoyl]amino]-1-phenyl-6-oxo, acetate,
4H-[1,2,4]triazolo[4,3-a][1,4]benzodiazepine-5(6H)-propanoic acid,8-[[4-(aminoiminomethyl)picolinoyl]amino]-1-phenyl-6-oxo, acetate,
4H-[1,2,3,4]tetrazolo[1,5-a][1,4]benzodiazepine-5(6H)-propanoic acid,8-[[4-(aminoiminomethyl)phenyl]methoxy]-6-oxo, acetate,
4H-[1,2,3,4]tetrazolo[1,5-a][1,4]benzodiazepine-5(6H)-propanoic acid,8-[[4-(aminoiminomethyl)phenyl]ethynyl]-6-oxo, acetate,
4H-[1,2,3,4]tetrazolo[4,3-a][1,4]benzodiazepine-5(6H)-propanoic acid,8-[[4-(aminoiminomethyl)benzoyl]amino]-6-oxo, acetate, 4H-[1,2,3,4]tetrazolo[1,5-a][1,4]benzodiazepine-5(6H)-propanoic acid,8-[[4-(aminoiminomethyl)picolinoyl]amino]-6-oxo, acetate, 4H-imidazo[1,2-a][1,4]benzodiazepine-5(6H)-(R)-2-methyl,(S)-3-methyl propanoic acid, 8-[[4-(aminoiminomethyl)phenyl]ethynyl]-1-methyl-6-oxo, acetate, 4H-imidazo[1,2-a][1,4]benzodiazepine-5(6H)-(R)-2-methyl,(S)-3-methyl propanoic acid, 8-[[4-(aminoiminomethyl)-3-chloro-phenyl]ethynyl]-1-methyl-6-oxo, acetate, 4H-imidazo[1,2-a][1,4]benzodiazepine-5(6H)-(R)-2-methyl,(S)-3-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(R)-2-methyl,(S)-3-methyl propanoic acid, 8-[[4-(aminoiminomethyl)-pyridyl]ethynyl]-1-methyl-6-oxo, acetate, 4H-imidazo[1,2-a][1,4]benzodiazepine-5(6H)-(S)-2-methyl,(R)-3-methyl propanoic acid, 8-[[4-(aminoiminomethyl)phenyl]ethynyl]-1-methyl-6-oxo, acetate, 4H-imidazo[1,2-a][1,4]benzodiazepine-5(6H)-(S)-2-methyl,(R)-3-methyl propanoic acid, 8-[[4-(aminoiminomethyl)-3-chloro-phenyl]ethynyl]-1-methyl-6-oxo, acetate, 4H-imidazo[1,2-a][1,4]benzodiazepine-5(6H)-(S)-2-methyl,(R)-3-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(S)-2-methyl,(R)-3-methyl propanoic acid, 8-[[4-(aminoiminomethyl)-pyridyl]ethynyl]-1-methyl-6-oxo, acetate, 4H-imidazo[1,2-a][1,4]benzodiazepine-5(6H)-(R)-2-methyl propanoic acid, 8-[[4-(aminoiminomethyl)phenyl]ethynyl]-1-methyl-6-oxo, acetate, 4H-imidazo[1,2-a][1,4]benzodiazepine-5(6H)-(R)-2-methyl propanoic acid, 8-[[4-(aminoiminomethyl)-3-chloro-phenyl]ethynyl]-1-methyl-6-oxo, acetate, 4H-imidazo[1,2-a][1,4]benzodiazepine-5(6H)-(R)-2-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(R)-2-methyl propanoic acid, 8-[[4-(aminoiminomethyl)-pyridyl]ethynyl]-1-methyl-6-oxo, acetate, 4H-imidazo[1,2-a][1,4]benzodiazepine-5(6H)-(S)-2-methyl propanoic acid, 8-[[4-(aminoiminomethyl)phenyl]ethynyl]-1-methyl-6-oxo, acetate, 4H-imidazo[1,2-a][1,4]benzodiazepine-5(6H)-(S)-2-methyl propanoic acid, 8-[[4-(aminoiminomethyl)-3-chloro-phenyl]ethynyl]-1-methyl-6-oxo, acetate, 4H-imidazo[1,2-a][1,4]benzodiazepine-5(6H)-(S)-2-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(S)-2-methyl propanoic acid, 8-[[4-(aminoiminomethyl)-]pyridyl]ethynyl]-1-methyl-6-oxo, acetate, 4H-imidazo[1,2-a][1,4]benzodiazepine-5(6H)-(S)-3-methyl propanoic acid, 8-[[4-(aminoiminomethyl)phenyl]ethynyl]-1-methyl-6-oxo, acetate, 4H-imidazo[1,2-a][1,4]benzodiazepine-5(6H)-(S)-3-methyl propanoic acid, 8-[[4-(aminoiminomethyl)-3-chloro-phenyl]ethynyl]-1-methyl-6-oxo, acetate, 4H-imidazo[1,2-a][1,4]benzodiazepine-5(6H)-(S)-3-methyl propanoic acid, 8-[[4-(aminoiminomethyl)-2-chloro-phenyl]ethynyl]-1-methyl-6-oxo, acetate, 4H-imidazo[1,2-a][1,4]benzodiazepine-5(6H)-(S)-3-methyl propanoic acid, 8-[[4-(aminoiminomethyl)-]pyridyl]ethynyl]-1-methyl-6-oxo, acetate, 4H-[1,2,3,4]tetrazolo[4,3a][1,4]benzodiazepine-5(6H)-(R)-2-methyl,(S)-3-methyl-propanoic acid,8-[[4-(aminoiminomethyl)phenyl]methoxy-6-oxo, acetate, 4H-[1,2,3,4]tetrazolo[4,3a][1,4]benzodiazepine-5(6H)-(S)-2-methyl,(R)-3-methyl-propanoic acid,8-[[4-(aminoiminomethyl)phenyl]methoxy-6-oxo, acetate, 4H-[1,2,3,4]tetrazolo[4,3a][1,4]benzodiazepine-5(6H)-(R)-2-methyl, propanoic acid,8-[[4-(aminoiminomethyl)phenyl]methoxy-6-oxo, acetate, 4H-[1,2,3,4]tetrazolo[4,3a][1,4]benzodiazepine-5(6H)-(S)-2-methyl, propanoic acid,8-[[4-(aminoiminomethyl)phenyl]methoxy-6-oxo, acetate, 4H-[1,2,3,4]tetrazolo[4,3a][1,4]benzodiazepine-5(6H)-(S)-3-methyl, propanoic acid,8-[[4-(aminoiminomethyl)phenyl]methoxy-6-oxo, acetate, 4H-[1,2,3,4]tetrazolo[4,3a][1,4]benzodiazepine-5(6H)-(R)-2-methyl,(S)-3-methyl-propanoic acid,8-[[4-(aminoiminomethyl)-7-chloro-benzoyl]amino-6-oxo, acetate, 4H-[1,2,3,4]tetrazolo[4,3a][1,4]benzodiazepine-5(6H)-(R)-2-methyl,(S)-3-methyl-propanoic acid,8-[[4-(aminoiminomethyl)-benzoyl]amino-6-oxo, acetate, 4H-[1,2,3,4]tetrazolo[4,3a][1,4]benzodiazepine-5(6H)-(S)-2-methyl,(R)-3-methyl-propanoic acid,8-[[4-(aminoiminomethyl)-7-chloro-benzoyl]amino]-6-oxo, acetate, 4H-[1,2,3,4]tetrazolo[4,3a][1,4]benzodiazepine-5(6H)-(S)-2-methyl,(R)-3-methyl-propanoic acid,8-[[4-(aminoiminomethyl)-benzoyl]amino]-6-oxo, acetate, 4H-[1,2,3,4]tetrazolo[4,3a][1,4]benzodiazepine-5(6H)-(R)-2-methyl, propanoic acid,8-[[4-(aminoiminomethyl)-7-chloro-benzoyl]amino-6-oxo, acetate, 4H-[1,2,3,4]tetrazolo[4,3a][1,4]benzodiazepine-5(6H)-(R)-2-methyl, propanoic acid,8-[[4-(aminoiminomethyl)-benzoyl]amino]-6-oxo, acetate, 4H-[1,2,3,4]tetrazolo[4,3a][1,4]benzodiazepine-5(6H)-(S)-2-methyl, propanoic acid,8-[[4-(aminoiminomethyl)-7-chloro-benzoyl]amino-6-oxo, acetate, 4H-[1,2,3,4]tetrazolo[4,3a][1,4]benzodiazepine-5(6H)-(S)-2-methyl, propanoic acid,8-[[4-(aminoiminomethyl)-benzoyl]amino]-6-oxo, acetate, 4H-[1,2,3,4]tetrazolo[4,3a][1,4]benzodiazepine-5(6H)-(S)-3-methyl, propanoic acid,8-[[4-(aminoiminomethyl)-7-chloro-benzoyl]amino-6-oxo, acetate, 4H-[1,2,3,4]tetrazolo[4,3a][1,4]benzodiazepine-5(6H)-(S)-3-methyl, propanoic acid,8-[[4-(aminoiminomethyl)-benzoyl]amino]-6-oxo, acetate.

8. A pharmaceutical composition comprising a pharmaceutically acceptable excipient and a platelet aggregation reducing amount of the compound of claims 1–7.

9. A method of inhibiting platelet aggregation in a mammal comprising administering to the mammal a platelet aggregation inhibiting amount of the composition of claim 8.

10. A method for reducing platelet aggregation in a mammal comprising administering a pharmaceutically effective amount of the composition of claim 8 to the mammal.

11. A method for treating a mammal having an increased propensity for thrombus formation comprising administering a pharmaceutically effective amount of the composition of claim 8 to the mammal.

12. The method of claim 11 further comprising administering the composition in combination with a thrombolytic agent.

13. The method of claim 11 further comprising administering the composition in combination with an anticoagulant.

* * * * *